US011407800B2

(12) United States Patent
Limphong et al.

(10) Patent No.: US 11,407,800 B2
(45) Date of Patent: Aug. 9, 2022

(54) TRANSLATABLE MOLECULES AND SYNTHESIS THEREOF

(71) Applicant: Arcturus Therapeutics, Inc., San Diego, CA (US)

(72) Inventors: Pattraranee Limphong, San Diego, CA (US); Kiyoshi Tachikawa, San Diego, CA (US); Padmanabh Chivukula, San Diego, CA (US); Daiki Matsuda, San Diego, CA (US); Arisa Cale, San Diego, CA (US)

(73) Assignee: ARCTURUS THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 15/907,123

(22) Filed: Feb. 27, 2018

(65) Prior Publication Data

US 2018/0327471 A1 Nov. 15, 2018

Related U.S. Application Data

(60) Provisional application No. 62/465,073, filed on Feb. 28, 2017.

(51) Int. Cl.
| | | |
|---|---|---|
| *C12N 15/10* | (2006.01) | |
| *C07K 14/505* | (2006.01) | |
| *C07K 14/745* | (2006.01) | |
| *C07K 14/575* | (2006.01) | |
| *C07K 14/81* | (2006.01) | |
| *A61K 38/48* | (2006.01) | |
| *A61K 38/17* | (2006.01) | |
| *A61K 38/18* | (2006.01) | |
| *A61K 31/7115* | (2006.01) | |
| *A61K 38/00* | (2006.01) | |

(52) U.S. Cl.
CPC ........ *C07K 14/505* (2013.01); *A61K 31/7115* (2013.01); *A61K 38/1709* (2013.01); *A61K 38/1816* (2013.01); *A61K 38/482* (2013.01); *A61K 38/4846* (2013.01); *C07K 14/575* (2013.01); *C07K 14/745* (2013.01); *C07K 14/81* (2013.01); *A61K 38/00* (2013.01)

(58) Field of Classification Search
None
See application file for complete search history.

(56) References Cited

U.S. PATENT DOCUMENTS

| | | |
|---|---|---|
| 7,659,391 B2 | 2/2010 | De Backer |
| 8,093,367 B2 | 1/2012 | Kore |
| 8,304,529 B2 | 11/2012 | Kore |
| 8,748,089 B2 | 6/2014 | Kariko |
| 9,149,506 B2 | 10/2015 | Chakraborty |
| 9,751,925 B2 | 9/2017 | Hoge |
| 10,072,057 B2 | 9/2018 | Hoge |
| 2009/0226906 A1 | 9/2009 | Xie |
| 2013/0123481 A1 | 5/2013 | De Fougerolles |
| 2015/0064235 A1 | 3/2015 | Bancel |
| 2015/0104476 A1 | 4/2015 | Von Der |
| 2015/0246139 A1* | 9/2015 | Bancel ................. A61K 9/1272 514/44 R |
| 2016/0237134 A1 | 8/2016 | Hoge |
| 2017/0362627 A1* | 12/2017 | Reynders, III ..... A61K 31/7088 |
| 2019/0382774 A1* | 12/2019 | Hoge .................... C12N 15/85 |

FOREIGN PATENT DOCUMENTS

| | | |
|---|---|---|
| WO | WO 2015/051169 | 4/2015 |
| WO | WO 2015/061491 | 4/2015 |
| WO | WO 2015/124935 | 8/2015 |
| WO | WO 2016/070166 | 5/2016 |
| WO | WO 2016/077125 | 5/2016 |

OTHER PUBLICATIONS

Li et al., Bioconjugate Chemistry, Feb. 24, 2016, pp. 849-853 plus supplemental material—total of 10 pages (Year: 2016).*
Beckert et al.,"Synthesis of RNA by In Vitro Transcription" in RNA, Methods in Molecular Biology 703, edited by H. Nielsen, pp. 29-41, 2011.*
Kozak, Molecular and Cellular Biology, Leader length and secondary structure modulate mRNA function under conditions of stress, 1988, pp. 2737-2744, vol. 8, No. 7.
Kozak, Journal of Cell Biology, The Scanning model fortranslation: An update, 1989, pp. 229-241, vol. 108.
Kozak, Proceedings National Academy of Science, Downstream secondary structure facilitates recognition of initiator codons by Eukaryotic Ribosomes, 1990, pp. 8301-8305, vol. 87.
Kozak, Journal of Biological Chemistry, Structural features in Eukaryotic mRNAs that modulate the initiation of translation, 1991, pp. 19867-19870, vol. 266, No. 30.

(Continued)

*Primary Examiner* — Sean McGarry

(74) *Attorney, Agent, or Firm* — Mintz, Levin, Cohn, Ferris, Glovsky and Popeo, P.C.

(57) ABSTRACT

A range of therapeutic mRNA molecules expressible to provide a target polypeptide or protein. The RNA molecules can contain one or more 5-methoxyuridines and 5-methylcytidines. Further provided are DNA templates, which can be transcribed to provide a target mRNA, and can have altered nucleotides, such as reduced deoxyadenosines. Also provided are processes for making the therapeutic mRNA molecules. The RNA molecules can be translated in vitro or in vivo to provide an active polypeptide or protein. The RNA molecules can be included in a composition used for preventing, treating, or ameliorating at least one symptom of a disease or condition in a subject in need thereof.

19 Claims, 21 Drawing Sheets

Specification includes a Sequence Listing.

(56) References Cited

OTHER PUBLICATIONS

United States Patent and Trademark Office, International Search Report and Written Opinion for PCT/US2018/020018, dated Jul. 26, 2018, 17 pages.
Wu et al. (Mar. 2020) "Synthesis of Low Immunogenicity RNA With High-temperature in Vitro Transcription", RNA, 26(3):345-360.

* cited by examiner

TRANSLATABLE MOLECULES AND SYNTHESIS THEREOF

SEQUENCE LISTING

This application includes a Sequence Listing submitted electronically as an ASCII file named ARC4097WO_SL.txt.

BACKGROUND OF THE INVENTION

The use of RNA molecules in therapeutics is a promising goal. Among other things, RNA molecules could be manipulated to affect or treat rare diseases that are not as readily approached by other means. It would be useful to utilize synthetic RNA to control or enhance the production and purity of a polypeptide or protein, especially one directly associated with a disease. However, realizing the potential of RNA therapeutics has long been difficult.

Drawbacks of using RNA molecules as medicinal agents include the general lack of control or ability to vary the structure to enhance therapeutic properties. There is a general lack of predictability for modifications or changes in chemical structures to modulate properties that are pertinent to drug success.

For example, increasing the level of a therapeutic moiety in vivo is a significant factor in drug success. Thus, compositions and methods to increase the translation efficiency of an RNA, and specifically increase the amount of a translated polypeptide or protein is a desirable result.

Further, structural modification that increases the efficiency of generating a translatable RNA, can improve the apparent and/or inherent activity of the RNA, thus contributing new therapeutic effects.

There is an urgent need for molecules, structures and compositions having translational activity to provide active polypeptides and proteins, both in vitro and in vivo. Such new molecules having functional cytoplasmic half-life for producing active peptides and proteins can yield new drug molecules and therapeutic modalities.

What is needed are translatable molecules, and methods of synthesis thereof, that can have increased specific activity, lifetime or other properties over native mRNA, to be used in methods and compositions for producing and delivering active polypeptides and proteins in medicines.

BRIEF SUMMARY

This invention relates to the fields of molecular biology, biopharmaceuticals and therapeutics generated with translatable molecules. More particularly, this invention relates to methods, structures and compositions for synthesis of molecules having translational activity for making active polypeptides or proteins, for use in vivo and as therapeutics.

This invention provides methods and compositions for a wide reaching platform to design and implement RNA agents for rare diseases, and other therapeutic modalities.

This disclosure includes methods and compositions for novel molecules having translational activity, which can be used to provide active polypeptides, proteins, or fragments thereof, in various settings.

In some aspects, this invention provides processes for making an RNA including steps for providing a DNA molecule that can be transcribed to provide the RNA. In the DNA, certain codons in an open reading frame of the DNA can be replaced with alternative codons, and codon in-frame position in a reading frame. The DNA molecule can be transcribed in the presence of nucleoside triphosphates, a 5' cap, and one or more chemically-modified nucleoside triphosphates to form a product mixture. An RNA can be isolated and purified from the mixture. The RNA may contain natural and chemically-modified nucleotides.

In certain aspects, this invention provides methods for synthesis of an RNA. Processes for making an RNA can include steps for providing a DNA molecule that can be transcribed to provide the RNA. In the DNA, certain deoxyadenosine nucleotides in an open reading frame of the DNA can be replaced with non-deoxyadenosine nucleotides. The DNA may further comprise a promoter for transcribing the non-coding strand. The DNA molecule can be transcribed in the presence of nucleoside triphosphates, a 5' cap, and one or more chemically-modified nucleoside triphosphates to form a product mixture. An RNA can be isolated and purified from the mixture. The RNA may contain natural and chemically-modified nucleotides.

The RNA product molecules made by a process of this invention can have functional cytoplasmic half-life for producing polypeptides and proteins. The peptides and proteins can be active for therapeutic modalities, as well as for use in vaccines and immunotherapies.

The RNA molecules made by a process of this invention can be translatable messenger molecules, which can have long half-life, particularly in the cytoplasm of a cell. The longer duration of the translatable messenger molecules of this invention can be significant for providing a translation product that is active for ameliorating, preventing or treating disease.

This disclosure provides a range of structures for translatable molecules having increased specific activity and/or lifetime over a native mRNA. The translatable molecules of this invention can be used in medicines, and for methods and compositions for producing and delivering active peptides and proteins.

This invention further provides processes for making translatable RNA molecules having enhanced properties for providing and delivering polypeptides and proteins.

Embodiments of this disclosure can provide a wide range of novel, translatable messenger RNA molecules. The translatable messenger molecules can contain various chemically modified nucleotides.

The translatable molecules of this invention can be used to provide polypeptides or proteins in vitro, ex vivo, or in vivo.

The translatable messenger molecules of this invention can be designed to provide high-efficiency expression of an expression product, polypeptide, protein, or fragment thereof. The expression can be in vitro, ex vivo, or in vivo.

In some embodiments, the messenger molecules of this invention have increased cytoplasmic half-life over a native, mature mRNA that provides the same expression product. The structures and compositions of this invention can provide increased functional half-life with respect to native, mature mRNAs.

In further aspects, a translatable messenger molecule of this invention can provide increased activity as a drug providing a polypeptide or protein product, as compared to a native, mature mRNA. In some embodiments, a translatable molecule can reduce the expected dose level that would be required for efficacious therapy.

In additional embodiments, this invention provides methods for ameliorating, preventing or treating a disease or condition in a subject comprising administering to the subject a composition containing a translatable molecule of this invention.

The disease or condition can be a rare disease, a chronic disease, a liver disease, or a cancer, among others.

In certain embodiments, this invention provides methods for producing a polypeptide or protein in vivo, by administering to a mammal a composition containing a translatable RNA molecule. The polypeptide or protein may be deficient in a disease or condition of a subject or mammal.

This invention further provides methods for producing a therapeutic polypeptide or protein in vitro, or in vivo, by transfecting a cell with a translatable molecule. The polypeptide or protein can be deficient in a disease or condition of a subject or mammal.

Embodiments of this invention include the following:

A RNA that is expressible to provide a target polypeptide or protein, wherein the occurrence of uridines in a coding sequence region of the RNA is reduced by at least 20% as compared to a wild type mRNA that is expressible to provide the target polypeptide or protein, and wherein the RNA contains one or more 5-methoxyuridines.

The RNA above, wherein 10-100% of the uridines in the RNA are 5-methoxyuridines. The RNA above, wherein the RNA contains one or more 5-methylcytidines. The RNA above, wherein 10-100% of the cytidines in the RNA are 5-methylcytidines.

The RNA above, wherein the occurrence of uridines in a coding sequence region of the RNA is reduced by at least 35% as compared to a wild type mRNA that is expressible to provide the target polypeptide or protein.

The RNA above, wherein the RNA is translatable for expression of a polypeptide or protein having at least 75% identity to the target polypeptide or protein. The RNA above, wherein the RNA is translatable for expression of a polypeptide or protein having at least 85% identity, or 90% identity, or 95% identity to the target polypeptide or protein.

The RNA above, wherein the RNA comprises a 5' cap, a 5' untranslated region, a coding region, a 3' untranslated region, and a tail region. The RNA above, wherein the RNA comprises a translation enhancer in a 5' or 3' untranslated region.

The RNA above, wherein the RNA is translatable in vitro, ex vivo, or in vivo. The RNA above, wherein the RNA comprises from 50 to 15,000 nucleotides. The RNA above, wherein the target polypeptide or protein is a polypeptide, a protein, a protein fragment, an antibody, an antibody fragment, a vaccine immunogen, or a vaccine toxoid.

The RNA above, wherein the RNA has at least 2-fold increased translation efficiency in vivo as compared to a native mRNA that expresses the target polypeptide or protein. The RNA above, wherein the RNA has at least 5-fold reduced immunogenicity as compared to a native mRNA that expresses the target polypeptide or protein.

The RNA above, wherein the target polypeptide or protein is an expression product, or a fragment thereof, of a gene selected from EPO, AAT, ADIPOQ, F9, TTR, and BIRC5.

Embodiments of this invention further contemplate a DNA encoding the RNA above.

In some aspects, this invention provides a composition comprising an RNA above and a pharmaceutically acceptable carrier. The carrier may comprise a transfection reagent, a nanoparticle, or a liposome.

This invention includes methods for preventing, treating, or ameliorating at least one symptom of a disease or condition in a subject in need thereof, the method comprising administering to the subject a composition above. The composition can be used in medical therapy, or in the treatment of the human or animal body.

In further embodiments, this invention includes a range of DNA templates that can be transcribable for expression of a target polypeptide or protein, the DNA template comprising a non-coding sequence template region, wherein deoxyadenosine nucleotides in the non-coding sequence template region are replaced with non-deoxyadenosine nucleotides, and wherein the occurrence of deoxyadenosines in the template region is reduced by at least 20% as compared to a wild type gene that is transcribable for expression of the target polypeptide or protein.

A DNA template may be double stranded, and comprise a coding non-template strand complementary to a non-coding template strand. A DNA template may have the occurrence of deoxyadenosines in the template region reduced by at least 35% as compared to a wild type gene that is transcribable for expression of the target polypeptide or protein. A DNA template may be transcribable for expression of a polypeptide or protein having at least 75% identity to the target polypeptide or protein. A DNA template can be transcribable for expression of a polypeptide or protein having at least 85% identity, or 90% identity, or 95% identity to the target polypeptide or protein. A DNA template may have a target polypeptide or protein being an expression product, or a fragment thereof, of a gene selected from EPO, AAT, ADIPOQ, F9, TTR, and BIRC5. A DNA template may comprise a plasmid, a linear polynucleotide, a PCR product, a synthetic oligonucleotide, a cloned oligonucleotide, or a reverse transcribed RNA.

This invention further contemplates processes for making an RNA, the RNA having an RNA coding region for expressing a target polypeptide or protein, the process comprising:

providing a DNA molecule comprising a non-coding template region encoding the RNA, wherein deoxyadenosine nucleotides in the portion of the non-coding template region that encodes the RNA coding region are replaced with non-deoxyadenosine nucleotides, and wherein the DNA further comprises a promoter for transcribing the template region;

transcribing the template region in the presence of nucleoside triphosphates and one or more chemically-modified nucleoside triphosphates to form a product mixture;

isolating the RNA, wherein the RNA comprises natural and chemically-modified nucleotides.

In a process above, the chemically-modified nucleosides can be 5-methoxyuridines. The chemically-modified nucleosides may be 5-methoxyuridines and 5-methylcytidines.

In some embodiments, the chemically-modified nucleosides can be selected from 5-hydroxyuridine, 5-methyluridine, 5,6-dihydro-5-methyluridine, 2'-O-methyluridine, 2'-O-methyl-5-methyluridine, 2'-fluoro-2'-deoxyuridine, 2'-amino-2'-deoxyuridine, 2'-azido-2'-deoxyuridine, 4-thiouridine, 5-hydroxymethyluridine, 5-carboxyuridine, 5-carboxymethylesteruridine, 5-formyluridine, 5-methoxyuridine, 5-propynyluridine, 5-bromouridine, 5-iodouridine, 5-fluorouridine, pseudouridine, 2'-O-methyl-pseudouridine, $N^1$-hydroxypseudouridine, $N^1$-methylpseudouridine, 2'-O-methyl-$N^1$-methylpseudouridine, $N^1$-ethylpseudouridine, $N^1$-hydroxymethylpseudouridine, and Arauridine.

In a process above, the chemically-modified nucleosides can replace 10-100% of the same, but non-chemically-modified nucleotides in the RNA, or 50-100% of the same, but non-chemically-modified nucleotides in the RNA, or 10-80% of the same, but non-chemically-modified nucleotides in the RNA, or 50-80% of the same, but non-chemically-modified nucleotides in the RNA.

In a process above, the occurrence of deoxyadenosines in the template region can be reduced by at least 20% as compared to a wild type gene that is transcribable for expression of the target polypeptide or protein. In a process above, the occurrence of deoxyadenosines in the template region is reduced by at least 35% as compared to a wild type gene that is transcribable for expression of the target polypeptide or protein.

In certain embodiments, the step of transcribing the DNA can be performed along with a 5' cap. The RNA may comprise a 5' cap, a 5' untranslated region, a coding region, a 3' untranslated region, and a tail region. The step of transcribing may be performed with an RNA polymerase, such as SP6, T7, or T3 phage RNA polymerase. The promoter can be double stranded.

In a process above, the level of double-stranded RNA impurities in the product mixture can be reduced at least 2-fold as compared to the same process without replacing the deoxyadenosine nucleotides. The level of double-stranded RNA impurities in the product mixture may be less than 5%, or less than 1%, or less than 0.1% of the total RNA.

Embodiments of this invention also contemplate a synthetic RNA comprising a product of a process above.

This invention includes compositions comprising an RNA above and a pharmaceutically acceptable carrier. The carrier can comprise a transfection reagent, a nanoparticle, or a liposome.

In some aspects, this invention includes methods for preventing, treating, or ameliorating at least one symptom of a disease or condition in a subject in need thereof, by administering to the subject a composition of an RNA above.

A composition may be used for medical therapy, or in the treatment of the human or animal body. A composition may be used for preparing or manufacturing a medicament for preventing, ameliorating, delaying onset or treating a disease or condition in a subject in need.

BRIEF DESCRIPTION OF THE DRAWINGS

As shown in FIG. 1, certain deoxyadenosine nucleotides may be replaced in the template by non-deoxyadenosine nucleotides, while codon assignment to a target product may be preserved (S101). The double stranded DNA further includes a double stranded promoter for transcribing the template strand, such as a T7 promoter. The DNA can be transcribed in the presence of nucleoside triphosphates, including optionally a 5' cap (shown), and along with one or more chemically modified nucleoside triphosphates to form a product mixture (S103). The ARC-RNA product can be isolated and purified from the product mixture (S105). The ARC-RNA product is a translatable molecule that contains natural and chemically modified nucleotides, with enhanced translational efficiency and properties.

As shown in FIG. 2, certain deoxyadenosine nucleotides may be replaced by non-deoxyadenosine nucleotides in the template, while codon assignment to a target product may be preserved (S101). The DNA further includes a promoter. The DNA can be transcribed in the presence of nucleoside triphosphates, including optionally a 5' cap, and along with one or more chemically modified nucleoside triphosphates to form a product mixture (S103). The ARC-RNA product can be isolated and purified from the product mixture (S105).

FIG. 4 shows surprisingly high translational efficiency of the ARC-RNA (5MeOU) compared to the wild type hEPO mRNA (UTP).

FIG. 5 shows surprisingly high translational efficiency of the ARC-RNA (5MeOU) compared to the wild type hF9 mRNA (UTP).

FIG. 6 shows the results of a dot blot for detecting double strand RNA impurity in the synthesis mixture (nitro cellulose membrane, J2 antibody to detect dsRNA). The ARC-RNA (5MeOU) synthesis product, which was translatable for hF9, showed surprisingly reduced dot blot intensity as compared to a wild type mRNA synthesis product, without 5MeOU, and with similarly reduced T. Thus, the ARC-RNA (5MeOU) synthesis process, with template reduced T composition, surprisingly reduced double strand RNA impurity levels in the synthesis mixture. The process for synthesizing the ARC-RNA (5MeOU) molecules of this invention provided a surprisingly reduced level of double strand RNA impurity.

FIG. 7 shows the results of a dot blot for detecting double strand RNA impurity in the synthesis mixture (nitro cellulose membrane, J2 antibody to detect dsRNA). The ARC-RNA (5MeOU) synthesis product, which was translatable for hAAT, showed surprisingly reduced dot blot intensity as compared to a wild type mRNA synthesis product, without 5MeOU, and with similarly reduced T. Thus, the ARC-RNA (5MeOU) synthesis process, with template reduced T composition, surprisingly reduced double strand RNA impurity levels in the synthesis mixture. The process for synthesizing the ARC-RNA (5MeOU) molecules of this invention provided a surprisingly reduced level of double strand RNA impurity.

FIG. 8 shows surprisingly high translational efficiency of the ARC-RNA (5MeOU) compared to the wild type human adiponectin mRNA (UTP). The translational efficiency of the ARC-RNA (5MeOU) was also surprisingly higher as compared to human adiponectin mRNA (N1MPU), a similar RNA made with $N^1$-methylpseudouridine (100%).

FIG. 9 shows the results of a dot blot for detecting double strand RNA impurity in the synthesis mixture (nitro cellulose membrane, J2 antibody to detect dsRNA). The ARC-RNA (5MeOU) synthesis product, which was translatable for human adiponectin, showed surprisingly reduced dot blot intensity as compared to a wild type mRNA synthesis product, without 5MeOU, and with similarly reduced T. Thus, the ARC-RNA (5MeOU) synthesis process, with template reduced T composition, surprisingly reduced double strand RNA impurity levels in the synthesis mixture. The process for synthesizing the ARC-RNA (5MeOU) molecules of this invention provided a surprisingly reduced level of double strand RNA impurity.

FIG. 10 shows surprisingly high translational efficiency of the ARC-RNA (5MeOU) compared to the wild type cynomolgus monkey cmEPO mRNA (UTP). The translational efficiency of the ARC-RNA (5MeOU) was also surprisingly higher as compared to cmEPO mRNA (N1MPU), a similar RNA made with $N^1$-methylpseudouridine (100%).

FIG. 11 shows the results of a dot blot for detecting double strand RNA impurity in the synthesis mixture (nitro cellulose membrane, J2 antibody to detect dsRNA). The ARC-RNA (5MeOU) synthesis product, which was translatable for mouse EPO, showed surprisingly reduced dot blot intensity as compared to a wild type mRNA synthesis product, without 5MeOU, and with similarly reduced T. Under the same conditions and synthesis, the ARC-RNA (5MC/5MeOU) synthesis product, which was translatable for mouse EPO, also showed surprisingly further reduced dot blot intensity as compared to a wild type mRNA synthesis product, without 5MC/5MeOU. Thus, the ARC-RNA (5MC/5MeOU) synthesis process, with template reduced T composition, surprisingly reduced double strand RNA impurity levels in the synthesis mixture. As shown in FIG. 11, similar advantageously reduced double strand RNA impurity levels were found in synthesis mixtures for monkey mAdipo mRNA and mfEPO mRNA.

FIG. 12 shows the results of a cytokine assay for IFN-α as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of IFN-α.

FIG. 13 shows the results of a cytokine assay for RANTES as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of RANTES.

FIG. 14 shows the results of a cytokine assay for IL-6 as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of IL-6.

FIG. 15 shows the results of a cytokine assay for MIP-1a as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of MIP-1a.

FIG. 16 shows the results for hEPO protein expression after hEPO ARC-mRNA was injected into mice at 0.3 mg/kg dose. hEPO in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased about 2-fold.

FIG. 17 shows the results for cmEPO protein expression after cmEPO ARC-mRNA was injected into mice at 0.3 mg/kg dose. cmEPO in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased greater than 3-fold.

FIG. 18 shows the results for hF9 protein expression after hF9 ARC-mRNA was injected into mice at 0.3 mg/kg dose. hF9 in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased about 2-fold.

FIG. 19 shows the results for hAdipo protein expression after hAdipo ARC-mRNA was injected into mice at 0.3 mg/kg dose. hAdipo in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased about 2-fold.

FIG. 20 shows the results for hAAT protein expression after hAAT ARC-mRNA was injected into mice at 0.3 mg/kg dose. hAAT in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased up to about 4-fold.

FIG. 21 shows the results of a cytokine assay as generated in mouse using an hEPO ARC-RNA (5MeOU) of this invention, detected in serum 6 hrs post injection. The ARC-RNAs synthesized with 5MeOU and a reduced T composition template showed markedly reduced immunogenicity as compared to a synthetic mRNA with the same sequence and containing only natural nucleotides. The hEPO ARC-RNA (5MeOU) did not stimulate cytokine responses in vivo as compared to the UTP control.

DESCRIPTION OF THE INVENTION

Figure 1:
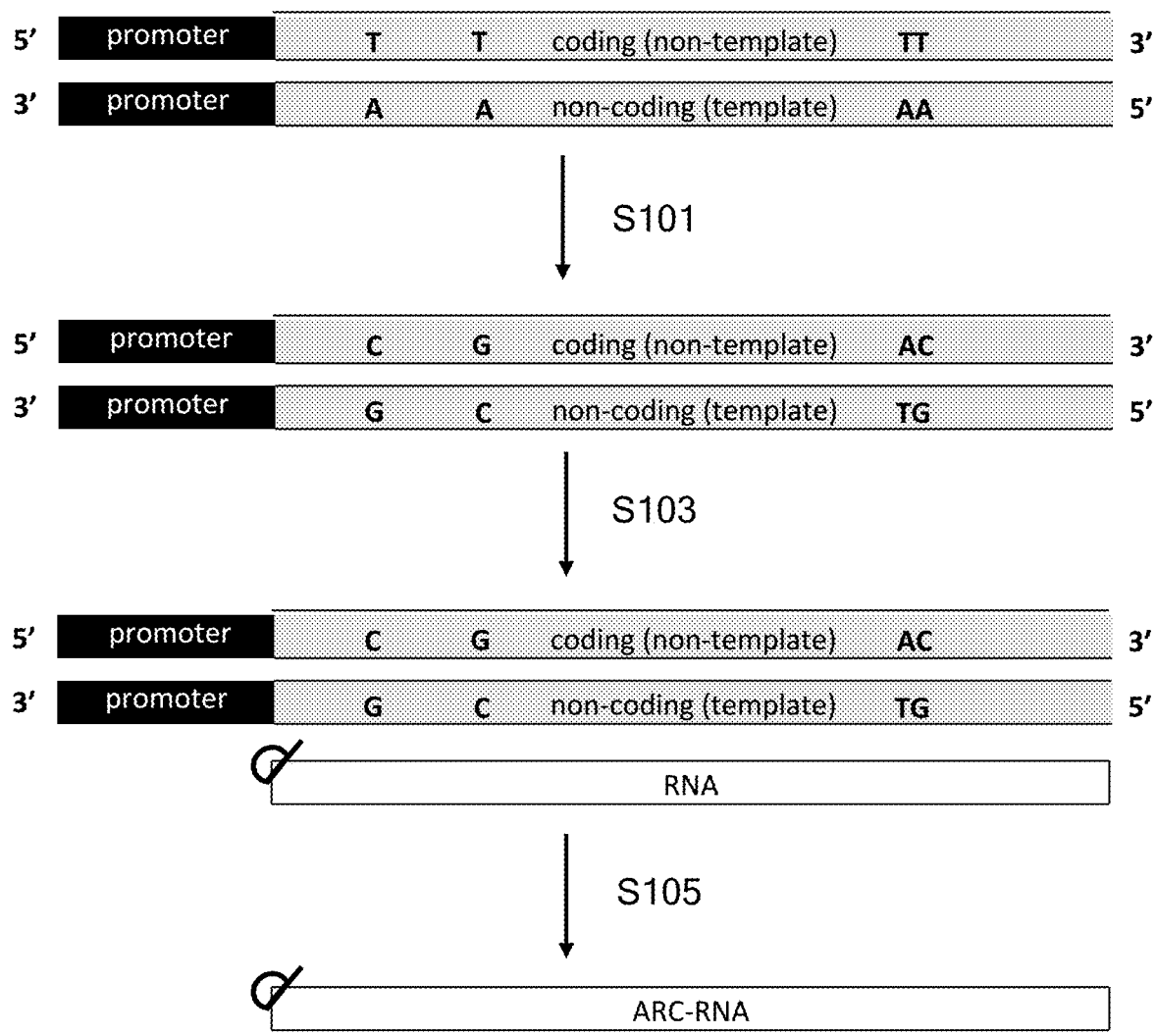
FIG. 1 shows a process for production of a translatable ARC-RNA molecule of this invention. A double stranded DNA molecule is provided having a non-coding template strand of nucleotides that can be transcribed to provide a targeted product RNA. The double stranded DNA contains an open reading frame in the template strand, which template is an alternative variation from a wild type or native version.

This invention provides a range of novel agents and compositions to be used for therapeutic applications. The molecules and compositions of this invention can be used for ameliorating, preventing or treating a disease, including, for example, rare diseases, and chronic diseases, among others.

In some embodiments, this invention encompasses synthetic, purified, and/or isolated translatable polynucleotide molecules for expressing a human polypeptide, protein, or fragment thereof, wherein the polynucleotide molecules comprise natural and chemically-modified nucleotides and encode the polypeptide, protein, or fragment.

Embodiments of this invention can provide nucleic acids that, when introduced into cells, can have improved properties such as increased expression levels, reduced immune response, and increased lifetime as compared to wild type nucleic acids.

In some embodiments, a translatable molecule of this invention can provide a modified mRNA. A modified mRNA can encode one or more biologically active peptides, polypeptides, or proteins. A modified mRNA can comprise one or more modifications as compared to wild type mRNA. Modifications of an mRNA may be located in any region of the molecule, including a coding region, an untranslated region, or a cap or tail region.

As used herein, the term "translatable" may be used interchangeably with the term "expressible." These terms can refer to the ability of polynucleotide, or a portion thereof, to provide a polypeptide, by transcription and/or translation events in a process using biological molecules, or in a cell, or in a natural biological setting. In some settings, translation is a process that can occur when a ribosome creates a polypeptide in a cell. In translation, a messenger RNA (mRNA) can be decoded by a ribosome to produce a specific amino acid chain, or polypeptide. A translatable oligomer or polynucleotide can provide a coding sequence region (usually, CDS), or portion thereof, that can be processed to provide a polypeptide, protein, or fragment thereof.

A translatable oligomer or polynucleotide of this invention can provide a coding sequence region, and can comprise various untranslated sequences, such as a 5' cap, a 5' untranslated region (5' UTR), a 3' untranslated region (3' UTR), and a tail region.

In some embodiments, a translatable molecule may include a 5' cap, a 5' UTR, a translation initiation sequence such as a Kozak sequence, a CDS, a 3' UTR, and a tail region.

In certain embodiments, a translatable molecule may include a 5' cap (m7GpppGm), a 5' UTR of tobacco etch virus (TEV), a Kozak sequence, a human CDS, a 3' UTR of *xenopus* beta-globin (XbG), and a tail region.

In additional embodiments, a human CDS may comprise a codon-modified sequence.

In certain embodiments, the level of G or C nucleotides of a region of a modified mRNA may be increased as compared to the level in the same region of the wild type mRNA, while codon assignment of the modified mRNA and the encoded amino acid sequence may be preserved. The increased level of G or C may be in any region of the molecule, including a coding region.

The level of GC content of a modified mRNA may be increased by at least 1%, or by at least 2%, or by at least 3%, or by at least 4%, or by at least 5%, or by at least 6%, or by at least 7%, or by at least 8%, or by at least 9%, or by at least 10%, or by at least 11%, or by at least 12%, or by at least 13%, or by at least 14%, or by at least 15%, or by at least 16%, or by at least 17%, or by at least 18%, as compared to the wild type mRNA.

The level of GC content of a modified mRNA may be increased by 1-3%, or by 4-6%, or by 7-9%, or by 10-12%, or by 13-15%, or by 16-20%, as compared to the wild type mRNA.

In further embodiments, the level of U nucleotides of a region of a modified mRNA may be decreased as compared to the level in the same region of the wild type mRNA, while codon assignment of the modified mRNA and the encoded amino acid sequence may be preserved. The decreased level of U may be in any region of the molecule, including a coding region.

The level of U content of a modified mRNA may be decreased by at least 1%, or by at least 2%, or by at least 3%, or by at least 4%, or by at least 5%, or by at least 6%, or by at least 7%, or by at least 8%, or by at least 9%, or by at least 10%, or by at least 12%, as compared to the wild type mRNA.

The level of U content of a modified mRNA may be decreased by 1%, or by 2%, or by 3%, or by 4%, or by 5%, or by 6%, or by 7%, or by 8%, or by 9%, or by 10%, as compared to the wild type mRNA.

In some embodiments, a translatable molecule of this invention may comprise a coding sequence that is at least 80%, 85%, 90%, 91%, 92%, 93%, 94%, 95%, 96%, 97%, 98%, 99% or more identical to a portion of a reference mRNA sequence, such as a human wild type mRNA sequence.

In some embodiments, a translatable molecule of this invention may comprise a coding sequence that has one, or two, or three, or four, or five, or six, or seven, or eight, or nine, or ten, or fifteen, or twenty or more synonymous or non-synonymous codon replacements as compared to a reference mRNA sequence, such as a human wild type mRNA sequence.

In some embodiments, a non-coding template sequence that is transcribable to provide a translatable molecule of this invention, when transcribed may provide a translatable molecule that is at least 80%, or 85%, or 90%, or 91%, or 92%, or 93%, or 94%, or 95%, or 96%, or 97%, or 98%, or 99% identical to a portion of a reference mRNA sequence, such as a human wild type mRNA sequence.

In some embodiments, a non-coding template sequence that is transcribable to provide a translatable molecule of this invention, when transcribed may provide a translatable molecule that has one, or two, or three, or four, or five, or six, or seven, or eight, or nine, or ten, or fifteen, or twenty or more synonymous or non-synonymous codon replacements as compared to a reference mRNA sequence, such as a human wild type mRNA sequence.

In some embodiments, a translatable molecule of this invention may be used to express a polypeptide that is at least 80%, 85%, 90%, 91%, 92%, 93%, 94%, 95%, 96%, 97%, 98%, 99% or more identical to a portion of a reference polypeptide or protein sequence, such as a human wild type protein sequence.

In some embodiments, a translatable molecule of this invention may be used to express a polypeptide that has one, or two, or three, or four, or five, or six, or seven, or eight, or nine, or ten, or fifteen, or twenty or more variant amino acid residues as compared to a reference polypeptide or protein sequence, such as a human wild type protein sequence.

In some embodiments, a translatable molecule of the invention may encode a fusion protein comprising a full length, or fragment or portion of a native human protein fused to another sequence, for example by N or C terminal fusion. In some embodiments, the N or C terminal sequence can be a signal sequence or a cellular targeting sequence.

A translatable molecule may comprise one or more LNA monomers.

The translatable molecules of this invention can be used in methods for ameliorating, preventing or treating a disease or condition associated with a polypeptide or protein. The translation efficiency of a translatable molecule of this invention can be increased as compared to a native mRNA.

A translatable molecule of this invention, which has one or more chemically modified nucleotides, can have reduced immunogenicity as compared to a native mRNA, or a synthetic mRNA with the same sequence and containing only natural nucleotides.

In some embodiments, a translatable molecule of this invention can have reduced immunogenicity as compared to a native mRNA. A translatable molecule can be less immunogenic than a synthetic RNA molecule with the same sequence and containing only natural nucleotides. Some methods for measuring immunogenicity include secretion of cytokines, for example, IL-12, IFN-α, TNF-α, RANTES, MIP-1a or b, IL-6, IFN-b, IFN-g or IL-8, and measuring expression of DC activation markers, for example, CD83, HLA-DR, CD80 and CD86.

In certain embodiments, the immunogenicity of a translatable molecule can be reduced by 2-fold, or 3-fold, or 5-fold, or 10-fold, or 20-fold, or more, as compared to a native mRNA, or as compared to a synthetic RNA molecule with the same sequence and containing only natural nucleotides.

A translatable molecule of this invention, which has one or more chemically modified nucleotides, can have increased translation efficiency as compared to a native mRNA, or a synthetic mRNA with the same sequence and containing only natural nucleotides.

In certain embodiments, the translation efficiency of a translatable molecule can be increased by 30%, or 50%, or 70%, or 100%, or 150%, or 200%, or more, as compared to a native mRNA, or as compared to a synthetic RNA molecule with the same sequence and containing only natural nucleotides. The translation efficiency may be performed in vitro, ex vivo, or in vivo.

Embodiments of this invention further encompass processes for making an RNA molecule for expressing a polypeptide or protein, wherein the RNA molecule comprises natural and chemically-modified nucleotides, and encodes the polypeptide or protein, or a fragment thereof. The processes can include transcribing a DNA template in the presence of chemically-modified nucleoside triphosphates to form a product mixture, and purifying the product mixture to isolate the RNA product. These processes may advantageously reduce the level of double-stranded RNA impurities in the product.

In a process of this invention, a translatable molecule of this invention can be synthesized with UTP replaced by 5-methoxy-UTP. The level of replacement can be 30% of UTP replaced by 5-methoxy-UTP, or 40% of UTP replaced by 5-methoxy-UTP, or 50% of UTP replaced by 5-methoxy-UTP, or 60% of UTP replaced by 5-methoxy-UTP, or 70% of UTP replaced by 5-methoxy-UTP, or 80% of UTP replaced by 5-methoxy-UTP, or 90% of UTP replaced by 5-methoxy-UTP, or 100% of UTP replaced by 5-methoxy-UTP.

In a process of this invention, a translatable molecule of this invention can be synthesized with CTP replaced by 5-methyl-CTP. The level of replacement can be 30% of CTP replaced by 5-methyl-CTP, or 40% of CTP replaced by 5-methyl-CTP, or 50% of CTP replaced by 5-methyl-CTP, or 60% of CTP replaced by 5-methyl-CTP, or 70% of CTP replaced by 5-methyl-CTP, or 80% of CTP replaced by 5-methyl-CTP, or 90% of CTP replaced by 5-methyl-CTP, or 100% of CTP replaced by 5-methyl-CTP.

The molecules of this invention can be translatable messenger RNA molecules. In some embodiments, the RNA agents can have long half-life, particularly in the cytoplasm. The long duration messenger molecules can be used for ameliorating, preventing, or treating disease associated with a polypeptide or protein level in a subject.

In some aspects, this invention provides processes for production of a translatable product RNA molecule. A double stranded DNA molecule can be provided having a non-coding template strand of nucleotides that can be transcribed to provide the product RNA. The double stranded DNA may contain an open reading frame in the template strand, which template is an alternative variation from a wild type or native version. In the template, certain deoxyadenosine nucleotides may be replaced by non-deoxyadenosine nucleotides, while codon assignment to a target RNA product may be preserved. The double stranded DNA may further include a double stranded promoter for transcribing the template strand, such as a T7 promoter. The DNA can be transcribed in the presence of nucleoside triphosphates, including optionally a 5' cap, and along with one or more chemically modified nucleoside triphosphates to form a product mixture. The product RNA product can be isolated and purified from the product mixture.

The product RNA can be a translatable molecule that contains natural and chemically modified nucleotides, and enhanced translational efficiency and resulting activity.

In further aspects, this invention provides processes for production of a translatable RNA molecule. A single stranded DNA molecule can be provided having a non-coding template strand of nucleotides that can be transcribed to provide the product RNA. The DNA may contain an open reading frame in the template strand, which template is an alternative variation from a wild type or native version. In the template, certain deoxyadenosine nucleotides may be replaced by non-deoxyadenosine nucleotides, while codon assignment to a target RNA product may be preserved. The DNA may further include a promoter. The DNA can be transcribed in the presence of nucleoside triphosphates, including optionally a 5' cap, and along with one or more chemically modified nucleoside triphosphates to form a product mixture. The product RNA can be isolated and purified from the product mixture.

The properties of the translatable compounds of this invention arise according to their molecular structure, and the structure of the molecule in its entirety, as a whole, can provide significant benefits based on those properties. Embodiments of this invention can provide translatable molecules having one or more properties that advantageously provide enhanced effectiveness in regulating protein expression or concentration, or modulating protein activity. The molecules and compositions of this invention can provide formulations for therapeutic agents for various diseases and conditions, which can provide clinical agents.

This invention provides a range of translatable molecules that are surprisingly translatable to provide active peptide or protein, in vitro and in vivo.

The translatable structures and compositions can have increased translational activity and cytoplasmic half-life. In these embodiments, the translatable structures and compositions can provide increased functional half-life in the cytoplasm of mammalian cells over native mRNA molecules. The inventive translatable molecules can have increased half-life of activity with respect to a corresponding native mRNA.

A wide range of novel translatable molecules are provided herein, each of which can incorporate specialized linker groups. The linker groups can be attached in a chain in the translatable molecule. Each linker group can also be attached to a nucleobase.

Processes for production of a translatable RNA molecule of this invention are illustrated in FIG. 1. A double stranded DNA molecule is provided having a non-coding template strand of nucleotides that can be transcribed to provide a targeted product RNA. The double stranded DNA contains an open reading frame in the template strand, which template is an alternative variation from a wild type or native version. As shown in FIG. 1, certain deoxyadenosine nucleotides may be replaced by non-deoxyadenosine nucleotides, while codon assignment to a target product may be preserved. The double stranded DNA further includes a double stranded promoter for transcribing the template strand, such as a T7 promoter. The DNA can be transcribed in the presence of nucleoside triphosphates, including optionally a 5' cap, and along with one or more chemically modified nucleoside triphosphates to form a product mixture. The RNA product can be isolated and purified from the product mixture. The RNA product is a translatable molecule that contains natural and chemically modified nucleotides, and enhanced translational efficiency and resulting activity.

Figure 2:
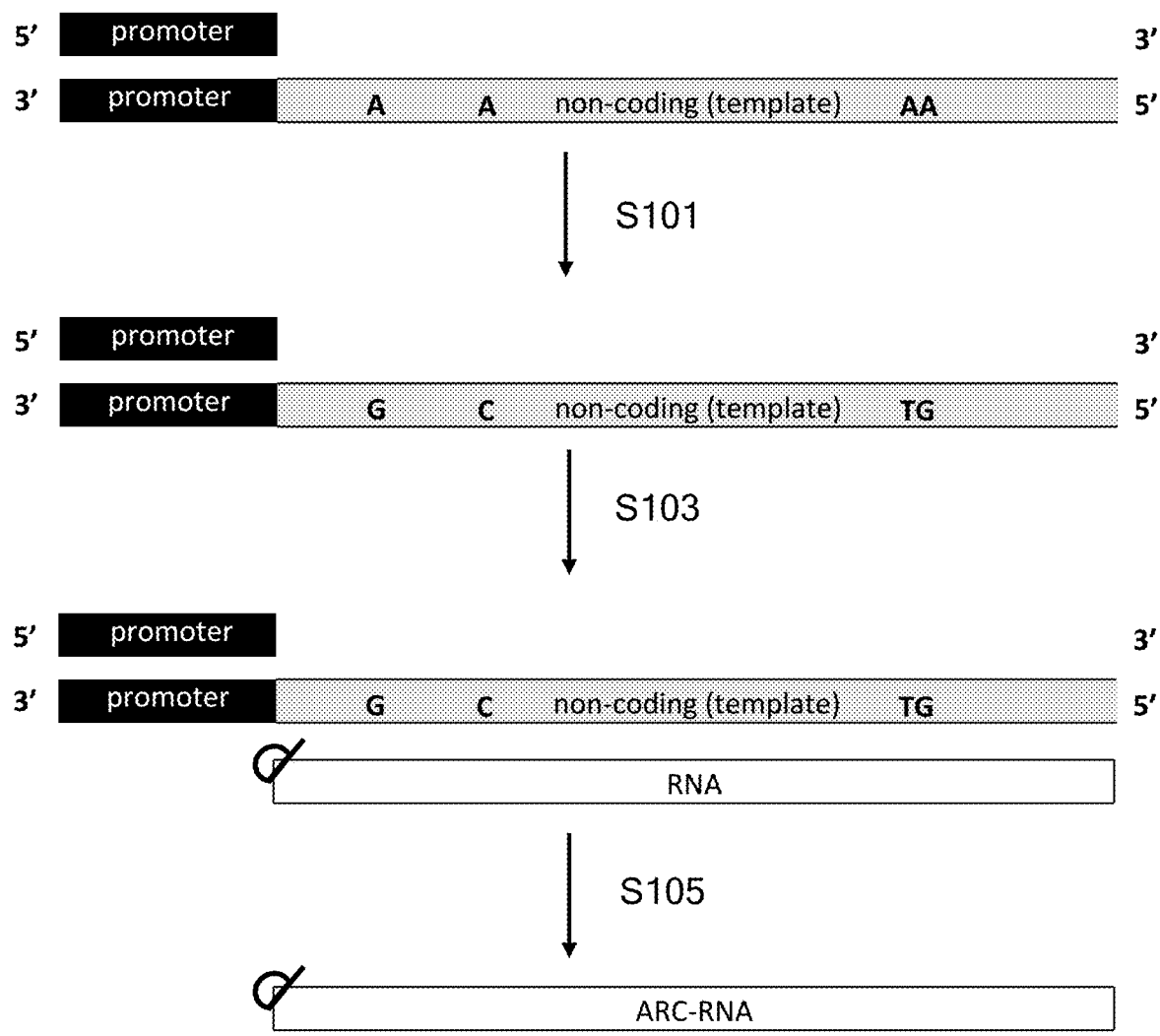
FIG. 2 shows a process for production of a translatable ARC-RNA molecule of this invention. A single stranded DNA molecule is provided having a non-coding template strand of nucleotides that can be transcribed to provide the product RNA. The DNA contains an open reading frame in the template strand, which template is an alternative variation from a wild type or native version.

Processes for production of a translatable RNA molecule of this invention are illustrated in FIG. 2. A single stranded DNA molecule is provided having a non-coding template strand of nucleotides that can be transcribed to provide the product RNA. The DNA contains an open reading frame in the template strand, which template is an alternative variation from a wild type or native version. As shown in FIG. 2, certain deoxyadenosine nucleotides may be replaced by non-deoxyadenosine nucleotides in the template, while codon assignment to a target product may be preserved. The DNA further includes a promoter. The DNA can be transcribed in the presence of nucleoside triphosphates, including optionally a 5' cap, and along with one or more chemically modified nucleoside triphosphates to form a product mixture. The RNA product can be isolated and purified from the product mixture.

Figure 3:
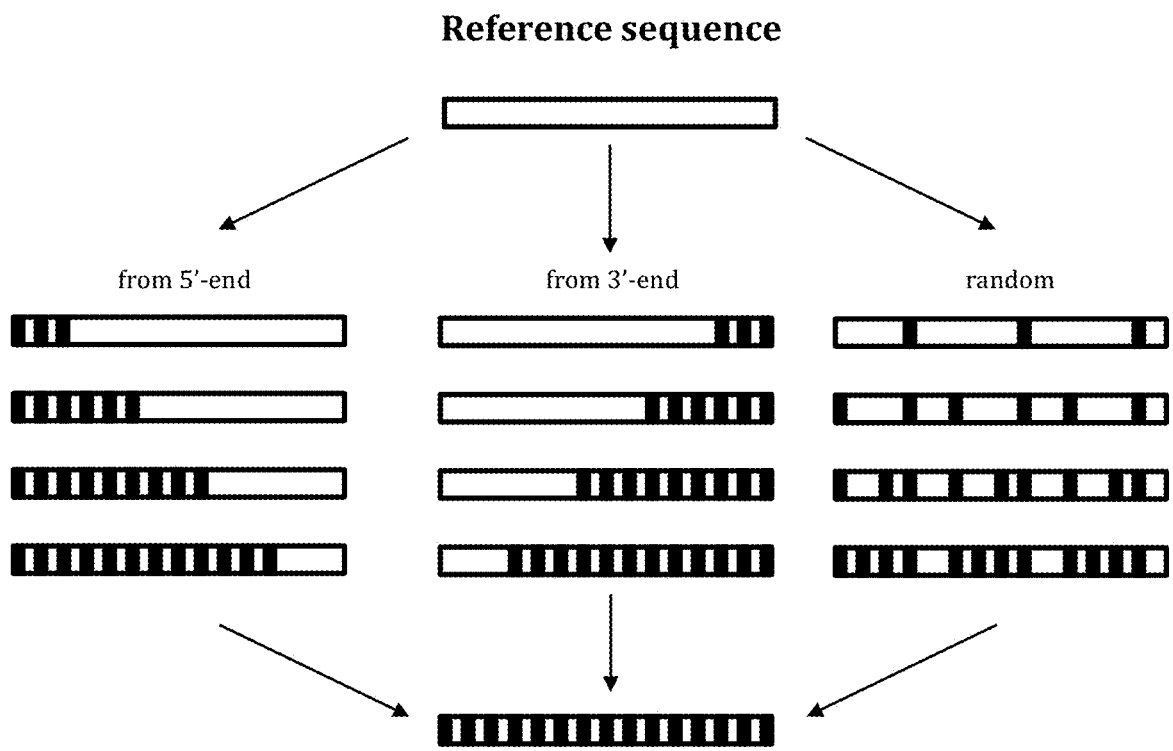
FIG. 3 shows embodiments of methods for providing templates for translatable molecules of this invention. Based on a reference sequence of an ORF of a template, certain deoxyadenosine nucleotides may be replaced in the template by non-deoxyadenosine nucleotides, while codon assignment to a target product may be preserved. In some methods, the deoxyadenosine nucleotides may be replaced beginning from the 5' end of the ORF. In further methods, the deoxyadenosine nucleotides may be replaced beginning from the 3' end of the ORF. In additional methods, the deoxyadenosine nucleotides may be replaced randomly throughout the ORF.

FIG. 3 shows embodiments of methods for providing templates for translatable molecules of this invention. Based on a reference sequence of an ORF of a template, certain deoxyadenosine nucleotides may be replaced in the template by non-deoxyadenosine nucleotides, while codon assignment to a target product may be preserved. In some methods, the deoxyadenosine nucleotides may be replaced beginning from the 5' end of the ORF. In further methods, the deoxyadenosine nucleotides may be replaced beginning from the 3' end of the ORF. In additional methods, the deoxyadenosine nucleotides may be replaced randomly throughout the ORF.

In some aspects, a linker group can be a monomer. Monomers can be attached to form a chain molecule. In a chain molecule of this invention, a linker group monomer can be attached at any point in the chain.

In certain aspects, linker group monomers can be attached in a chain molecule of this invention so that the linker group monomers reside near the ends of the chain, or at any position in the chain.

As used herein, a chain molecule can also be referred to as an oligomer.

In further aspects, the linker groups of a chain molecule can each be attached to a nucleobase. The presence of nucleobases in the chain molecule can provide a sequence of nucleobases in the chain molecule.

In certain embodiments, this invention provides translatable oligomer molecules having chain structures that incorporate novel combinations of the linker group monomers, along with certain natural nucleotides, or non-natural nucleotides, or modified nucleotides, or chemically-modified nucleotides.

The oligomer molecules of this invention can display a sequence of nucleobases, and can be designed to express a polypeptide or protein, in vitro, ex vivo, or in vivo. The expressed polypeptide or protein can have activity in various forms, including activity corresponding to protein expressed from natural mRNA, or activity corresponding to a negative or dominant negative protein.

In some aspects, this invention can provide active, translatable oligomer molecules having a base sequence that is complementary to at least a fragment of a native nucleic acid molecule of a cell.

In some embodiments, the cell can be a eukaryotic cell, a mammalian cell, or a human cell.

This invention provides structures, methods and compositions for translatable oligomeric agents that incorporate the linker group monomers. The oligomeric molecules of this invention can be used as active agents in formulations for therapeutics.

This invention provides a range of translatable molecules that are useful for providing therapeutic effects because of their longevity of activity in providing an expressed peptide or protein.

In certain embodiments, a translatable molecule can be structured as an oligomer composed of monomers. The oligomeric structures of this invention may contain one or more linker group monomers, along with certain nucleotides.

In certain embodiments, a translatable molecule may contain a sequence of nucleobases, and can be designed to express a peptide or protein of any isoform, in part by having sufficient homology with a native polynucleotide sequence.

In some embodiments, a translatable molecule can be from about 200 to about 12,000 monomers in length, or more. In certain embodiments, a translatable molecule can be from 200 to 12,000 monomers in length, or 200 to 10,000 monomers, or 200 to 8,000 monomers, or 200 to 6000 monomers, or 200 to 5000 monomers, or 200 to 4000 monomers, or 200 to 3600 monomers, or 200 to 3200 monomers, or 200 to 3000 monomers, or 200 to 2800 monomers, or 200 to 2600 monomers, or 200 to 2400 monomers, or 200 to 2200 monomers, or 600 to 3200 monomers, or 600 to 3000 monomers, or 600 to 2600 monomers.

In some embodiments, a translatable molecule can be from about 200 to about 12,000 bases in length, or more. In certain embodiments, a translatable molecule can be from 200 to 12,000 bases in length, or 200 to 10,000 bases, or 200 to 8,000 bases, or 200 to 6000 bases, or 200 to 5000 bases, or 200 to 4000 bases, or 200 to 3600 bases, or 200 to 3200 bases, or 200 to 3000 bases, or 200 to 2800 bases, or 200 to 2600 bases, or 200 to 2400 bases, or 200 to 2200 bases, or 600 to 3200 bases, or 600 to 3000 bases, or 600 to 2600 bases.

A translatable molecule of this invention may comprise a 5' cap, a 5' untranslated region of monomers, a coding region of monomers, a 3' untranslated region of monomers, and a tail region of monomers.

A translatable molecule of this invention may comprise regions of sequences or structures that are operable for translation in a cell, or which have the functionality of regions of an mRNA including, for example, a 5' cap, a 5' untranslated region, a coding region, a 3' untranslated region, and a polyA tail.

This invention further contemplates methods for delivering one or more vectors, or one or more translatable molecules to a cell.

In some embodiments, one or more translatable molecules can be delivered to a cell, in vitro, ex vivo, or in vivo. Viral and non-viral transfer methods as are known in the art can be used to introduce translatable molecules in mammalian cells. Translatable molecules can be delivered with a pharmaceutically acceptable vehicle, or for example, encapsulated in a liposome.

In some embodiments, translatable structures and compositions of this invention can reduce the number and frequency of transfections required for cell-fate manipulation in culture as compared to utilizing native compositions.

In additional aspects, this invention provides increased activity for mRNA-based drugs as compared to utilizing native compositions, and can reduce the dose levels required for efficacious therapy.

In further aspects, this invention provides increased activity for translatable or mRNA-based molecules, as compared to utilizing a native mRNA as active agent.

In some aspects, this invention can provide translatable molecules that may reduce the cellular innate immune response, as compared to that induced by a natural nucleic acid, peptide or protein.

This invention can provide synthetic translatable molecules that are refractory to deadenylation as compared to native molecules.

In certain embodiments, this invention can provide synthetic translatable molecules with increased specific activity and longer functional half-life as compared to native molecules. The synthetic translatable molecules of this invention can provide increased levels of ectopic protein expression. When using a translatable molecule as a vector, cellular-delivery can be at increased levels, and cytotoxic innate immune responses can be restrained so that higher levels of ectopic protein expression can be achieved. The translatable molecules of this invention can have increased specific activity and longer functional half-life than mRNAs.

In certain aspects, a translatable molecule may have a number of mutations from a native mRNA, or from a disease associated mRNA.

In further embodiments, this invention can provide translatable molecules having cleavable delivery and targeting moieties attached at a 3' end.

In general, the specific activity for a synthetic translatable molecule delivered by transfection can be viewed as the number of molecules of protein expressed per delivered transcript per unit time.

As used herein, translation efficiency refers to a measure of the production of a protein or polypeptide by translation of a messenger molecule in vitro or in vivo.

This invention provides a range of translatable molecules, which can contain one or more UNA monomers, and a number of nucleic acid monomers, wherein the translatable molecule can be translated to express a polypeptide or protein. UNA monomers are described in WO/2016/070166. In some embodiments, this invention includes a range of translatable molecules, which may contain one or more UNA monomers in a tail region, wherein the translatable molecule can be translated to express a polypeptide or protein. In some embodiments, a translatable molecule may comprise a 3' polyA tail containing one or more UNA monomers. In some embodiments, a 3' polyA tail may contain 2, 3, 4, 5, 10, or more UNA monomers.

In some embodiments, a translatable molecule can contain a modified 5' cap.

In further embodiments, a translatable molecule can contain a translation enhancing 5' untranslated region of monomers.

In additional embodiments, a translatable molecule can contain a translation enhancing 3' untranslated region of monomers.

A translatable molecule of this invention can exhibit increased translation efficiency in vivo as compared to a native mRNA that encodes the same translation product. For example, the translation efficiency can be increased by 10%, or 20%, or 30%, or 40%, or 50% or 100%, or more, as compared to a reference mRNA such as a native mRNA or human wild type mRNA.

In another aspect, a translatable molecule of this invention can exhibit at least 2-fold, 3-fold, 5-fold, or 10-fold increased translation efficiency in vivo as compared to a reference mRNA such as a native mRNA or human wild type mRNA.

In further aspects, a translatable molecule can provide increased levels of a polypeptide or protein in vivo as compared to a native mRNA that encodes the same polypeptide or protein. For example, the level of a polypeptide or protein can be increased by 10%, or 20%, or 30%, or 40%, or 50% or 100%, or more in vivo as compared to a reference mRNA such as a native mRNA or human wild type mRNA.

In a further aspect, a translatable molecule can produce at least 2-fold, 3-fold, 5-fold, or 10-fold increased levels of a polypeptide or protein in vivo as compared to a native mRNA or reference mRNA.

In additional embodiments, this invention provides methods for treating a disease or condition in a subject by administering to the subject a composition containing a translatable molecule.

Variant Templates in Processes for Translatable Molecules

A variant DNA template of this disclosure may exhibit advantages in processes for making a translatable molecule, and the efficiency of the translatable molecule. Variation of the template can be utilized to enhance incorporation of modified nucleotides or monomers in an RNA product of this invention. In certain aspects, variation of the template can be utilized to enhance the structural features of the translatable molecule. The enhanced structural features of the translatable molecule can provide unexpectedly advantageous properties, including translation efficiency to provide a polypeptide or protein product.

In some aspects of this invention, variation of the template may include reducing the occurrence or frequency of appearance of certain nucleotides in the template strand. Reducing the occurrence of a certain nucleotide can alter the structures and processes of this disclosure to provide forms, which achieve surprisingly improved properties of a translatable RNA product.

Aspects of this invention may require a variant DNA template in processes for making a translatable molecule. A DNA molecule can have a non-coding template strand of nucleotides that can be transcribed to provide a target RNA.

A target RNA can be any RNA, whether native or unknown, synthetic or derived from a natural source.

In some embodiments, a variant DNA template can be used for which an open reading frame of the template strand is transformed to an alternative form.

In certain embodiments, a DNA template can be used for which alternative nucleotides are used based on codon degeneracy.

In additional embodiments, a DNA template may have deoxyadenosine nucleotides replaced with non-deoxyadenosine nucleotides, while codon assignment may be preserved.

Embodiments of this invention advantageously utilize alternative codons in a DNA template of this invention to be used in processes for making a translatable RNA molecule. The variations that can be achieved in a DNA template of this invention can be far greater in scope than for cells and organisms, which may require preferred codons in many processes. In this invention, a wide range of alternative codons and positions can be used in a DNA template for transcribing an RNA molecule.

In further aspects of this invention, variation of the template may include reducing the occurrence or frequency of appearance of certain nucleotides in the template strand. For example, the occurrence of deoxyadenosine in a template may be reduced to a level below 25% of nucleotides in the template. In further examples, the occurrence of deoxyadenosine in a template may be reduced to a level below 20% of nucleotides in the template. In some examples, the occurrence of deoxyadenosine in a template may be reduced to a level below 16%, or 14% of nucleotides in the template. In certain examples, the occurrence of deoxyadenosine in a template may be reduced to a level below 12% of nucleotides in the template.

Inherent codon redundancy allows up to six different codons for a single amino acid. However, synonymous codons may not have equivalent preference in cells and organisms. Further, codon preference can vary among different genes, and may have functional effects. Codon degeneracy is in general poorly understood, with unpredictable effects on nucleic acid structures and processes. It is not generally known how codon alternatives affect ribosomes, protein folding, translation, and degradation of an RNA.

In some embodiments, the level of T can be reduced in a non-template strand, i.e. a coding strand, by replacing a triplet codon containing more than one T to another synonymous codon containing less T than the original triplet. For example, valine encoded by GTT can be replaced by GTC, GTA, or GTG. Serine encoded by TCT, TCC, TCA, TCG, AGT can be replaced by AGC. Complementary changes would be made in the template strand.

In certain embodiments, the level of T can be reduced in a non-template strand, i.e. a coding strand, by replacing all codons with synonymous codons where each replacement reduces the level of T.

In some aspects, in order to increase expression levels, a variant template can have a reduced number of rare codons. See, e.g. Mauro, A critical analysis of codon optimization in human therapeutics, Trends Mol Med 2014, Vol. 20(11), pp. 604-613.

In some aspects, any combination of synonymous codon replacements can be made in a variant template of this invention.

Various additional or synonymous codon replacements can be made as are known in the art.

Some examples of codon replacements in a coding non-template strand are shown in Table 1. For a variant template, complementary replacements are made in the template strand.

TABLE 1

Amino acid codons

| AA | Codons |
| --- | --- |
| Ala | GCA, GCC, GCG, GCT |
| Asx | AAC, AAT, GAC, GAT |
| Cys | TGC, TGT |
| Asp | GAC, GAT |
| Glu | GAA, GAG |
| Phe | TTC, TTT |
| Gly | GGA, GGC, GGG, GGT |
| His | CAC, CAT |
| Ile | ATA, ATC, ATT |
| Lys | AAA, AAG |
| Leu | CTA, CTC, CTG, CTT, TTA, TTG |
| Met | ATG |
| Asn | AAC, AAT |
| Pro | CCA, CCC, CCG, CCT |
| Gln | CAA, CAG |
| Arg | AGA, AGG, CGA, CGC, CGG, CGT |
| Ser | AGC, AGT, TCA, TCC, TCG, TCT |
| Thr | ACA, ACC, ACG, ACT |
| Val | GTA, GTC, GTG, GTT |
| Trp | TGG |
| Tyr | TAC, TAT |
| Glx | CAA, CAG, GAA, GAG |

Functional Variant Templates for Translatable Molecules

A functional variant DNA template of this disclosure may have a structure reflecting enhanced arrangement of alternative codons.

A functional variant template of this invention can be utilized to enhance incorporation of modified nucleotides or monomers in an RNA product.

In certain aspects, a functional variant template can be utilized to enhance the structural features of a translatable molecule. Examples of enhanced structural features of a translatable molecule include translation efficiency.

In some embodiments, a functional variant template may have reduced occurrence or frequency of appearance of certain nucleotides in the non-coding template strand. Reducing the occurrence of a certain nucleotide can alter the structures and processes of this disclosure to provide forms, which achieve surprisingly improved properties of a translatable RNA product.

In certain aspects, a functional variant template of this invention may have reduced occurrence or frequency of appearance of deoxyadenosine nucleotides in a non-coding template strand, where the deoxyadenosine nucleotides are reduced beginning at the 5' end of the template, and extending toward the 3' end.

In further aspects, a functional variant template of this invention may have reduced occurrence or frequency of appearance of deoxyadenosine nucleotides in a non-coding template strand, where the deoxyadenosine nucleotides are reduced beginning at the 3' end of the template, and extending toward the 5' end.

In additional aspects, a functional variant template of this invention may have reduced occurrence or frequency of appearance of deoxyadenosine nucleotides in a non-coding template strand, where the deoxyadenosine nucleotides are randomly reduced in the template structure.

In certain embodiments, a functional variant template of this invention may have all deoxyadenosine nucleotides in a non-coding template strand replaced by non-deoxyadenosine nucleotides in the template structure.

A DNA template that is transcribable for expression of a target polypeptide or protein can have a non-coding sequence template region, in which deoxyadenosine nucleotides in the non-coding sequence template region are replaced with non-deoxyadenosine nucleotides while codon assignment may be preserved, and in which the occurrence of deoxyadenosines in the template region is reduced by at least 20% as compared to a wild type gene that is transcribable for expression of the target polypeptide or protein. In some embodiments, the occurrence of deoxyadenosines in the template region is reduced by at least 25% as compared to a wild type gene that is transcribable for expression of the target polypeptide or protein. In further embodiments, the occurrence of deoxyadenosines in the template region is reduced by at least 30% as compared to a wild type gene that is transcribable for expression of the target polypeptide or protein. In additional embodiments, the occurrence of deoxyadenosines in the template region is reduced by at least 35% as compared to a wild type gene that is transcribable for expression of the target polypeptide or protein. The occurrence of deoxyadenosines in the template region may be reduced by at least 40%, or 45%, or 50% as compared to a wild type gene that is transcribable for expression of the target polypeptide or protein.

In some aspects, the occurrence of deoxythymidine in a non-template sequence region may be reduced by at least 20%, or 25%, or 30%, or 35%, or 40%, or 45%, or 50% as compared to a wild type gene that is transcribable for expression of the target polypeptide or protein.

Some examples of codon replacements in a coding non-template strand are shown in Table 2. For a functional variant template, complementary replacements are made in the template strand.

TABLE 2

Amino acid codons

| AA | From | To |
| --- | --- | --- |
| Asn | AAT | AAC |
| Thr | ACT | ACC |
| Ser | AGT | AGC |
| Ile | ATT | ATC |
| His | CAT | CAC |
| Pro | CCT | CCC |
| Arg | CGT | CGG |
| Lue | CTT | CTG |
| Asp | GAT | GAC |
| Ala | GCT | GCC |
| Gly | GGT | GGC |
| Val | GTT | GTG |
| Tyr | TAT | TAC |
| Ser | TCA | AGC |
| Ser | TCC | AGC |
| Ser | TCG | AGC |
| Ser | TCT | AGC |
| Cys | TGT | TGC |
| Leu | TTA | CTG |
| Leu | TTG | CTG |
| Phe | TTT | TTC |

Processes and Polynucleotides with Chemically-Modified Nucleotides

Embodiments of this invention can provide processes for production of translatable molecules, wherein the translatable molecules can comprise one or more kinds of chemically-modified nucleotides.

Embodiments of this invention contemplate processes for production of translatable molecules, where the translatable molecules incorporate one or more kinds of chemically-modified nucleotides, and the translatable molecules are produced with reduced levels of impurities, such as double stranded impurities.

In certain embodiments, the level of double stranded impurities in a process of this invention can be reduced by 2-fold, or 3-fold, or 5-fold, or 10-fold, or 20-fold, or more, as compared to a process using only natural NTPs.

In certain embodiments, this invention can provide processes for production of translatable molecules, where the translatable molecules incorporate one or more kinds of chemically-modified nucleotides, and the translatable molecules are produced with advantageously reduced levels of impurities, such as double stranded impurities, so that the product translatable molecules can be utilized without further purification.

Translatable molecules of this invention having chemically-modified nucleotides can provide enhanced properties for therapeutic use of the translatable molecules.

A translatable molecule of this invention having chemically-modified nucleotides can provide advantageously increased expression levels in vitro, ex vivo, or in vivo, as compared to a reference such as wild type mRNA.

In some aspects, a translatable molecule of this invention having chemically-modified nucleotides can provide advantageously reduced immune response in vitro, ex vivo, or in vivo, as compared to a reference such as wild type mRNA.

In certain aspects, a translatable molecule of this invention having chemically-modified nucleotides can provide advantageously increased intracellular lifetime in vitro, ex vivo, or in vivo, as compared to a reference such as wild type mRNA.

Examples of chemically-modified nucleotides include 5-methoxyuridine (5MeOU).

In certain embodiments, a translatable molecule of this invention can have uridines replaced by 5-methoxyuridines. The level of replacement can be 30% of uridines replaced by 5-methoxyuridine, or 40% of uridines replaced by 5-methoxyuridine, or 50% of uridines replaced by 5-methoxyuridine, or 60% of uridines replaced by 5-methoxyuridine, or 70% of uridines replaced by 5-methoxyuridine, or 80% of uridines replaced by 5-methoxyuridine, or 90% of uridines replaced by 5-methoxyuridine, or 100% of uridines replaced by 5-methoxyuridine.

Examples of combinations of chemically-modified nucleotides include the combination of 5-methoxyuridine (5MeOU) and 5-methylcytidine (5MC). In a combination of chemically-modified nucleotides, both kinds of chemically-modified nucleotides are incorporated into the same polynucleotide.

As used herein, in the context of oligomer sequences, the symbol N can represent any natural nucleotide monomer, or any modified nucleotide monomer.

As used herein, in the context of oligomer sequences, the symbol Q represents a non-natural, modified, or chemically-modified nucleotide monomer.

Additional examples of chemically-modified nucleotides include 5-hydroxyuridines, 5-alkyluridines, 5-hydroxyalkyluridines, 5-carboxyuridines, 5-carboxyalkylesteruridines, 5-formyluridines, 5-alkoxyuridines, 5-alkynyluridines, 5-halouridines, 2-thiouridines, and 6-alkyluridines.

Additional examples of chemically-modified nucleotides include 5-hydroxyuridine, 5-methyluridine, 5-hydroxymethyluridine, 5-carboxyuridine, 5-carboxymethylesteruridine, 5-formyluridine, 5-methoxyuridine, 5-propynyluridine, 5-bromouridine, 5-fluorouridine, 5-iodouridine, 2-thiouridine, and 6-methyluridine.

Additional examples of chemically-modified nucleotides include 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy)pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl)uridine, 2'-O-methylpseudouridine, 2-thio-2'-O-methyluridine, and 3,2'-O-dimethyluridine.

Additional examples of chemically-modified nucleotides include 5-hydroxycytidines, 5-alkylcytidines, 5-hydroxyalkylcytidines, 5-carboxycytidines, 5-formylcytidines, 5-alkoxycytidines, 5-alkynylcytidines, 5-halocytidines, 2-thiocytidines, $N^4$-alkylcytidines, $N^4$-aminocytidines, $N^4$-acetylcytidines, and $N^4,N^4$-dialkylcytidines.

Additional examples of chemically-modified nucleotides include 5-hydroxycytidine, 5-methylcytidine, 5-hydroxymethylcytidine, 5-carboxycytidine, 5-formylcytidine, 5-methoxycytidine, 5-propynylcytidine, 5-bromocytidine, 5-iodocytidine, 2-thiocytidine; $N^4$-methylcytidine, $N^4$-aminocytidine, $N^4$-acetylcytidine, and $N^4,N^4$-dimethylcytidine.

Additional examples of chemically-modified nucleotides include $N^6$-methyladenosine, 2-aminoadenosine, 3-methyladenosine, 8-azaadenosine, 7-deazaadenosine, 8-oxoadenosine, 8-bromoadenosine, 2-methylthio-$N^6$-methyladenosine, $N^6$-isopentenyladenosine, 2-methylthio-$N^6$-isopentenyladenosine, $N^6$-(cis-hydroxyi sopentenyl) adenosine, 2-methylthio-$N^6$-(cis-hydroxyisopentenyl) adenosine, $N^6$-glycinylcarbamoyladenosine, N6-threonylcarbamoyl-adenosine, $N^6$-methyl-$N^6$-threonylcarbamoyl-adenosine, 2-methylthio-$N^6$-threonylcarbamoyl-adenosine, $N^6,N^6$-dimethyladenosine, N6-hydroxynorvalylcarbamoyladenosine, 2-methylthio-$N^6$-hydroxynorvalylcarbamoyl-adenosine, $N^6$-acetyl-adenosine, 7-methyl-adenine, 2-methylthio-adenine, 2-methoxy-adenine, alpha-thio-adenosine, 2'-O-methyl-adenosine, $N^6$,2'-O-dimethyl-adenosine, $N^6,N^6$,2'-O-trimethyl-adenosine, 1,2'-O-dimethyl-adenosine, 2'-O-ribosyladenosine, 2-amino-$N^6$-methyl-purine, 1-thio-adenosine, 2'-F-ara-adenosine, 2'-F-adenosine, 2'-OH-ara-adenosine, and $N^6$-(19-amino-pentaoxanonadecyl)-adenosine.

Additional examples of modified or chemically-modified nucleotides include $N^1$-alkylguanosines, $N^2$-alkylguanosines, thienoguanosines, 7-deazaguanosines, 8-oxoguanosines, 8-bromoguanosines, $O^6$-alkylguanosines, xanthosines, inosines, and $N^1$-alkylinosines.

Additional examples of chemically-modified nucleotides include $N^1$-methylguanosine, $N^2$-methylguanosine, thienoguanosine, 7-deazaguanosine, 8-oxoguanosine, 8-bromoguanosine, $O^6$-methylguanosine, xanthosine, inosine, and $N^1$-methylinosine.

Additional examples of chemically-modified nucleotides include pseudouridines. Examples of pseudouridines include $N^1$-alkylpseudouridines, $N^1$-cycloalkylpseudouridines, $N^1$-hydroxypseudouridines, $N^1$-hydroxyalkylpseudouridines, $N^1$-phenylpseudouridines, $N^1$-phenylalkylpseudouridines, $N^1$-aminoalkylpseudouridines, $N^3$-alkylpseudouridines, $N^6$-alkylpseudouridines, $N^6$-alkoxypseudouridines, $N^6$-hydroxypseudouridines, $N^6$-hydroxyalkylpseudouridines, $N^6$-morpholinopseudouridines, $N^6$-phenylpseudouridines, and $N^6$-halopseudouridines. Examples of pseudouridines include $N^1$-alkyl-$N^6$-alkylpseudouridines, $N^1$-alkyl-$N^6$-alkoxypseudouridines, $N^1$-alkyl-$N^6$-hydroxypseudouridines, $N^1$-alkyl-$N^6$-hydroxyalkylpseudouridines, $N^1$-alkyl-$N^6$-morpholinopseudouridines, $N^1$-alkyl-$N^6$-phenylpseudouridines, and $N^1$-alkyl-$N^6$-halopseudouridines. In these examples, the alkyl, cycloalkyl, and phenyl substituents may be unsubstituted, or further substituted with alkyl, halo, haloalkyl, amino, or nitro substituents.

Additional examples of pseudouridines include $N^1$-methylpseudouridine, $N^1$-ethylpseudouridine, $N^1$-propylpseudouridine, $N^1$-cyclopropylpseudouridine, $N^1$-phenylpseudouridine, $N^1$-aminomethylpseudouridine, $N^3$-methylpseudouridine, $N^1$-hydroxypseudouridine, and $N^1$-hydroxymethylpseudouridine.

Additional examples of chemically-modified nucleotides include 5-hydroxyuridine, 5-methyluridine, 5,6-dihydro-5-methyluridine, 2'-O-methyluridine, 2'-O-methyl-5-methyluridine, 2'-fluoro-2'-deoxyuridine, 2'-amino-2'-deoxyuridine, 2'-azido-2'-deoxyuridine, 5-hydroxymethyluridine, 5-carboxyuridine, 5-carboxymethylesteruridine, 5-formyluridine, 5-methoxyuridine, 5-propynyluridine, 5-bromouridine, 5-iodouridine, 5-fluorouridine, pseudouridine, 2'-O-methylpseudouridine, $N^1$-hydroxypseudouridine, $N^1$-methylpseudouridine, 2'-O-methyl-$N^1$-methylpseudouridine, $N^1$-ethylpseudouridine, $N^1$-hydroxymethylpseudouridine, and Arauridine.

Additional examples of non-natural, modified, and chemically-modified nucleotide monomers include any such nucleotides known in the art, for example, 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Additional examples of non-natural, modified, and chemically-modified nucleotide monomers include 3'-end stabilized nucleotides, 3'-glyceryl nucleotides, 3'-inverted abasic nucleotides, and 3'-inverted thymidine.

Additional examples of non-natural, modified, and chemically-modified nucleotide monomers include locked nucleic acid nucleotides (LNA), glycol nucleic acids (GNA), 2'-O, 4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides.

Additional examples of non-natural, modified, and chemically-modified nucleotide monomers include 2',4'-Constrained 2'-O-Methoxyethyl (cMOE) and 2'-O-Ethyl (cEt) Modified DNAs.

Additional examples of non-natural, modified, and chemically-modified nucleotide monomers include 2'-amino nucleotides, 2'-O-amino nucleotides, 2'-C-allyl nucleotides, and 2'-O-allyl nucleotides.

Additional examples of non-natural, modified, and chemically-modified nucleotide monomers include nucleotide monomers with modified bases, such as 5-(3-amino)propyluridine and 5-(2-mercapto)ethyluridine.

Additional examples of non-natural, modified, and chemically-modified nucleotide monomers include 2'-O-aminopropyl substituted nucleotides.

Additional examples of non-natural, modified, and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Additional examples of nucleotide monomers include pseudouridine (psi-Uridine) and 1-methylpseudouridine.

Additional examples of chemically-modified nucleotide monomers include nucleotides having base modifications, nucleoside or nucleotide structure modifications, sugar modifications, or linkage modifications.

Examples of nucleic acid monomers include non-natural, modified, and chemically-modified nucleotides, including any such nucleotides known in the art.

Some examples of modified nucleotides are given in Saenger, Principles of Nucleic Acid Structure, Springer-Verlag, 1984; Rozenski J., Crain P. F., McCloskey J. A., The RNA Modification Database: 1999 update, Nucleic Acids Res., 1999; Vol. 27, pp. 196-197.

Modalities for Peptides and Proteins

An RNA molecule of this invention may be used for ameliorating, preventing or treating a disease through protein or enzyme modulation or replacement. An RNA molecule of this invention can be administered to regulate, modulate, increase, or decrease the concentration or effectiveness of a natural enzyme in a subject.

In some aspects, the protein can be an unmodified, natural enzyme for which the subject has an abnormal quantity.

In further embodiments, an RNA molecule can be delivered to cells or subjects, and translated to supply increased levels of a natural polypeptide or protein.

An RNA molecule of this invention may be used for ameliorating, preventing or treating a disease through modulation or introduction of a polypeptide or protein. In such embodiments, a translatable molecule of this invention can be administered to regulate, modulate, increase, or decrease the concentration or effectiveness of a peptide or protein in a subject, where the peptide or protein is non-natural or mutated, as compared to a native peptide or protein.

A polypeptide or protein delivered by an RNA molecule of this disclosure can be a modified, non-natural, exogenous, or synthetic polypeptide or protein, which has a pharmacological effect in a subject.

In some embodiments, an RNA molecule can be delivered to cells or subjects, and translated to supply a secretion or concentration of a peptide or protein.

A subject can be a human subject, a human patient, or a mammal.

Base sequences shown herein are from left to right, 5' to 3', unless stated otherwise.

A polypeptide, protein, or protein fragment provided by a polynucleotide of this disclosure can be a variant of a polypeptide or protein of interest. A variant of a polypeptide or protein can have at least about 50%, or 60%, or 70%, or 80%, or 90%, or 95% sequence identity to the polypeptide or protein of interest.

In some embodiments, a translatable molecule of this invention may encode a homolog, variant, or fragment thereof, of a human protein. A homolog or variant may have one or more amino acid substitutions, deletions, and/or insertions as compared to a wild type or naturally-occurring human protein, while retaining protein activity.

In further embodiments, a translatable molecule of this invention may encode a protein that is identical to human protein, or nearly identical.

For example, a translatable molecule may encode an amino acid sequence that is at least 80%, or 85%, or 90%, or 91%, or 92%, or 93%, or 94%, or 95%, or 96%, or 97%, or 98%, or 99% or more identical to the amino acid sequence of a reference polypeptide or protein, such as a human wild type protein.

In further examples, a translatable molecule may encode an amino acid sequence that may have one, or two, or three, or four, or five, or six, or seven, or eight, or nine, or ten, or fifteen, or twenty or more amino acid substitutions, deletions, and/or insertions as compared to the amino acid sequence of a reference polypeptide or protein, such as a human wild type protein.

Examples of polypeptides and proteins of this disclosure include human EPO, human Factor IX (hF9), human alpha-1-antitrypsin (hAAT), and human adiponectin (hAdipo), among others.

Diseases

Examples of diseases for enzyme modulation include lysosomal diseases, for example, Gaucher disease, Fabry disease, Mucopolysaccharidoses (MPS) and related diseases including MPS I, MPS II (Hunter syndrome), and MPS VI, as well as Glycogen storage disease type II.

Examples of diseases for enzyme modulation include hematologic diseases, for example, sickle-cell disease, thalassemia, methemoglobinemia, anemia due to deficiency of hemoglobin or $B_{12}$ intrinsic factor, spherocytosis, glucose-6-phosphate dehydrogenase deficiency, and pyruvate kinase deficiency.

Examples of diseases for enzyme modulation include hemophilia, Von Willebrand disease, Protein S deficiency, age-related macular degeneration, trinucleotide repeat disorders, muscular dystrophy, insertion mutation diseases, DNA repair-deficiency disorders, and deletion mutation diseases.

Examples of diseases and/or conditions for which the translatable molecules of this invention can be translatable to provide an active agent include those in Table 3.

TABLE 3

Rare diseases

| RARE DISEASE | DEFICIENCY |
|---|---|
| Aminoacylase 1 deficiency | Aminoacylase 1 |
| Apo A-I deficiency | Apo A-I |
| Carbamoyl phosphate synthetase 1 deficiency | Carbamoyl phosphate synthetase 1 |
| Ornithine transcarbamylase deficiency | Ornithine transcarbamylase |
| Plasminogen activator inhibitor type 1 deficiency | Plasminogen activator inhibitor type 1 |
| Flaujeac factor deficiency | Flaujeac factor (High-molecular-weight kininogen) |
| High-molecular-weight kininogen deficiency congenital | High-molecular-weight kininogen (Flaujeac factor) |
| PEPCK 1 deficiency | PEPCK 1 |
| Pyruvate kinase deficiency liver type | Pyruvate kinase liver type |
| Alpha 1-antitrypsin deficiency | Alpha 1-antitrypsin |
| Anti-plasmin deficiency congenital | Anti-plasmin |
| Apolipoprotein C 21 deficiency | Apolipoprotein C 21 |
| Butyrylcholinesterase deficiency | Butyrylcholinesterase |
| Complement component 2 deficiency | Complement component 2 |
| Complement component 8 deficiency type 2 | Complement component 8 type 2 |
| Congenital antithrombin deficiency type 1 | Antithrombin |
| Congenital antithrombin deficiency type 2 | Antithrombin, type 2 |
| Congenital antithrombin deficiency type 3 | Antithrombin, type 3 |
| Cortisone reductase deficiency 1 | Cortisone reductase |
| Factor VII deficiency | Factor VII |
| Factor X deficiency | Factor X |
| Factor XI deficiency | Factor XI |
| Factor XII deficiency | Factor XII |
| Factor XIII deficiency | Factor XIII |
| Fibrinogen deficiency congenital | Fibrinogen |
| Fructose-1 6-bisphosphatase deficiency | Fructose-1 6-bisphosphatase |
| Gamma aminobutyric acid transaminase deficiency | Gamma aminobutyric acid transaminase |
| Gamma-cystathionase deficiency | Gamma-cystathionase |
| Glut2 deficiency | Glut2 |
| GTP cyclohydrolase I deficiency | GTP cyclohydrolase I |
| Isolated growth hormone deficiency type 1B | Isolated growth hormone type 1B |
| Molybdenum cofactor deficiency | Molybdenum cofactor |
| Prekallikrein deficiency congenital | Prekallikrein |
| Proconvertin deficiency congenital | Proconvertin |
| Protein S deficiency | Protein S |
| Pseudocholinesterase deficiency | Pseudocholinesterase |
| Stuart factor deficiency congenital | Stuart factor |
| Tetrahydrobiopterin deficiency | Tetrahydrobiopterin |
| Type 1 plasminogen deficiency | Plasminogen |
| Urocanase deficiency | Urocanase |

TABLE 3-continued

Rare diseases

| RARE DISEASE | DEFICIENCY |
|---|---|
| Chondrodysplasia punctata with steroid sulfatase deficiency | Chondrodysplasia punctata with steroid sulfatase/X-linked chondrodysplasia punctata 1 |
| Homocystinuria due to CBS deficiency | CBS |
| Guanidinoacetate methyltransferase deficiency | Guanidinoacetate methyltransferase |
| Pulmonary surfactant protein B deficiency | Pulmonary surfactant protein B |
| Aminoacylase 1 deficiency | Aminoacylase 1 |
| Acid Sphingomyelinase Deficiency | Enzyme found in lysosomes, responsible for conversion of lipid sphingomyelin into lipid ceramide |
| Adenylosuccinate Lyase Deficiency | Neurological disorder, brain dysfunction (encephalopathy) and to delayed development of mental and movement abilities, autistic behaviors and seizures |
| Aggressive Angiomyxoma | Myxoid tumor involving the blood vessels, may be a non-metastasizing benign tumor |
| Albrights Hereditary Osteodystrophy | Inherited in an autosomal dominant pattern, lack of responsiveness to parathyroid hormone, low serum calcium, high serum phosphate |
| Carney Stratakis Syndrome | Very rare syndrome characterized by gastrointestinal stromal tumors and paragangliomas. |
| Carney Triad Syndrome | Characterized by the coexistence of 3 types of neoplasms, mainly in young women, including gastric gastrointestinal stromal tumor, pulmonary chondroma, and extra-adrenal paraganglioma |
| CDKL5 Mutation | Results in severe neurodevelopmental impairment and early onset, difficult to control seizures |
| CLOVES Syndrome | Complex vascular anomalies: Congenital, Lipomatous Overgrowth, Vascular malformations, Epidermal nevi and Scoliosis/Skeletal/Spinal anomalies |
| Cockayne Syndrome | Characterized by short stature and an appearance of premature aging, failure to gain weight, abnormally small head size, and impaired development of the nervous system |
| Congenital Disorder of Glycosylation type 1R | Rare inborn errors of metabolism involving deficient or defective glycosylation |
| Cowden Syndrome | Characterized by multiple noncancerous, tumor-like growths called hamartomas and an increased risk of developing certain cancers |
| DEND Syndrome | Generally severe form of neonatal diabetes mellitus characterized by a triad of developmental delay, epilepsy, and neonatal diabetes |
| Dercum's Disease | Characterized by multiple, and painful lipomas. These lipomas mainly occur on the trunk, the upper arms and upper legs |
| Febrile Infection-Related Epilepsy Syndrome | Explosive-onset, potentially fatal acute epileptic encephalopathy, develops in previously healthy children and adolescents following the onset of a non-specific febrile illness |
| Fibular Aplasia Tibial Campomelia Oligosyndactyly Syndrome | Unknown genetic basis and inheritance with variable expressivity and penetrance |
| Food Protein-Induced Enterocolitis Syndrome | A non-IgE mediated immune reaction in the gastrointestinal system to one or more specific foods, commonly characterized by profuse vomiting and diarrhea |
| Foreign Body Giant Cell Reactive Tissue Disease | Collection of fused macrophages which are generated in response to the presence of a large foreign body; particularly evident with implants that cause the body chronic inflammation and foreign body response |
| Galloway-Mowat | Physical features may include an unusually small head and additional abnormalities of the head and facial area; damage to clusters of capillaries in the kidneys resulting in abnormal kidney function; and, in many cases, protrusion of part of the stomach through an abnormal opening in the diaphragm |
| Gitelman syndrome | Autosomal recessive kidney disorder characterized by hypokalemic metabolic alkalosis with hypocalciuria, and hypomagnesemia. |
| Glycerol Kinase Deficiency | X-linked recessive enzyme defect that is heterozygous in nature, responsible gene in a region containing genes in which deletions can cause DMD and adrenal hypoplasia congenita |
| Glycogen Storage Disease type 9 | Caused by the inability to break down glycogen. The different forms of the condition can affect glycogen breakdown in liver cells, muscle cells or both |
| gm1 gangliosidosis | Autosomal recessive lysosomal storage disease characterized by accumulation of ganglioside substrates in lysosomes |

TABLE 3-continued

Rare diseases

| RARE DISEASE | DEFICIENCY |
| --- | --- |
| Hereditary spherocytosis | Affects red blood cells, shortage of red blood cells, yellowing of the eyes and skin, and an enlarged spleen |
| Hidradenitis Suppurativa Stage III | Disorder of the terminal follicular epithelium in the apocrine gland-bearing skin, frequently causing keloids, contractures, and immobility. Stage III is defined as multiple lesions, with more extensive sinus tracts and scarring |
| Horizonatal Gaze Palsy with Progressive Scoliosis | Disorder that affects vision and also causes an abnormal curvature of the spine |
| IMAGe syndrome | The combination of intrauterine growth restriction, metaphyseal dysplasia, adrenal hypoplasia congenita, and genital anomalies (only about 20 cases reported in the medical literature) |
| Isodicentric 15 | Chromosome abnormality in which a child is born with extra genetic material from chromosome 15 |
| isolated hemihyperplasia | One side of the body grows more than other, causing asymmetry |
| Juvenile Xanthogranuloma | Usually benign and self-limiting. It occurs most often in the skin of the head, neck, and trunk but can also occur in the arms, legs, feet, and buttocks |
| Kasabach-Merritt Syndrome | A vascular tumor leads to decreased platelet counts and sometimes other bleeding problems |
| Kniest Dysplasia | Disorder of bone growth characterized by short stature (dwarfism) with other skeletal abnormalities and problems with vision and hearing |
| Koolen de-Vries Syndrome | Disorder characterized by developmental delay and mild to moderate intellectual disability. They usually have weak muscle tone in childhood. About half have recurrent seizures |
| Lennox-Gastaut syndrome | Type of epilepsy with multiple different types of seizures, particularly tonic (stiffening) and atonic (drop) seizures. Intellectual development is usually, but not always, impaired |
| Lymphangiomatosis | Congenital and can affect any of the body's systems except the central nervous system (including the brain) |
| Lymphangiomiomytosis | Can occur either sporadically or in association with the tuberous sclerosis complex (TSC) and is often considered a forme fruste of TSC |
| MASA Syndrome | X-linked recessive neurological disorder |
| Mast Cell Activation disorder | Condition with signs and symptoms involving the skin, gastrointestinal, cardiovascular, respiratory, and neurologic systems |
| Mecp2 Duplication Syndrome | Genetic neurodevelopmental disorder characterized by low muscle tone, potentially severe intellectual disability, developmental delays, recurrent respiratory infections, speech abnormalities, seizures, and progressive spasticity |
| Mucha Habermann | Skin disorder |
| Neonatal Hemochromatosis | Severe liver disease of fetal or perinatal onset, associated with deposition of stainable iron in extrahepatic sites, disordered iron handling due to injury to the perinatal liver, as a form of fulminant hepatic failure |
| N-glycanase deficiency | The encoded enzyme may play a role in the proteasome-mediated degradation of misfolded glycoproteins |
| Opsoclonus Myoclonus Syndrome | Neurological disorder of unknown causes which appears to be the result of an autoimmune process involving the nervous system |
| Persistent genital arousal disorder | Results in a spontaneous, persistent, and uncontrollable genital arousal, with or without orgasm or genital engorgement, unrelated to any feelings of sexual desire |
| Pompe Disease | Inherited disorder caused by the buildup of glycogen in the body's cells. The accumulation of glycogen in certain organs and tissues, especially muscles, impairs their ability to function normally |
| Progressive Familial Intrahepatic Cholestasis | Disorder that causes progressive liver disease, which typically leads to liver failure. In people with PFIC, liver cells are less able to secrete a digestive fluid called bile. The buildup of bile in liver cells causes liver disease in affected individuals |
| Pseudohypoparathyroidism type 1a | Characterized by renal resistance to parathyroid hormone, resulting in hypocalcemia, hyperphosphatemia, and elevated PTH; resistance to other hormones including thyroid stimulating hormone, gonadotropins and growth-hormone-releasing hormone |

TABLE 3-continued

Rare diseases

| RARE DISEASE | DEFICIENCY |
|---|---|
| PTEN Hamartoma Tumor Syndrome | The gene was identified as a tumor suppressor that is mutated in a large number of cancers at high frequency |
| Schnitzler syndrome | Characterised by chronic hives and periodic fever, bone pain and joint pain (sometimes with joint inflammation), weight loss, malaise, fatigue, swollen lymph glands and enlarged spleen and liver |
| Scleroderma | Chronic hardening and tightening of the skin and connective tissues |
| Semi Lobar Holoprosencephany | Holoprosencephany: birth defect of the brain, which often can also affect facial features, including closely spaced eyes, small head size, and sometimes clefts of the lip and roof of the mouth. Semilobar holoprosencephaly is a subtype of holoprosencephaly characterised by an incomplete forebrain division |
| Sjogren's Syndrome | Immune system disorder characterized by dry eyes and dry mouth |
| Specific Antibody Deficiency Disease | Immune |
| SYNGAP 1 | A ras GTPase-activating protein that is critical for the development of cognition and proper synapse function |
| Trigeminal Trophic Syndrome | This is the wing of tissue at the end of the nose above the nostril. Trigeminal trophic syndrome is due to damage to the trigeminal nerve |
| Undiffentiated Connective Tissue Disease | Systemic autoimmune disease |
| X-linked hypophosphatemia | X-linked dominant form of rickets (or osteomalacia) that differs from most cases of rickets in that ingestion of vitamin D is relatively ineffective. It can cause bone deformity including short stature and genu varum |

Modalities for Immune Modulation

The RNA molecules of this invention can be translatable to provide an active protein. In certain embodiments, a translatable RNA molecule can provide an active RNA immunization agent, or an RNA vaccine component.

Embodiments of this invention can provide vaccination with RNA molecules that encode a target antigen. The RNA molecules can induce immune response following capture by antigen-presenting cells. Synthetic, isolated RNA molecules of this invention can provide control of immunogenic response parameters, as well as pharmacokinetic properties.

In certain aspects, this disclosure provides methods for RNA vaccines. Synthetic, isolated RNA molecules of this invention can be delivered to cells or subjects in molecular form, or in various carriers. Examples of carriers include liposomes, coated nanoparticles, or cells transfected with RNA agents. In certain embodiments, a RNA agent can be used as an adjuvant, or for stimulating an innate immune response.

The RNA agents of this invention can provide therapeutics effective at a low dose.

An RNA vaccine of this disclosure can advantageously provide a safe and efficacious genetic vaccine by inducing an immune response having both cellular and humoral components. In general, protein can be expressed using an RNA vaccine of this invention.

In some embodiments, an RNA vaccine can advantageously provide protein synthesis in the cytoplasm. In certain embodiments, an RNA vaccine of this invention can provide internalization, release and transport of an exogenous translatable RNA in the cytoplasm.

In certain aspects, an RNA vaccine of this invention can encode for a protein antigen that can be translated by host cells.

In further aspects, some RNA vaccines of this disclosure can encode for tumor antigens, viral antigens, or allergens.

Modalities for administering an RNA vaccine of this invention can include intravenous, intranodal, intradermal, subcutaneous and intrasplenic.

Embodiments of this invention further provide RNA vaccines having increased half-life of translation, which can be used to reduce the necessary dose and exposure to antigen, and reduce the risk of inducing tolerance.

An RNA vaccine of this invention can provide an immunological effect without the risk of integration of a component into the genome, and may reduce the risk of mutagenesis as compared to other genetic vaccines.

Additional embodiments of this disclosure include RNA molecules having translational activity, where the translational activity can be described by a cytoplasmic half-life in a mammalian cell. The half-life can be determined by the time required for 50% of the translatable molecule to be degraded in the cell.

A translatable molecule of this invention can be a precursor of an active molecule, which can be used in the treatment of a condition or disease in a subject.

In some embodiments, a translatable molecule of this invention can be a pharmacologically active molecule having increased half-life in the cytoplasm of mammalian cells.

Aspects of this invention provide structures and compositions for translatable molecules that are oligomeric compounds. The translatable compounds can be active agents for pharmaceutical compositions. Oligomeric molecules of this invention can be used as active agents in formulations for supplying peptide and protein therapeutics.

Oligomeric compounds of this invention can have a length of from about 200 to about 12,000 bases in length. Translatable oligomeric compounds of this invention can have a length of about 1800, or about 1900, or about 2000, or about 2100, or about 2200, or about 2300, or about 2400, or about 2500 bases.

In further aspects, the oligomeric, translatable compounds of this invention can be pharmacologically active molecules. A translatable molecule can be used as an active pharmaceutical ingredient for generating a peptide or protein active agent in vitro, in vivo, or ex vivo.

In some aspects, a translatable molecule of this invention can have any number of phosphorothioate intermonomer linkages in any intermonomer location.

In some embodiments, any one or more of the intermonomer linkages of a translatable molecule can be a phosphodiester, a phosphorothioate including dithioates, a chiral phosphorothioate, and other chemically modified forms.

Enhanced Translation

A translatable molecule of this invention can incorporate a region that enhances the translational efficiency of the molecule.

In general, translational enhancer regions as known in the art can be incorporated into the structure of a translatable molecule to increase peptide or protein yields.

A translatable molecule containing a translation enhancer region can provide increased production of peptide or protein.

In some embodiments, a translation enhancer region can comprise, or be located in a 5' or 3' untranslated region of a translatable molecule.

Examples of translation enhancer regions include naturally-occurring enhancer regions from TEV 5'UTR and *Xenopus* beta-globin 3'UTR.

Molecular Structure and Sequences

A translatable molecule can be designed to express a target peptide or protein. In some embodiments, the target peptide or protein can be associated with a condition or disease in a subject.

In some aspects, the base sequence of a translatable molecule can include a portion that is identical to at least an effective portion or domain of a base sequence of an mRNA, where an effective portion is sufficient to impart a therapeutic activity to a translation product of the translatable molecule.

In some aspects, this invention provides active translatable oligomer molecules having a base sequence identical to at least a fragment of a native nucleic acid molecule of a cell.

In certain embodiments, the base sequence of a translatable molecule can include a portion that is identical to a base sequence of an mRNA, except for one or more base mutations. The number of mutations for the translatable molecule should not exceed an amount that would produce a translation product of the translatable molecule having substantially less activity than the mRNA.

The oligomeric, translatable molecules of this invention can display a sequence of nucleobases, and can be designed to express a peptide or protein, in vitro, ex vivo, or in vivo. The expressed peptide or protein can have activity in various forms, including activity corresponding to protein expressed from a native or natural mRNA.

In some embodiments, a translatable molecule of this invention may have a chain length of about 200 to 15,000 monomers.

Molecular Cap Structure

A translatable molecule of this invention may have a 5'-end capped with one of various groups as are known in the art.

In some embodiments, a 5' cap may be a m7GpppGm cap.

In further embodiments, a 5' cap may be selected from m7GpppA, m7GpppC; unmethylated cap analogs (e.g., GpppG); dimethylated cap analog (e.g., m2,7GpppG), a trimethylated cap analog (e.g., m2,2,7GpppG), dimethylated symmetrical cap analogs (e.g., m7Gpppm7G), or anti reverse cap analogs (e.g., ARCA; m7, 2'OmeGpppG, m72'dGpppG, m7,3'OmeGpppG, m7,3'dGpppG and their tetraphosphate derivatives) (see, e.g., Jemiely, J. et al., RNA 9: 1108-1122 (2003).

In additional embodiments, a 5' cap may be an ARCA cap (3'-OMe-m7G(5')pppG).

The 5' cap may be an mCAP (m7G(5')ppp(5')G, $N^7$-Methyl-Guanosine-5'-Triphosphate-5'-Guanosine).

The 5' cap may be resistant to hydrolysis.

Some examples of 5' cap structures are given in WO2015/051169, WO2015/061491, U.S. Pat. Nos. 8,093,367, 8,304,529.

Untranslated Regions

In some embodiments, a translatable molecule may comprise a 5' untranslated region (5' UTR) and/or a 3' untranslated region (3' UTR).

In some embodiments, a translatable molecule may comprise a 5' UTR that is at least about 25, 50, 75, 100, 125, 150, 175, 200, 300, 400, or 500 nucleotides in length. In further embodiments, a 5' UTR may contain about 50 to 300 nucleotides, for example about 75 to 250 nucleotides, or about 100 to 200 nucleotides, or about 120 to 150 nucleotides, or about 135 nucleotides.

In some embodiments, a 5' UTR may be derived from a reference mRNA.

In some examples, a 5' UTR can be derived from an mRNA for a histone, a tubulin, a globin, a GAPDH, an actin, or a citric acid cycle enzyme.

In other embodiments, a 5' UTR sequence may include a partial sequence of a CMV immediate-early 1 (IE1) gene.

In some embodiments, a 5' UTR may comprise a sequence selected from the 5' UTR of human IL-6, alanine aminotransferase 1, human apolipoprotein E, human fibrinogen alpha chain, human transthyretin, human haptoglobin, human alpha-1-antichymotrypsin, human antithrombin, human alpha-1-antitrypsin, human albumin, human beta globin, human complement C3, human complement C5, SynK, AT1G58420, mouse beta globin, mouse albumin, and a tobacco etch virus, or fragments of any of the foregoing.

In further embodiments, a 5' UTR may be derived from a tobacco etch virus (TEV).

In some embodiments, the translatable oligomeric molecule may comprise an internal ribosome entry site (IRES). An IRES can allow for translation initiation in an end-independent manner. In certain embodiments, an IRES can be in a 5' UTR. In other embodiments, an IRES may be outside a 5' UTR.

In some embodiments, a translatable molecule may comprise a 3' UTR that is at least about 25, 50, 75, 100, 125, 150, 175, 200, 300, 400, or 500 nucleotides in length. In some embodiments, a 3' UTR may contain about 50 to 300 nucleotides, for example, about 75 to 250 nucleotides, or about 100 to 200 nucleotides, or about 140 to 175 nucleotides, or about 160 nucleotides.

In some embodiments, a 3' UTR can comprise a sequence selected from a 3' UTR of alanine aminotransferase 1, human apolipoprotein E, human fibrinogen alpha chain, human haptoglobin, human antithrombin, human alpha globin, human beta globin, human complement C3, human growth factor, human hepcidin, MALAT-1, mouse beta globin, mouse albumin, and *xenopus* beta globin, or fragments of any of the foregoing.

In some embodiments, a 3' UTR can be derived from *xenopus* beta globin.

Some examples of UTRs may be found in U.S. Pat. No. 9,149,506.

Stop Codon

In some embodiments, a translatable molecule may comprise a sequence downstream of a CDS that creates a triple stop codon. In some embodiments, a translatable molecule may comprise the sequence AUAAGUGAA (SEQ ID NO: 1) downstream of a CDS.

Translation Initiation

In some embodiments, a translatable molecule may comprise a translation initiation site.

In certain embodiments, a translation initiation site can be a Kozak sequence. Some examples are found in Kozak, Marilyn (1988) Mol. and Cell Biol., 8:2737-2744; Kozak, Marilyn (1991) J. Biol. Chem., 266:19867-19870; Kozak, Marilyn (1990) Proc Natl. Acad. Sci. USA, 87:8301-8305; and Kozak, Marilyn (1989) J. Cell Biol., 108:229-241.

In some embodiments, a translation initiation site can be inserted upstream of a CDS.

In further embodiments, a translation initiation site can be inserted downstream of a 5' UTR.

Molecular Tail Structure

In some embodiments, a translatable molecule can comprise a tail region, which can serve to protect the molecule from exonuclease degradation.

In some embodiments, the tail region can be a polyA tail.

A PolyA tail can be connected to a translatable molecule using a variety of methods known in the art. For example, using poly A polymerase to add tails to synthetic or in vitro transcribed RNA. Other methods include the use of a transcription vector to encode poly A tails or the use of a ligase (e.g., via splint ligation using a T4 RNA ligase and/or T4 DNA ligase), wherein polyA may be ligated to the 3' end of a sense RNA. In some embodiments, a combination of any of the above methods can be utilized.

In some embodiments, a translatable molecule can comprise a 3' polyA tail structure. The length of a polyA tail can be 5, 10, 15, 20, 25, 30, 35, 40, 45, 50, 100, 200, or 300 nucleotides, or longer. In some embodiments, a 3' polyA tail can contain about 5 to 300 adenosine nucleotides, e.g., about 30 to 250 adenosine nucleotides, or about 60 to 220 adenosine nucleotides, or about 80 to 200 adenosine nucleotides, or about 90 to about 150 adenosine nucleotides, or about 100 to about 120 adenosine nucleotides. In some examples, a 3' polyA tail can be about 100 nucleotides in length, or 115 nucleotides in length.

In some embodiments, a translatable molecule may comprise a 3' polyC tail structure. In some embodiments, the length of the polyC tail can be at least about 5, 10, 15, 20, 25, 30, 35, 40, 45, 50, 100, 200, or 300 nucleotides, or more. In some embodiments, a 3' polyC tail may contain about 5 to 300 cytosine nucleotides, for example, about 30 to 250 cytosine nucleotides, or about 60 to 220 cytosine nucleotides, or about 80 to about 200 cytosine nucleotides, or about 90 to 150 cytosine nucleotides, or about 100 to about 120 cytosine nucleotides. In some embodiments, a 3' polyC tail can be about 100 nucleotides in length, or 115 nucleotides in length.

In further aspects, a polyC tail may be connected to a polyA tail. A polyC tail may connect to the 5' end of a polyA tail, or to the 3' end of a polyA tail.

In some embodiments, the length of the poly A and/or poly C tail can be varied to affect the stability of a translatable molecule.

Genetic Basis for Translatable Molecules

In some embodiments, the translatable molecules of this invention can be structured to provide peptides or proteins that are nominally expressed by any portion of a genome.

Examples of genes for which a translatable molecule can be used to express the corresponding peptide or protein are set forth below.

Examples of genes for which a translatable molecule can be used to express the corresponding peptide or protein include: Neoplasia, PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc.

Examples of genes for which a translatable molecule can be used to express the corresponding peptide or protein include: Age-related Macular Degeneration, Schizophrenia, Aber; Cc12; Cc2; cp (ceruloplasmin); Timp3; cathepsinD; Vldlr; Ccr2 Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b.

Examples of genes for which a translatable molecule can be used to express the corresponding peptide or protein include: 5-HTT (Slc6a4); COMT; DRD (Drd1a); SLC6A3; DAOA; DTNBP1; Dao (Dao1).

Examples of genes for which a translatable molecule can be used to express the corresponding peptide or protein include: Trinucleotide Repeat Disorders, HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn 1 (DRPLA Dx); CBP (Creb-BP-global instability); VLDLR (Alzheimer's); Atxn7; Atxn10.

Examples of genes for which a translatable molecule can be used to express the corresponding peptide or protein include: Fragile X Syndrome, FMR2; FXR1; FXR2; mGLUR5.

Examples of genes for which a translatable molecule can be used to express the corresponding peptide or protein include: Secretase Related Disorders, APH-1 (alpha and beta); Presenilin (Psen1); nicastrin (Ncstn); PEN-2.

Examples of genes for which a translatable molecule can be used to express the corresponding peptide or protein include: Nos1.

Examples of genes for which a translatable molecule can be used to express the corresponding peptide or protein include: Parp1.

Examples of genes for which a translatable molecule can be used to express the corresponding peptide or protein include: Nat1; Nat2.

Examples of genes for which a translatable molecule can be used to express the corresponding peptide or protein include: Prion-related disorders, Prp.

Examples of genes for which a translatable molecule can be used to express the corresponding peptide or protein include: ALS disease, SOD1; ALS2; STEX; FUS; TARDBP; VEGF (VEGF-a; VEGF-b; VEGF-c).

Examples of genes for which a translatable molecule can be used to express the corresponding peptide or protein include: Drug addiction, Prkce (alcohol); Drd2; Drd4; ABAT (alcohol); GRIA2; Grm5; Grin1; Htr1b; Grin2a; Drd3; Pdyn; Gria1 (alcohol).

Examples of genes for which a translatable molecule can be used to express the corresponding peptide or protein include: Autism, Mecp2; BZRAP1; MDGA2; Sema5A; Neurexin 1; Fragile X (FMR2 (AFF2); FXR1; FXR2; Mglur5).

Examples of genes for which a translatable molecule can be used to express the corresponding peptide or protein include: Alzheimer's Disease, E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP.

Examples of genes for which a translatable molecule can be used to express the corresponding peptide or protein include: Inflammation, 1L-10; IL-1 (1L-1a; IL-1b); 1L-13; IL-17 (IL-17a (CTLA8); IL-17b; IL-17c; IL-17d; IL-17f); II-23; Cx3er1; ptpn22; TNFa; NOD2/CARD15 for IBD; IL-6; 1L-12 (1L-12a; 1L-12b); CTLA4; Cx3cl1.

Examples of genes for which a translatable molecule can be used to express the corresponding peptide or protein include: Parkinson's Disease, x-Synuclein; DJ-1; LRRK2; Parkin; PINK1.

Examples of genes for which a translatable molecule can be used to express the corresponding peptide or protein include: Blood and coagulation diseases and disorders, Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5); Bleeding disorders (TBXA2R, P2RX1, P2X1); Factor H and factor H-like 1 (HF 1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9 Factor IX, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1).

Examples of genes for which a translatable molecule can be used to express the corresponding peptide or protein include: Cell dysregulation and oncology diseases and disorders, B-cell non-Hodgkin lymphoma (BCL7A, BCL7); Leukemia (TAL1 TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN).

Examples of genes for which a translatable molecule can be used to express the corresponding peptide or protein include: Inflammation and immune related diseases and disorders, AIDS (KIR3DL1, NKAT3, NKB1, AMB11, KIR3DS1, IFNG, CXCL12, SDF1); Autoimmune lymphoproliferative syndrome (TNFRSF6, APT 1, FAS, CD95, ALPS1A); Combined immuno-deficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immuno-deficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f, 11-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs) (JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4).

Examples of genes for which a translatable molecule can be used to express the corresponding peptide or protein include: Metabolic, liver, kidney and protein diseases and disorders, Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRHIA, NAIC, TEX292, KIAA1988); Cystic fibrosis (CFTR, BG213071, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNFl1A, MODY3), Hepatic failure, early onset, and neurologic disorder (SCOD1, SCO1), Hepatic lipase deficiency (LIPC), Hepato-blastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63).

Examples of genes for which a translatable molecule can be used to express the corresponding peptide or protein include: Lipoprotein lipase, APOA1, APOC3 and APOA4.

Examples of genes for which a translatable molecule can be used to express the corresponding peptide or protein include: Muscular/skeletal diseases and disorders, Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facio-scapulohumeral muscular dystrophy (F SHMD 1A, F SHD 1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1).

Examples of genes for which a translatable molecule can be used to express the corresponding peptide or protein include: Neurological and neuronal diseases and disorders, ALS (SOD1, ALS2, STEX, FUS, TARDBP, VEGF (VEGF-a, VEGF-b, VEGF-c); Alzheimer's Disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIPIL, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizo-phrenia (Neuregulin1 (Nrg1), Erb4 (receptor for Neuregulin), Complexin1 (Cplx1), Tph1 Trypto-phan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Dis-orders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP—global instability), VLDLR (Alzheimer's), Atxn7, Atxn10).

Examples of genes for which a translatable molecule can be used to express the corresponding peptide or protein include: Occular diseases and disorders, Age-related macular degeneration (Aber, Cc12, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQPO, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2).

Examples of genes for which a translatable molecule can be used to express the corresponding peptide or protein include: Epilepsy, myoclonic, EPM2A, MELF, EPM2 Lafora type, 254780 Epilepsy, myoclonic, NHLRC1, EPM2A, EPM2B Lafora type, 254780.

Examples of genes for which a translatable molecule can be used to express the corresponding peptide or protein include: Duchenne muscular DMD, BMD dystrophy, 310200 (3) AIDS, delayed/rapid KIR3DL1, NKAT3, NKB1, AMB11, KIR3DS1 progression to (3).

Examples of genes for which a translatable molecule can be used to express the corresponding peptide or protein include: AIDS, delayed/rapid KIR3DL1, NKAT3, NKB1, AMB11, KIR3DS1 progression to (3) AIDS, rapid IFNG progression to, 609423 (3) AIDS, resistance to CXCL12, SDF1 (3).

Examples of genes for which a translatable molecule can be used to express the corresponding peptide or protein include: Alpha-1-Antitrypsin Deficiency, SERPINA1 [serpin peptidase inhibitor, clade A (alpha-1 antiproteinase, antitrypsin), member 1]; SERPINA2 [serpin peptidase inhibitor, clade A (alpha-1 antiproteinase, antitrypsin), member 2]; SERPINA3 [serpin peptidase inhibitor, clade A (alpha-1 antiproteinase, antitrypsin), member 3]; SERPINA5 [serpin peptidase inhibitor, clade A (alpha-1 antiproteinase, antitrypsin), member 5]; SERPINA6 [serpin peptidase inhibitor, clade A (alpha-1 antiproteinase, antitrypsin), member 6]; SERPINA7 [serpin peptidase inhibitor, clade A (alpha-1 antiproteinase, antitrypsin), member 7];" AND "SERPLNA6 (serpin peptidase inhibitor, clade A (alpha-1 antiproteinase, antitrypsin), member 6).

Examples of genes for which a translatable molecule can be used to express the corresponding peptide or protein include: PI3K/AKT Signaling, PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2RIA; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRKiA; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1.

Examples of genes for which a translatable molecule can be used to express the corresponding peptide or protein include: ERK/MAPK Signaling, PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRKiA; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK.

Examples of genes for which a translatable molecule can be used to express the corresponding peptide or protein include: Serine/Threonine-Protein Kinase, CDK16; PCTK1; CDK5R1.

Examples of genes for which a translatable molecule can be used to express the corresponding peptide or protein include: Glucocorticoid Receptor Signaling, RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1.

Examples of genes for which a translatable molecule can be used to express the corresponding peptide or protein include: Axonal Guidance Signaling, PRKCE; ITGAM; ROCK1; ITGA5; CXCR4; ADAM12; IGF1; RAC1; RAP1A; E1F4E; PRKCZ; NRP1; NTRK2; ARHGEF7; SMO; ROCK2; MAPK1; PGF; RAC2; PTPN11; GNAS; AKT2; PIK3CA; ERBB2; PRKC1; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA.

Examples of genes for which a translatable molecule can be used to express the corresponding peptide or protein include: Ephrin Receptor Signaling, PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK.

Examples of genes for which a translatable molecule can be used to express the corresponding peptide or protein include: Actin Cytoskeleton Signaling, ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRKIA; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK.

Examples of genes for which a translatable molecule can be used to express the corresponding peptide or protein include: Huntington's Disease Signaling, PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKC1; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3.

Examples of genes for which a translatable molecule can be used to express the corresponding peptide or protein include: Apoptosis Signaling, PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRKiA; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1.

Examples of genes for which a translatable molecule can be used to express the corresponding peptide or protein include: B Cell Receptor Signaling, RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1.

Examples of genes for which a translatable molecule can be used to express the corresponding peptide or protein include: Leukocyte Extravasation Signaling, ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9.

Examples of genes for which a translatable molecule can be used to express the corresponding peptide or protein include: Integrin Signaling, ACTN4; ITGAM; ROCK1; ITGA5; RAC1; PTEN; RAP1A; TLN1; ARHGEF7; MAPK1; RAC2; CAPNS1; AKT2; CAPN2; P1K3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3.

Examples of genes for which a translatable molecule can be used to express the corresponding peptide or protein include: Acute Phase Response Signaling, IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6.

Examples of genes for which a translatable molecule can be used to express the corresponding peptide or protein include: PTEN Signaling, ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1.

Examples of genes for which a translatable molecule can be used to express the corresponding peptide or protein include: p53 Signaling, PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; RIK3R1; RRM2B; APAF1; CTNNB1; SIRT1; CCND1; PRKDC; ATM; SFN; CDKN2A; JUN; SNAI2; GSK3B; BAX; AKT3.

Examples of genes for which a translatable molecule can be used to express the corresponding peptide or protein include: Aryl Hydrocarbon Receptor Signaling, HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2;

AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1.

Examples of genes for which a translatable molecule can be used to express the corresponding peptide or protein include: Xenobiotic Metabolism Signaling, PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1.

Examples of genes for which a translatable molecule can be used to express the corresponding peptide or protein include: SAPK/JNK Signaling, PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRKiA; MAP2K2; PIK3R1; MAP2K1; PAK3; CDC42; JUN; TTK; CSNK1A1; CRKL; BRAF; SGK.

Examples of genes for which a translatable molecule can be used to express the corresponding peptide or protein include: PPAr/RXR Signaling, PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ.

Examples of genes for which a translatable molecule can be used to express the corresponding peptide or protein include: NF-KB Signaling, IRAK1; EIF2AK2; EP300; INS; MYD88; PRKCZ: TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4: TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1.

Examples of genes for which a translatable molecule can be used to express the corresponding peptide or protein include: Neuregulin Signaling, ERBB4; PRKCE; ITGAM; ITGA5: PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6 KB1.

Examples of genes for which a translatable molecule can be used to express the corresponding peptide or protein include: Wnt & Beta catenin Signaling, CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2: ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2.

Examples of genes for which a translatable molecule can be used to express the corresponding peptide or protein include: Insulin Receptor Signaling, PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1.

Examples of genes for which a translatable molecule can be used to express the corresponding peptide or protein include: IL-6 Signaling, HSPB1; TRAF6; MAPKAPK2; ELK1; MAPK1; PTPN11; IKBKB; FOS; NFKB2: MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6.

Examples of genes for which a translatable molecule can be used to express the corresponding peptide or protein include: Hepatic Cholestasis, PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6.

Examples of genes for which a translatable molecule can be used to express the corresponding peptide or protein include: IGF-1 Signaling, IGF1; PRKCZ; ELK1; MAPK1; PTPN11; NEDD4; AKT2; PIK3CA; PRKC1; PTK2; FOS; PIK3CB; PIK3C3; MAPK8; 1GF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1.

Examples of genes for which a translatable molecule can be used to express the corresponding peptide or protein include: NRF2-mediated Oxidative Stress Response, PRKCE; EP300; SOD2; PRKCZ; MAPK1; SQSTM1; NQO1; PIK3CA; PRKC1; FOS; PIK3CB; P1K3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1.

Examples of genes for which a translatable molecule can be used to express the corresponding peptide or protein include: Hepatic, Fibrosis/Hepatic Stellate Cell Activation, EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; TNF; RELB; IL8; PDGFRA; NFKB1; TGFBR1; SMAD4; VEGFA; BAX; IL1R1; CCL2; HGF; MMP1; STAT1; IL6; CTGF; MMP9.

Examples of genes for which a translatable molecule can be used to express the corresponding peptide or protein include: PPAR Signaling, EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; TNF; INSR; RAF1; IKBKG; RELB; MAP3K7; CREBBP; MAP2K2; CHUK; PDGFRA; MAP2K1; NFKB1; JUN; IL1R1; HSP90AA1.

Examples of genes for which a translatable molecule can be used to express the corresponding peptide or protein include: Fc Epsilon RI Signaling, PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA.

Examples of genes for which a translatable molecule can be used to express the corresponding peptide or protein include: G-Protein Coupled Receptor Signaling, PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA.

Examples of genes for which a translatable molecule can be used to express the corresponding peptide or protein include: Inositol Phosphate Metabolism, PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRKiA; MAP2K2; PIP5K1A; PIK3R1; MAP2K1; PAK3; ATM; TTK; CSNK1A1; BRAF; SGK.

Examples of genes for which a translatable molecule can be used to express the corresponding peptide or protein include: PDGF Signaling, EIF2AK2; ELK1; ABL2; MAPK1; PIK3CA; FOS; PIK3CB; PIK3C3; MAPK8; CAV1; ABL1; MAPK3; KRAS; SRC; PIK3C2A; RAF1; MAP2K2; JAK1; JAK2; PIK3R1; PDGFRA; STAT3; SPHK1; MAP2K1; MYC; JUN; CRKL; PRKCA; SRF; STAT1; SPHK2.

Examples of genes for which a translatable molecule can be used to express the corresponding peptide or protein include: VEGF Signaling, ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA.

Examples of genes for which a translatable molecule can be used to express the corresponding peptide or protein include: Natural Killer Cell Signaling, PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA.

Examples of genes for which a translatable molecule can be used to express the corresponding peptide or protein include: Cell Cycle: G1/S Checkpoint Regulation, HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6.

Examples of genes for which a translatable molecule can be used to express the corresponding peptide or protein include: T Cell Receptor Signaling, RAC1; ELK1; MAPK1; IKBKB; CBL; PIK3CA; FOS; NFKB2; PIK3CB; PIK3C3; MAPK8; MAPK3; KRAS; RELA, PIK3C2A; BTK; LCK; RAF1; IKBKG; RELB, FYN; MAP2K2; PIK3R1; CHUK; MAP2K1; NFKB1; ITK; BCL10; JUN; VAV3.

Examples of genes for which a translatable molecule can be used to express the corresponding peptide or protein include: Death Receptor Signaling, CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3.

Examples of genes for which a translatable molecule can be used to express the corresponding peptide or protein include: FGF Signaling RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF.

Examples of genes for which a translatable molecule can be used to express the corresponding peptide or protein include: GM-CSF Signaling, LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1.

Examples of genes for which a translatable molecule can be used to express the corresponding peptide or protein include: Amyotrophic Lateral Sclerosis Signaling, BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3.

Examples of genes for which a translatable molecule can be used to express the corresponding peptide or protein include: JAK/Stat Signaling, PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1.

Examples of genes for which a translatable molecule can be used to express the corresponding peptide or protein include: Nicotinate and Nicotinamide Metabolism, PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRKiA; MAP2K2; MAP2K1; PAK3; NT5E; TTK; CSNK1A1; BRAF; SGK.

Examples of genes for which a translatable molecule can be used to express the corresponding peptide or protein include: Chemokine Signaling, CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA.

Examples of genes for which a translatable molecule can be used to express the corresponding peptide or protein include: IL-2 Signaling, ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A: LCK; RAF1; MAP2K2; JAK1; AKT1; PIK3R1; MAP2K1; JUN; AKT3.

Examples of genes for which a translatable molecule can be used to express the corresponding peptide or protein include: Synaptic Long Term Depression, PRKCE; IGF1; PRKCZ; PRDX6; LYN; MAPK1; GNAS; PRKC1; GNAQ; PPP2R1A; IGF1R; PRKID1; MAPK3; KRAS; GRN; PRKCD; NOS3; NOS2A; PPP2CA; YWHAZ; RAF1; MAP2K2; PPP2R5C; MAP2K1; PRKCA.

Examples of genes for which a translatable molecule can be used to express the corresponding peptide or protein include: Estrogen Receptor Signaling, TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2.

Examples of genes for which a translatable molecule can be used to express the corresponding peptide or protein include: Protein Ubiquitination Pathway, TRAF6; SMURF1; BIRC4; BRCA1; UCHL1; NEDD4; CBL; UBE2I; BTRC; HSPA5; USP7; USP10; FBXW7; USP9X; STUB 1; USP22; B2M; BIRC2; PARK2; USP8; USP1; VHL; HSP90AA1; BIRC3.

Examples of genes for which a translatable molecule can be used to express the corresponding peptide or protein include: IL-10 Signaling, TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6.

Examples of genes for which a translatable molecule can be used to express the corresponding peptide or protein include: VDR/RXR Activation, PRKCE; EP300; PRKCZ; RXRA; GADD45A; HES1; NCOR2; SP1; PRKC1; CDKN1B; PRKD1; PRKCD; RUNX2; KLF4; YY1; NCOA3; CDKN1A; NCOA2; SPP1; LRP5; CEBPB; FOXO1; PRKCA.

Examples of genes for which a translatable molecule can be used to express the corresponding peptide or protein include: TGF-beta Signaling, EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5.

Examples of genes for which a translatable molecule can be used to express the corresponding peptide or protein include: Toll-like Receptor Signaling, IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN.

Examples of genes for which a translatable molecule can be used to express the corresponding peptide or protein include: p38 MAPK Signaling, HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1.

Examples of genes for which a translatable molecule can be used to express the corresponding peptide or protein include: Neurotrophin/TRK Signaling, NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4.

Examples of genes for which a translatable molecule can be used to express the corresponding peptide or protein include: FXR/RXR Activation, INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1.

Examples of genes for which a translatable molecule can be used to express the corresponding peptide or protein include: Synaptic Long Term Potentiation, PRKCE; RAP1A; EP300; PRKCZ; MAPK1; CREB1; PRKC1; GNAQ; CAMK2A; PRKD1; MAPK3; KRAS; PRKCD; PPP1CC; RAF1; CREBBP; MAP2K2; MAP2K1; ATF4; PRKCA.

Examples of genes for which a translatable molecule can be used to express the corresponding peptide or protein include: Calcium Signaling, RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6.

Examples of genes for which a translatable molecule can be used to express the corresponding peptide or protein include: EGF Signaling, ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1.

Examples of genes for which a translatable molecule can be used to express the corresponding peptide or protein include: Hypoxia Signaling in the Cardiovascular System, EDN1; PTEN; EP300; NQO1; UBE21; CREB1; ARNT; HIF1A; SLC2A4; NOS3; TP53; LDHA; AKT1; ATM; VEGFA; JUN; ATF4; VHL; HSP90AA1.

Examples of genes for which a translatable molecule can be used to express the corresponding peptide or protein include: LPS/IL-1 Mediated Inhibition of RXR Function, IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1.

Examples of genes for which a translatable molecule can be used to express the corresponding peptide or protein include: LXR/RXR Activation, FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9.

Examples of genes for which a translatable molecule can be used to express the corresponding peptide or protein include: Amyloid Processing, PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP.

Examples of genes for which a translatable molecule can be used to express the corresponding peptide or protein include: IL-4 Signaling, AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1.

Examples of genes for which a translatable molecule can be used to express the corresponding peptide or protein include: Cell Cycle: G2/M DNA Damage Checkpoint Regulation, EP300; PCAF; BRCA1; GADD45A; PLK1; BTRC; CHEK1; ATR; CHEK2; YWHAZ; TP53; CDKN1A; PRKDC; ATM; SFN; CDKN2A.

Examples of genes for which a translatable molecule can be used to express the corresponding peptide or protein include: Nitric Oxide Signaling in the Cardiovascular System, KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1.

Examples of genes for which a translatable molecule can be used to express the corresponding peptide or protein include: Purine Metabolism NME2; SMARCA4; MYH9; RRM2; ADAR; EIF2AK4; PKM2; ENTPD1; RAD51; RRM2B; TJP2; RAD51C; NT5E; POLD1; NME1.

Examples of genes for which a translatable molecule can be used to express the corresponding peptide or protein include: cAMP-mediated Signaling, RAP1A; MAPK1; GNAS; CREB1; CAMK2A; MAPK3; SRC; RAF1; MAP2K2; STAT3; MAP2K1; BRAF; ATF4.

Examples of genes for which a translatable molecule can be used to express the corresponding peptide or protein include: Mitochondrial Dysfunction Notch Signaling, SOD2; MAPK8; CASP8; MAPK10; MAPK9; CASP9; PARK7; PSEN1; PARK2; APP; CASP3 HES1; JAG1; NUMB; NOTCH4; ADAM17; NOTCH2; PSEN1; NOTCH3; NOTCH1; DLL4.

Examples of genes for which a translatable molecule can be used to express the corresponding peptide or protein include: Endoplasmic Reticulum Stress Pathway, HSPA5; MAPK8; XBP1; TRAF2; ATF6; CASP9; ATF4; EIF2AK3; CASP3.

Examples of genes for which a translatable molecule can be used to express the corresponding peptide or protein include: Pyrimidine Metabolism, NME2; AICDA; RRM2; EIF2AK4; ENTPD1; RRM2B; NT5E; POLD1; NME1.

Examples of genes for which a translatable molecule can be used to express the corresponding peptide or protein include: Parkinson's Signaling, UCHL1; MAPK8; MAPK13; MAPK14; CASP9; PARK7; PARK2; CASP3.

Examples of genes for which a translatable molecule can be used to express the corresponding peptide or protein include: Cardiac & Beta Adrenergic Signaling, GNAS; GNAQ; PPP2R1A; GNB2L1; PPP2CA; PPP1CC; PPP2R5C.

Examples of genes for which a translatable molecule can be used to express the corresponding peptide or protein include: Glycolysis/Gluco-neogenesis, HK2; GCK; GPI; ALDH1A1; PKM2; LDHA; HK1.

Examples of genes for which a translatable molecule can be used to express the corresponding peptide or protein include: Interferon Signaling, IRF1; SOCS1; JAK1; JAK2; IFITM1; STAT1; IFIT3.

Examples of genes for which a translatable molecule can be used to express the corresponding peptide or protein include: Sonic Hedgehog Signaling, ARRB2; SMO; GLI2; DYRKiA; GLI1; GSK3B; DYRKIB.

Examples of genes for which a translatable molecule can be used to express the corresponding peptide or protein include: Glycerophospholipid Metabolism, PLD1; GRN; GPAM; YWHAZ; SPHK1; SPHK2.

Examples of genes for which a translatable molecule can be used to express the corresponding peptide or protein include: Phospholipid Degradation, PRDX6; PLD1; GRN; YWHAZ; SPHK1; SPHK2.

Examples of genes for which a translatable molecule can be used to express the corresponding peptide or protein include: Tryptophan Metabolism, SIAH2; PRMT5; NEDD4; ALDH1A1; CYP1B1; SIAH1.

Examples of genes for which a translatable molecule can be used to express the corresponding peptide or protein include: Lysine Degradation, SUV39H1; EHMT2; NSD1; SETD7; PPP2R5C.

Examples of genes for which a translatable molecule can be used to express the corresponding peptide or protein include: Nucleotide Excision, ERCC5; ERCC4; XPA; XPC; ERCC1.

Examples of genes for which a translatable molecule can be used to express the corresponding peptide or protein include: Repair Pathway Starch and Sucrose Metabolism, UCHL1; HK2; GCK; GPI; HK1.

Examples of genes for which a translatable molecule can be used to express the corresponding peptide or protein include: Aminosugars Metabolism, NQO1; HK2; GCK; HK1.

Examples of genes for which a translatable molecule can be used to express the corresponding peptide or protein include: Arachidonic Acid Metabolism, PRDX6; GRN; YWHAZ; CYP1B1.

Examples of genes for which a translatable molecule can be used to express the corresponding peptide or protein include: Circadian Rhythm Signaling, CSNK1E; CREB1; ATF4; NR1D1.

Examples of genes for which a translatable molecule can be used to express the corresponding peptide or protein include: Coagulation System, BDKRB1; F2R; SERPINE1; F3.

Examples of genes for which a translatable molecule can be used to express the corresponding peptide or protein include: Dopamine Receptor Signaling, PPP2R1A; PPP2CA; PPP1CC; PPP2R5C.

Examples of genes for which a translatable molecule can be used to express the corresponding peptide or protein include: Glutathione Metabolism, IDH2; GSTP1; ANPEP; IDH1.

Examples of genes for which a translatable molecule can be used to express the corresponding peptide or protein include: Glycerolipid Metabolism, ALDH1A1; GPAM; SPHK1; SPHK2.

Examples of genes for which a translatable molecule can be used to express the corresponding peptide or protein include: Linoleic Acid Metabolism, PRDX6; GRN; YWHAZ; CYP1B1.

Examples of genes for which a translatable molecule can be used to express the corresponding peptide or protein include: Methionine Metabolism, DNMT1; DNMT3B; AHCY; DNMT3A.

Examples of genes for which a translatable molecule can be used to express the corresponding peptide or protein include: Pyruvate Metabolism, GLO1; ALDH1A1; PKM2; LDHA.

Examples of genes for which a translatable molecule can be used to express the corresponding peptide or protein include: Arginine and Proline Metabolism, ALDH1A1; NOS3; NOS2A.

Examples of genes for which a translatable molecule can be used to express the corresponding peptide or protein include: Eicosanoid Signaling, PRDX6; GRN; YWHAZ.

Examples of genes for which a translatable molecule can be used to express the corresponding peptide or protein include: Fructose and Mannose Metabolism, HK2; GCK; HK1.

Examples of genes for which a translatable molecule can be used to express the corresponding peptide or protein include: Galactose Metabolism, HK2; GCK; HK1.

Examples of genes for which a translatable molecule can be used to express the corresponding peptide or protein include: Stilbene, Coumarine and Lignin Biosynthesis, PRDX6; PRDX1; TYR.

Examples of genes for which a translatable molecule can be used to express the corresponding peptide or protein include: Antigen Presentation Pathway, CALR; B2M.

Examples of genes for which a translatable molecule can be used to express the corresponding peptide or protein include: Biosynthesis of Steroids, NQO1; DHCR7.

Examples of genes for which a translatable molecule can be used to express the corresponding peptide or protein include: Butanoate Metabolism, ALDH1A1; NLGN1.

Examples of genes for which a translatable molecule can be used to express the corresponding peptide or protein include: Citrate Cycle, IDH2; IDH1.

Examples of genes for which a translatable molecule can be used to express the corresponding peptide or protein include: Fatty Acid Metabolism, ALDH1A1; CYP1B1.

Examples of genes for which a translatable molecule can be used to express the corresponding peptide or protein include: Glycerophospholipid Metabolism, PRDX6; CHKA.

Examples of genes for which a translatable molecule can be used to express the corresponding peptide or protein include: Histidine Metabolism, PRMT5; ALDH1A1.

Examples of genes for which a translatable molecule can be used to express the corresponding peptide or protein include: Inositol Metabolism, ERO1L; APEX1.

Examples of genes for which a translatable molecule can be used to express the corresponding peptide or protein include: Metabolism of Xenobiotics by Cytochrome p450, GSTP1; CYP1B1.

Examples of genes for which a translatable molecule can be used to express the corresponding peptide or protein include: Methane Metabolism, PRDX6; PRDX1.

Examples of genes for which a translatable molecule can be used to express the corresponding peptide or protein include: Phenylalanine Metabolism, PRDX6; PRDX1.

Examples of genes for which a translatable molecule can be used to express the corresponding peptide or protein include: Propanoate Metabolism, ALDH1A1; LDHA.

Examples of genes for which a translatable molecule can be used to express the corresponding peptide or protein include: Selenoamino Acid Metabolism, PRMT5; AHCY.

Examples of genes for which a translatable molecule can be used to express the corresponding peptide or protein include: Sphingolipid Metabolism, SPHK1; SPHK2.

Examples of genes for which a translatable molecule can be used to express the corresponding peptide or protein include: Aminophosphonate Metabolism, PRMT5.

Examples of genes for which a translatable molecule can be used to express the corresponding peptide or protein include: Androgen and Estrogen Metabolism, PRMT5.

Examples of genes for which a translatable molecule can be used to express the corresponding peptide or protein include: Ascorbate and Aldarate Metabolism, ALDH1A1.

Examples of genes for which a translatable molecule can be used to express the corresponding peptide or protein include: Bile Acid Biosynthesis, ALDH1A1.

Examples of genes for which a translatable molecule can be used to express the corresponding peptide or protein include: Cysteine Metabolism, LDHA.

Examples of genes for which a translatable molecule can be used to express the corresponding peptide or protein include: Fatty Acid Biosynthesis, FASN.

Examples of genes for which a translatable molecule can be used to express the corresponding peptide or protein include: Glutamate Receptor Signaling, GNB2L1.

Examples of genes for which a translatable molecule can be used to express the corresponding peptide or protein include: NRF2-mediated Oxidative Stress Response, PRDX1.

Examples of genes for which a translatable molecule can be used to express the corresponding peptide or protein include: Pentose Phosphate Pathway, GPI.

Examples of genes for which a translatable molecule can be used to express the corresponding peptide or protein include: Pentose and Glucuronate Interconversions, UCHL1.

Examples of genes for which a translatable molecule can be used to express the corresponding peptide or protein include: Retinol Metabolism, ALDH1A1.

Examples of genes for which a translatable molecule can be used to express the corresponding peptide or protein include: Riboflavin Metabolism, TYR.

Examples of genes for which a translatable molecule can be used to express the corresponding peptide or protein include: Tyrosine Metabolism, PRMT5, TYR.

Examples of genes for which a translatable molecule can be used to express the corresponding peptide or protein include: Ubiquinone Biosynthesis, PRMT5.

Examples of genes for which a translatable molecule can be used to express the corresponding peptide or protein include: Valine, Leucine and Isoleucine Degradation, ALDH1A1.

Examples of genes for which a translatable molecule can be used to express the corresponding peptide or protein include: Glycine, Serine and Threonine Metabolism, CHKA.

Examples of genes for which a translatable molecule can be used to express the corresponding peptide or protein include: Lysine Degradation, ALDH1A1.

Examples of genes for which a translatable molecule can be used to express the corresponding peptide or protein include: Pain/Taste, TRPM5; TRPA1.

Examples of genes for which a translatable molecule can be used to express the corresponding peptide or protein include: Pain, TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a.

Examples of genes for which a translatable molecule can be used to express the corresponding peptide or protein include: Mitochondrial Function, AIF; CytC; SMAC (Diablo); Aifm-1; Aifm-2.

Examples of genes for which a translatable molecule can be used to express the corresponding peptide or protein include: Developmental Neurology, BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab 1; unc-86 (Pou4fl or Brn3a); Numb; Reln.

Additional Synthesis Methods

In various aspects, this invention provides methods for synthesis of translatable molecules.

Translatable molecules of this invention can be synthesized and isolated using methods disclosed herein, as well as any pertinent techniques known in the art.

Some methods for preparing nucleic acids are given in, for example, Merino, Chemical Synthesis of Nucleoside Analogues, (2013); Gait, Oligonucleotide synthesis: a practical approach (1984); Herdewijn, Oligonucleotide Synthesis, Methods in Molecular Biology, Vol. 288 (2005).

In some embodiments, a translatable molecule can be made by in vitro transcription (IVT) reaction. A mix of nucleoside triphosphates (NTP) can be polymerized using T7 reagents, for example, to yield RNA from a DNA template. The DNA template can be degraded with RNase-free DNase, and the RNA column-separated.

In some embodiments, a ligase can be used to link a synthetic oligomer to the 3' end of an RNA molecule or an RNA transcript to form a translatable molecule. The synthetic oligomer that is ligated to the 3' end can provide the functionality of a polyA tail, and advantageously provide resistance to its removal by 3'-exoribonucleases. The ligated product translatable molecule can have increased specific activity and provide increased levels of ectopic protein expression.

In certain embodiments, ligated product translatable molecules of this invention can be made with an RNA transcript that has native specificity. The ligated product can be a synthetic molecule that retains the structure of the RNA transcript at the 5' end to ensure compatibility with the native specificity.

In further embodiments, ligated product translatable molecules of this invention can be made with an exogenous RNA transcript or non-natural RNA. The ligated product can be a synthetic molecule that retains the structure of the RNA.

In general, the canonical mRNA degradation pathway in cells includes the steps: (i) the polyA tail is gradually cut back to a stub by 3' exonucleases, shutting down the looping interaction required for efficient translation and leaving the cap open to attack; (ii) decapping complexes remove the 5' cap; (iii) the unprotected and translationally incompetent residuum of the transcript is degraded by 5' and 3' exonuclease activity.

Embodiments of this invention involve new translatable structures which can have increased translational activity over a native transcript. The translatable molecules can prevent exonucleases from trimming back the polyA tail in the process of de-adenylation.

Embodiments of this invention provide structures, compositions and methods for translatable molecules. Embodiments of this invention can provide translatable molecules containing one or more chemically modified monomers, as well as natural nucleotides, and having increased functional half-life.

Pharmaceutical Compositions

In some aspects, this invention provides pharmaceutical compositions containing a translatable compound and a pharmaceutically acceptable carrier.

A pharmaceutical composition can be capable of local or systemic administration. In some aspects, a pharmaceutical composition can be capable of any modality of administration. In certain aspects, the administration can be intravenous, subcutaneous, pulmonary, intramuscular, intraperitoneal, dermal, oral, or nasal administration.

Embodiments of this invention include pharmaceutical compositions containing a translatable compound in a lipid formulation.

In some embodiments, a pharmaceutical composition may comprise one or more lipids selected from cationic lipids, anionic lipids, sterols, pegylated lipids, and any combination of the foregoing.

In certain embodiments, a pharmaceutical composition can be substantially free of liposomes.

In further embodiments, a pharmaceutical composition can include liposomes or nanoparticles.

Some examples of lipids and lipid compositions for delivery of an active molecule of this invention are given in WO/2015/074085, which is hereby incorporated by reference in its entirety.

In additional embodiments, a pharmaceutical composition can contain an oligomeric compound within a viral or bacterial vector.

A pharmaceutical composition of this disclosure may include carriers, diluents or excipients as are known in the art. Examples of pharmaceutical compositions and methods are described, for example, in Remington's Pharmaceutical Sciences, Mack Publishing Co. (A. R. Gennaro ed. 1985), and Remington, The Science and Practice of Pharmacy, 21st Edition (2005).

Examples of excipients for a pharmaceutical composition include antioxidants, suspending agents, dispersing agents, preservatives, buffering agents, tonicity agents, and surfactants.

An effective dose of an agent or pharmaceutical formulation of this invention can be an amount that is sufficient to cause translation of a translatable molecule in a cell.

A therapeutically effective dose can be an amount of an agent or formulation that is sufficient to cause a therapeutic effect. A therapeutically effective dose can be administered in one or more separate administrations, and by different routes.

A therapeutically effective dose, upon administration, can result in serum levels of an active agent of 1-1000 pg/ml, or 1-1000 ng/ml, or 1-1000 µg/ml, or more.

A therapeutically effective dose of an active agent in vivo can be a dose of 0.001-0.01 mg/kg body weight, or 0.01-0.1 mg/kg, or 0.1-1 mg/kg, or 1-10 mg/kg, or 10-100 mg/kg.

A therapeutically effective dose of an active agent in vivo can be a dose of 0.001 mg/kg body weight, or 0.01 mg/kg, or 0.1 mg/kg, or 1 mg/kg, or 2 mg/kg, or 3 mg/kg, or 4 mg/kg, or 5 mg/kg, or more.

In Vitro Transcription (IVT) for Synthesis

The following protocol is for a 200 ul IVT reaction using NEB HiScribe T7 reagents, that should yield about 1 mg of RNA. 2.5×NTP mix was prepared as required by thawing individual 100 mM NTP stocks (ATP, GTP, CTP, and UTP nucleotides, or chemically modified counterparts) and pooling them together. For the IVT reaction, about 2-4 ug of the template was used for a 200 ul reaction. The 10×IVT reaction buffer, the 2.5×dNTP mix, the template DNA and the T7 RNA polymerase were mixed well by pipetting and incubated at 37° C. for 4 hours. To degrade the DNA template, the IVT reaction was diluted with 700 ul of nuclease-free water and then 10×DNase I buffer and 20 ul of the RNase-free DNase I are added to the IVT mix and incubated at 37° C. for 15 minutes. The diluted (to 1 ml) and DNase treated reaction was then purified by a Qiagen RNeasy Maxi columns as per the manufacturer's instructions with a final elution in RNase-free water. The purified RNA was then quantified by UV absorbance where the A260/A280 should be about 1.8-2.2, depending on the resuspension buffer used.

Enzymatic Capping of IVT mRNA

For enzymatic capping, a 50× scaled-up version of NEB's one-step capping and 2'O-methylation reaction was used, that is suitable for treating up to 1 mg of IVT transcripts. A 10 ug RNA in a 20 ul reaction was recommended, based on the assumption that transcript length would be as short as 100 nt. However, a higher substrate-to-reaction volume was acceptable for mRNA transcripts, which were generally longer (about 300-600 nt) in length. Before initiating the capping reaction, the RNA was denatured at 65° C. for 5 minutes and then snap chilled to relieve any secondary conformations. For the total 1 ml capping reaction, 1 mg denatured RNA in 700 ul of nuclease-free water was used along with 100 ul (10×) capping buffer, 50 ul (10 mM) GTP, 50 ul (4 mM) SAM, 50 ul of (10 U/ul) Vaccinia capping enzyme and 50 ul of mRNA cap 2'-O-methyltransferase at (50 U/ul) were combined and incubated at 37° C. for 1 hour. The resulting capped mRNA was eluted using RNASE free water, re-purified on an RNeasy column, quantified by nanodrop. The mRNA was also visualized on the gel by running 500 ng of the purified product per lane in a denaturing gel after denaturation and snap-chill to remove secondary structures.

Dot Blots mRNA samples (100 ng) were doted on of each mRNA Biodyne® pre-cut modified nylon membrane (Thermo Scientific, Catalog #77016) (0.45 m, 8×12 cm). The membrane was blocked by incubating 5% non-fat dried milk in TBS-T buffer (50 mM Tris HCl, 150 mM NaCl (pH 7.4) and 0.05% Tween20) for 1 hour, and then was incubated with primary antibody anti ds-RNA mAB J2 (English and Scientific Consulting K ft., Hungary, J2 monoclonal antibody (mAb), mouse, IgG2a, Batch # J2-1507, 1.0 mg/mL). After 1 hr incubation time, the membrane was washed using TBS-T buffer, each for 7 mins (4×7 min). Then the membrane was incubated with secondary antibody (Life Technologies, Goat anti-mouse IgG, (H+L), HRP Conjugate, Catalog #16066) for 1 hour at room temperature, following by washing 6 times with TBS-T (6×5 min), then once with TBS (5 min). The resulted membrane was incubated with ECL reagent (SUPERSIGNAL WEST PICO AND FEMTO MIX, Thermo Scientific, Catalog #34080 and 34095) for 3-4 min and exposed under white light inside Chemidoc-It$^2$ Imaging System

EXAMPLES

Example A: Cloning Example for Templates pIDT-SMART(Kan) (1962 bps, IDT DNA) was modified by point mutations to remove NotI and MluI restriction sites. At EcoRV site, the resulting plasmid was inserted with a 1226 bp DNA fragment containing the following DNA elements: stuffer DNA+T7 RNA promoter, 5' UTR from Tobacco Etch Virus (TEV), human EPO ORF, sequence containing 3' UTR from *Xenopus* beta globin (XbG) gene, polyA120, and BspQI restriction enzyme site+T7 terminator+stuffer DNA.

The resulting parental plasmid (pIDT-SMART-T7-TEV-hEPO-XbG-pA120) had total length of 3188 bps. The parental plasmid was used to clone the alternative ORFs.

Constructs containing TEV 5'UTR were constructed as follows. For Fluc, hEPO, and cmEPO constructs, the plasmid was linearized with NcoI and XhoI, and the synthesized ORF DNA fragments with NcoI and XhoI site were inserted by T4 DNA ligase. For hAdipo, hAAT, and F9 constructs, the synthesized ORF DNA fragments contained 20-25 bp of plasmid sequences flanking the designed ORFs, and cloned into the same linearized plasmid via a seamless cloning method.

SynK-cmEPO-XbG plasmid constructs were generated with synthesized DNA fragments containing SynK 5'UTR and cmEPO ORF with AflII and XhoI site. These fragments were cloned by T4 DNA ligase into the parental plasmid linearized with AflII and XhoI.

An example construct for hEPO is shown in Table 4.

TABLE 4

Cloning construct for hEPO

| DNA element | DNA Sequence |
| --- | --- |
| stuffer DNA + T7 RNA promoter | (SEQ ID NO: 2)<br>CGACACTGCTCGATCCGCTCGCACCGGGCTGGCAAGCCA<br>CGTTTGGTGTTGGACCCTCGTACAGAAGCTAATACGACT<br>CACTATA |
| TEV 5' UTR | (SEQ ID NO: 3)<br>AGGAAACTTAAGTCAACACAACATATACAAAACAAACGA<br>ATCTCAAGCAATCAAGCATTCTACTTCTATTGCAGCAATT<br>TAAATCATTTCTTTTAAAGCAAAAGCAATTTTCTGAAAAT<br>TTTCACCATTTACGAACGATAGCC |
| human EPO ORF | (SEQ ID NO: 4)<br>ATGGGGGTGCACGAATGTCCTGCCTGGCTGTGGCTTCTCC<br>TGTCCCTGCTGTCGCTCCCTCTGGGCCTCCCAGTCCTGGG<br>CGCCCCACCACGCCTCATCTGTGACAGCCGAGTCCTGGAG<br>AGGTACCTCTTGGAGGCCAAGGAGGCCGAGAATATCACG<br>ACGGGCTGTGCTGAACACTGCAGCTTGAATGAGAATATC<br>ACTGTCCCAGACACCAAAGTTAATTTCTATGCCTGGAAGA<br>GGATGGAGGTCGGGCAGCAGGCCGTAGAAGTCTGGCAGG<br>GCCTGGCCCTGCTGTCGGAAGCTGTCCTGCGGGGCCAGGC<br>CCTGTTGGTCAACTCTTCCCAGCCGTGGGAGCCCCTGCAG<br>CTGCATGTGGATAAAGCCGTCAGTGGCCTTCGCAGCCTCA<br>CCACTCTGCTTCGGGCTCTGGGAGCCCAGAAGGAAGCCA<br>TCTCCCCTCCAGATGCGGCCTCAGCTGCTCCACTCCGAAC<br>AATCACTGCTGACACTTTCCGCAAACTCTTCCGAGTCTAC<br>TCCAATTTCCTCCGGGGAAAGCTGAAGCTGTACACAGGG<br>GAGGCCTGCAGGACAGGGGACAGATGA |
| XbG 3' UTR | (SEQ ID NO: 5)<br>ATAAGTGAACTCGAGCTAGTGACTGACTAGGATCTGGTTA<br>CCACTAAACCAGCCTCAAGAACACCCGAATGGAGTCTCT<br>AAGCTACATAATACCAACTTACACTTACAAAATGTTGTCC<br>CCCAAAATGTAGCCATTCGTATCTGCTCCTAATAAAAAGA<br>AAGTTTCTTCACATTCTAG |
| polyA120 | (SEQ ID NO: 6)<br>AAAAAAAAAAAAAAAAAAAAAAAAAAAAAAAAAAAAAAAA<br>AAAAAAAAAAAAAAAAAAAAAAAAAAAAAAAAAAAAAAAA<br>AAAAAAAAAAAAAAAAAAAAAAAAAAAAAAAAAAAAAAAA<br>AAAAAAAA |
| BspQI site + T7 terminator + stuffer DNA | (SEQ ID NO: 7)<br>GAAGAGCGCTAGCGTCTTCAGCTGCACATAACCCCTTGG<br>GGCCTCTAAACGGGTCTTGAGGGGTTTTTTGCCTCTGACA<br>CATGCAGCTCCCGGGATCGACGAGAGCAGCGCGACTGG |

The nucleotide T and GC compositions of wildtype protein coding sequences are shown in Table 5.

TABLE 5

| Nucleotide T compositions of wildtype protein coding sequences | | |
| --- | --- | --- |
| Protein | T % | GC % |
| Fluc plus pGL3 | 25.8 | 47 |
| Human Adiponectin | 22.0 | 54 |
| Human AAT | 21.6 | 52 |
| Human F9 | 27.6 | 41 |
| Human EPO | 20.3 | 60 |
| Cynomolgus Monkey EPO | 20.4 | 60 |

Example B: Templates and mRNAs for hEPO

Figure 4:
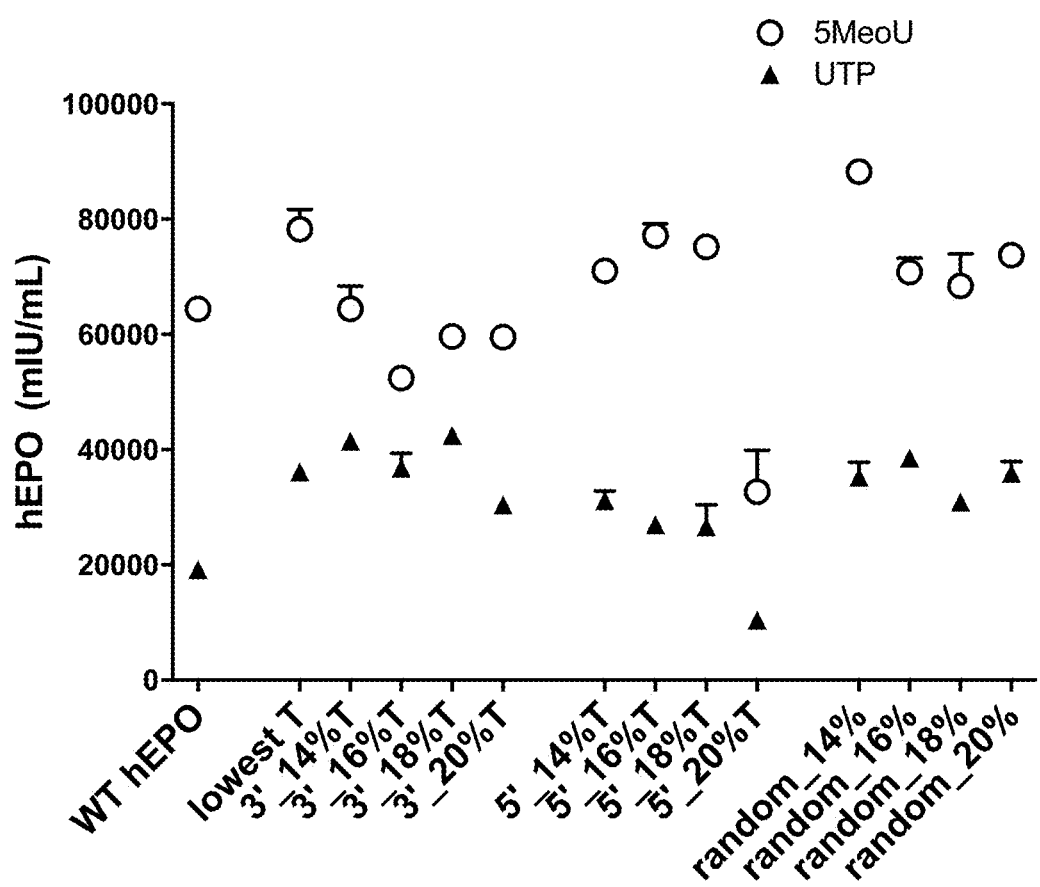
FIG. 4 shows the results of surprisingly increased human EPO protein production for a translatable molecule of this invention. Human EPO ARC-RNA was synthesized using a DNA template having reduced deoxyadenosine nucleotides in an open reading frame of the template strand, as well as reduced deoxythymidine nucleotides in the complementary non-template strand (reduced T). The synthesis was also carried out with 5-methoxyuridines (5MeOU, 100%). The ARC-RNA was transfected into HEPA1-6 cells using MES-SENGERMAX transfection reagents. The cell culture medium was collected 24 hrs after transfection. ELISA was used to detect the protein production with the ARC-RNA (5MeOU) as compared to wild type mRNA with similarly reduced T.

FIG. 4 shows the results of surprisingly increased human EPO protein production for a translatable molecule of this invention. Human EPO ARC-RNA was synthesized using a DNA template having reduced deoxyadenosine nucleotides in an open reading frame of the template strand, as well as reduced complementary deoxythymidine nucleotides in the non-template strand (reduced T). The synthesis was also carried out with 5-methoxyuridines (5MeOU, 100%). The ARC-RNA was transfected into HEPA1-6 cells using MES-SENGERMAX transfection reagents. The cell culture medium was collected 24 hrs after transfection. ELISA was used to detect the protein production with the ARC-RNA (5MeOU) as compared to wild type mRNA with similarly reduced T.

FIG. 4 shows surprisingly high translational efficiency of the ARC-mRNA (5MeOU) compared to the wild type hEPO mRNA (UTP). First, the ARC-mRNA (5MeOU) exhibited superior expression efficiency at all levels of template T composition as compared to the hEPO mRNA (UTP).

Further, FIG. 4 shows that ARC-mRNA (5MeOU) products exhibited unexpectedly superior expression efficiency at levels of template T composition of 13-16%, as compared to either wild type or "reduced T" hEPO mRNA (UTP).

Moreover, the ARC-mRNA (5MeOU) exhibited unexpectedly superior expression efficiency at 14% template T composition, when codon replacement was done randomly.

The compositions of the templates for hEPO are shown in Table 6.

TABLE 6

| Non-Template Nucleotide T compositions for hEPO | |
|---|---|
| hEPO | T % |
| hEPO_lowest_T | 13.1 |
| hEPO_3'_14% T | 13.9 |
| hEPO_3'_16% T | 16.0 |
| hEPO_3'_18% T | 17.9 |
| hEPO_3'_20% T | 19.9 |
| hEPO_5'_14% T | 13.9 |
| hEPO_5'_16% T | 16.0 |
| hEPO_5'_18% T | 17.9 |
| hEPO_5'_20% T | 19.9 |
| hEPO_random_14% | 13.9 |
| hEPO_random_16% | 16.0 |
| hEPO_random_18% | 17.9 |
| hEPO_random_20% | 19.9 |

Human EPO ORF reference. Sense strand, non-template. NM_000799.3:182-763 CDS *Homo sapiens* erythropoietin.

(SEQ ID NO: 8)

```
atgggggtgcacgaatgtcctgcctggctgtggcttctcctgtccctgctgtcgctccc tctgggcctcccagtcctgggcgccccaccacgcctcatctgtgacagccgagtcctgg agaggtacctcttggaggccaaggaggccgagaatatcacgacgggctgtgctgaacac tgcagcttgaatgagaatatcactgtcccagacaccaaagttaatttctatgcctggaa gaggatggaggtcgggcagcaggccgtagaagtctggcagggcctggccctgctgtcgg aagctgtcctgcggggccaggccctgttggtcaactcttcccagccgtgggagcccctg cagctgcatgtggataaagccgtcagtggccttcgcagcctcaccactctgcttcgggc tctgggagcccagaaggaagccatctcccctccagatgcggcctcagctgctccactcc gaacaatcactgctgacactttccgcaaactcttccgagtctactccaatttcctccgg ggaaagctgaagctgtacacaggggaggcctgcaggacaggggacagatga
``` hEPO sense strand, non-template. 3'_lowest_T.

(SEQ ID NO: 9)

```
ATGGGGGTGCACGAATGCCCCGCCTGGCTGTGGCTGCTCCTGAGCCTGC

TGAGCCTCCCCCTGGGCCTCCCAGTCCTGGGCGCCCCACCACGCCTCATCTGCGACAGC

CGAGTCCTGGAGAGGTACCTCCTGGAGGCCAAGGAGGCCGAGAACATCACGACGGGCTG

CGCCGAACACTGCAGCCTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTGAGCGAAGCCGTCCTGCGGGGCCAGGCCCTGCTGGTCAACAGCAGCCAGCCGTG

GGAGCCCCTGCAGCTGCACGTGGACAAAGCCGTCAGCGGCCTGCGCAGCCTCACCACCC

TGCTGCGGGCCCTGGGAGCCCAGAAGGAAGCCATCAGCCCCCAGACGCGGCCAGCGCC

GCCCCACTCCGAACAATCACCGCCGACACCTTCCGCAAACTCTTCCGAGTCTACAGCAA

CTTCCTCCGGGGAAAGCTGAAGCTGTACACAGGGGAGGCCTGCAGGACAGGGGACAGAT
```

GA

-continued hEPO sense strand, non-template. 3'_14%_T.
(SEQ ID NO: 10)
ATGGGGGTGCACGAATGTCCTGCCTGGCTGTGGCTTCTCCTGTCCCTGC

TGTCGCTCCCCCTGGGCCTCCCAGTCCTGGGCGCCCCACCACGCCTCATCTGCGACAGC

CGAGTCCTGGAGAGGTACCTCCTGGAGGCCAAGGAGGCCGAGAACATCACGACGGGCTG

CGCCGAACACTGCAGCCTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTGAGCGAAGCCGTCCTGCGGGGCCAGGCCCTGCTGGTCAACAGCAGCCAGCCGTG

GGAGCCCCTGCAGCTGCACGTGGACAAAGCCGTCAGCGGCCTGCGCAGCCTCACCACCC

TGCTGCGGGCCCTGGGAGCCCAGAAGGAAGCCATCAGCCCCCCAGACGCGGCCAGCGCC

GCCCCACTCCGAACAATCACCGCCGACACCTTCCGCAAACTCTTCCGAGTCTACAGCAA

CTTCCTCCGGGGAAAGCTGAAGCTGTACACAGGGGAGGCCTGCAGGACAGGGGACAGAT

GA hEPO sense strand, non-template. 3'_16%_T.
(SEQ ID NO: 11)
ATGGGGGTGCACGAATGTCCTGCCTGGCTGTGGCTTCTCCTGTCCCTGC

TGTCGCTCCCTCTGGGCCTCCCAGTCCTGGGCGCCCCACCACGCCTCATCTGTGACAGC

CGAGTCCTGGAGAGGTACCTCTTGGAGGCCAAGGAGGCCGAGAATATCACGACGGGCTG

TGCTGAACACTGCAGCTTGAATGAGAATATCACTGTCCCAGACACCAAAGTTAATTTCT

ACGCCTGGAAGAGGATGGAGGTCGGGCAGCAGGCCGTAGAAGTCTGGCAGGGCCTGGCC

CTGCTGAGCGAAGCCGTCCTGCGGGGCCAGGCCCTGCTGGTCAACAGCAGCCAGCCGTG

GGAGCCCCTGCAGCTGCACGTGGACAAAGCCGTCAGCGGCCTGCGCAGCCTCACCACCC

TGCTGCGGGCCCTGGGAGCCCAGAAGGAAGCCATCAGCCCCCCAGACGCGGCCAGCGCC

GCCCCACTCCGAACAATCACCGCCGACACCTTCCGCAAACTCTTCCGAGTCTACAGCAA

CTTCCTCCGGGGAAAGCTGAAGCTGTACACAGGGGAGGCCTGCAGGACAGGGGACAGAT

GA hEPO sense strand, non-template. 3'_18%_T.
(SEQ ID NO: 12)
ATGGGGGTGCACGAATGTCCTGCCTGGCTGTGGCTTCTCCTGTCCCTGC

TGTCGCTCCCTCTGGGCCTCCCAGTCCTGGGCGCCCCACCACGCCTCATCTGTGACAGC

CGAGTCCTGGAGAGGTACCTCTTGGAGGCCAAGGAGGCCGAGAATATCACGACGGGCTG

TGCTGAACACTGCAGCTTGAATGAGAATATCACTGTCCCAGACACCAAAGTTAATTTCT

ATGCCTGGAAGAGGATGGAGGTCGGGCAGCAGGCCGTAGAAGTCTGGCAGGGCCTGGCC

CTGCTGTCGGAAGCTGTCCTGCGGGGCCAGGCCCTGTTGGTCAACTCTTCCCAGCCGTG

GGAGCCCCTGCAGCTGCATGTGGATAAAGCCGTCAGTGGCCTTCGCAGCCTCACCACCC

TGCTGCGGGCCCTGGGAGCCCAGAAGGAAGCCATCAGCCCCCCAGACGCGGCCAGCGCC

GCCCCACTCCGAACAATCACCGCCGACACCTTCCGCAAACTCTTCCGAGTCTACAGCAA

CTTCCTCCGGGGAAAGCTGAAGCTGTACACAGGGGAGGCCTGCAGGACAGGGGACAGAT

GA hEPO sense strand, non-template. 3'_20%_T.
(SEQ ID NO: 13)
ATGGGGGTGCACGAATGTCCTGCCTGGCTGTGGCTTCTCCTGTCCCTGC

TGTCGCTCCCTCTGGGCCTCCCAGTCCTGGGCGCCCCACCACGCCTCATCTGTGACAGC

CGAGTCCTGGAGAGGTACCTCTTGGAGGCCAAGGAGGCCGAGAATATCACGACGGGCTG

-continued

TGCTGAACACTGCAGCTTGAATGAGAATATCACTGTCCCAGACACCAAAGTTAATTTCT

ATGCCTGGAAGAGGATGGAGGTCGGGCAGCAGGCCGTAGAAGTCTGGCAGGGCCTGGCC

CTGCTGTCGGAAGCTGTCCTGCGGGGCCAGGCCCTGTTGGTCAACTCTTCCCAGCCGTG

GGAGCCCCTGCAGCTGCATGTGGATAAAGCCGTCAGTGGCCTTCGCAGCCTCACCACTC

TGCTTCGGGCTCTGGGAGCCCAGAAGGAAGCCATCTCCCCTCCAGATGCGGCCTCAGCT

GCTCCACTCCGAACAATCACTGCTGACACTTTCCGCAAACTCTTCCGAGTCTACAGCAA

CTTCCTCCGGGGAAAGCTGAAGCTGTACACAGGGGAGGCCTGCAGGACAGGGGACAGAT

GA hEPO sense strand, non-template. 5'_14%_T.
(SEQ ID NO: 14)
ATGGGGGTGCACGAATGCCCCGCCTGGCTGTGGCTGCTCCTGAGCCTGC

TGAGCCTCCCCCTGGGCCTCCCAGTCCTGGGCGCCCCACCACGCCTCATCTGCGACAGC

CGAGTCCTGGAGAGGTACCTCTTGGAGGCCAAGGAGGCCGAGAACATCACGACGGGCTG

CGCCGAACACTGCAGCCTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTGAGCGAAGCCGTCCTGCGGGGCCAGGCCCTGCTGGTCAACAGCAGCCAGCCGTG

GGAGCCCCTGCAGCTGCACGTGGACAAAGCCGTCAGCGGCCTGCGCAGCCTCACCACCC

TGCTGCGGGCCCTGGGAGCCCAGAAGGAAGCCATCAGCCCCCCAGACGCGGCCAGCGCC

GCCCCACTCCGAACAATCACTGCTGACACTTTCCGCAAACTCTTCCGAGTCTACTCCAA

TTTCCTCCGGGGAAAGCTGAAGCTGTACACAGGGGAGGCCTGCAGGACAGGGGACAGAT

GA hEPO sense strand, non-template. 5'_16%_T.
(SEQ ID NO: 15)
ATGGGGGTGCACGAATGCCCCGCCTGGCTGTGGCTGCTCCTGAGCCTGC

TGAGCCTCCCCCTGGGCCTCCCAGTCCTGGGCGCCCCACCACGCCTCATCTGCGACAGC

CGAGTCCTGGAGAGGTACCTCTTGGAGGCCAAGGAGGCCGAGAACATCACGACGGGCTG

CGCCGAACACTGCAGCCTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTGAGCGAAGCCGTCCTGCGGGGCCAGGCCCTGCTGGTCAACAGCAGCCAGCCGTG

GGAGCCCCTGCAGCTGCACGTGGATAAAGCCGTCAGTGGCCTTCGCAGCCTCACCACTC

TGCTTCGGGCTCTGGGAGCCCAGAAGGAAGCCATCTCCCCTCCAGATGCGGCCTCAGCT

GCTCCACTCCGAACAATCACTGCTGACACTTTCCGCAAACTCTTCCGAGTCTACTCCAA

TTTCCTCCGGGGAAAGCTGAAGCTGTACACAGGGGAGGCCTGCAGGACAGGGGACAGAT

GA hEPO sense strand, non-template. 5'_18%_T.
(SEQ ID NO: 16)
ATGGGGGTGCACGAATGCCCCGCCTGGCTGTGGCTGCTCCTGAGCCTGC

TGAGCCTCCCCCTGGGCCTCCCAGTCCTGGGCGCCCCACCACGCCTCATCTGCGACAGC

CGAGTCCTGGAGAGGTACCTCTTGGAGGCCAAGGAGGCCGAGAACATCACGACGGGCTG

CGCCGAACACTGCAGCCTGAACGAGAACATCACTGTCCCAGACACCAAAGTTAATTTCT

ATGCCTGGAAGAGGATGGAGGTCGGGCAGCAGGCCGTAGAAGTCTGGCAGGGCCTGGCC

CTGCTGTCGGAAGCTGTCCTGCGGGGCCAGGCCCTGTTGGTCAACTCTTCCCAGCCGTG

GGAGCCCCTGCAGCTGCATGTGGATAAAGCCGTCAGTGGCCTTCGCAGCCTCACCACTC

TGCTTCGGGCTCTGGGAGCCCAGAAGGAAGCCATCTCCCCTCCAGATGCGGCCTCAGCT

```
GCTCCACTCCGAACAATCACTGCTGACACTTTCCGCAAACTCTTCCGAGTCTACTCCAA

TTTCCTCCGGGGAAAGCTGAAGCTGTACACAGGGGAGGCCTGCAGGACAGGGGACAGAT

GA hEPO sense strand, non-template. 5'_20%_T.
                                              (SEQ ID NO: 17)
ATGGGGGTGCACGAATGCCCCGCCTGGCTGTGGCTTCTCCTGTCCCTGC

TGTCGCTCCCTCTGGGCCTCCCAGTCCTGGGCGCCCCACCACGCCTCATCTGTGACAGC

CGAGTCCTGGAGAGGTACCTCTTGGAGGCCAAGGAGGCCGAGAATATCACGACGGGCTG

TGCTGAACACTGCAGCTTGAATGAGAATATCACTGTCCCAGACACCAAAGTTAATTTCT

ATGCCTGGAAGAGGATGGAGGTCGGGCAGCAGGCCGTAGAAGTCTGGCAGGGCCTGGCC

CTGCTGTCGGAAGCTGTCCTGCGGGGCCAGGCCCTGTTGGTCAACTCTTCCCAGCCGTG

GGAGCCCCTGCAGCTGCATGTGGATAAAGCCGTCAGTGGCCTTCGCAGCCTCACCACTC

TGCTTCGGGCTCTGGGAGCCCAGAAGGAAGCCATCTCCCCTCCAGATGCGGCCTCAGCT

GCTCCACTCCGAACAATCACTGCTGACACTTTCCGCAAACTCTTCCGAGTCTACTCCAA

TTTCCTCCGGGGAAAGCTGAAGCTGTACACAGGGGAGGCCTGCAGGACAGGGGACAGAT

GA hEPO sense strand, non-template. random_14%_T.
                                              (SEQ ID NO: 18)
ATGGGGGTGCACGAATGCCCTGCCTGGCTGTGGCTGCTCCTGAGCCTGC

TGAGCCTCCCCCTGGGCCTCCCAGTCCTGGGCGCCCCACCACGCCTCATCTGCGACAGC

CGAGTCCTGGAGAGGTACCTCCTGGAGGCCAAGGAGGCCGAGAACATCACGACGGGCTG

CGCCGAACACTGCAGCTTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTGAGCGAAGCCGTCCTGCGGGGCCAGGCCCTGCTGGTCAACAGCTCCCAGCCGTG

GGAGCCCCTGCAGCTGCACGTGGACAAAGCCGTCAGCGGCCTGCGCAGCCTCACCACCC

TGCTGCGGGCCCTGGGAGCCCAGAAGGAAGCCATCAGCCCCCCAGACGCGGCCAGCGCC

GCCCCACTCCGAACAATCACCGCTGACACCTTCCGCAAACTCTTCCGAGTCTACTCCAA

CTTCCTCCGGGGAAAGCTGAAGCTGTACACAGGGGAGGCCTGCAGGACAGGGGACAGAT

GA hEPO sense strand, non-template. random_16%_T.
                                              (SEQ ID NO: 19)
ATGGGGGTGCACGAATGTCCCGCCTGGCTGTGGCTGCTCCTGAGCCTGC

TGAGCCTCCCTCTGGGCCTCCCAGTCCTGGGCGCCCCACCACGCCTCATCTGCGACAGC

CGAGTCCTGGAGAGGTACCTCCTGGAGGCCAAGGAGGCCGAGAATATCACGACGGGCTG

TGCCGAACACTGCAGCTTGAACGAGAATATCACCGTCCCAGACACCAAAGTTAATTTCT

ATGCCTGGAAGAGGATGGAGGTCGGGCAGCAGGCCGTAGAAGTCTGGCAGGGCCTGGCC

CTGCTGTCGGAAGCTGTCCTGCGGGGCCAGGCCCTGCTGGTCAACAGCAGCCAGCCGTG

GGAGCCCCTGCAGCTGCACGTGGATAAAGCCGTCAGCGGCCTGCGCAGCCTCACCACCC

TGCTGCGGGCTCTGGGAGCCCAGAAGGAAGCCATCAGCCCTCCAGATGCGGCCAGCGCC

GCTCCACTCCGAACAATCACCGCCGACACTTTCCGCAAACTCTTCCGAGTCTACAGCAA

CTTCCTCCGGGGAAAGCTGAAGCTGTACACAGGGGAGGCCTGCAGGACAGGGGACAGAT

GA
``` hEPO sense strand, non-template. random_18%_T.
(SEQ ID NO: 20)
ATGGGGGTGCACGAATGTCCTGCCTGGCTGTGGCTTCTCCTGTCCCTGC

TGAGCCTCCCTCTGGGCCTCCCAGTCCTGGGCGCCCCACCACGCCTCATCTGTGACAGC

CGAGTCCTGGAGAGGTACCTCTTGGAGGCCAAGGAGGCCGAGAACATCACGACGGGCTG

CGCTGAACACTGCAGCCTGAATGAGAATATCACTGTCCCAGACACCAAAGTGAATTTCT

ATGCCTGGAAGAGGATGGAGGTCGGGCAGCAGGCCGTAGAAGTCTGGCAGGGCCTGGCC

CTGCTGAGCGAAGCCGTCCTGCGGGGCCAGGCCCTGTTGGTCAACAGCAGCCAGCCGTG

GGAGCCCCTGCAGCTGCATGTGGATAAAGCCGTCAGTGGCCTTCGCAGCCTCACCACTC

TGCTTCGGGCCCTGGGAGCCCAGAAGGAAGCCATCTCCCCTCCAGACGCGGCCTCAGCT

GCCCCACTCCGAACAATCACTGCTGACACTTTCCGCAAACTCTTCCGAGTCTACAGCAA

TTTCCTCCGGGGAAAGCTGAAGCTGTACACAGGGGAGGCCTGCAGGACAGGGGACAGAT

GA hEPO sense strand, non-template. random_20%_T.
(SEQ ID NO: 21)
ATGGGGGTGCACGAATGTCCTGCCTGGCTGTGGCTTCTCCTGTCCCTGC

TGTCGCTCCCTCTGGGCCTCCCAGTCCTGGGCGCCCCACCACGCCTCATCTGTGACAGC

CGAGTCCTGGAGAGGTACCTCTTGGAGGCCAAGGAGGCCGAGAATATCACGACGGGCTG

TGCTGAACACTGCAGCTTGAATGAGAATATCACTGTCCCAGACACCAAAGTTAACTTCT

ATGCCTGGAAGAGGATGGAGGTCGGGCAGCAGGCCGTAGAAGTCTGGCAGGGCCTGGCC

CTGCTGTCGGAAGCTGTCCTGCGGGGCCAGGCCCTGCTGGTCAACTCTTCCCAGCCGTG

GGAGCCCCTGCAGCTGCATGTGGATAAAGCCGTCAGTGGCCTTCGCAGCCTCACCACTC

TGCTTCGGGCTCTGGGAGCCCAGAAGGAAGCCATCTCCCCTCCAGATGCGGCCTCAGCT

GCTCCACTCCGAACAATCACTGCTGACACTTTCCGCAAACTCTTCCGAGTCTACTCCAA

TTTCCTCCGGGGAAAGCTGAAGCTGTACACAGGGGAGGCCTGCAGGACAGGGGACAGAT

GA

TEV-hEPO-XbG sense strand, non-template.
3'_lowest_T (1014 nt).
(SEQ ID NO: 22)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGCCCCGCC

TGGCTGTGGCTGCTCCTGAGCCTGCTGAGCCTCCCCCTGGGCCTCCCAGTCCTGGGCGC

CCCACCACGCCTCATCTGCGACAGCCGAGTCCTGGAGAGGTACCTCCTGGAGGCCAAGG

AGGCCGAGAACATCACGACGGGCTGCGCCGAACACTGCAGCCTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTGAGCGAAGCCGTCCTGCGGGGCCAGGCCC

TGCTGGTCAACAGCAGCCAGCCGTGGGAGCCCCTGCAGCTGCACGTGGACAAAGCCGTC

AGCGGCCTGCGCAGCCTCACCACCCTGCTGCGGGCCCTGGGAGCCCAGAAGGAAGCCAT

CAGCCCCCCAGACGCGGCCAGCGCCGCCCCACTCCGAACAATCACCGCCGACACCTTCC

GCAAACTCTTCCGAGTCTACAGCAACTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAAGA

AAGTTTCTTCACATTCTAGAAAAAAAAAAAAAAAAAAAAAAAAAAAAAAAAAA

AAAAAAAAAAAAAAAAAAAAAAAAAAAAAAAAAAAAAAAAAAAAAAAAAAAAAA

AAAAAAAAAAAAAAAAAAAAA

TEV-hEPO-XbG sense strand, non-template.
3'_14%_T (1014 nt).

(SEQ ID NO: 23)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGTCCTGCC

TGGCTGTGGCTTCTCCTGTCCCTGCTGTCGCTCCCCCTGGGCCTCCCAGTCCTGGGCGC

CCCACCACGCCTCATCTGCGACAGCCGAGTCCTGGAGAGGTACCTCCTGGAGGCCAAGG

AGGCCGAGAACATCACGACGGGCTGCGCCGAACACTGCAGCCTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTGAGCGAAGCCGTCCTGCGGGGCCAGGCCC

TGCTGGTCAACAGCAGCCAGCCGTGGGAGCCCCTGCAGCTGCACGTGGACAAAGCCGTC

AGCGGCCTGCGCAGCCTCACCACCCTGCTGCGGGCCCTGGGAGCCCAGAAGGAAGCCAT

CAGCCCCCCAGACGCGGCCAGCGCCGCCCCACTCCGAACAATCACCGCCGACACCTTCC

GCAAACTCTTCCGAGTCTACAGCAACTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAGA

AAGTTTCTTCACATTCTAGAAAAAAAAAAAAAAAAAAAAAAAAAAAAAAAAAA

AAAAAAAAAAAAAAAAAAAAAAAAAAAAAAAAAAAAAAAAAAAAAAAAAAAAAA

AAAAAAAAAAAAAAAAAAAA

TEV-hEPO-XbG sense strand, non-template.
3'_16%_T (1014 nt).

(SEQ ID NO: 24)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGTCCTGCC

TGGCTGTGGCTTCTCCTGTCCCTGCTGTCGCTCCCTCTGGGCCTCCCAGTCCTGGGCGC

CCCACCACGCCTCATCTGTGACAGCCGAGTCCTGGAGAGGTACCTCTTGGAGGCCAAGG

AGGCCGAGAATATCACGACGGGCTGTGCTGAACACTGCAGCTTGAATGAGAATATCACT

GTCCCAGACACCAAAGTTAATTTCTACGCCTGGAAGAGGATGGAGGTCGGGCAGCAGGC

CGTAGAAGTCTGGCAGGGCCTGGCCCTGCTGAGCGAAGCCGTCCTGCGGGGCCAGGCCC

TGCTGGTCAACAGCAGCCAGCCGTGGGAGCCCCTGCAGCTGCACGTGGACAAAGCCGTC

AGCGGCCTGCGCAGCCTCACCACCCTGCTGCGGGCCCTGGGAGCCCAGAAGGAAGCCAT

CAGCCCCCCAGACGCGGCCAGCGCCGCCCCACTCCGAACAATCACCGCCGACACCTTCC

GCAAACTCTTCCGAGTCTACAGCAACTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAGA

AAGTTTCTTCACATTCTAGAAAAAAAAAAAAAAAAAAAAAAAAAAAAAAAAAA

```
AAAAAAAAAAAAAAAAAAAAAAAAAAAAAAAAAAAAAAAAAAAAAAAAAAAA

AAAAAAAAAAAAAAAAAAAAA

TEV-hEPO-XbG sense strand, non-template.
3'_18%_T (1014 nt).
                                            (SEQ ID NO: 25)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGTCCTGCC

TGGCTGTGGCTTCTCCTGTCCCTGCTGTCGCTCCCTCTGGGCCTCCCAGTCCTGGGCGC

CCCACCACGCCTCATCTGTGACAGCCGAGTCCTGGAGAGGTACCTCTTGGAGGCCAAGG

AGGCCGAGAATATCACGACGGGCTGTGCTGAACACTGCAGCTTGAATGAGAATATCACT

GTCCCAGACACCAAAGTTAATTTCTATGCCTGGAAGAGGATGGAGGTCGGGCAGCAGGC

CGTAGAAGTCTGGCAGGGCCTGGCCCTGCTGTCGGAAGCTGTCCTGCGGGGCCAGGCCC

TGTTGGTCAACTCTTCCCAGCCGTGGGAGCCCCTGCAGCTGCATGTGGATAAAGCCGTC

AGTGGCCTTCGCAGCCTCACCACCCTGCTGCGGGCCCTGGGAGCCCAGAAGGAAGCCAT

CAGCCCCCCAGACGCGGCCAGCGCCGCCCCACTCCGAACAATCACCGCCGACACCTTCC

GCAAACTCTTCCGAGTCTACAGCAACTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAGA

AAGTTTCTTCACATTCTAGAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAA

AAAAAAAAAAAAAAAAAAAAA

TEV-hEPO-XbG sense strand, non-template.
3'_20%_T (1014 nt).
                                            (SEQ ID NO: 26)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGTCCTGCC

TGGCTGTGGCTTCTCCTGTCCCTGCTGTCGCTCCCTCTGGGCCTCCCAGTCCTGGGCGC

CCCACCACGCCTCATCTGTGACAGCCGAGTCCTGGAGAGGTACCTCTTGGAGGCCAAGG

AGGCCGAGAATATCACGACGGGCTGTGCTGAACACTGCAGCTTGAATGAGAATATCACT

GTCCCAGACACCAAAGTTAATTTCTATGCCTGGAAGAGGATGGAGGTCGGGCAGCAGGC

CGTAGAAGTCTGGCAGGGCCTGGCCCTGCTGTCGGAAGCTGTCCTGCGGGGCCAGGCCC

TGTTGGTCAACTCTTCCCAGCCGTGGGAGCCCCTGCAGCTGCATGTGGATAAAGCCGTC

AGTGGCCTTCGCAGCCTCACCACTCTGCTTCGGGCTCTGGGAGCCCAGAAGGAAGCCAT

CTCCCCTCCAGATGCGGCCTCAGCTGCTCCACTCCGAACAATCACTGCTGACACTTTCC

GCAAACTCTTCCGAGTCTACAGCAACTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAGA

AAGTTTCTTCACATTCTAGAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAA

AAAAAAAAAAAAAAAAAAAAA
```

TEV-hEPO-XbG sense strand, non-template.
5'_14%_T (1014 nt).

(SEQ ID NO: 27)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGCCCCGCC

TGGCTGTGGCTGCTCCTGAGCCTGCTGAGCCTCCCCCTGGGCCTCCCAGTCCTGGGCGC

CCCACCACGCCTCATCTGCGACAGCCGAGTCCTGGAGAGGTACCTCCTGGAGGCCAAGG

AGGCCGAGAACATCACGACGGGCTGCGCCGAACACTGCAGCCTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTGAGCGAAGCCGTCCTGCGGGGCCAGGCCC

TGCTGGTCAACAGCAGCCAGCCGTGGGAGCCCCTGCAGCTGCACGTGGACAAAGCCGTC

AGCGGCCTGCGCAGCCTCACCACCCTGCTGCGGGCCCTGGGAGCCCAGAAGGAAGCCAT

CAGCCCCCCAGACGCGGCCAGCGCCGCCCCACTCCGAACAATCACTGCTGACACTTTCC

GCAAACTCTTCCGAGTCTACTCCAATTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAGA

AAGTTTCTTCACATTCTAGAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAA

AAAAAAAAAAAAAAAAAAAA

TEV-hEPO-XbG sense strand, non-template.
5'_16%_T (1014 nt).

(SEQ ID NO: 28)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGCCCCGCC

TGGCTGTGGCTGCTCCTGAGCCTGCTGAGCCTCCCCCTGGGCCTCCCAGTCCTGGGCGC

CCCACCACGCCTCATCTGCGACAGCCGAGTCCTGGAGAGGTACCTCCTGGAGGCCAAGG

AGGCCGAGAACATCACGACGGGCTGCGCCGAACACTGCAGCCTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTGAGCGAAGCCGTCCTGCGGGGCCAGGCCC

TGCTGGTCAACAGCAGCCAGCCGTGGGAGCCCCTGCAGCTGCACGTGGATAAAGCCGTC

AGTGGCCTTCGCAGCCTCACCACTCTGCTTCGGGCTCTGGGAGCCCAGAAGGAAGCCAT

CTCCCCTCCAGATGCGGCCTCAGCTGCTCCACTCCGAACAATCACTGCTGACACTTTCC

GCAAACTCTTCCGAGTCTACTCCAATTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAGA

AAGTTTCTTCACATTCTAGAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAA

AAAAAAAAAAAAAAAAAAAA

-continued

TEV-hEPO-XbG sense strand, non-template.
5'_18%_T (1014 nt).
(SEQ ID NO: 29)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGCCCCGCC

TGGCTGTGGCTGCTCCTGAGCCTGCTGAGCCTCCCCCTGGGCCTCCCAGTCCTGGGCGC

CCCACCACGCCTCATCTGCGACAGCCGAGTCCTGGAGAGGTACCTCCTGGAGGCCAAGG

AGGCCGAGAACATCACGACGGGCTGCGCCGAACACTGCAGCCTGAACGAGAACATCACT

GTCCCAGACACCAAAGTTAATTTCTATGCCTGGAAGAGGATGGAGGTCGGGCAGCAGGC

CGTAGAAGTCTGGCAGGGCCTGGCCCTGCTGTCGGAAGCTGTCCTGCGGGGCCAGGCCC

TGTTGGTCAACTCTTCCCAGCCGTGGGAGCCCCTGCAGCTGCATGTGGATAAAGCCGTC

AGTGGCCTTCGCAGCCTCACCACTCTGCTTCGGGCTCTGGGAGCCCAGAAGGAAGCCAT

CTCCCCTCCAGATGCGGCCTCAGCTGCTCCACTCCGAACAATCACTGCTGACACTTTCC

GCAAACTCTTCCGAGTCTACTCCAATTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAGA

AAGTTTCTTCACATTCTAGAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAA

TEV-hEPO-XbG sense strand, non-template.
5'_20%_T (1014 nt).
(SEQ ID NO: 30)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGCCCCGCC

TGGCTGTGGCTTCTCCTGTCCCTGCTGTCGCTCCCTCTGGGCCTCCCAGTCCTGGGCGC

CCCACCACGCCTCATCTGTGACAGCCGAGTCCTGGAGAGGTACCTCTTGGAGGCCAAGG

AGGCCGAGAATATCACGACGGGCTGTGCTGAACACTGCAGCTTGAATGAGAATATCACT

GTCCCAGACACCAAAGTTAATTTCTATGCCTGGAAGAGGATGGAGGTCGGGCAGCAGGC

CGTAGAAGTCTGGCAGGGCCTGGCCCTGCTGTCGGAAGCTGTCCTGCGGGGCCAGGCCC

TGTTGGTCAACTCTTCCCAGCCGTGGGAGCCCCTGCAGCTGCATGTGGATAAAGCCGTC

AGTGGCCTTCGCAGCCTCACCACTCTGCTTCGGGCTCTGGGAGCCCAGAAGGAAGCCAT

CTCCCCTCCAGATGCGGCCTCAGCTGCTCCACTCCGAACAATCACTGCTGACACTTTCC

GCAAACTCTTCCGAGTCTACTCCAATTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAGA

AAGTTTCTTCACATTCTAGAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAA

TEV-hEPO-XbG sense strand, non-template.
random_14%_T (1014 nt).
(SEQ ID NO: 31)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGCCCTGCC

TGGCTGTGGCTGCTCCTGAGCCTGCTGAGCCTCCCCCTGGGCCTCCCAGTCCTGGGCGC

CCCACCACGCCTCATCTGCGACAGCCGAGTCCTGGAGAGGTACCTCCTGGAGGCCAAGG

AGGCCGAGAACATCACGACGGGCTGCGCCGAACACTGCAGCTTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTGAGCGAAGCCGTCCTGCGGGGCCAGGCCC

TGCTGGTCAACAGCTCCCAGCCGTGGGAGCCCCTGCAGCTGCACGTGGACAAAGCCGTC

AGCGGCCTGCGCAGCCTCACCACCCTGCTGCGGGCCCTGGGAGCCCAGAAGGAAGCCAT

CAGCCCCCCAGACGCGGCCAGCGCCGCCCCACTCCGAACAATCACCGCTGACACCTTCC

GCAAACTCTTCCGAGTCTACTCCAACTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAGA

AAGTTTCTTCACATTCTAGAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAA

TEV-hEPO-XbG sense strand, non-template.
random_16%_T (1014 nt).
(SEQ ID NO: 32)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGTCCCGCC

TGGCTGTGGCTGCTCCTGAGCCTGCTGAGCCTCCCTCTGGGCCTCCCAGTCCTGGGCGC

CCCACCACGCCTCATCTGCGACAGCCGAGTCCTGGAGAGGTACCTCCTGGAGGCCAAGG

AGGCCGAGAATATCACGACGGGCTGTGCCGAACACTGCAGCTTGAACGAGAATATCACC

GTCCCAGACACCAAAGTTAATTTCTATGCCTGGAAGAGGATGGAGGTCGGGCAGCAGGC

CGTAGAAGTCTGGCAGGGCCTGGCCCTGCTGTCGGAAGCTGTCCTGCGGGGCCAGGCCC

TGCTGGTCAACAGCAGCCAGCCGTGGGAGCCCCTGCAGCTGCACGTGGATAAAGCCGTC

AGCGGCCTGCGCAGCCTCACCACCCTGCTGCGGGCTCTGGGAGCCCAGAAGGAAGCCAT

CAGCCCTCCAGATGCGGCCAGCGCCGCTCCACTCCGAACAATCACCGCCGACACTTTCC

GCAAACTCTTCCGAGTCTACAGCAACTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAGA

AAGTTTCTTCACATTCTAGAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAA

TEV-hEPO-XbG sense strand, non-template.
random_18%_T (1014 nt).

(SEQ ID NO: 33)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGTCCTGCC

TGGCTGTGGCTTCTCCTGTCCCTGCTGAGCCTCCCTCTGGGCCTCCCAGTCCTGGGCGC

CCCACCACGCCTCATCTGTGACAGCCGAGTCCTGGAGAGGTACCTCTTGGAGGCCAAGG

AGGCCGAGAACATCACGACGGGCTGCGCTGAACACTGCAGCCTGAATGAGAATATCACT

GTCCCAGACACCAAAGTGAATTTCTATGCCTGGAAGAGGATGGAGGTCGGGCAGCAGGC

CGTAGAAGTCTGGCAGGGCCTGGCCCTGCTGAGCGAAGCCGTCCTGCGGGGCCAGGCCC

TGTTGGTCAACAGCAGCCAGCCGTGGGAGCCCCTGCAGCTGCATGTGGATAAAGCCGTC

AGTGGCCTTCGCAGCCTCACCACTCTGCTTCGGGCCCTGGGAGCCCAGAAGGAAGCCAT

CTCCCCTCCAGACGCGGCCTCAGCTGCCCCACTCCGAACAATCACTGCTGACACTTTCC

GCAAACTCTTCCGAGTCTACAGCAATTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAGA

AAGTTTCTTCACATTCTAGAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAA

TEV-hEPO-XbG sense strand, non-template.
random_20%_T (1014 nt).

(SEQ ID NO: 34)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGTCCTGCC

TGGCTGTGGCTTCTCCTGTCCCTGCTGTCGCTCCCTCTGGGCCTCCCAGTCCTGGGCGC

CCCACCACGCCTCATCTGTGACAGCCGAGTCCTGGAGAGGTACCTCTTGGAGGCCAAGG

AGGCCGAGAATATCACGACGGGCTGTGCTGAACACTGCAGCTTGAATGAGAATATCACT

GTCCCAGACACCAAAGTTAACTTCTATGCCTGGAAGAGGATGGAGGTCGGGCAGCAGGC

CGTAGAAGTCTGGCAGGGCCTGGCCCTGCTGTCGGAAGCTGTCCTGCGGGGCCAGGCCC

TGCTGGTCAACTCTTCCCAGCCGTGGGAGCCCCTGCAGCTGCATGTGGATAAAGCCGTC

AGTGGCCTTCGCAGCCTCACCACTCTGCTTCGGGCTCTGGGAGCCCAGAAGGAAGCCAT

CTCCCCTCCAGATGCGGCCTCAGCTGCTCCACTCCGAACAATCACTGCTGACACTTTCC

GCAAACTCTTCCGAGTCTACTCCAATTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAGA

-continued

AAGTTTCTTCACATTCTAGAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA

AAAAAAAAAAAAAAAAAAAA

TEV-hEPO-XbG ARC-mRNA. 3'_lowest_T (1014 nt).

(SEQ ID NO: 35)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

UGCUCCUGAGCCUGCUGAGCCUCCCCCUGGGCCUCCCAGUCCUGGGCGCCCCACCACGC

CUCAUCUGCGACAGCCGAGUCCUGGAGAGGUACCUCCUGGAGGCCAAGGAGGCCGAGAA

CAUCACGACGGGCUGCGCCGAACACUGCAGCCUGAACGAGAACAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUGAGCGAAGCCGUCCUGCGGGGCCAGGCCCUGCUGGUCAA

CAGCAGCCAGCCGUGGGAGCCCCUGCAGCUGCACGUGGACAAAGCCGUCAGCGGCCUGC

GCAGCCUCACCACCCUGCUGCGGGCCCUGGGAGCCCAGAAGGAAGCCAUCAGCCCCCCA

GACGCGGCCAGCGCCGCCCCACUCCGAACAAUCACCGCCGACACCUUCCGCAAACUCUU

CCGAGUCUACAGCAACUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCCAAAAUGUAGCCAUUCGUAUCUGCUCCUAAUAAAAAGAAAGUUUCUUC

ACAUUCUAGAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA

AAAAAAAAAA

TEV-hEPO-XbG ARC-mRNA. 3'_14%_T (1014 nt).

(SEQ ID NO: 36)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGUCCUGCCUGGCUGUGGC

UUCUCCUGUCCCUGCUGUCGCUCCCCCUGGGCCUCCCAGUCCUGGGCGCCCCACCACGC

CUCAUCUGCGACAGCCGAGUCCUGGAGAGGUACCUCCUGGAGGCCAAGGAGGCCGAGAA

CAUCACGACGGGCUGCGCCGAACACUGCAGCCUGAACGAGAACAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUGAGCGAAGCCGUCCUGCGGGGCCAGGCCCUGCUGGUCAA

CAGCAGCCAGCCGUGGGAGCCCCUGCAGCUGCACGUGGACAAAGCCGUCAGCGGCCUGC

GCAGCCUCACCACCCUGCUGCGGGCCCUGGGAGCCCAGAAGGAAGCCAUCAGCCCCCCA

GACGCGGCCAGCGCCGCCCCACUCCGAACAAUCACCGCCGACACCUUCCGCAAACUCUU

CCGAGUCUACAGCAACUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCCAAAAUGUAGCCAUUCGUAUCUGCUCCUAAUAAAAAGAAAGUUUCUUC

-continued

ACAUUCUAGAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAA

AAAAAAAAAA

TEV-hEPO-XbG ARC-mRNA. 3'_16%_T (1014 nt).

(SEQ ID NO: 37)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGUCCUGCCUGGCUGUGGC

UUCUCCUGUCCCUGCUGUCGCUCCCUCUGGGCCUCCCAGUCCUGGGCGCCCCACCACGC

CUCAUCUGUGACAGCCGAGUCCUGGAGAGGUACCUCUUGGAGGCCAAGGAGGCCGAGAA

UAUCACGACGGGCUGUGCUGAACACUGCAGCUUGAAUGAGAAUAUCACUGUCCCAGACA

CCAAAGUUAAUUUCUACGCCUGGAAGAGGAUGGAGGUCGGGCAGCAGGCCGUAGAAGUC

UGGCAGGGCCUGGCCCUGCUGAGCGAAGCCGUCCUGCGGGGCCAGGCCCUGCUGGUCAA

CAGCAGCCAGCCGUGGGAGCCCCUGCAGCUGCACGUGGACAAAGCCGUCAGCGGCCUGC

GCAGCCUCACCACCCUGCUGCGGGCCCUGGGAGCCCAGAAGGAAGCCAUCAGCCCCCCA

GACGCGGCCAGCGCCGCCCCACUCCGAACAAUCACCGCCGACACCUUCCGCAAACUCUU

CCGAGUCUACAGCAACUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCAAAAUGUAGCCAUUCGUAUCUGCUCCUAAUAAAAGAAAGUUUCUUC

ACAUUCUAGAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAA

AAAAAAAAAA

TEV-hEPO-XbG ARC-mRNA. 3'_18%_T (1014 nt).

(SEQ ID NO: 38)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGUCCUGCCUGGCUGUGGC

UUCUCCUGUCCCUGCUGUCGCUCCCUCUGGGCCUCCCAGUCCUGGGCGCCCCACCACGC

CUCAUCUGUGACAGCCGAGUCCUGGAGAGGUACCUCUUGGAGGCCAAGGAGGCCGAGAA

UAUCACGACGGGCUGUGCUGAACACUGCAGCUUGAAUGAGAAUAUCACUGUCCCAGACA

CCAAAGUUAAUUUCUAUGCCUGGAAGAGGAUGGAGGUCGGGCAGCAGGCCGUAGAAGUC

UGGCAGGGCCUGGCCCUGCUGUCGGAAGCUGUCCUGCGGGGCCAGGCCCUGUUGGUCAA

CUCUUCCCAGCCGUGGGAGCCCCUGCAGCUGCAUGUGGAUAAAGCCGUCAGUGGCCUUC

GCAGCCUCACCACCCUGCUGCGGGCCCUGGGAGCCCAGAAGGAAGCCAUCAGCCCCCCA

GACGCGGCCAGCGCCGCCCCACUCCGAACAAUCACCGCCGACACCUUCCGCAAACUCUU

CCGAGUCUACAGCAACUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCAAAAUGUAGCCAUUCGUAUCUGCUCCUAAUAAAAGAAAGUUUCUUC

ACAUUCUAGAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAA

TEV-hEPO-XbG ARC-mRNA. 3'_20%_T (1014 nt).
(SEQ ID NO: 39)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGUCCUGCCUGGCUGUGGC

UUCUCCUGUCCCUGCUGUCGCUCCCUCUGGGCCUCCCAGUCCUGGGCGCCCCACCACGC

CUCAUCUGUGACAGCCGAGUCCUGGAGAGGUACCUCUUGGAGGCCAAGGAGGCCGAGAA

UAUCACGACGGGCUGUGCUGAACACUGCAGCUUGAAUGAGAAUAUCACUGUCCCAGACA

CCAAAGUUAAUUUCUAUGCCUGGAAGAGGAUGGAGGUCGGGCAGCAGGCCGUAGAAGUC

UGGCAGGGCCUGGCCCUGCUGUCGGAAGCUGUCCUGCGGGGCCAGGCCCUGUUGGUCAA

CUCUUCCCAGCCGUGGGAGCCCCUGCAGCUGCAUGUGGAUAAAGCCGUCAGUGGCCUUC

GCAGCCUCACCACUCUGCUUCGGGCUCUGGGAGCCCAGAAGGAAGCCAUCUCCCCUCCA

GAUGCGGCCUCAGCUGCUCCACUCCGAACAAUCACUGCUGACACUUUCCGCAAACUCUU

CCGAGUCUACAGCAACUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCAAAAUGUAGCCAUUCGUAUCUGCUCCUAAUAAAAAGAAAGUUUCUUC

ACAUUCUAGAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAA

TEV-hEPO-XbG ARC-mRNA. 5'_14%_T (1014 nt).
(SEQ ID NO: 40)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

UGCUCCUGAGCCUGCUGAGCCUCCCCCUGGGCCUCCCAGUCCUGGGCGCCCCACCACGC

CUCAUCUGCGACAGCCGAGUCCUGGAGAGGUACCUCCUGGAGGCCAAGGAGGCCGAGAA

CAUCACGACGGGCUGCGCCGAACACUGCAGCCUGAACGAGAACAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUGAGCGAAGCCGUCCUGCGGGGCCAGGCCCUGCUGGUCAA

CAGCAGCCAGCCGUGGGAGCCCCUGCAGCUGCACGUGGACAAAGCCGUCAGCGGCCUGC

GCAGCCUCACCACCCUGCUGCGGGCCCUGGGAGCCCAGAAGGAAGCCAUCAGCCCCCCA

GACGCGGCCAGCGCCGCCCCACUCCGAACAAUCACUGCUGACACUUUCCGCAAACUCUU

CCGAGUCUACUCCAAUUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCAAAAUGUAGCCAUUCGUAUCUGCUCCUAAUAAAAAGAAAGUUUCUUC

ACAUUCUAGAAAAAAAAAAAAAAAAAAAAAAAAAAAAAAAAAAAAAAAAAAAAAAAAA

-continued
AAAAAAAAAAAAAAAAAAAAAAAAAAAAAAAAAAAAAAAAAAAAAAAAAAAA
AAAAAAAAAA

TEV-hEPO-XbG ARC-mRNA. 5'_16%_T (1014 nt).
(SEQ ID NO: 41)
5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

UGCUCCUGAGCCUGCUGAGCCUCCCCCUGGGCCUCCCAGUCCUGGGCGCCCCACCACGC

CUCAUCUGCGACAGCCGAGUCCUGGAGAGGUACCUCCUGGAGGCCAAGGAGGCCGAGAA

CAUCACGACGGGCUGCGCCGAACACUGCAGCCUGAACGAGAACAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUGAGCGAAGCCGUCCUGCGGGGCCAGGCCCUGCUGGUCAA

CAGCAGCCAGCCGUGGGAGCCCCUGCAGCUGCACGUGGAUAAAGCCGUCAGUGGCCUUC

GCAGCCUCACCACUCUGCUUCGGGCUCUGGGAGCCCAGAAGGAAGCCAUCUCCCCUCCA

GAUGCGGCCUCAGCUGCUCCACUCCGAACAAUCACUGCUGACACUUUCCGCAAACUCUU

CCGAGUCUACUCCAAUUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCAAAAUGUAGCCAUUCGUAUCUGCUCCUAAUAAAAGAAAGUUUCUUC

ACAUUCUAGAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAA

AAAAAAAAAA

TEV-hEPO-XbG ARC-mRNA. 5'_18%_T (1014 nt).
(SEQ ID NO: 42)
5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

UGCUCCUGAGCCUGCUGAGCCUCCCCCUGGGCCUCCCAGUCCUGGGCGCCCCACCACGC

CUCAUCUGCGACAGCCGAGUCCUGGAGAGGUACCUCCUGGAGGCCAAGGAGGCCGAGAA

CAUCACGACGGGCUGCGCCGAACACUGCAGCCUGAACGAGAACAUCACUGUCCCAGACA

CCAAAGUUAAUUUCUAUGCCUGGAAGAGGAUGGAGGUCGGGCAGCAGGCCGUAGAAGUC

UGGCAGGGCCUGGCCCUGCUGUCGGAAGCUGUCCUGCGGGGCCAGGCCCUGUUGGUCAA

CUCUUCCCAGCCGUGGGAGCCCCUGCAGCUGCAUGUGGAUAAAGCCGUCAGUGGCCUUC

GCAGCCUCACCACUCUGCUUCGGGCUCUGGGAGCCCAGAAGGAAGCCAUCUCCCCUCCA

GAUGCGGCCUCAGCUGCUCCACUCCGAACAAUCACUGCUGACACUUUCCGCAAACUCUU

CCGAGUCUACUCCAAUUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCAAAAUGUAGCCAUUCGUAUCUGCUCCUAAUAAAAGAAAGUUUCUUC

ACAUUCUAGAAAAAAAAAAAAAAAAAAAAAAAAAAAAAAAAAAAAAAAAAAAAAAAAAA

-continued

AAAAAAAAAAAAAAAAAAAAAAAAAAAAAAAAAAAAAAAAAAAAAAAAAAAAAAAAA

AAAAAAAAAA

TEV-hEPO-XbG ARC-mRNA. 5'_20%_T (1014 nt).

(SEQ ID NO: 43)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

UUCUCCUGUCCCUGCUGUCGCUCCCUCUGGGCCUCCCAGUCCUGGGCGCCCCACCACGC

CUCAUCUGUGACAGCCGAGUCCUGGAGAGGUACCUCUUGGAGGCCAAGGAGGCCGAGAA

UAUCACGACGGGCUGUGCUGAACACUGCAGCUUGAAUGAGAAUAUCACUGUCCCAGACA

CCAAAGUUAAUUUCUAUGCCUGGAAGAGGAUGGAGGUCGGGCAGCAGGCCGUAGAAGUC

UGGCAGGGCCUGGCCCUGCUGUCGGAAGCUGUCCUGCGGGGCCAGGCCCUGUUGGUCAA

CUCUUCCCAGCCGUGGGAGCCCCUGCAGCUGCAUGUGGAUAAAGCCGUCAGUGGCCUUC

GCAGCCUCACCACUCUGCUUCGGGCUCUGGGAGCCCAGAAGGAAGCCAUCUCCCCUCCA

GAUGCGGCCUCAGCUGCUCCACUCCGAACAAUCACUGCUGACACUUUCCGCAAACUCUU

CCGAGUCUACUCCAAUUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCAAAAUGUAGCCAUUCGUAUCUGCUCCUAAUAAAAGAAAGUUUCUUC

ACAUUCUAGAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAA

AAAAAAAAAA

TEV-hEPO-XbG ARC-mRNA. random_14%_T (1014 nt).

(SEQ ID NO: 44)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCUGCCUGGCUGUGGC

UGCUCCUGAGCCUGCUGAGCCUCCCCCUGGGCCUCCCAGUCCUGGGCGCCCCACCACGC

CUCAUCUGCGACAGCCGAGUCCUGGAGAGGUACCUCCUGGAGGCCAAGGAGGCCGAGAA

CAUCACGACGGGCUGCGCCGAACACUGCAGCUUGAACGAGAACAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUGAGCGAAGCCGUCCUGCGGGGCCAGGCCCUGCUGGUCAA

CAGCUCCCAGCCGUGGGAGCCCCUGCAGCUGCACGUGGACAAAGCCGUCAGCGGCCUGC

GCAGCCUCACCACCCUGCUGCGGGCCCUGGGAGCCCAGAAGGAAGCCAUCAGCCCCCCA

GACGCGGCCAGCGCCGCCCCACUCCGAACAAUCACCGCUGACACUUCCGCAAACUCUU

CCGAGUCUACUCCAACUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCAAAAUGUAGCCAUUCGUAUCUGCUCCUAAUAAAAGAAAGUUUCUUC

ACAUUCUAGAAAAAAAAAAAAAAAAAAAAAAAAAAAAAAAAAAAAAAAAAAAAAAAAAA

-continued
AAAAAAAAAAAAAAAAAAAAAAAAAAAAAAAAAAAAAAAAAAAAAAAAAAAAAAAAAA

AAAAAAAAAA

TEV-hEPO-XbG ARC-mRNA. random_16%_T (1014 nt).

(SEQ ID NO: 45)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGUCCCGCCUGGCUGUGGC

UGCUCCUGAGCCUGCUGAGCCUCCCUCUGGGCCUCCCAGUCCUGGGCGCCCCACCACGC

CUCAUCUGCGACAGCCGAGUCCUGGAGAGGUACCUCCUGGAGGCCAAGGAGGCCGAGAA

UAUCACGACGGGCUGUGCCGAACACUGCAGCUUGAACGAGAAUAUCACCGUCCCAGACA

CCAAAGUUAAUUUCUAUGCCUGGAAGAGGAUGGAGGUCGGGCAGCAGGCCGUAGAAGUC

UGGCAGGGCCUGGCCCUGCUGUCGGAAGCUGUCCUGCGGGGCCAGGCCCUGCUGGUCAA

CAGCAGCCAGCCGUGGGAGCCCCUGCAGCUGCACGUGGAUAAAGCCGUCAGCGGCCUGC

GCAGCCUCACCACCCUGCUGCGGGCUCUGGGGAGCCCAGAAGGAAGCCAUCAGCCCUCCA

GAUGCGGCCAGCGCCGCUCCACUCCGAACAAUCACCGCCGACACUUUCCGCAAACUCUU

CCGAGUCUACAGCAACUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCAAAAUGUAGCCAUUCGUAUCUGCUCCUAAUAAAAGAAAGUUUCUUC

ACAUUCUAGAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAA

TEV-hEPO-XbG ARC-mRNA. random_18%_T (1014 nt).

(SEQ ID NO: 46)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGUCCUGCCUGGCUGUGGC

UUCUCCUGUCCCUGCUGAGCCUCCCUCUGGGCCUCCCAGUCCUGGGCGCCCCACCACGC

CUCAUCUGUGACAGCCGAGUCCUGGAGAGGUACCUCUUGGAGGCCAAGGAGGCCGAGAA

CAUCACGACGGGCUGCGCUGAACACUGCAGCCUGAAUGAGAAUAUCACUGUCCCAGACA

CCAAAGUGAAUUUCUAUGCCUGGAAGAGGAUGGAGGUCGGGCAGCAGGCCGUAGAAGUC

UGGCAGGGCCUGGCCCUGCUGAGCGAAGCCGUCCUGCGGGGCCAGGCCCUGUUGGUCAA

CAGCAGCCAGCCGUGGGAGCCCCUGCAGCUGCAUGUGGAUAAAGCCGUCAGUGGCCUUC

GCAGCCUCACCACUCUGCUUCGGGCCCUGGGAGCCCAGAAGGAAGCCAUCUCCCCUCCA

GACGCGGCCUCAGCUGCCCCACUCCGAACAAUCACUGCUGACACUUUCCGCAAACUCUU

CCGAGUCUACAGCAAUUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCAAAAUGUAGCCAUUCGUAUCUGCUCCUAAUAAAAGAAAGUUUCUUC

ACAUUCUAGAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAAA

TEV-hEPO-XbG ARC-mRNA. random_20%_T (1014 nt).

(SEQ ID NO: 47)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGUCCUGCCUGGCUGUGGC

UUCUCCUGUCCCUGCUGUCGCUCCCUCUGGGCCUCCCAGUCCUGGGCGCCCCACCACGC

CUCAUCUGUGACAGCCGAGUCCUGGAGAGGUACCUCUUGGAGGCCAAGGAGGCCGAGAA

UAUCACGACGGGCUGUGCUGAACACUGCAGCUUGAAUGAGAAUAUCACUGUCCCAGACA

CCAAAGUUAACUUCUAUGCCUGGAAGAGGAUGGAGGUCGGGCAGCAGGCCGUAGAAGUC

UGGCAGGGCCUGGCCCUGCUGUCGGAAGCUGUCCUGCGGGGCCAGGCCCUGCUGGUCAA

CUCUUCCCAGCCGUGGGAGCCCCUGCAGCUGCAUGUGGAUAAAGCCGUCAGUGGCCUUC

GCAGCCUCACCACUCUGCUUCGGGCUCUGGGAGCCCAGAAGGAAGCCAUCUCCCCUCCA

GAUGCGGCCUCAGCUGCUCCACUCCGAACAAUCACUGCUGACACUUUCCGCAAACUCUU

CCGAGUCUACUCCAAUUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCCAAAAUGUAGCCAUUCGUAUCUGCUCCUAAUAAAAAGAAAGUUUCUUC

ACAUUCUAGAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAAA

Example C: Templates and mRNAs for hF9

Figure 5:
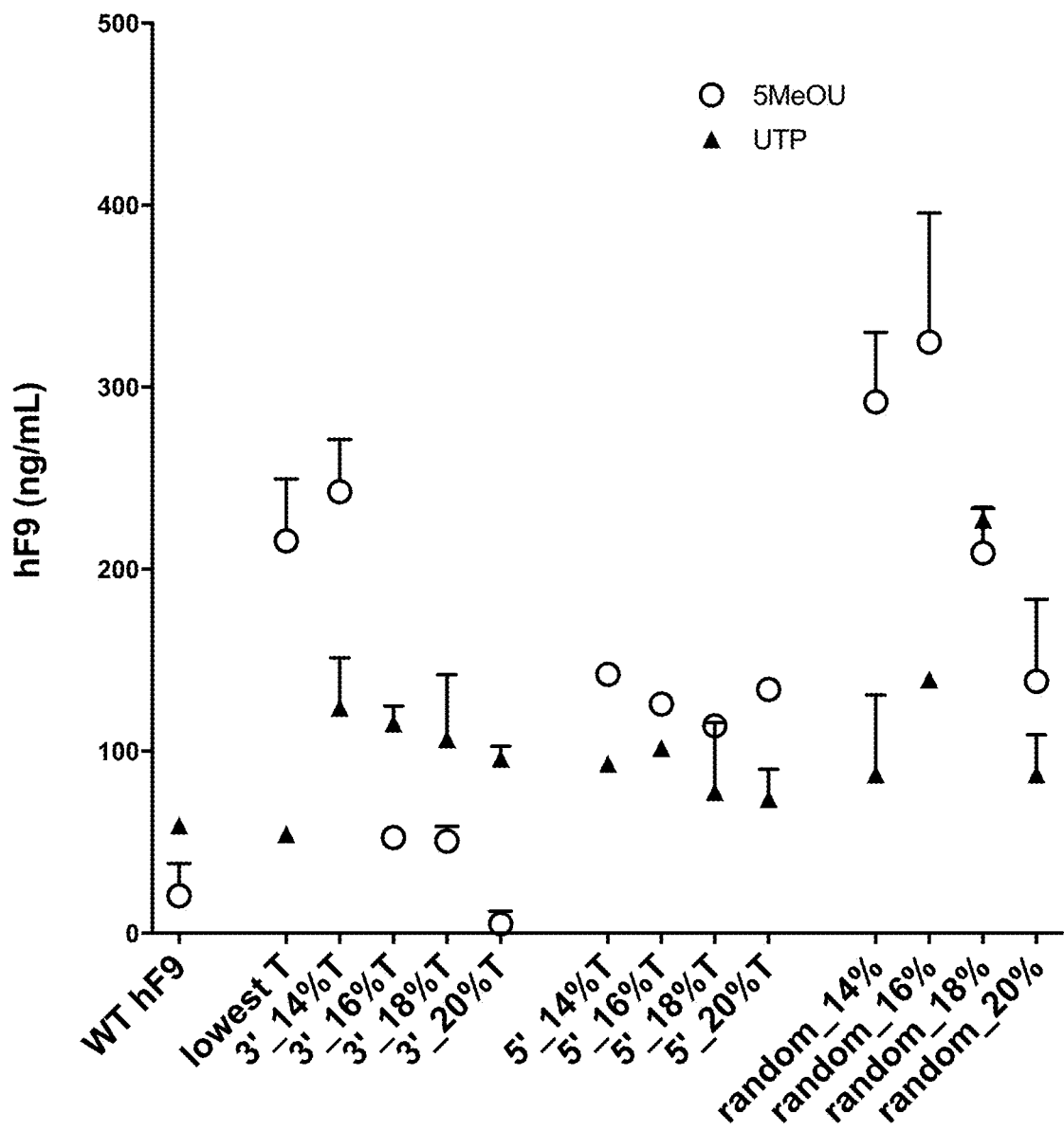
FIG. 5 shows the results of surprisingly increased human F9 protein production for a translatable molecule of this invention. Human F9 ARC-RNA was synthesized using a DNA template having reduced deoxyadenosine nucleotides in an open reading frame of the template strand, as well as reduced deoxythymidine nucleotides in the complementary non-template strand ("reduced T"). The synthesis was also carried out with 5-methoxyuridines (5MeOU, 100%). The ARC-RNA was transfected into HEPA1-6 cells using MES-SENGERMAX transfection reagents. The cell culture medium was collected 24 hrs after transfection. ELISA was used to detect the protein production with the ARC-RNA (5MeOU) as compared to wild type mRNA with similarly reduced T.

FIG. 5 shows the results of surprisingly increased human F9 protein production for a translatable molecule of this invention. Human F9 ARC-RNA was synthesized using a DNA template having reduced deoxyadenosine nucleotides in an open reading frame of the template strand, as well as reduced complementary deoxythymidine nucleotides in the non-template strand ("reduced T"). The synthesis was also carried out with 5-methoxyuridines (5MeOU, 1000). The ARC-RNA was transfected into HEPA1-6 cells using MES-SENGERMAX transfection reagents. The cell culture medium was collected 24 hrs after transfection. ELISA was used to detect the protein production with the ARC-RNA (5MeOU) as compared to wild type mRNA with similarly reduced T.

FIG. 5 shows surprisingly high translational efficiency of the ARC-mRNA (5MeOU) compared to the wild type hF9 mRNA (UTP). First, FIG. 5 shows that ARC-mRNA (5MeOU) products exhibited surprisingly superior expression efficiency at levels of template T composition of 13-14%. The increase of ARC-mRNA (5MeOU) expression efficiency at lower levels of template T composition of 13-14% is unexpectedly advantageous because neither the wild type nor "reduced T" hEPO mRNA (UTP) was increased at lower levels of template T composition.

Further, FIG. 5 shows that the ARC-mRNA (5MeOU) exhibited unexpectedly superior expression efficiency at 14-16% template T composition, when codon replacement was done randomly.

Figure 6:
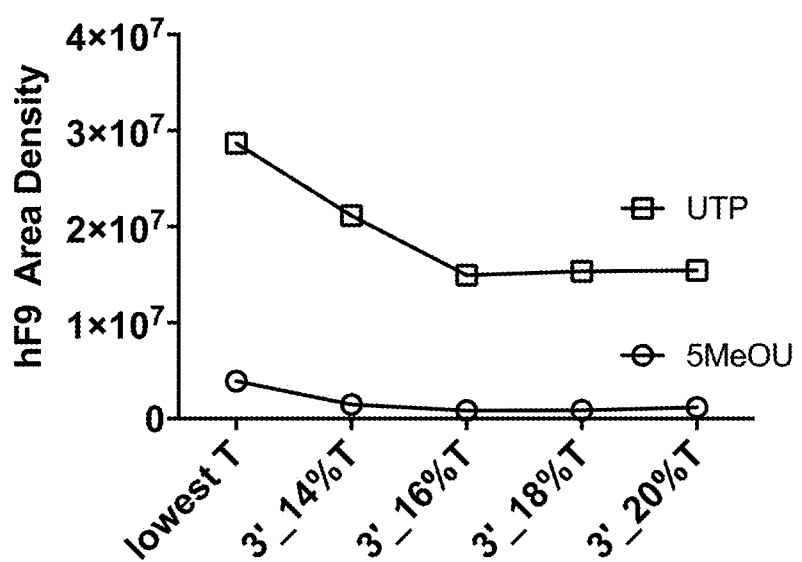
FIG. 6 shows the results of surprisingly reduced impurity levels in a process for synthesizing an hF9 translatable molecule of this invention.

FIG. 6 shows the results of surprisingly reduced impurity levels in a process for synthesizing an hF9 translatable molecule of this invention. FIG. 6 shows the results of a dot blot for detecting double strand RNA impurity in the synthesis mixture (nitro cellulose membrane, J2 antibody to detect dsRNA). The ARC-RNA (5MeOU) "reduced T" synthesis products, which were translatable for hF9, showed surprisingly reduced dot blot intensity as compared to similar "reduced T" mRNA (UTP) synthesis products. Thus, the ARC-RNA (5MeOU) synthesis process, with template reduced T composition, surprisingly reduced double strand RNA impurity levels in the synthesis mixture. The process for synthesizing the ARC-RNA (5MeOU) molecules of this invention with template reduced T composition provided a surprisingly reduced level of double strand RNA impurity. As shown in FIG. 6, this result is surprising because the "reduced T" mRNA (UTP) synthesis products exhibited increased levels of double strand RNA impurity at lower template T composition.

The compositions of the templates for hF9 are shown in Table 7.

TABLE 7

Non-Template Nucleotide T compositions for hF9

| hEPO | T % |
|---|---|
| hF9_lowest_T | 13.5 |
| hF9_3'_14% T | 14.1 |

TABLE 7-continued

Non-Template Nucleotide T compositions for hF9

| hEPO | T % |
|---|---|
| hF9_3'_16% T | 16.0 |
| hF9_3'_18% T | 18.0 |
| hF9_3'_20% T | 19.9 |
| hF9_5'_14% T | 14.1 |
| hF9_5'_16% T | 16.0 |
| hF9_5'_18% T | 18.0 |
| hF9_5'_20% T | 20.1 |
| hF9_random_14% | 14.1 |

TABLE 7-continued

Non-Template Nucleotide T compositions for hF9

| hEPO | T % |
|---|---|
| hF9_random_16% | 16.0 |
| hF9_random_18% | 18.0 |
| hF9_random_20% | 20.0 |

Human F9 ORF reference. Sense strand, non-template. NM_000133.3:30-1415 CDS *Homo sapiens* coagulation factor IX.

(SEQ ID NO: 48)

```
atgcagcgcgtgaacatgatcatggcagaatcaccaggcctcatcacca
tctgccttttaggatatctactcagtgctgaatgtacagttttcttgatcatgaaaac
gccaacaaaattctgaatcggccaaagaggtataattcaggtaaattggaagagtttgt
tcaagggaaccttgagagagaatgtatggaagaaaagtgtagttttgaagaagcacgag
aagttttgaaaacactgaaagaacaactgaattttggaagcagtatgttgatggagat
cagtgtgagtccaatccatgtttaaatggcggcagttgcaaggatgacattaattccta
tgaatgttggtgtccctttggatttgaaggaaagaactgtgaattagatgtaacatgta
acattaagaatggcagatgcgagcagttttgtaaaaatagtgctgataacaaggtggtt
tgctcctgtactgagggatatcgacttgcagaaaaccagaagtcctgtgaaccagcagt
gccatttccatgtggaagagtttctgtttcacaaacttctaagctcacccgtgctgaga
ctgttttcctgatgtggactatgtaaattctactgaagctgaaaccattttggataac
atcactcaaagcacccaatcatttaatgacttcactcgggttgttggtggagaagatgc
caaaccaggtcaattcccttggcaggttgttttgaatggtaaagttgatgcattctgtg
gaggctctatcgttaatgaaaaatggattgtaactgctgcccactgtgttgaaactggt
gttaaaattacagttgtcgcaggtgaacataatattgaggagacagaacatacagagca
aaagcgaaatgtgattcgaattattcctcaccacaactacaatgcagctattaataagt
acaaccatgacattgcccttctggaactggacgaacccttagtgctaaacagctacgtt
acacctatttgcattgctgacaaggaatacacgaacatcttcctcaaatttggatctgg
ctatgtaagtggctggggaagagtcttccacaaagggagatcagctttagttcttcagt
accttagagttccacttgttgaccgagccacatgtcttcgatctacaaagttcaccatc
tataacaacatgttctgtgctggcttccatgaaggaggtagagattcatgtcaaggaga
tagtgggggacccatgttactgaagtggaagggaccagtttcttaactggaattatta
gctggggtgaagagtgtgcaatgaaaggcaaatatggaatatataccaaggtatcccgg
tatgtcaactggattaaggaaaaaacaaagctcacttaa
``` hF9 sense strand, non-template. 3'_lowest_T.

(SEQ ID NO: 49)

```
ATGGGGGTGCACGAATGCCCCGCCTGGCTGTGGCTGCTCCTGAGCCTGC
TGAGCCTCCCCCTGGGCCTCCCAGTCCTGGGCGCCCCACCACGCCTCATCTGCGACAGC
CGAGTCCTGGAGAGGTACCTCCTGGAGGCCAAGGAGGCCGAGAACATCACGACGGGCTG
CGCCGAACACTGCAGCCTGAACGAGAACATCACCGTCCCAGACACCAAAGTGAACTTCT
ACGCCTGGAAGAGGATGGAGGTCGGGCAGCAGGCCGTAGAAGTCTGGCAGGGCCTGGCC
CTGCTGAGCGAAGCCGTCCTGCGGGGCCAGGCCCTGCTGGTCAACAGCAGCCAGCCGTG
GGAGCCCCTGCAGCTGCACGTGGACAAAGCCGTCAGCGGCCTGCGCAGCCTCACCACCC
```

TGCTGCGGGCCCTGGGAGCCCAGAAGGAAGCCATCAGCCCCCCAGACGCGGCCAGCGCC

GCCCCACTCCGAACAATCACCGCCGACACCTTCCGCAAACTCTTCCGAGTCTACAGCAA

CTTCCTCCGGGGAAAGCTGAAGCTGTACACAGGGGAGGCCTGCAGGACAGGGGACAGAT

GA hF9 sense strand, non-template. 3'_lowest_T.
(SEQ ID NO: 50)
ATGCAGCGCGTGAACATGATCATGGCAGAAAGCCCAGGCCTCATCACCA

TCTGCCTGCTGGGATACCTACTCAGCGCCGAATGCACAGTGTTCCTGGACCACGAAAAC

GCCAACAAAATCCTGAACCGGCCAAAGAGGTACAACAGCGGCAAACTGGAAGAGTTCGT

GCAAGGGAACCTGGAGAGAGAATGCATGGAAGAAAAGTGCAGCTTCGAAGAAGCACGAG

AAGTGTTCGAAAACACCGAAAGAACAACCGAATTCTGGAAGCAGTACGTGGACGGAGAC

CAGTGCGAGAGCAACCCATGCCTGAACGGCGGCAGCTGCAAGGACGACATCAACAGCTA

CGAATGCTGGTGCCCCTTCGGATTCGAAGGAAAGAACTGCGAACTGGACGTAACATGCA

ACATCAAGAACGGCAGATGCGAGCAGTTCTGCAAAAACAGCGCCGACAACAAGGTGGTG

TGCAGCTGCACCGAGGGATACCGACTGGCAGAAAACCAGAAGTCCTGCGAACCAGCAGT

GCCATTCCCATGCGGAAGAGTGAGCGTGAGCCAAACCAGCAAGCTCACCCGGGCCGAGA

CCGTGTTCCCCGACGTGGACTACGTAAACAGCACCGAAGCCGAAACCATCCTGGACAAC

ATCACCCAAAGCACCCAAAGCTTCAACGACTTCACCCGGGTGGTGGGCGGAGAAGACGC

CAAACCAGGCCAATTCCCCTGGCAGGTGGTGCTGAACGGCAAAGTGGACGCATTCTGCG

GAGGCAGCATCGTGAACGAAAAATGGATCGTAACCGCCGCCCACTGCGTGGAAACCGGC

GTGAAAATCACAGTGGTCGCAGGCGAACACAACATCGAGGAGACAGAACACACAGAGCA

AAAGCGAAACGTGATCCGAATCATCCCCCACCACAACTACAACGCAGCCATCAACAAGT

ACAACCACGACATCGCCCTGCTGGAACTGGACGAACCCCTGGTGCTAAACAGCTACGTG

ACACCCATCTGCATCGCCGACAAGGAATACACGAACATCTTCCTCAAATTCGGAAGCGG

CTACGTAAGCGGCTGGGGAAGAGTCTTCCACAAAGGGAGAAGCGCCCTGGTGCTGCAGT

ACCTGAGAGTGCCACTGGTGGACCGAGCCACATGCCTGCGAAGCACAAAGTTCACCATC

TACAACAACATGTTCTGCGCCGGCTTCCACGAAGGAGGCAGAGACAGCTGCCAAGGAGA

CAGCGGGGGACCCCACGTGACCGAAGTGGAAGGGACCAGCTTCCTGACCGGAATCATCA

GCTGGGGCGAAGAGTGCGCAATGAAAGGCAAATACGGAATATACACCAAGGTAAGCCGG

TACGTCAACTGGATCAAGGAAAAAACAAAGCTCACCTAA hF9 sense strand, non-template. 3'_14%_T.
(SEQ ID NO: 51)
ATGCAGCGCGTGAACATGATCATGGCAGAATCACCAGGCCTCATCACCA

TCTGCCTTTTAGGATATCTACTCAGTGCTGAATGTACAGTTTTCCTGGACCACGAAAAC

GCCAACAAAATCCTGAACCGGCCAAAGAGGTACAACAGCGGCAAACTGGAAGAGTTCGT

GCAAGGGAACCTGGAGAGAGAATGCATGGAAGAAAAGTGCAGCTTCGAAGAAGCACGAG

AAGTGTTCGAAAACACCGAAAGAACAACCGAATTCTGGAAGCAGTACGTGGACGGAGAC

CAGTGCGAGAGCAACCCATGCCTGAACGGCGGCAGCTGCAAGGACGACATCAACAGCTA

CGAATGCTGGTGCCCCTTCGGATTCGAAGGAAAGAACTGCGAACTGGACGTAACATGCA

ACATCAAGAACGGCAGATGCGAGCAGTTCTGCAAAAACAGCGCCGACAACAAGGTGGTG

TGCAGCTGCACCGAGGGATACCGACTGGCAGAAAACCAGAAGTCCTGCGAACCAGCAGT

GCCATTCCCATGCGGAAGAGTGAGCGTGAGCCAAACCAGCAAGCTCACCCGGGCCGAGA

```
CCGTGTTCCCCGACGTGGACTACGTAAACAGCACCGAAGCCGAAACCATCCTGGACAAC
ATCACCCAAAGCACCCAAAGCTTAACGACTTCACCCGGGTGGTGGGCGGAGAAGACGC
CAAACCAGGCCAATTCCCCTGGCAGGTGGTGCTGAACGGCAAAGTGGACGCATTCTGCG
GAGGCAGCATCGTGAACGAAAAATGGATCGTAACCGCCGCCCACTGCGTGGAAACCGGC
GTGAAAATCACAGTGGTCGCAGGCGAACACAACATCGAGGAGACAGAACACACAGAGCA
AAAGCGAAACGTGATCCGAATCATCCCCCACCACAACTACAACGCAGCCATCAACAAGT
ACAACCACGACATCGCCCTGCTGGAACTGGACGAACCCCTGGTGCTAAACAGCTACGTG
ACACCCATCTGCATCGCCGACAAGGAATACACGAACATCTTCCTCAAATTCGGAAGCGG
CTACGTAAGCGGCTGGGGAAGAGTCTTCCACAAAGGGAGAAGCGCCCTGGTGCTGCAGT
ACCTGAGAGTGCCACTGGTGGACCGAGCCACATGCCTGCGAAGCACAAAGTTCACCATC
TACAACAACATGTTCTGCGCCGGCTTCCACGAAGGAGGCAGAGACAGCTGCCAAGGAGA
CAGCGGGGACCCCACGTGACCGAAGTGGAAGGGACCAGCTTCCTGACCGGAATCATCA
GCTGGGGCGAAGAGTGCGCAATGAAAGGCAAATACGGAATATACACCAAGGTAAGCCGG
TACGTCAACTGGATCAAGGAAAAAACAAAGCTCACCTAA hF9 sense strand, non-template. 3'_16%_T.
                                                        (SEQ ID NO: 52)
ATGCAGCGCGTGAACATGATCATGGCAGAATCACCAGGCCTCATCACCA
TCTGCCTTTTAGGATATCTACTCAGTGCTGAATGTACAGTTTTTCTTGATCATGAAAAC
GCCAACAAAATTCTGAATCGGCCAAAGAGGTATAATTCAGGTAAATTGGAAGAGTTTGT
TCAAGGGAACCTTGAGAGAGAATGTATGGAAGAAAAGTGTAGTTTTGAAGAAGCACGAG
AAGTTTTTGAAAACACTGAAAGAACAACTGAATTTTGGAAGCAGTATGTTGATGGAGAT
CAGTGCGAGAGCAACCCATGCCTGAACGGCGGCAGCTGCAAGGACGACATCAACAGCTA
CGAATGCTGGTGCCCCTTCGGATTCGAAGGAAAGAACTGCGAACTGGACGTAACATGCA
ACATCAAGAACGGCAGATGCGAGCAGTTCTGCAAAAACAGCGCCGACAACAAGGTGGTG
TGCAGCTGCACCGAGGGATACCGACTGGCAGAAAACCAGAAGTCCTGCGAACCAGCAGT
GCCATTCCCATGCGGAAGAGTGAGCGTGAGCCAAACCAGCAAGCTCACCCGGGCCGAGA
CCGTGTTCCCCGACGTGGACTACGTAAACAGCACCGAAGCCGAAACCATCCTGGACAAC
ATCACCCAAAGCACCCAAAGCTTAACGACTTCACCCGGGTGGTGGGCGGAGAAGACGC
CAAACCAGGCCAATTCCCCTGGCAGGTGGTGCTGAACGGCAAAGTGGACGCATTCTGCG
GAGGCAGCATCGTGAACGAAAAATGGATCGTAACCGCCGCCCACTGCGTGGAAACCGGC
GTGAAAATCACAGTGGTCGCAGGCGAACACAACATCGAGGAGACAGAACACACAGAGCA
AAAGCGAAACGTGATCCGAATCATCCCCCACCACAACTACAACGCAGCCATCAACAAGT
ACAACCACGACATCGCCCTGCTGGAACTGGACGAACCCCTGGTGCTAAACAGCTACGTG
ACACCCATCTGCATCGCCGACAAGGAATACACGAACATCTTCCTCAAATTCGGAAGCGG
CTACGTAAGCGGCTGGGGAAGAGTCTTCCACAAAGGGAGAAGCGCCCTGGTGCTGCAGT
ACCTGAGAGTGCCACTGGTGGACCGAGCCACATGCCTGCGAAGCACAAAGTTCACCATC
TACAACAACATGTTCTGCGCCGGCTTCCACGAAGGAGGCAGAGACAGCTGCCAAGGAGA
CAGCGGGGACCCCACGTGACCGAAGTGGAAGGGACCAGCTTCCTGACCGGAATCATCA
GCTGGGGCGAAGAGTGCGCAATGAAAGGCAAATACGGAATATACACCAAGGTAAGCCGG
TACGTCAACTGGATCAAGGAAAAAACAAAGCTCACCTAA
``` hF9 sense strand, non-template. 3'_18%_T.

(SEQ ID NO: 53)

ATGCAGCGCGTGAACATGATCATGGCAGAATCACCAGGCCTCATCACCA

TCTGCCTTTTAGGATATCTACTCAGTGCTGAATGTACAGTTTTTCTTGATCATGAAAAC

GCCAACAAAATTCTGAATCGGCCAAAGAGGTATAATTCAGGTAAATTGGAAGAGTTTGT

TCAAGGGAACCTTGAGAGAGAATGTATGGAAGAAAAGTGTAGTTTTGAAGAAGCACGAG

AAGTTTTTGAAAACACTGAAAGAACAACTGAATTTTGGAAGCAGTATGTTGATGGAGAT

CAGTGTGAGTCCAATCCATGTTTAAATGGCGGCAGTTGCAAGGATGACATTAATTCCTA

TGAATGTTGGTGTCCCTTTGGATTTGAAGGAAAGAACTGTGAATTAGATGTAACATGTA

ACATTAAGAATGGCAGATGCGAGCAGTTTTGTAAAAATAGTGCTGATAACAAGGTGGTG

TGCAGCTGCACCGAGGGATACCGACTGGCAGAAAACCAGAAGTCCTGCGAACCAGCAGT

GCCATTCCCATGCGGAAGAGTGAGCGTGAGCCAAACCAGCAAGCTCACCCGGGCCGAGA

CCGTGTTCCCCGACGTGGACTACGTAAACAGCACCGAAGCCGAAACCATCCTGGACAAC

ATCACCCAAAGCACCCAAAGCTTCAACGACTTCACCCGGGTGGTGGGCGGAGAAGACGC

CAAACCAGGCCAATTCCCCTGGCAGGTGGTGCTGAACGGCAAAGTGGACGCATTCTGCG

GAGGCAGCATCGTGAACGAAAAATGGATCGTAACCGCCGCCCACTGCGTGGAAACCGGC

GTGAAAATCACAGTGGTCGCAGGCGAACACAACATCGAGGAGACAGAACACACAGAGCA

AAAGCGAAACGTGATCCGAATCATCCCCCACCACAACTACAACGCAGCCATCAACAAGT

ACAACCACGACATCGCCCTGCTGGAACTGGACGAACCCCTGGTGCTAAACAGCTACGTG

ACACCCATCTGCATCGCCGACAAGGAATACACGAACATCTTCCTCAAATTCGGAAGCGG

CTACGTAAGCGGCTGGGGAAGAGTCTTCCACAAAGGGAGAAGCGCCCTGGTGCTGCAGT

ACCTGAGAGTGCCACTGGTGGACCGAGCCACATGCCTGCGAAGCACAAAGTTCACCATC

TACAACAACATGTTCTGCGCCGGCTTCCACGAAGGAGGCAGAGACAGCTGCCAAGGAGA

CAGCGGGGGACCCCACGTGACCGAAGTGGAAGGGACCAGCTTCCTGACCGGAATCATCA

GCTGGGGCGAAGAGTGCGCAATGAAAGGCAAATACGGAATATACACCAAGGTAAGCCGG

TACGTCAACTGGATCAAGGAAAAAACAAAGCTCACCTAA hF9 sense strand, non-template. 3'_20%_T.

(SEQ ID NO: 54)

ATGCAGCGCGTGAACATGATCATGGCAGAATCACCAGGCCTCATCACCA

TCTGCCTTTTAGGATATCTACTCAGTGCTGAATGTACAGTTTTTCTTGATCATGAAAAC

GCCAACAAAATTCTGAATCGGCCAAAGAGGTATAATTCAGGTAAATTGGAAGAGTTTGT

TCAAGGGAACCTTGAGAGAGAATGTATGGAAGAAAAGTGTAGTTTTGAAGAAGCACGAG

AAGTTTTTGAAAACACTGAAAGAACAACTGAATTTTGGAAGCAGTATGTTGATGGAGAT

CAGTGTGAGTCCAATCCATGTTTAAATGGCGGCAGTTGCAAGGATGACATTAATTCCTA

TGAATGTTGGTGTCCCTTTGGATTTGAAGGAAAGAACTGTGAATTAGATGTAACATGTA

ACATTAAGAATGGCAGATGCGAGCAGTTTTGTAAAAATAGTGCTGATAACAAGGTGGTT

TGCTCCTGTACTGAGGGATATCGACTTGCAGAAAACCAGAAGTCCTGTGAACCAGCAGT

GCCATTTCCATGTGGAAGAGTTTCTGTTTCACAAACTTCTAAGCTCACCCGTGCTGAGA

CTGTTTTTCCTGATGTGGACTATGTAAATAGCACCGAAGCCGAAACCATCCTGGACAAC

ATCACCCAAAGCACCCAAAGCTTCAACGACTTCACCCGGGTGGTGGGCGGAGAAGACGC

CAAACCAGGCCAATTCCCCTGGCAGGTGGTGCTGAACGGCAAAGTGGACGCATTCTGCG

GAGGCAGCATCGTGAACGAAAAATGGATCGTAACCGCCGCCCACTGCGTGGAAACCGGC

```
GTGAAAATCACAGTGGTCGCAGGCGAACACAACATCGAGGAGACAGAACACACAGAGCA

AAAGCGAAACGTGATCCGAATCATCCCCCACCACAACTACAACGCAGCCATCAACAAGT

ACAACCACGACATCGCCCTGCTGGAACTGGACGAACCCCTGGTGCTAAACAGCTACGTG

ACACCCATCTGCATCGCCGACAAGGAATACACGAACATCTTCCTCAAATTCGGAAGCGG

CTACGTAAGCGGCTGGGGAAGAGTCTTCCACAAAGGGAGAAGCGCCCTGGTGCTGCAGT

ACCTGAGAGTGCCACTGGTGGACCGAGCCACATGCCTGCGAAGCACAAAGTTCACCATC

TACAACAACATGTTCTGCGCCGGCTTCCACGAAGGAGGCAGAGACAGCTGCCAAGGAGA

CAGCGGGGACCCCACGTGACCGAAGTGGAAGGGACCAGCTTCCTGACCGGAATCATCA

GCTGGGCGAAGAGTGCGCAATGAAAGGCAAATACGGAATATACACCAAGGTAAGCCGG

TACGTCAACTGGATCAAGGAAAAAACAAAGCTCACCTAA hF9 sense strand, non-template. 5'_14%_T.
                                                  (SEQ ID NO: 55)
ATGCAGCGCGTGAACATGATCATGGCAGAAAGCCCAGGCCTCATCACCA

TCTGCCTGCTGGGATACCTACTCAGCGCCGAATGCACAGTGTTCCTGGACCACGAAAAC

GCCAACAAAATCCTGAACCGGCCAAAGAGGTACAACAGCGGCAAACTGGAAGAGTTCGT

GCAAGGGAACCTGGAGAGAGAATGCATGGAAGAAAAGTGCAGCTTCGAAGAAGCACGAG

AAGTGTTCGAAAACACCGAAAGAACAACCGAATTCTGGAAGCAGTACGTGGACGGAGAC

CAGTGCGAGAGCAACCCATGCCTGAACGGCGGCAGCTGCAAGGACGACATCAACAGCTA

CGAATGCTGGTGCCCCTTCGGATTCGAAGGAAAGAACTGCGAACTGGACGTAACATGCA

ACATCAAGAACGGCAGATGCGAGCAGTTCTGCAAAAACAGCGCCGACAACAAGGTGGTG

TGCAGCTGCACCGAGGGATACCGACTGGCAGAAAACCAGAAGTCCTGCGAACCAGCAGT

GCCATTCCCATGCGGAAGAGTGAGCGTGAGCCAAACCAGCAAGCTCACCCGGGCCGAGA

CCGTGTTCCCCGACGTGGACTACGTAAACAGCACCGAAGCCGAAACCATCCTGGACAAC

ATCACCCAAAGCACCCAAAGCTTCAACGACTTCACCCGGGTGGTGGGCGGAGAAGACGC

CAAACCAGGCCAATTCCCCTGGCAGGTGGTGCTGAACGGCAAAGTGGACGCATTCTGCG

GAGGCAGCATCGTGAACGAAAAATGGATCGTAACCGCCGCCCACTGCGTGGAAACCGGC

GTGAAAATCACAGTGGTCGCAGGCGAACACAACATCGAGGAGACAGAACACACAGAGCA

AAAGCGAAACGTGATCCGAATCATCCCCCACCACAACTACAACGCAGCCATCAACAAGT

ACAACCACGACATCGCCCTGCTGGAACTGGACGAACCCCTGGTGCTAAACAGCTACGTG

ACACCCATCTGCATCGCCGACAAGGAATACACGAACATCTTCCTCAAATTCGGAAGCGG

CTACGTAAGCGGCTGGGGAAGAGTCTTCCACAAAGGGAGAAGCGCCCTGGTGCTGCAGT

ACCTGAGAGTGCCACTGGTGGACCGAGCCACATGCCTGCGAAGCACAAAGTTCACCATC

TACAACAACATGTTCTGCGCCGGCTTCCACGAAGGAGGCAGAGACAGCTGCCAAGGAGA

CAGCGGGGACCCCACGTGACCGAAGTGGAAGGGACCAGCTTCCTGACCGGAATCATCA

GCTGGGGTGAAGAGTGTGCAATGAAAGGCAAATATGGAATATATACCAAGGTATCCCGG

TATGTCAACTGGATTAAGGAAAAAACAAAGCTCACTTAA hF9 sense strand, non-template. 5'_16%_T.
                                                  (SEQ ID NO: 56)
ATGCAGCGCGTGAACATGATCATGGCAGAAAGCCCAGGCCTCATCACCA

TCTGCCTGCTGGGATACCTACTCAGCGCCGAATGCACAGTGTTCCTGGACCACGAAAAC

GCCAACAAAATCCTGAACCGGCCAAAGAGGTACAACAGCGGCAAACTGGAAGAGTTCGT

GCAAGGGAACCTGGAGAGAGAATGCATGGAAGAAAAGTGCAGCTTCGAAGAAGCACGAG

AAGTGTTCGAAAACACCGAAAGAACAACCGAATTCTGGAAGCAGTACGTGGACGGAGAC
```

-continued

```
CAGTGCGAGAGCAACCCATGCCTGAACGGCGGCAGCTGCAAGGACGACATCAACAGCTA

CGAATGCTGGTGCCCCTTCGGATTCGAAGGAAAGAACTGCGAACTGGACGTAACATGCA

ACATCAAGAACGGCAGATGCGAGCAGTTCTGCAAAAACAGCGCCGACAACAAGGTGGTG

TGCAGCTGCACCGAGGGATACCGACTGGCAGAAAACCAGAAGTCCTGCGAACCAGCAGT

GCCATTCCCATGCGGAAGAGTGAGCGTGAGCCAAACCAGCAAGCTCACCCGGGCCGAGA

CCGTGTTCCCCGACGTGGACTACGTAAACAGCACCGAAGCCGAAACCATCCTGGACAAC

ATCACCCAAAGCACCCAAAGCTTCAACGACTTCACCCGGGTGGTGGGCGGAGAAGACGC

CAAACCAGGCCAATTCCCCTGGCAGGTGGTGCTGAACGGCAAAGTGGACGCATTCTGCG

GAGGCAGCATCGTGAACGAAAAATGGATCGTAACCGCCGCCCACTGCGTGGAAACCGGC

GTGAAAATCACAGTGGTCGCAGGCGAACACAACATCGAGGAGACAGAACACACAGAGCA

AAAGCGAAACGTGATCCGAATCATCCCCCACCACAACTACAACGCAGCCATCAACAAGT

ACAACCACGACATCGCCCTGCTGGAACTGGACGAACCCCTGGTGCTAAACAGCTACGTG

ACACCCATCTGCATCGCCGACAAGGAATACACGAACATCTTCCTCAAATTCGGAAGCGG

CTACGTAAGCGGCTGGGGAAGAGTCTTCCACAAAGGGAGAAGCGCCCTGGTGCTTCAGT

ACCTTAGAGTTCCACTTGTTGACCGAGCCACATGTCTTCGATCTACAAAGTTCACCATC

TATAACAACATGTTCTGTGCTGGCTTCCATGAAGGAGGTAGAGATTCATGTCAAGGAGA

TAGTGGGGGACCCCATGTTACTGAAGTGGAAGGGACCAGTTTCTTAACTGGAATTATTA

GCTGGGGTGAAGAGTGTGCAATGAAAGGCAAATATGGAATATATACCAAGGTATCCCGG

TATGTCAACTGGATTAAGGAAAAAACAAAGCTCACTTAA
``` hF9 sense strand, non-template. 5'_18%_T.
(SEQ ID NO: 57)

```
ATGCAGCGCGTGAACATGATCATGGCAGAAAGCCCAGGCCTCATCACCA

TCTGCCTGCTGGGATACCTACTCAGCGCCGAATGCACAGTGTTCCTGGACCACGAAAAC

GCCAACAAAATCCTGAACCGGCCAAAGAGGTACAACAGCGGCAAACTGGAAGAGTTCGT

GCAAGGGAACCTGGAGAGAGAATGCATGGAAGAAAAGTGCAGCTTCGAAGAAGCACGAG

AAGTGTTCGAAAACACCGAAAGAACAACCGAATTCTGGAAGCAGTACGTGGACGGAGAC

CAGTGCGAGAGCAACCCATGCCTGAACGGCGGCAGCTGCAAGGACGACATCAACAGCTA

CGAATGCTGGTGCCCCTTCGGATTCGAAGGAAAGAACTGCGAACTGGACGTAACATGCA

ACATCAAGAACGGCAGATGCGAGCAGTTCTGCAAAAACAGCGCCGACAACAAGGTGGTG

TGCAGCTGCACCGAGGGATACCGACTGGCAGAAAACCAGAAGTCCTGCGAACCAGCAGT

GCCATTCCCATGCGGAAGAGTGAGCGTGAGCCAAACCAGCAAGCTCACCCGGGCCGAGA

CCGTGTTCCCCGACGTGGACTACGTAAACAGCACCGAAGCCGAAACCATCCTGGACAAC

ATCACCCAAAGCACCCAAAGCTTCAACGACTTCACCCGGGTGGTGGGCGGAGAAGACGC

CAAACCAGGCCAATTCCCCTGGCAGGTGGTGCTGAACGGCAAAGTGGACGCATTCTGCG

GAGGCAGCATCGTGAACGAAAAATGGATCGTAACCGCCGCCCACTGCGTGGAAACCGGC

GTGAAAATCACAGTGGTCGCAGGCGAACACAACATCGAGGAGACAGAACATACAGAGCA

AAAGCGAAATGTGATTCGAATTATTCCTCACCACAACTACAATGCAGCTATTAATAAGT

ACAACCATGACATTGCCCTTCTGGAACTGGACGAACCCTTAGTGCTAAACAGCTACGTT

ACACCTATTTGCATTGCTGACAAGGAATACACGAACATCTTCCTCAAATTTGGATCTGG

CTATGTAAGTGGCTGGGGAAGAGTCTTCCACAAAGGGAGATCAGCTTTAGTTCTTCAGT

ACCTTAGAGTTCCACTTGTTGACCGAGCCACATGTCTTCGATCTACAAAGTTCACCATC
```

-continued

TATAACAACATGTTCTGTGCTGGCTTCCATGAAGGAGGTAGAGATTCATGTCAAGGAGA

TAGTGGGGGACCCCATGTTACTGAAGTGGAAGGGACCAGTTTCTTAACTGGAATTATTA

GCTGGGGTGAAGAGTGTGCAATGAAAGGCAAATATGGAATATATACCAAGGTATCCCGG

TATGTCAACTGGATTAAGGAAAAAACAAAGCTCACTTAA hF9 sense strand, non-template. 5'_20%_T.

(SEQ ID NO: 58)
ATGCAGCGCGTGAACATGATCATGGCAGAAAGCCCAGGCCTCATCACCA

TCTGCCTGCTGGGATACCTACTCAGCGCCGAATGCACAGTGTTCCTGGACCACGAAAAC

GCCAACAAAATCCTGAACCGGCCAAAGAGGTACAACAGCGGCAAACTGGAAGAGTTCGT

GCAAGGGAACCTGGAGAGAGAATGCATGGAAGAAAAGTGCAGCTTCGAAGAAGCACGAG

AAGTGTTCGAAAACACCGAAAGAACAACCGAATTCTGGAAGCAGTACGTGGACGGAGAC

CAGTGCGAGAGCAACCCATGCCTGAACGGCGGCAGCTGCAAGGACGACATCAACAGCTA

CGAATGCTGGTGCCCCTTCGGATTCGAAGGAAAGAACTGCGAACTGGACGTAACATGCA

ACATCAAGAACGGCAGATGCGAGCAGTTCTGCAAAAACAGCGCCGACAACAAGGTGGTG

TGCAGCTGCACCGAGGGATACCGACTGGCAGAAAACCAGAAGTCCTGCGAACCAGCAGT

GCCATTCCCATGCGGAAGAGTGAGCGTGAGCCAAACCAGCAAGCTCACCCGGGCCGAGA

CCGTGTTCCCCGACGTGGACTACGTAAACAGCACCGAAGCCGAAACCATCCTGGACAAC

ATCACCCAAAGCACCCAAAGCTTCAACGACTTCACCCGGGTGGTGGGCGGAGAAGACGC

CAAACCAGGTCAATTCCCTTGGCAGGTTGTTTTGAATGGTAAAGTTGATGCATTCTGTG

GAGGCTCTATCGTTAATGAAAAATGGATTGTAACTGCTGCCCACTGTGTTGAAACTGGT

GTTAAAATTACAGTTGTCGCAGGTGAACATAATATTGAGGAGACAGAACATACAGAGCA

AAAGCGAAATGTGATTCGAATTATTCCTCACCACAACTACAATGCAGCTATTAATAAGT

ACAACCATGACATTGCCCTTCTGGAACTGGACGAACCCTTAGTGCTAAACAGCTACGTT

ACACCTATTTGCATTGCTGACAAGGAATACACGAACATCTTCCTCAAATTTGGATCTGG

CTATGTAAGTGGCTGGGGAAGAGTCTTCCACAAAGGGAGATCAGCTTTAGTTCTTCAGT

ACCTTAGAGTTCCACTTGTTGACCGAGCCACATGTCTTCGATCTACAAAGTTCACCATC

TATAACAACATGTTCTGTGCTGGCTTCCATGAAGGAGGTAGAGATTCATGTCAAGGAGA

TAGTGGGGGACCCCATGTTACTGAAGTGGAAGGGACCAGTTTCTTAACTGGAATTATTA

GCTGGGGTGAAGAGTGTGCAATGAAAGGCAAATATGGAATATATACCAAGGTATCCCGG

TATGTCAACTGGATTAAGGAAAAAACAAAGCTCACTTAA hF9 sense strand, non-template. random_14%_T.

(SEQ ID NO: 59)
ATGCAGCGCGTGAACATGATCATGGCAGAAAGCCCAGGCCTCATCACCA

TCTGCCTGCTGGGATATCTACTCAGCGCCGAATGCACAGTGTTCCTGGACCACGAAAAC

GCCAACAAAATCCTGAACCGGCCAAAGAGGTACAACAGCGGTAAACTGGAAGAGTTCGT

GCAAGGGAACCTGGAGAGAGAATGCATGGAAGAAAAGTGCAGCTTCGAAGAAGCACGAG

AAGTGTTCGAAAACACCGAAAGAACAACCGAATTCTGGAAGCAGTACGTGGACGGAGAC

CAGTGCGAGAGCAACCCATGCCTGAACGGCGGCAGCTGCAAGGACGACATCAACAGCTA

CGAATGCTGGTGCCCCTTCGGATTCGAAGGAAAGAACTGCGAACTGGACGTAACATGCA

ACATCAAGAACGGCAGATGCGAGCAGTTCTGCAAAAACAGCGCCGACAACAAGGTGGTG

TGCAGCTGCACCGAGGGATACCGACTTGCAGAAAACCAGAAGTCCTGCGAACCAGCAGT

GCCATTCCCATGCGGAAGAGTGAGCGTTAGCCAAACCAGCAAGCTCACCCGGGCCGAGA

CCGTGTTCCCCGACGTGGACTACGTAAACAGCACCGAAGCCGAAACCATCCTGGACAAC

-continued

ATCACCCAAAGCACCCAAAGCTTCAACGACTTCACCCGGGTGGTGGGCGGAGAAGACGC

CAAACCAGGCCAATTCCCCTGGCAGGTGGTGCTGAACGGCAAAGTGGACGCATTCTGCG

GAGGCAGCATCGTTAACGAAAAATGGATCGTAACCGCCGCCCACTGCGTGGAAACCGGC

GTGAAAATCACAGTGGTCGCAGGCGAACACAACATCGAGGAGACAGAACACACAGAGCA

AAAGCGAAACGTGATCCGAATCATCCCTCACCACAACTACAACGCAGCCATCAACAAGT

ACAACCACGACATCGCCCTGCTGGAACTGGACGAACCCTTAGTGCTAAACAGCTACGTG

ACACCCATCTGCATCGCCGACAAGGAATACACGAACATCTTCCTCAAATTCGGAAGCGG

CTACGTAAGCGGCTGGGGAAGAGTCTTCCACAAAGGGAGAAGCGCCCTGGTGCTGCAGT

ACCTGAGAGTGCCACTGGTGGACCGAGCCACATGCCTGCGAAGCACAAAGTTCACCATC

TACAACAACATGTTCTGCGCCGGCTTCCACGAAGGAGGCAGAGACAGCTGCCAAGGAGA

CAGCGGGGGACCCCACGTGACCGAAGTGGAAGGGACCAGCTTCCTGACCGGAATCATCA

GCTGGGGCGAAGAGTGTGCAATGAAAGGCAAATACGGAATATACACCAAGGTAAGCCGG

TACGTCAACTGGATCAAGGAAAAAACAAAGCTCACCTAA hF9 sense strand, non-template. random_16%_T.
(SEQ ID NO: 60)
ATGCAGCGCGTGAACATGATCATGGCAGAAAGCCCAGGCCTCATCACCA

TCTGCCTGCTGGGATACCTACTCAGTGCCGAATGTACAGTGTTCCTGGACCACGAAAAC

GCCAACAAAATCCTGAACCGGCCAAAGAGGTACAACTCAGGCAAACTGGAAGAGTTCGT

GCAAGGGAACCTGGAGAGAGAATGCATGGAAGAAAAGTGCAGCTTCGAAGAAGCACGAG

AAGTGTTTGAAAACACTGAAAGAACAACCGAATTTTGGAAGCAGTACGTGGATGGAGAT

CAGTGCGAGAGCAACCCATGCCTGAATGGCGGCAGCTGCAAGGACGACATCAACAGCTA

CGAATGCTGGTGCCCCTTCGGATTCGAAGGAAAGAACTGCGAACTGGACGTAACATGCA

ACATCAAGAACGGCAGATGCGAGCAGTTTTGTAAAAACAGCGCCGACAACAAGGTGGTG

TGCAGCTGCACCGAGGGATACCGACTGGCAGAAAACCAGAAGTCCTGCGAACCAGCAGT

GCCATTCCCATGCGGAAGAGTGTCTGTGTCACAAACCAGCAAGCTCACCCGGGCCGAGA

CCGTGTTCCCCGACGTGGACTACGTAAACAGCACCGAAGCCGAAACCATCCTGGATAAC

ATCACCCAAAGCACCCAAAGCTTCAATGACTTCACCCGGGTGGTGGGCGGAGAAGACGC

CAAACCAGGCCAATTCCCCTGGCAGGTTGTGCTGAACGGCAAAGTTGACGCATTCTGCG

GAGGCAGCATCGTGAACGAAAAATGGATCGTAACCGCTGCCCACTGCGTTGAAACCGGC

GTGAAAATCACAGTGGTCGCAGGCGAACACAACATTGAGGAGACAGAACACACAGAGCA

AAAGCGAAACGTGATCCGAATTATCCCCCACCACAACTACAACGCAGCCATTAATAAGT

ACAACCATGACATCGCCCTGCTGGAACTGGACGAACCCTTAGTGCTAAACAGCTACGTG

ACACCCATCTGCATCGCCGACAAGGAATACACGAACATCTTCCTCAAATTCGGAAGCGG

CTACGTAAGCGGCTGGGGAAGAGTCTTCCACAAAGGGAGAAGCGCCCTGGTTCTGCAGT

ACCTGAGAGTGCCACTGGTTGACCGAGCCACATGCCTGCGAAGCACAAAGTTCACCATC

TACAACAACATGTTCTGCGCCGGCTTCCATGAAGGAGGTAGAGACAGCTGTCAAGGAGA

CAGCGGGGGACCCCACGTTACTGAAGTGGAAGGGACCAGCTTCCTGACCGGAATCATCA

GCTGGGGCGAAGAGTGCGCAATGAAAGGCAAATACGGAATATATACCAAGGTAAGCCGG

TACGTCAACTGGATCAAGGAAAAAACAAAGCTCACTTAA

-continued hF9 sense strand, non-template. random_18%_T.
(SEQ ID NO: 61)
ATGCAGCGCGTGAACATGATCATGGCAGAATCACCAGGCCTCATCACCA

TCTGCCTGTTAGGATACCTACTCAGCGCCGAATGTACAGTGTTTCTTGACCACGAAAAC

GCCAACAAAATCCTGAATCGGCCAAAGAGGTATAACTCAGGTAAACTGGAAGAGTTTGT

GCAAGGGAACCTGGAGAGAGAATGCATGGAAGAAAGTGCAGCTTCGAAGAAGCACGAG

AAGTGTTCGAAAACACTGAAAGAACAACCGAATTTTGGAAGCAGTATGTGGATGGAGAC

CAGTGCGAGTCCAACCCATGCTTAAACGGCGGCAGTTGCAAGGACGACATCAACAGCTA

TGAATGCTGGTGCCCCTTCGGATTTGAAGGAAAGAACTGCGAACTGGACGTAACATGTA

ACATCAAGAATGGCAGATGCGAGCAGTTCTGTAAAAATAGCGCCGACAACAAGGTGGTG

TGCAGCTGTACCGAGGGATACCGACTGGCAGAAAACCAGAAGTCCTGCGAACCAGCAGT

GCCATTCCCATGCGGAAGAGTTAGCGTGAGCCAAACCAGCAAGCTCACCCGGGCCGAGA

CCGTGTTCCCTGACGTGGACTACGTAAACTCTACCGAAGCTGAAACCATCCTGGACAAC

ATCACTCAAAGCACCCAATCATTCAACGACTTCACCCGGGTGGTGGGCGGAGAAGATGC

CAAACCAGGTCAATTCCCTTGGCAGGTGGTGTTGAACGGCAAAGTGGACGCATTCTGTG

GAGGCAGCATCGTGAACGAAAAATGGATCGTAACTGCCGCCCACTGCGTGGAAACCGGC

GTGAAAATCACAGTGGTCGCAGGCGAACACAATATTGAGGAGACAGAACACACAGAGCA

AAAGCGAAATGTGATCCGAATTATCCCTCACCACAACTACAACGCAGCTATTAACAAGT

ACAACCACGACATTGCCCTGCTGGAACTGGACGAACCCCTGGTGCTAAACAGCTACGTT

ACACCTATCTGCATCGCCGACAAGGAATACACGAACATCTTCCTCAAATTCGGATCTGG

CTACGTAAGCGGCTGGGGAAGAGTCTTCCACAAAGGGAGATCAGCCCTGGTGCTTCAGT

ACCTTAGAGTGCCACTTGTGGACCGAGCCACATGCCTGCGAAGCACAAAGTTCACCATC

TACAACAACATGTTCTGTGCTGGCTTCCACGAAGGAGGTAGAGACAGCTGTCAAGGAGA

TAGCGGGGGACCCCACGTTACCGAAGTGGAAGGGACCAGCTTCTTAACTGGAATCATCA

GCTGGGGCGAAGAGTGCGCAATGAAAGGCAAATACGGAATATACACCAAGGTATCCCGG

TATGTCAACTGGATCAAGGAAAAAACAAAGCTCACCTAA hF9 sense strand, non-template. random_20%_T.
(SEQ ID NO: 62)
ATGCAGCGCGTGAACATGATCATGGCAGAAAGCCCAGGCCTCATCACCA

TCTGCCTTCTGGGATATCTACTCAGCGCCGAATGCACAGTTTTCCTTGACCACGAAAAC

GCCAACAAAATCCTGAATCGGCCAAAGAGGTATAATTCAGGTAAACTGGAAGAGTTTGT

TCAAGGGAACCTTGAGAGAGAATGCATGGAAGAAAGTGTAGTTTTGAAGAAGCACGAG

AAGTGTTCGAAAACACCGAAAGAACAACCGAATTTTGGAAGCAGTATGTGGATGGAGAC

CAGTGCGAGAGCAATCCATGCTTAAATGGCGGCAGCTGCAAGGACGACATTAATTCCTA

TGAATGCTGGTGCCCCCTTTGGATTCGAAGGAAAGAACTGCGAATTAGACGTAACATGCA

ACATCAAGAACGGCAGATGCGAGCAGTTTTGTAAAAATAGTGCTGACAACAAGGTGGTT

TGCAGCTGCACCGAGGGATACCGACTGGCAGAAAACCAGAAGTCCTGCGAACCAGCAGT

GCCATTCCCATGTGGAAGAGTTTCTGTGAGCCAAACTTCTAAGCTCACCCGTGCCGAGA

CCGTTTTCCCTGACGTGGACTATGTAAATTCTACCGAAGCCGAAACCATTTTGGATAAC

ATCACCCAAAGCACCCAAAGCTTTAACGACTTCACTCGGGTGGTTGGCGGAGAAGACGC

CAAACCAGGCCAATTCCCTTGGCAGGTGGTTCTGAATGGCAAAGTGGATGCATTCTGTG

GAGGCTCTATCGTGAACGAAAAATGGATCGTAACTGCCGCCCACTGCGTTGAAACCGGC

```
GTTAAAATTACAGTGGTCGCAGGCGAACACAATATTGAGGAGACAGAACACACAGAGCA

AAAGCGAAACGTGATTCGAATTATCCCTCACCACAACTACAATGCAGCCATTAACAAGT

ACAACCATGACATCGCCCTGCTGGAACTGGACGAACCCCTGGTGCTAAACAGCTACGTT

ACACCTATTTGCATCGCCGACAAGGAATACACGAACATCTTCCTCAAATTTGGATCTGG

CTATGTAAGCGGCTGGGGAAGAGTCTTCCACAAAGGGAGAAGCGCCCTGGTGCTTCAGT

ACCTGAGAGTGCCACTTGTGGACCGAGCCACATGTCTGCGAAGCACAAAGTTCACCATC

TACAACAACATGTTCTGCGCCGGCTTCCACGAAGGAGGTAGAGACTCATGCCAAGGAGA

TAGCGGGGGACCCCACGTGACCGAAGTGGAAGGGACCAGCTTCCTGACTGGAATTATTA

GCTGGGGCGAAGAGTGCGCAATGAAAGGCAAATATGGAATATACACCAAGGTAAGCCGG

TATGTCAACTGGATCAAGGAAAAAACAAAGCTCACCTAA

TEV-hF9-XbG sense strand, non-template.
3'_lowest_T. (1818 nt)
                                                   (SEQ ID NO: 63)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTGCTGGGATACCTACTCAGCGCCGAATG

CACAGTGTTCCTGGACCACGAAAACGCCAACAAAATCCTGAACCGGCCAAAGAGGTACA

ACAGCGGCAAACTGGAAGAGTTCGTGCAAGGGAACCTGGAGAGAGAATGCATGGAAGAA

AAGTGCAGCTTCGAAGAAGCACGAGAAGTGTTCGAAAACACCGAAAGAACAACCGAATT

CTGGAAGCAGTACGTGGACGGAGACCAGTGCGAGAGCAACCCATGCCTGAACGGCGGCA

GCTGCAAGGACGACATCAACAGCTACGAATGCTGGTGCCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTGGCAGAAA

ACCAGAAGTCCTGCGAACCAGCAGTGCCATTCCCATGCGGAAGAGTGAGCGTGAGCCAA

ACCAGCAAGCTCACCCGGGCCGAGACCGTGTTCCCCGACGTGGACTACGTAAACAGCAC

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCCCACCAC

AACTACAACGCAGCCATCAACAAGTACAACCACGACATCGCCCTGCTGGAACTGGACGA

ACCCCTGGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

GGGAGAAGCGCCCTGGTGCTGCAGTACCTGAGAGTGCCACTGGTGGACCGAGCCACATG

CCTGCGAAGCACAAAGTTCACCATCTACAACAACATGTTCTGCGCCGGCTTCCACGAAG

GAGGCAGAGACAGCTGCCAAGGAGACAGCGGGGGACCCCACGTGACCGAAGTGGAAGGG

ACCAGCTTCCTGACCGGAATCATCAGCTGGGGCGAAGAGTGCGCAATGAAAGGCAAATA

CGGAATATACACCAAGGTAAGCCGGTACGTCAACTGGATCAAGGAAAAAACAAAGCTCA

CCTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

AAAATGTAGCCATTCGTATCTGCTCCTAATAAAAAGAAAGTTTCTTCACATTCTAGAAA
```

-continued

AAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAA

TEV-hF9-XbG sense strand, non-template. 3'_14%_T.
(1818 nt)

(SEQ ID NO: 64)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAATCACCAGGCCTCATCACCATCTGCCTTTTAGGATATCTACTCAGTGCTGAATG

TACAGTTTTCCTGGACCACGAAAACGCCAACAAAATCCTGAACCGGCCAAAGAGGTACA

ACAGCGGCAAACTGGAAGAGTTCGTGCAAGGGAACCTGGAGAGAGAATGCATGGAAGAA

AAGTGCAGCTTCGAAGAAGCACGAGAAGTGTTCGAAAACACCGAAAGAACAACCGAATT

CTGGAAGCAGTACGTGGACGGAGACCAGTGCGAGAGCAACCCATGCCTGAACGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTGGCAGAAA

ACCAGAAGTCCTGCGAACCAGCAGTGCCATTCCCATGCGGAAGAGTGAGCGTGAGCCAA

ACCAGCAAGCTCACCCGGGCCGAGACCGTGTTCCCCGACGTGGACTACGTAAACAGCAC

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCCCACCAC

AACTACAACGCAGCCATCAACAAGTACAACCACGACATCGCCCTGCTGGAACTGGACGA

ACCCCTGGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

GGGAGAAGCGCCCTGGTGCTGCAGTACCTGAGAGTGCCACTGGTGGACCGAGCCACATG

CCTGCGAAGCACAAAGTTCACCATCTACAACAACATGTTCTGCGCCGGCTTCCACGAAG

GAGGCAGAGACAGCTGCCAAGGAGACAGCGGGGGACCCCACGTGACCGAAGTGGAAGGG

ACCAGCTTCCTGACCGGAATCATCAGCTGGGGCGAAGAGTGCGCAATGAAAGGCAAATA

CGGAATATACACCAAGGTAAGCCGGTACGTCAACTGGATCAAGGAAAAAACAAAGCTCA

CCTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

AAAATGTAGCCATTCGTATCTGCTCCTAATAAAAGAAAGTTTCTTCACATTCTAGAAA

AAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAA

TEV-hF9-XbG sense strand, non-template. 3'_16%_T.
(1818 nt)

(SEQ ID NO: 65)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAATCACCAGGCCTCATCACCATCTGCCTTTTAGGATATCTACTCAGTGCTGAATG

TACAGTTTTCTTGATCATGAAAACGCCAACAAAATTCTGAATCGGCCAAAGAGGTATA

-continued

```
ATTCAGGTAAATTGGAAGAGTTTGTTCAAGGGAACCTTGAGAGAGAATGTATGGAAGAA

AAGTGTAGTTTTGAAGAAGCACGAGAAGTTTTTGAAAACACTGAAAGAACAACTGAATT

TTGGAAGCAGTATGTTGATGGAGATCAGTGCGAGAGCAACCCATGCCTGAACGGCGGCA

GCTGCAAGGACGACATCAACAGCTACGATGCTGGTGCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTGGCAGAAA

ACCAGAAGTCCTGCGAACCAGCAGTGCCATTCCCATGCGGAAGAGTGAGCGTGAGCCAA

ACCAGCAAGCTCACCCGGGCCGAGACCGTGTTCCCCGACGTGGACTACGTAAACAGCAC

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCCCACCAC

AACTACAACGCAGCCATCAACAAGTACAACCACGACATCGCCCTGCTGGAACTGGACGA

ACCCCTGGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

GGGAGAAGCGCCCTGGTGCTGCAGTACCTGAGAGTGCCACTGGTGGACCGAGCCACATG

CCTGCGAAGCACAAAGTTCACCATCTACAACAACATGTTCTGCGCCGGCTTCCACGAAG

GAGGCAGAGACAGCTGCCAAGGAGACAGCGGGGGACCCCACGTGACCGAAGTGGAAGGG

ACCAGCTTCCTGACCGGAATCATCAGCTGGGGCGAAGAGTGCGCAATGAAAGGCAAATA

CGGAATATACACCAAGGTAAGCCGGTACGTCAACTGGATCAAGGAAAAAACAAAGCTCA

CCTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA
```

TEV-hF9-XbG sense strand, non-template. 3'_18%_T.
(1818 nt)

(SEQ ID NO: 66)

```
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAATCACCAGGCCTCATCACCATCTGCCTTTTAGGATATCTACTCAGTGCTGAATG

TACAGTTTTTCTTGATCATGAAAACGCCAACAAAATTCTGAATCGGCCAAAGAGGTATA

ATTCAGGTAAATTGGAAGAGTTTGTTCAAGGGAACCTTGAGAGAGAATGTATGGAAGAA

AAGTGTAGTTTTGAAGAAGCACGAGAAGTTTTTGAAAACACTGAAAGAACAACTGAATT

TTGGAAGCAGTATGTTGATGGAGATCAGTGTGAGTCCAATCCATGTTTAAATGGCGGCA

GTTGCAAGGATGACATTAATTCCTATGAATGTTGGTGTCCCTTTGGATTTGAAGGAAAG

AACTGTGAATTAGATGTAACATGTAACATTAAGAATGGCAGATGCGAGCAGTTTTGTAA

AAATAGTGCTGATAACAAGGTGGTGTGCAGCTGCACCGAGGGATACCGACTGGCAGAAA

ACCAGAAGTCCTGCGAACCAGCAGTGCCATTCCCATGCGGAAGAGTGAGCGTGAGCCAA

ACCAGCAAGCTCACCCGGGCCGAGACCGTGTTCCCCGACGTGGACTACGTAAACAGCAC
```

```
CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCCCACCAC

AACTACAACGCAGCCATCAACAAGTACAACCACGACATCGCCCTGCTGGAACTGGACGA

ACCCCTGGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

GGGAGAAGCGCCCTGGTGCTGCAGTACCTGAGAGTGCCACTGGTGGACCGAGCCACATG

CCTGCGAAGCACAAAGTTCACCATCTACAACAACATGTTCTGCGCCGGCTTCCACGAAG

GAGGCAGAGACAGCTGCCAAGGAGACAGCGGGGGACCCCACGTGACCGAAGTGGAAGGG

ACCAGCTTCCTGACCGGAATCATCAGCTGGGGCGAAGAGTGCGCAATGAAAGGCAAATA

CGGAATATACACCAAGGTAAGCCGGTACGTCAACTGGATCAAGGAAAAAACAAAGCTCA

CCTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAA

TEV-hF9-XbG sense strand, non-template. 3'_20%_T.
(1818 nt)
                                                    (SEQ ID NO: 67)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAATCACCAGGCCTCATCACCATCTGCCTTTTAGGATATCTACTCAGTGCTGAATG

TACAGTTTTTCTTGATCATGAAAACGCCAACAAAATTCTGAATCGGCCAAAGAGGTATA

ATTCAGGTAAATTGGAAGAGTTTGTTCAAGGGAACCTTGAGAGAGAATGTATGGAAGAA

AAGTGTAGTTTTGAAGAAGCACGAGAAGTTTTTGAAAACACTGAAAGAACAACTGAATT

TTGGAAGCAGTATGTTGATGGAGATCAGTGTGAGTCCAATCCATGTTTAAATGGCGGCA

GTTGCAAGGATGACATTAATTCCTATGAATGTTGGTGTCCCTTTGGATTTGAAGGAAAG

AACTGTGAATTAGATGTAACATGTAACATTAAGAATGGCAGATGCGAGCAGTTTTGTAA

AAATAGTGCTGATAACAAGGTGGTTTGCTCCTGTACTGAGGGATATCGACTTGCAGAAA

ACCAGAAGTCCTGTGAACCAGCAGTGCCATTTCCATGTGGAAGAGTTTCTGTTTCACAA

ACTTCTAAGCTCACCCGTGCTGAGACTGTTTTTCCTGATGTGGACTATGTAAATAGCAC

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCCCACCAC

AACTACAACGCAGCCATCAACAAGTACAACCACGACATCGCCCTGCTGGAACTGGACGA

ACCCCTGGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA
```

```
GGGAGAAGCGCCCTGGTGCTGCAGTACCTGAGAGTGCCACTGGTGGACCGAGCCACATG

CCTGCGAAGCACAAAGTTCACCATCTACAACAACATGTTCTGCGCCGGCTTCCACGAAG

GAGGCAGAGACAGCTGCCAAGGAGACAGCGGGGGACCCCACGTGACCGAAGTGGAAGGG

ACCAGCTTCCTGACCGGAATCATCAGCTGGGGCGAAGAGTGCGCAATGAAAGGCAAATA

CGGAATATACACCAAGGTAAGCCGGTACGTCAACTGGATCAAGGAAAAAACAAAGCTCA

CCTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA
```

TEV-hF9-XbG sense strand, non-template. 5'_14%_T.
(1818 nt)

(SEQ ID NO: 68)

```
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTGCTGGGATACCTACTCAGCGCCGAATG

CACAGTGTTCCTGGACCACGAAAACGCCAACAAAATCCTGAACCGGCCAAAGAGGTACA

ACAGCGGCAAACTGGAAGAGTTCGTGCAAGGGAACCTGGAGAGAGAATGCATGGAAGAA

AAGTGCAGCTTCGAAGAAGCACGAGAAGTGTTCGAAAACACCGAAAGAACAACCGAATT

CTGGAAGCAGTACGTGGACGGAGACCAGTGCGAGAGCAACCCATGCCTGAACGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTGGCAGAAA

ACCAGAAGTCCTGCGAACCAGCAGTGCCATTCCCATGCGGAAGAGTGAGCGTGAGCCAA

ACCAGCAAGCTCACCCGGGCCGAGACCGTGTTCCCCGACGTGGACTACGTAAACAGCAC

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCCCACCAC

AACTACAACGCAGCCATCAACAAGTACAACCACGACATCGCCCTGCTGGAACTGGACGA

ACCCCTGGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

GGGAGAAGCGCCCTGGTGCTGCAGTACCTGAGAGTGCCACTGGTGGACCGAGCCACATG

CCTGCGAAGCACAAAGTTCACCATCTACAACAACATGTTCTGCGCCGGCTTCCACGAAG

GAGGCAGAGACAGCTGCCAAGGAGACAGCGGGGGACCCCACGTGACCGAAGTGGAAGGG

ACCAGCTTCCTGACCGGAATCATCAGCTGGGGTGAAGAGTGTGCAATGAAAGGCAAATA

TGGAATATATACCAAGGTATCCCGGTATGTCAACTGGATTAAGGAAAAAACAAAGCTCA

CTTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

AAAATGTAGCCATTCGTATCTGCTCCTAATAAAAAGAAAGTTTCTTCACATTCTAGAAA
```

-continued

AAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAA

TEV-hF9-XbG sense strand, non-template. 5'_16%_T.
(1818 nt)

(SEQ ID NO: 69)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTGCTGGGATACCTACTCAGCGCCGAATG

CACAGTGTTCCTGGACCACGAAAACGCCAACAAAATCCTGAACCGGCCAAAGAGGTACA

ACAGCGGCAAACTGGAAGAGTTCGTGCAAGGGAACCTGGAGAGAGAATGCATGGAAGAA

AAGTGCAGCTTCGAAGAAGCACGAGAAGTGTTCGAAAACACCGAAAGAACAACCGAATT

CTGGAAGCAGTACGTGGACGGAGACCAGTGCGAGAGCAACCCATGCCTGAACGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTGGCAGAAA

ACCAGAAGTCCTGCGAACCAGCAGTGCCATTCCCATGCGGAAGAGTGAGCGTGAGCCAA

ACCAGCAAGCTCACCCGGGCCGAGACCGTGTTCCCCGACGTGGACTACGTAAACAGCAC

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCCCACCAC

AACTACAACGCAGCCATCAACAAGTACAACCACGACATCGCCCTGCTGGAACTGGACGA

ACCCCTGGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

GGGAGAAGCGCCCTGGTGCTTCAGTACCTTAGAGTTCCACTTGTTGACCGAGCCACATG

TCTTCGATCTACAAAGTTCACCATCTATAACAACATGTTCTGTGCTGGCTTCCATGAAG

GAGGTAGAGATTCATGTCAAGGAGATAGTGGGGGACCCCATGTTACTGAAGTGGAAGGG

ACCAGTTTCTTAACTGGAATTATTAGCTGGGGTGAAGAGTGTGCAATGAAAGGCAAATA

TGGAATATATACCAAGGTATCCCGGTATGTCAACTGGATTAAGGAAAAAACAAAGCTCA

CTTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAA

TEV-hF9-XbG sense strand, non-template. 5'_18%_T.
(1818 nt)

(SEQ ID NO: 70)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTGCTGGGATACCTACTCAGCGCCGAATG

-continued

```
CACAGTGTTCCTGGACCACGAAAACGCCAACAAATCCTGAACCGGCCAAAGAGGTACA

ACAGCGGCAAACTGGAAGAGTTCGTGCAAGGGAACCTGGAGAGAGAATGCATGGAAGAA

AAGTGCAGCTTCGAAGAAGCACGAGAAGTGTTCGAAAACACCGAAAGAACAACCGAATT

CTGGAAGCAGTACGTGGACGGAGACCAGTGCGAGAGCAACCCATGCCTGAACGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTGGCAGAAA

ACCAGAAGTCCTGCGAACCAGCAGTGCCATTCCCATGCGGAAGAGTGAGCGTGAGCCAA

ACCAGCAAGCTCACCCGGGCCGAGACCGTGTTCCCCGACGTGGACTACGTAAACAGCAC

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACATACAGAGCAAAAGCGAAATGTGATTCGAATTATTCCTCACCAC

AACTACAATGCAGCTATTAATAAGTACAACCATGACATTGCCCTTCTGGAACTGGACGA

ACCCTTAGTGCTAAACAGCTACGTTACACCTATTTGCATTGCTGACAAGGAATACACGA

ACATCTTCCTCAAATTTGGATCTGGCTATGTAAGTGGCTGGGGAAGAGTCTTCCACAAA

GGGAGATCAGCTTTAGTTCTTCAGTACCTTAGAGTTCCACTTGTTGACCGAGCCACATG

TCTTCGATCTACAAAGTTCACCATCTATAACAACATGTTCTGTGCTGGCTTCCATGAAG

GAGGTAGAGATTCATGTCAAGGAGATAGTGGGGGACCCCATGTTACTGAAGTGGAAGGG

ACCAGTTTCTTAACTGGAATTATTAGCTGGGGTGAAGAGTGTGCAATGAAAGGCAAATA

TGGAATATATACCAAGGTATCCCGGTATGTCAACTGGATTAAGGAAAAAACAAAGCTCA

CTTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAA

TEV-hF9-XbG sense strand, non-template. 5'_20%_T.
(1818 nt)
                                            (SEQ ID NO: 71)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTGCTGGGATACCTACTCAGCGCCGAATG

CACAGTGTTCCTGGACCACGAAAACGCCAACAAATCCTGAACCGGCCAAAGAGGTACA

ACAGCGGCAAACTGGAAGAGTTCGTGCAAGGGAACCTGGAGAGAGAATGCATGGAAGAA

AAGTGCAGCTTCGAAGAAGCACGAGAAGTGTTCGAAAACACCGAAAGAACAACCGAATT

CTGGAAGCAGTACGTGGACGGAGACCAGTGCGAGAGCAACCCATGCCTGAACGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTGGCAGAAA

ACCAGAAGTCCTGCGAACCAGCAGTGCCATTCCCATGCGGAAGAGTGAGCGTGAGCCAA
```

-continued
```
ACCAGCAAGCTCACCCGGGCCGAGACCGTGTTCCCCGACGTGGACTACGTAAACAGCAC

CGAAGCCGAAACCATCCTGGACAACATCACCCAAAGCACCCAAAGCTTCAACGACTTCA

CCCGGGTGGTGGGCGGAGAAGACGCCAAACCAGGTCAATTCCCTTGGCAGGTTGTTTTG

AATGGTAAAGTTGATGCATTCTGTGGAGGCTCTATCGTTAATGAAAAATGGATTGTAAC

TGCTGCCCACTGTGTTGAAACTGGTGTTAAAATTACAGTTGTCGCAGGTGAACATAATA

TTGAGGAGACAGAACATACAGAGCAAAAGCGAAATGTGATTCGAATTATTCCTCACCAC

AACTACAATGCAGCTATTAATAAGTACAACCATGACATTGCCCTTCTGGAACTGGACGA

ACCCTTAGTGCTAAACAGCTACGTTACACCTATTTGCATTGCTGACAAGGAATACACGA

ACATCTTCCTCAAATTTGGATCTGGCTATGTAAGTGGCTGGGGAAGAGTCTTCCACAAA

GGGAGATCAGCTTTAGTTCTTCAGTACCTTAGAGTTCCACTTGTTGACCGAGCCACATG

TCTTCGATCTACAAAGTTCACCATCTATAACAACATGTTCTGTGCTGGCTTCCATGAAG

GAGGTAGAGATTCATGTCAAGGAGATAGTGGGGGACCCCATGTTACTGAAGTGGAAGGG

ACCAGTTTCTTAACTGGAATTATTAGCTGGGGTGAAGAGTGTGCAATGAAAGGCAAATA

TGGAATATATACCAAGGTATCCCGGTATGTCAACTGGATTAAGGAAAAAACAAAGCTCA

CTTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAA

TEV-hF9-XbG sense strand, non-template.
random_14%_T. (1818 nt)
                                                    (SEQ ID NO: 72)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTGCTGGGATATCTACTCAGCGCCGAATG

CACAGTGTTCCTGGACCACGAAAACGCCAACAAAATCCTGAACCGGCCAAAGAGGTACA

ACAGCGGTAAACTGGAAGAGTTCGTGCAAGGGAACCTGGAGAGAGAATGCATGGAAGAA

AAGTGCAGCTTCGAAGAAGCACGAGAAGTGTTCGAAAACACCGAAAGAACAACCGAATT

CTGGAAGCAGTACGTGGACGGAGACCAGTGCGAGAGCAACCCATGCCTGAACGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTTGCAGAAA

ACCAGAAGTCCTGCGAACCAGCAGTGCCATTCCCATGCGGAAGAGTGAGCGTTAGCCAA

ACCAGCAAGCTCACCCGGGCCGAGACCGTGTTCCCCGACGTGGACTACGTAAACAGCAC

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTTAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCTCACCAC

AACTACAACGCAGCCATCAACAAGTACAACCACGACATCGCCCTGCTGGAACTGGACGA

ACCCTTAGTGCTAAACAGCTACGTGACACCCATCTGCATCGCCGACAAGGAATACACGA
```

-continued

ACATCTTCCTCAAATTCGGAAGCGGCTACGTAAGCGGCTGGGGAAGAGTCTTCCACAAA

GGGAGAAGCGCCCTGGTGCTGCAGTACCTGAGAGTGCCACTGGTGGACCGAGCCACATG

CCTGCGAAGCACAAAGTTCACCATCTACAACAACATGTTCTGCGCCGGCTTCCACGAAG

GAGGCAGAGACAGCTGCCAAGGAGACAGCGGGGGACCCCACGTGACCGAAGTGGAAGGG

ACCAGCTTCCTGACCGGAATCATCAGCTGGGGCGAAGAGTGTGCAATGAAAGGCAAATA

CGGAATATACACCAAGGTAAGCCGGTACGTCAACTGGATCAAGGAAAAAACAAAGCTCA

CCTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA

TEV-hF9-XbG sense strand, non-template.
random_16%_T. (1818 nt)

(SEQ ID NO: 73)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTGCTGGGATACCTACTCAGTGCCGAATG

TACAGTGTTCCTGGACCACGAAAACGCCAACAAAATCCTGAACCGGCCAAAGAGGTACA

ACTCAGGCAAACTGGAAGAGTTCGTGCAAGGGAACCTGGAGAGAGAATGCATGGAAGAA

AAGTGCAGCTTCGAAGAAGCACGAGAAGTGTTTGAAAACACTGAAAGAACAACCGAATT

TTGGAAGCAGTACGTGGATGGAGATCAGTGCGAGAGCAACCCATGCCTGAATGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTTTGTAA

AAACAGCGCCGACAACAAGGTGGTGTGCAGCTGCACCGAGGGATACCGACTGGCAGAAA

ACCAGAAGTCCTGCGAACCAGCAGTGCCATTCCCATGCGGAAGAGTGTCTGTGTCACAA

ACCAGCAAGCTCACCCGGGCCGAGACCGTGTTCCCCGACGTGGACTACGTAAACAGCAC

CGAAGCCGAAACCATCCTGGATAACATCACCCAAAGCACCCAAAGCTTCAATGACTTCA

CCCGGGTGGTGGGCGGAGAAGACGCCAAACCAGGCCAATTCCCCTGGCAGGTTGTGCTG

AACGGCAAAGTTGACGCATTCTGCGGAGGCAGCATCGTGAACGAAAAATGGATCGTAAC

CGCTGCCCACTGCGTTGAAACCGGCGTGAAAATCACAGTGGTCGCAGGCGAACACAACA

TTGAGGAGACAGAACACACAGAGCAAAAGCGAAACGTGATCCGAATTATCCCCCACCAC

AACTACAACGCAGCCATTAATAAGTACAACCATGACATCGCCCTGCTGGAACTGGACGA

ACCCTTAGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

GGGAGAAGCGCCCTGGTTCTGCAGTACCTGAGAGTGCCACTGGTTGACCGAGCCACATG

CCTGCGAAGCACAAAGTTCACCATCTACAACAACATGTTCTGCGCCGGCTTCCATGAAG

GAGGTAGAGACAGCTGTCAAGGAGACAGCGGGGGACCCCACGTTACTGAAGTGGAAGGG

ACCAGCTTCCTGACCGGAATCATCAGCTGGGGCGAAGAGTGCGCAATGAAAGGCAAATA

CGGAATATATACCAAGGTAAGCCGGTACGTCAACTGGATCAAGGAAAAAACAAAGCTCA

CTTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

```
AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAA

TEV-hF9-XbG sense strand, non-template.
random_18%_T. (1818 nt)
                                                       (SEQ ID NO: 74)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAATCACCAGGCCTCATCACCATCTGCCTGTTAGGATACCTACTCAGCGCCGAATG

TACAGTGTTTCTTGACCACGAAAACGCCAACAAAATCCTGAATCGGCCAAAGAGGTATA

ACTCAGGTAAACTGGAAGAGTTTGTGCAAGGGAACCTGGAGAGAATGCATGGAAGAA

AAGTGCAGCTTCGAAGAAGCACGAGAAGTGTTCGAAAACACTGAAAGAACAACCGAATT

TTGGAAGCAGTATGTGGATGGAGACCAGTGCGAGTCCAACCCATGCTTAAACGGCGGCA

GTTGCAAGGACGACATCAACAGCTATGAATGCTGGTGCCCCTTCGGATTTGAAGGAAAG

AACTGCGAACTGGACGTAACATGTAACATCAAGAATGGCAGATGCGAGCAGTTCTGTAA

AAATAGCGCCGACAACAAGGTGGTGTGCAGCTGTACCGAGGGATACCGACTGGCAGAAA

ACCAGAAGTCCTGCGAACCAGCAGTGCCATTCCCATGCGGAAGAGTTAGCGTGAGCCAA

ACCAGCAAGCTCACCCGGGCCGAGACCGTGTTCCCTGACGTGGACTACGTAAACTCTAC

CGAAGCTGAAACCATCCTGGACAACATCACTCAAAGCACCCAATCATTCAACGACTTCA

CCCCGGGTGGTGGGCGGAGAAGATGCCAAACCAGGTCAATTCCCTTGGCAGGTGGTGTTG

AACGGCAAAGTGGACGCATTCTGTGGAGGCAGCATCGTGAACGAAAAATGGATCGTAAC

TGCCGCCCACTGCGTGGAAACCGGCGTGAAAATCACAGTGGTCGCAGGCGAACACAATA

TTGAGGAGACAGAACACACAGAGCAAAAGCGAAATGTGATCCGAATTATCCCTCACCAC

AACTACAACGCAGCTATTAACAAGTACAACCACGACATTGCCCTGCTGGAACTGGACGA

ACCCCTGGTGCTAAACAGCTACGTTACACCTATCTGCATCGCCGACAAGGAATACACGA

ACATCTTCCTCAAATTCGGATCTGGCTACGTAAGCGGCTGGGGAAGAGTCTTCCACAAA

GGGAGATCAGCCCTGGTGCTTCAGTACCTTAGAGTGCCACTTGTGGACCGAGCCACATG

CCTGCGAAGCACAAAGTTCACCATCTACAACAACATGTTCTGTGCTGGCTTCCACGAAG

GAGGTAGAGACAGCTGTCAAGGAGATAGCGGGGGACCCCACGTTACCGAAGTGGAAGGG

ACCAGCTTCTTAACTGGAATCATCAGCTGGGGCGAAGAGTGCGCAATGAAAGGCAAATA

CGGAATATACACCAAGGTATCCCGGTATGTCAACTGGATCAAGGAAAAAACAAAGCTCA

CCTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAA

TEV-hF9-XbG sense strand, non-template.
random_20%_T. (1818 nt)
                                                       (SEQ ID NO: 75)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTTCTGGGATATCTACTCAGCGCCGAATG
```

```
CACAGTTTTCCTTGACCACGAAAACGCCAACAAAATCCTGAATCGGCCAAAGAGGTATA

ATTCAGGTAAACTGGAAGAGTTTGTTCAAGGGAACCTTGAGAGAGAATGCATGGAAGAA

AAGTGTAGTTTTGAAGAAGCACGAGAAGTGTTCGAAAACACCGAAAGAACAACCGAATT

TTGGAAGCAGTATGTGGATGGAGACCAGTGCGAGAGCAATCCATGCTTAAATGGCGGCA

GCTGCAAGGACGACATTAATTCCTATGAATGCTGGTGCCCCTTTGGATTCGAAGGAAAG

AACTGCGAATTAGACGTAACATGCAACATCAAGAACGGCAGATGCGAGCAGTTTTGTAA

AAATAGTGCTGACAACAAGGTGGTTTGCAGCTGCACCGAGGGATACCGACTGGCAGAAA

ACCAGAAGTCCTGCGAACCAGCAGTGCCATTCCCATGTGGAAGAGTTTCTGTGAGCCAA

ACTTCTAAGCTCACCCGTGCCGAGACCGTTTTCCCTGACGTGGACTATGTAAATTCTAC

CGAAGCCGAAACCATTTTGGATAACATCACCCAAAGCACCCAAAGCTTTAACGACTTCA

CTCGGGTGGTTGGCGGAGAAGACGCCAAACCAGGCCAATTCCCTTGGCAGGTGGTTCTG

AATGGCAAAGTGGATGCATTCTGTGGAGGCTCTATCGTGAACGAAAAATGGATCGTAAC

TGCCGCCCACTGCGTTGAAACCGGCGTTAAAATTACAGTGGTCGCAGGCGAACACAATA

TTGAGGAGACAGAACACACAGAGCAAAAGCGAAACGTGATTCGAATTATCCCTCACCAC

AACTACAATGCAGCCATTAACAAGTACAACCATGACATCGCCCTGCTGGAACTGGACGA

ACCCCTGGTGCTAAACAGCTACGTTACACCTATTTGCATCGCCGACAAGGAATACACGA

ACATCTTCCTCAAATTTGGATCTGGCTATGTAAGCGGCTGGGGAAGAGTCTTCCACAAA

GGGAGAAGCGCCCTGGTGCTTCAGTACCTGAGAGTGCCACTTGTGGACCGAGCCACATG

TCTGCGAAGCACAAAGTTCACCATCTACAACAACATGTTCTGCGCCGGCTTCCACGAAG

GAGGTAGAGACTCATGCCAAGGAGATAGCGGGGGACCCCACGTGACCGAAGTGGAAGGG

ACCAGCTTCCTGACTGGAATTATTAGCTGGGGCGAAGAGTGCGCAATGAAAGGCAAATA

TGGAATATACACCAAGGTAAGCCGGTATGTCAACTGGATCAAGGAAAAAACAAAGCTCA

CCTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA
TEV-hF9-XbG ARC-mRNA. 3'_lowest_T. (1818 nt)
                                                (SEQ ID NO: 76)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAAGCC

CAGGCCUCAUCACCAUCUGCCUGCUGGGAUACCUACUCAGCGCCGAAUGCACAGUGUUC

CUGGACCACGAAAACGCCAACAAAAUCCUGAACCGGCCAAAGAGGUACAACAGCGGCAA

ACUGGAAGAGUUCGUGCAAGGGAACCUGGAGAGAGAAUGCAUGGAAGAAAAGUGCAGCU

UCGAAGAAGCACGAGAAGUGUUCGAAAACACCGAAAGAACAACCGAAUUCUGGAAGCAG

UACGUGGACGGAGACCAGUGCGAGAGCAACCCAUGCCUGAACGGCGGCAGCUGCAAGGA

CGACAUCAACAGCUACGAAUGCUGGUGCCCCUUCGGAUUCGAAGGAAAGAACUGCGAAC

UGGACGUAACAUGCAACAUCAAGAACGGCAGAUGCGAGCAGUUCUGCAAAAACAGCGCC

GACAACAAGGUGGUGUGCAGCUGCACCGAGGGAUACCGACUGGCAGAAAACCAGAAGUC
```

```
CUGCGAACCAGCAGUGCCAUUCCCAUGCGGAAGAGUGAGCGUGAGCCAAACCAGCAAGC

UCACCCGGGCCGAGACCGUGUUCCCCGACGUGGACUACGUAAACAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUGAACGAAAAAUGGAUCGUAACCGCCGCCCAC

UGCGUGGAAACCGGCGUGAAAAUCACAGUGGUCGCAGGCGAACACAACAUCGAGGAGAC

AGAACACACAGAGCAAAAGCGAAACGUGAUCCGAAUCAUCCCCCACCACAACUACAACG

CAGCCAUCAACAAGUACAACCACGACAUCGCCCUGCUGGAACUGGACGAACCCCUGGUG

CUAAACAGCUACGUGACACCCAUCUGCAUCGCCGACAAGGAAUACACGAACAUCUUCCU

CAAAUUCGGAAGCGGCUACGUAAGCGGCUGGGGAAGAGUCUUCCACAAAGGGAGAAGCG

CCCUGGUGCUGCAGUACCUGAGAGUGCCACUGGUGGACCGAGCCACAUGCCUGCGAAGC

ACAAAGUUCACCAUCUACAACAACAUGUUCUGCGCCGGCUUCCACGAAGGAGGCAGAGA

CAGCUGCCAAGGAGACAGCGGGGGACCCCACGUGACCGAAGUGGAAGGGACCAGCUUCC

UGACCGGAAUCAUCAGCUGGGGCGAAGAGUGCGCAAUGAAAGGCAAAUACGGAAUAUAC

ACCAAGGUAAGCCGGUACGUCAACUGGAUCAAGGAAAAAACAAAGCUCACCUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAA

TEV-hF9-XbG ARC-mRNA. 3'_14%_T. (1818 nt)
                                                                (SEQ ID NO: 77)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAUCAC

CAGGCCUCAUCACCAUCUGCCUUUUAGGAUAUCUACUCAGUGCUGAAUGUACAGUUUUC

CUGGACCACGAAAACGCCAACAAAAUCCUGAACCGGCCAAAGAGGUACAACAGCGGCAA

ACUGGAAGAGUUCGUGCAAGGGAACCUGGAGAGAGAAUGCAUGGAAGAAAAGUGCAGCU

UCGAAGAAGCACGAGAAGUGUUCGAAAACACCGAAAGAACAACCGAAUUCUGGAAGCAG

UACGUGGACGGAGACCAGUGCGAGAGCAACCCAUGCCUGAACGGCGGCAGCUGCAAGGA

CGACAUCAACAGCUACGAAUGCUGGUGCCCCUUCGGAUUCGAAGGAAAGAACUGCGAAC

UGGACGUAACAUGCAACAUCAAGAACGGCAGAUGCGAGCAGUUCUGCAAAAACAGCGCC

GACAACAAGGUGGGUGCAGCUGCACCGAGGGAUACCGACUGGCAGAAAACCAGAAGUC

CUGCGAACCAGCAGUGCCAUUCCCAUGCGGAAGAGUGAGCGUGAGCCAAACCAGCAAGC

UCACCCGGGCCGAGACCGUGUUCCCCGACGUGGACUACGUAAACAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUGAACGAAAAAUGGAUCGUAACCGCCGCCCAC

UGCGUGGAAACCGGCGUGAAAAUCACAGUGGUCGCAGGCGAACACAACAUCGAGGAGAC

AGAACACACAGAGCAAAAGCGAAACGUGAUCCGAAUCAUCCCCCACCACAACUACAACG

CAGCCAUCAACAAGUACAACCACGACAUCGCCCUGCUGGAACUGGACGAACCCCUGGUG
```

-continued

CUAAACAGCUACGUGACACCCAUCUGCAUCGCCGACAAGGAAUACACGAACAUCUUCCU

CAAAUUCGGAAGCGGCUACGUAAGCGGCUGGGGAAGAGUCUUCCACAAAGGGAGAAGCG

CCCUGGUGCUGCAGUACCUGAGAGUGCCACUGGUGGACCGAGCCACAUGCCUGCGAAGC

ACAAAGUUCACCAUCUACAACAACAUGUUCUGCGCCGGCUUCCACGAAGGAGGCAGAGA

CAGCUGCCAAGGAGACAGCGGGGGACCCCACGUGACCGAAGUGGAAGGGACCAGCUUCC

UGACCGGAAUCAUCAGCUGGGGCGAAGAGUGCGCAAUGAAAGGCAAAUACGGAAUAUAC

ACCAAGGUAAGCCGGUACGUCAACUGGAUCAAGGAAAAAACAAAGCUCACCUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA

TEV-hF9-XbG ARC-mRNA. 3'_16%_T. (1818 nt)
(SEQ ID NO: 78)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAUCAC

CAGGCCUCAUCACCAUCUGCCUUUUAGGAUAUCUACUCAGUGCUGAAUGUACAGUUUUU

CUUGAUCAUGAAAACGCCAACAAAAUUCUGAAUCGGCCAAAGAGGUAUAAUUCAGGUAA

AUUGGAAGAGUUUGUUCAAGGGAACCUUGAGAGAGAAUGUAUGGAAGAAAAGUGUAGUU

UUGAAGAAGCACGAGAAGUUUUUGAAAACACUGAAAGAACAACUGAAUUUUGGAAGCAG

UAUGUUGAUGGAGAUCAGUGCGAGAGCAACCCAUGCCUGAACGGCGGCAGCUGCAAGGA

CGACAUCAACAGCUACGAAUGCUGGUGCCCCUUCGGAUUCGAAGGAAAGAACUGCGAAC

UGGACGUAACAUGCAACAUCAAGAACGGCAGAUGCGAGCAGUUCUGCAAAAACAGCGCC

GACAACAAGGUGGUGUGCAGCUGCACCGAGGGAUACCGACUGGCAGAAAACCAGAAGUC

CUGCGAACCAGCAGUGCCAUUCCCAUGCGGAAGAGUGAGCGUGAGCCAAACCAGCAAGC

UCACCCGGGCCGAGACCGUGUUCCCCGACGUGGACUACGUAAACAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUGAACGAAAAAUGGAUCGUAACCGCCGCCCAC

UGCGUGGAAACCGGCGUGAAAAUCACAGUGGUCGCAGGCGAACACAACAUCGAGGAGAC

AGAACACACAGAGCAAAAGCGAAACGUGAUCCGAAUCAUCCCCCACCACAACUACAACG

CAGCCAUCAACAAGUACAACCACGACAUCGCCCUGCUGGAACUGGACGAACCCCUGGUG

CUAAACAGCUACGUGACACCCAUCUGCAUCGCCGACAAGGAAUACACGAACAUCUUCCU

CAAAUUCGGAAGCGGCUACGUAAGCGGCUGGGGAAGAGUCUUCCACAAAGGGAGAAGCG

CCCUGGUGCUGCAGUACCUGAGAGUGCCACUGGUGGACCGAGCCACAUGCCUGCGAAGC

ACAAAGUUCACCAUCUACAACAACAUGUUCUGCGCCGGCUUCCACGAAGGAGGCAGAGA

CAGCUGCCAAGGAGACAGCGGGGGACCCCACGUGACCGAAGUGGAAGGGACCAGCUUCC

UGACCGGAAUCAUCAGCUGGGGCGAAGAGUGCGCAAUGAAAGGCAAAUACGGAAUAUAC

ACCAAGGUAAGCCGGUACGUCAACUGGAUCAAGGAAAAAACAAAGCUCACCUAACUCGA

-continued

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA

TEV-hF9-XbG ARC-mRNA. 3'_18%_T. (1818 nt)

(SEQ ID NO: 79)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAUCAC

CAGGCCUCAUCACCAUCUGCCUUUUAGGAUAUCUACUCAGUGCUGAAUGUACAGUUUUU

CUUGAUCAUGAAAACGCCAACAAAAUUCUGAAUCGGCCAAAGAGGUAUAAUUCAGGUAA

AUUGGAAGAGUUUGUUCAAGGGAACCUUGAGAGAGAAUGUAUGGAAGAAAAGUGUAGUU

UUGAAGAAGCACGAGAAGUUUUUGAAAACACUGAAAGAACAACUGAAUUUUGGAAGCAG

UAUGUUGAUGGAGAUCAGUGUGAGUCCAAUCCAUGUUUAAAUGGCGGCAGUUGCAAGGA

UGACAUUAAUUCCUAUGAAUGUUGGUGUCCCUUUGGAUUUGAAGGAAAGAACUGUGAAU

UAGAUGUAACAUGUAACAUUAAGAAUGGCAGAUGCGAGCAGUUUUGUAAAAAUAGUGCU

GAUAACAAGGUGGUGUGCAGCUGCACCGAGGGAUACCGACUGGCAGAAAACCAGAAGUC

CUGCGAACCAGCAGUGCCAUUCCCAUGCGGAAGAGUGAGCGUGAGCCAAACCAGCAAGC

UCACCCGGGCCGAGACCGUGUUCCCCGACGUGGACUACGUAAACAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUGAACGAAAAAUGGAUCGUAACCGCCGCCCAC

UGCGUGGAAACCGGCGUGAAAAUCACAGUGGUCGCAGGCGAACACAACAUCGAGGAGAC

AGAACACACAGAGCAAAAGCGAAACGUGAUCCGAAUCAUCCCCCACCACAACUACAACG

CAGCCAUCAACAAGUACAACCACGACAUCGCCCUGCUGGAACUGGACGAACCCCUGGUG

CUAAACAGCUACGUGACACCCAUCUGCAUCGCCGACAAGGAAUACACGAACAUCUUCCU

CAAAUUCGGAAGCGGCUACGUAAGCGGCUGGGGAAGAGUCUUCCACAAAGGGAGAAGCG

CCCUGGUGCUGCAGUACCUGAGAGUGCCACUGGUGGACCGAGCCACAUGCCUGCGAAGC

ACAAAGUUCACCAUCUACAACAACAUGUUCUGCGCCGGCUUCCACGAAGGAGGCAGAGA

CAGCUGCCAAGGAGACAGCGGGGGACCCCACGUGACCGAAGUGGAAGGGACCAGCUUCC

UGACCGGAAUCAUCAGCUGGGGCGAAGAGUGCGCAAUGAAAGGCAAAUACGGAAUAUAC

ACCAAGGUAAGCCGGUACGUCAACUGGAUCAAGGAAAAAACAAAGCUCACCUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA

TEV-hF9-XbG ARC-mRNA. 3'_20%_T. (1818 nt)

(SEQ ID NO: 80)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAUCAC

CAGGCCUCAUCACCAUCUGCCUUUUAGGAUAUCUACUCAGUGCUGAAUGUACAGUUUUU

CUUGAUCAUGAAAACGCCAACAAAAUUCUGAAUCGGCCAAAGAGGUAUAAUUCAGGUAA

AUUGGAAGAGUUUGUUCAAGGGAACCUUGAGAGAGAAUGUAUGGAAGAAAAGUGUAGUU

UUGAAGAAGCACGAGAAGUUUUUGAAAACACUGAAAGAACAACUGAAUUUUGGAAGCAG

UAUGUUGAUGGAGAUCAGUGUGAGUCCAAUCCAUGUUUAAAUGGCGGCAGUUGCAAGGA

UGACAUUAAUUCCUAUGAAUGUUGGUGUCCCUUUGGAUUUGAAGGAAAGAACUGUGAAU

UAGAUGUAACAUGUAACAUUAAGAAUGGCAGAUGCGAGCAGUUUUGUAAAAAUAGUGCU

GAUAACAAGGUGGUUUGCUCCUGUACUGAGGGAUAUCGACUUGCAGAAAACCAGAAGUC

CUGUGAACCAGCAGUGCCAUUUCCAUGUGGAAGAGUUUCUGUUUCACAAACUUCUAAGC

UCACCCGUGCUGAGACUGUUUUUCCUGAUGUGGACUAUGUAAAUAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUGAACGAAAAAUGGAUCGUAACCGCCGCCCAC

UGCGUGGAAACCGGCGUGAAAAUCACAGUGGUCGCAGGCGAACACAACAUCGAGGAGAC

AGAACACACAGAGCAAAAGCGAAACGUGAUCCGAAUCAUCCCCCACCACAACUACAACG

CAGCCAUCAACAAGUACAACCACGACAUCGCCCUGCUGGAACUGGACGAACCCCUGGUG

CUAAACAGCUACGUGACACCCAUCUGCAUCGCCGACAAGGAAUACACGAACAUCUUCCU

CAAAUUCGGAAGCGGCUACGUAAGCGGCUGGGGAAGAGUCUUCCACAAAGGGAGAAGCG

CCCUGGUGCUGCAGUACCUGAGAGUGCCACUGGUGGACCGAGCCACAUGCCUGCGAAGC

ACAAAGUUCACCAUCUACAACAACAUGUUCUGCGCCGGCUUCCACGAAGGAGGCAGAGA

CAGCUGCCAAGGAGACAGCGGGGGACCCCACGUGACCGAAGUGGAAGGGACCAGCUUCC

UGACCGGAAUCAUCAGCUGGGGCGAAGAGUGCGCAAUGAAAGGCAAAUACGGAAUAUAC

ACCAAGGUAAGCCGGUACGUCAACUGGAUCAAGGAAAAAACAAAGCUCACCUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA

TEV-hF9-XbG ARC-mRNA. 5'_14%_T. (1818 nt)

(SEQ ID NO: 81)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAAGCC

CAGGCCUCAUCACCAUCUGCCUGCUGGGAUACCUACUCAGCGCCGAAUGCACAGUGUUC

CUGGACCACGAAAACGCCAACAAAAUCCUGAACCGGCCAAAGAGGUACAACAGCGGCAA

```
ACUGGAAGAGUUCGUGCAAGGGAACCUGGAGAGAGAAUGCAUGGAAGAAAAGUGCAGCU

UCGAAGAAGCACGAGAAGUGUUCGAAAACACCGAAAGAACAACCGAAUUCUGGAAGCAG

UACGUGGACGGAGACCAGUGCGAGAGCAACCCAUGCCUGAACGGCGGCAGCUGCAAGGA

CGACAUCAACAGCUACGAAUGCUGGUGCCCCUUCGGAUUCGAAGGAAAGAACUGCGAAC

UGGACGUAACAUGCAACAUCAAGAACGGCAGAUGCGAGCAGUUCUGCAAAAACAGCGCC

GACAACAAGGUGGUGUGCAGCUGCACCGAGGGAUACCGACUGGCAGAAAACCAGAAGUC

CUGCGAACCAGCAGUGCCAUUCCCAUGCGGAAGAGUGAGCGUGAGCCAAACCAGCAAGC

UCACCCGGGCCGAGACCGUGUUCCCCGACGUGGACUACGUAAACAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUGAACGAAAAAUGGAUCGUAACCGCCGCCCAC

UGCGUGGAAACCGGCGUGAAAAUCACAGUGGUCGCAGGCGAACACAACAUCGAGGAGAC

AGAACACACAGAGCAAAAGCGAAACGUGAUCCGAAUCAUCCCCCACCACAACUACAACG

CAGCCAUCAACAAGUACAACCACGACAUCGCCCUGCUGGAACUGGACGAACCCCUGGUG

CUAAACAGCUACGUGACACCCAUCUGCAUCGCCGACAAGGAAUACACGAACAUCUUCCU

CAAAUUCGGAAGCGGCUACGUAAGCGGCUGGGGAAGAGUCUUCCACAAAGGGAGAAGCG

CCCUGGUGCUGCAGUACCUGAGAGUGCCACUGGUGGACCGAGCCACAUGCCUGCGAAGC

ACAAAGUUCACCAUCUACAACAACAUGUUCUGCGCCGGCUUCCACGAAGGAGGCAGAGA

CAGCUGCCAAGGAGACAGCGGGGGACCCCACGUGACCGAAGUGGAAGGGACCAGCUUCC

UGACCGGAAUCAUCAGCUGGGGUGAAGAGUGUGCAAUGAAAGGCAAAUAUGGAAUAUAU

ACCAAGGUAUCCCGGUAUGUCAACUGGAUUAAGGAAAAAACAAAGCUCACUUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA
```

TEV-hF9-XbG ARC-mRNA. 5'_16%_T. (1818 nt)  (SEQ ID NO: 82)

5'-cap-

```
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAAGCC

CAGGCCUCAUCACCAUCUGCCUGCUGGGAUACCUACUCAGCGCCGAAUGCACAGUGUUC

CUGGACCACGAAAACGCCAACAAAAUCCUGAACCGGCCAAAGAGGUACAACAGCGGCAA

ACUGGAAGAGUUCGUGCAAGGGAACCUGGAGAGAGAAUGCAUGGAAGAAAAGUGCAGCU

UCGAAGAAGCACGAGAAGUGUUCGAAAACACCGAAAGAACAACCGAAUUCUGGAAGCAG

UACGUGGACGGAGACCAGUGCGAGAGCAACCCAUGCCUGAACGGCGGCAGCUGCAAGGA

CGACAUCAACAGCUACGAAUGCUGGUGCCCCUUCGGAUUCGAAGGAAAGAACUGCGAAC

UGGACGUAACAUGCAACAUCAAGAACGGCAGAUGCGAGCAGUUCUGCAAAAACAGCGCC

GACAACAAGGUGGUGUGCAGCUGCACCGAGGGAUACCGACUGGCAGAAAACCAGAAGUC

CUGCGAACCAGCAGUGCCAUUCCCAUGCGGAAGAGUGAGCGUGAGCCAAACCAGCAAGC

UCACCCGGGCCGAGACCGUGUUCCCCGACGUGGACUACGUAAACAGCACCGAAGCCGAA
```

-continued

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUGAACGAAAAAUGGAUCGUAACCGCCGCCCAC

UGCGUGGAAACCGGCGUGAAAAUCACAGUGGUCGCAGGCGAACACAACAUCGAGGAGAC

AGAACACACAGAGCAAAAGCGAAACGUGAUCCGAAUCAUCCCCCACCACAACUACAACG

CAGCCAUCAACAAGUACAACCACGACAUCGCCCUGCUGGAACUGGACGAACCCCUGGUG

CUAAACAGCUACGUGACACCCAUCUGCAUCGCCGACAAGGAAUACACGAACAUCUUCCU

CAAAUUCGGAAGCGGCUACGUAAGCGGCUGGGGAAGAGUCUUCCACAAAGGGAGAAGCG

CCCUGGUGCUUCAGUACCUUAGAGUUCCACUUGUUGACCGAGCCACAUGUCUUCGAUCU

ACAAAGUUCACCAUCUAUAACAACAUGUUCUGUGCUGGCUUCCAUGAAGGAGGUAGAGA

UUCAUGUCAAGGAGAUAGUGGGGGACCCCAUGUUACUGAAGUGGAAGGGACCAGUUUCU

UAACUGGAAUUAUUAGCUGGGGUGAAGAGUGUGCAAUGAAAGGCAAAUAUGGAAUAUAU

ACCAAGGUAUCCCGGUAUGUCAACUGGAUUAAGGAAAAAACAAAGCUCACUUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA

TEV-hF9-XbG ARC-mRNA. 5'_18%_T. (1818 nt)
(SEQ ID NO: 83)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAAGCC

CAGGCCUCAUCACCAUCUGCCUGCUGGGAUACCUACUCAGCGCCGAAUGCACAGUGUUC

CUGGACCACGAAAACGCCAACAAAAUCCUGAACCGGCCAAAGAGGUACAACAGCGGCAA

ACUGGAAGAGUUCGUGCAAGGGAACCUGGAGAGAGAAUGCAUGGAAGAAAAGUGCAGCU

UCGAAGAAGCACGAGAAGUGUUCGAAAACACCGAAAGAACAACCGAAUUCUGGAAGCAG

UACGUGGACGGAGACCAGUGCGAGAGCAACCCAUGCCUGAACGGCGGCAGCUGCAAGGA

CGACAUCAACAGCUACGAAUGCUGGUGCCCCUUCGGAUUCGAAGGAAAGAACUGCGAAC

UGGACGUAACAUGCAACAUCAAGAACGGCAGAUGCGAGCAGUUCUGCAAAAACAGCGCC

GACAACAAGGUGGUGUGCAGCUGCACCGAGGGAUACCGACUGGCAGAAAACCAGAAGUC

CUGCGAACCAGCAGUGCCAUUCCCAUGCGGAAGAGUGAGCGUGAGCCAAACCAGCAAGC

UCACCCGGGCCGAGACCGUGUUCCCCGACGUGGACUACGUAAACAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUGAACGAAAAAUGGAUCGUAACCGCCGCCCAC

UGCGUGGAAACCGGCGUGAAAAUCACAGUGGUCGCAGGCGAACACAACAUCGAGGAGAC

AGAACAUACAGAGCAAAAGCGAAAUGUGAUUCGAAUUAUUCCUCACCACAACUACAAUG

CAGCUAUUAAUAAGUACAACCAUGACAUUGCCCUUCUGGAACUGGACGAACCCUUAGUG

CUAAACAGCUACGUUACACCUAUUUGCAUUGCUGACAAGGAAUACACGAACAUCUUCCU

-continued

CAAAUUUGGAUCUGGCUAUGUAAGUGGCUGGGGAAGAGUCUUCCACAAAGGGAGAUCAG

CUUUAGUUCUUCAGUACCUUAGAGUUCCACUUGUUGACCGAGCCACAUGUCUUCGAUCU

ACAAAGUUCACCAUCUAUAACAACAUGUUCUGUGCUGGCUUCCAUGAAGGAGGUAGAGA

UUCAUGUCAAGGAGAUAGUGGGGGACCCCAUGUUACUGAAGUGGAAGGGACCAGUUUCU

UAACUGGAAUUAUUAGCUGGGGUGAAGAGUGUGCAAUGAAAGGCAAAUAUGGAAUAUAU

ACCAAGGUAUCCCGGUAUGUCAACUGGAUUAAGGAAAAAACAAAGCUCACUUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAA

TEV-hF9-XbG ARC-mRNA. 5'_20%_T. (1818 nt)
(SEQ ID NO: 84)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAAGCC

CAGGCCUCAUCACCAUCUGCCUGCUGGGAUACCUACUCAGCGCCGAAUGCACAGUGUUC

CUGGACCACGAAAACGCCAACAAAAUCCUGAACCGGCCAAAGAGGUACAACAGCGGCAA

ACUGGAAGAGUUCGUGCAAGGGAACCUGGAGAGAGAAUGCAUGGAAGAAAAGUGCAGCU

UCGAAGAAGCACGAGAAGUGUUCGAAAACACCGAAAGAACAACCGAAUUCUGGAAGCAG

UACGUGGACGGAGACCAGUGCGAGAGCAACCCAUGCCUGAACGGCGGCAGCUGCAAGGA

CGACAUCAACAGCUACGAAUGCUGGUGCCCCUUCGGAUUCGAAGGAAAGAACUGCGAAC

UGGACGUAACAUGCAACAUCAAGAACGGCAGAUGCGAGCAGUUCUGCAAAAACAGCGCC

GACAACAAGGUGGUGUGCAGCUGCACCGAGGGAUACCGACUGGCAGAAAACCAGAAGUC

CUGCGAACCAGCAGUGCCAUUCCCAUGCGGAAGAGUGAGCGUGAGCCAAACCAGCAAGC

UCACCCGGGCCGAGACCGUGUUCCCCGACGUGGACUACGUAAACAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGUCAAUUCCCUUGGCAGGUUGUUUUGAAUGGUAAAG

UUGAUGCAUUCUGUGGAGGCUCUAUCGUUAAUGAAAAAUGGAUUGUAACUGCUGCCCAC

UGUGUUGAAACUGGUGUUAAAAUUACAGUUGUCGCAGGUGAACAUAAUAUUGAGGAGAC

AGAACAUACAGAGCAAAAGCGAAAUGUGAUUCGAAUUAUUCCUCACCACAACUACAAUG

CAGCUAUUAAUAAGUACAACCAUGACAUUGCCCUUCUGGAACUGGACGAACCCUUAGUG

CUAAACAGCUACGUUACACCUAUUUGCAUUGCUGACAAGGAAUACACGAACAUCUUCCU

CAAAUUUGGAUCUGGCUAUGUAAGUGGCUGGGGAAGAGUCUUCCACAAAGGGAGAUCAG

CUUUAGUUCUUCAGUACCUUAGAGUUCCACUUGUUGACCGAGCCACAUGUCUUCGAUCU

ACAAAGUUCACCAUCUAUAACAACAUGUUCUGUGCUGGCUUCCAUGAAGGAGGUAGAGA

UUCAUGUCAAGGAGAUAGUGGGGGACCCCAUGUUACUGAAGUGGAAGGGACCAGUUUCU

UAACUGGAAUUAUUAGCUGGGGUGAAGAGUGUGCAAUGAAAGGCAAAUAUGGAAUAUAU

ACCAAGGUAUCCCGGUAUGUCAACUGGAUUAAGGAAAAAACAAAGCUCACUUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

-continued

CAUUCGUAUCUGCUCCUAAUAAAAAGAAAGUUUCUUCACAUUCUAGAAAAAAAAAAAA
AAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAA

TEV-hF9-XbG ARC-mRNA. random_14%_T. (1818 nt)
(SEQ ID NO: 85)
5'-cap-
AGGAAACUUAAGUCAACACAACAUAUACAAAACAAACGAAUCUCAAGCAAUCAAGCAUU
CUACUUCUAUUGCAGCAAUUUAAAUCAUUUCUUUUAAAGCAAAAGCAAUUUUCUGAAAA
UUUUCACCAUUUACGAACGAUAGCCAUGCAGCGCGUGAACAUGAUCAUGGCAGAAAGCC
CAGGCCUCAUCACCAUCUGCCUGCUGGGAUAUCUACUCAGCGCCGAAUGCACAGUGUUC
CUGGACCACGAAAACGCCAACAAAAUCCUGAACCGGCCAAAGAGGUACAACAGCGGUAA
ACUGGAAGAGUUCGUGCAAGGGAACCUGGAGAGAGAAUGCAUGGAAGAAAAGUGCAGCU
UCGAAGAAGCACGAGAAGUGUUCGAAAACACCGAAAGAACAACCGAAUUCUGGAAGCAG
UACGUGGACGGAGACCAGUGCGAGAGCAACCCAUGCCUGAACGGCGGCAGCUGCAAGGA
CGACAUCAACAGCUACGAAUGCUGGUGCCCCUUCGGAUUCGAAGGAAAGAACUGCGAAC
UGGACGUAACAUGCAACAUCAAGAACGGCAGAUGCGAGCAGUUCUGCAAAAACAGCGCC
GACAACAAGGUGGUGUGCAGCUGCACCGAGGGAUACCGACUUGCAGAAAACCAGAAGUC
CUGCGAACCAGCAGUGCCAUUCCCAUGCGGAAGAGUGAGCGUUAGCCAAACCAGCAAGC
UCACCCGGGCCGAGACCGUGUUCCCCGACGUGGACUACGUAAACAGCACCGAAGCCGAA
ACCAUCCUGGACAACAUCACCCAAAGCACCCAAAGCUUCAACGACUUCACCCGGGUGGU
GGGCGGAGAAGACGCCAAACCAGGCCAAUUCCCCUGGCAGGUGGUGCUGAACGGCAAAG
UGGACGCAUUCUGCGGAGGCAGCAUCGUUAACGAAAAAUGGAUCGUAACCGCCGCCCAC
UGCGUGGAAACCGGCGUGAAAAUCACAGUGGUCGCAGGCGAACACAACAUCGAGGAGAC
AGAACACACAGAGCAAAAGCGAAACGUGAUCCGAAUCAUCCCUCACCACAACUACAACG
CAGCCAUCAACAAGUACAACCACGACAUCGCCCUGCUGGAACUGGACGAACCCUUAGUG
CUAAACAGCUACGUGACACCCAUCUGCAUCGCCGACAAGGAAUACACGAACAUCUUCCU
CAAAUUCGGAAGCGGCUACGUAAGCGGCUGGGGAAGAGUCUUCCACAAAGGGAGAAGCG
CCCUGGUGCUGCAGUACCUGAGAGUGCCACUGGUGGACCGAGCCACAUGCCUGCGAAGC
ACAAAGUUCACCAUCUACAACAACAUGUUCUGCGCCGGCUUCCACGAAGGAGGCAGAGA
CAGCUGCCAAGGAGACAGCGGGGGACCCCACGUGACCGAAGUGGAAGGGACCAGCUUCC
UGACCGGAAUCAUCAGCUGGGGCGAAGAGUGUGCAAUGAAAGGCAAAUACGGAAUAUAC
ACCAAGGUAAGCCGGUACGUCAACUGGAUCAAGGAAAAAACAAAGCUCACCUAACUCGA
GCUAGUGACUGACUAGGAUCUGGUUACCACUAAACCAGCCUCAAGAACACCCGAAUGGA
GUCUCUAAGCUACAUAAUACCAACUUACACUUACAAAAUGUUGUCCCCCAAAAUGUAGC
CAUUCGUAUCUGCUCCUAAUAAAAAGAAAGUUUCUUCACAUUCUAGAAAAAAAAAAAA
AAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAA TEV-hF9-XbG ARC-mRNA. random_16%_T. (1818 nt)
(SEQ ID NO: 86)
5'-cap-
AGGAAACUUAAGUCAACACAACAUAUACAAAACAAACGAAUCUCAAGCAAUCAAGCAUU
CUACUUCUAUUGCAGCAAUUUAAAUCAUUUCUUUUAAAGCAAAAGCAAUUUUCUGAAAA -continued

UUUUCACCAUUUACGAACGAUAGCCAUGCAGCGCGUGAACAUGAUCAUGGCAGAAAGCC

CAGGCCUCAUCACCAUCUGCCUGCUGGGAUACCUACUCAGUGCCGAAUGUACAGUGUUC

CUGGACCACGAAAACGCCAACAAAAUCCUGAACCGGCCAAAGAGGUACAACUCAGGCAA

ACUGGAAGAGUUCGUGCAAGGGAACCUGGAGAGAGAAUGCAUGGAAGAAAAGUGCAGCU

UCGAAGAAGCACGAGAAGUGUUUGAAAACACUGAAAGAACAACCGAAUUUUGGAAGCAG

UACGUGGAUGGAGAUCAGUGCGAGAGCAACCCAUGCCUGAAUGGCGGCAGCUGCAAGGA

CGACAUCAACAGCUACGAAUGCUGGUGCCCCUUCGGAUUCGAAGGAAAGAACUGCGAAC

UGGACGUAACAUGCAACAUCAAGAACGGCAGAUGCGAGCAGUUUUGUAAAAACAGCGCC

GACAACAAGGUGGUGUGCAGCUGCACCGAGGGAUACCGACUGGCAGAAAACCAGAAGUC

CUGCGAACCAGCAGUGCCAUUCCCAUGCGGAAGAGUGUCUGUGUCACAAACCAGCAAGC

UCACCCGGGCCGAGACCGUGUUCCCCGACGUGGACUACGUAAACAGCACCGAAGCCGAA

ACCAUCCUGGAUAACAUCACCCAAAGCACCCAAAGCUUCAAUGACUUCACCCGGGUGGU

GGGCGGAGAAGACGCCAAACCAGGCCAAUUCCCCUGGCAGGUUGUGCUGAACGGCAAAG

UUGACGCAUUCUGCGGAGGCAGCAUCGUGAACGAAAAAUGGAUCGUAACCGCUGCCCAC

UGCGUUGAAACCGGCGUGAAAAUCACAGUGGUCGCAGGCGAACACAACAUUGAGGAGAC

AGAACACACAGAGCAAAAGCGAAACGUGAUCCGAAUUAUCCCCCACCACAACUACAACG

CAGCCAUUAAUAAGUACAACCAUGACAUCGCCCUGCUGGAACUGGACGAACCCUUAGUG

CUAAACAGCUACGUGACACCCAUCUGCAUCGCCGACAAGGAAUACACGAACAUCUUCCU

CAAAUUCGGAAGCGGCUACGUAAGCGGCUGGGGAAGAGUCUUCCACAAAGGGAGAAGCG

CCCUGGUUCUGCAGUACCUGAGAGUGCCACUGGUUGACCGAGCCACAUGCCUGCGAAGC

ACAAAGUUCACCAUCUACAACAACAUGUUCUGCGCCGGCUUCCAUGAAGGAGGUAGAGA

CAGCUGUCAAGGAGACAGCGGGGGACCCCACGUUACUGAAGUGGAAGGGACCAGCUUCC

UGACCGGAAUCAUCAGCUGGGGCGAAGAGUGCGCAAUGAAAGGCAAAUACGGAAUAUAU

ACCAAGGUAAGCCGGUACGUCAACUGGAUCAAGGAAAAAACAAAGCUCACUUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAA

TEV-hF9-XbG ARC-mRNA. random_18%_T. (1818 nt)

(SEQ ID NO: 87)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAUCAC

CAGGCCUCAUCACCAUCUGCCUGUUAGGAUACCUACUCAGCGCCGAAUGUACAGUGUUU

CUUGACCACGAAAACGCCAACAAAAUCCUGAAUCGGCCAAAGAGGUAUAACUCAGGUAA

ACUGGAAGAGUUUGUGCAAGGGAACCUGGAGAGAGAAUGCAUGGAAGAAAAGUGCAGCU

UCGAAGAAGCACGAGAAGUGUUCGAAAACACUGAAAGAACAACCGAAUUUUGGAAGCAG

UAUGUGGAUGGAGACCAGUGCGAGUCCAACCCAUGCUUAAACGGCGGCAGUUGCAAGGA

CGACAUCAACAGCUAUGAAUGCUGGUGCCCCUUCGGAUUUGAAGGAAAGAACUGCGAAC

UGGACGUAACAUGUAACAUCAAGAAUGGCAGAUGCGAGCAGUUCUGUAAAAAUAGCGCC

```
GACAACAAGGUGGUGUGCAGCUGUACCGAGGGAUACCGACUGGCAGAAAACCAGAAGUC

CUGCGAACCAGCAGUGCCAUUCCCAUGCGGAAGAGUUAGCGUGAGCCAAACCAGCAAGC

UCACCCGGGCCGAGACCGUGUUCCCUGACGUGGACUACGUAAACUCUACCGAAGCUGAA

ACCAUCCUGGACAACAUCACUCAAAGCACCCAAUCAUUCAACGACUUCACCCGGGUGGU

GGGCGGAGAAGAUGCCAAACCAGGUCAAUUCCCUUGGCAGGUGGUGUUGAACGGCAAAG

UGGACGCAUUCUGUGGAGGCAGCAUCGUGAACGAAAAAUGGAUCGUAACUGCCGCCCAC

UGCGUGGAAACCGGCGUGAAAAUCACAGUGGUCGCAGGCGAACACAAUAUUGAGGAGAC

AGAACACACAGAGCAAAAGCGAAAUGUGAUCCGAAUUAUCCCUCACCACAACUACAACG

CAGCUAUUAACAAGUACAACCACGACAUUGCCCUGCUGGAACUGGACGAACCCCUGGUG

CUAAACAGCUACGUUACACCUAUCUGCAUCGCCGACAAGGAAUACACGAACAUCUUCCU

CAAAUUCGGAUCUGGCUACGUAAGCGGCUGGGGAAGAGUCUUCCACAAAGGGAGAUCAG

CCCUGGUGCUUCAGUACCUUAGAGUGCCACUUGUGGACCGAGCCACAUGCCUGCGAAGC

ACAAAGUUCACCAUCUACAACAACAUGUUCUGUGCUGGCUUCCACGAAGGAGGUAGAGA

CAGCUGUCAAGGAGAUAGCGGGGGACCCCACGUUACCGAAGUGGAAGGGACCAGCUUCU

UAACUGGAAUCAUCAGCUGGGGCGAAGAGUGCGCAAUGAAAGGCAAAUACGGAAUAUAC

ACCAAGGUAUCCCGGUAUGUCAACUGGAUCAAGGAAAAAACAAAGCUCACCUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAA

TEV-hF9-XbG ARC-mRNA. random_20%_T. (1818 nt)
                                                (SEQ ID NO: 88)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAAGCC

CAGGCCUCAUCACCAUCUGCCUUCUGGGAUAUCUACUCAGCGCCGAAUGCACAGUUUUC

CUUGACCACGAAAACGCCAACAAAAUCCUGAAUCGGCCAAAGAGGUAUAAUUCAGGUAA

ACUGGAAGAGUUUGUUCAAGGGAACCUUGAGAGAGAAUGCAUGGAAGAAAAGUGUAGUU

UUGAAGAAGCACGAGAAGUGUUCGAAAACACCGAAAGAACAACCGAAUUUUGGAAGCAG

UAUGUGGAUGGAGACCAGUGCGAGAGCAAUCCAUGCUUAAAUGGCGGCAGCUGCAAGGA

CGACAUUAAUUCCUAUGAAUGCUGGUGCCCCUUUGGAUUCGAAGGAAAGAACUGCGAAU

UAGACGUAACAUGCAACAUCAAGAACGGCAGAUGCGAGCAGUUUUGUAAAAAUAGUGCU

GACAACAAGGUGGUUUGCAGCUGCACCGAGGGAUACCGACUGGCAGAAAACCAGAAGUC

CUGCGAACCAGCAGUGCCAUUCCCAUGUGGAAGAGUUUCUGUGAGCCAAACUUCUAAGC

UCACCCGUGCCGAGACCGUUUUCCCUGACGUGGACUAUGUAAAUUCUACCGAAGCCGAA

ACCAUUUUGGAUAACAUCACCCAAAGCACCCAAAGCUUUAACGACUUCACUCGGGUGGU

UGGCGGAGAAGACGCCAAACCAGGCCAAUUCCCUUGGCAGGUGGUUCUGAAUGGCAAAG

UGGAUGCAUUCUGUGGAGGCUCUAUCGUGAACGAAAAAUGGAUCGUAACUGCCGCCCAC

UGCGUUGAAACCGGCGUUAAAAUUACAGUGGUCGCAGGCGAACACAAUAUUGAGGAGAC
```

```
-continued
AGAACACACAGAGCAAAAGCGAAACGUGAUUCGAAUUAUCCCUCACCACAACUACAAUG

CAGCCAUUAACAAGUACAACCAUGACAUCGCCCUGCUGGAACUGGACGAACCCCUGGUG

CUAAACAGCUACGUUACACCUAUUUGCAUCGCCGACAAGGAAUACACGAACAUCUUCCU

CAAAUUUGGAUCUGGCUAUGUAAGCGGCUGGGGAAGAGUCUUCCACAAAGGGAGAAGCG

CCCUGGUGCUUCAGUACCUGAGAGUGCCACUUGUGGACCGAGCCACAUGUCUGCGAAGC

ACAAAGUUCACCAUCUACAACAACAUGUUCUGCGCCGGCUUCCACGAAGGAGGUAGAGA

CUCAUGCCAAGGAGAUAGCGGGGGACCCCACGUGACCGAAGUGGAAGGGACCAGCUUCC

UGACUGGAAUUAUUAGCUGGGGCGAAGAGUGCGCAAUGAAAGGCAAAUAUGGAAUAUAC

ACCAAGGUAAGCCGGUAUGUCAACUGGAUCAAGGAAAAAACAAAGCUCACCUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAA
```

Example D: Templates and mRNAs for Human Alpha-1-Antitrypsin (hAAT)

Figure 7:
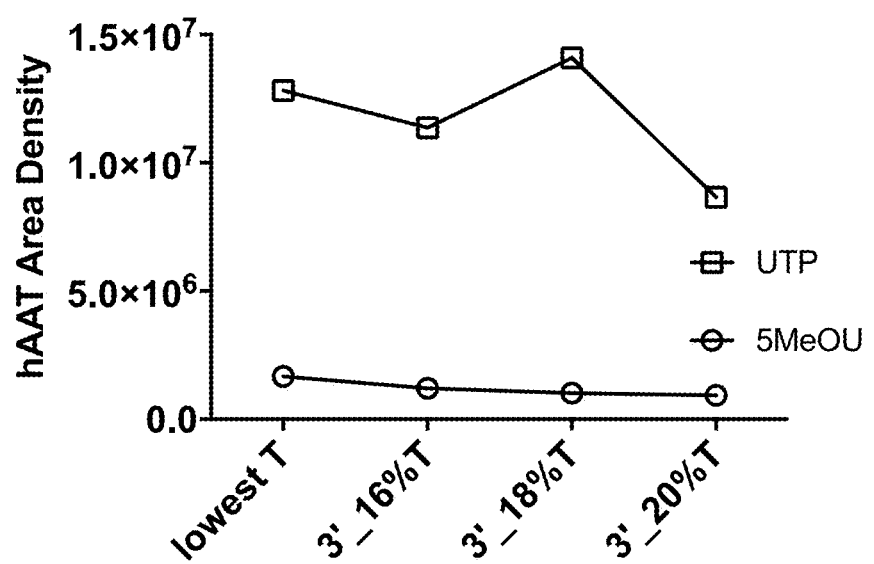
FIG. 7 shows the results of surprisingly reduced impurity levels in a process for synthesizing an hAAT translatable molecule of this invention.

FIG. 7 shows the results of surprisingly reduced impurity levels in a process for synthesizing an hAAT translatable molecule of this invention. FIG. 7 shows the results of a dot blot for detecting double strand RNA impurity in the synthesis mixture (nitro cellulose membrane, J2 antibody to detect dsRNA). The ARC-RNA (5MeOU) "reduced T" synthesis products, which were translatable for hAAT, showed surprisingly reduced dot blot intensity as compared to similar "reduced T" mRNA (UTP) synthesis products. Thus, the ARC-RNA (5MeOU) synthesis process, with template reduced T composition, surprisingly reduced double strand RNA impurity levels in the synthesis mixture. The process for synthesizing the ARC-RNA (5MeOU) molecules of this invention with template reduced T composition provided a surprisingly reduced level of double strand RNA impurity. As shown in FIG. 7, this result is surprising because the "reduced T" mRNA (UTP) synthesis products exhibited increased levels of double strand RNA impurity at lower template T composition.

The compositions of the templates for hAAT are shown in Table 8.

TABLE 8

| Non-Template Nucleotide T compositions for hAAT | |
|---|---|
| hEPO | T % |
| hAAT_lowest_T | 14.0 |
| hAAT_3'_16% T | 16.1 |
| hAAT_3'_18% T | 18.1 |
| hAAT_3'_20% T | 20.0 |
| hAAT_5'_16% T | 16.1 |
| hAAT_5'_18% T | 18.1 |
| hAAT_5'_20% T | 20.0 |
| hAAT_random_16% | 16.1 |
| hAAT_random_18% | 18.1 |
| hAAT_random_20% | 20.0 |

Human AAT ORF reference. Sense strand, non-template. NM_000295.4:262-1518 Homo sapiens serpin family A member 1 (SERPINA1).

```
                                                      (SEQ ID NO: 89)
        atgccgtcttctgtctcgtggggcatcctcctgctggcaggcctgtgct gcctggtccctgtctccctggctgaggatccccagggagatgctgcccagaagacagat acatcccaccatgatcaggatcacccaaccttcaacaagatcacccccaacctggctga gttcgccttcagcctataccgccagctggcacaccagtccaacagcaccaatatcttct tctccccagtgagcatcgctacagcctttgcaatgctctccctggggaccaaggctgac actcacgatgaaatcctggagggcctgaatttcaacctcacggagattccggaggctca gatccatgaaggcttccaggaactcctccgtaccctcaaccagccagacagccagctcc agctgaccaccggcaatggcctgttcctcagcgagggcctgaagctagtggataagttt ttggaggatgttaaaaagttgtaccactcagaagccttcactgtcaacttcggggacac cgaagaggccaagaaacagatcaacgattacgtggagaagggtactcaagggaaaattg tggatttggtcaaggagcttgacagagacacagttttttgctctggtgaattacatcttc
```

-continued tttaaaggcaaatgggagagacccttttgaagtcaaggacaccgaggaagaggacttcca cgtggaccaggtgaccaccgtgaaggtgcctatgatgaagcgtttaggcatgtttaaca tccagcactgtaagaagctgtccagctgggtgctgctgatgaaatacctgggcaatgcc accgccatcttcttcctgcctgatgaggggaaactacagcacctggaaaatgaactcac ccacgatatcatcaccaagttcctggaaaatgaagacagaaggtctgccagcttacatt tacccaaactgtccattactggaacctatgatctgaagagcgtcctgggtcaactgggc atcactaaggtcttcagcaatggggctgacctctccggggtcacagaggaggcacccct gaagctctccaaggccgtgcataaggctgtgctgaccatcgacgagaaagggactgaag ctgctggggccatgttttagaggccatacccatgtctatcccccccgaggtcaagttc aacaaaccctttgtcttcttaatgattgaacaaaataccaagtctccctcttcatggg aaaagtggtgaatcccacccaaaaataa hAAT sense strand, non-template. 3'_lowest_T.

(SEQ ID NO: 90)
ATGCCGAGCAGCGTCAGCTGGGGCATCCTCCTGCTGGCAGGCCTGTGCT

GCCTGGTCCCCGTCAGCCTGGCCGAGGACCCCCAGGGAGACGCCGCCCAGAAGACAGAC

ACAAGCCACCACGACCAGGACCACCCAACCTTCAACAAGATCACCCCCAACCTGGCCGA

GTTCGCCTTCAGCCTATACCGCCAGCTGGCACACCAGAGCAACAGCACCAACATCTTCT

TCAGCCCAGTGAGCATCGCCACAGCCTTCGCAATGCTCAGCCTGGGGACCAAGGCCGAC

ACCCACGACGAAATCCTGGAGGGCCTGAACTTCAACCTCACGGAGATCCCGGAGGCCCA

GATCCACGAAGGCTTCCAGGAACTCCTCCGGACCCTCAACCAGCCAGACAGCCAGCTCC

AGCTGACCACCGGCAACGGCCTGTTCCTCAGCGAGGGCCTGAAGCTAGTGGACAAGTTC

CTGGAGGACGTGAAAAAGCTGTACCACAGCGAAGCCTTCACCGTCAACTTCGGGGACAC

CGAAGAGGCCAAGAAACAGATCAACGACTACGTGGAGAAGGGCACCCAAGGGAAAATCG

TGGACCTGGTCAAGGAGCTGGACAGAGACACAGTGTTCGCCCTGGTGAACTACATCTTC

TTCAAAGGCAAATGGGAGAGACCCTTCGAAGTCAAGGACACCGAGGAAGAGGACTTCCA

CGTGGACCAGGTGACCACCGTGAAGGTGCCCATGATGAAGCGGCTGGGCATGTTCAACA

TCCAGCACTGCAAGAAGCTGAGCAGCTGGGTGCTGCTGATGAAATACCTGGGCAACGCC

ACCGCCATCTTCTTCCTGCCCGACGAGGGGAAACTACAGCACCTGGAAAACGAACTCAC

CCACGACATCATCACCAAGTTCCTGGAAAACGAAGACAGAAGGAGCGCCAGCCTGCACC

TGCCCAAACTGAGCATCACCGGAACCTACGACCTGAAGTCCGTGCTGGGCCAACTGGGC

ATCACCAAGGTCTTCAGCAACGGGGCCGACCTCAGCGGGGTCACAGAGGAGGCACCCCT

GAAGCTCAGCAAGGCCGTGCACAAGGCCGTGCTGACCATCGACGAGAAAGGGACCGAAG

CCGCCGGGGCCATGTTCCTGGAGGCCATACCCATGAGCATCCCCCCCGAGGTCAAGTTC

AACAAACCCTTCGTCTTCCTGATGATCGAACAAAACACCAAGAGCCCCCTCTTCATGGG

AAAAGTGGTGAACCCCACCCAAAAATAA hAAT sense strand, non-template. 3'_16%_T.

(SEQ ID NO: 91)
ATGCCGTCTTCTGTCTCGTGGGGCATCCTCCTGCTGGCAGGCCTGTGCT

GCCTGGTCCCTGTCTCCCTGGCTGAGGATCCCCAGGGAGATGCTGCCCAGAAGACAGAT

ACATCCCACCATGATCAGGATCACCCAACCTTCAACAAGATCACCCCCAACCTGGCTGA

GTTCGCCTTCAGCCTATACCGCCAGCTGGCACACCAGTCCAACAGCACCAATATCTTCT

TCTCCCCAGTGAGCATCGCTACAGCCTTTGCAATGCTCTCCCTGGGGACCAAGGCTGAC

ACTCACGATGAAATCCTGGAGGGCCTGAACTTCAACCTCACGGAGATCCCGGAGGCCCA

-continued

GATCCACGAAGGCTTCCAGGAACTCCTCCGGACCCTCAACCAGCCAGACAGCCAGCTCC

AGCTGACCACCGGCAACGGCCTGTTCCTCAGCGAGGGCCTGAAGCTAGTGGACAAGTTC

CTGGAGGACGTGAAAAAGCTGTACCACAGCGAAGCCTTCACCGTCAACTTCGGGGACAC

CGAAGAGGCCAAGAAACAGATCAACGACTACGTGGAGAAGGGCACCCAAGGGAAAATCG

TGGACCTGGTCAAGGAGCTGGACAGAGACACAGTGTTCGCCCTGGTGAACTACATCTTC

TTCAAAGGCAAATGGGAGAGACCCTTCGAAGTCAAGGACACCGAGGAAGAGGACTTCCA

CGTGGACCAGGTGACCACCGTGAAGGTGCCCATGATGAAGCGGCTGGGCATGTTCAACA

TCCAGCACTGCAAGAAGCTGAGCAGCTGGGTGCTGCTGATGAAATACCTGGGCAACGCC

ACCGCCATCTTCTTCCTGCCCGACGAGGGGAAACTACAGCACCTGGAAAACGAACTCAC

CCACGACATCATCACCAAGTTCCTGGAAAACGAAGACAGAAGGAGCGCCAGCCTGCACC

TGCCCAAACTGAGCATCACCGGAACCTACGACCTGAAGTCCGTGCTGGGCCAACTGGGC

ATCACCAAGGTCTTCAGCAACGGGGCCGACCTCAGCGGGGTCACAGAGGAGGCACCCCT

GAAGCTCAGCAAGGCCGTGCACAAGGCCGTGCTGACCATCGACGAGAAAGGGACCGAAG

CCGCCGGGGCCATGTTCCTGGAGGCCATACCCATGAGCATCCCCCCCGAGGTCAAGTTC

AACAAACCCTTCGTCTTCCTGATGATCGAACAAAACACCAAGAGCCCCCTCTTCATGGG

AAAAGTGGTGAACCCCACCCAAAAATAA hAAT sense strand, non-template. 3'_18%_T.

(SEQ ID NO: 92)

ATGCCGTCTTCTGTCTCGTGGGGCATCCTCCTGCTGGCAGGCCTGTGCT

GCCTGGTCCCTGTCTCCCTGGCTGAGGATCCCCAGGGAGATGCTGCCCAGAAGACAGAT

ACATCCACCATGATCAGGATCACCCAACCTTCAACAAGATCACCCCCAACCTGGCTGA

GTTCGCCTTCAGCCTATACCGCCAGCTGGCACACCAGTCCAACAGCACCAATATCTTCT

TCTCCCCAGTGAGCATCGCTACAGCCTTTGCAATGCTCTCCCTGGGGACCAAGGCTGAC

ACTCACGATGAAATCCTGGAGGGCCTGAATTTCAACCTCACGGAGATTCCGGAGGCTCA

GATCCATGAAGGCTTCCAGGAACTCCTCCGTACCCTCAACCAGCCAGACAGCCAGCTCC

AGCTGACCACCGGCAATGGCCTGTTCCTCAGCGAGGGCCTGAAGCTAGTGGATAAGTTT

TTGGAGGATGTTAAAAAGTTGTACCACTCAGAAGCCTTCACTGTCAACTTCGGGGACAC

CGAAGAGGCCAAGAAACAGATCAACGATTACGTGGAGAAGGGTACTCAAGGGAAAATTG

TGGATTTGGTCAAGGAGCTTGACAGAGACACAGTTTTTGCTCTGGTGAATTACATCTTC

TTCAAAGGCAAATGGGAGAGACCCTTCGAAGTCAAGGACACCGAGGAAGAGGACTTCCA

CGTGGACCAGGTGACCACCGTGAAGGTGCCCATGATGAAGCGGCTGGGCATGTTCAACA

TCCAGCACTGCAAGAAGCTGAGCAGCTGGGTGCTGCTGATGAAATACCTGGGCAACGCC

ACCGCCATCTTCTTCCTGCCCGACGAGGGGAAACTACAGCACCTGGAAAACGAACTCAC

CCACGACATCATCACCAAGTTCCTGGAAAACGAAGACAGAAGGAGCGCCAGCCTGCACC

TGCCCAAACTGAGCATCACCGGAACCTACGACCTGAAGTCCGTGCTGGGCCAACTGGGC

ATCACCAAGGTCTTCAGCAACGGGGCCGACCTCAGCGGGGTCACAGAGGAGGCACCCCT

GAAGCTCAGCAAGGCCGTGCACAAGGCCGTGCTGACCATCGACGAGAAAGGGACCGAAG

CCGCCGGGGCCATGTTCCTGGAGGCCATACCCATGAGCATCCCCCCCGAGGTCAAGTTC

AACAAACCCTTCGTCTTCCTGATGATCGAACAAAACACCAAGAGCCCCCTCTTCATGGG

AAAAGTGGTGAACCCCACCCAAAAATAA hAAT sense strand, non-template. 3'_20%_T.

(SEQ ID NO: 93)

ATGCCGTCTTCTGTCTCGTGGGGCATCCTCCTGCTGGCAGGCCTGTGCT

GCCTGGTCCCTGTCTCCCTGGCTGAGGATCCCCAGGGAGATGCTGCCCAGAAGACAGAT

ACATCCCACCATGATCAGGATCACCCAACCTTCAACAAGATCACCCCCAACCTGGCTGA

GTTCGCCTTCAGCCTATACCGCCAGCTGGCACACCAGTCCAACAGCACCAATATCTTCT

TCTCCCCAGTGAGCATCGCTACAGCCTTTGCAATGCTCTCCCTGGGGACCAAGGCTGAC

ACTCACGATGAAATCCTGGAGGGCCTGAATTTCAACCTCACGGAGATTCCGGAGGCTCA

GATCCATGAAGGCTTCCAGGAACTCCTCCGTACCCTCAACCAGCCAGACAGCCAGCTCC

AGCTGACCACCGGCAATGGCCTGTTCCTCAGCGAGGGCCTGAAGCTAGTGGATAAGTTT

TTGGAGGATGTTAAAAAGTTGTACCACTCAGAAGCCTTCACTGTCAACTTCGGGGACAC

CGAAGAGGCCAAGAAACAGATCAACGATTACGTGGAGAAGGGTACTCAAGGGAAAATTG

TGGATTTGGTCAAGGAGCTTGACAGAGACACAGTTTTTGCTCTGGTGAATTACATCTTC

TTTAAAGGCAAATGGGAGAGACCCTTTGAAGTCAAGGACACCGAGGAAGAGGACTTCCA

CGTGGACCAGGTGACCACCGTGAAGGTGCCTATGATGAAGCGTTTAGGCATGTTTAACA

TCCAGCACTGTAAGAAGCTGTCCAGCTGGGTGCTGCTGATGAAATACCTGGGCAATGCC

ACCGCCATCTTCTTCCTGCCTGATGAGGGGAAACTACAGCACCTGGAAAATGAACTCAC

CCACGATATCATCACCAAGTTCCTGGAAAATGAAGACAGAAGGTCTGCCAGCTTACATT

TACCCAAACTGTCCATTACTGGAACCTATGATCTGAAGTCCGTGCTGGGTCAACTGGGC

ATCACCAAGGTCTTCAGCAACGGGGCCGACCTCAGCGGGGTCACAGAGGAGGCACCCCT

GAAGCTCAGCAAGGCCGTGCACAAGGCCGTGCTGACCATCGACGAGAAAGGGACCGAAG

CCGCCGGGGCCATGTTCCTGGAGGCCATACCCATGAGCATCCCCCCCGAGGTCAAGTTC

AACAAACCCTTCGTCTTCCTGATGATCGAACAAAACACCAAGAGCCCCCTCTTCATGGG

AAAAGTGGTGAACCCCACCCAAAAATAA hAAT sense strand, non-template. 5'_16%_T.

(SEQ ID NO: 94)

ATGCCGAGCAGCGTCAGCTGGGGCATCCTCCTGCTGGCAGGCCTGTGCT

GCCTGGTCCCCGTCAGCCTGGCCGAGGACCCCCAGGGAGACGCCGCCCAGAAGACAGAC

ACAAGCCACCACGACCAGGACCACCCAACCTTCAACAAGATCACCCCCAACCTGGCCGA

GTTCGCCTTCAGCCTATACCGCCAGCTGGCACACCAGAGCAACAGCACCAACATCTTCT

TCAGCCCAGTGAGCATCGCCACAGCCTTCGCAATGCTCAGCCTGGGGACCAAGGCCGAC

ACCCACGACGAAATCCTGGAGGGCCTGAACTTCAACCTCACGGAGATCCCGGAGGCCCA

GATCCACGAAGGCTTCCAGGAACTCCTCCGGACCCTCAACCAGCCAGACAGCCAGCTCC

AGCTGACCACCGGCAACGGCCTGTTCCTCAGCGAGGGCCTGAAGCTAGTGGACAAGTTC

CTGGAGGACGTGAAAAAGCTGTACCACAGCGAAGCCTTCACCGTCAACTTCGGGGACAC

CGAAGAGGCCAAGAAACAGATCAACGACTACGTGGAGAAGGGCACCCAAGGGAAAATCG

TGGACCTGGTCAAGGAGCTGGACAGAGACACAGTGTTCGCCCTGGTGAACTACATCTTC

TTCAAAGGCAAATGGGAGAGACCCTTCGAAGTCAAGGACACCGAGGAAGAGGACTTCCA

CGTGGACCAGGTGACCACCGTGAAGGTGCCCATGATGAAGCGGCTGGGCATGTTCAACA

TCCAGCACTGCAAGAAGCTGAGCAGCTGGGTGCTGCTGATGAAATACCTGGGCAACGCC

ACCGCCATCTTCTTCCTGCCCGACGAGGGGAAACTACAGCACCTGGAAAACGAACTCAC

CCACGACATCATCACCAAGTTCCTGGAAAACGAAGACAGAAGGAGCGCCAGCCTGCACC

-continued

TGCCCAAACTGAGCATTACTGGAACCTATGATCTGAAGTCCGTGCTGGGTCAACTGGGC

ATCACTAAGGTCTTCAGCAATGGGGCTGACCTCTCCGGGGTCACAGAGGAGGCACCCCT

GAAGCTCTCCAAGGCCGTGCATAAGGCTGTGCTGACCATCGACGAGAAAGGGACTGAAG

CTGCTGGGGCCATGTTTTTAGAGGCCATACCCATGTCTATCCCCCCCGAGGTCAAGTTC

AACAAACCCTTTGTCTTCTTAATGATTGAACAAAATACCAAGTCTCCCCTCTTCATGGG

AAAAGTGGTGAATCCCACCCAAAAATAA hAAT sense strand, non-template. 5'_18%_T.
(SEQ ID NO: 95)
ATGCCGAGCAGCGTCAGCTGGGGCATCCTCCTGCTGGCAGGCCTGTGCT

GCCTGGTCCCCGTCAGCCTGGCCGAGGACCCCCAGGGAGACGCCGCCCAGAAGACAGAC

ACAAGCCACCACGACCAGGACCACCCAACCTTCAACAAGATCACCCCCAACCTGGCCGA

GTTCGCCTTCAGCCTATACCGCCAGCTGGCACACCAGAGCAACAGCACCAACATCTTCT

TCAGCCCAGTGAGCATCGCCACAGCCTTCGCAATGCTCAGCCTGGGGACCAAGGCCGAC

ACCCACGACGAAATCCTGGAGGGCCTGAACTTCAACCTCACGGAGATCCCGGAGGCCCA

GATCCACGAAGGCTTCCAGGAACTCCTCCGGACCCTCAACCAGCCAGACAGCCAGCTCC

AGCTGACCACCGGCAACGGCCTGTTCCTCAGCGAGGGCCTGAAGCTAGTGGACAAGTTC

CTGGAGGACGTGAAAAAGCTGTACCACAGCGAAGCCTTCACCGTCAACTTCGGGGACAC

CGAAGAGGCCAAGAAACAGATCAACGACTACGTGGAGAAGGGCACCCAAGGGAAAATCG

TGGACCTGGTCAAGGAGCTTGACAGAGACACAGTTTTTGCTCTGGTGAATTACATCTTC

TTTAAAGGCAAATGGGAGAGACCCTTTGAAGTCAAGGACACCGAGGAAGAGGACTTCCA

CGTGGACCAGGTGACCACCGTGAAGGTGCCTATGATGAAGCGTTTAGGCATGTTTAACA

TCCAGCACTGTAAGAAGCTGTCCAGCTGGGTGCTGCTGATGAAATACCTGGGCAATGCC

ACCGCCATCTTCTTCCTGCCTGATGAGGGGAAACTACAGCACCTGGAAAATGAACTCAC

CCACGATATCATCACCAAGTTCCTGGAAAATGAAGACAGAAGGTCTGCCAGCTTACATT

TACCCAAACTGTCCATTACTGGAACCTATGATCTGAAGTCCGTGCTGGGTCAACTGGGC

ATCACTAAGGTCTTCAGCAATGGGGCTGACCTCTCCGGGGTCACAGAGGAGGCACCCCT

GAAGCTCTCCAAGGCCGTGCATAAGGCTGTGCTGACCATCGACGAGAAAGGGACTGAAG

CTGCTGGGGCCATGTTTTTAGAGGCCATACCCATGTCTATCCCCCCCGAGGTCAAGTTC

AACAAACCCTTTGTCTTCTTAATGATTGAACAAAATACCAAGTCTCCCCTCTTCATGGG

AAAAGTGGTGAATCCCACCCAAAAATAA hAAT sense strand, non-template. 5'_20%_T.
(SEQ ID NO: 96)
ATGCCGAGCAGCGTCAGCTGGGGCATCCTCCTGCTGGCAGGCCTGTGCT

GCCTGGTCCCCGTCAGCCTGGCCGAGGACCCCCAGGGAGACGCCGCCCAGAAGACAGAC

ACAAGCCACCACGACCAGGACCACCCAACCTTCAACAAGATCACCCCCAACCTGGCCGA

GTTCGCCTTCAGCCTATACCGCCAGCTGGCACACCAGAGCAACAGCACCAACATCTTCT

TCAGCCCAGTGAGCATCGCCACAGCCTTTGCAATGCTCTCCCTGGGGACCAAGGCTGAC

ACTCACGATGAAATCCTGGAGGGCCTGAATTTCAACCTCACGGAGATTCCGGAGGCTCA

GATCCATGAAGGCTTCCAGGAACTCCTCCGTACCCTCAACCAGCCAGACAGCCAGCTCC

AGCTGACCACCGGCAATGGCCTGTTCCTCAGCGAGGGCCTGAAGCTAGTGGATAAGTTT

TTGGAGGATGTTAAAAAGTTGTACCACTCAGAAGCCTTCACTGTCAACTTCGGGGACAC

CGAAGAGGCCAAGAAACAGATCAACGATTACGTGGAGAAGGGTACTCAAGGGAAAATTG

TGGATTTGGTCAAGGAGCTTGACAGAGACACAGTTTTTGCTCTGGTGAATTACATCTTC

-continued

```
TTTAAAGGCAAATGGGAGAGACCCTTTGAAGTCAAGGACACCGAGGAAGAGGACTTCCA

CGTGGACCAGGTGACCACCGTGAAGGTGCCTATGATGAAGCGTTTAGGCATGTTTAACA

TCCAGCACTGTAAGAAGCTGTCCAGCTGGGTGCTGCTGATGAAATACCTGGGCAATGCC

ACCGCCATCTTCTTCCTGCCTGATGAGGGGAAACTACAGCACCTGGAAAATGAACTCAC

CCACGATATCATCACCAAGTTCCTGGAAAATGAAGACAGAAGGTCTGCCAGCTTACATT

TACCCAAACTGTCCATTACTGGAACCTATGATCTGAAGTCCGTGCTGGGTCAACTGGGC

ATCACTAAGGTCTTCAGCAATGGGGCTGACCTCTCCGGGGTCACAGAGGAGGCACCCCT

GAAGCTCTCCAAGGCCGTGCATAAGGCTGTGCTGACCATCGACGAGAAAGGGACTGAAG

CTGCTGGGGCCATGTTTTTAGAGGCCATACCCATGTCTATCCCCCCCGAGGTCAAGTTC

AACAAACCCTTTGTCTTCTTAATGATTGAACAAAATACCAAGTCTCCCCTCTTCATGGG

AAAAGTGGTGAATCCCACCCAAAAATAA
``` hAAT sense strand, non-template. random_16%_T.
                                                          (SEQ ID NO: 97)

```
ATGCCGAGCAGCGTCTCGTGGGGCATCCTCCTGCTGGCAGGCCTGTGCT

GCCTGGTCCCCGTCAGCCTGGCCGAGGACCCCCAGGGAGATGCTGCCCAGAAGACAGAC

ACATCCACCACGACCAGGACCACCCAACCTTCAACAAGATCACCCCCAACCTGGCTGA

GTTCGCCTTCAGCCTATACCGCCAGCTGGCACACCAGAGCAACAGCACCAATATCTTCT

TCAGCCCAGTGAGCATCGCTACAGCCTTCGCAATGCTCAGCCTGGGGACCAAGGCCGAC

ACCCACGATGAAATCCTGGAGGGCCTGAATTTCAACCTCACGGAGATCCCGGAGGCTCA

GATCCACGAAGGCTTCCAGGAACTCCTCCGGACCCTCAACCAGCCAGACAGCCAGCTCC

AGCTGACCACCGGCAACGGCCTGTTCCTCAGCGAGGGCCTGAAGCTAGTGGACAAGTTC

CTGGAGGACGTTAAAAAGCTGTACCACAGCGAAGCCTTCACCGTCAACTTCGGGGACAC

CGAAGAGGCCAAGAAACAGATCAACGATTACGTGGAGAAGGGCACCCAAGGGAAAATCG

TGGACCTGGTCAAGGAGCTTGACAGAGACACAGTGTTTGCCCTGGTGAACTACATCTTC

TTCAAAGGCAAATGGGAGAGACCCTTCGAAGTCAAGGACACCGAGGAAGAGGACTTCCA

CGTGGACCAGGTGACCACCGTGAAGGTGCCCATGATGAAGCGGTTAGGCATGTTCAACA

TCCAGCACTGCAAGAAGCTGAGCAGCTGGGTGCTGCTGATGAAATACCTGGGCAACGCC

ACCGCCATCTTCTTCCTGCCCGACGAGGGGAAACTACAGCACCTGGAAAACGAACTCAC

CCACGACATCATCACCAAGTTCCTGGAAAACGAAGACAGAAGGAGCGCCAGCCTGCATC

TGCCCAAACTGAGCATTACTGGAACCTACGATCTGAAGTCCGTGCTGGGTCAACTGGGC

ATCACCAAGGTCTTCAGCAATGGGGCCGACCTCAGCGGGGTCACAGAGGAGGCACCCCT

GAAGCTCAGCAAGGCCGTGCACAAGGCTGTGCTGACCATCGACGAGAAAGGGACCGAAG

CCGCTGGGGCCATGTTCCTGGAGGCCATACCCATGAGCATCCCCCCCGAGGTCAAGTTC

AACAAACCCTTTGTCTTCCTGATGATCGAACAAAACACCAAGTCTCCCCTCTTCATGGG

AAAAGTGGTGAACCCCACCCAAAAATAA
``` hAAT sense strand, non-template. random_18%_T.
                                                          (SEQ ID NO: 98)

```
ATGCCGTCTTCTGTCTCGTGGGGCATCCTCCTGCTGGCAGGCCTGTGCT

GCCTGGTCCCCGTCTCCCTGGCTGAGGACCCCCAGGGAGATGCCGCCCAGAAGACAGAC

ACATCCACCATGACCAGGACCACCCAACCTTCAACAAGATCACCCCCAACCTGGCCGA

GTTCGCCTTCAGCCTATACCGCCAGCTGGCACACCAGAGCAACAGCACCAACATCTTCT

TCTCCCCAGTGAGCATCGCCACAGCCTTTGCAATGCTCTCCCTGGGGACCAAGGCCGAC
```

-continued

ACCCACGACGAAATCCTGGAGGGCCTGAATTTCAACCTCACGGAGATCCCGGAGGCTCA

GATCCATGAAGGCTTCCAGGAACTCCTCCGGACCCTCAACCAGCCAGACAGCCAGCTCC

AGCTGACCACCGGCAATGGCCTGTTCCTCAGCGAGGGCCTGAAGCTAGTGGATAAGTTC

CTGGAGGATGTTAAAAAGCTGTACCACAGCGAAGCCTTCACCGTCAACTTCGGGGACAC

CGAAGAGGCCAAGAAACAGATCAACGATTACGTGGAGAAGGGCACCCAAGGGAAAATCG

TGGACCTGGTCAAGGAGCTTGACAGAGACACAGTGTTTGCTCTGGTGAATTACATCTTC

TTTAAAGGCAAATGGGAGAGACCCTTTGAAGTCAAGGACACCGAGGAAGAGGACTTCCA

CGTGGACCAGGTGACCACCGTGAAGGTGCCTATGATGAAGCGGTTAGGCATGTTTAACA

TCCAGCACTGCAAGAAGCTGAGCAGCTGGGTGCTGCTGATGAAATACCTGGGCAATGCC

ACCGCCATCTTCTTCCTGCCTGATGAGGGGAAACTACAGCACCTGGAAAACGAACTCAC

CCACGACATCATCACCAAGTTCCTGGAAAATGAAGACAGAAGGTCTGCCAGCTTACACT

TACCCAAACTGAGCATTACTGGAACCTACGATCTGAAGTCCGTGCTGGGCCAACTGGGC

ATCACTAAGGTCTTCAGCAACGGGGCTGACCTCTCCGGGGTCACAGAGGAGGCACCCCT

GAAGCTCAGCAAGGCCGTGCACAAGGCTGTGCTGACCATCGACGAGAAAGGGACCGAAG

CTGCCGGGGCCATGTTTCTGGAGGCCATACCCATGTCTATCCCCCCCGAGGTCAAGTTC

AACAAACCCTTTGTCTTCCTGATGATCGAACAAAATACCAAGAGCCCCCTCTTCATGGG

AAAAGTGGTGAACCCCACCCAAAAATAA hAAT sense strand, non-template. random_20%_T.

(SEQ ID NO: 99)

ATGCCGAGCAGCGTCAGCTGGGGCATCCTCCTGCTGGCAGGCCTGTGCT

GCCTGGTCCCTGTCTCCCTGGCTGAGGATCCCCAGGGAGATGCTGCCCAGAAGACAGAT

ACATCCCACCATGATCAGGATCACCCAACCTTCAACAAGATCACCCCCAACCTGGCTGA

GTTCGCCTTCAGCCTATACCGCCAGCTGGCACACCAGTCCAACAGCACCAATATCTTCT

TCTCCCCAGTGAGCATCGCTACAGCCTTCGCAATGCTCTCCCTGGGGACCAAGGCTGAC

ACTCACGATGAAATCCTGGAGGGCCTGAATTTCAACCTCACGGAGATTCCGGAGGCCCA

GATCCATGAAGGCTTCCAGGAACTCCTCCGTACCCTCAACCAGCCAGACAGCCAGCTCC

AGCTGACCACCGGCAATGGCCTGTTCCTCAGCGAGGGCCTGAAGCTAGTGGATAAGTTT

TTGGAGGATGTTAAAAAGCTGTACCACAGCGAAGCCTTCACTGTCAACTTCGGGGACAC

CGAAGAGGCCAAGAAACAGATCAACGATTACGTGGAGAAGGGTACTCAAGGGAAAATTG

TGGATTTGGTCAAGGAGCTTGACAGAGACACAGTTTTTGCTCTGGTGAATTACATCTTC

TTCAAAGGCAAATGGGAGAGACCCTTTGAAGTCAAGGACACCGAGGAAGAGGACTTCCA

CGTGGACCAGGTGACCACCGTGAAGGTGCCTATGATGAAGCGGTTAGGCATGTTCAACA

TCCAGCACTGTAAGAAGCTGTCCAGCTGGGTGCTGCTGATGAAATACCTGGGCAATGCC

ACCGCCATCTTCTTCCTGCCTGATGAGGGGAAACTACAGCACCTGGAAAATGAACTCAC

CCACGATATCATCACCAAGTTCCTGGAAAATGAAGACAGAAGGAGCGCCAGCTTACATT

TACCCAAACTGAGCATTACTGGAACCTACGATCTGAAGTCCGTGCTGGGTCAACTGGGC

ATCACTAAGGTCTTCAGCAACGGGGCTGACCTCTCCGGGGTCACAGAGGAGGCACCCCT

GAAGCTCTCCAAGGCCGTGCATAAGGCTGTGCTGACCATCGACGAGAAAGGGACTGAAG

CTGCTGGGGCCATGTTTTTAGAGGCCATACCCATGTCTATCCCCCCCGAGGTCAAGTTC

AACAAACCCTTTGTCTTCCTGATGATCGAACAAAATACCAAGAGCCCCCTCTTCATGGG

AAAAGTGGTGAATCCCACCCAAAAATAA

TEV-hAAT-XbG sense strand, non-template.
3'_lowest_T. (1689 nt)
(SEQ ID NO: 100)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGAGCAGCGTCAGCTGGGGC

ATCCTCCTGCTGGCAGGCCTGTGCTGCCTGGTCCCCGTCAGCCTGGCCGAGGACCCCCA

GGGAGACGCCGCCCAGAAGACAGACACAAGCCACCACGACCAGGACCACCCAACCTTCA

ACAAGATCACCCCCAACCTGGCCGAGTTCGCCTTCAGCCTATACCGCCAGCTGGCACAC

CAGAGCAACAGCACCAACATCTTCTTCAGCCCAGTGAGCATCGCCACAGCCTTCGCAAT

GCTCAGCCTGGGGACCAAGGCCGACACCCACGACGAAATCCTGGAGGGCCTGAACTTCA

ACCTCACGGAGATCCCGGAGGCCCAGATCCACGAAGGCTTCCAGGAACTCCTCCGGACC

CTCAACCAGCCAGACAGCCAGCTCCAGCTGACCACCGGCAACGGCCTGTTCCTCAGCGA

GGGCCTGAAGCTAGTGGACAAGTTCCTGGAGGACGTGAAAAAGCTGTACCACAGCGAAG

CCTTCACCGTCAACTTCGGGGACACCGAAGAGGCCAAGAAACAGATCAACGACTACGTG

GAGAAGGGCACCCAAGGGAAAATCGTGGACCTGGTCAAGGAGCTGGACAGAGACACAGT

GTTCGCCCTGGTGAACTACATCTTCTTCAAAGGCAAATGGGAGAGACCCTTCGAAGTCA

AGGACACCGAGGAAGAGGACTTCCACGTGGACCAGGTGACCACCGTGAAGGTGCCCATG

ATGAAGCGGCTGGGCATGTTCAACATCCAGCACTGCAAGAAGCTGAGCAGCTGGGTGCT

GCTGATGAAATACCTGGGCAACGCCACCGCCATCTTCTTCCTGCCCGACGAGGGGAAAC

TACAGCACCTGGAAAACGAACTCACCCACGACATCATCACCAAGTTCCTGGAAAACGAA

GACAGAAGGAGCGCCAGCCTGCACCTGCCCAAACTGAGCATCACCGGAACCTACGACCT

GAAGTCCGTGCTGGGCCAACTGGGCATCACCAAGGTCTTCAGCAACGGGGCCGACCTCA

GCGGGGTCACAGAGGAGGCACCCCTGAAGCTCAGCAAGGCCGTGCACAAGGCCGTGCTG

ACCATCGACGAGAAAGGGACCGAAGCCGCCGGGGCCATGTTCCTGGAGGCCATACCCAT

GAGCATCCCCCCCGAGGTCAAGTTCAACAAACCCTTCGTCTTCCTGATGATCGAACAAA

ACACCAAGAGCCCCCTCTTCATGGGAAAAGTGGTGAACCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAAGAAAGTTTCTTCACATTCTAGAAAAAAAAAAAAAA

AAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAA

TEV-hAAT-XbG sense strand, non-template.
3'_16%_T. (1689 nt)
(SEQ ID NO: 101)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGTCTTCTGTCTCGTGGGGC

ATCCTCCTGCTGGCAGGCCTGTGCTGCCTGGTCCCTGTCTCCCTGGCTGAGGATCCCCA

GGGAGATGCTGCCCAGAAGACAGATACATCCCACCATGATCAGGATCACCCAACCTTCA

ACAAGATCACCCCCAACCTGGCTGAGTTCGCCTTCAGCCTATACCGCCAGCTGGCACAC

CAGTCCAACAGCACCAATATCTTCTTCTCCCCAGTGAGCATCGCTACAGCCTTTGCAAT

GCTCTCCCTGGGGACCAAGGCTGACACTCACGATGAAATCCTGGAGGGCCTGAACTTCA

-continued

ACCTCACGGAGATCCCGGAGGCCCAGATCCACGAAGGCTTCCAGGAACTCCTCCGGACC

CTCAACCAGCCAGACAGCCAGCTCCAGCTGACCACCGGCAACGGCCTGTTCCTCAGCGA

GGGCCTGAAGCTAGTGGACAAGTTCCTGGAGGACGTGAAAAAGCTGTACCACAGCGAAG

CCTTCACCGTCAACTTCGGGGACACCGAAGAGGCCAAGAAACAGATCAACGACTACGTG

GAGAAGGGCACCCAAGGGAAAATCGTGGACCTGGTCAAGGAGCTGGACAGAGACACAGT

GTTCGCCCTGGTGAACTACATCTTCTTCAAAGGCAAATGGGAGAGACCCTTCGAAGTCA

AGGACACCGAGGAAGAGGACTTCCACGTGGACCAGGTGACCACCGTGAAGGTGCCCATG

ATGAAGCGGCTGGGCATGTTCAACATCCAGCACTGCAAGAAGCTGAGCAGCTGGGTGCT

GCTGATGAAATACCTGGGCAACGCCACCGCCATCTTCTTCCTGCCCGACGAGGGGAAAC

TACAGCACCTGGAAAACGAACTCACCCACGACATCATCACCAAGTTCCTGGAAAACGAA

GACAGAAGGAGCGCCAGCCTGCACCTGCCCAAACTGAGCATCACCGGAACCTACGACCT

GAAGTCCGTGCTGGGCCAACTGGGCATCACCAAGGTCTTCAGCAACGGGGCCGACCTCA

GCGGGGTCACAGAGGAGGCACCCCTGAAGCTCAGCAAGGCCGTGCACAAGGCCGTGCTG

ACCATCGACGAGAAAGGGACCGAAGCCGCCGGGGCCATGTTCCTGGAGGCCATACCCAT

GAGCATCCCCCCCGAGGTCAAGTTCAACAAACCCTTCGTCTTCCTGATGATCGAACAAA

ACACCAAGAGCCCCCTCTTCATGGGAAAAGTGGTGAACCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAAGAAAGTTTCTTCACATTCTAGAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA

TEV-hAAT-XbG sense strand, non-template.
3'_18%_T. (1689 nt)

(SEQ ID NO: 102)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGTCTTCTGTCTCGTGGGGC

ATCCTCCTGCTGGCAGGCCTGTGCTGCCTGGTCCCTGTCTCCCTGGCTGAGGATCCCCA

GGGAGATGCTGCCCAGAAGACAGATACATCCCACCATGATCAGGATCACCCAACCTTCA

ACAAGATCACCCCCAACCTGGCTGAGTTCGCCTTCAGCCTATACCGCCAGCTGGCACAC

CAGTCCAACAGCACCAATATCTTCTTCTCCCCAGTGAGCATCGCTACAGCCTTTGCAAT

GCTCTCCCTGGGGACCAAGGCTGACACTCACGATGAAATCCTGGAGGGCCTGAATTTCA

ACCTCACGGAGATTCCGGAGGCTCAGATCCATGAAGGCTTCCAGGAACTCCTCCGTACC

CTCAACCAGCCAGACAGCCAGCTCCAGCTGACCACCGGCAATGGCCTGTTCCTCAGCGA

GGGCCTGAAGCTAGTGGATAAGTTTTTGGAGGATGTTAAAAAGTTGTACCACTCAGAAG

CCTTCACTGTCAACTTCGGGGACACCGAAGAGGCCAAGAAACAGATCAACGATTACGTG

GAGAAGGGTACTCAAGGGAAAATTGTGGATTTGGTCAAGGAGCTTGACAGAGACACAGT

TTTTGCTCTGGTGAATTACATCTTCTTCAAAGGCAAATGGGAGAGACCCTTCGAAGTCA

AGGACACCGAGGAAGAGGACTTCCACGTGGACCAGGTGACCACCGTGAAGGTGCCCATG

ATGAAGCGGCTGGGCATGTTCAACATCCAGCACTGCAAGAAGCTGAGCAGCTGGGTGCT

GCTGATGAAATACCTGGGCAACGCCACCGCCATCTTCTTCCTGCCCGACGAGGGGAAAC

TACAGCACCTGGAAAACGAACTCACCCACGACATCATCACCAAGTTCCTGGAAAACGAA

-continued

```
GACAGAAGGAGCGCCAGCCTGCACCTGCCCAAACTGAGCATCACCGGAACCTACGACCT

GAAGTCCGTGCTGGGCCAACTGGGCATCACCAAGGTCTTCAGCAACGGGGCCGACCTCA

GCGGGGTCACAGAGGAGGCACCCCTGAAGCTCAGCAAGGCCGTGCACAAGGCCGTGCTG

ACCATCGACGAGAAAGGGACCGAAGCCGCCGGGGCCATGTTCCTGGAGGCCATACCCAT

GAGCATCCCCCCCGAGGTCAAGTTCAACAAACCCTTCGTCTTCCTGATGATCGAACAAA

ACACCAAGAGCCCCCTCTTCATGGGAAAAGTGGTGAACCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAGAAAGTTTCTTCACATTCTAGAAAAAAAAAAAAA

AAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA
```

TEV-hAAT-XbG sense strand, non-template.
3'_20%_T. (1689 nt)

(SEQ ID NO: 103)

```
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGTCTTCTGTCTCGTGGGGC

ATCCTCCTGCTGGCAGGCCTGTGCTGCCTGGTCCCTGTCTCCTGGCTGAGGATCCCCA

GGGAGATGCTGCCCAGAAGACAGATACATCCCACCATGATCAGGATCACCCAACCTTCA

ACAAGATCACCCCCAACCTGGCTGAGTTCGCCTTCAGCCTATACCGCCAGCTGGCACAC

CAGTCCAACAGCACCAATATCTTCTTCTCCCCAGTGAGCATCGCTACAGCCTTTGCAAT

GCTCTCCCTGGGGACCAAGGCTGACACTCACGATGAAATCCTGGAGGGCCTGAATTTCA

ACCTCACGGAGATTCCGGAGGCTCAGATCCATGAAGGCTTCCAGGAACTCCTCCGTACC

CTCAACCAGCCAGACAGCCAGCTCCAGCTGACCACCGGCAATGGCCTGTTCCTCAGCGA

GGGCCTGAAGCTAGTGGATAAGTTTTTGGAGGATGTTAAAAAGTTGTACCACTCAGAAG

CCTTCACTGTCAACTTCGGGGACACCGAAGAGGCCAAGAAACAGATCAACGATTACGTG

GAGAAGGGTACTCAAGGGAAAATTGTGGATTTGGTCAAGGAGCTTGACAGAGACACAGT

TTTTGCTCTGGTGAATTACATCTTCTTTAAAGGCAAATGGGAGAGACCCTTTGAAGTCA

AGGACACCGAGGAAGAGGACTTCCACGTGGACCAGGTGACCACCGTGAAGGTGCCTATG

ATGAAGCGTTTAGGCATGTTTAACATCCAGCACTGTAAGAAGCTGTCCAGCTGGGTGCT

GCTGATGAAATACCTGGGCAATGCCACCGCCATCTTCTTCCTGCCTGATGAGGGGAAAC

TACAGCACCTGGAAAATGAACTCACCCACGATATCATCACCAAGTTCCTGGAAAATGAA

GACAGAAGGTCTGCCAGCTTACATTTACCCAAACTGTCCATTACTGGAACCTATGATCT

GAAGTCCGTGCTGGGTCAACTGGGCATCACCAAGGTCTTCAGCAACGGGGCCGACCTCA

GCGGGGTCACAGAGGAGGCACCCCTGAAGCTCAGCAAGGCCGTGCACAAGGCCGTGCTG

ACCATCGACGAGAAAGGGACCGAAGCCGCCGGGGCCATGTTCCTGGAGGCCATACCCAT

GAGCATCCCCCCCGAGGTCAAGTTCAACAAACCCTTCGTCTTCCTGATGATCGAACAAA

ACACCAAGAGCCCCCTCTTCATGGGAAAAGTGGTGAACCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAGAAAGTTTCTTCACATTCTAGAAAAAAAAAAAAA
```

-continued

AAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA

TEV-hAAT-XbG sense strand, non-template.
5'_16%_T. (1689 nt)
(SEQ ID NO: 104)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGAGCAGCGTCAGCTGGGGC

ATCCTCCTGCTGGCAGGCCTGTGCTGCCTGGTCCCCGTCAGCCTGGCCGAGGACCCCCA

GGGAGACGCCGCCCAGAAGACAGACACAAGCCACCACGACCAGGACCACCCAACCTTCA

ACAAGATCACCCCCAACCTGGCCGAGTTCGCCTTCAGCCTATACCGCCAGCTGGCACAC

CAGAGCAACAGCACCAACATCTTCTTCAGCCCAGTGAGCATCGCCACAGCCTTCGCAAT

GCTCAGCCTGGGGACCAAGGCCGACACCCACGACGAAATCCTGGAGGGCCTGAACTTCA

ACCTCACGGAGATCCCGGAGGCCCAGATCCACGAAGGCTTCCAGGAACTCCTCCGGACC

CTCAACCAGCCAGACAGCCAGCTCCAGCTGACCACCGGCAACGGCCTGTTCCTCAGCGA

GGGCCTGAAGCTAGTGGACAAGTTCCTGGAGGACGTGAAAAAGCTGTACCACAGCGAAG

CCTTCACCGTCAACTTCGGGGACACCGAAGAGGCCAAGAAACAGATCAACGACTACGTG

GAGAAGGGCACCCAAGGGAAAATCGTGGACCTGGTCAAGGAGCTGGACAGAGACACAGT

GTTCGCCCTGGTGAACTACATCTTCTTCAAAGGCAAATGGGAGAGACCCTTCGAAGTCA

AGGACACCGAGGAAGAGGACTTCCACGTGGACCAGGTGACCACCGTGAAGGTGCCCATG

ATGAAGCGGCTGGGCATGTTCAACATCCAGCACTGCAAGAAGCTGAGCAGCTGGGTGCT

GCTGATGAAATACCTGGGCAACGCCACCGCCATCTTCTTCCTGCCCGACGAGGGGAAAC

TACAGCACCTGGAAAACGAACTCACCCACGACATCATCACCAAGTTCCTGGAAAACGAA

GACAGAAGGAGCGCCAGCCTGCACCTGCCCAAACTGAGCATTACTGGAACCTATGATCT

GAAGTCCGTGCTGGGTCAACTGGGCATCACTAAGGTCTTCAGCAATGGGGCTGACCTCT

CCGGGGTCACAGAGGAGGCACCCCTGAAGCTCTCCAAGGCCGTGCATAAGGCTGTGCTG

ACCATCGACGAGAAAGGGACTGAAGCTGCTGGGGCCATGTTTTTAGAGGCCATACCCAT

GTCTATCCCCCCCGAGGTCAAGTTCAACAAACCCTTTGTCTTCTTAATGATTGAACAAA

ATACCAAGTCTCCCCTCTTCATGGGAAAAGTGGTGAATCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAAGAAAGTTTCTTCACATTCTAGAAAAAAAAAAAAA

AAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA

TEV-hAAT-XbG sense strand, non-template.
5'_18%_T. (1689 nt)
(SEQ ID NO: 105)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGAGCAGCGTCAGCTGGGGC

ATCCTCCTGCTGGCAGGCCTGTGCTGCCTGGTCCCCGTCAGCCTGGCCGAGGACCCCCA

GGGAGACGCCGCCCAGAAGACAGACACAAGCCACCACGACCAGGACCACCCAACCTTCA

ACAAGATCACCCCCAACCTGGCCGAGTTCGCCTTCAGCCTATACCGCCAGCTGGCACAC

-continued

```
CAGAGCAACAGCACCAACATCTTCTTCAGCCCAGTGAGCATCGCCACAGCCTTCGCAAT
GCTCAGCCTGGGGACCAAGGCCGACACCCACGACGAAATCCTGGAGGGCCTGAACTTCA
ACCTCACGGAGATCCCGGAGGCCCAGATCCACGAAGGCTTCCAGGAACTCCTCCGGACC
CTCAACCAGCCAGACAGCCAGCTCCAGCTGACCACCGGCAACGGCCTGTTCCTCAGCGA
GGGCCTGAAGCTAGTGGACAAGTTCCTGGAGGACGTGAAAAAGCTGTACCACAGCGAAG
CCTTCACCGTCAACTTCGGGGACACCGAAGAGGCCAAGAAACAGATCAACGACTACGTG
GAGAAGGGCACCCAAGGGAAAATCGTGGACCTGGTCAAGGAGCTTGACAGAGACACAGT
TTTTGCTCTGGTGAATTACATCTTCTTTAAAGGCAAATGGGAGAGACCCTTTGAAGTCA
AGGACACCGAGGAAGAGGACTTCCACGTGGACCAGGTGACCACCGTGAAGGTGCCTATG
ATGAAGCGTTTAGGCATGTTTAACATCCAGCACTGTAAGAAGCTGTCCAGCTGGGTGCT
GCTGATGAAATACCTGGGCAATGCCACCGCCATCTTCTTCCTGCCTGATGAGGGGAAAC
TACAGCACCTGGAAAATGAACTCACCCACGATATCATCACCAAGTTCCTGGAAAATGAA
GACAGAAGGTCTGCCAGCTTACATTTACCCAAACTGTCCATTACTGGAACCTATGATCT
GAAGTCCGTGCTGGGTCAACTGGGCATCACTAAGGTCTTCAGCAATGGGGCTGACCTCT
CCGGGGTCACAGAGGAGGCACCCCTGAAGCTCTCCAAGGCCGTGCATAAGGCTGTGCTG
ACCATCGACGAGAAAGGGACTGAAGCTGCTGGGGCCATGTTTTTAGAGGCCATACCCAT
GTCTATCCCCCCCGAGGTCAAGTTCAACAAACCCTTTGTCTTCTTAATGATTGAACAAA
ATACCAAGTCTCCCCTCTTCATGGGAAAAGTGGTGAATCCCACCCAAAAATAACTCGAG
CTAGTGACTGACTAGGATCTGGTTACCACTAAACCAGCCTCAAGAACACCCGAATGGAG
TCTCTAAGCTACATAATACCAACTTACACTTACAAAATGTTGTCCCCCAAAATGTAGCC
ATTCGTATCTGCTCCTAATAAAAAGAAAGTTTCTTCACATTCTAGAAAAAAAAAAAAAA
AAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAA
```

TEV-hAAT-XbG sense strand, non-template.
5'_20%_T. (1689 nt)

(SEQ ID NO: 106)

```
AGGAAACTTAAGTCAACACAACATATACAAAACAAACGAATCTCAAGCA
ATCAAGCATTCTACTTCTATTGCAGCAATTTAAATCATTTCTTTTAAAGCAAAAGCAAT
TTTCTGAAAATTTTCACCATTTACGAACGATAGCCATGCCGAGCAGCGTCAGCTGGGGC
ATCCTCCTGCTGGCAGGCCTGTGCTGCCTGGTCCCCGTCAGCCTGGCCGAGGACCCCCA
GGGAGACGCCGCCCAGAAGACAGACACAAGCCACCACGACCAGGACCACCCAACCTTCA
ACAAGATCACCCCCAACCTGGCCGAGTTCGCCTTCAGCCTATACCGCCAGCTGGCACAC
CAGAGCAACAGCACCAACATCTTCTTCAGCCCAGTGAGCATCGCCACAGCCTTTGCAAT
GCTCTCCCTGGGGACCAAGGCTGACACTCACGATGAAATCCTGGAGGGCCTGAATTTCA
ACCTCACGGAGATTCCGGAGGCTCAGATCCATGAAGGCTTCCAGGAACTCCTCCGTACC
CTCAACCAGCCAGACAGCCAGCTCCAGCTGACCACCGGCAATGGCCTGTTCCTCAGCGA
GGGCCTGAAGCTAGTGGATAAGTTTTTGGAGGATGTTAAAAAGTTGTACCACTCAGAAG
CCTTCACTGTCAACTTCGGGGACACCGAAGAGGCCAAGAAACAGATCAACGATTACGTG
GAGAAGGGTACTCAAGGGAAAATTGTGGATTTGGTCAAGGAGCTTGACAGAGACACAGT
TTTTGCTCTGGTGAATTACATCTTCTTTAAAGGCAAATGGGAGAGACCCTTTGAAGTCA
AGGACACCGAGGAAGAGGACTTCCACGTGGACCAGGTGACCACCGTGAAGGTGCCTATG
ATGAAGCGTTTAGGCATGTTTAACATCCAGCACTGTAAGAAGCTGTCCAGCTGGGTGCT
```

```
GCTGATGAAATACCTGGGCAATGCCACCGCCATCTTCTTCCTGCCTGATGAGGGGAAAC

TACAGCACCTGGAAAATGAACTCACCCACGATATCATCACCAAGTTCCTGGAAAATGAA

GACAGAAGGTCTGCCAGCTTACATTTACCCAAACTGTCCATTACTGGAACCTATGATCT

GAAGTCCGTGCTGGGTCAACTGGGCATCACTAAGGTCTTCAGCAATGGGGCTGACCTCT

CCGGGGTCACAGAGGAGGCACCCCTGAAGCTCTCCAAGGCCGTGCATAAGGCTGTGCTG

ACCATCGACGAGAAAGGGACTGAAGCTGCTGGGGCCATGTTTTTAGAGGCCATACCCAT

GTCTATCCCCCCCGAGGTCAAGTTCAACAAACCCTTTGTCTTCTTAATGATTGAACAAA

ATACCAAGTCTCCCCTCTTCATGGGAAAAGTGGTGAATCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAGAAAGTTTCTTCACATTCTAGAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA
```

TEV-hAAT-XbG sense strand, non-template.
random_16%_T. (1689 nt)

(SEQ ID NO: 107)

```
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGAGCAGCGTCTCGTGGGC

ATCCTCCTGCTGGCAGGCCTGTGCTGCCTGGTCCCCGTCAGCCTGGCCGAGGACCCCCA

GGGAGATGCTGCCCAGAAGACAGACACATCCCACCACGACCAGGACCACCCAACCTTCA

ACAAGATCACCCCCAACCTGGCTGAGTTCGCCTTCAGCCTATACCGCCAGCTGGCACAC

CAGAGCAACAGCACCAATATCTTCTTCAGCCCAGTGAGCATCGCTACAGCCTTCGCAAT

GCTCAGCCTGGGGACCAAGGCCGACACCCACGATGAAATCCTGGAGGGCCTGAATTTCA

ACCTCACGGAGATCCCGGAGGCTCAGATCCACGAAGGCTTCCAGGAACTCCTCCGGACC

CTCAACCAGCCAGACAGCCAGCTCCAGCTGACCACCGGCAACGGCCTGTTCCTCAGCGA

GGGCCTGAAGCTAGTGGACAAGTTCCTGGAGGACGTTAAAAAGCTGTACCACAGCGAAG

CCTTCACCGTCAACTTCGGGGACACCGAAGAGGCCAAGAAACAGATCAACGATTACGTG

GAGAAGGGCACCCAAGGGAAAATCGTGGACCTGGTCAAGGAGCTTGACAGAGACACAGT

GTTTGCCCTGGTGAACTACATCTTCTTCAAAGGCAAATGGGAGAGACCCTTCGAAGTCA

AGGACACCGAGGAAGAGGACTTCCACGTGGACCAGGTGACCACCGTGAAGGTGCCCATG

ATGAAGCGGTTAGGCATGTTCAACATCCAGCACTGCAAGAAGCTGAGCAGCTGGGTGCT

GCTGATGAAATACCTGGGCAACGCCACCGCCATCTTCTTCCTGCCCGACGAGGGGAAAC

TACAGCACCTGGAAAACGAACTCACCCACGACATCATCACCAAGTTCCTGGAAAACGAA

GACAGAAGGAGCGCCAGCCTGCATCTGCCCAAACTGAGCATTACTGGAACCTACGATCT

GAAGTCCGTGCTGGGTCAACTGGGCATCACCAAGGTCTTCAGCAATGGGCCGACCTCA

GCGGGGTCACAGAGGAGGCACCCCTGAAGCTCAGCAAGGCCGTGCACAAGGCTGTGCTG

ACCATCGACGAGAAAGGGACCGAAGCCGCTGGGGCCATGTTCCTGGAGGCCATACCCAT

GAGCATCCCCCCCGAGGTCAAGTTCAACAAACCCTTTGTCTTCCTGATGATCGAACAAA

ACACCAAGTCTCCCCTCTTCATGGGAAAAGTGGTGAACCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC
```

ATTCGTATCTGCTCCTAATAAAAAGAAAGTTTCTTCACATTCTAGAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA

TEV-hAAT-XbG sense strand, non-template.
random_18%_T. (1689 nt)

(SEQ ID NO: 108)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGTCTTCTGTCTCGTGGGGC

ATCCTCCTGCTGGCAGGCCTGTGCTGCCTGGTCCCCGTCTCCCTGGCTGAGGACCCCCA

GGGAGATGCCGCCCAGAAGACAGACACATCCCACCATGACCAGGACCACCCAACCTTCA

ACAAGATCACCCCCAACCTGGCCGAGTTCGCCTTCAGCCTATACCGCCAGCTGGCACAC

CAGAGCAACAGCACCAACATCTTCTTCTCCCCAGTGAGCATCGCCACAGCCTTTGCAAT

GCTCTCCCTGGGGACCAAGGCCGACACCCACGACGAAATCCTGGAGGGCCTGAATTTCA

ACCTCACGGAGATCCCGGAGGCTCAGATCCATGAAGGCTTCCAGGAACTCCTCCGGACC

CTCAACCAGCCAGACAGCCAGCTCCAGCTGACCACCGGCAATGGCCTGTTCCTCAGCGA

GGGCCTGAAGCTAGTGGATAAGTTCCTGGAGGATGTTAAAAAGCTGTACCACAGCGAAG

CCTTCACCGTCAACTTCGGGGACACCGAAGAGGCCAAGAAACAGATCAACGATTACGTG

GAGAAGGGCACCCAAGGGAAAATCGTGGACCTGGTCAAGGAGCTTGACAGAGACACAGT

GTTTGCTCTGGTGAATTACATCTTCTTTAAAGGCAAATGGGAGAGACCCTTTGAAGTCA

AGGACACCGAGGAAGAGGACTTCCACGTGGACCAGGTGACCACCGTGAAGGTGCCTATG

ATGAAGCGGTTAGGCATGTTTAACATCCAGCACTGCAAGAAGCTGAGCAGCTGGGTGCT

GCTGATGAAATACCTGGGCAATGCCACCGCCATCTTCTTCCTGCCTGATGAGGGGAAAC

TACAGCACCTGGAAAACGAACTCACCCACGACATCATCACCAAGTTCCTGGAAAATGAA

GACAGAAGGTCTGCCAGCTTACACTTACCCAAACTGAGCATTACTGGAACCTACGATCT

GAAGTCCGTGCTGGGCCAACTGGGCATCACTAAGGTCTTCAGCAACGGGGCTGACCTCT

CCGGGGTCACAGAGGAGGCACCCCTGAAGCTCAGCAAGGCCGTGCACAAGGCTGTGCTG

ACCATCGACGAGAAAGGGACCGAAGCTGCCGGGGCCATGTTTCTGGAGGCCATACCCAT

GTCTATCCCCCCCGAGGTCAAGTTCAACAAACCCTTTGTCTTCCTGATGATCGAACAAA

ATACCAAGAGCCCCCTCTTCATGGGAAAAGTGGTGAACCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAAGAAAGTTTCTTCACATTCTAGAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA

TEV-hAAT-XbG sense strand, non-template.
random_20%_T. (1689 nt)

(SEQ ID NO: 109)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGAGCAGCGTCAGCTGGGGC

ATCCTCCTGCTGGCAGGCCTGTGCTGCCTGGTCCCTGTCTCCCTGGCTGAGGATCCCCA

GGGAGATGCTGCCCAGAAGACAGATACATCCCACCATGATCAGGATCACCCAACCTTCA

ACAAGATCACCCCCAACCTGGCTGAGTTCGCCTTCAGCCTATACCGCCAGCTGGCACAC

-continued

```
CAGTCCAACAGCACCAATATCTTCTTCTCCCCAGTGAGCATCGCTACAGCCTTCGCAAT

GCTCTCCCTGGGGACCAAGGCTGACACTCACGATGAAATCCTGGAGGGCCTGAATTTCA

ACCTCACGGAGATTCCGGAGGCCCAGATCCATGAAGGCTTCCAGGAACTCCTCCGTACC

CTCAACCAGCCAGACAGCCAGCTCCAGCTGACCACCGGCAATGGCCTGTTCCTCAGCGA

GGGCCTGAAGCTAGTGGATAAGTTTTTGGAGGATGTTAAAAAGCTGTACCACAGCGAAG

CCTTCACTGTCAACTTCGGGGACACCGAAGAGGCCAAGAAACAGATCAACGATTACGTG

GAGAAGGGTACTCAAGGGAAAATTGTGGATTTGGTCAAGGAGCTTGACAGAGACACAGT

TTTTGCTCTGGTGAATTACATCTTCTTCAAAGGCAAATGGGAGAGACCCTTTGAAGTCA

AGGACACCGAGGAAGAGGACTTCCACGTGGACCAGGTGACCACCGTGAAGGTGCCTATG

ATGAAGCGGTTAGGCATGTTCAACATCCAGCACTGTAAGAAGCTGTCCAGCTGGGTGCT

GCTGATGAAATACCTGGGCAATGCCACCGCCATCTTCTTCCTGCCTGATGAGGGGAAAC

TACAGCACCTGGAAAATGAACTCACCCACGATATCATCACCAAGTTCCTGGAAAATGAA

GACAGAAGGAGCGCCAGCTTACATTTACCCAAACTGAGCATTACTGGAACCTACGATCT

GAAGTCCGTGCTGGGTCAACTGGGCATCACTAAGGTCTTCAGCAACGGGGCTGACCTCT

CCGGGGTCACAGAGGAGGCACCCCTGAAGCTCTCCAAGGCCGTGCATAAGGCTGTGCTG

ACCATCGACGAGAAAGGGACTGAAGCTGCTGGGGCCATGTTTTTAGAGGCCATACCCAT

GTCTATCCCCCCCGAGGTCAAGTTCAACAAACCCTTTGTCTTCCTGATGATCGAACAAA

ATACCAAGAGCCCCTCTTCATGGGAAAAGTGGTGAATCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAGAAAGTTTCTTCACATTCTAGAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAA
```

TEV-hAAT-XbG ARC-mRNA. 3'_lowest_T.
(1689 nt)

(SEQ ID NO: 110)

```
5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGAGCAGCGUCAGCUGGGGCAUCCUCCUGC

UGGCAGGCCUGUGCUGCCUGGUCCCCGUCAGCCUGGCCGAGGACCCCCAGGGAGACGCC

GCCCAGAAGACAGACACAAGCCACCACGACCAGGACCACCCAACCUUCAACAAGAUCAC

CCCCAACCUGGCCGAGUUCGCCUUCAGCCUAUACCGCCAGCUGGCACACCAGAGCAACA

GCACCAACAUCUUCUUCAGCCCAGUGAGCAUCGCCACAGCCUUCGCAAUGCUCAGCCUG

GGGACCAAGGCCGACACCCACGACGAAAUCCUGGAGGGCCUGAACUUCAACCUCACGGA

GAUCCCGGAGGCCCAGAUCCACGAAGGCUUCCAGGAACUCCUCCGGACCCUCAACCAGC

CAGACAGCCAGCUCCAGCUGACCACCGGCAACGGCCUGUUCCUCAGCGAGGGCCUGAAG

CUAGUGGACAAGUUCCUGGAGGACGUGAAAAAGCUGUACCACAGCGAAGCCUUCACCGU

CAACUUCGGGGACACCGAAGAGGCCAAGAAACAGAUCAACGACUACGUGGAGAAGGGCA

CCCAAGGGAAAAUCGUGGACCUGGUCAAGGAGCUGGACAGAGACACAGUGUUCGCCCUG

GUGAACUACAUCUUCUUCAAAGGCAAAUGGGAGAGACCCUUCGAAGUCAAGGACACCGA

GGAAGAGGACUUCCACGUGGACCAGGUGACCACCGUGAAGGUGCCCAUGAUGAAGCGGC
```

-continued

UGGGCAUGUUCAACAUCCAGCACUGCAAGAAGCUGAGCAGCUGGGUGCUGCUGAUGAAA

UACCUGGGCAACGCCACCGCCAUCUUCUUCCUGCCCGACGAGGGGAAACUACAGCACCU

GGAAAACGAACUCACCCACGACAUCAUCACCAAGUUCCUGGAAAACGAAGACAGAAGGA

GCGCCAGCCUGCACCUGCCCAAACUGAGCAUCACCGGAACCUACGACCUGAAGUCCGUG

CUGGGCCAACUGGGCAUCACCAAGGUCUUCAGCAACGGGGCCGACCUCAGCGGGGUCAC

AGAGGAGGCACCCCUGAAGCUCAGCAAGGCCGUGCACAAGGCCGUGCUGACCAUCGACG

AGAAAGGGACCGAAGCCGCCGGGGCCAUGUUCCUGGAGGCCAUACCCAUGAGCAUCCCC

CCCGAGGUCAAGUUCAACAAACCCUUCGUCUUCCUGAUGAUCGAACAAAACACCAAGAG

CCCCCUCUUCAUGGGAAAAGUGGUGAACCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAGAAAGUUUCUUCACAUUCUAGAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAA

TEV-hAAT-XbG ARC-mRNA. 3'_16%_T.
(1689 nt)
(SEQ ID NO: 111)
5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGUCUUCUGUCUCGUGGGGCAUCCUCCUGC

UGGCAGGCCUGUGCUGCCUGGUCCCUGUCUCCCUGGCUGAGGAUCCCCAGGGAGAUGCU

GCCCAGAAGACAGAUACAUCCCACCAUGAUCAGGAUCACCCAACCUUCAACAAGAUCAC

CCCCAACCUGGCUGAGUUCGCCUUCAGCCUAUACCGCCAGCUGGCACACCAGUCCAACA

GCACCAAUAUCUUCUUCUCCCCAGUGAGCAUCGCUACAGCCUUUGCAAUGCUCUCCCUG

GGGACCAAGGCUGACACUCACGAUGAAAUCCUGGAGGGCCUGAACUUCAACCUCACGGA

GAUCCCGGAGGCCCAGAUCCACGAAGGCUUCCAGGAACUCCUCCGGACCCUCAACCAGC

CAGACAGCCAGCUCCAGCUGACCACCGGCAACGGCCUGUUCCUCAGCGAGGGCCUGAAG

CUAGUGGACAAGUUCCUGGAGGACGUGAAAAAGCUGUACCACAGCGAAGCCUUCACCGU

CAACUUCGGGGACACCGAAGAGGCCAAGAAACAGAUCAACGACUACGUGGAGAAGGGCA

CCCAAGGGAAAAUCGUGGACCUGGUCAAGGAGCUGGACAGAGACACAGUGUUCGCCCUG

GUGAACUACAUCUUCUUCAAAGGCAAAUGGGAGAGACCCUUCGAAGUCAAGGACACCGA

GGAAGAGGACUUCCACGUGGACCAGGUGACCACCGUGAAGGUGCCCAUGAUGAAGCGGC

UGGGCAUGUUCAACAUCCAGCACUGCAAGAAGCUGAGCAGCUGGGUGCUGCUGAUGAAA

UACCUGGGCAACGCCACCGCCAUCUUCUUCCUGCCCGACGAGGGGAAACUACAGCACCU

GGAAAACGAACUCACCCACGACAUCAUCACCAAGUUCCUGGAAAACGAAGACAGAAGGA

GCGCCAGCCUGCACCUGCCCAAACUGAGCAUCACCGGAACCUACGACCUGAAGUCCGUG

CUGGGCCAACUGGGCAUCACCAAGGUCUUCAGCAACGGGGCCGACCUCAGCGGGGUCAC

AGAGGAGGCACCCCUGAAGCUCAGCAAGGCCGUGCACAAGGCCGUGCUGACCAUCGACG

AGAAAGGGACCGAAGCCGCCGGGGCCAUGUUCCUGGAGGCCAUACCCAUGAGCAUCCCC

CCCGAGGUCAAGUUCAACAAACCCUUCGUCUUCCUGAUGAUCGAACAAAACACCAAGAG

CCCCCUCUUCAUGGGAAAAGUGGUGAACCCCACCCAAAAAUAACUCGAGCUAGUGACUG

ACUAGGAUCUGGUUACCACUAAACCAGCCUCAAGAACACCCGAAUGGAGUCUCUAAGCU

```
ACAUAAUACCAACUUACACUUACAAAAUGUUGUCCCCCAAAAUGUAGCCAUUCGUAUCU

GCUCCUAAUAAAAAGAAAGUUUCUUCACAUUCUAGAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAA
```

TEV-hAAT-XbG ARC-mRNA. 3'_18%_T. (1689 nt)

(SEQ ID NO: 112)

```
5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGUCUUCUGUCUCGUGGGGCAUCCUCCUGC

UGGCAGGCCUGUGCUGCCUGGUCCCUGUCUCCCUGGCUGAGGAUCCCCAGGGAGAUGCU

GCCCAGAAGACAGAUACAUCCCACCAUGAUCAGGAUCACCCAACCUUCAACAAGAUCAC

CCCCAACCUGGCUGAGUUCGCCUUCAGCCUAUACCGCCAGCUGGCACACCAGUCCAACA

GCACCAAUAUCUUCUUCUCCCCAGUGAGCAUCGCUACAGCCUUUGCAAUGCUCUCCCUG

GGGACCAAGGCUGACACUCACGAUGAAAUCCUGGAGGGCCUGAAUUUCAACCUCACGGA

GAUUCCGGAGGCUCAGAUCCAUGAAGGCUUCCAGGAACUCCUCCGUACCCUCAACCAGC

CAGACAGCCAGCUCCAGCUGACCACCGGCAAUGGCCUGUUCCUCAGCGAGGGCCUGAAG

CUAGUGGAUAAGUUUUUGGAGGAUGUUAAAAAGUUGUACCACUCAGAAGCCUUCACUGU

CAACUUCGGGGACACCGAAGAGGCCAAGAAACAGAUCAACGAUUACGUGGAGAAGGGUA

CUCAAGGGAAAAUUGUGGAUUUGGUCAAGGAGCUUGACAGAGACACAGUUUUUGCUCUG

GUGAAUUACAUCUUCUUCAAAGGCAAAUGGGAGAGACCCUUCGAAGUCAAGGACACCGA

GGAAGAGGACUUCCACGUGGACCAGGUGACCACCGUGAAGGUGCCCAUGAUGAAGCGGC

UGGGCAUGUUCAACAUCCAGCACUGCAAGAAGCUGAGCAGCUGGGUGCUGCUGAUGAAA

UACCUGGGCAACGCCACCGCCAUCUUCUUCCUGCCCGACGAGGGGAAACUACAGCACCU

GGAAAACGAACUCACCCACGACAUCAUCACCAAGUUCCUGGAAAACGAAGACAGAAGGA

GCGCCAGCCUGCACCUGCCCAAACUGAGCAUCACCGGAACCUACGACCUGAAGUCCGUG

CUGGGCCAACUGGGCAUCACCAAGGUCUUCAGCAACGGGGCCGACCUCAGCGGGGUCAC

AGAGGAGGCACCCCUGAAGCUCAGCAAGGCCGUGCACAAGGCCGUGCUGACCAUCGACG

AGAAAGGGACCGAAGCCGCCGGGGCCAUGUUCCUGGAGGCCAUACCCAUGAGCAUCCCC

CCCGAGGUCAAGUUCAACAAACCCUUCGUCUUCCUGAUGAUCGAACAAAACACCAAGAG

CCCCCUCUUCAUGGGAAAAGUGGUGAACCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAAGAAAGUUUCUUCACAUUCUAGAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAA
```

TEV-hAAT-XbG ARC-mRNA. 3'_20%_T. (1689 nt)

(SEQ ID NO: 113)

```
5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGUCUUCUGUCUCGUGGGGCAUCCUCCUGC
```

-continued

UGGCAGGCCUGUGCUGCCUGGUCCCUGUCUCCCUGGCUGAGGAUCCCCAGGGAGAUGCU

GCCCAGAAGACAGAUACAUCCCACCAUGAUCAGGAUCACCCAACCUUCAACAAGAUCAC

CCCCAACCUGGCUGAGUUCGCCUUCAGCCUAUACCGCCAGCUGGCACACCAGUCCAACA

GCACCAAUAUCUUCUUCUCCCCAGUGAGCAUCGCUACAGCCUUUGCAAUGCUCUCCCUG

GGGACCAAGGCUGACACUCACGAUGAAAUCCUGGAGGGCCUGAAUUUCAACCUCACGGA

GAUUCCGGAGGCUCAGAUCCAUGAAGGCUUCCAGGAACUCCUCCGUACCCUCAACCAGC

CAGACAGCCAGCUCCAGCUGACCACCGGCAAUGGCCUGUUCCUCAGCGAGGGCCUGAAG

CUAGUGGAUAAGUUUUUGGAGGAUGUUAAAAAGUUGUACCACUCAGAAGCCUUCACUGU

CAACUUCGGGGACACCGAAGAGGCCAAGAAACAGAUCAACGAUUACGUGGAGAAGGGUA

CUCAAGGGAAAAUUGUGGAUUUGGUCAAGGAGCUUGACAGAGACACAGUUUUUGCUCUG

GUGAAUUACAUCUUCUUUAAAGGCAAAUGGGAGAGACCCUUUGAAGUCAAGGACACCGA

GGAAGAGGACUUCCACGUGGACCAGGUGACCACCGUGAAGGUGCCUAUGAUGAAGCGUU

UAGGCAUGUUUAACAUCCAGCACUGUAAGAAGCUGUCCAGCUGGGUGCUGCUGAUGAAA

UACCUGGGCAAUGCCACCGCCAUCUUCUUCCUGCCUGAUGAGGGGAAACUACAGCACCU

GGAAAAUGAACUCACCCACGAUAUCAUCACCAAGUUCCUGGAAAAUGAAGACAGAAGGU

CUGCCAGCUUACAUUUACCCAAACUGUCCAUUACUGGAACCUAUGAUCUGAAGUCCGUG

CUGGGUCAACUGGGCAUCACCAAGGUCUUCAGCAACGGGGCCGACCUCAGCGGGGUCAC

AGAGGAGGCACCCCUGAAGCUCAGCAAGGCCGUGCACAAGGCCGUGCUGACCAUCGACG

AGAAAGGGACCGAAGCCGCCGGGGCCAUGUUCCUGGAGGCCAUACCCAUGAGCAUCCCC

CCCGAGGUCAAGUUCAACAAACCCUUCGUCUUCCUGAUGAUCGAACAAAACACCAAGAG

CCCCCUCUUCAUGGGAAAAGUGGUGAACCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAGAAAGUUUCUUCACAUUCUAGAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAA

TEV-hAAT-XbG ARC-mRNA. 5'_16%_T. (1689
nt)
(SEQ ID NO: 114)
5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGAGCAGCGUCAGCUGGGGCAUCCUCCUGC

UGGCAGGCCUGUGCUGCCUGGUCCCGUCAGCCUGGCCGAGGACCCCCAGGGAGACGCC

GCCCAGAAGACAGACACAAGCCACCACGACCAGGACCACCCAACCUUCAACAAGAUCAC

CCCCAACCUGGCCGAGUUCGCCUUCAGCCUAUACCGCCAGCUGGCACACCAGAGCAACA

GCACCAACAUCUUCUUCAGCCCAGUGAGCAUCGCCACAGCCUUCGCAAUGCUCAGCCUG

GGGACCAAGGCCGACACCCACGACGAAAUCCUGGAGGGCCUGAACUUCAACCUCACGGA

GAUCCCGGAGGCCCAGAUCCACGAAGGCUUCCAGGAACUCCUCCGGACCCUCAACCAGC

CAGACAGCCAGCUCCAGCUGACCACCGGCAACGGCCUGUUCCUCAGCGAGGGCCUGAAG

CUAGUGGACAAGUUCCUGGAGGACGUGAAAAAGCUGUACCACAGCGAAGCCUUCACCGU

CAACUUCGGGGACACCGAAGAGGCCAAGAAACAGAUCAACGACUACGUGGAGAAGGGCA

CCCAAGGGAAAAUCGUGGACCUGGUCAAGGAGCUGGACAGAGACACAGUGUUCGCCCUG

```
GUGAACUACAUCUUCUUCAAAGGCAAAUGGGAGAGACCCUUCGAAGUCAAGGACACCGA

GGAAGAGGACUUCCACGUGGACCAGGUGACCACCGUGAAGGUGCCCAUGAUGAAGCGGC

UGGGCAUGUUCAACAUCCAGCACUGCAAGAAGCUGAGCAGCUGGGUGCUGCUGAUGAAA

UACCUGGGCAACGCCACCGCCAUCUUCUUCCUGCCCGACGAGGGGAAACUACAGCACCU

GGAAAACGAACUCACCCACGACAUCAUCACCAAGUUCCUGGAAAACGAAGACAGAAGGA

GCGCCAGCCUGCACCUGCCCAAACUGAGCAUUACUGGAACCUAUGAUCUGAAGUCCGUG

CUGGGUCAACUGGGCAUCACUAAGGUCUUCAGCAAUGGGGCUGACCUCUCCGGGGUCAC

AGAGGAGGCACCCCUGAAGCUCUCCAAGGCCGUGCAUAAGGCUGUGCUGACCAUCGACG

AGAAAGGGACUGAAGCUGCUGGGGCCAUGUUUUUAGAGGCCAUACCCAUGUCUAUCCCC

CCCGAGGUCAAGUUCAACAAACCCUUUGUCUUCUUAAUGAUUGAACAAAAUACCAAGUC

UCCCCUCUUCAUGGGAAAAGUGGUGAAUCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCAAAAUGUAGCCAUUCGUAUCU

GCUCCUAAUAAAAAGAAAGUUUCUUCACAUUCUAGAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAA

TEV-hAAT-XbG ARC-mRNA. 5'_18%_T. (1689
nt)
                                                    (SEQ ID NO: 115)
5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGAGCAGCGUCAGCUGGGGCAUCCUCCUGC

UGGCAGGCCUGUGCUGCCUGGUCCCCGUCAGCCUGGCCGAGGACCCCCAGGGAGACGCC

GCCCAGAAGACAGACACAAGCCACCACGACCAGGACCACCCAACCUUCAACAAGAUCAC

CCCCAACCUGGCCGAGUUCGCCUUCAGCCUAUACCGCCAGCUGGCACACCAGAGCAACA

GCACCAACAUCUUCUUCAGCCCAGUGAGCAUCGCCACAGCCUUCGCAAUGCUCAGCCUG

GGGACCAAGGCCGACACCCACGACGAAAUCCUGGAGGGCCUGAACUUCAACCUCACGGA

GAUCCCGGAGGCCCAGAUCCACGAAGGCUUCCAGGAACUCCUCCGGACCCUCAACCAGC

CAGACAGCCAGCUCCAGCUGACCACCGGCAACGGCCUGUUCCUCAGCGAGGGCCUGAAG

CUAGUGGACAAGUUCCUGGAGGACGUGAAAAAGCUGUACCACAGCGAAGCCUUCACCGU

CAACUUCGGGGACACCGAAGAGGCCAAGAAACAGAUCAACGACUACGUGGAGAAGGGCA

CCCAAGGGAAAAUCGUGGACCUGGUCAAGGAGCUUGACAGAGACACAGUUUUUGCUCUG

GUGAAUUACAUCUUCUUUAAAGGCAAAUGGGAGAGACCCUUUGAAGUCAAGGACACCGA

GGAAGAGGACUUCCACGUGGACCAGGUGACCACCGUGAAGGUGCCUAUGAUGAAGCGUU

UAGGCAUGUUUAACAUCCAGCACUGUAAGAAGCUGUCCAGCUGGGUGCUGCUGAUGAAA

UACCUGGGCAAUGCCACCGCCAUCUUCUUCCUGCCUGAUGAGGGGAAACUACAGCACCU

GGAAAAUGAACUCACCCACGAUAUCAUCACCAAGUUCCUGGAAAAUGAAGACAGAAGGU

CUGCCAGCUUACAUUUACCCAAACUGUCCAUUACUGGAACCUAUGAUCUGAAGUCCGUG

CUGGGUCAACUGGGCAUCACUAAGGUCUUCAGCAAUGGGGCUGACCUCUCCGGGGUCAC

AGAGGAGGCACCCCUGAAGCUCUCCAAGGCCGUGCAUAAGGCUGUGCUGACCAUCGACG

AGAAAGGGACUGAAGCUGCUGGGGCCAUGUUUUUAGAGGCCAUACCCAUGUCUAUCCCC
```

CCCGAGGUCAAGUUCAACAAACCCUUUGUCUUCUUAAUGAUUGAACAAAAUACCAAGUC

UCCCCUCUUCAUGGGAAAAGUGGUGAAUCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAGAAAGUUUCUUCACAUUCUAGAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAA

TEV-hAAT-XbG ARC-mRNA. 5'_20%_T. (1689 nt)

(SEQ ID NO: 116)

5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGAGCAGCGUCAGCUGGGGCAUCCUCCUGC

UGGCAGGCCUGUGCUGCCUGGUCCCCGUCAGCCUGGCCGAGGACCCCCAGGGAGACGCC

GCCCAGAAGACAGACACAAGCCACCACGACCAGGACCACCCAACCUUCAACAAGAUCAC

CCCCAACCUGGCCGAGUUCGCCUUCAGCCUAUACCGCCAGCUGGCACACCAGAGCAACA

GCACCAACAUCUUCUUCAGCCCAGUGAGCAUCGCCACAGCCUUUGCAAUGCUCUCCCUG

GGGACCAAGGCUGACACUCACGAUGAAAUCCUGGAGGGCCUGAAUUUCAACCUCACGGA

GAUUCCGGAGGCUCAGAUCCAUGAAGGCUUCCAGGAACUCUCCGUACCCUCAACCAGC

CAGACAGCCAGCUCCAGCUGACCACCGGCAAUGGCCUGUUCCUCAGCGAGGGCCUGAAG

CUAGUGGAUAAGUUUUUGGAGGAUGUUAAAAAGUUGUACCACUCAGAAGCCUUCACUGU

CAACUUCGGGGACACCGAAGAGGCCAAGAAACAGAUCAACGAUUACGUGGAGAAGGGUA

CUCAAGGGAAAAUUGUGGAUUUGGUCAAGGAGCUUGACAGAGACACAGUUUUUGCUCUG

GUGAAUUACAUCUUCUUUAAAGGCAAAUGGGAGAGACCCUUUGAAGUCAAGGACACCGA

GGAAGAGGACUUCCACGUGGACCAGGUGACCACCGUGAAGGUGCCUAUGAUGAAGCGUU

UAGGCAUGUUUAACAUCCAGCACUGUAAGAAGCUGUCCAGCUGGGUGCUGCUGAUGAAA

UACCUGGGCAAUGCCACCGCCAUCUUCUUCCUGCCUGAUGAGGGGAAACUACAGCACCU

GGAAAAUGAACUCACCCACGAUAUCAUCACCAAGUUCCUGGAAAAUGAAGACAGAAGGU

CUGCCAGCUUACAUUUACCCAAACUGUCCAUUACUGGAACCUAUGAUCUGAAGUCCGUG

CUGGGUCAACUGGGCAUCACUAAGGUCUUCAGCAAUGGGGCUGACCUCUCCGGGGUCAC

AGAGGAGGCACCCCUGAAGCUCUCCAAGGCCGUGCAUAAGGCUGUGCUGACCAUCGACG

AGAAAGGGACUGAAGCUGCUGGGGCCAUGUUUUUAGAGGCCAUACCCAUGUCUAUCCCC

CCCGAGGUCAAGUUCAACAAACCCUUUGUCUUCUUAAUGAUUGAACAAAAUACCAAGUC

UCCCCUCUUCAUGGGAAAAGUGGUGAAUCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAGAAAGUUUCUUCACAUUCUAGAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAA

-continued

TEV-hAAT-XbG ARC-mRNA.
random_16%_T. (1689 nt)

(SEQ ID NO: 117)

5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUCUGAAAA

UUUUCACCAUUUACGAACGAUAGCCAUGCCGAGCAGCGUCUCGUGGGGCAUCCUCCUGC

UGGCAGGCCUGUGCUGCCUGGUCCCCGUCAGCCUGGCCGAGGACCCCCAGGGAGAUGCU

GCCCAGAAGACAGACACAUCCCACCACGACCAGGACCACCCAACCUUCAACAAGAUCAC

CCCCAACCUGGCUGAGUUCGCCUUCAGCCUAUACCGCCAGCUGGCACACCAGAGCAACA

GCACCAAUAUCUUCUUCAGCCCAGUGAGCAUCGCUACAGCCUUCGCAAUGCUCAGCCUG

GGGACCAAGGCCGACACCCACGAUGAAAUCCUGGAGGGCCUGAAUUUCAACCUCACGGA

GAUCCCGGAGGCUCAGAUCCACGAAGGCUUCCAGGAACUCCUCCGGACCCUCAACCAGC

CAGACAGCCAGCUCCAGCUGACCACCGGCAACGGCCUGUUCCUCAGCGAGGGCCUGAAG

CUAGUGGACAAGUUCCUGGAGGACGUUAAAAAGCUGUACCACAGCGAAGCCUUCACCGU

CAACUUCGGGGACACCGAAGAGGCCAAGAAACAGAUCAACGAUUACGUGGAGAAGGGCA

CCCAAGGGAAAAUCGUGGACCUGGUCAAGGAGCUUGACAGAGACACAGUGUUUGCCCUG

GUGAACUACAUCUUCUUCAAAGGCAAAUGGGAGAGACCCUUCGAAGUCAAGGACACCGA

GGAAGAGGACUUCCACGUGGACCAGGUGACCACCGUGAAGGUGCCCAUGAUGAAGCGGU

UAGGCAUGUUCAACAUCCAGCACUGCAAGAAGCUGAGCAGCUGGGUGCUGCUGAUGAAA

UACCUGGGCAACGCCACCGCCAUCUUCUUCCUGCCCGACGAGGGGAAACUACAGCACCU

GGAAAACGAACUCACCCACGACAUCAUCACCAAGUUCCUGGAAAACGAAGACAGAAGGA

GCGCCAGCCUGCAUCUGCCCAAACUGAGCAUUACUGGAACCUACGAUCUGAAGUCCGUG

CUGGGUCAACUGGGCAUCACCAAGGUCUUCAGCAAUGGGGCCGACCUCAGCGGGGUCAC

AGAGGAGGCACCCCUGAAGCUCAGCAAGGCCGUGCACAAGGCUGUGCUGACCAUCGACG

AGAAAGGGACCGAAGCCGCUGGGGCCAUGUUCCUGGAGGCCAUACCCAUGAGCAUCCCC

CCCGAGGUCAAGUUCAACAAACCCUUUGUCUUCCUGAUGAUCGAACAAAACACCAAGUC

UCCCCUCUUCAUGGGAAAAGUGGUGAACCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAGAAAGUUUCUUCACAUUCUAGAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAA

TEV-hAAT-XbG ARC-mRNA. random_18%_T.
(1689 nt)

(SEQ ID NO: 118)

5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUCUGAAAA

UUUUCACCAUUUACGAACGAUAGCCAUGCCGUCUUCUGUCUCGUGGGGCAUCCUCCUGC

UGGCAGGCCUGUGCUGCCUGGUCCCCGUCUCCCUGGCUGAGGACCCCCAGGGAGAUGCC

GCCCAGAAGACAGACACAUCCCACCAUGACCAGGACCACCCAACCUUCAACAAGAUCAC

CCCCAACCUGGCCGAGUUCGCCUUCAGCCUAUACCGCCAGCUGGCACACCAGAGCAACA

GCACCAACAUCUUCUUCUCCCCAGUGAGCAUCGCCACAGCCUUUGCAAUGCUCUCCCUG

```
GGGACCAAGGCCGACACCCACGACGAAAUCCUGGAGGGCCUGAAUUUCAACCUCACGGA

GAUCCCGGAGGCUCAGAUCCAUGAAGGCUUCCAGGAACUCCUCCGGACCCUCAACCAGC

CAGACAGCCAGCUCCAGCUGACCACCGGCAAUGGCCUGUUCCUCAGCGAGGGCCUGAAG

CUAGUGGAUAAGUUCCUGGAGGAUGUUAAAAAGCUGUACCACAGCGAAGCCUUCACCGU

CAACUUCGGGGACACCGAAGAGGCCAAGAAACAGAUCAACGAUUACGUGGAGAAGGGCA

CCCAAGGGAAAAUCGUGGACCUGGUCAAGGAGCUUGACAGAGACACAGUGUUUGCUCUG

GUGAAUUACAUCUUCUUUAAAGGCAAAUGGGAGAGACCCUUUGAAGUCAAGGACACCGA

GGAAGAGGACUUCCACGUGGACCAGGUGACCACCGUGAAGGUGCCUAUGAUGAAGCGGU

UAGGCAUGUUUAACAUCCAGCACUGCAAGAAGCUGAGCAGCUGGGUGCUGCUGAUGAAA

UACCUGGGCAAUGCCACCGCCAUCUUCUUCCUGCCUGAUGAGGGGAAACUACAGCACCU

GGAAAACGAACUCACCCACGACAUCAUCACCAAGUUCCUGGAAAAUGAAGACAGAAGGU

CUGCCAGCUUACACUUACCCAAACUGAGCAUUACUGGAACCUACGAUCUGAAGUCCGUG

CUGGGCCAACUGGGCAUCACUAAGGUCUUCAGCAACGGGGCUGACCUCUCCGGGGUCAC

AGAGGAGGCACCCCUGAAGCUCAGCAAGGCCGUGCACAAGGCUGUGCUGACCAUCGACG

AGAAAGGGACCGAAGCUGCCGGGGCCAUGUUUCUGGAGGCCAUACCCAUGUCUAUCCCC

CCCGAGGUCAAGUUCAACAAACCCUUUGUCUUCCUGAUGAUCGAACAAAAUACCAAGAG

CCCCCUCUUCAUGGGAAAAGUGGUGAACCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAGAAAGUUUCUUCACAUUCUAGAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAA

TEV-hAAT-XbG ARC-mRNA. random_20%_T.
(1689 nt)
                                                    (SEQ ID NO: 119)
5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGAGCAGCGUCAGCUGGGGCAUCCUCCUGC

UGGCAGGCCUGUGCUGCCUGGUCCCUGUCUCCCUGGCUGAGGAUCCCCAGGGAGAUGCU

GCCCAGAAGACAGAUACAUCCCACCAUGAUCAGGAUCACCCAACCUUCAACAAGAUCAC

CCCCAACCUGGCUGAGUUCGCCUUCAGCCUAUACCGCCAGCUGGCACACCAGUCCAACA

GCACCAAUAUCUUCUUCUCCCCAGUGAGCAUCGCUACAGCCUUCGCAAUGCUCUCCCUG

GGGACCAAGGCUGACACUCACGAUGAAAUCCUGGAGGGCCUGAAUUUCAACCUCACGGA

GAUUCCGGAGGCCCAGAUCCAUGAAGGCUUCCAGGAACUCCUCCGUACCCUCAACCAGC

CAGACAGCCAGCUCCAGCUGACCACCGGCAAUGGCCUGUUCCUCAGCGAGGGCCUGAAG

CUAGUGGAUAAGUUUUUGGAGGAUGUUAAAAAGCUGUACCACAGCGAAGCCUUCACUGU

CAACUUCGGGGACACCGAAGAGGCCAAGAAACAGAUCAACGAUUACGUGGAGAAGGGUA

CUCAAGGGAAAAUUGUGGAUUUGGUCAAGGAGCUUGACAGAGACACAGUUUUUGCUCUG

GUGAAUUACAUCUUCUUCAAAGGCAAAUGGGAGAGACCCUUUGAAGUCAAGGACACCGA

GGAAGAGGACUUCCACGUGGACCAGGUGACCACCGUGAAGGUGCCUAUGAUGAAGCGGU

UAGGCAUGUUCAACAUCCAGCACUGUAAGAAGCUGUCCAGCUGGGUGCUGCUGAUGAAA

UACCUGGGCAAUGCCACCGCCAUCUUCUUCCUGCCUGAUGAGGGGAAACUACAGCACCU
```

-continued

```
GGAAAAUGAACUCACCCACGAUAUCAUCACCAAGUUCCUGGAAAAUGAAGACAGAAGGA

GCGCCAGCUUACAUUUACCCAAACUGAGCAUUACUGGAACCUACGAUCUGAAGUCCGUG

CUGGGUCAACUGGGCAUCACUAAGGUCUUCAGCAACGGGGCUGACCUCUCCGGGGUCAC

AGAGGAGGCACCCCUGAAGCUCUCCAAGGCCGUGCAUAAGGCUGUGCUGACCAUCGACG

AGAAAGGGACUGAAGCUGCUGGGGCCAUGUUUUAGAGGCCAUACCCAUGUCUAUCCCC

CCCGAGGUCAAGUUCAACAAACCCUUUGUCUUCCUGAUGAUCGAACAAAAUACCAAGAG

CCCCCUCUUCAUGGGAAAAGUGGUGAAUCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAAGAAAGUUUCUUCACAUUCUAGAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAA
```

Example E: Templates and mRNAs for Human Adiponectin (hAdipo)

Figure 8:
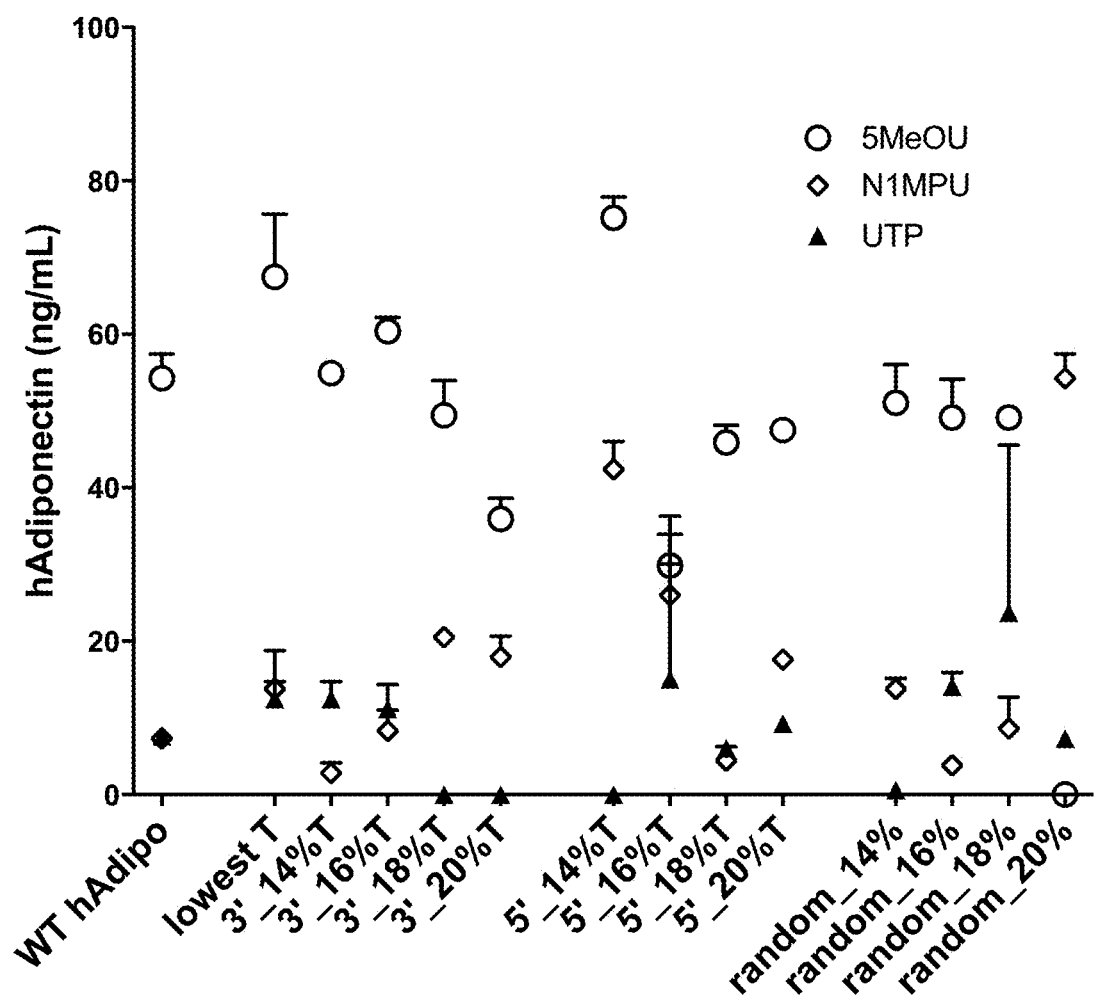
FIG. 8 shows the results of surprisingly increased human adiponectin protein production for a translatable molecule of this invention. Human adiponectin ARC-RNA was synthesized using a DNA template having reduced deoxyadenosine nucleotides in an open reading frame of the template strand, as well as reduced deoxythymidine nucleotides in the complementary non-template strand ("reduced T"). The synthesis was also carried out with 5-methoxyuridines (5MeOU, 100%). The ARC-RNA was transfected into HEPA1-6 cells using MESSENGERMAX transfection reagents. The cell culture medium was collected 24 hrs after transfection. ELISA was used to detect the protein production with the ARC-RNA (5MeOU) as compared to wild type mRNA with similarly reduced T.

FIG. 8 shows the results of surprisingly increased human adiponectin protein production for a translatable molecule of this invention. Human adiponectin ARC-RNA was synthesized using a DNA template having reduced deoxyadenosine nucleotides in an open reading frame of the template strand, as well as reduced complementary deoxythymidine nucleotides in the non-template strand ("reduced T"). The synthesis was also carried out with 5-methoxyuridines (5MeOU, 100%). The ARC-RNA was transfected into HEPA1-6 cells using MESSENGERMAX transfection reagents. The cell culture medium was collected 24 hrs after transfection. ELISA was used to detect the protein production with the ARC-RNA (5MeOU) as compared to wild type mRNA with similarly reduced T.

FIG. 8 shows surprisingly high translational efficiency of the ARC-mRNA (5MeOU) compared to the wild type hAdipo mRNA (UTP). First, the ARC-mRNA (5MeOU) exhibited superior expression efficiency at all levels of template T composition as compared to the hAdipo mRNA (UTP). Further, the ARC-mRNA (5MeOU) exhibited unexpectedly superior expression efficiency at all levels of template T composition as compared to the hAdipo mRNA (N1MPU).

Moreover, FIG. 8 shows that ARC-mRNA (5MeOU) products exhibited superior expression efficiency at levels of template T composition of 12-14%. The increase of ARC-mRNA (5MeOU) expression efficiency at lower levels of template T composition of 12-14% was unexpectedly advantageous because the "reduced T" hAdipo mRNA (UTP) was not increased at lower levels of template T composition.

In addition, FIG. 8 shows that the translational efficiency of the ARC-RNA (5MeOU) was also surprisingly higher as compared to WT human adiponectin mRNA (N1MPU), a similar RNA made with $N^1$-methylpseudouridine (100%).

Figure 9:
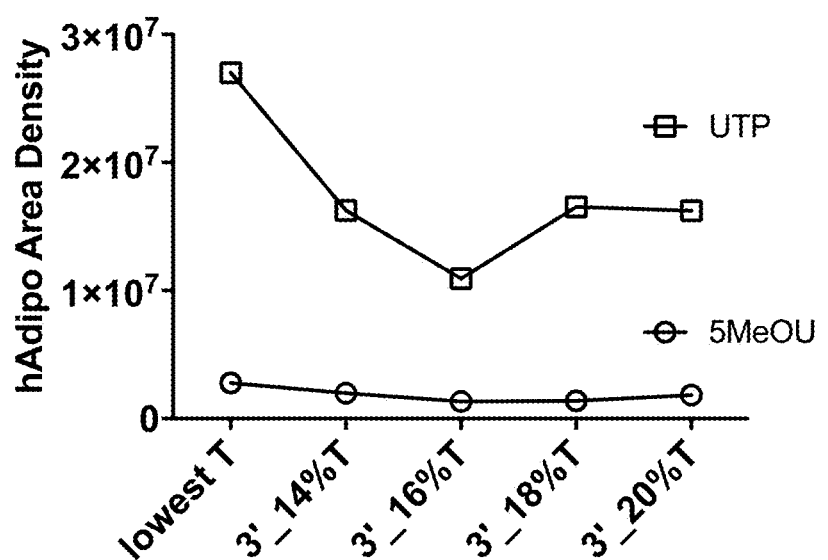
FIG. 9 shows the results of surprisingly reduced impurity levels in a process for synthesizing a human adiponectin translatable molecule of this invention.

FIG. 9 shows the results of surprisingly reduced impurity levels in a process for synthesizing an hAdipo translatable molecule of this invention. FIG. 9 shows the results of a dot blot for detecting double strand RNA impurity in the synthesis mixture (nitro cellulose membrane, J2 antibody to detect dsRNA). The ARC-RNA (5MeOU) "reduced T" synthesis products, which were translatable for hAdipo, showed surprisingly reduced dot blot intensity as compared to similar "reduced T" mRNA (UTP) synthesis products. Thus, the ARC-RNA (5MeOU) synthesis process, with template reduced T composition, surprisingly reduced double strand RNA impurity levels in the synthesis mixture. The process for synthesizing the ARC-RNA (5MeOU) molecules of this invention with template reduced T composition provided a surprisingly reduced level of double strand RNA impurity. As shown in FIG. 9, this result is surprising because the "reduced T" mRNA (UTP) synthesis products exhibited increased levels of double strand RNA impurity at lower template T composition.

The compositions of the templates for hAdipo are shown in Table 9.

TABLE 9

Non-Template Nucleotide T compositions for hAdipo

| hEPO | T % |
| --- | --- |
| hAdipo__lowest__T | 12.2 |
| hAdipo__3'__14% T | 13.9 |
| hAdipo__3'__16% T | 15.9 |
| hAdipo__3'__18% T | 18.0 |
| hAdipo__3'__20% T | 20.0 |
| hAdipo__5'__14% T | 13.9 |
| hAdipo__5'__16% T | 15.9 |
| hAdipo__5'__18% T | 18.0 |
| hAdipo__5'__20% T | 20.0 |
| hAdipo__random__14% | 13.9 |
| hAdipo__random__16% | 15.9 |
| hAdipo__random__18% | 18.0 |
| hAdipo__random__20% | 20.0 |

Human Adipo ORF reference. Sense strand, non-template. NM_001177800.1:136-870 *Homo sapiens* adiponectin, C1Q and collagen domain containing (ADIPOQ).

(SEQ ID NO: 120)
atgctgttgctgggagctgttctactgctattagctctgcccggtcatg accaggaaaccacgactcaagggcccggagtcctgcttcccctgcccaaggggcctgc acaggttggatggcgggcatcccagggcatccgggccataatggggccccaggccgtga tggcagagatggcacccctggtgagaagggtgagaaaggagatccaggtcttattggtc ctaagggagacatcggtgaaaccggagtacccggggctgaaggtccccgaggctttccg ggaatccaaggcaggaaaggagaacctggagaaggtgcctatgtataccgctcagcatt cagtgtgggattggagacttacgttactatccccaacatgcccattcgctttaccaaga tcttctacaatcagcaaaaccactatgatggctccactggtaaattccactgcaacatt cctgggctgtactactttgcctaccacatcacagtctatatgaaggatgtgaaggtcag cctcttcaagaaggacaaggctatgctcttcacctatgatcagtaccaggaaaataatg tggaccaggcctccggctctgtgctcctgcatctggaggtgggcgaccaagtctggctc caggtgtatggggaaggagagcgtaatggactctatgctgataatgacaatgactccac cttcacaggctttcttctctaccatgacaccaactga hAdipo sense strand, non-template. 3'_lowest_T.
(SEQ ID NO: 121)
ATGCTGCTGCTGGGAGCCGTGCTACTGCTACTGGCCCTGCCCGGCCACG

ACCAGGAAACCACGACCCAAGGGCCCGGAGTCCTGCTGCCCCTGCCCAAGGGGGCCTGC

ACAGGCTGGATGGCGGGCATCCCAGGGCACCCGGGCCACAACGGGGCCCCAGGCCGGGA

CGGCAGAGACGGCACCCCCGGCGAGAAGGGCGAGAAAGGAGACCCAGGCCTGATCGGCC

CCAAGGGAGACATCGGCGAAACCGGAGTACCCGGGGCCGAAGGCCCCCGAGGCTTCCCG

GGAATCCAAGGCAGGAAAGGAGAACCCGGAGAAGGCGCCTACGTATACCGCAGCGCATT

CAGCGTGGGACTGGAGACCTACGTGACCATCCCCAACATGCCCATCCGCTTCACCAAGA

TCTTCTACAACCAGCAAAACCACTACGACGGCAGCACCGGCAAATTCCACTGCAACATC

CCCGGGCTGTACTACTTCGCCTACCACATCACAGTCTACATGAAGGACGTGAAGGTCAG

CCTCTTCAAGAAGGACAAGGCCATGCTGTTCACCTACGACCAGTACCAGGAAAACAACG

TGGACCAGGCCAGCGGCAGCGTGCTCCTGCACCTGGAGGTGGGCGACCAAGTCTGGCTC

CAGGTGTACGGGGAAGGAGAGCGGAACGGACTCTACGCCGACAACGACAACGACAGCAC

CTTCACAGGCTTCCTGCTCTACCACGACACCAACTGA hAdipo sense strand, non-template. 3'_14%_T.
(SEQ ID NO: 122)
ATGCTGTTGCTGGGAGCTGTTCTACTGCTATTAGCTCTGCCCGGTCATG

ACCAGGAAACCACGACTCAAGGGCCCGGAGTCCTGCTTCCCCTGCCCAAGGGGGCCTGC

ACAGGTTGGATGGCGGGCATCCCAGGGCATCCGGGCCATAACGGGGCCCCAGGCCGGGA

CGGCAGAGACGGCACCCCCGGCGAGAAGGGCGAGAAAGGAGACCCAGGCCTGATCGGCC

CCAAGGGAGACATCGGCGAAACCGGAGTACCCGGGGCCGAAGGCCCCCGAGGCTTCCCG

GGAATCCAAGGCAGGAAAGGAGAACCCGGAGAAGGCGCCTACGTATACCGCAGCGCATT

CAGCGTGGGACTGGAGACCTACGTGACCATCCCCAACATGCCCATCCGCTTCACCAAGA

TCTTCTACAACCAGCAAAACCACTACGACGGCAGCACCGGCAAATTCCACTGCAACATC

CCCGGGCTGTACTACTTCGCCTACCACATCACAGTCTACATGAAGGACGTGAAGGTCAG

CCTCTTCAAGAAGGACAAGGCCATGCTGTTCACCTACGACCAGTACCAGGAAAACAACG

TGGACCAGGCCAGCGGCAGCGTGCTCCTGCACCTGGAGGTGGGCGACCAAGTCTGGCTC

CAGGTGTACGGGGAAGGAGAGCGGAACGGACTCTACGCCGACAACGACAACGACAGCAC

CTTCACAGGCTTCCTGCTCTACCACGACACCAACTGA

-continued hAdipo sense strand, non-template. 3'_16%_T.
(SEQ ID NO: 123)
ATGCTGTTGCTGGGAGCTGTTCTACTGCTATTAGCTCTGCCCGGTCATG

ACCAGGAAACCACGACTCAAGGGCCCGGAGTCCTGCTTCCCCTGCCCAAGGGGGCCTGC

ACAGGTTGGATGGCGGGCATCCCAGGGCATCCGGGCCATAATGGGGCCCCAGGCCGTGA

TGGCAGAGATGGCACCCCTGGTGAGAAGGGTGAGAAAGGAGATCCAGGTCTTATTGGTC

CTAAGGGAGACATCGGTGAAACCGGAGTACCCGGGGCTGAAGGCCCCCGAGGCTTCCCG

GGAATCCAAGGCAGGAAAGGAGAACCCGGAGAAGGCGCCTACGTATACCGCAGCGCATT

CAGCGTGGGACTGGAGACCTACGTGACCATCCCCAACATGCCCATCCGCTTCACCAAGA

TCTTCTACAACCAGCAAAACCACTACGACGGCAGCACCGGCAAATTCCACTGCAACATC

CCCGGGCTGTACTACTTCGCCTACCACATCACAGTCTACATGAAGGACGTGAAGGTCAG

CCTCTTCAAGAAGGACAAGGCCATGCTGTTCACCTACGACCAGTACCAGGAAAACAACG

TGGACCAGGCCAGCGGCAGCGTGCTCCTGCACCTGGAGGTGGGCGACCAAGTCTGGCTC

CAGGTGTACGGGAAGGAGAGCGGAACGGACTCTACGCCGACAACGACAACGACAGCAC

CTTCACAGGCTTCCTGCTCTACCACGACACCAACTGA hAdipo sense strand, non-template. 3'_18%_T.
(SEQ ID NO: 124)
ATGCTGTTGCTGGGAGCTGTTCTACTGCTATTAGCTCTGCCCGGTCATG

ACCAGGAAACCACGACTCAAGGGCCCGGAGTCCTGCTTCCCCTGCCCAAGGGGGCCTGC

ACAGGTTGGATGGCGGGCATCCCAGGGCATCCGGGCCATAATGGGGCCCCAGGCCGTGA

TGGCAGAGATGGCACCCCTGGTGAGAAGGGTGAGAAAGGAGATCCAGGTCTTATTGGTC

CTAAGGGAGACATCGGTGAAACCGGAGTACCCGGGGCTGAAGGTCCCCGAGGCTTTCCG

GGAATCCAAGGCAGGAAAGGAGAACCTGGAGAAGGTGCCTATGTATACCGCTCAGCATT

CAGTGTGGGATTGGAGACTTACGTTACTATCCCCAACATGCCCATTCGCTTTACCAAGA

TCTTCTACAATCAGCAAAACCACTATGACGGCAGCACCGGCAAATTCCACTGCAACATC

CCCGGGCTGTACTACTTCGCCTACCACATCACAGTCTACATGAAGGACGTGAAGGTCAG

CCTCTTCAAGAAGGACAAGGCCATGCTGTTCACCTACGACCAGTACCAGGAAAACAACG

TGGACCAGGCCAGCGGCAGCGTGCTCCTGCACCTGGAGGTGGGCGACCAAGTCTGGCTC

CAGGTGTACGGGAAGGAGAGCGGAACGGACTCTACGCCGACAACGACAACGACAGCAC

CTTCACAGGCTTCCTGCTCTACCACGACACCAACTGA hAdipo sense strand, non-template. 3'_20%_T.
(SEQ ID NO: 125)
ATGCTGTTGCTGGGAGCTGTTCTACTGCTATTAGCTCTGCCCGGTCATG

ACCAGGAAACCACGACTCAAGGGCCCGGAGTCCTGCTTCCCCTGCCCAAGGGGGCCTGC

ACAGGTTGGATGGCGGGCATCCCAGGGCATCCGGGCCATAATGGGGCCCCAGGCCGTGA

TGGCAGAGATGGCACCCCTGGTGAGAAGGGTGAGAAAGGAGATCCAGGTCTTATTGGTC

CTAAGGGAGACATCGGTGAAACCGGAGTACCCGGGGCTGAAGGTCCCCGAGGCTTTCCG

GGAATCCAAGGCAGGAAAGGAGAACCTGGAGAAGGTGCCTATGTATACCGCTCAGCATT

CAGTGTGGGATTGGAGACTTACGTTACTATCCCCAACATGCCCATTCGCTTTACCAAGA

TCTTCTACAATCAGCAAAACCACTATGATGGCTCCACTGGTAAATTCCACTGCAACATT

CCTGGGCTGTACTACTTTGCCTACCACATCACAGTCTATATGAAGGATGTGAAGGTCAG

CCTCTTCAAGAAGGACAAGGCTATGCTGTTCACCTATGATCAGTACCAGGAAAATAATG

TGGACCAGGCCTCCGGCAGCGTGCTCCTGCACCTGGAGGTGGGCGACCAAGTCTGGCTC

-continued
CAGGTGTACGGGGAAGGAGAGCGGAACGGACTCTACGCCGACAACGACAACGACAGCAC

CTTCACAGGCTTCCTGCTCTACCACGACACCAACTGA hAdipo sense strand, non-template. 5'_14%_T.
(SEQ ID NO: 126)
ATGCTGCTGCTGGGAGCCGTGCTACTGCTACTGGCCCTGCCCGGCCACG

ACCAGGAAACCACGACCCAAGGGCCCGGAGTCCTGCTGCCCCTGCCCAAGGGGGCCTGC

ACAGGCTGGATGGCGGGCATCCCAGGGCACCCGGGCCACAACGGGGCCCCAGGCCGGGA

CGGCAGAGACGGCACCCCCGGCGAGAAGGGCGAGAAAGGAGACCCAGGCCTGATCGGCC

CCAAGGGAGACATCGGCGAAACCGGAGTACCCGGGGCCGAAGGCCCCCGAGGCTTCCCG

GGAATCCAAGGCAGGAAAGGAGAACCCGGAGAAGGCGCCTACGTATACCGCAGCGCATT

CAGCGTGGGACTGGAGACCTACGTGACCATCCCCAACATGCCCATCCGCTTCACCAAGA

TCTTCTACAACCAGCAAAACCACTACGACGGCAGCACCGGCAAATTCCACTGCAACATC

CCCGGGCTGTACTACTTCGCCTACCACATCACAGTCTACATGAAGGACGTGAAGGTCAG

CCTCTTCAAGAAGGACAAGGCCATGCTGTTCACCTACGACCAGTACCAGGAAAACAACG

TGGACCAGGCCAGCGGCAGCGTGCTCCTGCACCTGGAGGTGGGCGACCAAGTCTGGCTC

CAGGTGTATGGGAAGGAGAGCGTAATGGACTCTATGCTGATAATGACAATGACTCCAC

CTTCACAGGCTTTCTTCTCTACCATGACACCAACTGA hAdipo sense strand, non-template. 5'_16%_T.
(SEQ ID NO: 127)
ATGCTGCTGCTGGGAGCCGTGCTACTGCTACTGGCCCTGCCCGGCCACG

ACCAGGAAACCACGACCCAAGGGCCCGGAGTCCTGCTGCCCCTGCCCAAGGGGGCCTGC

ACAGGCTGGATGGCGGGCATCCCAGGGCACCCGGGCCACAACGGGGCCCCAGGCCGGGA

CGGCAGAGACGGCACCCCCGGCGAGAAGGGCGAGAAAGGAGACCCAGGCCTGATCGGCC

CCAAGGGAGACATCGGCGAAACCGGAGTACCCGGGGCCGAAGGCCCCCGAGGCTTCCCG

GGAATCCAAGGCAGGAAAGGAGAACCCGGAGAAGGCGCCTACGTATACCGCAGCGCATT

CAGCGTGGGACTGGAGACCTACGTGACCATCCCCAACATGCCCATCCGCTTCACCAAGA

TCTTCTACAACCAGCAAAACCACTACGACGGCAGCACCGGTAAATTCCACTGCAACATT

CCTGGGCTGTACTACTTTGCCTACCACATCACAGTCTATATGAAGGATGTGAAGGTCAG

CCTCTTCAAGAAGGACAAGGCTATGCTGTTCACCTATGATCAGTACCAGGAAAATAATG

TGGACCAGGCCTCCGGCTCTGTGCTCCTGCATCTGGAGGTGGGCGACCAAGTCTGGCTC

CAGGTGTATGGGAAGGAGAGCGTAATGGACTCTATGCTGATAATGACAATGACTCCAC

CTTCACAGGCTTTCTTCTCTACCATGACACCAACTGA hAdipo sense strand, non-template. 5'_18%_T.
(SEQ ID NO: 128)
ATGCTGCTGCTGGGAGCCGTGCTACTGCTACTGGCCCTGCCCGGCCACG

ACCAGGAAACCACGACCCAAGGGCCCGGAGTCCTGCTGCCCCTGCCCAAGGGGGCCTGC

ACAGGCTGGATGGCGGGCATCCCAGGGCACCCGGGCCACAACGGGGCCCCAGGCCGGGA

CGGCAGAGACGGCACCCCCGGCGAGAAGGGCGAGAAAGGAGACCCAGGCCTGATCGGCC

CCAAGGGAGACATCGGCGAAACCGGAGTACCCGGGGCCGAAGGCCCCCGAGGCTTCCCG

GGAATCCAAGGCAGGAAAGGAGAACCCGGAGAAGGTGCCTATGTATACCGCTCAGCATT

CAGTGTGGGATTGGAGACTTACGTTACTATCCCCAACATGCCCATTCGCTTTACCAAGA

TCTTCTACAATCAGCAAAACCACTATGATGGCTCCACTGGTAAATTCCACTGCAACATT

CCTGGGCTGTACTACTTTGCCTACCACATCACAGTCTATATGAAGGATGTGAAGGTCAG

CCTCTTCAAGAAGGACAAGGCTATGCTGTTCACCTATGATCAGTACCAGGAAAATAATG

```
TGGACCAGGCCTCCGGCTCTGTGCTCCTGCATCTGGAGGTGGGCGACCAAGTCTGGCTC

CAGGTGTATGGGAAGGAGAGCGTAATGGACTCTATGCTGATAATGACAATGACTCCAC

CTTCACAGGCTTTCTTCTCTACCATGACACCAACTGA hAdipo sense strand, non-template. 5'_20%_T.
                                                  (SEQ ID NO: 129)
ATGCTGCTGCTGGGAGCCGTGCTACTGCTACTGGCCCTGCCCGGCCACG

ACCAGGAAACCACGACCCAAGGGCCCGGAGTCCTGCTGCCCCTGCCCAAGGGGGCCTGC

ACAGGCTGGATGGCGGGCATCCCAGGGCACCCGGGCCACAACGGGGCCCCAGGCCGGGA

CGGCAGAGATGGCACCCCTGGTGAGAAGGGTGAGAAAGGAGATCCAGGTCTTATTGGTC

CTAAGGGAGACATCGGTGAAACCGGAGTACCCGGGGCTGAAGGTCCCCGAGGCTTTCCG

GGAATCCAAGGCAGGAAAGGAGAACCTGGAGAAGGTGCCTATGTATACCGCTCAGCATT

CAGTGTGGGATTGGAGACTTACGTTACTATCCCCAACATGCCCATTCGCTTTACCAAGA

TCTTCTACAATCAGCAAAACCACTATGATGGCTCCACTGGTAAATTCCACTGCAACATT

CCTGGGCTGTACTACTTTGCCTACCACATCACAGTCTATATGAAGGATGTGAAGGTCAG

CCTCTTCAAGAAGGACAAGGCTATGCTGTTCACCTATGATCAGTACCAGGAAAATAATG

TGGACCAGGCCTCCGGCTCTGTGCTCCTGCATCTGGAGGTGGGCGACCAAGTCTGGCTC

CAGGTGTATGGGAAGGAGAGCGTAATGGACTCTATGCTGATAATGACAATGACTCCAC

CTTCACAGGCTTTCTTCTCTACCATGACACCAACTGA hAdipo sense strand, non-template. random_14%_T.
                                                  (SEQ ID NO: 130)
ATGCTGTTGCTGGGAGCCGTGCTACTGCTACTGGCCCTGCCCGGCCACG

ACCAGGAAACCACGACTCAAGGGCCCGGAGTCCTGCTGCCCCTGCCCAAGGGGGCCTGC

ACAGGTTGGATGGCGGGCATCCCAGGGCACCCGGGCCACAATGGGGCCCCAGGCCGGGA

TGGCAGAGACGGCACCCCCGGCGAGAAGGGCGAGAAAGGAGATCCAGGCCTGATCGGTC

CCAAGGGAGACATCGGCGAAACCGGAGTACCCGGGGCCGAAGGCCCCCGAGGCTTCCCG

GGAATCCAAGGCAGGAAAGGAGAACCCGGAGAAGGCGCCTATGTATACCGCAGCGCATT

CAGTGTGGGATTGGAGACCTACGTGACCATCCCCAACATGCCCATCCGCTTCACCAAGA

TCTTCTACAACCAGCAAAACCACTACGACGGCAGCACCGGCAAATTCCACTGCAACATC

CCCGGGCTGTACTACTTTGCCTACCACATCACAGTCTACATGAAGGACGTGAAGGTCAG

CCTCTTCAAGAAGGACAAGGCCATGCTGTTCACCTACGACCAGTACCAGGAAAACAACG

TGGACCAGGCCAGCGGCAGCGTGCTCCTGCACCTGGAGGTGGGCGACCAAGTCTGGCTC

CAGGTGTACGGGAAGGAGAGCGTAACGGACTCTACGCCGACAACGACAACGACAGCAC

CTTCACAGGCTTCCTGCTCTACCACGACACCAACTGA hAdipo sense strand, non-template. random_16%_T.
                                                  (SEQ ID NO: 131)
ATGCTGCTGCTGGGAGCCGTGCTACTGCTACTGGCTCTGCCCGGTCACG

ACCAGGAAACCACGACTCAAGGGCCCGGAGTCCTGCTGCCCCTGCCCAAGGGGGCCTGC

ACAGGTTGGATGGCGGGCATCCCAGGGCATCCGGGCCATAACGGGGCCCCAGGCCGGGA

TGGCAGAGACGGCACCCCTGGCGAGAAGGGTGAGAAAGGAGACCCAGGCCTGATCGGCC

CTAAGGGAGACATCGGCGAAACCGGAGTACCCGGGGCCGAAGGCCCCCGAGGCTTCCCG

GGAATCCAAGGCAGGAAAGGAGAACCCGGAGAAGGCGCCTATGTATACCGCAGCGCATT

CAGTGTGGGATTGGAGACTTACGTTACCATCCCCAACATGCCCATTCGCTTCACCAAGA

TCTTCTACAACCAGCAAAACCACTACGACGGCAGCACCGGTAAATTCCACTGCAACATC
```

```
CCTGGGCTGTACTACTTTGCCTACCACATCACAGTCTATATGAAGGATGTGAAGGTCAG

CCTCTTCAAGAAGGACAAGGCTATGCTGTTCACCTACGATCAGTACCAGGAAAATAATG

TGGACCAGGCCAGCGGCAGCGTGCTCCTGCACCTGGAGGTGGGCGACCAAGTCTGGCTC

CAGGTGTACGGGGAAGGAGAGCGGAACGGACTCTACGCCGACAACGACAATGACAGCAC

CTTCACAGGCTTCCTGCTCTACCATGACACCAACTGA hAdipo sense strand, non-template. random_18%_T.
                                                   (SEQ ID NO: 132)
ATGCTGTTGCTGGGAGCCGTTCTACTGCTACTGGCTCTGCCCGGCCATG

ACCAGGAAACCACGACCCAAGGGCCCGGAGTCCTGCTTCCCCTGCCCAAGGGGGCCTGC

ACAGGTTGGATGGCGGGCATCCCAGGGCACCCGGGCCATAATGGGGCCCCAGGCCGTGA

TGGCAGAGACGGCACCCCCGGCGAGAAGGGTGAGAAAGGAGATCCAGGTCTGATCGGTC

CTAAGGGAGACATCGGCGAAACCGGAGTACCCGGGGCTGAAGGTCCCCGAGGCTTTCCG

GGAATCCAAGGCAGGAAAGGAGAACCTGGAGAAGGCGCCTACGTATACCGCAGCGCATT

CAGCGTGGGACTGGAGACCTACGTGACCATCCCCAACATGCCCATCCGCTTTACCAAGA

TCTTCTACAATCAGCAAAACCACTATGACGGCTCCACTGGCAAATTCCACTGCAACATT

CCCGGGCTGTACTACTTTGCCTACCACATCACAGTCTATATGAAGGATGTGAAGGTCAG

CCTCTTCAAGAAGGACAAGGCCATGCTGTTCACCTACGATCAGTACCAGGAAAACAATG

TGGACCAGGCCAGCGGCTCTGTGCTCCTGCATCTGGAGGTGGGCGACCAAGTCTGGCTC

CAGGTGTACGGGGAAGGAGAGCGTAACGGACTCTATGCCGATAATGACAATGACTCCAC

CTTCACAGGCTTTCTTCTCTACCATGACACCAACTGA hAdipo sense strand, non-template. random_20%_T.
                                                   (SEQ ID NO: 133)
ATGCTGTTGCTGGGAGCCGTTCTACTGCTATTAGCTCTGCCCGGTCATG

ACCAGGAAACCACGACTCAAGGGCCCGGAGTCCTGCTGCCCCTGCCCAAGGGGGCCTGC

ACAGGTTGGATGGCGGGCATCCCAGGGCATCCGGGCCATAATGGGGCCCCAGGCCGTGA

CGGCAGAGATGGCACCCCCGGTGAGAAGGGTGAGAAAGGAGACCCAGGTCTTATTGGCC

CTAAGGGAGACATCGGTGAAACCGGAGTACCCGGGGCTGAAGGCCCCCGAGGCTTTCCG

GGAATCCAAGGCAGGAAAGGAGAACCTGGAGAAGGCGCCTATGTATACCGCAGCGCATT

CAGTGTGGGATTGGAGACTTACGTTACTATCCCCAACATGCCCATTCGCTTTACCAAGA

TCTTCTACAATCAGCAAAACCACTATGATGGCAGCACCGGTAAATTCCACTGCAACATC

CCTGGGCTGTACTACTTTGCCTACCACATCACAGTCTATATGAAGGATGTGAAGGTCAG

CCTCTTCAAGAAGGACAAGGCTATGCTGTTCACCTATGACCAGTACCAGGAAATAATG

TGGACCAGGCCTCCGGCTCTGTGCTCCTGCATCTGGAGGTGGGCGACCAAGTCTGGCTC

CAGGTGTATGGGAAGGAGAGCGTAATGGACTCTACGCTGATAATGACAATGACTCCAC

CTTCACAGGCTTTCTGCTCTACCATGACACCAACTGA

TEV-hAdipo-XbG sense strand, non-template.
3'_lowest_T. (1167 nt)
                                                   (SEQ ID NO: 134)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGCTGCTGGGAGCCGTGCTA

CTGCTACTGGCCCTGCCCGGCCACGACCAGGAAACCACGACCCAAGGGCCCGGAGTCCT

GCTGCCCCTGCCCAAGGGGGCCTGCACAGGCTGGATGGCGGGCATCCCAGGGCACCCGG

GCCACAACGGGGCCCCAGGCCGGGACGGCAGAGACGGCACCCCCGGCGAGAAGGGCGAG
```

```
AAAGGAGACCCAGGCCTGATCGGCCCCAAGGGAGACATCGGCGAAACCGGAGTACCCGG

GGCCGAAGGCCCCCGAGGCTTCCCGGGAATCCAAGGCAGGAAAGGAGAACCCGGAGAAG

GCGCCTACGTATACCGCAGCGCATTCAGCGTGGGACTGGAGACCTACGTGACCATCCCC

AACATGCCCATCCGCTTCACCAAGATCTTCTACAACCAGCAAAACCACTACGACGGCAG

CACCGGCAAATTCCACTGCAACATCCCCGGGCTGTACTACTTCGCCTACCACATCACAG

TCTACATGAAGGACGTGAAGGTCAGCCTCTTCAAGAAGGACAAGGCCATGCTGTTCACC

TACGACCAGTACCAGGAAAACAACGTGGACCAGGCCAGCGGCAGCGTGCTCCTGCACCT

GGAGGTGGGCGACCAAGTCTGGCTCCAGGTGTACGGGGAAGGAGAGCGGAACGGACTCT

ACGCCGACAACGACAACGACAGCACCTTCACAGGCTTCCTGCTCTACCACGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAA

TEV-hAdipo-XbG sense strand, non-template.
3'_14%_T. (1167 nt)
                                          (SEQ ID NO: 135)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGTTGCTGGGAGCTGTTCTA

CTGCTATTAGCTCTGCCCGGTCATGACCAGGAAACCACGACTCAAGGGCCCGGAGTCCT

GCTTCCCCTGCCCAAGGGGGCCTGCACAGGTTGGATGGCGGGCATCCCAGGGCATCCGG

GCCATAACGGGGCCCCAGGCCGGGACGGCAGAGACGGCACCCCCGGCGAGAAGGGCGAG

AAAGGAGACCCAGGCCTGATCGGCCCCAAGGGAGACATCGGCGAAACCGGAGTACCCGG

GGCCGAAGGCCCCCGAGGCTTCCCGGGAATCCAAGGCAGGAAAGGAGAACCCGGAGAAG

GCGCCTACGTATACCGCAGCGCATTCAGCGTGGGACTGGAGACCTACGTGACCATCCCC

AACATGCCCATCCGCTTCACCAAGATCTTCTACAACCAGCAAAACCACTACGACGGCAG

CACCGGCAAATTCCACTGCAACATCCCCGGGCTGTACTACTTCGCCTACCACATCACAG

TCTACATGAAGGACGTGAAGGTCAGCCTCTTCAAGAAGGACAAGGCCATGCTGTTCACC

TACGACCAGTACCAGGAAAACAACGTGGACCAGGCCAGCGGCAGCGTGCTCCTGCACCT

GGAGGTGGGCGACCAAGTCTGGCTCCAGGTGTACGGGGAAGGAGAGCGGAACGGACTCT

ACGCCGACAACGACAACGACAGCACCTTCACAGGCTTCCTGCTCTACCACGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAA

TEV-hAdipo-XbG sense strand, non-template.
3'_16%_T. (1167 nt)
                                          (SEQ ID NO: 136)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGTTGCTGGGAGCTGTTCTA

CTGCTATTAGCTCTGCCCGGTCATGACCAGGAAACCACGACTCAAGGGCCCGGAGTCCT
```

-continued

GCTTCCCCTGCCCAAGGGGGCCTGCACAGGTTGGATGGCGGGCATCCCAGGGCATCCGG

GCCATAATGGGGCCCCAGGCCGTGATGGCAGAGATGGCACCCCTGGTGAGAAGGGTGAG

AAAGGAGATCCAGGTCTTATTGGTCCTAAGGGAGACATCGGTGAAACCGGAGTACCCGG

GGCTGAAGGCCCCCGAGGCTTCCCGGGAATCCAAGGCAGGAAAGGAGAACCCGGAGAAG

GCGCCTACGTATACCGCAGCGCATTCAGCGTGGGACTGGAGACCTACGTGACCATCCCC

AACATGCCCATCCGCTTCACCAAGATCTTCTACAACCAGCAAAACCACTACGACGGCAG

CACCGGCAAATTCCACTGCAACATCCCCGGGCTGTACTACTTCGCCTACCACATCACAG

TCTACATGAAGGACGTGAAGGTCAGCCTCTTCAAGAAGGACAAGGCCATGCTGTTCACC

TACGACCAGTACCAGGAAAACAACGTGGACCAGGCCAGCGGCAGCGTGCTCCTGCACCT

GGAGGTGGGCGACCAAGTCTGGCTCCAGGTGTACGGGGAAGGAGAGCGGAACGGACTCT

ACGCCGACAACGACAACGACAGCACCTTCACAGGCTTCCTGCTCTACCACGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAGAAAGTTTCTTCACATTCTAGAAAAA

AAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAA

TEV-hAdipo-XbG sense strand, non-template.
3'_18%_T. (1167 nt)

(SEQ ID NO: 137)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGTTGCTGGGAGCTGTTCTA

CTGCTATTAGCTCTGCCCGGTCATGACCAGGAAACCACGACTCAAGGGCCCGGAGTCCT

GCTTCCCCTGCCCAAGGGGGCCTGCACAGGTTGGATGGCGGGCATCCCAGGGCATCCGG

GCCATAATGGGGCCCCAGGCCGTGATGGCAGAGATGGCACCCCTGGTGAGAAGGGTGAG

AAAGGAGATCCAGGTCTTATTGGTCCTAAGGGAGACATCGGTGAAACCGGAGTACCCGG

GGCTGAAGGTCCCCGAGGCTTTCCGGGAATCCAAGGCAGGAAAGGAGAACCTGGAGAAG

GTGCCTATGTATACCGCTCAGCATTCAGTGTGGGATTGGAGACTTACGTTACTATCCCC

AACATGCCCATTCGCTTTACCAAGATCTTCTACAATCAGCAAAACCACTATGACGGCAG

CACCGGCAAATTCCACTGCAACATCCCCGGGCTGTACTACTTCGCCTACCACATCACAG

TCTACATGAAGGACGTGAAGGTCAGCCTCTTCAAGAAGGACAAGGCCATGCTGTTCACC

TACGACCAGTACCAGGAAAACAACGTGGACCAGGCCAGCGGCAGCGTGCTCCTGCACCT

GGAGGTGGGCGACCAAGTCTGGCTCCAGGTGTACGGGGAAGGAGAGCGGAACGGACTCT

ACGCCGACAACGACAACGACAGCACCTTCACAGGCTTCCTGCTCTACCACGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAGAAAGTTTCTTCACATTCTAGAAAAA

AAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAA

TEV-hAdipo-XbG sense strand, non-template.
3'_20%_T. (1167 nt)

(SEQ ID NO: 138)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGTTGCTGGGAGCTGTTCTA

CTGCTATTAGCTCTGCCCGGTCATGACCAGGAAACCACGACTCAAGGGCCCGGAGTCCT

GCTTCCCCTGCCCAAGGGGGCCTGCACAGGTTGGATGGCGGGCATCCCAGGGCATCCGG

GCCATAATGGGGCCCCAGGCCGTGATGGCAGAGATGGCACCCCTGGTGAGAAGGGTGAG

AAAGGAGATCCAGGTCTTATTGGTCCTAAGGGAGACATCGGTGAAACCGGAGTACCCGG

GGCTGAAGGTCCCCGAGGCTTTCCGGGAATCCAAGGCAGGAAAGGAGAACCTGGAGAAG

GTGCCTATGTATACCGCTCAGCATTCAGTGTGGGATTGGAGACTTACGTTACTATCCCC

AACATGCCCATTCGCTTTACCAAGATCTTCTACAATCAGCAAAACCACTATGATGGCTC

CACTGGTAAATTCCACTGCAACATTCCTGGGCTGTACTACTTTGCCTACCACATCACAG

TCTATATGAAGGATGTGAAGGTCAGCCTCTTCAAGAAGGACAAGGCTATGCTGTTCACC

TATGATCAGTACCAGGAAAATAATGTGGACCAGGCCTCCGGCAGCGTGCTCCTGCACCT

GGAGGTGGGCGACCAAGTCTGGCTCCAGGTGTACGGGGAAGGAGAGCGGAACGGACTCT

ACGCCGACAACGACAACGACAGCACCTTCACAGGCTTCCTGCTCTACCACGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

TEV-hAdipo-XbG sense strand, non-template.
5'_14%_T. (1167 nt)

(SEQ ID NO: 139)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGCTGCTGGGAGCCGTGCTA

CTGCTACTGGCCCTGCCCGGCCACGACCAGGAAACCACGACCCAAGGGCCCGGAGTCCT

GCTGCCCCTGCCCAAGGGGGCCTGCACAGGCTGGATGGCGGGCATCCCAGGGCACCCGG

GCCACAACGGGGCCCCAGGCCGGGACGGCAGAGACGGCACCCCCGGCGAGAAGGGCGAG

AAAGGAGACCCAGGCCTGATCGGCCCCAAGGGAGACATCGGCGAAACCGGAGTACCCGG

GGCCGAAGGCCCCCGAGGCTTCCCGGGAATCCAAGGCAGGAAAGGAGAACCCGGAGAAG

GCGCCTACGTATACCGCAGCGCATTCAGCGTGGGACTGGAGACCTACGTGACCATCCCC

AACATGCCCATCCGCTTCACCAAGATCTTCTACAACCAGCAAAACCACTACGACGGCAG

CACCGGCAAATTCCACTGCAACATCCCCGGGCTGTACTACTTCGCCTACCACATCACAG

TCTACATGAAGGACGTGAAGGTCAGCCTCTTCAAGAAGGACAAGGCCATGCTGTTCACC

TACGACCAGTACCAGGAAAACAACGTGGACCAGGCCAGCGGCAGCGTGCTCCTGCACCT

GGAGGTGGGCGACCAAGTCTGGCTCCAGGTGTATGGGGAAGGAGAGCGTAATGGACTCT

ATGCTGATAATGACAATGACTCCACCTTCACAGGCTTTCTTCTCTACCATGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAA

TEV-hAdipo-XbG sense strand, non-template.
5'_16%_T. (1167 nt)

(SEQ ID NO: 140)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGCTGCTGGGAGCCGTGCTA

CTGCTACTGGCCCTGCCCGGCCACGACCAGGAAACCACGACCCAAGGGCCCGGAGTCCT

GCTGCCCCTGCCCAAGGGGGCCTGCACAGGCTGGATGGCGGGCATCCCAGGGCACCCGG

GCCACAACGGGCCCCAGGCCGGGACGGCAGAGACGGCACCCCCGGCGAGAAGGGCGAG

AAAGGAGACCCAGGCCTGATCGGCCCCAAGGGAGACATCGGCGAAACCGGAGTACCCGG

GGCCGAAGGCCCCCGAGGCTTCCCGGGAATCCAAGGCAGGAAAGGAGAACCCGGAGAAG

GCGCCTACGTATACCGCAGCGCATTCAGCGTGGGACTGGAGACCTACGTGACCATCCCC

AACATGCCCATCCGCTTCACCAAGATCTTCTACAACCAGCAAAACCACTACGACGGCAG

CACCGGTAAATTCCACTGCAACATTCCTGGGCTGTACTACTTTGCCTACCACATCACAG

TCTATATGAAGGATGTGAAGGTCAGCCTCTTCAAGAAGGACAAGGCTATGCTGTTCACC

TATGATCAGTACCAGGAAAATAATGTGGACCAGGCCTCCGGCTCTGTGCTCCTGCATCT

GGAGGTGGGCGACCAAGTCTGGCTCCAGGTGTATGGGGAAGGAGAGCGTAATGGACTCT

ATGCTGATAATGACAATGACTCCACCTTCACAGGCTTTCTTCTCTACCATGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAA

TEV-hAdipo-XbG sense strand, non-template.
5'_18%_T. (1167 nt)

(SEQ ID NO: 141)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGCTGCTGGGAGCCGTGCTA

CTGCTACTGGCCCTGCCCGGCCACGACCAGGAAACCACGACCCAAGGGCCCGGAGTCCT

GCTGCCCCTGCCCAAGGGGGCCTGCACAGGCTGGATGGCGGGCATCCCAGGGCACCCGG

GCCACAACGGGCCCCAGGCCGGGACGGCAGAGACGGCACCCCCGGCGAGAAGGGCGAG

AAAGGAGACCCAGGCCTGATCGGCCCCAAGGGAGACATCGGCGAAACCGGAGTACCCGG

GGCCGAAGGCCCCCGAGGCTTCCCGGGAATCCAAGGCAGGAAAGGAGAACCCGGAGAAG

GTGCCTATGTATACCGCTCAGCATTCAGTGTGGGATTGGAGACTTACGTTACTATCCCC

AACATGCCCATTCGCTTTACCAAGATCTTCTACAATCAGCAAAACCACTATGATGGCTC

CACTGGTAAATTCCACTGCAACATTCCTGGGCTGTACTACTTTGCCTACCACATCACAG

TCTATATGAAGGATGTGAAGGTCAGCCTCTTCAAGAAGGACAAGGCTATGCTGTTCACC

TATGATCAGTACCAGGAAAATAATGTGGACCAGGCCTCCGGCTCTGTGCTCCTGCATCT

GGAGGTGGGCGACCAAGTCTGGCTCCAGGTGTATGGGGAAGGAGAGCGTAATGGACTCT

ATGCTGATAATGACAATGACTCCACCTTCACAGGCTTTCTTCTCTACCATGACACCAAC

```
TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAA
```

TEV-hAdipo-XbG sense strand, non-template.
5'_20%_T. (1167 nt)

(SEQ ID NO: 142)
```
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGCTGCTGGGAGCCGTGCTA

CTGCTACTGGCCCTGCCCGGCCACGACCAGGAAACCACGACCCAAGGGCCCGGAGTCCT

GCTGCCCCTGCCCAAGGGGGCCTGCACAGGCTGGATGGCGGGCATCCCAGGGCACCCGG

GCCACAACGGGGCCCCAGGCCGGGACGGCAGAGATGGCACCCCTGGTGAGAAGGGTGAG

AAAGGAGATCCAGGTCTTATTGGTCCTAAGGGAGACATCGGTGAAACCGGAGTACCCGG

GGCTGAAGGTCCCCGAGGCTTTCCGGGAATCCAAGGCAGGAAAGGAGAACCTGGAGAAG

GTGCCTATGTATACCGCTCAGCATTCAGTGTGGGATTGGAGACTTACGTTACTATCCCC

AACATGCCCATTCGCTTTACCAAGATCTTCTACAATCAGCAAAACCACTATGATGGCTC

CACTGGTAAATTCCACTGCAACATTCCTGGGCTGTACTACTTTGCCTACCACATCACAG

TCTATATGAAGGATGTGAAGGTCAGCCTCTTCAAGAAGGACAAGGCTATGCTGTTCACC

TATGATCAGTACCAGGAAAATAATGTGGACCAGGCCTCCGGCTCTGTGCTCCTGCATCT

GGAGGTGGGCGACCAAGTCTGGCTCCAGGTGTATGGGGAAGGAGAGCGTAATGGACTCT

ATGCTGATAATGACAATGACTCCACCTTCACAGGCTTTCTTCTCTACCATGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAA
```

TEV-hAdipo-XbG sense strand, non-template.
random_14%_T. (1167 nt)

(SEQ ID NO: 143)
```
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGTTGCTGGGAGCCGTGCTA

CTGCTACTGGCCCTGCCCGGCCACGACCAGGAAACCACGACTCAAGGGCCCGGAGTCCT

GCTGCCCCTGCCCAAGGGGGCCTGCACAGGTTGGATGGCGGGCATCCCAGGGCACCCGG

GCCACAATGGGGCCCCAGGCCGGGATGGCAGAGACGGCACCCCCGGCGAGAAGGGCGAG

AAAGGAGATCCAGGCCTGATCGGTCCCAAGGGAGACATCGGCGAAACCGGAGTACCCGG

GGCCGAAGGCCCCCGAGGCTTCCCGGGAATCCAAGGCAGGAAAGGAGAACCCGGAGAAG

GCGCCTATGTATACCGCAGCGCATTCAGTGTGGGATTGGAGACCTACGTGACCATCCCC

AACATGCCCATCCGCTTCACCAAGATCTTCTACAACCAGCAAAACCACTACGACGGCAG

CACCGGCAAATTCCACTGCAACATCCCCGGGCTGTACTACTTTGCCTACCACATCACAG

TCTACATGAAGGACGTGAAGGTCAGCCTCTTCAAGAAGGACAAGGCCATGCTGTTCACC
```

-continued

TACGACCAGTACCAGGAAAACAACGTGGACCAGGCCAGCGGCAGCGTGCTCCTGCACCT

GGAGGTGGGCGACCAAGTCTGGCTCCAGGTGTACGGGGAAGGAGAGCGTAACGGACTCT

ACGCCGACAACGACAACGACAGCACCTTCACAGGCTTCCTGCTCTACCACGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAA

TEV-hAdipo-XbG sense strand, non-template.
random_16%_T. (1167 nt)

(SEQ ID NO: 144)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGCTGCTGGGAGCCGTGCTA

CTGCTACTGGCTCTGCCCGGTCACGACCAGGAAACCACGACTCAAGGGCCCGGAGTCCT

GCTGCCCCTGCCCAAGGGGGCCTGCACAGGTTGGATGGCGGGCATCCCAGGGCATCCGG

GCCATAACGGGGCCCCAGGCCGGGATGGCAGAGACGGCACCCCTGGCGAGAAGGGTGAG

AAAGGAGACCCAGGCCTGATCGGCCCTAAGGGAGACATCGGCGAAACCGGAGTACCCGG

GGCCGAAGGCCCCCGAGGCTTCCCGGGAATCCAAGGCAGGAAAGGAGAACCCGGAGAAG

GCGCCTATGTATACCGCAGCGCATTCAGTGTGGGATTGGAGACTTACGTTACCATCCCC

AACATGCCCATTCGCTTCACCAAGATCTTCTACAACCAGCAAAACCACTACGACGGCAG

CACCGGTAAATTCCACTGCAACATCCCTGGGCTGTACTACTTTGCCTACCACATCACAG

TCTATATGAAGGATGTGAAGGTCAGCCTCTTCAAGAAGGACAAGGCTATGCTGTTCACC

TACGATCAGTACCAGGAAAATAATGTGGACCAGGCCAGCGGCAGCGTGCTCCTGCACCT

GGAGGTGGGCGACCAAGTCTGGCTCCAGGTGTACGGGGAAGGAGAGCGGAACGGACTCT

ACGCCGACAACGACAATGACAGCACCTTCACAGGCTTCCTGCTCTACCATGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAA

TEV-hAdipo-XbG sense strand, non-template.
random_18%_T. (1167 nt)

(SEQ ID NO: 145)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGTTGCTGGGAGCCGTTCTA

CTGCTACTGGCTCTGCCCGGCCATGACCAGGAAACCACGACCCAAGGGCCCGGAGTCCT

GCTTCCCCTGCCCAAGGGGGCCTGCACAGGTTGGATGGCGGGCATCCCAGGGCACCCGG

GCCATAATGGGCCCCAGGCCGTGATGGCAGAGACGGCACCCCCGGCGAGAAGGGTGAG

AAAGGAGATCCAGGTCTGATCGGTCCTAAGGGAGACATCGGCGAAACCGGAGTACCCGG

GGCTGAAGGTCCCCGAGGCTTTCCGGGAATCCAAGGCAGGAAAGGAGAACCTGGAGAAG

GCGCCTACGTATACCGCAGCGCATTCAGCGTGGGACTGGAGACCTACGTGACCATCCCC

AACATGCCCATCCGCTTTACCAAGATCTTCTACAATCAGCAAAACCACTATGACGGCTC

-continued

CACTGGCAAATTCCACTGCAACATTCCCGGGCTGTACTACTTTGCCTACCACATCACAG

TCTATATGAAGGATGTGAAGGTCAGCCTCTTCAAGAAGGACAAGGCCATGCTGTTCACC

TACGATCAGTACCAGGAAAACAATGTGGACCAGGCCAGCGGCTCTGTGCTCCTGCATCT

GGAGGTGGGCGACCAAGTCTGGCTCCAGGTGTACGGGGAAGGAGAGCGTAACGGACTCT

ATGCCGATAATGACAATGACTCCACCTTCACAGGCTTTCTTCTCTACCATGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAGAAAGTTTCTTCACATTCTAGAAAAA

AAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAA

TEV-hAdipo-XbG sense strand, non-template.
random_20%_T. (1167 nt)

(SEQ ID NO: 146)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGTTGCTGGGAGCCGTTCTA

CTGCTATTAGCTCTGCCCGGTCATGACCAGGAAACCACGACTCAAGGGCCCGGAGTCCT

GCTGCCCCTGCCCAAGGGGGCCTGCACAGGTTGGATGGCGGGCATCCCAGGGCATCCGG

GCCATAATGGGGCCCCAGGCCGTGACGGCAGAGATGGCACCCCCGGTGAGAAGGGTGAG

AAAGGAGACCCAGGTCTTATTGGCCCTAAGGGAGACATCGGTGAAACCGGAGTACCCGG

GGCTGAAGGCCCCCGAGGCTTTCCGGGAATCCAAGGCAGGAAAGGAGAACCTGGAGAAG

GCGCCTATGTATACCGCAGCGCATTCAGTGTGGGATTGGAGACTTACGTTACTATCCCC

AACATGCCCATTCGCTTTACCAAGATCTTCTACAATCAGCAAAACCACTATGATGGCAG

CACCGGTAAATTCCACTGCAACATCCCTGGGCTGTACTACTTTGCCTACCACATCACAG

TCTATATGAAGGATGTGAAGGTCAGCCTCTTCAAGAAGGACAAGGCTATGCTGTTCACC

TATGACCAGTACCAGGAAAATAATGTGGACCAGGCCTCCGGCTCTGTGCTCCTGCATCT

GGAGGTGGGCGACCAAGTCTGGCTCCAGGTGTATGGGGAAGGAGAGCGTAATGGACTCT

ACGCTGATAATGACAATGACTCCACCTTCACAGGCTTTCTGCTCTACCATGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAGAAAGTTTCTTCACATTCTAGAAAAA

AAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAA

TEV-hAdipo-XbG ARC-mRNA. 3'_lowest_T.
(1167 nt)

(SEQ ID NO: 147)

5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGCUGCUGGGAGCCGUGCUACUGCUACUGG

CCCUGCCCGGCCACGACCAGGAAACCACGACCCAAGGGCCCGGAGUCCUGCUGCCCCUG

CCCAAGGGGGCCUGCACAGGCUGGAUGGCGGGCAUCCCAGGGCACCCGGGCCACAACGG

GGCCCCAGGCCGGGACGGCAGAGACGGCACCCCCGGCGAGAAGGGCGAGAAAGGAGACC

CAGGCCUGAUCGGCCCCAAGGGAGACAUCGGCGAAACCGGAGUACCCGGGGCCGAAGGC

-continued

CCCCGAGGCUUCCCGGGAAUCCAAGGCAGGAAAGGAGAACCCGGAGAAGGCGCCUACGU
AUACCGCAGCGCAUUCAGCGUGGGACUGGAGACCUACGUGACCAUCCCCAACAUGCCCA
UCCGCUUCACCAAGAUCUUCUACAACCAGCAAAACCACUACGACGGCAGCACCGGCAAA
UUCCACUGCAACAUCCCCGGGCUGUACUACUUCGCCUACCACAUCACAGUCUACAUGAA
GGACGUGAAGGUCAGCCUCUUCAAGAAGGACAAGGCCAUGCUGUUCACCUACGACCAGU
ACCAGGAAAACAACGUGGACCAGGCCAGCGGCAGCGUGCUCCUGCACCUGGAGGUGGGC
GACCAAGUCUGGCUCCAGGUGUACGGGGAAGGAGAGCGGAACGGACUCUACGCCGACAA
CGACAACGACAGCACCUUCACAGGCUUCCUGCUCUACCACGACACCAACUGACUCGAGC
UAGUGACUGACUAGGAUCUGGUUACCACUAAACCAGCCUCAAGAACACCCGAAUGGAGU
CUCUAAGCUACAUAAUACCAACUUACACUUACAAAAUGUUGUCCCCCAAAAUGUAGCCA
UUCGUAUCUGCUCCUAAUAAAAAGAAAGUUUCUUCACAUUCUAGAAAAAAAAAAAAAA
AAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAA

TEV-hAdipo-XbG ARC-mRNA. 3'_14%_T. (1167 nt)

(SEQ ID NO: 148)

5'-cap-
AGGAAACUUAAGUCAACACAACAUAUACAAAACAAACGAAUCUCAAGCAAUCAAGCAUU
CUACUUCUAUUGCAGCAAUUUAAAUCAUUUCUUUUAAAGCAAAAGCAAUUUUCUGAAAA
UUUUCACCAUUUACGAACGAUAGCCAUGCUGUUGCUGGGAGCUGUUCUACUGCUAUUAG
CUCUGCCCGGUCAUGACCAGGAAACCACGACUCAAGGGCCCGGAGUCCUGCUUCCCCUG
CCCAAGGGGGCCUGCACAGGUUGGAUGGCGGGCAUCCCAGGGCAUCCGGGCCAUAACGG
GGCCCCAGGCCGGGACGGCAGAGACGGCACCCCCGGCGAGAAGGGCGAGAAAGGAGACC
CAGGCCUGAUCGGCCCCAAGGGAGACAUCGGCGAAACCGGAGUACCCGGGGCCGAAGGC
CCCCGAGGCUUCCCGGGAAUCCAAGGCAGGAAAGGAGAACCCGGAGAAGGCGCCUACGU
AUACCGCAGCGCAUUCAGCGUGGGACUGGAGACCUACGUGACCAUCCCCAACAUGCCCA
UCCGCUUCACCAAGAUCUUCUACAACCAGCAAAACCACUACGACGGCAGCACCGGCAAA
UUCCACUGCAACAUCCCCGGGCUGUACUACUUCGCCUACCACAUCACAGUCUACAUGAA
GGACGUGAAGGUCAGCCUCUUCAAGAAGGACAAGGCCAUGCUGUUCACCUACGACCAGU
ACCAGGAAAACAACGUGGACCAGGCCAGCGGCAGCGUGCUCCUGCACCUGGAGGUGGGC
GACCAAGUCUGGCUCCAGGUGUACGGGGAAGGAGAGCGGAACGGACUCUACGCCGACAA
CGACAACGACAGCACCUUCACAGGCUUCCUGCUCUACCACGACACCAACUGACUCGAGC
UAGUGACUGACUAGGAUCUGGUUACCACUAAACCAGCCUCAAGAACACCCGAAUGGAGU
CUCUAAGCUACAUAAUACCAACUUACACUUACAAAAUGUUGUCCCCCAAAAUGUAGCCA
UUCGUAUCUGCUCCUAAUAAAAAGAAAGUUUCUUCACAUUCUAGAAAAAAAAAAAAAA
AAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAA TEV-hAdipo-XbG ARC-mRNA. 3'_16%_T. (1167 nt)

(SEQ ID NO: 149)

5'-cap-
AGGAAACUUAAGUCAACACAACAUAUACAAAACAAACGAAUCUCAAGCAAUCAAGCAUU
CUACUUCUAUUGCAGCAAUUUAAAUCAUUUCUUUUAAAGCAAAAGCAAUUUUCUGAAAA
UUUUCACCAUUUACGAACGAUAGCCAUGCUGUUGCUGGGAGCUGUUCUACUGCUAUUAG -continued

CUCUGCCCGGUCAUGACCAGGAAACCACGACUCAAGGGCCCGGAGUCCUGCUUCCCUG

CCCAAGGGGGCCUGCACAGGUUGGAUGGCGGGCAUCCCAGGGCAUCCGGGCAUAAUGG

GGCCCCAGGCCGUGAUGGCAGAGAUGGCACCCCUGGUGAGAAGGGUGAGAAAGGAGAUC

CAGGUCUUAUUGGUCCUAAGGGAGACAUCGGUGAAACCGGAGUACCCGGGGCUGAAGGC

CCCCGAGGCUUCCCGGGAAUCCAAGGCAGGAAAGGAGAACCCGGAGAAGGCGCCUACGU

AUACCGCAGCGCAUUCAGCGUGGGACUGGAGACCUACGUGACCAUCCCCAACAUGCCCA

UCCGCUUCACCAAGAUCUUCUACAACCAGCAAAACCACUACGACGGCAGCACCGGCAAA

UUCCACUGCAACAUCCCCGGGCUGUACUACUUCGCCUACCACAUCACAGUCUACAUGAA

GGACGUGAAGGUCAGCCUCUUCAAGAAGGACAAGGCCAUGCUGUUCACCUACGACCAGU

ACCAGGAAAACAACGUGGACCAGGCCAGCGGCAGCGUGCUCCUGCACCUGGAGGUGGGC

GACCAAGUCUGGCUCCAGGUGUACGGGGAAGGAGAGCGGAACGGACUCUACGCCGACAA

CGACAACGACAGCACCUUCACAGGCUUCCUGCUCUACCACGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCAAAAUGUAGCCA

UUCGUAUCUGCUCCUAAUAAAAAGAAAGUUUCUUCACAUUCUAGAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAA

TEV-hAdipo-XbG ARC-mRNA. 3'_18%_T. (1167
nt)
(SEQ ID NO: 150)
5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGUUGCUGGGAGCUGUUCUACUGCUAUUAG

CUCUGCCCGGUCAUGACCAGGAAACCACGACUCAAGGGCCCGGAGUCCUGCUUCCCUG

CCCAAGGGGGCCUGCACAGGUUGGAUGGCGGGCAUCCCAGGGCAUCCGGGCAUAAUGG

GGCCCCAGGCCGUGAUGGCAGAGAUGGCACCCCUGGUGAGAAGGGUGAGAAAGGAGAUC

CAGGUCUUAUUGGUCCUAAGGGAGACAUCGGUGAAACCGGAGUACCCGGGGCUGAAGGU

CCCCGAGGCUUUCCGGGAAUCCAAGGCAGGAAAGGAGAACCUGGAGAAGGUGCCUAUGU

AUACCGCUCAGCAUUCAGUGUGGGAUUGGAGACUUACGUUACUAUCCCCAACAUGCCCA

UUCGCUUUACCAAGAUCUUCUACAAUCAGCAAAACCACUAUGACGGCAGCACCGGCAAA

UUCCACUGCAACAUCCCCGGGCUGUACUACUUCGCCUACCACAUCACAGUCUACAUGAA

GGACGUGAAGGUCAGCCUCUUCAAGAAGGACAAGGCCAUGCUGUUCACCUACGACCAGU

ACCAGGAAAACAACGUGGACCAGGCCAGCGGCAGCGUGCUCCUGCACCUGGAGGUGGGC

GACCAAGUCUGGCUCCAGGUGUACGGGGAAGGAGAGCGGAACGGACUCUACGCCGACAA

CGACAACGACAGCACCUUCACAGGCUUCCUGCUCUACCACGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCAAAAUGUAGCCA

UUCGUAUCUGCUCCUAAUAAAAAGAAAGUUUCUUCACAUUCUAGAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAA

TEV-hAdipo-XbG ARC-mRNA. 3'_20%_T. (1167 nt)

(SEQ ID NO: 151)

5'-cap-
AGGAAACUUAAGUCAACACAACAUAUACAAAACAAACGAAUCUCAAGCAAUCAAGCAUU
CUACUUCUAUUGCAGCAAUUUAAAUCAUUUCUUUUAAAGCAAAAGCAAUUUCUGAAAA
UUUUCACCAUUUACGAACGAUAGCCAUGCUGUUGCUGGGAGCUGUUCUACUGCUAUUAG
CUCUGCCCGGUCAUGACCAGGAAACCACGACUCAAGGGCCCGGAGUCCUGCUUCCCCUG
CCCAAGGGGGCCUGCACAGGUUGGAUGGCGGGCAUCCCAGGGCAUCCGGGCCAUAAUGG
GGCCCCAGGCCGUGAUGGCAGAGAUGGCACCCCUGGUGAGAAGGGUGAGAAAGGAGAUC
CAGGUCUUAUUGGUCCUAAGGGAGACAUCGGUGAAACCGGAGUACCCGGGGCUGAAGGU
CCCCGAGGCUUUCCGGGAAUCCAAGGCAGGAAAGGAGAACCUGGAGAAGGUGCCUAUGU
AUACCGCUCAGCAUUCAGUGUGGGAUUGGAGACUUACGUUACUAUCCCCAACAUGCCCA
UUCGCUUUACCAAGAUCUUCUACAAUCAGCAAAACCACUAUGAUGGCUCCACUGGUAAA
UUCCACUGCAACAUUCCUGGGCUGUACUACUUUGCCUACCACAUCACAGUCUAUAUGAA
GGAUGUGAAGGUCAGCCUCUUCAAGAAGGACAAGGCUAUGCUGUUCACCUAUGAUCAGU
ACCAGGAAAAUAAUGUGGACCAGGCCUCCGGCAGCGUGCUCCUGCACCUGGAGGUGGGC
GACCAAGUCUGGCUCCAGGUGUACGGGGAAGGAGAGCGGAACGGACUCUACGCCGACAA
CGACAACGACAGCACCUUCACAGGCUUCCUGCUCUACCACGACACCAACUGACUCGAGC
UAGUGACUGACUAGGAUCUGGUUACCACUAAACCAGCCUCAAGAACACCCGAAUGGAGU
CUCUAAGCUACAUAAUACCAACUUACACUUACAAAAUGUUGUCCCCCAAAAUGUAGCCA
UUCGUAUCUGCUCCUAAUAAAAAGAAAGUUUCUUCACAUUCUAGAAAAAAAAAAAAAA
AAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAA TEV-hAdipo-XbG ARC-mRNA. 5'_14%_T. (1167 nt)

(SEQ ID NO: 152)

5'-cap-
AGGAAACUUAAGUCAACACAACAUAUACAAAACAAACGAAUCUCAAGCAAUCAAGCAUU
CUACUUCUAUUGCAGCAAUUUAAAUCAUUUCUUUUAAAGCAAAAGCAAUUUCUGAAAA
UUUUCACCAUUUACGAACGAUAGCCAUGCUGCUGCUGGGAGCCGUGCUACUGCUACUGG
CCCUGCCCGGCCACGACCAGGAAACCACGACCCAAGGGCCCGGAGUCCUGCUGCCCCUG
CCCAAGGGGGCCUGCACAGGCUGGAUGGCGGGCAUCCCAGGGCACCCGGGCCACAACGG
GGCCCCAGGCCGGGACGGCAGAGACGGCACCCCCGGCGAGAAGGGCGAGAAAGGAGACC
CAGGCCUGAUCGGCCCCAAGGGAGACAUCGGCGAAACCGGAGUACCCGGGGCCGAAGGC
CCCCGAGGCUUCCCGGGAAUCCAAGGCAGGAAAGGAGAACCCGGAGAAGGCGCCUACGU
AUACCGCAGCGCAUUCAGCGUGGGACUGGAGACCUACGUGACCAUCCCCAACAUGCCCA
UCCGCUUCACCAAGAUCUUCUACAACCAGCAAAACCACUACGACGGCAGCACCGGCAAA
UUCCACUGCAACAUCCCCGGGCUGUACUACUUCGCCUACCACAUCACAGUCUACAUGAA
GGACGUGAAGGUCAGCCUCUUCAAGAAGGACAAGGCCAUGCUGUUCACCUACGACCAGU
ACCAGGAAAACAACGUGGACCAGGCCAGCGGCAGCGUGCUCCUGCACCUGGAGGUGGGC
GACCAAGUCUGGCUCCAGGUGUAUGGGGAAGGAGAGCGUAAUGGACUCUAUGCUGAUAA
UGACAAUGACUCCACCUUCACAGGCUUUCUUCUCUACCAUGACACCAACUGACUCGAGC
UAGUGACUGACUAGGAUCUGGUUACCACUAAACCAGCCUCAAGAACACCCGAAUGGAGU -continued
CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA

TEV-hAdipo-XbG ARC-mRNA. 5'_16%_T. (1167 nt)

(SEQ ID NO: 153)

5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGCUGCUGGGAGCCGUGCUACUGCUACUGG

CCCUGCCCGGCCACGACCAGGAAACCACGACCCAAGGGCCCGGAGUCCUGCUGCCCCUG

CCCAAGGGGGCCUGCACAGGCUGGAUGGCGGGCAUCCCAGGGCACCCGGGCCACAACGG

GGCCCCAGGCCGGGACGGCAGAGACGGCACCCCCGGCGAGAAGGGCGAGAAAGGAGACC

CAGGCCUGAUCGGCCCCAAGGGAGACAUCGGCGAAACCGGAGUACCCGGGGCCGAAGGC

CCCCGAGGCUUCCCGGGAAUCCAAGGCAGGAAAGGAGAACCCGGAGAAGGCGCCUACGU

AUACCGCAGCGCAUUCAGCGUGGGACUGGAGACCUACGUGACCAUCCCCAACAUGCCCA

UCCGCUUCACCAAGAUCUUCUACAACCAGCAAAACCACUACGACGGCAGCACCGGUAAA

UUCCACUGCAACAUUCCUGGGCUGUACUACUUUGCCUACCACAUCACAGUCUAUAUGAA

GGAUGUGAAGGUCAGCCUCUUCAAGAAGGACAAGGCUAUGCUGUUCACCUAUGAUCAGU

ACCAGGAAAUAAUGUGGACCAGGCCUCCGGCUCUGUGCUCCUGCAUCUGGAGGUGGGC

GACCAAGUCUGGCUCCAGGUGUAUGGGGAAGGAGAGCGUAAUGGACUCUAUGCUGAUAA

UGACAAUGACUCCACCUUCACAGGCUUUCUUCUCUACCAUGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA

TEV-hAdipo-XbG ARC-mRNA. 5'_18%_T. (1167 nt)

(SEQ ID NO: 154)

5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGCUGCUGGGAGCCGUGCUACUGCUACUGG

CCCUGCCCGGCCACGACCAGGAAACCACGACCCAAGGGCCCGGAGUCCUGCUGCCCCUG

CCCAAGGGGGCCUGCACAGGCUGGAUGGCGGGCAUCCCAGGGCACCCGGGCCACAACGG

GGCCCCAGGCCGGGACGGCAGAGACGGCACCCCCGGCGAGAAGGGCGAGAAAGGAGACC

CAGGCCUGAUCGGCCCCAAGGGAGACAUCGGCGAAACCGGAGUACCCGGGGCCGAAGGC

CCCCGAGGCUUCCCGGGAAUCCAAGGCAGGAAAGGAGAACCCGGAGAAGGUGCCUAUGU

AUACCGCUCAGCAUUCAGUGUGGGAUUGGAGACUUACGUUACUAUCCCCAACAUGCCCA

UUCGCUUUACCAAGAUCUUCUACAAUCAGCAAAACCACUAUGAUGGCUCCACUGGUAAA

UUCCACUGCAACAUUCCUGGGCUGUACUACUUUGCCUACCACAUCACAGUCUAUAUGAA

GGAUGUGAAGGUCAGCCUCUUCAAGAAGGACAAGGCUAUGCUGUUCACCUAUGAUCAGU

ACCAGGAAAUAAUGUGGACCAGGCCUCCGGCUCUGUGCUCCUGCAUCUGGAGGUGGGC

GACCAAGUCUGGCUCCAGGUGUAUGGGGAAGGAGAGCGUAAUGGACUCUAUGCUGAUAA

UGACAAUGACUCCACCUUCACAGGCUUUCUUCUCUACCAUGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAA

TEV-hAdipo-XbG ARC-mRNA. 5'_20%_T. (1167
nt)
(SEQ ID NO: 155)
5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGCUGCUGGGAGCCGUGCUACUGCUACUGG

CCCUGCCCGGCCACGACCAGGAAACCACGACCCAAGGGCCCGGAGUCCUGCUGCCCCUG

CCCAAGGGGGCCUGCACAGGCUGGAUGGCGGGCAUCCCAGGGCACCCGGGCCACAACGG

GGCCCCAGGCCGGGACGGCAGAGAUGGCACCCCUGGUGAGAAGGGUGAGAAAGGAGAUC

CAGGUCUUAUUGGUCCUAAGGGAGACAUCGGUGAAACCGGAGUACCCGGGGCUGAAGGU

CCCCGAGGCUUUCCGGGAAUCCAAGGCAGGAAAGGAGAACCUGGAGAAGGUGCCUAUGU

AUACCGCUCAGCAUUCAGUGUGGGAUUGGAGACUUACGUUACUAUCCCCAACAUGCCCA

UUCGCUUUACCAAGAUCUUCUACAAUCAGCAAAACCACUAUGAUGGCUCCACUGGUAAA

UUCCACUGCAACAUUCCUGGGCUGUACUACUUUGCCUACCACAUCACAGUCUAUAUGAA

GGAUGUGAAGGUCAGCCUCUUCAAGAAGGACAAGGCUAUGCUGUUCACCUAUGAUCAGU

ACCAGGAAAAUAAUGUGGACCAGGCCUCCGGCUCUGUGCUCCUGCAUCGGAGGUGGGC

GACCAAGUCUGGCUCCAGGUGUAUGGGGAAGGAGAGCGUAAUGGACUCUAUGCUGAUAA

UGACAAUGACUCCACCUUCACAGGCUUUCUUCUCUACCAUGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAA

TEV-hAdipo-XbG ARC-mRNA. random_14%_T.
(1167 nt)
(SEQ ID NO: 156)
5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGUUGCUGGGAGCCGUGCUACUGCUACUGG

CCCUGCCCGGCCACGACCAGGAAACCACGACUCAAGGGCCCGGAGUCCUGCUGCCCCUG

CCCAAGGGGGCCUGCACAGGUUGGAUGGCGGGCAUCCCAGGGCACCCGGGCCACAAUGG

GGCCCCAGGCCGGGAUGGCAGAGACGGCACCCCCGGCGAGAAGGGCGAGAAAGGAGAUC

CAGGCCUGAUCGGUCCCAAGGGAGACAUCGGCGAAACCGGAGUACCCGGGGCCGAAGGC

CCCCGAGGCUUUCCCGGGAAUCCAAGGCAGGAAAGGAGAACCCGGAGAAGGCGCCUAUGU

AUACCGCAGCGCAUUCAGUGUGGGAUUGGAGACCUACGUGACCAUCCCCAACAUGCCCA

```
UCCGCUUCACCAAGAUCUUCUACAACCAGCAAAACCACUACGACGGCAGCACCGGCAAA

UUCCACUGCAACAUCCCCGGGCUGUACUACUUUGCCUACCACAUCACAGUCUACAUGAA

GGACGUGAAGGUCAGCCUCUUCAAGAAGGACAAGGCCAUGCUGUUCACCUACGACCAGU

ACCAGGAAAACAACGUGGACCAGGCCAGCGGCAGCGUGCUCCUGCACCUGGAGGUGGGC

GACCAAGUCUGGCUCCAGGUGUACGGGGAAGGAGAGCGUAACGGACUCUACGCCGACAA

CGACAACGACAGCACCUUCACAGGCUUCCUGCUCUACCACGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAA
```

TEV-hAdipo-XbG ARC-mRNA. random_16%_T.
(1167 nt)
(SEQ ID NO: 157)
5'-cap-
```
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGCUGCUGGGAGCCGUGCUACUGCUACUGG

CUCUGCCCGGUCACGACCAGGAAACCACGACUCAAGGGCCCGGAGUCCUGCUGCCCCUG

CCCAAGGGGGCCUGCACAGGUUGGAUGGCGGGCAUCCCAGGGCAUCCGGGCCAUAACGG

GGCCCCAGGCCGGGAUGGCAGAGACGGCACCCCUGGCGAGAAGGGUGAGAAAGGAGACC

CAGGCCUGAUCGGCCCUAAGGGAGACAUCGGCGAAACCGGAGUACCCGGGGCCGAAGGC

CCCCGAGGCUUCCCGGGAAUCCAAGGCAGGAAAGGAGAACCCGGAGAAGGCGCCUAUGU

AUACCGCAGCGCAUUCAGUGUGGGAUUGGAGACUUACGUUACCAUCCCCAACAUGCCCA

UUCGCUUCACCAAGAUCUUCUACAACCAGCAAAACCACUACGACGGCAGCACCGGUAAA

UUCCACUGCAACAUCCCUGGGCUGUACUACUUUGCCUACCACAUCACAGUCUAUAUGAA

GGAUGUGAAGGUCAGCCUCUUCAAGAAGGACAAGGCUAUGCUGUUCACCUACGAUCAGU

ACCAGGAAAAUAAUGUGGACCAGGCCAGCGGCAGCGUGCUCCUGCACCUGGAGGUGGGC

GACCAAGUCUGGCUCCAGGUGUACGGGGAAGGAGAGCGGAACGGACUCUACGCCGACAA

CGACAAUGACAGCACCUUCACAGGCUUCCUGCUCUACCAUGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAA
```

TEV-hAdipo-XbG ARC-mRNA. random_18%_T.
(1167 nt)
(SEQ ID NO: 158)
5'-cap-
```
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGUUGCUGGGAGCCGUUCUACUGCUACUGG

CUCUGCCCGGCCAUGACCAGGAAACCACGACCCAAGGGCCCGGAGUCCUGCUUCCCCUG

CCCAAGGGGGCCUGCACAGGUUGGAUGGCGGGCAUCCCAGGGCACCCGGGCCAUAAUGG

GGCCCCAGGCCGUGAUGGCAGAGACGGCACCCCCGGCGAGAAGGGUGAGAAAGGAGAUC
```

```
CAGGUCUGAUCGGUCCUAAGGGAGACAUCGGCGAAACCGGAGUACCCGGGGCUGAAGGU

CCCCGAGGCUUUCCGGGAAUCCAAGGCAGGAAAGGAGAACCUGGAGAAGGCGCCUACGU

AUACCGCAGCGCAUUCAGCGUGGGACUGGAGACCUACGUGACCAUCCCCAACAUGCCCA

UCCGCUUUACCAAGAUCUUCUACAAUCAGCAAAACCACUAUGACGGCUCCACUGGCAAA

UUCCACUGCAACAUUCCCGGGCUGUACUACUUUGCCUACCACAUCACAGUCUAUAUGAA

GGAUGUGAAGGUCAGCCUCUUCAAGAAGGACAAGGCCAUGCUGUUCACCUACGAUCAGU

ACCAGGAAAACAAUGUGGACCAGGCCAGCGGCUCUGUGCUCCUGCAUCUGGAGGUGGGC

GACCAAGUCUGGCUCCAGGUGUACGGGGAAGGAGAGCGUAACGGACUCUAUGCCGAUAA

UGACAAUGACUCCACCUUCACAGGCUUUCUUCUCUACCAUGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAA

TEV-hAdipo-XbG ARC-mRNA. random_20%_T.
(1167 nt)
                                                      (SEQ ID NO: 159)
5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGUUGCUGGGAGCCGUUCUACUGCUAUUAG

CUCUGCCCGGUCAUGACCAGGAAACCACGACUCAAGGGCCCGGAGUCCUGCUGCCCCUG

CCCAAGGGGGCCUGCACAGGUUGGAUGGCGGGCAUCCCAGGGCAUCCGGGCCAUAAUGG

GGCCCCAGGCCGUGACGGCAGAGAUGGCACCCCCGGUGAGAAGGGUGAGAAAGGAGACC

CAGGUCUUAUUGGCCCUAAGGGAGACAUCGGUGAAACCGGAGUACCCGGGGCUGAAGGC

CCCCGAGGCUUUCCGGGAAUCCAAGGCAGGAAAGGAGAACCUGGAGAAGGCGCCUAUGU

AUACCGCAGCGCAUUCAGUGUGGGAUUGGAGACUUACGUUACUAUCCCCAACAUGCCCA

UUCGCUUUACCAAGAUCUUCUACAAUCAGCAAAACCACUAUGAUGGCAGCACCGGUAAA

UUCCACUGCAACAUCCCUGGGCUGUACUACUUUGCCUACCACAUCACAGUCUAUAUGAA

GGAUGUGAAGGUCAGCCUCUUCAAGAAGGACAAGGCUAUGCUGUUCACCUAUGACCAGU

ACCAGGAAAAUAAUGUGGACCAGGCCUCCGGCUCUGUGCUCCUGCAUCUGGAGGUGGGC

GACCAAGUCUGGCUCCAGGUGUAUGGGGAAGGAGAGCGUAAUGGACUCUACGCUGAUAA

UGACAAUGACUCCACCUUCACAGGCUUUCUGCUCUACCAUGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAA
```

Example F: Templates and mRNAs for Cynomolgus Monkey EPO (cmEPO)

Figure 10:
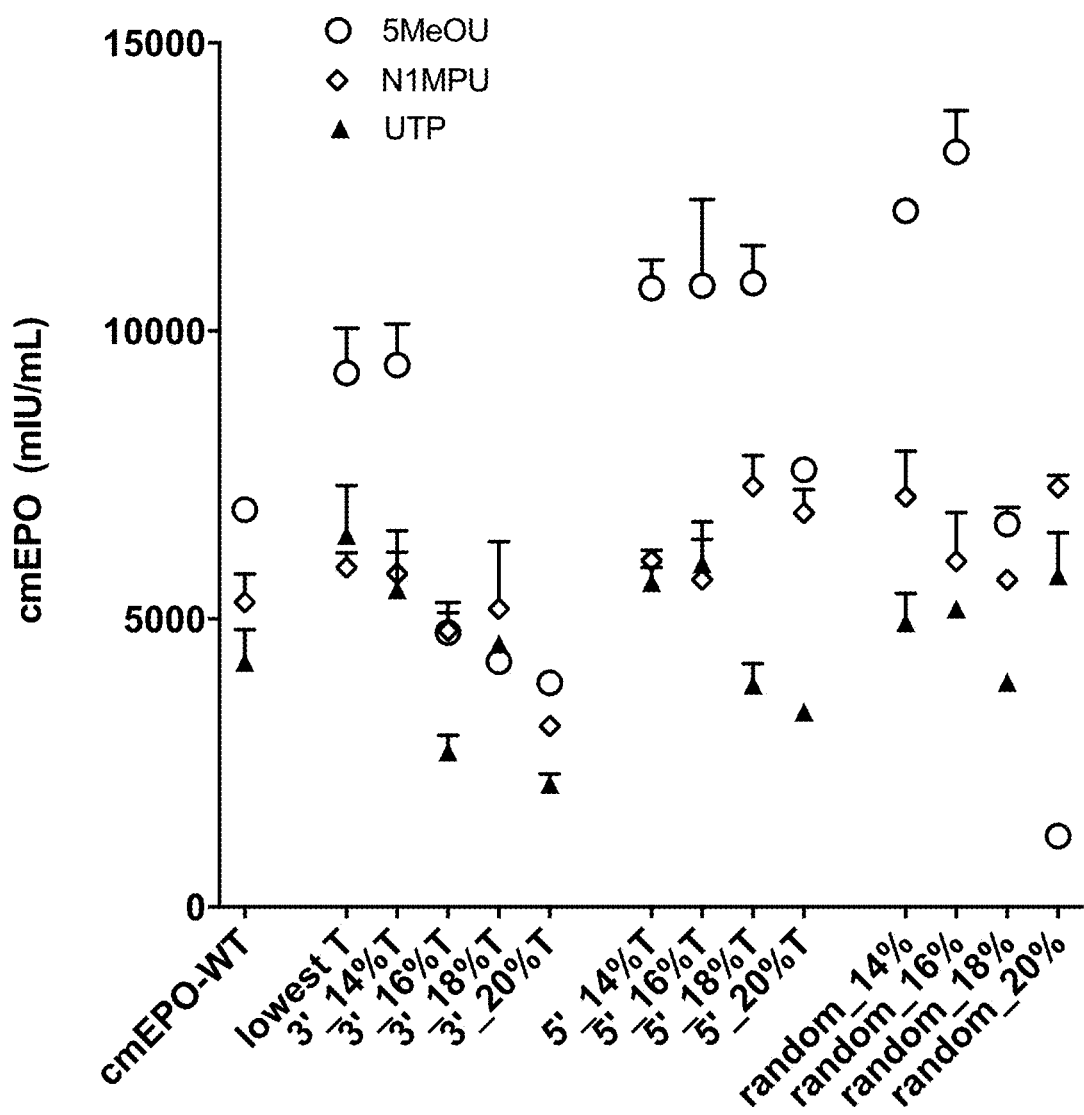
FIG. 10 shows the results of surprisingly increased cynomolgus monkey EPO protein production for a translatable molecule of this invention. Cynomolgus monkey cmEPO ARC-RNA was synthesized using a DNA template having reduced deoxyadenosine nucleotides in an open reading frame of the template strand, as well as reduced complementary deoxythymidine nucleotides in the non-template strand ("reduced T"). The synthesis was also carried out with 5-methoxyuridines (5MeOU, 100%). The ARC-RNA was transfected into HEPA1-6 cells using MESSENGERMAX transfection reagents. The cell culture medium was collected 24 hrs after transfection. ELISA was used to detect the protein production with the ARC-RNA (5MeOU) as compared to wild type mRNA with similarly reduced T.

FIG. 10 shows the results of surprisingly increased cynomolgus monkey EPO protein production for a translatable molecule of this invention. Cynomolgus monkey EPO ARC-RNA was synthesized using a DNA template having reduced deoxyadenosine nucleotides in an open reading frame of the template strand, as well as reduced complementary deoxythymidine nucleotides in the non-template strand ("reduced T"). The synthesis was also carried out with 5-methoxyuridines (5MeOU, 100%). The ARC-RNA was transfected into HEPA1-6 cells using MESSENGERMAX transfection reagents. The cell culture medium was collected 24 hrs after transfection. ELISA was used to detect the protein production with the ARC-RNA (5MeOU) as compared to wild type mRNA with similarly reduced T.

FIG. 10 shows surprisingly high translational efficiency of the ARC-mRNA (5MeOU) compared to the wild type cmEPO mRNA (UTP). First, FIG. 10 shows that ARC-mRNA (5MeOU) products exhibited surprisingly superior expression efficiency at levels of template T composition of 13-16%. Further, FIG. 10 shows that ARC-mRNA (5MeOU) products exhibited surprisingly superior expression efficiency at levels of template T composition of 13-16% as compared to cmEPO mRNA (N1MPU).

Further, FIG. 10 shows that the ARC-mRNA (5MeOU) exhibited unexpectedly superior expression efficiency at 14-16% template T composition, when codon replacement was done randomly.

In addition, FIG. 10 shows that the translational efficiency of the ARC-RNA (5MeOU) was also surprisingly higher as compared to WT cmEPO mRNA (N1MPU), a similar RNA made with $N^1$-methylpseudouridine (100%).

The compositions of the templates for cmEPO are shown in Table 10.

TABLE 10

| Non-Template Nucleotide T compositions for cmEPO | |
|---|---|
| hEPO | T % |
| mEPO_lowest_T | 13.5 |
| mEPO_3'_14% T | 14.0 |
| mEPO_3'_16% T | 15.9 |
| mEPO_3'_18% T | 18.0 |
| mEPO_3'_20% T | 19.9 |
| mEPO_5'_14% T | 14.0 |
| mEPO_5'_16% T | 15.9 |
| mEPO_5'_18% T | 18.0 |
| mEPO_5'_20% T | 19.9 |
| mEPO_random_14% | 14.0 |
| mEPO_random_16% | 15.9 |
| mEPO_random_18% | 18.0 |
| mEPO_random_20% | 19.9 |

Cynomolgus Monkey EPO ORF reference. Sense strand, non-template. NM_001284561.1:220-798 *Macaca fascicularis* erythropoietin (cmEPO).

(SEQ ID NO: 160)

```
atgggggtgcacgaatgtcctgcctggctgtggcttctcctgtctctgc tgtcgctccctctgggcctcccagtcccgggcgccccaccacgcctcatctgtgacagc cgagtcctggagaggtacctcttggaggccaaggaggccgagaatgtcacgatgggctg ttccgaaagctgcagcttgaatgagaatatcaccgtcccagacaccaaagttaacttct atgcctggaagaggatggaggtcgggcagcaggctgtagaagtctggcagggcctggcc ctgctctcagaagctgtcctgcggggccaggccgtgttggccaactcttcccagcctt cgagcccctgcagctgcacatggataaagccatcagtggccttcgcagcatcaccactc tgcttcgggcgctgggagcccaggaagccatctccctcccagatgcggcctcggctgct ccactccgaaccatcactgctgacactttctgcaaactcttccgagtctactccaattt cctccggggaaagctgaagctgtacacggggaggcctgcaggagaggggacagatga
``` cmEPO sense strand, non-template. 3'_lowest_T.

(SEQ ID NO: 161)

```
ATGGGGGTGCACGAATGCCCCGCCTGGCTGTGGCTGCTCCTGAGCCTGC

TGAGCCTCCCCCTGGGCCTCCCAGTCCCGGGCGCCCCACCACGCCTCATCTGCGACAGC

CGAGTCCTGGAGAGGTACCTCCTGGAGGCCAAGGAGGCCGAGAACGTCACGATGGGCTG

CAGCGAAAGCTGCAGCCTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTCAGCGAAGCCGTCCTGCGGGGCCAGGCCGTGCTGGCCAACAGCAGCCAGCCCTT

CGAGCCCCTGCAGCTGCACATGGACAAAGCCATCAGCGGCCTGCGCAGCATCACCACCC

TGCTGCGGGCGCTGGGAGCCCAGGAAGCCATCAGCCTCCCAGACGCGGCCAGCGCCGCC

CCACTCCGAACCATCACCGCCGACACCTTCTGCAAACTCTTCCGAGTCTACAGCAACTT

CCTCCGGGGAAAGCTGAAGCTGTACACGGGGGAGGCCTGCAGGAGAGGGGACAGATGA
``` cmEPO sense strand, non-template. 3'_14%_T.

(SEQ ID NO: 162)

```
ATGGGGGTGCACGAATGTCCTGCCTGGCTGTGGCTTCTCCTGAGCCTGC

TGAGCCTCCCCCTGGGCCTCCCAGTCCCGGGCGCCCCACCACGCCTCATCTGCGACAGC

CGAGTCCTGGAGAGGTACCTCCTGGAGGCCAAGGAGGCCGAGAACGTCACGATGGGCTG

CAGCGAAAGCTGCAGCCTGAACGAGAACATCACCGTCCCAGACACCAAAGTGAACTTCT
```

```
ACGCCTGGAAGAGGATGGAGGTCGGGCAGCAGGCCGTAGAAGTCTGGCAGGGCCTGGCC

CTGCTCAGCGAAGCCGTCCTGCGGGGCCAGGCCGTGCTGGCCAACAGCAGCCAGCCCTT

CGAGCCCCTGCAGCTGCACATGGACAAAGCCATCAGCGGCCTGCGCAGCATCACCACCC

TGCTGCGGGCGCTGGGAGCCCAGGAAGCCATCAGCCTCCCAGACGCGGCCAGCGCCGCC

CCACTCCGAACCATCACCGCCGACACCTTCTGCAAACTCTTCCGAGTCTACAGCAACTT

CCTCCGGGGAAAGCTGAAGCTGTACACGGGGGAGGCCTGCAGGAGAGGGGACAGATGA cmEPO sense strand, non-template. 3'_16%_T.
                                                  (SEQ ID NO: 163)
ATGGGGGTGCACGAATGTCCTGCCTGGCTGTGGCTTCTCCTGTCTCTGC

TGTCGCTCCCTCTGGGCCTCCCAGTCCCGGGCGCCCCACCACGCCTCATCTGTGACAGC

CGAGTCCTGGAGAGGTACCTCTTGGAGGCCAAGGAGGCCGAGAATGTCACGATGGGCTG

TTCCGAAAGCTGCAGCTTGAATGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTCAGCGAAGCCGTCCTGCGGGGCCAGGCCGTGCTGGCCAACAGCAGCCAGCCCTT

CGAGCCCCTGCAGCTGCACATGGACAAAGCCATCAGCGGCCTGCGCAGCATCACCACCC

TGCTGCGGGCGCTGGGAGCCCAGGAAGCCATCAGCCTCCCAGACGCGGCCAGCGCCGCC

CCACTCCGAACCATCACCGCCGACACCTTCTGCAAACTCTTCCGAGTCTACAGCAACTT

CCTCCGGGGAAAGCTGAAGCTGTACACGGGGGAGGCCTGCAGGAGAGGGGACAGATGA cmEPO sense strand, non-template. 3'_18%_T.
                                                  (SEQ ID NO: 164)
ATGGGGGTGCACGAATGTCCTGCCTGGCTGTGGCTTCTCCTGTCTCTGC

TGTCGCTCCCTCTGGGCCTCCCAGTCCCGGGCGCCCCACCACGCCTCATCTGTGACAGC

CGAGTCCTGGAGAGGTACCTCTTGGAGGCCAAGGAGGCCGAGAATGTCACGATGGGCTG

TTCCGAAAGCTGCAGCTTGAATGAGAATATCACCGTCCCAGACACCAAAGTTAACTTCT

ATGCCTGGAAGAGGATGGAGGTCGGGCAGCAGGCTGTAGAAGTCTGGCAGGGCCTGGCC

CTGCTCTCAGAAGCTGTCCTGCGGGGCCAGGCCGTGTTGGCCAACTCTTCCCAGCCTTT

CGAGCCCCTGCAGCTGCACATGGATAAAGCCATCAGCGGCCTGCGCAGCATCACCACCC

TGCTGCGGGCGCTGGGAGCCCAGGAAGCCATCAGCCTCCCAGACGCGGCCAGCGCCGCC

CCACTCCGAACCATCACCGCCGACACCTTCTGCAAACTCTTCCGAGTCTACAGCAACTT

CCTCCGGGGAAAGCTGAAGCTGTACACGGGGGAGGCCTGCAGGAGAGGGGACAGATGA cmEPO sense strand, non-template. 3'_20%_T.
                                                  (SEQ ID NO: 165)
ATGGGGGTGCACGAATGTCCTGCCTGGCTGTGGCTTCTCCTGTCTCTGC

TGTCGCTCCCTCTGGGCCTCCCAGTCCCGGGCGCCCCACCACGCCTCATCTGTGACAGC

CGAGTCCTGGAGAGGTACCTCTTGGAGGCCAAGGAGGCCGAGAATGTCACGATGGGCTG

TTCCGAAAGCTGCAGCTTGAATGAGAATATCACCGTCCCAGACACCAAAGTTAACTTCT

ATGCCTGGAAGAGGATGGAGGTCGGGCAGCAGGCTGTAGAAGTCTGGCAGGGCCTGGCC

CTGCTCTCAGAAGCTGTCCTGCGGGGCCAGGCCGTGTTGGCCAACTCTTCCCAGCCTTT

CGAGCCCCTGCAGCTGCACATGGATAAAGCCATCAGTGGCCTTCGCAGCATCACCACTC

TGCTTCGGGCGCTGGGAGCCCAGGAAGCCATCTCCCTCCCAGATGCGGCCTCGGCTGCT

CCACTCCGAACCATCACTGCTGACACCTTCTGCAAACTCTTCCGAGTCTACAGCAACTT

CCTCCGGGGAAAGCTGAAGCTGTACACGGGGGAGGCCTGCAGGAGAGGGGACAGATGA
```

-continued cmEPO sense strand, non-template. 5'_14%_T.
(SEQ ID NO: 166)
ATGGGGGTGCACGAATGCCCCGCCTGGCTGTGGCTGCTCCTGAGCCTGC

TGAGCCTCCCCCTGGGCCTCCCAGTCCCGGGCGCCCCACCACGCCTCATCTGCGACAGC

CGAGTCCTGGAGAGGTACCTCCTGGAGGCCAAGGAGGCCGAGAACGTCACGATGGGCTG

CAGCGAAAGCTGCAGCCTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTCAGCGAAGCCGTCCTGCGGGGCCAGGCCGTGCTGGCCAACAGCAGCCAGCCCTT

CGAGCCCCTGCAGCTGCACATGGACAAAGCCATCAGCGGCCTGCGCAGCATCACCACCC

TGCTGCGGGCGCTGGGAGCCCAGGAAGCCATCAGCCTCCCAGACGCGGCCAGCGCCGCC

CCACTCCGAACCATCACCGCCGACACTTTCTGCAAACTCTTCCGAGTCTACTCCAATTT

CCTCCGGGGAAAGCTGAAGCTGTACACGGGGGAGGCCTGCAGGAGAGGGGACAGATGA cmEPO sense strand, non-template. 5'_16%_T.
(SEQ ID NO: 167)
ATGGGGGTGCACGAATGCCCCGCCTGGCTGTGGCTGCTCCTGAGCCTGC

TGAGCCTCCCCCTGGGCCTCCCAGTCCCGGGCGCCCCACCACGCCTCATCTGCGACAGC

CGAGTCCTGGAGAGGTACCTCCTGGAGGCCAAGGAGGCCGAGAACGTCACGATGGGCTG

CAGCGAAAGCTGCAGCCTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTCAGCGAAGCCGTCCTGCGGGGCCAGGCCGTGCTGGCCAACAGCAGCCAGCCCTT

CGAGCCCCTGCAGCTGCACATGGACAAAGCCATCAGTGGCCTTCGCAGCATCACCACTC

TGCTTCGGGCGCTGGGAGCCCAGGAAGCCATCTCCCTCCCAGATGCGGCCTCGGCTGCT

CCACTCCGAACCATCACTGCTGACACTTTCTGCAAACTCTTCCGAGTCTACTCCAATTT

CCTCCGGGGAAAGCTGAAGCTGTACACGGGGGAGGCCTGCAGGAGAGGGGACAGATGA cmEPO sense strand, non-template. 5'_18%_T.
(SEQ ID NO: 168)
ATGGGGGTGCACGAATGCCCCGCCTGGCTGTGGCTGCTCCTGAGCCTGC

TGAGCCTCCCCCTGGGCCTCCCAGTCCCGGGCGCCCCACCACGCCTCATCTGCGACAGC

CGAGTCCTGGAGAGGTACCTCCTGGAGGCCAAGGAGGCCGAGAACGTCACGATGGGCTG

CAGCGAAAGCTGCAGCCTGAACGAGAATATCACCGTCCCAGACACCAAAGTTAACTTCT

ATGCCTGGAAGAGGATGGAGGTCGGGCAGCAGGCTGTAGAAGTCTGGCAGGGCCTGGCC

CTGCTCTCAGAAGCTGTCCTGCGGGGCCAGGCCGTGTTGGCCAACTCTTCCCAGCCTTT

CGAGCCCCTGCAGCTGCACATGGATAAAGCCATCAGTGGCCTTCGCAGCATCACCACTC

TGCTTCGGGCGCTGGGAGCCCAGGAAGCCATCTCCCTCCCAGATGCGGCCTCGGCTGCT

CCACTCCGAACCATCACTGCTGACACTTTCTGCAAACTCTTCCGAGTCTACTCCAATTT

CCTCCGGGGAAAGCTGAAGCTGTACACGGGGGAGGCCTGCAGGAGAGGGGACAGATGA cmEPO sense strand, non-template. 5'_20%_T.
(SEQ ID NO: 169)
ATGGGGGTGCACGAATGCCCCGCCTGGCTGTGGCTGCTCCTGTCTCTGC

TGTCGCTCCCTCTGGGCCTCCCAGTCCCGGGCGCCCCACCACGCCTCATCTGTGACAGC

CGAGTCCTGGAGAGGTACCTCTTGGAGGCCAAGGAGGCCGAGAATGTCACGATGGGCTG

TTCCGAAAGCTGCAGCTTGAATGAGAATATCACCGTCCCAGACACCAAAGTTAACTTCT

ATGCCTGGAAGAGGATGGAGGTCGGGCAGCAGGCTGTAGAAGTCTGGCAGGGCCTGGCC

CTGCTCTCAGAAGCTGTCCTGCGGGGCCAGGCCGTGTTGGCCAACTCTTCCCAGCCTTT

```
CGAGCCCCTGCAGCTGCACATGGATAAAGCCATCAGTGGCCTTCGCAGCATCACCACTC

TGCTTCGGGCGCTGGGAGCCCAGGAAGCCATCTCCCTCCCAGATGCGGCCTCGGCTGCT

CCACTCCGAACCATCACTGCTGACACTTTCTGCAAACTCTTCCGAGTCTACTCCAATTT

CCTCCGGGGAAAGCTGAAGCTGTACACGGGGGAGGCCTGCAGGAGAGGGGACAGATGA cmEPO sense strand, non-template. random_14%_T.
                                                 (SEQ ID NO: 170)
ATGGGGGTGCACGAATGCCCCGCCTGGCTGTGGCTGCTCCTGAGCCTGC

TGAGCCTCCCTCTGGGCCTCCCAGTCCCGGGCGCCCCACCACGCCTCATCTGCGACAGC

CGAGTCCTGGAGAGGTACCTCCTGGAGGCCAAGGAGGCCGAGAACGTCACGATGGGCTG

CAGCGAAAGCTGCAGCCTGAACGAGAATATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTCAGCGAAGCCGTCCTGCGGGGCCAGGCCGTGCTGGCCAACAGCAGCCAGCCTTT

CGAGCCCCTGCAGCTGCACATGGACAAAGCCATCAGCGGCCTGCGCAGCATCACCACCC

TGCTGCGGGCGCTGGGAGCCCAGGAAGCCATCAGCCTCCCAGACGCGGCCAGCGCCGCC

CCACTCCGAACCATCACCGCCGACACCTTCTGCAAACTCTTCCGAGTCTACAGCAACTT

CCTCCGGGGAAAGCTGAAGCTGTACACGGGGGAGGCCTGCAGGAGAGGGGACAGATGA cmEPO sense strand, non-template. random_16%_T.
                                                 (SEQ ID NO: 171)
ATGGGGGTGCACGAATGCCCCGCCTGGCTGTGGCTTCTCCTGAGCCTGC

TGTCGCTCCCCCTGGGCCTCCCAGTCCCGGGCGCCCCACCACGCCTCATCTGCGACAGC

CGAGTCCTGGAGAGGTACCTCCTGGAGGCCAAGGAGGCCGAGAACGTCACGATGGGCTG

CTCCGAAAGCTGCAGCTTGAATGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTCTCAGAAGCCGTCCTGCGGGGCCAGGCCGTGCTGGCCAACAGCAGCCAGCCTTT

CGAGCCCCTGCAGCTGCACATGGATAAAGCCATCAGCGGCCTTCGCAGCATCACCACTC

TGCTGCGGGCGCTGGGAGCCCAGGAAGCCATCTCCCTCCCAGATGCGGCCAGCGCTGCC

CCACTCCGAACCATCACTGCCGACACCTTCTGCAAACTCTTCCGAGTCTACAGCAACTT

CCTCCGGGGAAAGCTGAAGCTGTACACGGGGAGGCCTGCAGGAGAGGGGACAGATGA cmEPO sense strand, non-template. random_18%_T.
                                                 (SEQ ID NO: 172)
ATGGGGGTGCACGAATGCCCCGCCTGGCTGTGGCTTCTCCTGTCTCTGC

TGAGCCTCCCTCTGGGCCTCCCAGTCCCGGGCGCCCCACCACGCCTCATCTGTGACAGC

CGAGTCCTGGAGAGGTACCTCTTGGAGGCCAAGGAGGCCGAGAACGTCACGATGGGCTG

TTCCGAAAGCTGCAGCTTGAACGAGAATATCACCGTCCCAGACACCAAAGTGAACTTCT

ATGCCTGGAAGAGGATGGAGGTCGGGCAGCAGGCTGTAGAAGTCTGGCAGGGCCTGGCC

CTGCTCAGCGAAGCCGTCCTGCGGGGCCAGGCCGTGTTGGCCAACAGCTCCCAGCCCTT

CGAGCCCCTGCAGCTGCACATGGACAAAGCCATCAGTGGCCTGCGCAGCATCACCACTC

TGCTTCGGGCGCTGGGAGCCCAGGAAGCCATCTCCCTCCCAGATGCGGCCAGCGCTGCT

CCACTCCGAACCATCACTGCTGACACTTTCTGCAAACTCTTCCGAGTCTACTCCAATTT

CCTCCGGGGAAAGCTGAAGCTGTACACGGGGGAGGCCTGCAGGAGAGGGGACAGATGA cmEPO sense strand, non-template. random_20%_T.
                                                 (SEQ ID NO: 173)
ATGGGGGTGCACGAATGCCCTGCCTGGCTGTGGCTTCTCCTGTCTCTGC

TGTCGCTCCCTCTGGGCCTCCCAGTCCCGGGCGCCCCACCACGCCTCATCTGTGACAGC

CGAGTCCTGGAGAGGTACCTCTTGGAGGCCAAGGAGGCCGAGAATGTCACGATGGGCTG
```

```
TTCCGAAAGCTGCAGCCTGAATGAGAATATCACCGTCCCAGACACCAAAGTTAACTTCT

ATGCCTGGAAGAGGATGGAGGTCGGGCAGCAGGCTGTAGAAGTCTGGCAGGGCCTGGCC

CTGCTCTCAGAAGCTGTCCTGCGGGGCCAGGCCGTGTTGGCCAACTCTTCCCAGCCTTT

CGAGCCCCTGCAGCTGCACATGGATAAAGCCATCAGTGGCCTTCGCAGCATCACCACTC

TGCTGCGGGCGCTGGGAGCCCAGGAAGCCATCTCCCTCCCAGATGCGGCCTCGGCTGCT

CCACTCCGAACCATCACTGCTGACACTTTCTGCAAACTCTTCCGAGTCTACTCCAATTT

CCTCCGGGGAAAGCTGAAGCTGTACACGGGGGAGGCCTGCAGGAGAGGGGACAGATGA

SynK-cmEPO-XbG sense strand, non-template.
3'_lowest_T. (913 nt)
                                              (SEQ ID NO: 174)
AGGAAACTTAAGAACTTAAAAAAAAAAATCAAAATGGCCGCCACCATGG

GGGTGCACGAATGCCCCGCCTGGCTGTGGCTGCTCCTGAGCCTGCTGAGCCTCCCCCTG

GGCCTCCCAGTCCCGGGCGCCCCACCACGCCTCATCTGCGACAGCCGAGTCCTGGAGAG

GTACCTCCTGGAGGCCAAGGAGGCCGAGAACGTCACGATGGGCTGCAGCGAAAGCTGCA

GCCTGAACGAGAACATCACCGTCCCAGACACCAAAGTGAACTTCTACGCCTGGAAGAGG

ATGGAGGTCGGGCAGCAGGCCGTAGAAGTCTGGCAGGGCCTGGCCCTGCTCAGCGAAGC

CGTCCTGCGGGCCAGGCCGTGCTGGCCAACAGCAGCCAGCCCTTCGAGCCCCTGCAGC

TGCACATGGACAAAGCCATCAGCGGCCTGCGCAGCATCACCACCCTGCTGCGGGCGCTG

GGAGCCCAGGAAGCCATCAGCCTCCCAGACGCGGCCAGCGCCGCCCCACTCCGAACCAT

CACCGCCGACACCTTCTGCAAACTCTTCCGAGTCTACAGCAACTTCCTCCGGGGAAAGC

TGAAGCTGTACACGGGGGAGGCCTGCAGGAGAGGGGACAGATGACTCGAGCTAGTGACT

GACTAGGATCTGGTTACCACTAAACCAGCCTCAAGAACACCCGAATGGAGTCTCTAAGC

TACATAATACCAACTTACACTTACAAAATGTTGTCCCCCAAAATGTAGCCATTCGTATC

TGCTCCTAATAAAAGAAAGTTTCTTCACATTCTAGAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAA

SynK-cmEPO-XbG sense strand, non-template.
3'_14%_T. (913 nt)
                                              (SEQ ID NO: 175)
AGGAAACTTAAGAACTTAAAAAAAAAAATCAAAATGGCCGCCACCATGG

GGGTGCACGAATGTCCTGCCTGGCTGTGGCTTCTCCTGAGCCTGCTGAGCCTCCCCCTG

GGCCTCCCAGTCCCGGGCGCCCCACCACGCCTCATCTGCGACAGCCGAGTCCTGGAGAG

GTACCTCCTGGAGGCCAAGGAGGCCGAGAACGTCACGATGGGCTGCAGCGAAAGCTGCA

GCCTGAACGAGAACATCACCGTCCCAGACACCAAAGTGAACTTCTACGCCTGGAAGAGG

ATGGAGGTCGGGCAGCAGGCCGTAGAAGTCTGGCAGGGCCTGGCCCTGCTCAGCGAAGC

CGTCCTGCGGGCCAGGCCGTGCTGGCCAACAGCAGCCAGCCCTTCGAGCCCCTGCAGC

TGCACATGGACAAAGCCATCAGCGGCCTGCGCAGCATCACCACCCTGCTGCGGGCGCTG

GGAGCCCAGGAAGCCATCAGCCTCCCAGACGCGGCCAGCGCCGCCCCACTCCGAACCAT

CACCGCCGACACCTTCTGCAAACTCTTCCGAGTCTACAGCAACTTCCTCCGGGGAAAGC

TGAAGCTGTACACGGGGGAGGCCTGCAGGAGAGGGGACAGATGACTCGAGCTAGTGACT

GACTAGGATCTGGTTACCACTAAACCAGCCTCAAGAACACCCGAATGGAGTCTCTAAGC

TACATAATACCAACTTACACTTACAAAATGTTGTCCCCCAAAATGTAGCCATTCGTATC

TGCTCCTAATAAAAGAAAGTTTCTTCACATTCTAGAAAAAAAAAAAAAAAAAAAAAAA
```

```
AAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAA

SynK-cmEPO-XbG sense strand, non-template.
5'_14%_T. (913 nt)
                                              (SEQ ID NO: 176)
AGGAAACTTAAGAACTTAAAAAAAAAAATCAAAATGGCCGCCACCATGG

GGGTGCACGAATGCCCCGCCTGGCTGTGGCTGCTCCTGAGCCTGCTGAGCCTCCCCCTG

GGCCTCCCAGTCCCGGGCGCCCCACCACGCCTCATCTGCGACAGCCGAGTCCTGGAGAG

GTACCTCCTGGAGGCCAAGGAGGCCGAGAACGTCACGATGGGCTGCAGCGAAAGCTGCA

GCCTGAACGAGAACATCACCGTCCCAGACACCAAAGTGAACTTCTACGCCTGGAAGAGG

ATGGAGGTCGGGCAGCAGGCCGTAGAAGTCTGGCAGGGCCTGGCCCTGCTCAGCGAAGC

CGTCCTGCGGGGCCAGGCCGTGCTGGCCAACAGCAGCCAGCCCTTCGAGCCCCTGCAGC

TGCACATGGACAAAGCCATCAGCGGCCTGCGCAGCATCACCACCCTGCTGCGGGCGCTG

GGAGCCCAGGAAGCCATCAGCCTCCCAGACGCGGCCAGCGCCGCCCCACTCCGAACCAT

CACCGCCGACACTTTCTGCAAACTCTTCCGAGTCTACTCCAATTTCCTCCGGGGAAAGC

TGAAGCTGTACACGGGGGAGGCCTGCAGGAGAGGGGACAGATGACTCGAGCTAGTGACT

GACTAGGATCTGGTTACCACTAAACCAGCCTCAAGAACACCCGAATGGAGTCTCTAAGC

TACATAATACCAACTTACACTTACAAAATGTTGTCCCCCAAAATGTAGCCATTCGTATC

TGCTCCTAATAAAAGAAAGTTTCTTCACATTCTAGAAAAAAAAAAAAAAAAAAAAAAA

AAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAA

SynK-cmEPO-XbG sense strand, non-template.
random_14%_T. (913 nt)
                                              (SEQ ID NO: 177)
AGGAAACTTAAGAACTTAAAAAAAAAAATCAAAATGGCCGCCACCATGG

GGGTGCACGAATGCCCCGCCTGGCTGTGGCTGCTCCTGAGCCTGCTGAGCCTCCCTCTG

GGCCTCCCAGTCCCGGGCGCCCCACCACGCCTCATCTGCGACAGCCGAGTCCTGGAGAG

GTACCTCCTGGAGGCCAAGGAGGCCGAGAACGTCACGATGGGCTGCAGCGAAAGCTGCA

GCCTGAACGAGAATATCACCGTCCCAGACACCAAAGTGAACTTCTACGCCTGGAAGAGG

ATGGAGGTCGGGCAGCAGGCCGTAGAAGTCTGGCAGGGCCTGGCCCTGCTCAGCGAAGC

CGTCCTGCGGGGCCAGGCCGTGCTGGCCAACAGCAGCCAGCCTTTCGAGCCCCTGCAGC

TGCACATGGACAAAGCCATCAGCGGCCTGCGCAGCATCACCACCCTGCTGCGGGCGCTG

GGAGCCCAGGAAGCCATCAGCCTCCCAGACGCGGCCAGCGCCGCCCCACTCCGAACCAT

CACCGCCGACACCTTCTGCAAACTCTTCCGAGTCTACAGCAACTTCCTCCGGGGAAAGC

TGAAGCTGTACACGGGGGAGGCCTGCAGGAGAGGGGACAGATGACTCGAGCTAGTGACT

GACTAGGATCTGGTTACCACTAAACCAGCCTCAAGAACACCCGAATGGAGTCTCTAAGC

TACATAATACCAACTTACACTTACAAAATGTTGTCCCCCAAAATGTAGCCATTCGTATC

TGCTCCTAATAAAAGAAAGTTTCTTCACATTCTAGAAAAAAAAAAAAAAAAAAAAAAA

AAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAA
```

SynK-cmEPO-XbG ARC-mRNA. 3'_lowest_T.
(913nt)
(SEQ ID NO: 178)
5'-cap-

AGGAAACUUAAGAACUUAAAAAAAAAAAUCAAAAUGGCCGCCACCAUGGGGGUGCACGA

AUGCCCCGCCUGGCUGUGGCUGCUCCUGAGCCUGCUGAGCCUCCCCCUGGGCCUCCCAG

UCCCGGGCGCCCCACCACGCCUCAUCUGCGACAGCCGAGUCCGGAGAGGUACCUCCUG

GAGGCCAAGGAGGCCGAGAACGUCACGAUGGGCUGCAGCGAAAGCUGCAGCCUGAACGA

GAACAUCACCGUCCCAGACACCAAAGUGAACUUCUACGCCUGGAAGAGGAUGGAGGUCG

GGCAGCAGGCCGUAGAAGUCUGGCAGGGCCUGGCCCUGCUCAGCGAAGCCGUCCUGCGG

GGCCAGGCCGUGCUGGCCAACAGCAGCCAGCCCUUCGAGCCCCUGCAGCUGCACAUGGA

CAAAGCCAUCAGCGGCCUGCGCAGCAUCACCACCCUGCUGCGGGCGCUGGGAGCCCAGG

AAGCCAUCAGCCUCCCAGACGCGGCCAGCGCCGCCCCACUCCGAACCAUCACCGCCGAC

ACCUUCUGCAAACUCUUCCGAGUCUACAGCAACUUCCUCCGGGGAAAGCUGAAGCUGUA

CACGGGGGAGGCCUGCAGGAGAGGGGACAGAUGACUCGAGCUAGUGACUGACUAGGAUC

UGGUUACCACUAAACCAGCCUCAAGAACACCCGAAUGGAGUCUCUAAGCUACAUAAUAC

CAACUUACACUUACAAAAUGUUGUCCCCCAAAAUGUAGCCAUUCGUAUCUGCUCCUAAU

AAAAAGAAAGUUUCUUCACAUUCUAGAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAA

SynK-cmEPO-XbG ARC-mRNA. 3'_14%_T.
(913nt)
(SEQ ID NO: 179)
5'-cap-

AGGAAACUUAAGAACUUAAAAAAAAAAAUCAAAAUGGCCGCCACCAUGGGGGUGCACGA

AUGUCCUGCCUGGCUGUGGCUUCUCCUGAGCCUGCUGAGCCUCCCCCUGGGCCUCCCAG

UCCCGGGCGCCCCACCACGCCUCAUCUGCGACAGCCGAGUCCGGAGAGGUACCUCCUG

GAGGCCAAGGAGGCCGAGAACGUCACGAUGGGCUGCAGCGAAAGCUGCAGCCUGAACGA

GAACAUCACCGUCCCAGACACCAAAGUGAACUUCUACGCCUGGAAGAGGAUGGAGGUCG

GGCAGCAGGCCGUAGAAGUCUGGCAGGGCCUGGCCCUGCUCAGCGAAGCCGUCCUGCGG

GGCCAGGCCGUGCUGGCCAACAGCAGCCAGCCCUUCGAGCCCCUGCAGCUGCACAUGGA

CAAAGCCAUCAGCGGCCUGCGCAGCAUCACCACCCUGCUGCGGGCGCUGGGAGCCCAGG

AAGCCAUCAGCCUCCCAGACGCGGCCAGCGCCGCCCCACUCCGAACCAUCACCGCCGAC

ACCUUCUGCAAACUCUUCCGAGUCUACAGCAACUUCCUCCGGGGAAAGCUGAAGCUGUA

CACGGGGGAGGCCUGCAGGAGAGGGGACAGAUGACUCGAGCUAGUGACUGACUAGGAUC

UGGUUACCACUAAACCAGCCUCAAGAACACCCGAAUGGAGUCUCUAAGCUACAUAAUAC

CAACUUACACUUACAAAAUGUUGUCCCCCAAAAUGUAGCCAUUCGUAUCUGCUCCUAAU

AAAAAGAAAGUUUCUUCACAUUCUAGAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAA

SynK-cmEPO-XbG ARC-mRNA. 5'_14%_T.
(913nt)

(SEQ ID NO: 180)

5'-cap-

AGGAAACUUAAGAACUUAAAAAAAAAAAAUCAAAAUGGCCGCCACCAUGGGGGUGCACGA

AUGCCCCGCCUGGCUGUGGCUGCUCCUGAGCCUGCUGAGCCUCCCCCUGGGGCCUCCCAG

UCCCGGGCGCCCCACCACGCCUCAUCUGCGACAGCCGAGUCCUGGAGAGGUACCUCCUG

GAGGCCAAGGAGGCCGAGAACGUCACGAUGGGCUGCAGCGAAAGCUGCAGCCUGAACGA

GAACAUCACCGUCCCAGACACCAAAGUGAACUUCUACGCCUGGAAGAGGAUGGAGGUCG

GGCAGCAGGCCGUAGAAGUCUGGCAGGGCCUGGCCCUGCUCAGCGAAGCCGUCCUGCGG

GGCCAGGCCGUGCUGGCCAACAGCAGCCAGCCCUUCGAGCCCCUGCAGCUGCACAUGGA

CAAAGCCAUCAGCGGCCUGCGCAGCAUCACCACCCUGCUGCGGGCGCUGGGAGCCCAGG

AAGCCAUCAGCCUCCCAGACGCGGCCAGCGCCGCCCCACUCCGAACCAUCACCGCCGAC

ACUUUCUGCAAACUCUUCCGAGUCUACUCCAAUUUCCUCCGGGGAAAGCUGAAGCUGUA

CACGGGGGAGGCCUGCAGGAGAGGGGACAGAUGACUCGAGCUAGUGACUGACUAGGAUC

UGGUUACCACUAAACCAGCCUCAAGAACACCCGAAUGGAGUCUCUAAGCUACAUAAUAC

CAACUUACACUUACAAAAUGUUGUCCCCCAAAAUGUAGCCAUUCGUAUCUGCUCCUAAU

AAAAAGAAAGUUUCUUCACAUUCUAGAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAA

SynK-cmEPO-XbG ARC-mRNA. random_14%_T.
(913 nt)

(SEQ ID NO: 181)

5'-cap-

AGGAAACUUAAGAACUUAAAAAAAAAAAAUCAAAAUGGCCGCCACCAUGGGGGUGCACGA

AUGCCCCGCCUGGCUGUGGCUGCUCCUGAGCCUGCUGAGCCUCCCUCUGGGGCCUCCCAG

UCCCGGGCGCCCCACCACGCCUCAUCUGCGACAGCCGAGUCCUGGAGAGGUACCUCCUG

GAGGCCAAGGAGGCCGAGAACGUCACGAUGGGCUGCAGCGAAAGCUGCAGCCUGAACGA

GAAUAUCACCGUCCCAGACACCAAAGUGAACUUCUACGCCUGGAAGAGGAUGGAGGUCG

GGCAGCAGGCCGUAGAAGUCUGGCAGGGCCUGGCCCUGCUCAGCGAAGCCGUCCUGCGG

GGCCAGGCCGUGCUGGCCAACAGCAGCCAGCCUUUCGAGCCCCUGCAGCUGCACAUGGA

CAAAGCCAUCAGCGGCCUGCGCAGCAUCACCACCCUGCUGCGGGCGCUGGGAGCCCAGG

AAGCCAUCAGCCUCCCAGACGCGGCCAGCGCCGCCCCACUCCGAACCAUCACCGCCGAC

ACCUUCUGCAAACUCUUCCGAGUCUACAGCAACUUCCUCCGGGGAAAGCUGAAGCUGUA

CACGGGGGAGGCCUGCAGGAGAGGGGACAGAUGACUCGAGCUAGUGACUGACUAGGAUC

UGGUUACCACUAAACCAGCCUCAAGAACACCCGAAUGGAGUCUCUAAGCUACAUAAUAC

CAACUUACACUUACAAAAUGUUGUCCCCCAAAAUGUAGCCAUUCGUAUCUGCUCCUAAU

AAAAAGAAAGUUUCUUCACAUUCUAGAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAAAAAAAAAAAAAAAAAAA

TEV-cmEPO-XbG sense strand, non-template.
3'_lowest_T. (1011 nt)

(SEQ ID NO: 182)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

-continued

TTTCTGAAAATTTTCACCATTTACGAACGATAGCCATGGGGGTGCACGAATGCCCCGCC

TGGCTGTGGCTGCTCCTGAGCCTGCTGAGCCTCCCCCTGGGCCTCCCAGTCCCGGGCGC

CCCACCACGCCTCATCTGCGACAGCCGAGTCCTGGAGAGGTACCTCCTGGAGGCCAAGG

AGGCCGAGAACGTCACGATGGGCTGCAGCGAAAGCTGCAGCCTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTCAGCGAAGCCGTCCTGCGGGGCCAGGCCG

TGCTGGCCAACAGCAGCCAGCCCTTCGAGCCCCTGCAGCTGCACATGGACAAAGCCATC

AGCGGCCTGCGCAGCATCACCACCCTGCTGCGGGCGCTGGGAGCCCAGGAAGCCATCAG

CCTCCCAGACGCGGCCAGCGCCGCCCCACTCCGAACCATCACCGCCGACACCTTCTGCA

AACTCTTCCGAGTCTACAGCAACTTCCTCCGGGGAAAGCTGAAGCTGTACACGGGGGAG

GCCTGCAGGAGAGGGGACAGATGACTCGAGCTAGTGACTGACTAGGATCTGGTTACCAC

TAAACCAGCCTCAAGAACACCCGAATGGAGTCTCTAAGCTACATAATACCAACTTACAC

TTACAAAATGTTGTCCCCCAAAATGTAGCCATTCGTATCTGCTCCTAATAAAAGAAAG

TTTCTTCACATTCTAGAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAAAAAAAA

TEV-cmEPO-XbG sense strand, non-template.
3'_14%_T. (1011 nt)

(SEQ ID NO: 183)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGTCCTGCC

TGGCTGTGGCTTCTCCTGAGCCTGCTGAGCCTCCCCCTGGGCCTCCCAGTCCCGGGCGC

CCCACCACGCCTCATCTGCGACAGCCGAGTCCTGGAGAGGTACCTCCTGGAGGCCAAGG

AGGCCGAGAACGTCACGATGGGCTGCAGCGAAAGCTGCAGCCTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTCAGCGAAGCCGTCCTGCGGGGCCAGGCCG

TGCTGGCCAACAGCAGCCAGCCCTTCGAGCCCCTGCAGCTGCACATGGACAAAGCCATC

AGCGGCCTGCGCAGCATCACCACCCTGCTGCGGGCGCTGGGAGCCCAGGAAGCCATCAG

CCTCCCAGACGCGGCCAGCGCCGCCCCACTCCGAACCATCACCGCCGACACCTTCTGCA

AACTCTTCCGAGTCTACAGCAACTTCCTCCGGGGAAAGCTGAAGCTGTACACGGGGGAG

GCCTGCAGGAGAGGGGACAGATGACTCGAGCTAGTGACTGACTAGGATCTGGTTACCAC

TAAACCAGCCTCAAGAACACCCGAATGGAGTCTCTAAGCTACATAATACCAACTTACAC

TTACAAAATGTTGTCCCCCAAAATGTAGCCATTCGTATCTGCTCCTAATAAAAGAAAG

TTTCTTCACATTCTAGAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAAAAAAAAAA

TEV-cmEPO-XbG sense strand, non-template.
5'_14%_T. (1011 nt)

(SEQ ID NO: 184)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGCCCCGCC

-continued

TGGCTGTGGCTGCTCCTGAGCCTGCTGAGCCTCCCCCTGGGCCTCCCAGTCCCGGGCGC

CCCACCACGCCTCATCTGCGACAGCCGAGTCCTGGAGAGGTACCTCCTGGAGGCCAAGG

AGGCCGAGAACGTCACGATGGGCTGCAGCGAAAGCTGCAGCCTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTCAGCGAAGCCGTCCTGCGGGGCCAGGCCG

TGCTGGCCAACAGCAGCCAGCCCTTCGAGCCCCTGCAGCTGCACATGGACAAAGCCATC

AGCGGCCTGCGCAGCATCACCACCCTGCTGCGGGCGCTGGGAGCCCAGGAAGCCATCAG

CCTCCCAGACGCGGCCAGCGCCGCCCCACTCCGAACCATCACCGCCGACACTTTCTGCA

AACTCTTCCGAGTCTACTCCAATTTCCTCCGGGGAAAGCTGAAGCTGTACACGGGGGAG

GCCTGCAGGAGAGGGGACAGATGACTCGAGCTAGTGACTGACTAGGATCTGGTTACCAC

TAAACCAGCCTCAAGAACACCCGAATGGAGTCTCTAAGCTACATAATACCAACTTACAC

TTACAAAATGTTGTCCCCCAAAATGTAGCCATTCGTATCTGCTCCTAATAAAAAGAAAG

TTTCTTCACATTCTAGAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAA

TEV-cmEPO-XbG sense strand, non-template.
random_14%_T. (1011 nt)

(SEQ ID NO: 185)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGCCCCGCC

TGGCTGTGGCTGCTCCTGAGCCTGCTGAGCCTCCCTCTGGGCCTCCCAGTCCCGGGCGC

CCCACCACGCCTCATCTGCGACAGCCGAGTCCTGGAGAGGTACCTCCTGGAGGCCAAGG

AGGCCGAGAACGTCACGATGGGCTGCAGCGAAAGCTGCAGCCTGAACGAGAATATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTCAGCGAAGCCGTCCTGCGGGGCCAGGCCG

TGCTGGCCAACAGCAGCCAGCCTTTCGAGCCCCTGCAGCTGCACATGGACAAAGCCATC

AGCGGCCTGCGCAGCATCACCACCCTGCTGCGGGCGCTGGGAGCCCAGGAAGCCATCAG

CCTCCCAGACGCGGCCAGCGCCGCCCCACTCCGAACCATCACCGCCGACACCTTCTGCA

AACTCTTCCGAGTCTACAGCAACTTCCTCCGGGGAAAGCTGAAGCTGTACACGGGGGAG

GCCTGCAGGAGAGGGGACAGATGACTCGAGCTAGTGACTGACTAGGATCTGGTTACCAC

TAAACCAGCCTCAAGAACACCCGAATGGAGTCTCTAAGCTACATAATACCAACTTACAC

TTACAAAATGTTGTCCCCCAAAATGTAGCCATTCGTATCTGCTCCTAATAAAAAGAAAG

TTTCTTCACATTCTAGAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAA

TEV-cmEPO-XbG ARC-mRNA. 3'_lowest_T.
(1011 nt)

(SEQ ID NO: 186)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

UGCUCCUGAGCCUGCUGAGCCUCCCCCUGGGCCUCCCAGUCCCGGGCGCCCCACCACGC

-continued

CUCAUCUGCGACAGCCGAGUCCUGGAGAGGUACCUCCUGGAGGCCAAGGAGGCCGAGAA

CGUCACGAUGGGCUGCAGCGAAAGCUGCAGCCUGAACGAGAACAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUCAGCGAAGCCGUCCUGCGGGGCCAGGCCGUGCUGGCCAA

CAGCAGCCAGCCCUUCGAGCCCCUGCAGCUGCACAUGGACAAAGCCAUCAGCGGCCUGC

GCAGCAUCACCACCCUGCUGCGGGCGCUGGGAGCCCAGGAAGCCAUCAGCCUCCCAGAC

GCGGCCAGCGCCGCCCCACUCCGAACCAUCACCGCCGACACCUUCUGCAAACUCUUCCG

AGUCUACAGCAACUUCCUCCGGGGAAAGCUGAAGCUGUACACGGGGGAGGCCUGCAGGA

GAGGGGACAGAUGACUCGAGCUAGUGACUGACUAGGAUCUGGUUACCACUAAACCAGCC

UCAAGAACACCCGAAUGGAGUCUCUAAGCUACAUAAUACCAACUUACACUUACAAAAUG

UUGUCCCCCAAAAUGUAGCCAUUCGUAUCUGCUCCUAAUAAAAAGAAAGUUUCUUCACA

UUCUAGAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAA

TEV-cmEPO-XbG ARC-mRNA. 3'_14%_T.
(1011 nt)
(SEQ ID NO: 187)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGUCCUGCCUGGCUGUGGC

UUCUCCUGAGCCUGCUGAGCCUCCCCCUGGGCCUCCCAGUCCCGGGCGCCCCACCACGC

CUCAUCUGCGACAGCCGAGUCCUGGAGAGGUACCUCCUGGAGGCCAAGGAGGCCGAGAA

CGUCACGAUGGGCUGCAGCGAAAGCUGCAGCCUGAACGAGAACAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUCAGCGAAGCCGUCCUGCGGGGCCAGGCCGUGCUGGCCAA

CAGCAGCCAGCCCUUCGAGCCCCUGCAGCUGCACAUGGACAAAGCCAUCAGCGGCCUGC

GCAGCAUCACCACCCUGCUGCGGGCGCUGGGAGCCCAGGAAGCCAUCAGCCUCCCAGAC

GCGGCCAGCGCCGCCCCACUCCGAACCAUCACCGCCGACACCUUCUGCAAACUCUUCCG

AGUCUACAGCAACUUCCUCCGGGGAAAGCUGAAGCUGUACACGGGGGAGGCCUGCAGGA

GAGGGGACAGAUGACUCGAGCUAGUGACUGACUAGGAUCUGGUUACCACUAAACCAGCC

UCAAGAACACCCGAAUGGAGUCUCUAAGCUACAUAAUACCAACUUACACUUACAAAAUG

UUGUCCCCCAAAAUGUAGCCAUUCGUAUCUGCUCCUAAUAAAAAGAAAGUUUCUUCACA

UUCUAGAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAA

TEV-cmEPO-XbG ARC-mRNA. 5'_14%_T.
(1011 nt)
(SEQ ID NO: 188)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

```
UGCUCCUGAGCCUGCUGAGCCUCCCCUGGGCCUCCCAGUCCCGGGCGCCCCACCACGC

CUCAUCUGCGACAGCCGAGUCCUGGAGAGGUACCUCCUGGAGGCCAAGGAGGCCGAGAA

CGUCACGAUGGGCUGCAGCGAAAGCUGCAGCCUGAACGAGAACAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUCAGCGAAGCCGUCCUGCGGGGCCAGGCCGUGCUGGCCAA

CAGCAGCCAGCCCUUCGAGCCCCUGCAGCUGCACAUGGACAAAGCCAUCAGCGGCCUGC

GCAGCAUCACCACCCUGCUGCGGGCGCUGGGAGCCCAGGAAGCCAUCAGCCUCCCAGAC

GCGGCCAGCGCCGCCCCACUCCGAACCAUCACCGCCGACACUUUCUGCAAACUCUUCCG

AGUCUACUCCAAUUUCCUCCGGGGAAAGCUGAAGCUGUACACGGGGGAGGCCUGCAGGA

GAGGGGACAGAUGACUCGAGCUAGUGACUGACUAGGAUCUGGUUACCACUAAACCAGCC

UCAAGAACACCCGAAUGGAGUCUCUAAGCUACAUAAUACCAACUUACACUUACAAAAUG

UUGUCCCCCAAAAUGUAGCCAUUCGUAUCUGCUCCUAAUAAAAGAAAGUUUCUUCACA

UUCUAGAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAA

TEV-cmEPO-XbG ARC-mRNA. random_14%_T.
(1011 nt)
                                                (SEQ ID NO: 189)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

UGCUCCUGAGCCUGCUGAGCCUCCCUCUGGGCCUCCCAGUCCCGGGCGCCCCACCACGC

CUCAUCUGCGACAGCCGAGUCCUGGAGAGGUACCUCCUGGAGGCCAAGGAGGCCGAGAA

CGUCACGAUGGGCUGCAGCGAAAGCUGCAGCCUGAACGAGAAUAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUCAGCGAAGCCGUCCUGCGGGGCCAGGCCGUGCUGGCCAA

CAGCAGCCAGCCUUUCGAGCCCCUGCAGCUGCACAUGGACAAAGCCAUCAGCGGCCUGC

GCAGCAUCACCACCCUGCUGCGGGCGCUGGGAGCCCAGGAAGCCAUCAGCCUCCCAGAC

GCGGCCAGCGCCGCCCCACUCCGAACCAUCACCGCCGACACCUUCUGCAAACUCUUCCG

AGUCUACAGCAACUUCCUCCGGGGAAAGCUGAAGCUGUACACGGGGGAGGCCUGCAGGA

GAGGGGACAGAUGACUCGAGCUAGUGACUGACUAGGAUCUGGUUACCACUAAACCAGCC

UCAAGAACACCCGAAUGGAGUCUCUAAGCUACAUAAUACCAACUUACACUUACAAAAUG

UUGUCCCCCAAAAUGUAGCCAUUCGUAUCUGCUCCUAAUAAAAGAAAGUUUCUUCACA

UUCUAGAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

AAAAAAAA
```

Example G: Templates and mRNAs for Fluc. Photinus Luciferase (Fluc+, Promega; Fluc)

The compositions of the templates for Fluc are shown in Table 11.

TABLE 11

Non-Template Nucleotide T compositions for Fluc

| hEPO | T % |
|---|---|
| Fluc_lowest_T | 14.3 |
| Fluc_3'_16% T | 16.0 |
| Fluc_3'_18% T | 18.0 |
| Fluc_3'_20% T | 20.0 |

TABLE 11-continued

Non-Template Nucleotide T compositions for Fluc

| hEPO | T % |
|---|---|
| Fluc_5'_16% T | 15.9 |
| Fluc_5'_18% T | 18.0 |
| Fluc_5'_20% T | 20.0 |
| Fluc_random_16% | 16.0 |
| Fluc_random_18% | 18.0 |
| Fluc_random_20% | 20.0 |

Fluc ORF reference. Sense strand, non-template. Fluc_plus_pGL3_Promega (U47295.2:88-1740 Cloning vector pGL3-Basic).

(SEQ ID NO: 190)
```
atggaagacgccaaaaacataaagaaaggcccggcgccattctatccgc
tggaagatggaaccgctggagagcaactgcataaggctatgaagagatacgccctggtt
cctggaacaattgcttttacagatgcacatatcgaggtggacatcacttacgctgagta
cttcgaaatgtccgttcggttggcagaagctatgaaacgatatgggctgaatacaaatc
acagaatcgtcgtatgcagtgaaaactctcttcaattctttatgccggtgttgggcgcg
ttatttatcggagttgcagttgcgcccgcgaacgacatttataatgaacgtgaattgct
caacagtatgggcatttcgcagcctaccgtggtgttcgtttccaaaaaggggttgcaaa
aattttgaacgtgcaaaaaaagctcccaatcatccaaaaaattattatcatggattct
aaaacggattaccagggatttcagtcgatgtacacgttcgtcacatctcatctacctcc
cggttttaatgaatacgattttgtgccagagtccttcgatagggacaagacaattgcac
tgatcatgaactcctctggatctactggtctgcctaaaggtgtcgctctgcctcataga
actgcctgcgtgagattctcgcatgccagagatcctattttttggcaatcaaatcattcc
ggatactgcgattttaagtgttgttccattccatcacggttttggaatgtttactacac
tcggatatttgatatgtggatttcgagtcgtcttaatgtatagatttgaagaagagctg
tttctgaggagccttcaggattacaagattcaaagtgcgctgctggtgccaaccctatt
ctccttcttcgccaaaagcactctgattgacaaatacgatttatctaatttacacgaaa
ttgcttctggtggcgctccctctctaaggaagtcggggaagcggttgccaagaggttc
catctgccaggtatcaggcaaggatatgggctcactgagactacatcagctattctgat
tacacccgaggggatgataaaccgggcgcggtcggtaaagttgttccattttttgaag
cgaaggttgtggatctggataccgggaaaacgctgggcgttaatcaaagaggcgaactg
tgtgtgagaggtcctatgattatgtccggttatgtaaacaatccggaagcgaccaacgc
cttgattgacaaggatggatggctacattctggagacatagcttactgggacgaagacg
aacacttcttcatcgttgaccgcctgaagtctctgattaagtacaaaggctatcaggtg
gctcccgctgaattggaatccatcttgctccaacaccccaacatcttcgacgcaggtgt
cgcaggtcttcccgacgatgacgccggtgaacttcccgcgccgttgttgttttggagc
acggaaagacgatgacggaaaaagagatcgtggattacgtcgccagtcaagtaacaacc
gcgaaaagttgcgcggaggagttgtgtttgtggacgaagtaccgaaaggtcttaccgg
aaaactcgacgcaagaaaaatcagagagatcctcataaaggccaagaagggcggaaaga
tcgccgtgtaa
```

-continued

Fluc sense strand, non-template. lowest_T.
(SEQ ID NO: 191)
ATGGAAGACGCCAAAAACATAAAGAAAGGCCCGGCGCCATTCTACCCGC

TGGAAGACGGAACCGCCGGAGAGCAACTGCACAAGGCCATGAAGAGATACGCCCTGGTG

CCCGGAACAATCGCCTTCACAGACGCACACATCGAGGTGGACATCACCTACGCCGAGTA

CTTCGAAATGAGCGTGCGGCTGGCAGAAGCCATGAAACGATACGGGCTGAACACAAACC

ACAGAATCGTCGTATGCAGCGAAAACAGCCTGCAATTCTTCATGCCGGTGCTGGGCGCG

CTGTTCATCGGAGTGGCAGTGGCGCCCGCGAACGACATCTACAACGAACGGGAACTGCT

CAACAGCATGGGCATCAGCCAGCCCACCGTGGTGTTCGTGAGCAAAAAGGGGCTGCAAA

AAATCCTGAACGTGCAAAAAAAGCTCCCAATCATCCAAAAAATCATCATCATGGACAGC

AAAACGGACTACCAGGGATTCCAGAGCATGTACACGTTCGTCACAAGCCACCTACCCCC

CGGCTTCAACGAATACGACTTCGTGCCAGAGAGCTTCGACAGGGACAAGACAATCGCAC

TGATCATGAACAGCAGCGGAAGCACCGGCCTGCCCAAAGGCGTCGCCCTGCCCCACAGA

ACCGCCTGCGTGAGATTCAGCCACGCCAGAGACCCCATCTTCGGCAACCAAATCATCCC

GGACACCGCGATCCTGAGCGTGGTGCCATTCCACCACGGCTTCGGAATGTTCACCACAC

TCGGATACCTGATATGCGGATTCCGAGTCGTCCTGATGTACAGATTCGAGGAGGAGCTG

TTCCTGAGGAGCCTGCAGGACTACAAGATCCAAAGCGCGCTGCTGGTGCCAACCCTATT

CAGCTTCTTCGCCAAAAGCACCCTGATCGACAAATACGACCTGAGCAACCTGCACGAAA

TCGCCAGCGGCGGCGCCCCCCTCAGCAAGGAAGTCGGGGAAGCGGTGGCCAAGAGGTTC

CACCTGCCAGGCATCAGGCAAGGATACGGGCTCACCGAGACCACAAGCGCCATCCTGAT

CACACCCGAGGGGACGACAAACCGGGCGCGGTCGGCAAAGTGGTGCCATTCTTCGAAG

CGAAGGTGGTGGACCTGGACACCGGGAAAACGCTGGGCGTGAACCAAAGAGGCGAACTG

TGCGTGAGAGGCCCCATGATCATGAGCGGCTACGTAAACAACCCGGAAGCGACCAACGC

CCTGATCGACAAGGACGGATGGCTACACAGCGGAGACATAGCCTACTGGGACGAAGACG

AACACTTCTTCATCGTGGACCGCCTGAAGTCCCTGATCAAGTACAAAGGCTACCAGGTG

GCCCCCGCCGAACTGGAAAGCATCCTGCTCCAACACCCCAACATCTTCGACGCAGGCGT

CGCAGGCCTGCCCGACGACGACGCCGGCGAACTGCCCGCCGCCGTGGTGGTGCTGGAGC

ACGGAAAGACGATGACGGAAAAAGAGATCGTGGACTACGTCGCCAGCCAAGTAACAACC

GCGAAAAAGCTGCGCGGAGGAGTGGTGTTCGTGGACGAAGTACCGAAAGGCCTGACCGG

AAAACTCGACGCAAGAAAAATCAGAGAGATCCTCATAAAGGCCAAGAAGGGCGGAAAGA

TCGCCGTGTAA

Fluc sense strand, non-template. 3'_16%_T.
(SEQ ID NO: 192)
ATGGAAGACGCCAAAAACATAAAGAAAGGCCCGGCGCCATTCTATCCGC

TGGAAGATGGAACCGCTGGAGAGCAACTGCATAAGGCTATGAAGAGATACGCCCTGGTT

CCTGGAACAATTGCTTTTACAGATGCACATATCGAGGTGGACATCACTTACGCTGAGTA

CTTCGAAATGTCCGTTCGGTTGGCAGAAGCTATGAAACGATATGGGCTGAATACAAATC

ACAGAATCGTCGTATGCAGTGAAAACTCTCTTCAATTCTTTATGCCGGTGTTGGGCGCG

TTATTTATCGGAGTGGCAGTGGCGCCCGCGAACGACATCTACAACGAACGGGAACTGCT

CAACAGCATGGGCATCAGCCAGCCCACCGTGGTGTTCGTGAGCAAAAAGGGGCTGCAAA

AAATCCTGAACGTGCAAAAAAAGCTCCCAATCATCCAAAAAATCATCATCATGGACAGC

AAAACGGACTACCAGGGATTCCAGAGCATGTACACGTTCGTCACAAGCCACCTACCCCC

```
                         -continued
CGGCTTCAACGAATACGACTTCGTGCCAGAGAGCTTCGACAGGGACAAGACAATCGCAC

TGATCATGAACAGCAGCGGAAGCACCGGCCTGCCCAAAGGCGTCGCCCTGCCCCACAGA

ACCGCCTGCGTGAGATTCAGCCACGCCAGAGACCCCATCTTCGGCAACCAAATCATCCC

GGACACCGCGATCCTGAGCGTGGTGCCATTCCACCACGGCTTCGGAATGTTCACCACAC

TCGGATACCTGATATGCGGATTCCGAGTCGTCCTGATGTACAGATTCGAGGAGGAGCTG

TTCCTGAGGAGCCTGCAGGACTACAAGATCCAAAGCGCGCTGCTGGTGCCAACCCTATT

CAGCTTCTTCGCCAAAAGCACCCTGATCGACAAATACGACCTGAGCAACCTGCACGAAA

TCGCCAGCGGCGGCGCCCCCCTCAGCAAGGAAGTCGGGGAAGCGGTGGCCAAGAGGTTC

CACCTGCCAGGCATCAGGCAAGGATACGGGCTCACCGAGACCACAAGCGCCATCCTGAT

CACACCCGAGGGGGACGACAAACCGGGCGCGGTCGGCAAAGTGGTGCCATTCTTCGAAG

CGAAGGTGGTGGACCTGGACACCGGGAAAACGCTGGGCGTGAACCAAAGAGGCGAACTG

TGCGTGAGAGGCCCCATGATCATGAGCGGCTACGTAAACAACCCGGAAGCGACCAACGC

CCTGATCGACAAGGACGGATGGCTACACAGCGGAGACATAGCCTACTGGGACGAAGACG

AACACTTCTTCATCGTGGACCGCCTGAAGTCCCTGATCAAGTACAAAGGCTACCAGGTG

GCCCCCGCCGAACTGGAAAGCATCCTGCTCCAACACCCCAACATCTTCGACGCAGGCGT

CGCAGGCCTGCCCGACGACGACGCCGGCGAACTGCCCGCCGCCGTGGTGGTGCTGGAGC

ACGGAAAGACGATGACGGAAAAAGAGATCGTGGACTACGTCGCCAGCCAAGTAACAACC

GCGAAAAAGCTGCGCGGAGGAGTGGTGTTCGTGGACGAAGTACCGAAAGGCCTGACCGG

AAAACTCGACGCAAGAAAAATCAGAGAGATCCTCATAAAGGCCAAGAAGGGCGGAAAGA

TCGCCGTGTAA
```

Example H: Reduced Impurities in a Process for ARC-mRNA

Figure 11:
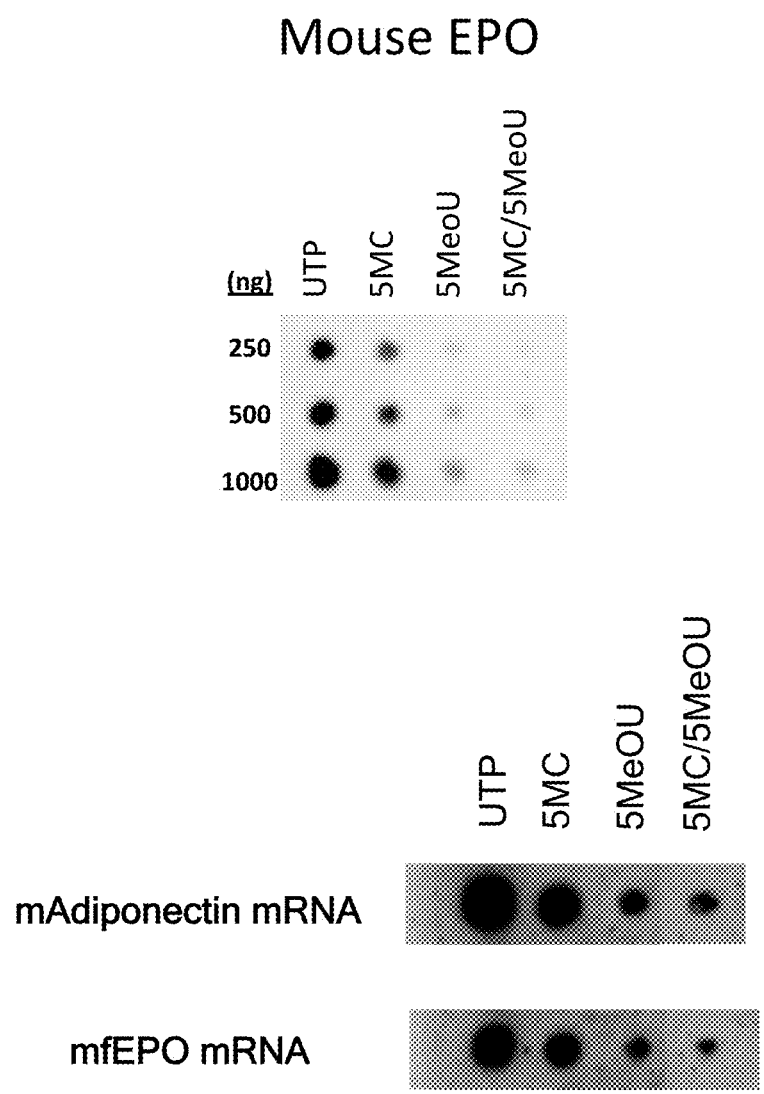
FIG. 11 shows the results of surprisingly reduced impurity levels in a process for synthesizing a mouse EPO translatable molecule of this invention.

FIG. 11 shows the results of surprisingly reduced impurity levels in a process for synthesizing a mouse EPO translatable molecule of this invention. FIG. 11 shows the results of a dot blot for detecting double strand RNA impurity in the synthesis mixture (nitro cellulose membrane, J2 antibody to detect dsRNA). The ARC-RNA (5MeOU) synthesis product, which was translatable for mouse EPO, showed surprisingly reduced dot blot intensity as compared to a wild type mRNA synthesis product, without 5MeOU, and with similarly reduced T. Under the same conditions and synthesis, the ARC-RNA (5MC/5MeOU) synthesis product, which was translatable for mouse EPO, also showed surprisingly further reduced dot blot intensity as compared to a wild type mRNA synthesis product, without 5MC/5MeOU. Thus, the ARC-RNA (5MC/5MeOU) synthesis process, with template reduced T composition, surprisingly reduced double strand RNA impurity levels in the synthesis mixture. As shown in FIG. 11, similar advantageously reduced double strand RNA impurity levels were found in synthesis mixtures for monkey mAdipo mRNA and mfEPO mRNA.

The double strand RNA impurity levels for mouse EPO for FIG. 11 are shown in Table 12.

TABLE 12

| Area density | |
|---|---|
| Mouse EPO | Area density |
| UTP | 15,674 |
| 5MC | 7,663 |

TABLE 12-continued

| Area density | |
|---|---|
| Mouse EPO | Area density |
| 5MeOU | 1,108 |
| 5MC/5MeOU | 506 |

The double strand RNA impurity levels for mfEPO for FIG. 11 are shown in Table 13.

TABLE 13

| Area density | |
|---|---|
| Mouse EPO | Area density |
| UTP | 17,874 |
| 5MC | 11,238 |
| 5MeOU | 4,801 |
| 5MC/5MeOU | 3,386 |

Example I: Reduced Immunogenicity for ARC-mRNA

Figure 12:
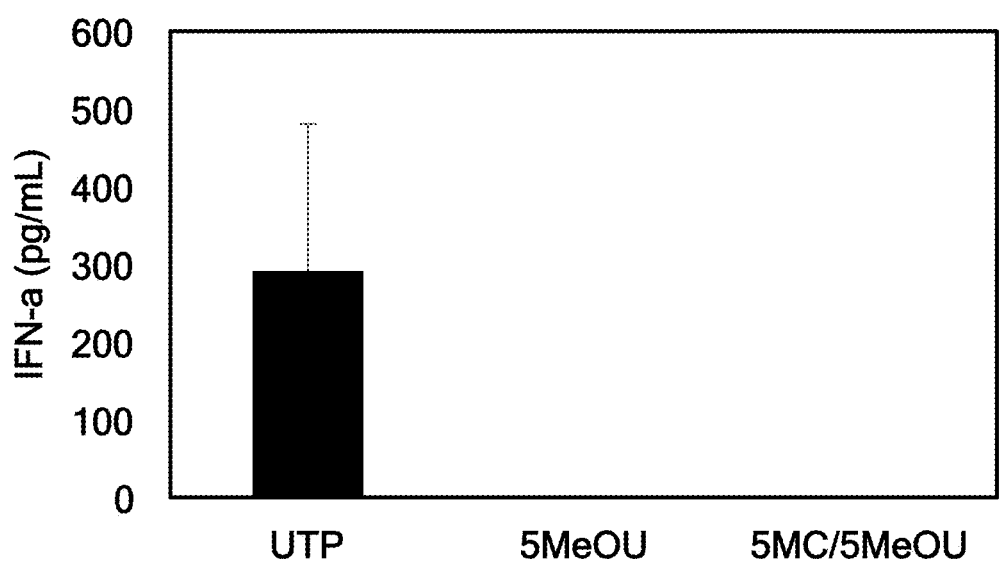
FIG. 12 shows the results of reduced immunogenicity for a translatable molecule of this invention.

FIG. 12 shows the results of reduced immunogenicity for a translatable molecule of this invention. FIG. 12 shows the results of a cytokine assay for IFN-a as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of IFN-a.

Figure 13:
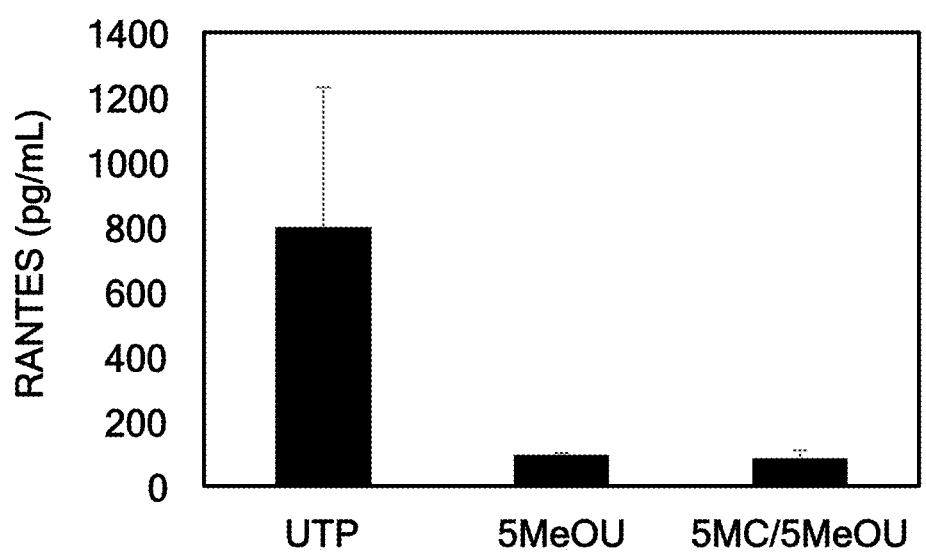
FIG. 13 shows the results of reduced immunogenicity for a translatable molecule of this invention.

FIG. 13 shows the results of reduced immunogenicity for a translatable molecule of this invention. FIG. 13 shows the results of a cytokine assay for RANTES as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of RANTES.

Figure 14:
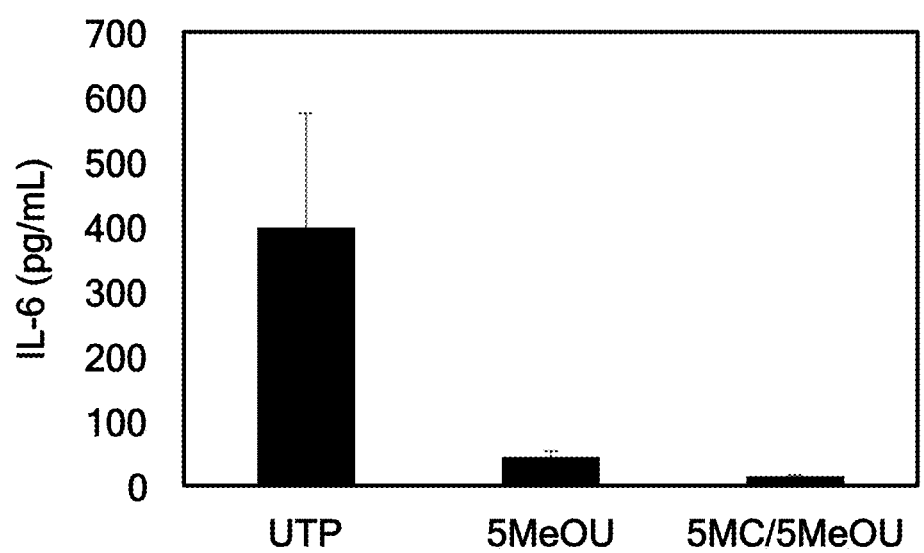
FIG. 14 shows the results of reduced immunogenicity for a translatable molecule of this invention.

FIG. 14 shows the results of reduced immunogenicity for a translatable molecule of this invention. FIG. 14 shows the results of a cytokine assay for IL-6 as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of IL-6.

Figure 15:
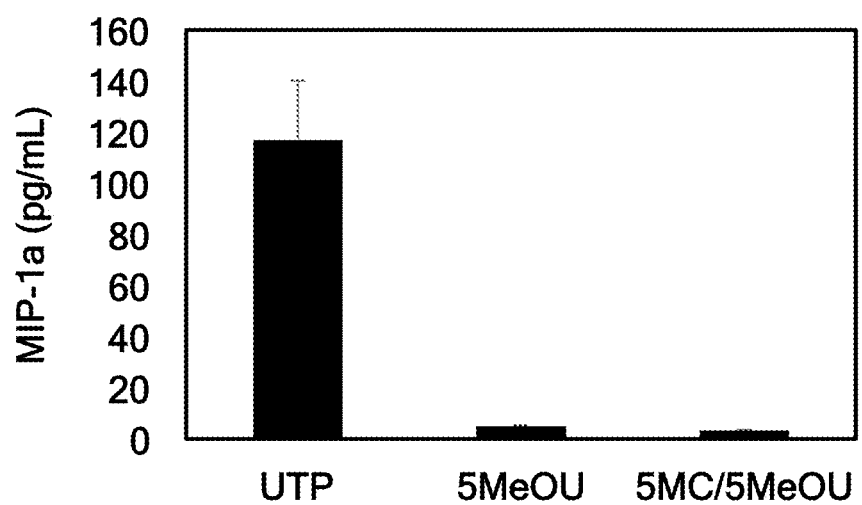
FIG. 15 shows the results of reduced immunogenicity for a translatable molecule of this invention.

FIG. 15 shows the results of reduced immunogenicity for a translatable molecule of this invention. FIG. 15 shows the results of a cytokine assay for MIP-1a as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of MIP-1a.

Example J: Enhanced Expression for ARC-mRNA

Figure 16:
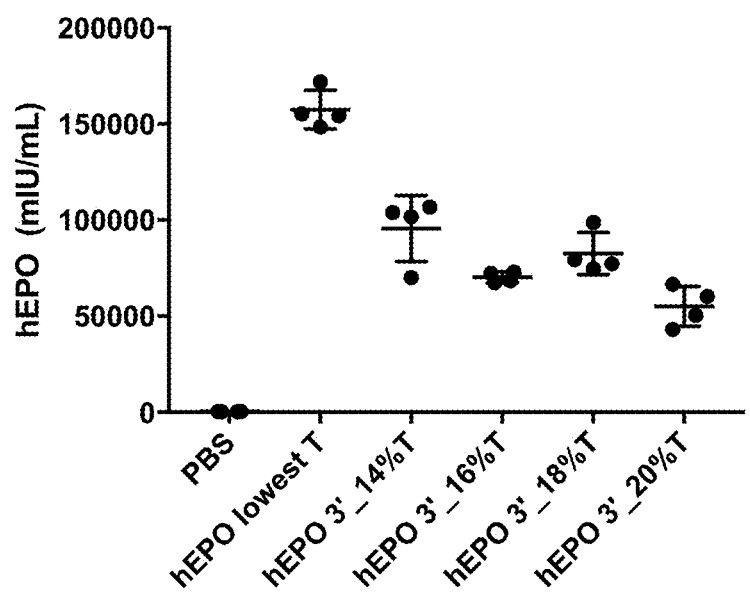
FIG. 16 shows the results of surprisingly increased human EPO protein production in vivo for a translatable molecule of this invention.

FIG. 16 shows the results of surprisingly increased human EPO protein production in vivo for a translatable molecule of this invention. FIG. 16 shows the results for hEPO protein expression after hEPO ARC-mRNA was injected into mice at 0.3 mg/kg dose. hEPO in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased about 2-fold.

Figure 17:
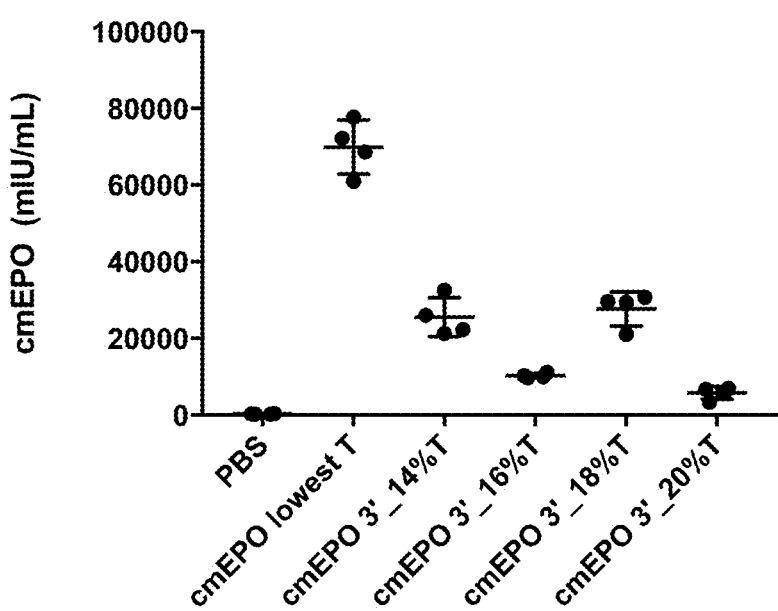
FIG. 17 shows the results of surprisingly increased cynomolgus monkey EPO protein production in vivo for a translatable molecule of this invention.

FIG. 17 shows the results of surprisingly increased cynomolgus monkey EPO protein production in vivo for a translatable molecule of this invention. FIG. 17 shows the results for cmEPO protein expression after cmEPO ARC-mRNA was injected into mice at 0.3 mg/kg dose. cmEPO in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased greater than 3-fold.

Figure 18:
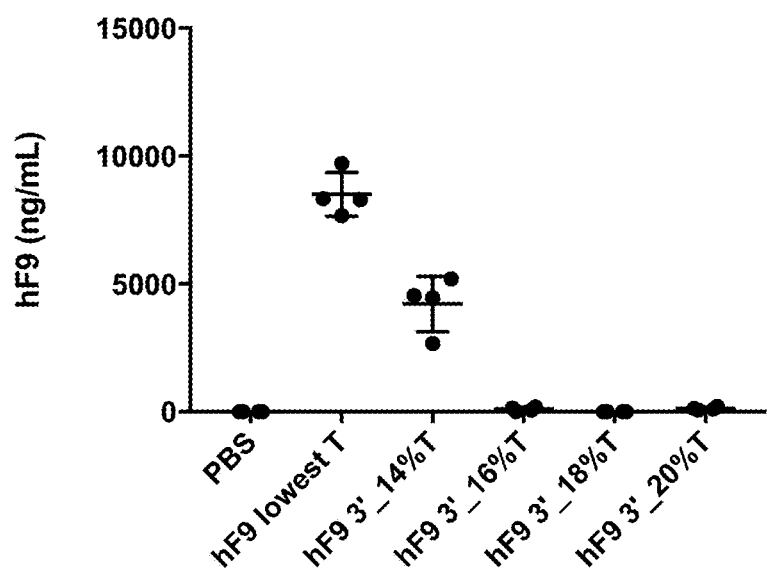
FIG. 18 shows the results of surprisingly increased human F9 protein production in vivo for a translatable molecule of this invention.

FIG. 18 shows the results of surprisingly increased human F9 protein production in vivo for a translatable molecule of this invention. FIG. 18 shows the results for hF9 protein expression after hF9 ARC-mRNA was injected into mice at 0.3 mg/kg dose. hF9 in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased about 2-fold.

Figure 19:
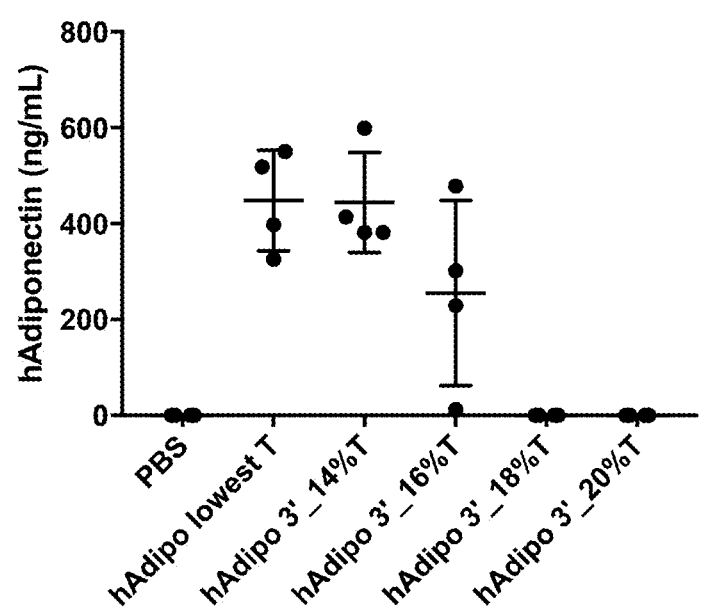
FIG. 19 shows the results of surprisingly increased human adiponectin protein production in vivo for a translatable molecule of this invention.

FIG. 19 shows the results of surprisingly increased human adiponectin protein production in vivo for a translatable molecule of this invention. FIG. 19 shows the results for hAdipo protein expression after hAdipo ARC-mRNA was injected into mice at 0.3 mg/kg dose. hAdipo in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased about 2-fold.

Figure 20:
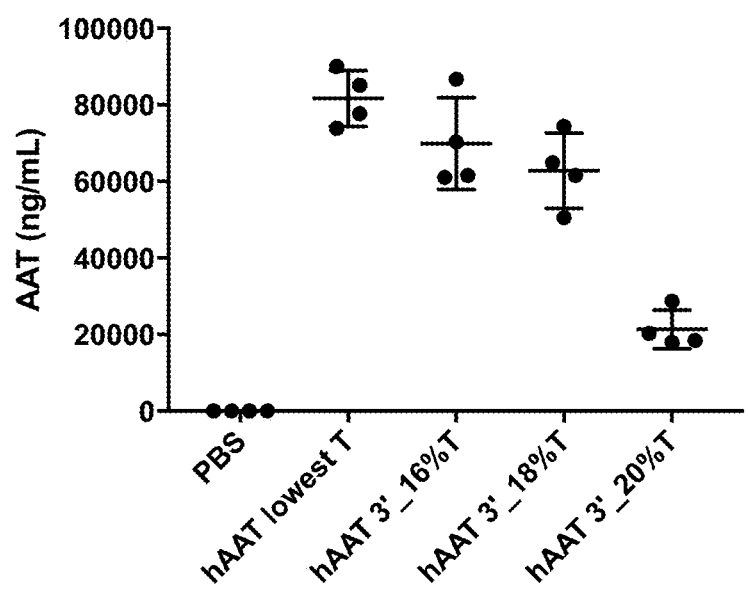
FIG. 20 shows the results of surprisingly increased human AAT protein production in vivo for a translatable molecule of this invention.

FIG. 20 shows the results of surprisingly increased human AAT protein production in vivo for a translatable molecule of this invention. FIG. 20 shows the results for hAAT protein expression after hAAT ARC-mRNA was injected into mice at 0.3 mg/kg dose. hAAT in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased up to about 4-fold.

Example K: Reduced Immunogenicity for ARC-mRNA

Figure 21:
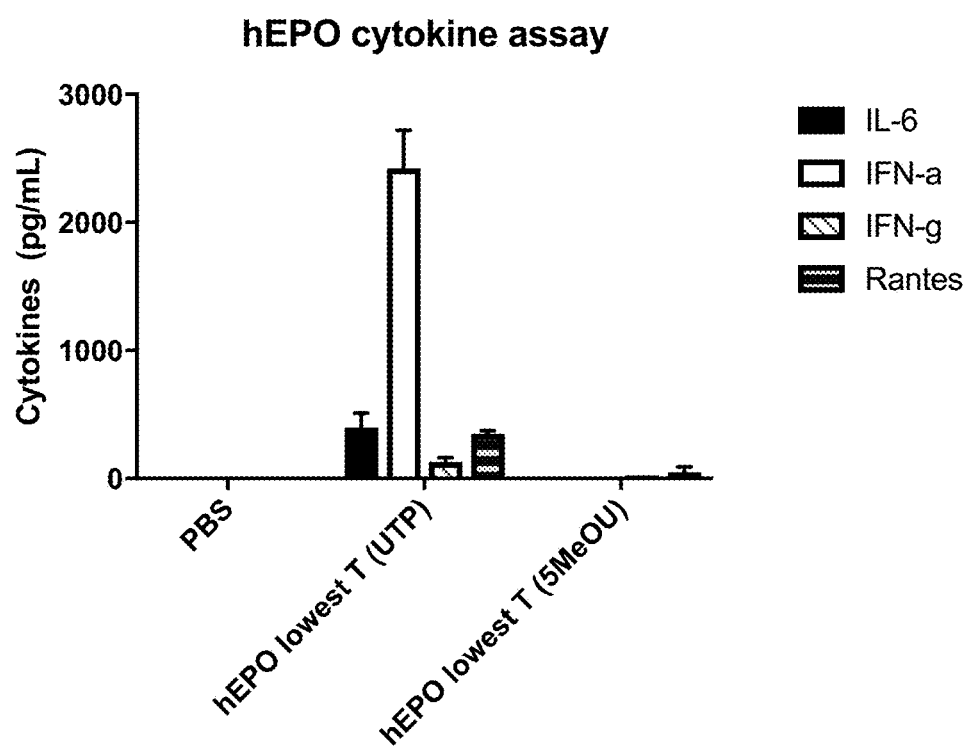
FIG. 21 shows the results of reduced immunogenicity for a translatable molecule of this invention in vivo.

FIG. 21 shows the results of reduced immunogenicity for a translatable molecule of this invention in vivo. FIG. 21 shows the results of a cytokine assay as generated in mouse using an hEPO ARC-RNA (5MeOU) of this invention, detected in serum 6 hrs post injection. The ARC-RNAs synthesized with 5MeOU and a reduced T composition template showed markedly reduced immunogenicity as compared to a synthetic mRNA with the same sequence and containing only natural nucleotides. The hEPO ARC-RNA (5MeOU) did not stimulate cytokine responses in vivo as compared to the UTP control.

All publications, patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprise," "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limiting of the remainder of the disclosure in any way.

All of the features disclosed in this specification may be combined in any combination. Each feature disclosed in this specification may be replaced by an alternative feature serving the same, equivalent, or similar purpose.

What is claimed is:

1. A composition comprising a modified messenger RNA (mRNA), wherein
   i. the modified mRNA comprises a coding region of a wild-type mRNA that is expressible, wherein
      a. one or more codons of the coding region have been replaced such that the occurrence of uridine monomers in the coding region is reduced by at least 20% as compared to the coding region of the wild-type mRNA; and
      b. the modified mRNA encodes a polypeptide or protein having at least 75% identity to a target polypeptide or protein of interest; and
   ii. the modified mRNA contains one or more 5-methoxyuridines,
wherein the composition comprises an at least three-fold lower level of double stranded RNA as compared to a composition comprising an mRNA having the same coding region sequence with a similarly reduced occurrence of uridine monomers in the coding region as the modified mRNA and lacking 5-methoxyuridine, and
wherein the composition is a synthesis mixture comprising about 0.01 μg/μl to 0.02 μg/μl of template DNA encoding the modified mRNA.

2. The composition of claim 1, wherein 10-100% of the uridine monomers in the modified mRNA are 5-methoxyuridines, or wherein 50-80% of the uridine monomers in the modified mRNA are 5-methoxyuridines.

3. The composition of claim 1, wherein the modified mRNA contains one or more 5-methylcytidines.

4. The composition of claim 1, wherein 10-100% of the cytidines in the modified mRNA are 5-methylcytidines.

5. The composition of claim 1, wherein one or more codons of the coding region have been replaced such that the occurrence of uridine monomers in the coding region of the modified mRNA is reduced by at least 35% as compared to the coding region of the wild-type mRNA.

6. The composition of claim 1, wherein the uridine monomers are replaced beginning from the 5' end of the coding region, or beginning from the 3' end of the coding region, or randomly throughout the coding region.

7. The composition of claim 1, wherein the modified mRNA is selected from SEQ ID NOs: 35-47, 76-88, 110-119, and 147-159, wherein one or more of the uridines are 5-methoxyuridines.

8. The composition of claim 1, wherein the modified mRNA encodes a polypeptide or protein having at least 85% identity to the target polypeptide or protein of interest.

9. The composition of claim 1, wherein the modified mRNA comprises a 5' cap, a 5' untranslated region, a coding region, a 3' untranslated region, and a tail region.

10. The composition of claim 1, wherein the modified mRNA comprises a translation enhancer in a 5' or 3' untranslated region.

11. The composition of claim 1, wherein the modified mRNA is translatable in vitro, ex vivo, or in vivo.

12. The composition of claim 1, wherein the modified mRNA comprises from 50 to 15,000 nucleotides.

13. The composition of claim 1, wherein the target polypeptide or protein of interest is a polypeptide, a protein, a protein fragment, an antibody, an antibody fragment, a vaccine immunogen, or a vaccine toxoid.

14. The composition of claim 1, wherein the modified mRNA has at least 2-fold increased translation efficiency in vivo as compared to a native mRNA that expresses the target polypeptide or protein of interest.

15. The composition of claim 1, wherein the modified mRNA has at least 5-fold reduced immunogenicity as compared to a native mRNA that expresses the target polypeptide or protein of interest.

16. The composition of claim 1, wherein the target polypeptide or protein of interest is an expression product, or a fragment thereof, of a gene selected from EPO, AAT, ADIPOQ, F9, TTR, and BIRC5.

17. A composition comprising a DNA template encoding a modified mRNA, wherein i. the modified mRNA comprises a coding region of a wild-type mRNA that is expressible, wherein
        a. one or more codons of the coding region have been replaced such that the occurrence of uridine monomers in the coding region is reduced by at least 20% as compared to the coding region of the wild-type mRNA; and
        b. the modified mRNA encodes a polypeptide or protein having at least 75% identity to a target polypeptide or protein of interest; and
    ii. the modified mRNA contains one or more 5-methoxyuridines, wherein the composition comprises an at least three-fold lower level of double stranded RNA as compared to a composition comprising an mRNA having the same coding region sequence with a similarly reduced occurrence of uridine monomers in the coding region as the modified mRNA and lacking 5-methoxyuridine, and wherein the composition is a synthesis mixture comprising about 0.01 μg/μl to 0.02 μg/μl of the template DNA encoding the modified mRNA.

18. The composition of claim 1, wherein the synthesis mixture comprises about 0.01 μg/μl or about 0.02 μg/μl of template DNA encoding the modified mRNA.

19. The composition of claim 1, wherein the synthesis mixture is an in vitro transcription (IVT) reaction.

* * * * *

SEQUENCE LISTING

```
<160> NUMBER OF SEQ ID NOS: 192

<210> SEQ ID NO 1
<211> LENGTH: 9
<212> TYPE: RNA
<213> ORGANISM: Unknown
<220> FEATURE:
<223> OTHER INFORMATION: Description of Unknown:
      Translatable molecule peptide

<400> SEQUENCE: 1 auaagugaa                                                                  9

<210> SEQ ID NO 2
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgacactgct cgatccgctc gcaccgggct ggcaagccac gtttggtgtt ggaccctcgt         60
acagaagcta atacgactca ctata                                               85

<210> SEQ ID NO 3
<211> LENGTH: 143
<212> TYPE: DNA
<213> ORGANISM: Tobacco etch virus

<400> SEQUENCE: 3
aggaaactta agtcaacaca acatatacaa aacaaacgaa tctcaagcaa tcaagcattc         60
tacttctatt gcagcaattt aaatcatttc ttttaaagca aaagcaattt tctgaaaatt        120
ttcaccattt acgaacgata gcc                                                143

<210> SEQ ID NO 4
<211> LENGTH: 582
<212> TYPE: DNA
<213> ORGANISM: Homo sapiens

<400> SEQUENCE: 4 atggggtgc acgaatgtcc tgcctggctg tggcttctcc tgtccctgct gtcgctccct          60
ctgggcctcc cagtcctggg cgccccacca cgcctcatct gtgacagccg agtcctggag        120
aggtacctct tggaggccaa ggaggccgag aatatcacga cgggctgtgc tgaacactgc        180
agcttgaatg agaatatcac tgtcccagac accaaagtta atttctatgc ctggaagagg        240
atggaggtcg ggcagcaggc cgtagaagtc tggcagggcc tggccctgct gtcggaagct        300
gtcctgcggg gccaggccct gttggtcaac tcttcccagc cgtgggagcc cctgcagctg        360
catgtggata aagccgtcag tggccttcgc agcctcacca ctctgcttcg ggctctggga        420
gcccagaagg aagccatctc ccctccagat gcggcctcag ctgctccact ccgaacaatc        480
actgctgaca ctttccgcaa actcttccga gtctactcca atttcctccg gggaaagctg        540
aagctgtaca caggggaggc ctgcaggaca ggggacagat ga                           582

<210> SEQ ID NO 5
<211> LENGTH: 178
<212> TYPE: DNA
```

<213> ORGANISM: Xenopus sp.

<400> SEQUENCE: 5

```
ataagtgaac tcgagctagt gactgactag gatctggtta ccactaaacc agcctcaaga    60
acacccgaat ggagtctcta agctacataa taccaactta cacttacaaa atgttgtccc   120
ccaaaatgta gccattcgta tctgctccta ataaaaagaa agtttcttca cattctag    178
```

<210> SEQ ID NO 6
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aaaaaaaaaa   120
```

<210> SEQ ID NO 7
<211> LENGTH: 118
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
gaagagcgct agcgtcttca gctgcacata accccttggg gcctctaaac gggtcttgag    60
gggttttttg cctctgacac atgcagctcc cggggatcga cgagagcagc gcgactgg    118
```

<210> SEQ ID NO 8
<211> LENGTH: 582
<212> TYPE: DNA
<213> ORGANISM: Homo sapiens

<400> SEQUENCE: 8

```
atgggggtgc acgaatgtcc tgcctggctg tggcttctcc tgtccctgct gtcgctccct    60
ctgggcctcc cagtcctggg cgccccacca cgcctcatct gtgacagccg agtcctggag   120
aggtacctct tggaggccaa ggaggccgag aatatcacga cgggctgtgc tgaacactgc   180
agcttgaatg agaatatcac tgtcccagac accaaagtta atttctatgc ctggaagagg   240
atggaggtcg ggcagcaggc cgtagaagtc tggcagggcc tggccctgct gtcggaagct   300
gtcctgcggg gccaggccct gttggtcaac tcttcccagc cgtgggagcc cctgcagctg   360
catgtggata agccgtcag tggccttcgc agcctcacca ctctgcttcg ggctctggga   420
gcccagaagg aagccatctc ccctccagat gcggcctcag ctgctccact ccgaacaatc   480
actgctgaca ctttccgcaa actcttccga gtctactcca atttcctccg gggaaagctg   540
aagctgtaca caggggaggc ctgcaggaca ggggacagat ga                      582
```

<210> SEQ ID NO 9
<211> LENGTH: 582
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

-continued

```
atggggtgc acgaatgccc cgcctggctg tggctgctcc tgagcctgct gagcctcccc    60
ctgggcctcc cagtcctggg cgccccacca cgcctcatct gcgacagccg agtcctggag   120
aggtacctcc tggaggccaa ggaggccgag aacatcacga cgggctgcgc cgaacactgc   180
agcctgaacg agaacatcac cgtcccagac accaaagtga acttctacgc ctggaagagg   240
atggaggtcg ggcagcaggc cgtagaagtc tggcagggcc tggccctgct gagcgaagcc   300
gtcctgcggg gccaggccct gctggtcaac agcagccagc cgtgggagcc cctgcagctg   360
cacgtggaca aagccgtcag cggcctgcgc agcctcacca ccctgctgcg ggccctggga   420
gcccagaagg aagccatcag ccccccagac gcggccagcg ccgccccact ccgaacaatc   480
accgccgaca ccttccgcaa actcttccga gtctacagca acttcctccg gggaaagctg   540
aagctgtaca caggggaggc ctgcaggaca ggggacagat ga                     582
```

<210> SEQ ID NO 10
<211> LENGTH: 582
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
atggggtgc acgaatgtcc tgcctggctg tggcttctcc tgtccctgct gtcgctcccc    60
ctgggcctcc cagtcctggg cgccccacca cgcctcatct gcgacagccg agtcctggag   120
aggtacctcc tggaggccaa ggaggccgag aacatcacga cgggctgcgc cgaacactgc   180
agcctgaacg agaacatcac cgtcccagac accaaagtga acttctacgc ctggaagagg   240
atggaggtcg ggcagcaggc cgtagaagtc tggcagggcc tggccctgct gagcgaagcc   300
gtcctgcggg gccaggccct gctggtcaac agcagccagc cgtgggagcc cctgcagctg   360
cacgtggaca aagccgtcag cggcctgcgc agcctcacca ccctgctgcg ggccctggga   420
gcccagaagg aagccatcag ccccccagac gcggccagcg ccgccccact ccgaacaatc   480
accgccgaca ccttccgcaa actcttccga gtctacagca acttcctccg gggaaagctg   540
aagctgtaca caggggaggc ctgcaggaca ggggacagat ga                     582
```

<210> SEQ ID NO 11
<211> LENGTH: 582
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
atggggtgc acgaatgtcc tgcctggctg tggcttctcc tgtccctgct gtcgctccct    60
ctgggcctcc cagtcctggg cgccccacca cgcctcatct gtgacagccg agtcctggag   120
aggtacctct tggaggccaa ggaggccgag aatatcacga cgggctgtgc tgaacactgc   180
agcttgaatg agaatatcac tgtcccagac accaaagtta atttctacgc ctggaagagg   240
atggaggtcg ggcagcaggc cgtagaagtc tggcagggcc tggccctgct gagcgaagcc   300
gtcctgcggg gccaggccct gctggtcaac agcagccagc cgtgggagcc cctgcagctg   360
cacgtggaca aagccgtcag cggcctgcgc agcctcacca ccctgctgcg ggccctggga   420
gcccagaagg aagccatcag ccccccagac gcggccagcg ccgccccact ccgaacaatc   480
accgccgaca ccttccgcaa actcttccga gtctacagca acttcctccg gggaaagctg   540
```

```
aagctgtaca cagggaggc ctgcaggaca ggggacagat ga              582
```

<210> SEQ ID NO 12
<211> LENGTH: 582
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
atggggtgc acgaatgtcc tgcctggctg tggcttctcc tgtccctgct gtcgctccct    60
ctgggcctcc cagtcctggg cgccccacca cgcctcatct gtgacagccg agtcctggag   120
aggtacctct tggaggccaa ggaggccgag aatatcacga cgggctgtgc tgaacactgc   180
agcttgaatg agaatatcac tgtcccagac accaaagtta atttctatgc ctggaagagg   240
atggaggtcg ggcagcaggc cgtagaagtc tggcagggcc tggccctgct gtcggaagct   300
gtcctgcggg gccaggccct gttggtcaac tcttcccagc cgtgggagcc cctgcagctg   360
catgtggata aagccgtcag tggccttcgc agcctcacca ccctgctgcg ggccctggga   420
gcccagaagg aagccatcag ccccccagac gcggccagcg ccgccccact ccgaacaatc   480
accgccgaca ccttccgcaa actcttccga gtctacagca acttcctccg ggaaagctg    540
aagctgtaca caggggaggc ctgcaggaca ggggacagat ga                      582
```

<210> SEQ ID NO 13
<211> LENGTH: 582
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
atggggtgc acgaatgtcc tgcctggctg tggcttctcc tgtccctgct gtcgctccct    60
ctgggcctcc cagtcctggg cgccccacca cgcctcatct gtgacagccg agtcctggag   120
aggtacctct tggaggccaa ggaggccgag aatatcacga cgggctgtgc tgaacactgc   180
agcttgaatg agaatatcac tgtcccagac accaaagtta atttctatgc ctggaagagg   240
atggaggtcg ggcagcaggc cgtagaagtc tggcagggcc tggccctgct gtcggaagct   300
gtcctgcggg gccaggccct gttggtcaac tcttcccagc cgtgggagcc cctgcagctg   360
catgtggata aagccgtcag tggccttcgc agcctcacca ctctgctcg ggctctggga    420
gcccagaagg aagccatctc ccctccagat gcggcctcag ctgctccact ccgaacaatc   480
actgctgaca ctttccgcaa actcttccga gtctacagca acttcctccg ggaaagctg    540
aagctgtaca caggggaggc ctgcaggaca ggggacagat ga                      582
```

<210> SEQ ID NO 14
<211> LENGTH: 582
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
atggggtgc acgaatgccc cgcctggctg tggctgctcc tgagcctgct gagcctcccc    60
ctgggcctcc cagtcctggg cgccccacca cgcctcatct gcgacagccg agtcctggag   120
```

| | |
|---|---|
| aggtacctcc tggaggccaa ggaggccgag aacatcacga cgggctgcgc cgaacactgc | 180 |
| agcctgaacg agaacatcac cgtcccagac accaaagtga acttctacgc ctggaagagg | 240 |
| atggaggtcg ggcagcaggc cgtagaagtc tggcagggcc tggccctgct gagcgaagcc | 300 |
| gtcctgcggg gccaggccct gctggtcaac agcagccagc cgtgggagcc cctgcagctg | 360 |
| cacgtggaca aagccgtcag cggcctgcgc agcctcacca ccctgctgcg ggccctggga | 420 |
| gcccagaagg aagccatcag ccccccagac gcggccagcg ccgccccact ccgaacaatc | 480 |
| actgctgaca ctttccgcaa actcttccga gtctactcca atttcctccg gggaaagctg | 540 |
| aagctgtaca caggggaggc ctgcaggaca ggggacagat ga | 582 |

<210> SEQ ID NO 15
<211> LENGTH: 582
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

| | |
|---|---|
| atgggggtgc acgaatgccc cgcctggctg tggctgctcc tgagcctgct gagcctcccc | 60 |
| ctgggcctcc cagtcctggg cgccccacca cgcctcatct gcgacagccg agtcctggag | 120 |
| aggtacctcc tggaggccaa ggaggccgag aacatcacga cgggctgcgc cgaacactgc | 180 |
| agcctgaacg agaacatcac cgtcccagac accaaagtga acttctacgc ctggaagagg | 240 |
| atggaggtcg ggcagcaggc cgtagaagtc tggcagggcc tggccctgct gagcgaagcc | 300 |
| gtcctgcggg gccaggccct gctggtcaac agcagccagc cgtgggagcc cctgcagctg | 360 |
| cacgtggata aagccgtcag tggccttcgc agcctcacca ctctgcttcg ggctctggga | 420 |
| gcccagaagg aagccatctc ccctccagat gcggcctcag ctgctccact ccgaacaatc | 480 |
| actgctgaca ctttccgcaa actcttccga gtctactcca atttcctccg gggaaagctg | 540 |
| aagctgtaca caggggaggc ctgcaggaca ggggacagat ga | 582 |

<210> SEQ ID NO 16
<211> LENGTH: 582
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

| | |
|---|---|
| atgggggtgc acgaatgccc cgcctggctg tggctgctcc tgagcctgct gagcctcccc | 60 |
| ctgggcctcc cagtcctggg cgccccacca cgcctcatct gcgacagccg agtcctggag | 120 |
| aggtacctcc tggaggccaa ggaggccgag aacatcacga cgggctgcgc cgaacactgc | 180 |
| agcctgaacg agaacatcac tgtcccagac accaaagtta atttctatgc ctggaagagg | 240 |
| atggaggtcg ggcagcaggc cgtagaagtc tggcagggcc tggccctgct gtcggaagct | 300 |
| gtcctgcggg gccaggccct gttggtcaac tcttcccagc cgtgggagcc cctgcagctg | 360 |
| catgtggata aagccgtcag tggccttcgc agcctcacca ctctgcttcg ggctctggga | 420 |
| gcccagaagg aagccatctc ccctccagat gcggcctcag ctgctccact ccgaacaatc | 480 |
| actgctgaca ctttccgcaa actcttccga gtctactcca atttcctccg gggaaagctg | 540 |
| aagctgtaca caggggaggc ctgcaggaca ggggacagat ga | 582 |

<210> SEQ ID NO 17
<211> LENGTH: 582
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atgggggtgc acgaatgccc cgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacga cgggctgtgc tgaacactgc     180
agcttgaatg agaatatcac tgtcccagac accaaagtta atttctatgc ctggaagagg     240
atggaggtcg ggcagcaggc cgtagaagtc tggcagggcc tggccctgct gtcggaagct     300
gtcctgcggg gccaggccct gttggtcaac tcttcccagc cgtgggagcc cctgcagctg     360
catgtggata aagccgtcag tggccttcgc agcctcacca ctctgcttcg ggctctggga     420
gcccagaagg aagccatctc ccctccagat gcggcctcag ctgctccact ccgaacaatc     480
actgctgaca ctttccgcaa actcttccga gtctactcca atttcctccg gggaaagctg     540
aagctgtaca caggggaggc ctgcaggaca ggggacagat ga                        582

<210> SEQ ID NO 18
<211> LENGTH: 582
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atgggggtgc acgaatgccc tgcctggctg tggctgctcc tgagcctgct gagcctcccc      60
ctgggcctcc cagtcctggg cgccccacca cgcctcatct gcgacagccg agtcctggag     120
aggtacctcc tggaggccaa ggaggccgag aacatcacga cgggctgcgc cgaacactgc     180
agcttgaacg agaacatcac cgtcccagac accaaagtga acttctacgc ctggaagagg     240
atggaggtcg ggcagcaggc cgtagaagtc tggcagggcc tggccctgct gagcgaagcc     300
gtcctgcggg gccaggccct gctggtcaac agctcccagc cgtgggagcc cctgcagctg     360
cacgtggaca aagccgtcag cggcctgcgc agcctcacca ccctgctgcg ggccctggga     420
gcccagaagg aagccatcag ccccccagac gcggccagcg ccgccccact ccgaacaatc     480
accgctgaca ccttccgcaa actcttccga gtctactcca acttcctccg gggaaagctg     540
aagctgtaca caggggaggc ctgcaggaca ggggacagat ga                        582

<210> SEQ ID NO 19
<211> LENGTH: 582
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atgggggtgc acgaatgtcc cgcctggctg tggctgctcc tgagcctgct gagcctccct      60
ctgggcctcc cagtcctggg cgccccacca cgcctcatct gcgacagccg agtcctggag     120
aggtacctcc tggaggccaa ggaggccgag aatatcacga cgggctgtgc cgaacactgc     180

-continued

```
agcttgaacg agaatatcac cgtcccagac accaaagtta atttctatgc ctggaagagg      240
atggaggtcg ggcagcaggc cgtagaagtc tggcagggcc tggccctgct gtcggaagct      300
gtcctgcggg gccaggccct gctggtcaac agcagccagc cgtgggagcc cctgcagctg      360
cacgtggata aagccgtcag cggcctgcgc agcctcacca ccctgctgcg ggctctggga      420
gcccagaagg aagccatcag ccctccagat gcggccagcg ccgctccact ccgaacaatc      480
accgccgaca ctttccgcaa actcttccga gtctacagca acttcctccg gggaaagctg      540
aagctgtaca caggggaggc ctgcaggaca ggggacagat ga                         582
```

<210> SEQ ID NO 20
<211> LENGTH: 582
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
atgggggtgc acgaatgtcc tgcctggctg tggcttctcc tgtccctgct gagcctccct      60
ctgggcctcc cagtcctggg cgccccacca cgcctcatct gtgacagccg agtcctggag     120
aggtacctct tggaggccaa ggaggccgag aacatcacga cgggctgcgc tgaacactgc     180
agcctgaatg agaatatcac tgtcccagac accaaagtga atttctatgc ctggaagagg     240
atggaggtcg ggcagcaggc cgtagaagtc tggcagggcc tggccctgct gagcgaagcc     300
gtcctgcggg gccaggccct gttggtcaac agcagccagc cgtgggagcc cctgcagctg     360
catgtggata aagccgtcag tggccttcgc agcctcacca ctctgcttcg ggccctggga     420
gcccagaagg aagccatctc ccctccagac gcggcctcag ctgccccact ccgaacaatc     480
actgctgaca ctttccgcaa actcttccga gtctacagca atttcctccg gggaaagctg     540
aagctgtaca caggggaggc ctgcaggaca ggggacagat ga                        582
```

<210> SEQ ID NO 21
<211> LENGTH: 582
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
atgggggtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacga cgggctgtgc tgaacactgc     180
agcttgaatg agaatatcac tgtcccagac accaaagtta acttctatgc ctggaagagg     240
atggaggtcg ggcagcaggc cgtagaagtc tggcagggcc tggccctgct gtcggaagct     300
gtcctgcggg gccaggccct gctggtcaac tcttcccagc cgtgggagcc cctgcagctg     360
catgtggata aagccgtcag tggccttcgc agcctcacca ctctgcttcg ggctctggga     420
gcccagaagg aagccatctc ccctccagat gcggcctcag ctgctccact ccgaacaatc     480
actgctgaca ctttccgcaa actcttccga gtctactcca atttcctccg gggaaagctg     540
aagctgtaca caggggaggc ctgcaggaca ggggacagat ga                        582
```

<210> SEQ ID NO 22
<211> LENGTH: 1014

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
aggaaactta agtcaacaca acatatacaa aacaaacgaa tctcaagcaa tcaagcattc        60
tacttctatt gcagcaattt aaatcatttc ttttaaagca aaagcaattt tctgaaaatt       120
ttcaccattt acgaacgata gccatggggg tgcacgaatg ccccgcctgg ctgtggctgc       180
tcctgagcct gctgagcctc ccctgggcc tcccagtcct gggcgcccca ccacgcctca        240
tctgcgacag ccgagtcctg gagaggtacc tcctggaggc caaggaggcc gagaacatca       300
cgacgggctg cgccgaacac tgcagcctga acgagaacat caccgtccca gacaccaaag       360
tgaacttcta cgcctggaag aggatggagg tcggcagca ggccgtagaa gtctggcagg        420
gcctggccct gctgagcgaa gccgtcctgc ggggccaggc cctgctggtc aacagcagcc       480
agccgtggga gccctgcag ctgcacgtgg acaaagccgt cagcggcctg cgcagcctca        540
ccaccctgct gcgggccctg ggagcccaga aggaagccat cagcccccca gacgcggcca       600
gcgccgcccc actccgaaca atcaccgccg acaccttccg caaactcttc cgagtctaca       660
gcaacttcct ccggggaaag ctgaagctgt acacagggga ggcctgcagg acaggggaca       720
gatgactcga gctagtgact gactaggatc tggttaccac taaaccagcc tcaagaacac       780
ccgaatggag tctctaagct acataatacc aacttacact tacaaaatgt tgtcccccaa       840
aatgtagcca ttcgtatctg ctcctaataa aagaaagtt tcttcacatt ctagaaaaaa        900
aaaaaaaaaa aaaaaaaaaa aaaaaaaaaa aaaaaaaaaa aaaaaaaaaa aaaaaaaaaa       960
aaaaaaaaaa aaaaaaaaaa aaaaaaaaaa aaaaaaaaaa aaaaaaaaaa aaaa            1014

<210> SEQ ID NO 23
<211> LENGTH: 1014
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
aggaaactta agtcaacaca acatatacaa aacaaacgaa tctcaagcaa tcaagcattc        60
tacttctatt gcagcaattt aaatcatttc ttttaaagca aaagcaattt tctgaaaatt       120
ttcaccattt acgaacgata gccatggggg tgcacgaatg tcctgcctgg ctgtggcttc       180
tcctgtccct gctgtcgctc ccctgggcc tcccagtcct gggcgcccca ccacgcctca        240
tctgcgacag ccgagtcctg gagaggtacc tcctggaggc caaggaggcc gagaacatca       300
cgacgggctg cgccgaacac tgcagcctga acgagaacat caccgtccca gacaccaaag       360
tgaacttcta cgcctggaag aggatggagg tcgggcagca ggccgtagaa gtctggcagg      420
gcctggccct gctgagcgaa gccgtcctgc ggggccaggc cctgctggtc aacagcagcc       480
agccgtggga gccctgcag ctgcacgtgg acaaagccgt cagcggcctg cgcagcctca        540
ccaccctgct gcgggccctg ggagcccaga aggaagccat cagcccccca gacgcggcca       600
gcgccgcccc actccgaaca atcaccgccg acaccttccg caaactcttc cgagtctaca       660
gcaacttcct ccggggaaag ctgaagctgt acacagggga ggcctgcagg acaggggaca       720
gatgactcga gctagtgact gactaggatc tggttaccac taaaccagcc tcaagaacac       780
```

| | |
|---|---|
| ccgaatggag tctctaagct acataatacc aacttacact tacaaaatgt tgtcccccaa | 840 |
| aatgtagcca ttcgtatctg ctcctaataa aagaaagtt tcttcacatt ctagaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaa | 1014 |

<210> SEQ ID NO 24
<211> LENGTH: 1014
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

| | |
|---|---|
| aggaaactta agtcaacaca acatatacaa aacaaacgaa tctcaagcaa tcaagcattc | 60 |
| tacttctatt gcagcaattt aaatcatttc ttttaaagca aaagcaattt tctgaaaatt | 120 |
| ttcaccattt acgaacgata gccatggggg tgcacgaatg tcctgcctgg ctgtggcttc | 180 |
| tcctgtccct gctgtcgctc cctctgggcc tcccagtcct gggcgcccca ccacgcctca | 240 |
| tctgtgacag ccgagtcctg gagaggtacc tcttggaggc caaggaggcc gagaatatca | 300 |
| cgacgggctg tgctgaacac tgcagcttga atgagaatat cactgtccca gacaccaaag | 360 |
| ttaatttcta cgcctggaag aggatggagg tcgggcagca ggccgtagaa gtctggcagg | 420 |
| gcctggccct gctgagcgaa gccgtcctgc ggggccaggc cctgctggtc aacagcagcc | 480 |
| agccgtggga gccctgcag ctgcacgtgg acaaagccgt cagcggcctg cgcagcctca | 540 |
| ccaccctgct gcgggccctg ggagcccaga aggaagccat cagcccccca gacgcggcca | 600 |
| gcgccgcccc actccgaaca atcaccgccg acaccttccg caaactcttc cgagtctaca | 660 |
| gcaacttcct ccggggaaag ctgaagctgt acacagggga ggcctgcagg caggggaca | 720 |
| gatgactcga gctagtgact gactaggatc tggttaccac taaaccagcc tcaagaacac | 780 |
| ccgaatggag tctctaagct acataatacc aacttacact tacaaaatgt tgtcccccaa | 840 |
| aatgtagcca ttcgtatctg ctcctaataa aagaaagtt tcttcacatt ctagaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaa | 1014 |

<210> SEQ ID NO 25
<211> LENGTH: 1014
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

| | |
|---|---|
| aggaaactta agtcaacaca acatatacaa aacaaacgaa tctcaagcaa tcaagcattc | 60 |
| tacttctatt gcagcaattt aaatcatttc ttttaaagca aaagcaattt tctgaaaatt | 120 |
| ttcaccattt acgaacgata gccatggggg tgcacgaatg tcctgcctgg ctgtggcttc | 180 |
| tcctgtccct gctgtcgctc cctctgggcc tcccagtcct gggcgcccca ccacgcctca | 240 |
| tctgtgacag ccgagtcctg gagaggtacc tcttggaggc caaggaggcc gagaatatca | 300 |
| cgacgggctg tgctgaacac tgcagcttga atgagaatat cactgtccca gacaccaaag | 360 |
| ttaatttcta tgcctggaag aggatggagg tcgggcagca ggccgtagaa gtctggcagg | 420 |
| gcctggccct gctgtcggaa gctgtcctgc ggggccaggc cctgttggtc aactcttccc | 480 |

```
agccgtggga gcccctgcag ctgcatgtgg ataaagccgt cagtggcctt cgcagcctca      540
ccaccctgct gcgggccctg ggagcccaga aggaagccat cagcccccca gacgcggcca      600
gcgccgcccc actccgaaca atcaccgccg acaccttccg caaactcttc cgagtctaca      660
gcaacttcct ccggggaaag ctgaagctgt acacagggga ggcctgcagg acagggggaca     720 gatgactcga gctagtgact gactaggatc tggttaccac taaaccagcc tcaagaacac      780
ccgaatggag tctctaagct acataatacc aacttacact tacaaaatgt tgtcccccaa      840
aatgtagcca ttcgtatctg ctcctaataa aagaaagtt tcttcacatt ctagaaaaaa       900
aaaaaaaaaa aaaaaaaaaa aaaaaaaaaa aaaaaaaaaa aaaaaaaaaa aaaaaaaaaa      960
aaaaaaaaaa aaaaaaaaaa aaaaaaaaaa aaaaaaaaaa aaaaaaaaaa aaaa           1014
```

<210> SEQ ID NO 26
<211> LENGTH: 1014
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
aggaaactta agtcaacaca acatatacaa acaaacgaa tctcaagcaa tcaagcattc        60
tacttctatt gcagcaattt aaatcatttc ttttaaagca aaagcaattt tctgaaaatt      120
ttcaccattt acgaacgata gccatggggg tgcacgaatg tcctgcctgg ctgtggcttc      180
tcctgtccct gctgtcgctc cctctgggcc tccagtcct gggcgccca ccacgcctca       240 tctgtgacag ccgagtcctg gagaggtacc tcttggaggc caaggaggcc gagaatatca      300
cgacgggctg tgctgaacac tgcagcttga atgagaatat cactgtccca gacaccaaag      360
ttaatttcta tgcctggaag aggatggagg tcgggcagca ggccgtagaa gtctggcagg      420
gcctggccct gctgtcggaa gctgtcctgc ggggccaggc cctgttggtc aactcttccc      480
agccgtggga gcccctgcag ctgcatgtgg ataaagccgt cagtggcctt cgcagcctca      540
ccactctgct tcgggctctg ggagcccaga aggaagccat ctcccctcca gatgcggcct      600
cagctgctcc actccgaaca atcactgctg acactttccg caaactcttc cgagtctaca      660
gcaacttcct ccggggaaag ctgaagctgt acacagggga ggcctgcagg acagggggaca     720 gatgactcga gctagtgact gactaggatc tggttaccac taaaccagcc tcaagaacac      780
ccgaatggag tctctaagct acataatacc aacttacact tacaaaatgt tgtcccccaa      840
aatgtagcca ttcgtatctg ctcctaataa aagaaagtt tcttcacatt ctagaaaaaa       900
aaaaaaaaaa aaaaaaaaaa aaaaaaaaaa aaaaaaaaaa aaaaaaaaaa aaaaaaaaaa      960
aaaaaaaaaa aaaaaaaaaa aaaaaaaaaa aaaaaaaaaa aaaaaaaaaa aaaa           1014
```

<210> SEQ ID NO 27
<211> LENGTH: 1014
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
aggaaactta agtcaacaca acatatacaa acaaacgaa tctcaagcaa tcaagcattc        60
tacttctatt gcagcaattt aaatcatttc ttttaaagca aaagcaattt tctgaaaatt      120
```

```
ttcaccattt acgaacgata gccatggggg tgcacgaatg ccccgcctgg ctgtggctgc      180
tcctgagcct gctgagcctc ccctgggcc tcccagtcct gggcgcccca ccacgcctca      240
tctgcgacag ccgagtcctg gagaggtacc tcctggaggc caaggaggcc gagaacatca      300
cgacgggctg cgccgaacac tgcagcctga acgagaacat caccgtccca gacaccaaag      360
tgaacttcta cgcctggaag aggatggagg tcgggcagca ggccgtagaa gtctggcagg      420
gcctggccct gctgagcgaa gccgtcctgc ggggccaggc cctgctggtc aacagcagcc      480
agccgtggga gcccctgcag ctgcacgtgg acaaagccgt cagcggcctg cgcagcctca      540
ccaccctgct gcgggccctg ggagcccaga aggaagccat cagcccccca gacgcggcca      600
gcgccgcccc actccgaaca atcactgctg acactttccg caaactcttc cgagtctact      660
ccaatttcct ccggggaaag ctgaagctgt acacagggga ggcctgcagg acagggdaca      720
gatgactcga gctagtgact gactaggatc tggttaccac taaaccagcc tcaagaacac      780
ccgaatggag tctctaagct acataatacc aacttacact tacaaaatgt tgtcccccaa      840
aatgtagcca ttcgtatctg ctcctaataa aagaaagtt tcttcacatt ctagaaaaaa      900
aaaaaaaaaa aaaaaaaaaa aaaaaaaaaa aaaaaaaaaa aaaaaaaaaa aaaaaaaaaa      960
aaaaaaaaaa aaaaaaaaaa aaaaaaaaaa aaaaaaaaaa aaaaaaaaaa aaaa           1014
```

<210> SEQ ID NO 28
<211> LENGTH: 1014
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
aggaaactta agtcaacaca acatatacaa acaaacgaa tctcaagcaa tcaagcattc      60
tacttctatt gcagcaattt aaatcatttc ttttaaagca aaagcaattt tctgaaaatt      120
ttcaccattt acgaacgata gccatggggg tgcacgaatg ccccgcctgg ctgtggctgc      180
tcctgagcct gctgagcctc ccctgggcc tcccagtcct gggcgcccca ccacgcctca      240
tctgcgacag ccgagtcctg gagaggtacc tcctggaggc caaggaggcc gagaacatca      300
cgacgggctg cgccgaacac tgcagcctga acgagaacat caccgtccca gacaccaaag      360
tgaacttcta cgcctggaag aggatggagg tcgggcagca ggccgtagaa gtctggcagg      420
gcctggccct gctgagcgaa gccgtcctgc ggggccaggc cctgctggtc aacagcagcc      480
agccgtggga gcccctgcag ctgcacgtgg ataaagccgt cagtggcctt cgcagcctca      540
ccactctgct tcgggctctg ggagcccaga aggaagccat ctcccctcca gatgcggcct      600
cagctgctcc actccgaaca atcactgctg acactttccg caaactcttc cgagtctact      660
ccaatttcct ccggggaaag ctgaagctgt acacagggga ggcctgcagg acagggdaca      720
gatgactcga gctagtgact gactaggatc tggttaccac taaaccagcc tcaagaacac      780
ccgaatggag tctctaagct acataatacc aacttacact tacaaaatgt tgtcccccaa      840
aatgtagcca ttcgtatctg ctcctaataa aagaaagtt tcttcacatt ctagaaaaaa      900
aaaaaaaaaa aaaaaaaaaa aaaaaaaaaa aaaaaaaaaa aaaaaaaaaa aaaaaaaaaa      960
aaaaaaaaaa aaaaaaaaaa aaaaaaaaaa aaaaaaaaaa aaaaaaaaaa aaaa           1014
```

<210> SEQ ID NO 29
<211> LENGTH: 1014
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 29

```
aggaaactta agtcaacaca acatatacaa aacaaacgaa tctcaagcaa tcaagcattc    60
tacttctatt gcagcaattt aaatcatttc ttttaaagca aaagcaattt tctgaaaatt   120
ttcaccattt acgaacgata gccatggggg tgcacgaatg ccccgcctgg ctgtggctgc   180
tcctgagcct gctgagcctc ccctgggcc tcccagtcct gggcgcccca ccacgcctca    240
tctgcgacag ccgagtcctg gagaggtacc tcctggaggc caaggaggcc gagaacatca   300
cgacgggctg cgccgaacac tgcagcctga cgagaacat cactgtccca gacaccaaag    360
ttaatttcta tgcctggaag aggatggagg tcgggcagca ggccgtagaa gtctggcagg   420
gcctggccct gctgtcggaa gctgtcctgc ggggccaggc cctgttggtc aactcttccc   480
agccgtggga gccctgcag ctgcatgtgg ataaagccgt cagtggcctt cgcagcctca    540
ccactctgct tcgggctctg ggagcccaga aggaagccat ctcccctcca gatgcggcct   600
cagctgctcc actccgaaca atcactgctg acactttccg caaactcttc cgagtctact   660
ccaatttcct ccggggaaag ctgaagctgt acacagggga ggcctgcagg acaggggaca   720
gatgactcga gctagtgact gactaggatc tggttaccac taaaccagcc tcaagaacac   780
ccgaatggag tctctaagct acataatacc aacttacact tacaaaatgt tgtcccccaa   840
aatgtagcca ttcgtatctg ctcctaataa aagaaagtt tcttcacatt ctagaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaa         1014
```

<210> SEQ ID NO 30
<211> LENGTH: 1014
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
aggaaactta agtcaacaca acatatacaa aacaaacgaa tctcaagcaa tcaagcattc    60
tacttctatt gcagcaattt aaatcatttc ttttaaagca aaagcaattt tctgaaaatt   120
ttcaccattt acgaacgata gccatggggg tgcacgaatg ccccgcctgg ctgtggcttc   180
tcctgtccct gctgtcgctc cctctgggcc tcccagtcct gggcgcccca ccacgcctca   240
tctgtgacag ccgagtcctg gagaggtacc tcttggaggc caaggaggcc gagaatatca   300
cgacgggctg tgctgaacac tgcagcttga atgagaatat cactgtccca gacaccaaag   360
ttaatttcta tgcctggaag aggatggagg tcgggcagca ggccgtagaa gtctggcagg   420
gcctggccct gctgtcggaa gctgtcctgc ggggccaggc cctgttggtc aactcttccc   480
agccgtggga gccctgcag ctgcatgtgg ataaagccgt cagtggcctt cgcagcctca    540
ccactctgct tcgggctctg ggagcccaga aggaagccat ctcccctcca gatgcggcct   600
cagctgctcc actccgaaca atcactgctg acactttccg caaactcttc cgagtctact   660
ccaatttcct ccggggaaag ctgaagctgt acacagggga ggcctgcagg acaggggaca   720
gatgactcga gctagtgact gactaggatc tggttaccac taaaccagcc tcaagaacac   780
ccgaatggag tctctaagct acataatacc aacttacact tacaaaatgt tgtcccccaa   840
```

```
aatgtagcca ttcgtatctg ctcctaataa aagaaagtt tcttcacatt ctagaaaaaa      900
aaaaaaaaaa aaaaaaaaaa aaaaaaaaaa aaaaaaaaaa aaaaaaaaaa aaaaaaaaaa      960
aaaaaaaaaa aaaaaaaaaa aaaaaaaaaa aaaaaaaaaa aaaaaaaaaa aaaa           1014
```

<210> SEQ ID NO 31
<211> LENGTH: 1014
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
aggaaactta agtcaacaca acatatacaa acaaacgaa tctcaagcaa tcaagcattc        60
tacttctatt gcagcaattt aaatcatttc ttttaaagca aaagcaattt tctgaaaatt      120
ttcaccattt acgaacgata gccatggggg tgcacgaatg ccctgcctgg ctgtggctgc      180
tcctgagcct gctgagcctc ccctgggcc tcccagtcct gggcgcccca ccacgcctca      240
tctgcgacag ccgagtcctg gagaggtacc tcctggaggc caaggaggcc gagaacatca      300
cgacgggctg cgccgaacac tgcagcttga acgagaacat caccgtccca gacaccaaag      360
tgaacttcta cgcctggaag aggatggagg tcgggcagca ggccgtagaa gtctggcagg      420
gcctggccct gctgagcgaa gccgtcctgc ggggccaggc cctgctggtc aacagctccc      480
agccgtggga gcccctgcag ctgcacgtgg acaaagccgt cagcggcctg cgcagcctca      540
ccaccctgct gcgggccctg ggagcccaga aggaagccat cagcccccca gacgcggcca      600
gcgccgcccc actccgaaca atcaccgctg acaccttccg caaactcttc cgagtctact      660
ccaacttcct ccggggaaag ctgaagctgt acacaggggga ggcctgcagg acaggggaca      720
gatgactcga gctagtgact gactaggatc tggttaccac taaaccagcc tcaagaacac      780
ccgaatggag tctctaagct acataatacc aacttacact tacaaaatgt tgtcccccaa      840
aatgtagcca ttcgtatctg ctcctaataa aagaaagtt tcttcacatt ctagaaaaaa      900
aaaaaaaaaa aaaaaaaaaa aaaaaaaaaa aaaaaaaaaa aaaaaaaaaa aaaaaaaaaa      960
aaaaaaaaaa aaaaaaaaaa aaaaaaaaaa aaaaaaaaaa aaaaaaaaaa aaaa           1014
```

<210> SEQ ID NO 32
<211> LENGTH: 1014
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
aggaaactta agtcaacaca acatatacaa acaaacgaa tctcaagcaa tcaagcattc        60
tacttctatt gcagcaattt aaatcatttc ttttaaagca aaagcaattt tctgaaaatt      120
ttcaccattt acgaacgata gccatggggg tgcacgaatg ccccgcctgg ctgtggctgc      180
tcctgagcct gctgagcctc cctctgggcc tcccagtcct gggcgcccca ccacgcctca      240
tctgcgacag ccgagtcctg gagaggtacc tcctggaggc caaggaggcc gagaatatca      300
cgacgggctg tgccgaacac tgcagcttga acgagaatat caccgtccca gacaccaaag      360
ttaatttcta tgcctggaag aggatggagg tcgggcagca ggccgtagaa gtctggcagg      420
gcctggccct gctgtcggaa gctgtcctgc ggggccaggc cctgctggtc aacagcagcc      480
```

| | |
|---|---|
| agccgtggga gccnctgcag ctgcacgtgg ataaagccgt cagcggcctg cgcagcctca | 540 |
| ccaccctgct gcgggctctg ggagcccaga aggaagccat cagccctcca gatgcggcca | 600 |
| gcgccgctcc actccgaaca atcaccgccg acactttccg caaactcttc cgagtctaca | 660 |
| gcaacttcct ccggggaaag ctgaagctgt acacagggga ggcctgcagg acaggggaca | 720 |
| gatgactcga gctagtgact gactaggatc tggttaccac taaaccagcc tcaagaacac | 780 |
| ccgaatggag tctctaagct acataatacc aacttacact tacaaaatgt tgtcccccaa | 840 |
| aatgtagcca ttcgtatctg ctcctaataa aagaaagtt tcttcacatt ctagaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaa | 1014 |

<210> SEQ ID NO 33
<211> LENGTH: 1014
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

| | |
|---|---|
| aggaaactta agtcaacaca acatatacaa acaaacgaa tctcaagcaa tcaagcattc | 60 |
| tacttctatt gcagcaattt aaatcatttc ttttaaagca aaagcaattt tctgaaaatt | 120 |
| ttcaccattt acgaacgata gccatggggg tgcacgaatg tcctgcctgg ctgtggcttc | 180 |
| tcctgtccct gctgagcctc cctctgggcc tcccagtcct gggcgcccca ccacgcctca | 240 |
| tctgtgacag ccgagtcctg gagaggtacc tcttggaggc caaggaggcc gagaacatca | 300 |
| cgacgggctg cgctgaacac tgcagcctga atgagaatat cactgtccca gacaccaaag | 360 |
| tgaatttcta tgcctggaag aggatggagg tcggcagca ggccgtagaa gtctggcagg | 420 |
| gcctggccct gctgagcgaa gccgtcctgc ggggccaggc cctgttggtc aacagcagcc | 480 |
| agccgtggga gccnctgcag ctgcatgtgg ataaagccgt cagtggcctt cgcagcctca | 540 |
| ccactctgct cgggccctg ggagcccaga aggaagccat ctcccctcca gacgcggcct | 600 |
| cagctgcccc actccgaaca atcactgctg acactttccg caaactcttc cgagtctaca | 660 |
| gcaatttcct ccggggaaag ctgaagctgt acacagggga ggcctgcagg acaggggaca | 720 |
| gatgactcga gctagtgact gactaggatc tggttaccac taaaccagcc tcaagaacac | 780 |
| ccgaatggag tctctaagct acataatacc aacttacact tacaaaatgt tgtcccccaa | 840 |
| aatgtagcca ttcgtatctg ctcctaataa aagaaagtt tcttcacatt ctagaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaa | 1014 |

<210> SEQ ID NO 34
<211> LENGTH: 1014
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

| | |
|---|---|
| aggaaactta agtcaacaca acatatacaa acaaacgaa tctcaagcaa tcaagcattc | 60 |
| tacttctatt gcagcaattt aaatcatttc ttttaaagca aaagcaattt tctgaaaatt | 120 |
| ttcaccattt acgaacgata gccatggggg tgcacgaatg tcctgcctgg ctgtggcttc | 180 |

```
tcctgtccct gctgtcgctc cctctgggcc tcccagtcct gggcgcccca ccacgcctca    240
tctgtgacag ccgagtcctg gagaggtacc tcttggaggc caaggaggcc gagaatatca    300
cgacgggctg tgctgaacac tgcagcttga atgagaatat cactgtccca gacaccaaag    360
ttaacttcta tgcctggaag aggatggagg tcgggcagca ggccgtagaa gtctggcagg    420
gcctggccct gctgtcggaa gctgtcctgc ggggccaggc cctgctggtc aactcttccc    480
agccgtggga gccctgcag ctgcatgtgg ataaagccgt cagtggcctt cgcagcctca     540
ccactctgct tcgggctctg ggagcccaga aggaagccat ctccctcca gatgcggcct     600 cagctgctcc actccgaaca atcactgctg acactttccg caaactcttc cgagtctact    660
ccaatttcct ccggggaaag ctgaagctgt acacagggga ggcctgcagg acagggggaca   720 gatgactcga gctagtgact gactaggatc tggttaccac taaaccagcc tcaagaacac    780
ccgaatggag tctctaagct acataatacc aacttacact tacaaaatgt tgtcccccaa    840
aatgtagcca ttcgtatctg ctcctaataa aagaaagtt tcttcacatt ctagaaaaaa     900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaa         1014
```

<210> SEQ ID NO 35
<211> LENGTH: 1014
<212> TYPE: RNA
<213> ORGANISM: Artificial Sequence
<220> FEATURE:
<223> OTHER INFORMATION: Description of Artificial Sequence: Synthetic
    polynucleotide

<400> SEQUENCE: 35

```
aggaaacuua agucaacaca acauauacaa aacaaacgaa ucucaagcaa ucaagcauuc     60
uacuucuauu gcagcaauuu aaaucauuuc uuuuaaagca aaagcaauuu ucugaaaauu    120
uucaccauuu acgaacgaua gccauggggg ugcacgaaug ccccgccugg cuguggcugc    180
uccugagccu gcugagccuc ccccugggcc ucccaguccu gggcgcccca ccacgccuca    240
ucugcgacag ccgaguccug gagagguacc uccuggaggc caaggaggcc gagaacauca    300
cgacgggcug cgccgaacac ugcagccuga acgagaacau caccguccca gacaccaaag    360
ugaacuucua cgccuggaag aggauggagg ucgggcagca ggccguagaa gucuggcagg    420
gccuggcccu gcugagcgaa gccguccugc ggggccaggc ccugcugguc aacagcagcc    480
agccguggga gcccugcag cugcacgugg acaaagccgu cagcggccug cgcagccuca    540
ccacccugcu gcgggcccug ggagcccaga aggaagccau cagcccccca gacgcggcca    600
gcgccgcccc acuccgaaca auccaccgccg acaccuuccg caaacucuuc cgagucuaca    660
gcaacuuccu ccggggaaag cugaagcugu acacagggga ggccugcagg acagggggaca   720 gaugacucga gcuagugacu gacuaggauc ugguuaccac uaaaccagcc ucaagaacac    780
ccgaauggag ucucuaagcu acauaauacc aacuuacacu uacaaaaugu uguccccaa     840 aauguagcca uucguaucug cuccuaauaa aagaaaguu ucuucacauu cuagaaaaaa     900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaa         1014
```

<210> SEQ ID NO 36
<211> LENGTH: 1014
<212> TYPE: RNA
<213> ORGANISM: Artificial Sequence
<220> FEATURE:
<223> OTHER INFORMATION: Description of Artificial Sequence: Synthetic
       polynucleotide

<400> SEQUENCE: 36

```
aggaaacuua agucaacaca acauauacaa acaaacgaa ucucaagcaa ucaagcauuc      60
uacuucuauu gcagcaauuu aaaucauuuc uuuuaaagca aaagcaauuu ucugaaaauu    120
uucaccauuu acgaacgaua gccauggggg ugcacgaaug uccugccugg cuguggcuuc    180
uccugucccu gcugucgcuc ccccugggcc ucccaguccu gggcgcccca ccacgccuca    240
ucugcgacag ccgaguccug gagagguacc uccuggaggc caaggaggcc gagaacauca    300
cgacgggcug cgccgaacac ugcagccuga acgagaacau caccguccca gacaccaaag    360
ugaacuucua cgccuggaag aggauggagg ucgggcagca ggccguagaa gucuggcagg    420
gccuggcccu gcugagcgaa gccguccugc ggggccaggc ccugcugguc aacagcagcc    480
agccguggga gccccugcag cugcacgugg acaaagccgu cagcggccug cgcagccuca    540
ccacccugcu gcgggcccug ggagcccaga aggaagccau cagcccccca gacgcggcca    600
gcgccgcccc acuccgaaca aucaccgccg acaccuuccg caaacucuuc cgagucuaca    660
gcaacuuccu ccggggaaag cugaagcugu acacagggga ggccugcagg cagggaca     720 gaugacucga gcuagugacu gacuaggauc ugguuaccac uaaaccagcc ucaagaacac    780
ccgaauggag ucucuaagcu acauaauacc aacuuacacu uacaaaaugu ugucccccaa    840
aauguagcca uucguaucug cuccuaauaa aagaaaguu ucuucacauu cuagaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaa         1014
```

<210> SEQ ID NO 37
<211> LENGTH: 1014
<212> TYPE: RNA
<213> ORGANISM: Artificial Sequence
<220> FEATURE:
<223> OTHER INFORMATION: Description of Artificial Sequence: Synthetic
       polynucleotide

<400> SEQUENCE: 37

```
aggaaacuua agucaacaca acauauacaa acaaacgaa ucucaagcaa ucaagcauuc      60
uacuucuauu gcagcaauuu aaaucauuuc uuuuaaagca aaagcaauuu ucugaaaauu    120
uucaccauuu acgaacgaua gccauggggg ugcacgaaug uccugccugg cuguggcuuc    180
uccugucccu gcugucgcuc ccucugggcc ucccaguccu gggcgcccca ccacgccuca    240
ucugugacag ccgaguccug gagagguacc ucuuggaggc caaggaggcc gagaauauca    300
cgacgggcug ugcugaacac ugcagcuuga augagaauau cacuguccca gacaccaaag    360
uuaauuucua cgccuggaag aggauggagg ucgggcagca ggccguagaa gucuggcagg    420
gccuggcccu gcugagcgaa gccguccugc ggggccaggc ccugcugguc aacagcagcc    480
agccguggga gccccugcag cugcacgugg acaaagccgu cagcggccug cgcagccuca    540
ccacccugcu gcgggcccug ggagcccaga aggaagccau cagcccccca gacgcggcca    600
gcgccgcccc acuccgaaca aucaccgccg acaccuuccg caaacucuuc cgagucuaca    660
gcaacuuccu ccggggaaag cugaagcugu acacagggga ggccugcagg cagggaca     720 gaugacucga gcuagugacu gacuaggauc ugguuaccac uaaaccagcc ucaagaacac    780
ccgaauggag ucucuaagcu acauaauacc aacuuacacu uacaaaaugu ugucccccaa    840
```

| aauguagcca uucguaucug cuccuaauaa aaagaaaguu ucuucacauu cuagaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaa | 1014 |

<210> SEQ ID NO 38
<211> LENGTH: 1014
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 38

| aggaaacuua agucaacaca acauauacaa aacaaacgaa ucucaagcaa ucaagcauuc | 60 |
| uacuucuauu gcagcaauuu aaaucauuuc uuuuaaagca aaagcaauuu ucugaaaauu | 120 |
| uucaccauuu acgaacgaua gccauggggg ugcacgaaug uccugccugg cuguggcuuc | 180 |
| uccugucccu gcugucgcuc ccucggggcc ucccaguccu gggcgcccca ccacgccuca | 240 |
| ucugugacag ccgaguccug gagagguacc ucuuggaggc caaggaggcc gagaauauca | 300 |
| cgacgggcug ugcugaacac ugcagcuuga augagaauau cacuguccca gacaccaaag | 360 |
| uuaauuucua ugccuggaag aggauggagg ucgggcagca ggccguagaa gucuggcagg | 420 |
| gccuggcccu gcugucggaa gcuguccugc ggggccaggc ccuguugguc aacucuuccc | 480 |
| agccguggga gccccugcag cugcaugugg auaaagccgu caguggccuu cgcagccuca | 540 |
| ccacccugcu gcgggcccug ggagcccaga aggaagccau cagcccccca gacgcggcca | 600 |
| gcgccgcccc acuccgaaca aucaccgccg acaccuuccg caaacucuuc cgagucuaca | 660 |
| gcaacuuccu ccgggggaaag cugaagcugu acacagggga ggccugcagg acaggggaca | 720 |
| gaugacucga gcuagugacu gacuaggauc ugguuaccac uaaaccagcc ucaagaacac | 780 |
| ccgaauggag ucucuaagcu acauaauacc aacuuacacu uacaaaaugu gucccccaa | 840 |
| aauguagcca uucguaucug cuccuaauaa aaagaaaguu ucuucacauu cuagaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaa | 1014 |

<210> SEQ ID NO 39
<211> LENGTH: 1014
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 39

| aggaaacuua agucaacaca acauauacaa aacaaacgaa ucucaagcaa ucaagcauuc | 60 |
| uacuucuauu gcagcaauuu aaaucauuuc uuuuaaagca aaagcaauuu ucugaaaauu | 120 |
| uucaccauuu acgaacgaua gccauggggg ugcacgaaug uccugccugg cuguggcuuc | 180 |
| uccugucccu gcugucgcuc ccucggggcc ucccaguccu gggcgcccca ccacgccuca | 240 |
| ucugugacag ccgaguccug gagagguacc ucuuggaggc caaggaggcc gagaauauca | 300 |
| cgacgggcug ugcugaacac ugcagcuuga augagaauau cacuguccca gacaccaaag | 360 |
| uuaauuucua ugccuggaag aggauggagg ucgggcagca ggccguagaa gucuggcagg | 420 |
| gccuggcccu gcugucggaa gcuguccugc ggggccaggc ccuguugguc aacucuuccc | 480 |
| agccguggga gccccugcag cugcaugugg auaaagccgu caguggccuu cgcagccuca | 540 |

```
ccacucugcu ucgggcucug ggagcccaga aggaagccau cuccccucca gaugcggccu    600
cagcugcucc acuccgaaca aucacugcug acacuuuccg caaacucuuc cgagucuaca    660
gcaacuuccu ccggggaaag cugaagcugu acacagggga ggccugcagg acaggggaca    720
gaugacucga gcuagugacu gacuaggauc ugguuaccac uaaaccagcc ucaagaacac    780
ccgaauggag ucucuaagcu acauaauacc aacuuacacu uacaaaaugu gucccccaa     840 aauguagcca uucguaucug cuccuaauaa aaagaaaguu ucuucacauu cuagaaaaaa    900
aaaaaaaaaa aaaaaaaaaa aaaaaaaaaa aaaaaaaaaa aaaaaaaaaa aaaaaaaaaa   960
aaaaaaaaaa aaaaaaaaaa aaaaaaaaaa aaaaaaaaaa aaaaaaaaaa aaaa         1014
```

<210> SEQ ID NO 40
<211> LENGTH: 1014
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 40

```
aggaaacuua agucaacaca acauauacaa aacaaacgaa ucucaagcaa ucaagcauuc    60
uacuucuauu gcagcaauuu aaaucauuuc uuuuaaagca aaagcaauuu ucugaaaauu   120
uucaccauuu acgaacgaua gccauggggg ugcacgaaug ccccgccugg cuguggcugc   180
uccugagccu gcugagccuc ccccugggcc ucccaguccu gggcgcccca ccacgcccuca   240 ucugcgacag ccgaguccug gagagguacc uccuggaggc caaggaggcc gagaacauca    300
cgacgggcug cgccgaacac ugcagccuga acgagaacau caccguccca gacaccaaag    360
ugaacuucua cgccuggaag aggauggagg ucgggcagca ggccguagaa gucuggcagg    420
gccuggcccu gcugagcgaa gccguccugc ggggccaggc ccugcugguc aacagcagcc    480
agccguggga gccccugcag cugcacgugg acaaagccgu cagcggccug cgcagccuca    540
ccacccugcu gcgggcccug ggagcccaga aggaagccau cagcccccca gacgcggcca    600
gcgccgcccc acuccgaaca aucacugcug acacuuuccg caaacucuuc cgagucuacu    660
ccaauuuccu ccggggaaag cugaagcugu acacagggga ggccugcagg acaggggaca    720
gaugacucga gcuagugacu gacuaggauc ugguuaccac uaaaccagcc ucaagaacac    780
ccgaauggag ucucuaagcu acauaauacc aacuuacacu uacaaaaugu gucccccaa     840 aauguagcca uucguaucug cuccuaauaa aaagaaaguu ucuucacauu cuagaaaaaa    900
aaaaaaaaaa aaaaaaaaaa aaaaaaaaaa aaaaaaaaaa aaaaaaaaaa aaaaaaaaaa   960
aaaaaaaaaa aaaaaaaaaa aaaaaaaaaa aaaaaaaaaa aaaaaaaaaa aaaa         1014
```

<210> SEQ ID NO 41
<211> LENGTH: 1014
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 41

```
aggaaacuua agucaacaca acauauacaa aacaaacgaa ucucaagcaa ucaagcauuc    60
uacuucuauu gcagcaauuu aaaucauuuc uuuuaaagca aaagcaauuu ucugaaaauu   120
uucaccauuu acgaacgaua gccauggggg ugcacgaaug ccccgccugg cuguggcugc   180
```

```
uccugagccu gcugagccuc ccccugggcc ucccaguccu gggcgcccca ccacgccuca    240
ucugcgacag ccgaguccug gagagguacc uccuggaggc caaggaggcc gagaacauca    300
cgacgggcug cgccgaacac ugcagccuga acgagaacau caccguccca gacaccaaag    360
ugaacuucua cgccuggaag aggauggagu cgggcagca ggccguagaa gucuggcagg    420
gccuggcccu gcugagcgaa gccguccugc ggggccaggc ccugcugguc aacagcagcc    480
agccguggga gccccugcag cugcacgugg auaaagccgu caguggccuu cgcagccuca    540
ccacucugcu ucgggcucug ggagcccaga aggaagccau cuccccucca gaugcggccu    600
cagcugcucc acuccgaaca aucacugcug acacuuuccg caaacucuuc cgagucuacu    660
ccaauuuccu ccggggaaag cugaagcugu acacagggga ggccugcagg caggggaca    720 gaugacucga gcuagugacu gacuaggauc ugguuaccac uaaaccagcc ucaagaacac    780
ccgaauggag ucucuaagcu acauaauacc aacuuacacu uacaaaaugu gucccccaa    840 aauguagcca uucguaucug cuccuaauaa aaagaaaguu ucuucacauu cuagaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaa         1014

<210> SEQ ID NO 42
<211> LENGTH: 1014
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 42
aggaaacuua agucaacaca acauauacaa aacaaacgaa ucucaagcaa ucaagcauuc    60
uacuucuauu gcagcaauuu aaaucauuuc uuuuaaagca aaagcaauuu ucugaaaauu    120
uucaccauuu acgaacgaua gccaugggg ugcacgaaug ccccgccugg cuguggcugc    180
uccugagccu gcugagccuc ccccugggcc ucccaguccu gggcgcccca ccacgccuca    240
ucugcgacag ccgaguccug gagagguacc uccuggaggc caaggaggcc gagaacauca    300
cgacgggcug cgccgaacac ugcagccuga acgagaacau cacuguccca gacaccaaag    360
uuaauuucua ugccuggaag aggauggagu cgggcagca ggccguagaa gucuggcagg    420
gccuggcccu gcugucggaa gcuguccugc ggggccaggc ccuguugguc aacucuuccc    480
agccguggga gccccugcag cugcaugugg auaaagccgu caguggccuu cgcagccuca    540
ccacucugcu ucgggcucug ggagcccaga aggaagccau cuccccucca gaugcggccu    600
cagcugcucc acuccgaaca aucacugcug acacuuuccg caaacucuuc cgagucuacu    660
ccaauuuccu ccggggaaag cugaagcugu acacagggga ggccugcagg caggggaca    720 gaugacucga gcuagugacu gacuaggauc ugguuaccac uaaaccagcc ucaagaacac    780
ccgaauggag ucucuaagcu acauaauacc aacuuacacu uacaaaaugu gucccccaa    840 aauguagcca uucguaucug cuccuaauaa aaagaaaguu ucuucacauu cuagaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaa         1014

<210> SEQ ID NO 43
<211> LENGTH: 1014
<212> TYPE: RNA
<213> ORGANISM: Artificial Sequence
<220> FEATURE:
```

<223> OTHER INFORMATION: Description of Artificial Sequence: Synthetic
polynucleotide

<400> SEQUENCE: 43

```
aggaaacuua agucaacaca acauauacaa aacaaacgaa ucucaagcaa ucaagcauuc      60
uacuucuauu gcagcaauuu aaaucauuuc uuuuaaagca aaagcaauuu ucugaaaauu     120
uucaccauuu acgaacgaua gccauggggg ugcacgaaug ccccgccugg cuguggcuuc     180
uccugucccu gcgucgcuc ccucugggcc ucccaguccu gggcgcccca ccacgccuca      240
ucugugacag ccgagaccug gagagguacc ucuuggaggc caaggaggcc gagaauauca     300
cgacgggcug ugcugaacac ugcagcuuga augagaauau cacuguccca gacaccaaag    360
uuaauuucua ugccuggaag aggauggagg ucgggcagca ggccguagaa gucuggcagg    420
gccuggcccu gcgucggaa gcugccugc ggggccaggc ccuguggguc aacucuuccc      480
agccguggga gccccugcag cugcaugugg auaaagccgu caguggccuu cgcagccuca    540
ccacucugcu ucgggcucug ggagcccaga aggaagccau cuccccucca gaugcggccu    600
cagcugcucc acuccgaaca aucacugcug acacuuuccg caaacucuuc cgagucuacu    660
ccaauuuccu ccggggaaag cugaagcugu acacagggga ggccugcagg acaggggaca    720
gaugacucga gcuagugacu gacuaggauc ugguuaccac uaaaccagcc ucaagaacac    780
ccgaauggag ucucuaagcu acauaauacc aacuuacacu uacaaaaugu gucccccaa    840
aaugauagcca uucguaucug cuccuaauaa aaagaaaguu ucuucacauu cuagaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaa          1014
```

<210> SEQ ID NO 44
<211> LENGTH: 1014
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 44

```
aggaaacuua agucaacaca acauauacaa aacaaacgaa ucucaagcaa ucaagcauuc      60
uacuucuauu gcagcaauuu aaaucauuuc uuuuaaagca aaagcaauuu ucugaaaauu    120
uucaccauuu acgaacgaua gccauggggg ugcacgaaug cccugccugg cuguggcugc    180
uccugagccu gcgagccuc ccccugggcc ucccaguccu gggcgcccca ccacgccuca     240
ucugcgacag ccgagaccug gagagguacc uccuggaggc caaggaggcc gagaacauca    300
cgacgggcug cgccgaacac ugcagcuuga acgagaacau caccguccca gacaccaaag    360
ugaacuucua cgccuggaag aggauggagg ucgggcagca ggccguagaa gucuggcagg    420
gccuggcccu gcgagcgaa gccguccugc ggggccaggc ccugcugguc aacagccccc      480
agccguggga gccccugcag cugcacgugg acaaagccgu cagcggccug cgcagccuca    540
ccaccccugcu gcgggcccug ggagcccaga aggaagccau cagcccccca gacgcggcca    600
gcgccgcccc acuccgaaca aucaccgcug acaccuuccg caaacucuuc cgagucuacu    660
ccaacuuccu ccggggaaag cugaagcugu acacagggga ggccugcagg acaggggaca    720
gaugacucga gcuagugacu gacuaggauc ugguuaccac uaaaccagcc ucaagaacac    780
ccgaauggag ucucuaagcu acauaauacc aacuuacacu uacaaaaugu gucccccaa    840
aauguagcca uucguaucug cuccuaauaa aaagaaaguu ucuucacauu cuagaaaaaa    900
```

```
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaa         1014

<210> SEQ ID NO 45
<211> LENGTH: 1014
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 45
aggaaacuua agucaacaca acauauacaa aacaaacgaa ucucaagcaa ucaagcauuc     60
uacuucuauu gcagcaauuu aaaucauuuc uuuuaaagca aaagcaauuu ucugaaaauu    120
uucaccauuu acgaacgaua gccauggggg ugcacgaaug ucccgccugg cuguggcugc    180
uccugagccu gcugaccuc ccucugggcc ucccaguccu gggcgcccca ccacgccuca    240
ucugcgacag ccgaguccug gagagguacc uccuggaggc caaggaggcc gagaauauca    300
cgacgggcug ugccgaacac ugcagcuuga acgagaauau caccgucccca gacaccaaag    360 uuaauuucua ugccuggaag aggauggagg ucgggcagca ggccguagaa gucuggcagg    420
gccuggcccu gcugucggaa gcuguccugc ggggccaggc ccugcugguc aacagcagcc    480
agccguggga gccccugcag cugcacgugg auaaagccgu cagcggccug cgcagccuca    540
ccacccugcu gcgggcucug ggagcccaga aggaagccau cagcccucca gaugcggcca    600
gcgccgcucc acuccgaaca auccaccgccg acacuuuccg caaacucuuc cgagucuaca    660
gcaacuuccu ccggggaaag cugaagcugu acacagggga ggccugcagg acaggggaca    720
gaugacucga gcuagugacu gacuaggauc ugguuaccac uaaaccagcc ucaagaacac    780
ccgaauggag ucucuaagcu acauaauacc aacuuacacu uacaaaaugu ugucccccaa    840
aauguagcca uucguaucug cuccuaauaa aaagaaaguu ucuucacauu cuagaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaa         1014

<210> SEQ ID NO 46
<211> LENGTH: 1014
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 46
aggaaacuua agucaacaca acauauacaa aacaaacgaa ucucaagcaa ucaagcauuc     60
uacuucuauu gcagcaauuu aaaucauuuc uuuuaaagca aaagcaauuu ucugaaaauu    120
uucaccauuu acgaacgaua gccauggggg ugcacgaaug uccugccugg cuguggcuuc    180
uccugucccu gcugagccuc ccucugggcc ucccaguccu gggcgcccca ccacgccuca    240
ucugugacag ccgaguccug gagagguacc ucuggaggc caaggaggcc gagaacauca    300
cgacgggcug cgcugaacac ugcagccuga augagaauau cacugucccca gacaccaaag    360 ugaauuucua ugccuggaag aggauggagg ucgggcagca ggccguagaa gucuggcagg    420
gccuggcccu gcugagcgaa gccguccugc ggggccaggc ccuguugguc aacagcagcc    480
agccguggga gccccugcag cugcauggg auaaagccgu cagugccuu cgcagccuca    540
```

| | | |
|---|---|---|
| ccacucugcu ucgggcccug ggagcccaga aggaagccau cuccccucca gacgcggccu | 600 | |
| cagcugcccc acuccgaaca aucacugcug acacuuuccg caaacucuuc cgagucuaca | 660 | |
| gcaauuuccu ccggggaaag cugaagcugu acacagggga ggccugcagg caggggaca | 720 | |
| gaugacucga gcuagugacu gacuaggauc ugguuaccac uaaaccagcc ucaagaacac | 780 | |
| ccgaauggag ucucuaagcu acauaauacc aacuuacacu uacaaaaugu uguccccaa | 840 | |
| aauguagcca uucguaucug cuccuaauaa aaagaaaguu ucuucacauu cuagaaaaaa | 900 | |
| aaaaaaaaaa aaaaaaaaaa aaaaaaaaaa aaaaaaaaaa aaaaaaaaaa aaaaaaaaaa | 960 | |
| aaaaaaaaaa aaaaaaaaaa aaaaaaaaaa aaaaaaaaaa aaaaaaaaaa aaaa | 1014 | |

<210> SEQ ID NO 47
<211> LENGTH: 1014
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 47

| | | |
|---|---|---|
| aggaaacuua agucaacaca acauauacaa aacaaacgaa ucucaagcaa ucaagcauuc | 60 | |
| uacuucuauu gcagcaauuu aaaucauuuc uuuuaaagca aaagcaauuu ucugaaaauu | 120 | |
| uucaccauuu acgaacgaua gccauggggg ugcacgaaug uccugccugg cuguggcuuc | 180 | |
| uccuguccu gcugucgcuc ccucugggcc ucccagccu gggcgcccca ccacgccuca | 240 | |
| ucugugacag ccgaguccug gagagguacc ucuuggaggc caaggaggcc gagaauauca | 300 | |
| cgacgggcug ugcugaacac ugcagcuuga augagaauau cacuguccca gacaccaaag | 360 | |
| uuaacuucua ugccuggaag aggauggagg ucgggcagca ggccguagaa gucuggcagg | 420 | |
| gccuggcccu gcugucggaa gcuguccugc ggggccaggc ccugcugguc aacucuuccc | 480 | |
| agccguggga gccccugcag cugcauguug auaaagccgu cagugccuu cgcagccuca | 540 | |
| ccacucugcu ucgggcucug ggagcccaga aggaagccau cuccccucca gaugcggccu | 600 | |
| cagcugcucc acuccgaaca aucacugcug acacuuuccg caaacucuuc cgagucuacu | 660 | |
| ccaauuuccu ccggggaaag cugaagcugu acacagggga ggccugcagg caggggaca | 720 | |
| gaugacucga gcuagugacu gacuaggauc ugguuaccac uaaaccagcc ucaagaacac | 780 | |
| ccgaauggag ucucuaagcu acauaauacc aacuuacacu uacaaaaugu uguccccaa | 840 | |
| aauguagcca uucguaucug cuccuaauaa aaagaaaguu ucuucacauu cuagaaaaaa | 900 | |
| aaaaaaaaaa aaaaaaaaaa aaaaaaaaaa aaaaaaaaaa aaaaaaaaaa aaaaaaaaaa | 960 | |
| aaaaaaaaaa aaaaaaaaaa aaaaaaaaaa aaaaaaaaaa aaaaaaaaaa aaaa | 1014 | |

<210> SEQ ID NO 48
<211> LENGTH: 1386
<212> TYPE: DNA
<213> ORGANISM: Homo sapiens

<400> SEQUENCE: 48

| | | |
|---|---|---|
| atgcagcgcg tgaacatgat catggcagaa tcaccaggcc tcatcaccat ctgccttta | 60 | |
| ggatatctac tcagtgctga atgtacagtt tttcttgatc atgaaaacgc caacaaaatt | 120 | |
| ctgaatcggc aaagaggta taattcaggt aaattggaag agtttgttca agggaacctt | 180 | |
| gagagagaat gtatggaaga aaagtgtagt tttgaagaag cacagaagt ttttgaaaac | 240 | |
| actgaaagaa caactgaatt ttggaagcag tatgttgatg gagatcagtg tgagtccaat | 300 | |

```
ccatgtttaa atggcggcag ttgcaaggat gacattaatt cctatgaatg ttggtgtccc    360
tttggatttg aaggaaagaa ctgtgaatta gatgtaacat gtaacattaa gaatggcaga    420
tgcgagcagt tttgtaaaaa tagtgctgat aacaaggtgg tttgctcctg tactgaggga    480
tatcgacttg cagaaaacca gaagtcctgt gaaccagcag tgccatttcc atgtggaaga    540
gtttctgttt cacaaacttc taagctcacc cgtgctgaga ctgttttttcc tgatgtggac    600 tatgtaaatt ctactgaagc tgaaaccatt ttggataaca tcactcaaag cacccaatca    660
tttaatgact tcactcgggt tgttggtgga gaagatgcca aaccaggtca attcccttgg    720
caggttgttt tgaatggtaa agttgatgca ttctgtggag gctctatcgt taatgaaaaa    780
tggattgtaa ctgctgccca ctgtgttgaa actggtgtta aaattacagt tgtcgcaggt    840
gaacataata ttgaggagac agaacataca gagcaaaagc gaaatgtgat tcgaattatt    900
cctcaccaca actacaatgc agctattaat aagtacaacc atgacattgc ccttctggaa    960
ctggacgaac ccttagtgct aaacagctac gttacaccta tttgcattgc tgacaaggaa   1020
tacacgaaca tcttcctcaa atttggatct ggctatgtaa gtggctgggg aagagtcttc   1080
cacaaaggga gatcagcttt agttcttcag taccttagag ttccacttgt tgaccgagcc   1140
acatgtcttc gatctacaaa gttcaccatc tataacaaca tgttctgtgc tggcttccat   1200
gaaggaggta gagattcatg tcaaggagat agtgggggac ccatgttac tgaagtggaa    1260 gggaccagtt tcttaactgg aattattagc tggggtgaag agtgtgcaat gaaaggcaaa   1320
tatggaatat ataccaaggt atcccggtat gtcaactgga ttaaggaaaa aacaaagctc   1380
acttaa                                                              1386

<210> SEQ ID NO 49
<211> LENGTH: 582
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
atgggggtgc acgaatgccc cgcctggctg tggctgctcc tgagcctgct gagcctcccc     60
ctgggcctcc cagtcctggg cgccccacca cgcctcatct gcgacagccg agtcctggag    120
aggtacctcc tggaggccaa ggaggccgag aacatcacga cgggctgcgc cgaacactgc    180
agcctgaacg agaacatcac cgtcccagac accaaagtga acttctacgc ctggaagagg    240
atggaggtcg ggcagcaggc cgtagaagtc tggcagggcc tggccctgct gagcgaagcc    300
gtcctgcggg gccaggccct gctggtcaac agcagccagc cgtgggagcc cctgcagctg    360
cacgtggaca aagccgtcag cggcctgcgc agcctcacca cctgctgcg ggccctggga    420 gcccagaagg aagccatcag ccccccagac gcggccagcg ccgccccact ccgaacaatc    480
accgccgaca ccttccgcaa actcttccga gtctacagca cttcctccg gggaaagctg    540 aagctgtaca caggggaggc ctgcaggaca ggggacagat ga                      582

<210> SEQ ID NO 50
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
```

| | |
|---|---|
| atgcagcgcg tgaacatgat catggcagaa agcccaggcc tcatcaccat ctgcctgctg | 60 |
| ggatacctac tcagcgccga atgcacagtg ttcctggacc acgaaaacgc caacaaaatc | 120 |
| ctgaaccggc caagagggta caacagcggc aaactggaag agttcgtgca agggaacctg | 180 |
| gagagagaat gcatggaaga aaagtgcagc ttcgaagaag cacgagaagt gttcgaaaac | 240 |
| accgaaagaa caaccgaatt ctggaagcag tacgtggacg agaccagtg cgagagcaac | 300 |
| ccatgcctga acggcggcag ctgcaaggac gacatcaaca gctacgaatg ctggtgcccc | 360 |
| ttcggattcg aaggaaagaa ctgcgaactg gacgtaacat gcaacatcaa gaacggcaga | 420 |
| tgcgagcagt tctgcaaaaa cagcgccgac aacaaggtgg tgtgcagctg caccgaggga | 480 |
| taccgactgg cagaaaacca gaagtcctgc gaaccagcag tgccattccc atgcggaaga | 540 |
| gtgagcgtga gccaaaccag caagctcacc cgggccgaga ccgtgttccc cgacgtggac | 600 |
| tacgtaaaca gcaccgaagc cgaaaccatc ctggacaaca tcacccaaag cacccaaagc | 660 |
| ttcaacgact cacccgggt ggtgggcgga gaagacgcca aaccaggcca attcccctgg | 720 |
| caggtggtgc tgaacggcaa agtggacgca ttctgcggag gcagcatcgt gaacgaaaaa | 780 |
| tggatcgtaa ccgccgccca ctgcgtggaa accggcgtga aaatcacagt ggtcgcaggc | 840 |
| gaacacaaca tcgaggagac agaacacaca gagcaaaagc gaaacgtgat ccgaatcatc | 900 |
| ccccaccaca actacaacgc agccatcaac aagtacaacc acgacatcgc cctgctggaa | 960 |
| ctggacgaac ccctggtgct aaacagctac gtgacaccca tctgcatcgc cgacaaggaa | 1020 |
| tacacgaaca tcttcctcaa attcggaagc ggctacgtaa gcggctgggg aagagtcttc | 1080 |
| cacaaaggga gcgcgccct ggtgctgcag tacctgagag tgccactggt ggaccgagcc | 1140 |
| acatgcctgc gaagcacaaa gttcaccatc tacaacaaca tgttctgcgc cggcttccac | 1200 |
| gaaggaggca gagacagctg ccaaggagac agcggggggac cccacgtgac cgaagtggaa | 1260 |
| gggaccagct tcctgaccgg aatcatcagc tggggcgaag agtgcgcaat gaaaggcaaa | 1320 |
| tacggaatat acaccaaggt aagccggtac gtcaactgga tcaaggaaaa aacaaagctc | 1380 |
| acctaa | 1386 |

<210> SEQ ID NO 51
<211> LENGTH: 1386
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

| | |
|---|---|
| atgcagcgcg tgaacatgat catggcagaa tcaccaggcc tcatcaccat ctgccttta | 60 |
| ggatatctac tcagtgctga atgtacagtt ttcctggacc acgaaaacgc caacaaaatc | 120 |
| ctgaaccggc caagagggta caacagcggc aaactggaag agttcgtgca agggaacctg | 180 |
| gagagagaat gcatggaaga aaagtgcagc ttcgaagaag cacgagaagt gttcgaaaac | 240 |
| accgaaagaa caaccgaatt ctggaagcag tacgtggacg agaccagtg cgagagcaac | 300 |
| ccatgcctga acggcggcag ctgcaaggac gacatcaaca gctacgaatg ctggtgcccc | 360 |
| ttcggattcg aaggaaagaa ctgcgaactg gacgtaacat gcaacatcaa gaacggcaga | 420 |
| tgcgagcagt tctgcaaaaa cagcgccgac aacaaggtgg tgtgcagctg caccgaggga | 480 |
| taccgactgg cagaaaacca gaagtcctgc gaaccagcag tgccattccc atgcggaaga | 540 |
| gtgagcgtga gccaaaccag caagctcacc cgggccgaga ccgtgttccc cgacgtggac | 600 |

```
tacgtaaaca gcaccgaagc cgaaaccatc ctggacaaca tcacccaaag cacccaaagc      660
ttcaacgact tcacccgggt ggtgggcgga gaagacgcca aaccaggcca attcccctgg      720
caggtggtgc tgaacggcaa agtggacgca ttctgcggag gcagcatcgt gaacgaaaaa      780
tggatcgtaa ccgccgccca ctgcgtggaa accggcgtga aaatcacagt ggtcgcaggc      840
gaacacaaca tcgaggagac agaacacaca gagcaaaagc gaaacgtgat ccgaatcatc      900
ccccaccaca actacaacgc agccatcaac aagtacaacc acgacatcgc cctgctggaa      960
ctggacgaac ccctggtgct aaacagctac gtgacaccca tctgcatcgc cgacaaggaa     1020
tacacgaaca tcttcctcaa attcggaagc ggctacgtaa gcggctgggg aagagtcttc     1080
cacaaaggga gaagcgccct ggtgctgcag tacctgagag tgccactggt ggaccgagcc     1140
acatgcctgc gaagcacaaa gttcaccatc tacaacaaca tgttctgcgc cggcttccac     1200
gaaggaggca gagacagctg ccaaggagac agcgggggac cccacgtgac cgaagtggaa     1260
gggaccagct tcctgaccgg aatcatcagc tggggcgaag agtgcgcaat gaaaggcaaa     1320
tacggaatat acaccaaggt aagccggtac gtcaactgga tcaaggaaaa aacaaagctc     1380
acctaa                                                                1386
```

<210> SEQ ID NO 52
<211> LENGTH: 1386
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

```
atgcagcgcg tgaacatgat catggcagaa tcaccaggcc tcatcaccat ctgcctttta       60
ggatatctac tcagtgctga atgtacagtt tttcttgatc atgaaaacgc caacaaaatt      120
ctgaatcggc caaagaggta taattcaggt aaattggaag agtttgttca agggaacctt      180
gagagagaat gtatggaaga aaagtgtagt tttgaagaag cacgagaagt ttttgaaaac      240
actgaaagaa caactgaatt ttggaagcag tatgttgatg gagatcagtg cgagagcaac      300
ccatgcctga acggcggcag ctgcaaggac gacatcaaca gctacgaatg ctggtgcccc      360
ttcggattcg aaggaaagaa ctgcgaactg gacgtaacat gcaacatcaa gaacggcaga      420
tgcgagcagt tctgcaaaaa cagcgccgac aacaaggtgg tgtgcagctg caccgaggga      480
taccgactgg cagaaaacca gaagtcctgc gaaccagcag tgccattccc atgcggaaga      540
gtgagcgtga gccaaaccag caagctcacc cgggccgaga ccgtgttccc cgacgtggac      600
tacgtaaaca gcaccgaagc cgaaaccatc ctggacaaca tcacccaaag cacccaaagc      660
ttcaacgact tcacccgggt ggtgggcgga gaagacgcca aaccaggcca attcccctgg      720
caggtggtgc tgaacggcaa agtggacgca ttctgcggag gcagcatcgt gaacgaaaaa      780
tggatcgtaa ccgccgccca ctgcgtggaa accggcgtga aaatcacagt ggtcgcaggc      840
gaacacaaca tcgaggagac agaacacaca gagcaaaagc gaaacgtgat ccgaatcatc      900
ccccaccaca actacaacgc agccatcaac aagtacaacc acgacatcgc cctgctggaa      960
ctggacgaac ccctggtgct aaacagctac gtgacaccca tctgcatcgc cgacaaggaa     1020
tacacgaaca tcttcctcaa attcggaagc ggctacgtaa gcggctgggg aagagtcttc     1080
cacaaaggga gaagcgccct ggtgctgcag tacctgagag tgccactggt ggaccgagcc     1140
acatgcctgc gaagcacaaa gttcaccatc tacaacaaca tgttctgcgc cggcttccac     1200
```

```
gaaggaggca gagacagctg ccaaggagac agcgggggac cccacgtgac cgaagtggaa   1260
gggaccagct tcctgaccgg aatcatcagc tggggcgaag agtgcgcaat gaaaggcaaa   1320
tacggaatat acaccaaggt aagccggtac gtcaactgga tcaaggaaaa aacaaagctc   1380
acctaa                                                               1386
```

<210> SEQ ID NO 53
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
atgcagcgcg tgaacatgat catggcagaa tcaccaggcc tcatcaccat ctgccttta     60 ggatatctac tcagtgctga atgtacagtt tttcttgatc atgaaaacgc caacaaaatt   120
ctgaatcggc caaagaggta taattcaggt aaattgaag agtttgttca agggaacctt    180
gagagagaat gtatggaaga aaagtgtagt tttgaagaag cacgagaagt ttttgaaaac   240
actgaaagaa caactgaatt ttggaagcag tatgttgatg gagatcagtg tgagtccaat   300
ccatgtttaa atggcggcag ttgcaaggat gacattaatt cctatgaatg ttggtgtccc   360
tttggatttg aaggaaagaa ctgtgaatta gatgtaacat gtaacattaa gaatggcaga   420
tgcgagcagt tttgtaaaaa tagtgctgat aacaaggtgg tgtgcagctg caccgaggga   480
taccgactgg cagaaaacca gaagtcctgc gaaccagcta tgccattccc atgcggaaga   540
gtgagcgtga gccaaaccag caagctcacc cgggccgaga ccgtgttccc cgacgtggac   600
tacgtaaaca gcaccgaagc cgaaaccatc ctggacaaca tcacccaaag cacccaaagc   660
ttcaacgact cacccgggt ggtgggcgga gaagacgcca accaggcca ttcccctgg     720 caggtggtgc tgaacggcaa agtggacgca ttctgcggag cagcatcgt gaacgaaaaa    780 tggatcgtaa ccgccgccca ctgcgtggaa accggcgtga aaatcacagt ggtcgcaggc   840
gaacacaaca tcgaggagac agaacacaca gagcaaaagc gaaacgtgat ccgaatcatc   900
ccccaccaca actacaacgc agccatcaac aagtacaacc acgacatcgc cctgctggaa   960
ctggacgaac ccctggtgct aaacagctac gtgacacca tctgcatcgc cgacaaggaa   1020
tacacgaaca tcttcctcaa attcggaagc ggctacgtaa gcggctgggg aagagtcttc   1080
cacaaaggga aagcgccct ggtgctgcag tacctgagag tgccactggt ggaccgagcc   1140
acatgcctgc gaagcacaaa gttcaccatc tacaacaaca tgttctgcgc cggcttccac   1200
gaaggaggca gagacagctg ccaaggagac agcgggggac cccacgtgac cgaagtggaa   1260
gggaccagct tcctgaccgg aatcatcagc tggggcgaag agtgcgcaat gaaaggcaaa   1320
tacggaatat acaccaaggt aagccggtac gtcaactgga tcaaggaaaa aacaaagctc   1380
acctaa                                                               1386
```

<210> SEQ ID NO 54
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

| | |
|---|---|
| atgcagcgcg tgaacatgat catggcagaa tcaccaggcc tcatcaccat ctgcctttta | 60 |
| ggatatctac tcagtgctga atgtacagtt tttcttgatc atgaaaacgc caacaaaatt | 120 |
| ctgaatcggc caaagaggta taattcaggt aaattggaag agtttgttca agggaacctt | 180 |
| gagagagaat gtatggaaga aaagtgtagt tttgaagaag cacgagaagt ttttgaaaac | 240 |
| actgaaagaa caactgaatt tggaagcag tatgttgatg gagatcagtg tgagtccaat | 300 |
| ccatgtttaa atggcggcag ttgcaaggat gacattaatt cctatgaatg ttggtgtccc | 360 |
| tttggatttg aaggaaagaa ctgtgaatta gatgtaacat gtaacattaa gaatggcaga | 420 |
| tgcgagcagt tttgtaaaaa tagtgctgat aacaaggtgg tttgctcctg tactgaggga | 480 |
| tatcgacttg cagaaaacca gaagtcctgt gaaccagcag tgccatttcc atgtggaaga | 540 |
| gtttctgttt cacaaacttc taagctcacc cgtgctgaga ctgttttttcc tgatgtggac | 600 |
| tatgtaaata gcaccgaagc cgaaaccatc ctggacaaca tcacccaaag cacccaaagc | 660 |
| ttcaacgact caccccgggt ggtgggcgga gaagacgcca aaccaggcca attcccctgg | 720 |
| caggtggtgc tgaacggcaa agtggacgca ttctgcggag cagcatcgt gaacgaaaaa | 780 |
| tggatcgtaa ccgccgccca ctgcgtggaa accggcgtga aaatcacagt ggtcgcaggc | 840 |
| gaacacaaca tcgaggagac agaacacaca gagcaaaagc gaaacgtgat ccgaatcatc | 900 |
| ccccaccaca actacaacgc agccatcaac aagtacaacc acgacatcgc cctgctggaa | 960 |
| ctggacgaac ccctggtgct aaacagctac gtgacaccca tctgcatcgc cgacaaggaa | 1020 |
| tacacgaaca tcttcctcaa attcggaagc ggctacgtaa gcggctgggg aagagtcttc | 1080 |
| cacaaaggga aagcgccct ggtgctgcag tacctgagag tgccactggt ggaccgagcc | 1140 |
| acatgcctgc gaagcacaaa gttcaccatc tacaacaaca tgttctgcgc cggcttccac | 1200 |
| gaaggaggca gagacagctg ccaaggagac agcgggggac ccacgtgac cgaagtggaa | 1260 |
| gggaccagct tcctgaccgg aatcatcagc tggggcgaag agtgcgcaat gaaaggcaaa | 1320 |
| tacggaatat acaccaaggt aagccggtac gtcaactgga tcaaggaaaa aacaaagctc | 1380 |
| acctaa | 1386 |

<210> SEQ ID NO 55
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

| | |
|---|---|
| atgcagcgcg tgaacatgat catggcagaa agcccaggcc tcatcaccat ctgcctgctg | 60 |
| ggataccctac tcagcgccga atgcacacgtg ttcctggacc acgaaaacgc caacaaaatc | 120 |
| ctgaaccggc caaagaggta caacagcggc aaactggaag agttcgtgca agggaacctg | 180 |
| gagagagaat gcatggaaga aaagtgcagc ttcgaagaag cacgagaagt gttcgaaaac | 240 |
| accgaaagaa caaccgaatt ctggaagcag tacgtggacg agaccagtg cgagagcaac | 300 |
| ccatgcctga acggcggcag ctgcaaggac gacatcaaca gctacgaatg ctggtgcccc | 360 |
| ttcggattcg aaggaaagaa ctgcgaactg gacgtaacat gcaacatcaa gaacggcaga | 420 |
| tgcgagcagt tctgcaaaaa cagcgccgac aacaaggtgg tgtgcagctg caccgaggga | 480 |
| taccgactgg cagaaaacca gaagtcctgc gaaccagcag tgccatttcc atgcggaaga | 540 |
| gtgagcgtga gccaaaccag caagctcacc cgggccgaga ccgtgttccc cgacgtggac | 600 |

| | |
|---|---|
| tacgtaaaca gcaccgaagc cgaaaccatc ctggacaaca tcacccaaag cacccaaagc | 660 |
| ttcaacgact tcacccgggt ggtgggcgga gaagacgcca aaccaggcca attcccctgg | 720 |
| caggtggtgc tgaacggcaa agtggacgca ttctgcggag gcagcatcgt gaacgaaaaa | 780 |
| tggatcgtaa ccgccgccca ctgcgtggaa accggcgtga aaatcacagt ggtcgcaggc | 840 |
| gaacacaaca tcgaggagac agaacacaca gagcaaaagc gaaacgtgat ccgaatcatc | 900 |
| ccccaccaca actacaacgc agccatcaac aagtacaacc acgacatcgc cctgctggaa | 960 |
| ctggacgaac ccctggtgct aaacagctac gtgacaccca tctgcatcgc cgacaaggaa | 1020 |
| tacacgaaca tcttcctcaa attcggaagc ggctacgtaa gcggctgggg aagagtcttc | 1080 |
| cacaaaggga gaagcgccct ggtgctgcag tacctgagag tgccactggt ggaccgagcc | 1140 |
| acatgcctgc gaagcacaaa gttcaccatc tacaacaaca tgttctgcgc cggcttccac | 1200 |
| gaaggaggca gagacagctg ccaaggagac agcgggggac cccacgtgac cgaagtggaa | 1260 |
| gggaccagct tcctgaccgg aatcatcagc tggggtgaag agtgtgcaat gaaaggcaaa | 1320 |
| tatggaatat ataccaaggt atcccggtat gtcaactgga ttaaggaaaa aacaaagctc | 1380 |
| acttaa | 1386 |

<210> SEQ ID NO 56
<211> LENGTH: 1386
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

| | |
|---|---|
| atgcagcgcg tgaacatgat catggcagaa agcccaggcc tcatcaccat ctgcctgctg | 60 |
| ggatacctac tcagcgccga atgcacagtg ttcctggacc acgaaaacgc caacaaaatc | 120 |
| ctgaaccggc aaagaggta caacagcggc aaactggaag agttcgtgca agggaacctg | 180 |
| gagagagaat gcatggaaga aaagtgcagc ttcgaagaag cacgagaagt gttcgaaaac | 240 |
| accgaaagaa caaccgaatt ctggaagcag tacgtggacg gagaccagtg cgagagcaac | 300 |
| ccatgcctga acggcggcag ctgcaaggac gacatcaaca gctacgaatg ctggtgcccc | 360 |
| ttcggattcg aaggaaagaa ctgcgaactg gacgtaacat gcaacatcaa gaacggcaga | 420 |
| tgcgagcagt tctgcaaaaa cagcgccgac aacaaggtgg tgtgcagctg caccgaggga | 480 |
| taccgactgg cagaaaacca gaagtcctgc gaaccagcag tgccattccc atgcggaaga | 540 |
| gtgagcgtga gccaaaccag caagctcacc cgggccgaga ccgtgttccc cgacgtggac | 600 |
| tacgtaaaca gcaccgaagc cgaaaccatc ctggacaaca tcacccaaag cacccaaagc | 660 |
| ttcaacgact tcacccgggt ggtgggcgga gaagacgcca aaccaggcca attcccctgg | 720 |
| caggtggtgc tgaacggcaa agtggacgca ttctgcggag gcagcatcgt gaacgaaaaa | 780 |
| tggatcgtaa ccgccgccca ctgcgtggaa accggcgtga aaatcacagt ggtcgcaggc | 840 |
| gaacacaaca tcgaggagac agaacacaca gagcaaaagc gaaacgtgat ccgaatcatc | 900 |
| ccccaccaca actacaacgc agccatcaac aagtacaacc acgacatcgc cctgctggaa | 960 |
| ctggacgaac ccctggtgct aaacagctac gtgacaccca tctgcatcgc cgacaaggaa | 1020 |
| tacacgaaca tcttcctcaa attcggaagc ggctacgtaa gcggctgggg aagagtcttc | 1080 |
| cacaaaggga gaagcgccct ggtgcttcag taccttagag ttccacttgt tgaccgagcc | 1140 |
| acatgtcttc gatctacaaa gttcaccatc tataacaaca tgttctgtgc tggcttccat | 1200 |

```
gaaggaggta gagattcatg tcaaggagat agtgggggac cccatgttac tgaagtggaa    1260
gggaccagtt tcttaactgg aattattagc tggggtgaag agtgtgcaat gaaaggcaaa    1320
tatggaatat ataccaaggt atcccggtat gtcaactgga ttaaggaaaa aacaaagctc    1380
acttaa                                                               1386
```

<210> SEQ ID NO 57
<211> LENGTH: 1386
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57

```
atgcagcgcg tgaacatgat catggcagaa agcccaggcc tcatcaccat ctgcctgctg      60
ggatacctac tcagcgccga atgcacagtg ttcctggacc acgaaaacgc caacaaaatc     120
ctgaaccggc aaagaggta caacagcggc aaactggaag agttcgtgca agggaacctg     180
gagagagaat gcatggaaga aaagtgcagc ttcgaagaag cacgagaagt gttcgaaaac     240
accgaaagaa caaccgaatt ctggaagcag tacgtggacg agaccagtg cgagagcaac     300 ccatgcctga acggcggcag ctgcaaggac gacatcaaca gctacgaatg ctggtgcccc     360
ttcggattcg aaggaaagaa ctgcgaactg gacgtaacat gcaacatcaa gaacggcaga     420
tgcgagcagt tctgcaaaaa cagcgccgac aacaaggtgg tgtgcagctg caccgaggga     480
taccgactgg cagaaaacca gaagtcctgc gaaccagcag tgccattccc atgcggaaga     540
gtgagcgtga gccaaaccag caagctcacc cgggccgaga ccgtgttccc cgacgtggac     600
tacgtaaaca gcaccgaagc cgaaaccatc ctggacaaca tcacccaaag cacccaaagc     660
ttcaacgact tcacccgggt ggtgggcgga gaagacgcca accaggcca ttcccctgg      720 caggtggtgc tgaacggcaa agtggacgca ttctgcggag cagcatcgt gaacgaaaaa     780 tggatcgtaa ccgccgccca ctgcgtggaa accggcgtga aaatcacagt ggtcgcaggc     840
gaacacaaca tcgaggagac agaacataca gagcaaaagc gaaatgtgat tcgaattatt     900
cctcaccaca actacaatgc agctattaat aagtacaacc atgacattgc ccttctggaa     960
ctggacgaac ccttagtgct aaacagctac gttacaccta tttgcattgc tgacaaggaa    1020
tacacgaaca tcttcctcaa atttggatct ggctatgtaa gtggctgggg aagagtcttc    1080
cacaaaggga gatcagcttt agttcttcag taccttagag ttccacttgt tgaccgagcc    1140
acatgtcttc gatctacaaa gttcaccatc tataacaaca tgttctgtgc tggcttccat    1200
gaaggaggta gagattcatg tcaaggagat agtgggggac cccatgttac tgaagtggaa    1260
gggaccagtt tcttaactgg aattattagc tggggtgaag agtgtgcaat gaaaggcaaa    1320
tatggaatat ataccaaggt atcccggtat gtcaactgga ttaaggaaaa aacaaagctc    1380
acttaa                                                               1386
```

<210> SEQ ID NO 58
<211> LENGTH: 1386
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
atgcagcgcg tgaacatgat catggcagaa agcccaggcc tcatcaccat ctgcctgctg      60
```

```
ggatacctac tcagcgccga atgcacagtg ttcctggacc acgaaaacgc caacaaaatc    120
ctgaaccggc caaagaggta caacagcggc aaactggaag agttcgtgca agggaacctg    180
gagagagaat gcatggaaga aaagtgcagc ttcgaagaag cacgagaagt gttcgaaaac    240
accgaaagaa caaccgaatt ctggaagcag tacgtggacg agaccagtg cgagagcaac     300 ccatgcctga acggcggcag ctgcaaggac gacatcaaca gctacgaatg ctggtgcccc    360
ttcggattcg aaggaaagaa ctgcgaactg acgtaacat gcaacatcaa gaacggcaga     420
tgcgagcagt tctgcaaaaa cagcgccgac aacaaggtgg tgtgcagctg caccgaggga    480
taccgactgg cagaaaacca gaagtcctgc gaaccagcag tgccattccc atgcggaaga    540
gtgagcgtga gccaaaccag caagctcacc cgggccgaga ccgtgttccc cgacgtggac    600
tacgtaaaca gcaccgaagc cgaaaccatc ctggacaaca tcacccaaag caccccaaagc   660 ttcaacgact tcacccgggt ggtgggcgga gaagacgcca accaggtca attcccttgg     720 caggttgttt tgaatggtaa agttgatgca ttctgtggag gctctatcgt taatgaaaaa    780
tggattgtaa ctgctgccca ctgtgttgaa actggtgtta aaattacagt tgtcgcaggt    840
gaacataata ttgaggagac agaacataca gagcaaaagc gaaatgtgat tcgaattatt    900
cctcaccaca actacaatgc agctattaat aagtacaacc atgacattgc ccttctggaa    960
ctggacgaac cttagtgct aaacagctac gttacaccta tttgcattgc tgacaaggaa    1020
tacacgaaca tcttcctcaa atttggatct ggctatgtaa gtggctgggg aagagtcttc    1080
cacaaaggga gatcagcttt agttcttcag taccttagag ttccacttgt tgaccgagcc    1140
acatgtcttc gatctacaaa gttcaccatc tataacaaca tgttctgtgc tggcttccat    1200
gaaggaggta gagattcatg tcaaggagat agtgggggac ccatgttac tgaagtggaa    1260 gggaccagtt tcttaactgg aattattagc tggggtgaag agtgtgcaat gaaaggcaaa    1320
tatggaatat ataccaaggt atcccggtat gtcaactgga ttaaggaaaa aacaaagctc    1380
acttaa                                                              1386
```

<210> SEQ ID NO 59
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
atgcagcgcg tgaacatgat catggcagaa agcccaggcc tcatcaccat ctgcctgctg     60
ggatatctac tcagcgccga atgcacagtg ttcctggacc acgaaaacgc caacaaaatc    120
ctgaaccggc caaagaggta caacagcggt aaactggaag agttcgtgca agggaacctg    180
gagagagaat gcatggaaga aaagtgcagc ttcgaagaag cacgagaagt gttcgaaaac    240
accgaaagaa caaccgaatt ctggaagcag tacgtggacg agaccagtg cgagagcaac     300 ccatgcctga acggcggcag ctgcaaggac gacatcaaca gctacgaatg ctggtgcccc    360
ttcggattcg aaggaaagaa ctgcgaactg acgtaacat gcaacatcaa gaacggcaga     420
tgcgagcagt tctgcaaaaa cagcgccgac aacaaggtgg tgtgcagctg caccgaggga    480
taccgacttg cagaaaacca gaagtcctgc gaaccagcag tgccattccc atgcggaaga    540
gtgagcgtta gccaaaccag caagctcacc cgggccgaga ccgtgttccc cgacgtggac    600
tacgtaaaca gcaccgaagc cgaaaccatc ctggacaaca tcacccaaag cacccaaagc    660
```

```
ttcaacgact tcacccgggt ggtgggcgga gaagacgcca aaccaggcca attcccctgg    720
caggtggtgc tgaacggcaa agtggacgca ttctgcggag gcagcatcgt taacgaaaaa    780
tggatcgtaa ccgccgccca ctgcgtggaa accggcgtga aaatcacagt ggtcgcaggc    840
gaacacaaca tcgaggagac agaacacaca gagcaaaagc gaaacgtgat ccgaatcatc    900
cctcaccaca actacaacgc agccatcaac aagtacaacc acgacatcgc cctgctggaa    960
ctggacgaac ccttagtgct aaacagctac gtgacaccca tctgcatcgc cgacaaggaa   1020
tacacgaaca tcttcctcaa attcggaagc ggctacgtaa gcggctgggg aagagtcttc   1080
cacaaaggga gaagcgccct ggtgctgcag tacctgagag tgccactggt ggaccgagcc   1140
acatgcctgc gaagcacaaa gttcaccatc tacaacaaca tgttctgcgc cggcttccac   1200
gaaggaggca gagacagctg ccaaggagac agcgggggac cccacgtgac cgaagtggaa   1260
gggaccagct tcctgaccgg aatcatcagc tggggcgaag agtgtgcaat gaaaggcaaa   1320
tacggaatat acaccaaggt aagccggtac gtcaactgga tcaaggaaaa aacaaagctc   1380
acctaa                                                              1386
```

<210> SEQ ID NO 60
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
atgcagcgcg tgaacatgat catggcagaa agcccaggcc tcatcaccat ctgcctgctg     60
ggatacctac tcagtgccga atgtacagtg ttcctggacc acgaaaacgc caacaaaatc    120
ctgaaccggc aaagaggta caactcaggc aaactggaag agttcgtgca agggaacctg    180
gagagagaat gcatggaaga aaagtgcagc ttcgaagaag cacgagaagt gtttgaaaac    240
actgaaagaa caaccgaatt ttggaagcag tacgtggatg gagatcagtg cgagagcaac    300
ccatgcctga atggcggcag ctgcaaggac gacatcaaca gctacgaatg ctggtgcccc    360
ttcggattcg aaggaaagaa ctgcgaactg gacgtaacat gcaacatcaa gaacggcaga    420
tgcgagcagt tttgtaaaaa cagcgccgac aacaaggtgg tgtgcagctg caccgaggga    480
taccgactgg cagaaaacca gaagtcctgc gaaccagcag tgccattccc atgcggaaga    540
gtgtctgtgt cacaaaccag caagctcacc cgggccgaga ccgtgttccc cgacgtggac    600
tacgtaaaca gcaccgaagc cgaaaccatc ctggataaca tcacccaaag cacccaaagc    660
ttcaatgact cacccgggt ggtgggcgga gaagacgcca aaccaggcca attcccctgg    720
caggttgtgc tgaacggcaa agttgacgca ttctgcggag gcagcatcgt gaacgaaaaa    780
tggatcgtaa ccgctgccca ctgcgttgaa accggcgtga aaatcacagt ggtcgcaggc    840
gaacacaaca ttgaggagac agaacacaca gagcaaaagc gaaacgtgat ccgaattatc    900
ccccaccaca actacaacgc agccattaat aagtacaacc atgacatcgc cctgctggaa    960
ctggacgaac ccttagtgct aaacagctac gtgacaccca tctgcatcgc cgacaaggaa   1020
tacacgaaca tcttcctcaa attcggaagc ggctacgtaa gcggctgggg aagagtcttc   1080
cacaaaggga gaagcgccct ggttctgcag tacctgagag tgccactggt tgaccgagcc   1140
acatgcctgc gaagcacaaa gttcaccatc tacaacaaca tgttctgcgc cggcttccat   1200
gaaggaggta gagacagctg tcaaggagac agcgggggac cccacgttac tgaagtggaa   1260
```

```
gggaccagct tcctgaccgg aatcatcagc tggggcgaag agtgcgcaat gaaaggcaaa    1320
tacggaatat ataccaaggt aagccggtac gtcaactgga tcaaggaaaa aacaaagctc    1380
acttaa                                                               1386
```

<210> SEQ ID NO 61
<211> LENGTH: 1386
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61

```
atgcagcgcg tgaacatgat catggcagaa tcaccaggcc tcatcaccat ctgcctgtta      60
ggatacctac tcagcgccga atgtacagtg tttcttgacc acgaaaacgc caacaaaatc     120
ctgaatcggc caaagaggta taactcaggt aaactggaag agtttgtgca agggaacctg     180
gagagagaat gcatggaaga aaagtgcagc ttcgaagaag cacgagaagt gttcgaaaac     240
actgaaagaa caaccgaatt ttggaagcag tatgtggatg gagaccagtg cgagtccaac     300
ccatgcttaa acggcggcag ttgcaaggac gacatcaaca gctatgaatg ctggtgcccc     360
ttcggatttg aaggaaagaa ctgcgaactg gacgtaacat gtaacatcaa gaatggcaga     420
tgcgagcagt tctgtaaaaa tagcgccgac aacaaggtgg tgtgcagctg taccgaggga     480
taccgactgg cagaaaacca gaagtcctgc gaaccagcag tgccattccc atgcggaaga     540
gttagcgtga gccaaaccag caagctcacc cgggccgaga ccgtgttccc tgacgtggac     600
tacgtaaact ctaccgaagc tgaaaccatc ctggacaaca tcactcaaag cacccaatca     660
ttcaacgact caccgggt ggtgggcgga gaagatgcca aaccaggtca attcccttgg     720
caggtggtgt tgaacggcaa agtggacgca ttctgtggag gcagcatcgt gaacgaaaaa     780
tggatcgtaa ctgccgccca ctgcgtggaa accggcgtga aaatcacagt ggtcgcaggc     840
gaacacaata ttgaggagac agaacacaca gagcaaaagc gaaatgtgat ccgaattatc     900
cctcaccaca actacaacgc agctattaac aagtacaacc acgacattgc cctgctggaa     960
ctggacgaac ccctggtgct aaacagctac gttacaccta tctgcatcgc cgacaaggaa    1020
tacacgaaca tcttcctcaa attcggatct ggctacgtaa gcggctgggg aagagtcttc    1080
cacaaaggga atcagccct ggtgcttcag taccttagag tgccacttgt ggaccgagcc    1140
acatgcctgc gaagcacaaa gttcaccatc tacaacaaca tgttctgtgc tggcttccac    1200
gaaggaggta gagacagctg tcaaggagat agcggggac cccacgttac cgaagtggaa    1260
gggaccagct tcttaactgg aatcatcagc tggggcgaag agtgcgcaat gaaaggcaaa    1320
tacggaatat acaccaaggt atcccggtat gtcaactgga tcaaggaaaa aacaaagctc    1380
acctaa                                                              1386
```

<210> SEQ ID NO 62
<211> LENGTH: 1386
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62

```
atgcagcgcg tgaacatgat catggcagaa agcccaggcc tcatcaccat ctgccttctg      60
```

| | |
|---|---|
| ggatatctac tcagcgccga atgcacagtt ttccttgacc acgaaaacgc caacaaaatc | 120 |
| ctgaatcggc caaagaggta taattcaggt aaactggaag agtttgttca agggaacctt | 180 |
| gagagagaat gcatggaaga aaagtgtagt tttgaagaag cacgagaagt gttcgaaaac | 240 |
| accgaaagaa caaccgaatt ttggaagcag tatgtggatg agaccagtg cgagagcaat | 300 |
| ccatgcttaa atggcggcag ctgcaaggac gacattaatt cctatgaatg ctggtgcccc | 360 |
| tttggattcg aaggaaagaa ctgcgaatta gacgtaacat gcaacatcaa gaacggcaga | 420 |
| tgcgagcagt tttgtaaaaa tagtgctgac aacaaggtgg tttgcagctg caccgaggga | 480 |
| taccgactgg cagaaaacca gaagtcctgc gaaccagcag tgccattccc atgtggaaga | 540 |
| gtttctgtga gccaaacttc taagctcacc cgtgccgaga ccgttttccc tgacgtggac | 600 |
| tatgtaaatt ctaccgaagc cgaaaccatt ttggataaca tcacccaaag cacccaaagc | 660 |
| tttaacgact tcactcgggt ggttggcgga gaagacgcca aaccaggcca attcccttgg | 720 |
| caggtggttc tgaatggcaa agtggatgca ttctgtggag gctctatcgt gaacgaaaaa | 780 |
| tggatcgtaa ctgccgccca ctgcgttgaa accggcgtta aaattacagt ggtcgcaggc | 840 |
| gaacacaata ttgaggagac agaacacaca gagcaaaagc gaaacgtgat tcgaattatc | 900 |
| cctcaccaca actacaatgc agccattaac aagtacaacc atgacatcgc cctgctggaa | 960 |
| ctggacgaac ccctggtgct aaacagctac gttacaccta tttgcatcgc cgacaaggaa | 1020 |
| tacacgaaca tcttcctcaa atttggatct ggctatgtaa gcggctgggg aagagtcttc | 1080 |
| cacaaaggga aagcgcccct ggtgcttcag tacctgagag tgccacttgt ggaccgagcc | 1140 |
| acatgtctgc gaagcacaaa gttcaccatc tacaacaaca tgttctgcgc cggcttccac | 1200 |
| gaaggaggta gagactcatg ccaaggagat agcgggggac cccacgtgac cgaagtggaa | 1260 |
| gggaccagct tcctgactgg aattattagc tggggcgaag agtgcgcaat gaaaggcaaa | 1320 |
| tatggaatat acaccaaggt aagccggtat gtcaactgga tcaaggaaaa aacaaagctc | 1380 |
| acctaa | 1386 |

<210> SEQ ID NO 63
<211> LENGTH: 1818
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 63

| | |
|---|---|
| aggaaactta agtcaacaca acatatacaa aacaaacgaa tctcaagcaa tcaagcattc | 60 |
| tacttctatt gcagcaattt aaatcatttc ttttaaagca aaagcaattt tctgaaaatt | 120 |
| ttcaccattt acgaacgata gccatgcagc gcgtgaacat gatcatggca gaaagcccag | 180 |
| gcctcatcac catctgcctg ctgggatacc tactcagcgc cgaatgcaca gtgttcctgg | 240 |
| accacgaaaa cgccaacaaa atcctgaacc ggccaaagag gtacaacagc ggcaaactgg | 300 |
| aagagttcgt gcaagggaac ctggagagag aatgcatgga agaaaagtgc agcttcgaag | 360 |
| aagcacgaga agtgttcgaa aacaccgaaa gaacaaccga attctggaag cagtacgtgg | 420 |
| acggagacca gtgcgagagc aacccatgcc tgaacgcgg cagctgcaag gacgacatca | 480 |
| acagctacga atgctggtgc cccttcggat tcgaaggaaa gaactgcgaa ctggacgtaa | 540 |
| catgcaacat caagaacggc agatgcgagc agttctgcaa aaacagcgcc gacaacaagg | 600 |
| tggtgtgcag ctgcaccgag ggataccgac tggcagaaaa ccagaagtcc tgcgaaccag | 660 |

```
cagtgccatt cccatgcgga agagtgagcg tgagccaaac cagcaagctc acccgggccg    720
agaccgtgtt ccccgacgtg gactacgtaa acagcaccga agccgaaacc atcctggaca    780
acatcaccca aagcacccaa agcttcaacg acttcacccg ggtggtgggc ggagaagacg    840
ccaaaccagg ccaattcccc tggcaggtgg tgctgaacgg caaagtggac gcattctgcg    900
gaggcagcat cgtgaacgaa aaatggatcg taaccgccgc ccactgcgtg aaaccggcg    960 tgaaaatcac agtggtcgca ggcgaacaca acatcgagga gacagaacac acagagcaaa   1020
agcgaaacgt gatccgaatc atcccccacc acaactacaa cgcagccatc aacaagtaca   1080
accacgacat cgccctgctg gaactggacg aaccccgggt gctaaacagc tacgtgacac   1140
ccatctgcat cgccgacaag gaatacacga acatcttcct caaattcgga agcggctacg   1200
taagcggctg gggaagagtc ttccacaaag ggagaagcgc cctggtgctg cagtacctga   1260
gagtgccact ggtggaccga gccacatgcc tgcgaagcac aaagttcacc atctacaaca   1320
acatgttctg cgccggcttc cacgaaggag gcagagacag ctgccaagga gacagcgggg   1380
gaccccacgt gaccgaagtg gaagggacca gcttcctgac cggaatcatc agctggggcg   1440
aagagtgcgc aatgaaaggc aaatacggaa tatacaccaa ggtaagccgg tacgtcaact   1500
ggatcaagga aaaacaaag ctcacctaac tcgagctagt gactgactag gatctggtta   1560
ccactaaacc agcctcaaga cacccgaat ggagtctcta agctacataa taccaactta   1620
cacttacaaa atgttgtccc ccaaaatgta gccattcgta tctgctccta ataaaagaa   1680 agtttcttca cattctagaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaa                                                 1818
```

<210> SEQ ID NO 64
<211> LENGTH: 1818
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64

```
aggaaactta agtcaacaca acatatacaa aacaaacgaa tctcaagcaa tcaagcattc     60
tacttctatt gcagcaattt aaatcatttc ttttaaagca aaagcaattt tctgaaaatt    120
ttcaccattt acgaacgata gccatgcagc gcgtgaacat gatcatggca gaatcaccag    180
gcctcatcac catctgcctt ttaggatatc tactcagtgc tgaatgtaca gttttcctgg    240
accacgaaaa cgccaacaaa atcctgaacc ggccaaagag gtacaacagc ggcaaactgg    300
aagagttcgt gcaagggaac ctggagagag aatgcatgga agaaaagtgc agcttcgaag    360
aagcacgaga agtgttcgaa aacaccgaaa gaacaaccga attctggaag cagtacgtgg    420
acggagacca gtgcgagagc aacccatgcc tgaacggcgg cagctgcaag gacgacatca    480
acagctacga atgctggtgc cccttcggat tcgaaggaaa gaactgcgaa ctggacgtaa    540
catgcaacat caagaacggc agatgcgagc agttctgcaa aaacagcgcc gacaacaagg    600
tggtgtgcag ctgcaccgag ggataccgac tggcagaaaa ccagaagtcc tgcgaaccag    660
cagtgccatt cccatgcgga agagtgagcg tgagccaaac cagcaagctc acccgggccg    720
agaccgtgtt ccccgacgtg gactacgtaa acagcaccga agccgaaacc atcctggaca    780
acatcaccca aagcacccaa agcttcaacg acttcacccg ggtggtgggc ggagaagacg    840
```

```
ccaaaccagg ccaattcccc tggcaggtgg tgctgaacgg caaagtggac gcattctgcg      900
gaggcagcat cgtgaacgaa aaatggatcg taaccgccgc ccactgcgtg gaaaccggcg      960
tgaaaatcac agtggtcgca ggcgaacaca acatcgagga gacagaacac acagagcaaa     1020
agcgaaacgt gatccgaatc atcccccacc acaactacaa cgcagccatc aacaagtaca     1080
accacgacat cgccctgctg gaactggacg aacccctggt gctaaacagc tacgtgacac     1140
ccatctgcat cgccgacaag gaatacgacga acatcttcct caaattcgga agcggctacg     1200
taagcggctg gggaagagtc ttccacaaag ggagaagcgc cctggtgctg cagtacctga     1260
gagtgccact ggtggaccga gccacatgcc tgcgaagcac aaagttcacc atctacaaca     1320
acatgttctg cgccggcttc cacgaaggag gcagagacag ctgccaagga gacagcgggg     1380
gaccccacgt gaccgaagtg gaagggacca gcttcctgac cggaatcatc agctggggcg     1440
aagagtgcgc aatgaaaggc aaatacggaa tatacaccaa ggtaagccgg tacgtcaact     1500
ggatcaagga aaaacaaag ctcacctaac tcgagctagt gactgactag gatctggtta     1560
ccactaaacc agcctcaaga cacccgaat ggagtctcta agctacataa taccaactta     1620
cacttacaaa atgttgtccc ccaaaatgta gccattcgta tctgctccta ataaaaagaa     1680
agtttcttca cattctagaa aaaaaaaaaa aaaaaaaaaa aaaaaaaaaa aaaaaaaaaa     1740
aaaaaaaaaa aaaaaaaaaa aaaaaaaaaa aaaaaaaaaa aaaaaaaaaa aaaaaaaaaa     1800
aaaaaaaaaa aaaaaaaa                                                   1818
```

<210> SEQ ID NO 65
<211> LENGTH: 1818
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
aggaaactta agtcaacaca acatatacaa aacaaacgaa tctcaagcaa tcaagcattc       60
tacttctatt gcagcaattt aaatcatttc ttttaaagca aaagcaattt tctgaaaatt      120
ttcaccattt acgaacgata gccatgcagc gcgtgaacat gatcatggca gaatcaccag      180
gcctcatcac catctgcctt ttaggatatc tactcagtgc tgaatgtaca gttttcttg      240 atcatgaaaa cgccaacaaa attctgaatc ggccaaagag gtataattca ggtaaattgg      300
aagagtttgt tcaagggaac cttgagagag aatgtatgga agaaaagtgt agttttgaag      360
aagcacgaga agttttttgaa aacactgaaa gaacaactga attttggaag cagtatgttg      420
atggagatca gtgcgagagc aacccatgcc tgaacggcgg cagctgcaag gacgacatca      480
acagctacga atgctggtgc cccttcggat tcgaaggaaa gaactgcgaa ctggacgtaa      540
catgcaacat caagaacggc agatgcgagc agttctgcaa aaacagcgcc gacaacaagg      600
tggtgtgcag ctgcaccgag ggataccgac tggcagaaaa ccagaagtcc tgcgaaccag      660
cagtgccatt cccatgcgga agagtgagcg tgagccaaac cagcaagctc acccgggccg      720
agaccgtgtt ccccgacgtg gactacgtaa acagcaccga agccgaaacc atcctggaca      780
acatcaccca agcacccaa agcttcaacg acttcacccg ggtggtgggc ggagaagacg      840
ccaaaccagg ccaattcccc tggcaggtgg tgctgaacgg caaagtggac gcattctgcg      900
gaggcagcat cgtgaacgaa aaatggatcg taaccgccgc ccactgcgtg gaaaccggcg      960
tgaaaatcac agtggtcgca ggcgaacaca acatcgagga gacagaacac acagagcaaa     1020
```

```
agcgaaacgt gatccgaatc atcccccacc acaactacaa cgcagccatc aacaagtaca    1080
accacgacat cgccctgctg gaactggacg aaccccctggt gctaaacagc tacgtgacac    1140
ccatctgcat cgccgacaag gaatacacga acatcttcct caaattcgga agcggctacg    1200
taagcggctg gggaagagtc ttccacaaag ggagaagcgc cctggtgctg cagtacctga    1260
gagtgccact ggtggaccga gccacatgcc tgcgaagcac aaagttcacc atctacaaca    1320
acatgttctg cgccggcttc cacgaaggag gcagagacag ctgccaagga gacagcgggg    1380
gaccccacgt gaccgaagtg aagggaccga gcttcctgac cggaatcatc agctggggcg    1440
aagagtgcgc aatgaaaggc aaatacgaaa tataccacaa ggtaagccgg tacgtcaact    1500
ggatcaagga aaaaacaaag ctcacctaac tcgagctagt gactgactag gatctggtta    1560
ccactaaacc agcctcaaga acacccgaat ggagtctcta agctacataa taccaactta    1620
cacttacaaa atgttgtccc ccaaaatgta gccattcgta tctgctccta ataaaaagaa    1680
agtttcttca cattctagaa aaaaaaaaaa aaaaaaaaaa aaaaaaaaaa aaaaaaaaa    1740 aaaaaaaaaa aaaaaaaaaa aaaaaaaaaa aaaaaaaaaa aaaaaaaaaa aaaaaaaaaa    1800
aaaaaaaaaa aaaaaaaa                                                 1818
```

<210> SEQ ID NO 66
<211> LENGTH: 1818
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

```
aggaaactta agtcaacaca acatatacaa aacaaacgaa tctcaagcaa tcaagcattc      60
tacttctatt gcagcaattt aaatcatttc tttaaagca aaagcaattt tctgaaaatt    120
ttcaccattt acgaacgata gccatggcagc gcgtgaacat gatcatggca gaatcaccag    180
gcctcatcac catctgcctt ttaggatatc tactcagtgc tgaatgtaca gttttcttg    240 atcatgaaaa cgccaacaaa attctgaatc ggccaaagag gtataattca ggtaaattgg    300
aagagtttgt tcaagggaac cttgagagag aatgtatgga agaaaagtgt agttttgaag    360
aagcacgaga agttttttgaa aacactgaaa gaacaactga attttggaag cagtatgttg    420
atggagatca gtgtgagtcc aatccatgtt taaatggcgg cagttgcaag gatgacatta    480
attcctatga atgttggtgt ccctttggat ttgaggaaaa gaactgtgaa ttagatgtaa    540
catgtaacat taagaatggc agatgcgagc agttttgtaa aaatagtgct gataacaagg    600
tggtgtgcag ctgcaccgag ggataccgac tggcagaaaa ccagaagtcc tgcgaaccag    660
cagtgccatt cccatgcgga agagtgagcg tgagccaaac cagcaagctc acccgggccg    720
agaccgtgtt ccccgacgtg gactacgtaa acagcaccga agccgaaacc atcctggaca    780
acatcaccca agcacccaa agcttcaacg acttcacccg gtggtgggc ggagaagacg    840 ccaaaccagg ccaattcccc tggcaggtgg tgctgaacgg caaagtggac gcattctgcg    900
gaggcagcat cgtgaacgaa aaatggatcg taaccgccgc ccactgcgtg gaaaccggcg    960
tgaaaatcac agtggtcgca ggcgaacaca acatcgagga gacagaacac acagagcaaa    1020
agcgaaacgt gatccgaatc atcccccacc acaactacaa cgcagccatc aacaagtaca    1080
accacgacat cgccctgctg gaactggacg aaccccctggt gctaaacagc tacgtgacac    1140
ccatctgcat cgccgacaag gaatacacga acatcttcct caaattcgga agcggctacg    1200
```

| | | |
|---|---|---|
| taagcggctg gggaagagtc ttccacaaag ggagaagcgc cctggtgctg cagtacctga | 1260 | |
| gagtgccact ggtggaccga gccacatgcc tgcgaagcac aaagttcacc atctacaaca | 1320 | |
| acatgttctg cgccggcttc cacgaaggag gcagagacag ctgccaagga gacagcgggg | 1380 | |
| gaccccacgt gaccgaagtg aagggacca gcttcctgac cggaatcatc agctggggcg | 1440 | |
| aagagtgcgc aatgaaaggc aaatacggaa tatacaccaa ggtaagccgg tacgtcaact | 1500 | |
| ggatcaagga aaaacaaag ctcacctaac tcgagctagt gactgactag gatctggtta | 1560 | |
| ccactaaacc agcctcaaga cacccgaat ggagtctcta agctacataa taccaactta | 1620 | |
| cacttacaaa atgttgtccc ccaaaatgta gccattcgta tctgctccta ataaaaagaa | 1680 | |
| agtttcttca cattctagaa aaaaaaaaaa aaaaaaaaaa aaaaaaaaaa aaaaaaaaaa | 1740 | |
| aaaaaaaaaa aaaaaaaaaa aaaaaaaaaa aaaaaaaaaa aaaaaaaaaa aaaaaaaaaa | 1800 | |
| aaaaaaaaaa aaaaaaaa | 1818 | |

<210> SEQ ID NO 67
<211> LENGTH: 1818
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

| | | |
|---|---|---|
| aggaaactta agtcaacaca acatatacaa acaaacgaa tctcaagcaa tcaagcattc | 60 | |
| tacttctatt gcagcaattt aaatcatttc ttttaaagca aaagcaattt tctgaaaatt | 120 | |
| ttcaccattt acgaacgata gccatgcagc gcgtgaacat gatcatggca gaatcaccag | 180 | |
| gcctcatcac catctgcctt ttaggatatc tactcagtgc tgaatgtaca gttttcttg | 240 | |
| atcatgaaaa cgccaacaaa attctgaatc ggccaaagag gtataattca ggtaaattgg | 300 | |
| aagagtttgt tcaagggaac cttgagagag aatgtatgga agaaaagtgt agttttgaag | 360 | |
| aagcacgaga agttttttgaa aacactgaaa gaacaactga atttttggaag cagtatgttg | 420 | |
| atggagatca gtgtgagtcc aatccatgtt taaatggcgg cagttgcaag gatgacatta | 480 | |
| attcctatga atgttggtgt cccttttggat ttgaaggaaa gaactgtgaa ttagatgtaa | 540 | |
| catgtaacat taagaatggc agatgcgagc agttttgtaa aaatagtgct gataacaagg | 600 | |
| tggtttgctc ctgtactgag ggatatcgac ttgcagaaaa ccagaagtcc tgtgaaccag | 660 | |
| cagtgccatt tccatgtgga agagtttctg tttcacaaac ttctaagctc acccgtgctg | 720 | |
| agactgtttt tcctgatgtg gactatgtaa atagcaccga agccgaaacc atcctggaca | 780 | |
| acatcaccca aagcacccaa agcttcaacg acttcacccg ggtggtgggc ggagaagacg | 840 | |
| ccaaccagc ccaattcccc tggcaggtgg tgctgaacgg caaagtggac gcattctgcg | 900 | |
| gaggcagcat cgtgaacgaa aaatggatcg taaccgccgc ccactgcgtg gaaaccggcg | 960 | |
| tgaaaatcac agtggtcgca ggcgaacaca acatcgagga gacagaacac acagagcaaa | 1020 | |
| agcgaaacgt gatccgaatc atcccccacc acaactacaa cgcagccatc aacaagtaca | 1080 | |
| accacgacat cgccctgctg gaactggacg aaccctggt gctaaacagc tacgtgacac | 1140 | |
| ccatctgcat cgccgacaag gaatacacga acatcttcct caaattcgga agcggctacg | 1200 | |
| taagcggctg gggaagagtc ttccacaaag ggagaagcgc cctggtgctg cagtacctga | 1260 | |
| gagtgccact ggtggaccga gccacatgcc tgcgaagcac aaagttcacc atctacaaca | 1320 | |
| acatgttctg cgccggcttc cacgaaggag gcagagacag ctgccaagga gacagcgggg | 1380 | |

```
gaccccacgt gaccgaagtg aagggacca gcttcctgac cggaatcatc agctggggcg    1440
aagagtgcgc aatgaaaggc aaatacgaaa tatacaccaa ggtaagccgg tacgtcaact    1500
ggatcaagga aaaaacaaag ctcacctaac tcgagctagt gactgactag gatctggtta    1560
ccactaaacc agcctcaaga acacccgaat ggagtctcta agctacataa taccaactta    1620
cacttacaaa atgttgtccc ccaaaatgta gccattcgta tctgctccta ataaaaagaa    1680
agtttcttca cattctagaa aaaaaaaaaa aaaaaaaaaa aaaaaaaaaa aaaaaaaaa     1740 aaaaaaaaaa aaaaaaaaaa aaaaaaaaaa aaaaaaaaaa aaaaaaaaaa aaaaaaaaaa    1800
aaaaaaaaaa aaaaaaaa                                                  1818
```

<210> SEQ ID NO 68
<211> LENGTH: 1818
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
aggaaactta agtcaacaca acatatacaa aacaaacgaa tctcaagcaa tcaagcattc      60
tacttctatt gcagcaattt aaatcatttc ttttaaagca aaagcaattt tctgaaaatt     120
ttcaccattt acgaacgata gccatgcagc gcgtgaacat gatcatggca gaaagcccag     180
gcctcatcac catctgcctg ctgggatacc tactcagcgc cgaatgcaca gtgttcctgg     240
accacgaaaa cgccaacaaa atcctgaacc ggccaaagag gtacaacagc ggcaaactgg     300
aagagttcgt gcaagggaac ctggagagag aatgcatgga agaaaagtgc agcttcgaag     360
aagcacgaga agtgttcgaa acaccgaaa gaacaaccga attctggaag cagtacgtgg      420
acggagacca gtgcgagagc aacccatgcc tgaacggcgg cagctgcaag gacgcatca      480 acagctacga atgctggtgc cccttcggat cgaaggaaa gaactgcgaa ctggacgtaa      540
catgcaacat caagaacggc agatgcgagc agttctgcaa aaacagcgcc gacaacaagg     600
tggtgtgcag ctgcaccgag ggataccgac tggcagaaaa ccagaagtcc tgcgaaccag     660
cagtgccatt cccatgcgga agagtgagcg tgagccaaac cagcaagctc acccgggccg     720
agaccgtgtt ccccgacgtg gactacgtaa acagcaccga agccgaaacc atcctggaca     780
acatcaccca aagcacccaa agcttcaacg acttcacccg ggtggtgggc ggagaagacg     840
ccaaaccagg ccaattcccc tggcaggtgg tgctgaacgg caagtggac gcattctgcg      900 gaggcagcat cgtgaacgaa aaatggatcg taaccgccgc ccactgcgtg gaaaccggcg     960
tgaaaatcac agtggtcgca ggcgaacaca cactcgagga acagaacac acagagcaaa    1020 agcgaaacgt gatccgaatc atcccccacc acaactacaa cgcagccatc aacaagtaca    1080
accacgacat cgccctgctg gaactggacg aaccctggt gctaaacagc tacgtgacac     1140
ccatctgcat cgccgacaag gaatacacga acatcttcct caaattcgga agcggctacg    1200
taagcggctg gggaagagtc ttccacaaag ggagaagcgc cctggtgctg cagtacctga    1260
gagtgccact ggtggaccga gccacatgcc tgcgaagcac aaagttcacc atctacaaca    1320
acatgttctg cgccggcttc cacgaaggag gcagagacag ctgccaagga gacagcgggg    1380
gaccccacgt gaccgaagtg aagggaccag cttcctgac cggaatcatc agctggggtg     1440
aagagtgtgc aatgaaaggc aaatatgaaa tatataccaa ggtatcccgg tatgtcaact    1500
ggattaagga aaaaacaaag ctcacttaac tcgagctagt gactgactag gatctggtta    1560
```

```
ccactaaacc agcctcaaga acacccgaat ggagtctcta agctacataa taccaactta    1620
cacttacaaa atgttgtccc ccaaaatgta gccattcgta tctgctccta ataaaaagaa    1680
agtttcttca cattctagaa aaaaaaaaaa aaaaaaaaaa aaaaaaaaaa aaaaaaaaaa    1740
aaaaaaaaaa aaaaaaaaaa aaaaaaaaaa aaaaaaaaaa aaaaaaaaaa aaaaaaaaaa    1800
aaaaaaaaaa aaaaaaaa                                                 1818
```

<210> SEQ ID NO 69
<211> LENGTH: 1818
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
aggaaactta agtcaacaca acatatacaa acaaacgaa tctcaagcaa tcaagcattc      60
tacttctatt gcagcaattt aaatcatttc ttttaaagca aaagcaattt tctgaaaatt    120
ttcaccattt acgaacgata gccatgcagc gcgtgaacat gatcatggca gaaagcccag    180
gcctcatcac catctgcctg ctgggatacc tactcagcgc cgaatgcaca gtgttcctgg    240
accacgaaaa cgccaacaaa atcctgaacc ggccaaagag gtacaacagc ggcaaactgg    300
aagagttcgt gcaagggaac ctggagagag aatgcatgga agaaaagtgc agcttcgaag    360
aagcacgaga agtgttcgaa aacaccgaaa gaacaaccga attctggaag cagtacgtgg    420
acggagacca gtgcgagagc aacccatgcc tgaacggcgg cagctgcaag gacgacatca    480
acagctacga atgctggtgc cccttcggat tcgaaggaaa gaactgcgaa ctggacgtaa    540
catgcaacat caagaacggc agatgcgagc agttctgcaa aaacagcgcc gacaacaagg    600
tggtgtgcag ctgcaccgag ggataccgac tggcagaaaa ccagaagtcc tgcgaaccag    660
cagtgccatt cccatgcgga agagtgagcg tgagccaaac cagcaagctc acccgggccg    720
agaccgtgtt ccccgacgtg gactacgtaa acagcaccga agccgaaacc atcctggaca    780
acatcaccca aagcacccaa agcttcaacg acttcacccg ggtggtgggc ggagaagacg    840
ccaaaccagg ccaattcccc tggcaggtgg tgctgaacgg caaagtggac gcattctgcg    900
gaggcagcat cgtgaacgaa aaatggatcg taaccgccgc ccactgcgtg gaaaccggcg    960
tgaaaatcac agtggtcgca ggcgaacaca acatcgagga gacagaacac acagagcaaa   1020
agcgaaacgt gatccgaatc atcccccacc acaactacaa cgcagccatc aacaagtaca   1080
accacgacat cgccctgctg gaactggacg aaccctggt gctaaacagc tacgtgacac    1140
ccatctgcat cgccgacaag gaatacacga acatcttcct caaattcgga agcggctacg   1200
taagcggctg gggaagagtc ttccacaaag ggagaagcgc cctggtgctt cagtaccttag   1260 gagttccact tgttgaccga gccacatgtc ttcgatctac aaagttcacc atctataaca    1320
acatgttctg tgctggcttc catgaaggag gtagagattc atgtcaagga gatagtgggg   1380
gaccccatgt tactgaagtg aagggacca gtttcttaac tggaattatt agctggggtg    1440
aagagtgtgc aatgaaaggc aaatatggaa tatataccaa ggtatcccgg tatgtcaact   1500
ggattaagga aaaaacaaag ctcacttaac tcgagctagt gactgactag gatctggtta   1560
ccactaaacc agcctcaaga acacccgaat ggagtctcta agctacataa taccaactta    1620
cacttacaaa atgttgtccc ccaaaatgta gccattcgta tctgctccta ataaaaagaa    1680
agtttcttca cattctagaa aaaaaaaaaa aaaaaaaaaa aaaaaaaaaa aaaaaaaaaa    1740
```
aaaaaaaaaa aaaaaaaaa aaaaaaaaaa aaaaaaaaaa aaaaaaaaaa aaaaaaaaaa    1800
aaaaaaaaaa aaaaaaaa                                                 1818

<210> SEQ ID NO 70
<211> LENGTH: 1818
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
aggaaactta agtcaacaca acatatacaa aacaaacgaa tctcaagcaa tcaagcattc      60
tacttctatt gcagcaattt aaatcatttc ttttaaagca aaagcaattt tctgaaaatt     120
ttcaccattt acgaacgata gccatgcagc gcgtgaacat gatcatggca gaaagcccag     180
gcctcatcac catctgcctg ctgggatacc tactcagcgc cgaatgcaca gtgttcctgg     240
accacgaaaa cgccaacaaa atcctgaacc ggccaaagag gtacaacagc ggcaaactgg     300
aagagttcgt gcaagggaac ctggagagag aatgcatgga agaaaagtgc agcttcgaag     360
aagcacgaga gtgttcgaa aacaccgaaa gaacaaccga attctggaag cagtacgtgg      420
acggagacca gtgcgagagc aacccatgcc tgaacggcgg cagctgcaag gacgacatca     480
acagctacga atgctggtgc cccttcggat tcgaaggaaa gaactgcgaa ctggacgtaa     540
catgcaacat caagaacggc agatgcgagc agttctgcaa aacagcgcc gacaacaagg      600 tggtgtgcag ctgcaccgag ggataccgac tggcagaaaa ccagaagtcc tgcgaaccag     660
cagtgccatt cccatgcgga agagtgagcg tgagccaaac cagcaagctc acccgggccg     720
agaccgtgtt ccccgacgtg gactacgtaa acagcaccga agccgaaacc atcctggaca     780
acatcaccca aagcacccaa agcttcaacg acttcacccg ggtggtgggc ggagaagacg     840
ccaaaccagg ccaattcccc tggcaggtgg tgctgaacgg caaagtggac gcattctgcg     900
gaggcagcat cgtgaacgaa aaatggatcg taaccgccgc ccactgcgtg gaaaccggcg     960
tgaaaatcac agtggtcgca ggcgaacaca catcgagga cagaacat acagagcaaa       1020 agcgaaatgt gattcgaatt attcctcacc acaactacaa tgcagctatt aataagtaca     1080
accatgacat tgcccttctg gaactggacg aacccttagt gctaaacagc tacgttacac     1140
ctatttgcat tgctgacaag gaatacacga acatcttcct caaatttgga tctggctatg     1200
taagtggctg gggaagagtc ttccacaaag ggagatcagc tttagttctt cagtaccta     1260 gagttccact tgttgaccga gccacatgtc ttcgatctac aaagttcacc atctataaca     1320
acatgttctg tgctggcttc catgaaggag gtagagattc atgtcaagga gatagtgggg     1380
gaccccatgt tactgaagtg gaagggacca gttttcttaac tggaattatt agctggggtg     1440
aagagtgtgc aatgaaaggc aaatatggaa tataccaa ggtatcccgg tatgtcaact       1500
ggattaagga aaaacaaag ctcacttaac tcgagctagt gactgactag gatctggtta      1560
ccactaaacc agcctcaaga acaccgaat ggagtctcta agctacataa taccaactta      1620
cacttacaaa atgttgtccc ccaaaatgta gccattcgta tctgctccta ataaaaagaa     1680
agtttcttca cattctagaa aaaaaaaaa aaaaaaaaa aaaaaaaaa aaaaaaaaa         1740 aaaaaaaaaa aaaaaaaaaa aaaaaaaaa aaaaaaaaa aaaaaaaaa aaaaaaaaa         1800 aaaaaaaaaa aaaaaaaa                                                 1818

<210> SEQ ID NO 71

<211> LENGTH: 1818
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

| | |
|---|---|
| aggaaactta agtcaacaca acatatacaa aacaaacgaa tctcaagcaa tcaagcattc | 60 |
| tacttctatt gcagcaattt aaatcatttc ttttaaagca aaagcaattt tctgaaaatt | 120 |
| ttcaccattt acgaacgata gccatgcagc gcgtgaacat gatcatggca gaaagcccag | 180 |
| gcctcatcac catctgcctg ctgggatacc tactcagcgc cgaatgcaca gtgttcctgg | 240 |
| accacgaaaa cgccaacaaa atcctgaacc ggccaaagag gtacaacagc ggcaaactgg | 300 |
| aagagttcgt gcaagggaac ctggagagag aatgcatgga agaaaagtgc agcttcgaag | 360 |
| aagcacgaga agtgttcgaa aacaccgaaa gaacaaccga attctggaag cagtacgtgg | 420 |
| acggagacca gtgcgagagc aacccatgcc tgaacggcgg cagctgcaag gacgacatca | 480 |
| acagctacga atgctggtgc cccttcggat tcgaaggaaa gaactgcgaa ctggacgtaa | 540 |
| catgcaacat caagaacggc agatgcgagc agttctgcaa aaacagcgcc gacaacaagg | 600 |
| tggtgtgcag ctgcaccgag ggataccgac tggcagaaaa ccagaagtcc tgcgaaccag | 660 |
| cagtgccatt cccatgcgga agagtgagcg tgagccaaac cagcaagctc acccgggccg | 720 |
| agaccgtgtt ccccgacgtg gactacgtaa acagcaccga agccgaaacc atcctggaca | 780 |
| acatcaccca aagcacccaa agcttcaacg acttcacccg ggtggtgggc ggagaagacg | 840 |
| ccaaaccagg tcaattccct tggcaggttg ttttgaatgg taaagttgat gcattctgtg | 900 |
| gaggctctat cgttaatgaa aaatggattg taactgctgc ccactgtgtt gaaactggtg | 960 |
| ttaaaattac agttgtcgca ggtgaacata atattgagga gacagaacat acagagcaaa | 1020 |
| agcgaaatgt gattcgaatt attcctcacc acaactacaa tgcagctatt aataagtaca | 1080 |
| accatgacat tgcccttctg gaactggacg aaccettagt gctaaacagc tacgttacac | 1140 |
| ctatttgcat tgctgacaag gaatacgaga acatcttcct caaatttgga tctggctatg | 1200 |
| taagtggctg gggaagagtc ttccacaaag ggagatcagc tttagttctt cagtaccttaa | 1260 |
| gagttccact tgttgaccga gccacatgtc ttcgatctac aaagttcacc atctataaca | 1320 |
| acatgttctg tgctggcttc catgaaggag gtagagatta tgtcaagga gatagtgggg | 1380 |
| gaccccatgt tactgaagtg gagggacca gtttcttaac tggaattatt agctggggtg | 1440 |
| aagagtgtgc aatgaaaggc aaatatggaa tatataccaa ggtatcccgg tatgtcaact | 1500 |
| ggattaagga aaaacaaag ctcacttaac tcgagctagt gactgactag gatctggtta | 1560 |
| ccactaaacc agcctcaaga acaccgaat ggagtctcta agctacataa taccaactta | 1620 |
| cacttacaaa atgttgtccc ccaaaatgta gccattcgta tctgctccta ataaaaagaa | 1680 |
| agtttcttca cattctagaa aaaaaaaaaaaa aaaaaaaaa aaaaaaaaa aaaaaaaaa | 1740 |
| aaaaaaaaa aaaaaaaaa aaaaaaaaa aaaaaaaaa aaaaaaaaa aaaaaaaaa | 1800 |
| aaaaaaaaaa aaaaaaa | 1818 |

<210> SEQ ID NO 72
<211> LENGTH: 1818
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
aggaaactta agtcaacaca acatatacaa aacaaacgaa tctcaagcaa tcaagcattc    60
tacttctatt gcagcaattt aaatcatttc ttttaaagca aaagcaattt tctgaaaatt   120
ttcaccattt acgaacgata gccatgcagc gcgtgaacat gatcatggca gaaagcccag   180
gcctcatcac catctgcctg ctgggatatc tactcagcgc cgaatgcaca gtgttcctgg   240
accacgaaaa cgccaacaaa atcctgaacc ggccaaagag gtacaacagc ggtaaactgg   300
aagagttcgt gcaagggaac ctggagagag aatgcatgga agaaaagtgc agcttcgaag   360
aagcacgaga gtgttcgaa acaccgaaa gaacaaccga attctggaag cagtacgtgg   420
acggagacca gtgcgagagc aacccatgcc tgaacggcgg cagctgcaag gacgacatca   480
acagctacga atgctggtgc cccttcggat tcgaaggaaa gaactgcgaa ctggacgtaa   540
catgcaacat caagaacggc agatgcgagc agttctgcaa aaacagcgcc gacaacaagg   600
tggtgtgcag ctgcaccgag ggataccgac ttgcagaaaa ccagaagtcc tgcgaaccag   660
cagtgccatt cccatgcgga agagtgagcg ttagccaaac cagcaagctc acccgggccg   720
agaccgtgtt ccccgacgtg gactacgtaa acagcaccga agccgaaacc atcctggaca   780
acatcaccca aagcacccaa agcttcaacg acttcacccg ggtggtgggc ggagaagacg   840
ccaaaccagg ccaattcccc tggcaggtgg tgctgaacgg caaagtggac gcattctgcg   900
gaggcagcat cgttaacgaa aaatggatcg taaccgccgc ccactgcgtg gaaaccggcg   960
tgaaaatcac agtggtcgca ggcgaacaca catcgagga cagaacac acagagcaaa  1020
agcgaaacgt gatccgaatc atccctcacc acaactacaa cgcagccatc aacaagtaca  1080
accacgacat cgccctgctg gaactggacg aaccttagt gctaaacagc tacgtgacac  1140
ccatctgcat cgccgacaag gaatacacga acatcttcct caaattcgga agcggctacg  1200
taagcggctg gggaagagtc ttccacaaag ggagaagcgc cctggtgctg cagtacctga  1260
gagtgccact ggtggaccga gccacatgcc tgcgaagcac aaagttcacc atctacaaca  1320
acatgttctg cgccggcttc cacgaaggag gcagagacag ctgccaagga gacagcgggg  1380
gaccccacgt gaccgaagtg gaagggacca gcttcctgac cggaatcatc agctggggcg  1440
aagagtgtgc aatgaaaggc aaatacggaa tatacaccaa ggtaagccgg tacgtcaact  1500
ggatcaagga aaaaacaaag ctcacctaac tcgagctagt gactgactag gatctggtta  1560
ccactaaacc agcctcaaga cacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaa                                                 1818
```

<210> SEQ ID NO 73
<211> LENGTH: 1818
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73

```
aggaaactta agtcaacaca acatatacaa aacaaacgaa tctcaagcaa tcaagcattc    60
tacttctatt gcagcaattt aaatcatttc ttttaaagca aaagcaattt tctgaaaatt   120
```

```
ttcaccattt acgaacgata gccatgcagc gcgtgaacat gatcatggca gaaagcccag      180
gcctcatcac catctgcctg ctgggatacc tactcagtgc cgaatgtaca gtgttcctgg      240
accacgaaaa cgccaacaaa atcctgaacc ggccaaagag gtacaactca ggcaaactgg      300
aagagttcgt gcaagggaac ctggagagag aatgcatgga agaaaagtgc agcttcgaag      360
aagcacgaga agtgtttgaa aacactgaaa gaacaaccga attttggaag cagtacgtgg      420
atggagatca gtgcgagagc aacccatgcc tgaatggcgg cagctgcaag gacgacatca      480
acagctacga atgctggtgc cccttcggat tcgaaggaaa gaactgcgaa ctggacgtaa      540
catgcaacat caagaacggc agatgcgagc agttttgtaa aaacagcgcc gacaacaagg      600
tggtgtgcag ctgcaccgag ggataccgac tggcagaaaa ccagaagtcc tgcgaaccag      660
cagtgccatt cccatgcgga agagtgtctg tgtcacaaac cagcaagctc acccgggccg      720
agaccgtgtt ccccgacgtg gactacgtaa acagcaccga agccgaaacc atcctggata      780
acatcaccca aagcacccaa agcttcaatg acttcacccg ggtggtgggc ggagaagacg      840
ccaaaccagg ccaattcccc tggcaggttg tgctgaacgg caaagttgac gcattctgcg      900
gaggcagcat cgtgaacgaa aaatggatcg taaccgctgc ccactgcgtt gaaaccggcg      960
tgaaaatcac agtggtcgca ggcgaacaca acattgagga gacagaacac acagagcaaa     1020
agcgaaacgt gatccgaatt atcccccacc acaactacaa cgcagccatt aataagtaca     1080
accatgacat cgccctgctg gaactggacg aaccttagt gctaaacagc tacgtgacac      1140
ccatctgcat cgccgacaag gaatacgacga acatcttcct caaattcgga agcggctacg     1200
taagcggctg gggaagagtc ttccacaaag ggagaagcgc cctggttctg cagtacctga     1260
gagtgccact ggttgaccga gccacatgcc tgcgaagcac aaagttcacc atctacaaca     1320
acatgttctg cgccggcttc catgaaggag gtagagacag ctgtcaagga gacagcgggg     1380
gaccccacgt tactgaagtg gaagggacca gcttcctgac cggaatcatc agctggggcg     1440
aagagtgcgc aatgaaaggc aaatacggaa tatataccaa ggtaagccgg tacgtcaact     1500
ggatcaagga aaaacaaag ctcacttaac tcgagctagt gactgactag gatctggtta      1560
ccactaaacc agcctcaaga acaccgaat ggagtctcta agctacataa taccaactta       1620
cacttacaaa atgttgtccc ccaaaatgta gccattcgta tctgctccta ataaaagaa       1680 agtttcttca cattctagaa aaaaaaaaa aaaaaaaaaa aaaaaaaaaa aaaaaaaaaa       1740
aaaaaaaaaa aaaaaaaaaa aaaaaaaaaa aaaaaaaaaa aaaaaaaaaa aaaaaaaaaa     1800
aaaaaaaaaa aaaaaaaa                                                    1818
```

<210> SEQ ID NO 74
<211> LENGTH: 1818
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
aggaaactta agtcaacaca acatatacaa aacaaacgaa tctcaagcaa tcaagcattc       60
tacttctatt gcagcaattt aaatcatttc ttttaaagca aagcaatttt tctgaaaatt      120
ttcaccattt acgaacgata gccatgcagc gcgtgaacat gatcatggca gaatcaccag      180
gcctcatcac catctgcctg ttaggatacc tactcagcgc cgaatgtaca gtgtttcttg      240
accacgaaaa cgccaacaaa atcctgaatc ggccaaagag gtataactca ggtaaactgg      300
```

```
aagagtttgt gcaagggaac ctggagagag aatgcatgga agaaaagtgc agcttcgaag    360
aagcacgaga agtgttcgaa aacactgaaa gaacaaccga attttggaag cagtatgtgg    420
atggagacca gtgcgagtcc aacccatgct taaacggcgg cagttgcaag gacgacatca    480
acagctatga atgctggtgc cccttcggat ttgaaggaaa gaactgcgaa ctggacgtaa    540
catgtaacat caagaatggc agatgcgagc agttctgtaa aaatagcgcc gacaacaagg    600
tggtgtgcag ctgtaccgag ggataccgac tggcagaaaa ccagaagtcc tgcgaaccag    660
cagtgccatt cccatgcgga agagttagcg tgagccaaac cagcaagctc acccgggccg    720
agaccgtgtt ccctgacgtg gactacgtaa actctaccga agctgaaacc atcctggaca    780
acatcactca aagcacccaa tcattcaacg acttcacccg ggtggtgggc ggagaagatg    840
ccaaaccagg tcaattccct tggcaggtgg tgttgaacgg caaagtggac gcattctgtg    900
gaggcagcat cgtgaacgaa aaatggatcg taactgccgc ccactgcgtg gaaaccggcg    960
tgaaaatcac agtggtcgca ggcgaacaca atattgagga cagaacac acagagcaaa     1020 agcgaaatgt gatccgaatt atccctcacc acaactacaa cgcagctatt aacaagtaca    1080
accacgacat tgccctgctg gaactggacg aaccccctggt gctaaacagc tacgttacac    1140
ctatctgcat cgccgacaag gaatacacga acatcttcct caaattcgga tctggctacg    1200
taagcggctg gggaagagtc ttccacaaag ggagatcagc cctggtgctt cagtaccta    1260 gagtgccact tgtggaccga gccacatgcc tgcgaagcac aaagttcacc atctacaaca    1320
acatgttctg tgctggcttc cacgaaggag gtagagacac ctgtcaagga gatagcgggg    1380
gaccccacgt taccgaagtg gaagggacca gcttcttaac tggaatcatc agctggggcg    1440
aagagtgcgc aatgaaaggc aaatacggaa tatacaccaa ggtatcccgg tatgtcaact    1500
ggatcaagga aaaacaaag ctcacctaac tcgagctagt gactgactag gatctggtta     1560
ccactaaacc agcctcaaga cacccgaat ggagtctcta agctacataa taccaactta     1620
cacttacaaa atgttgtccc ccaaaatgta gccattcgta tctgctccta ataaaagaa    1680 agtttcttca cattctagaa aaaaaaaaa aaaaaaaaa aaaaaaaaa aaaaaaaaa        1740 aaaaaaaaa aaaaaaaaa aaaaaaaaa aaaaaaaaa aaaaaaaaa aaaaaaaaa         1800 aaaaaaaaa aaaaaaaa                                                  1818
```

<210> SEQ ID NO 75
<211> LENGTH: 1818
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75

```
aggaaactta agtcaacaca acatatacaa aacaaacgaa tctcaagcaa tcaagcattc     60
tacttctatt gcagcaattt aaatcatttc ttttaaagca aaagcaattt tctgaaaatt    120
ttcaccattt acgaacgata gccatgcagc gcgtgaacat gatcatggca gaaagcccag    180
gcctcatcac catctgcctt ctgggatatc tactcagcgc cgaatgcaca gttttccttg    240
accacgaaaa cgccaacaaa atcctgaatc ggccaaagag gtataattca ggtaaactgg    300
aagagtttgt tcaagggaac cttgagagag aatgcatgga agaaaagtgt agttttgaag    360
aagcacgaga agtgttcgaa aacaccgaaa gaacaaccga attttggaag cagtatgtgg    420
atggagacca gtgcgagagc aatccatgct taaatggcgg cagctgcaag gacgacatta    480
```

```
attcctatga atgctggtgc cccttttggat tcgaaggaaa gaactgcgaa ttagacgtaa      540
catgcaacat caagaacggc agatgcgagc agttttgtaa aaatagtgct gacaacaagg      600
tggtttgcag ctgcaccgag ggataccgac tggcagaaaa ccagaagtcc tgcgaaccag      660
cagtgccatt cccatgtgga agagtttctg tgagccaaac ttctaagctc acccgtgccg      720
agaccgtttt ccctgacgtg gactatgtaa attctaccga agccgaaacc attttggata      780
acatcaccca aagcacccaa agctttaacg acttcactcg ggtggttggc ggagaagacg      840
ccaaaccagg ccaattccct tggcaggtgg ttctgaatgg caaagtggat gcattctgtg      900
gaggctctat cgtgaacgaa aaatggatcg taactgccgc ccactgcgtt gaaaccggcg      960
ttaaaattac agtggtcgca ggcgaacaca atattgagga cagaacacac acagagcaaa     1020
agcgaaacgt gattcgaatt atccctcacc acaactacaa tgcagccatt aacaagtaca     1080
accatgacat cgccctgctg gaactggacg aaccccctggt gctaaacagc tacgttacac     1140
ctatttgcat cgccgacaag gaatacgacga acatcttcct caaatttgga tctggctatg     1200
taagcggctg gggaagagtc ttccacaaag ggagaagcgc cctggtgctt cagtacctga     1260
gagtgccact tgtggaccga gccacatgtc tgcgaagcac aaagttcacc atctacaaca     1320
acatgttctg cgccggcttc cacgaaggag gtagagactc atgccaagga gatagcgggg     1380
gaccccacgt gaccgaagtg gaagggacca gcttcctgac tggaattatt agctggggcg     1440
aagagtgcgc aatgaaaggc aaatatggaa tatacaccaa ggtaagccgg tatgtcaact     1500
ggatcaagga aaaacaaag ctcacctaac tcgagctagt gactgactag gatctggtta     1560
ccactaaacc agcctcaaga cacccgaat ggagtctcta agctacataa taccaactta     1620
cacttacaaa atgttgtccc ccaaaatgta gccattcgta tctgctccta ataaaaagaa     1680
agtttcttca cattctagaa aaaaaaaaaa aaaaaaaaa aaaaaaaaaa aaaaaaaaa      1740 aaaaaaaaaa aaaaaaaaaa aaaaaaaaaa aaaaaaaaaa aaaaaaaaaa aaaaaaaaaa     1800
aaaaaaaaaa aaaaaaaa                                                  1818
```

<210> SEQ ID NO 76
<211> LENGTH: 1818
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 76

```
aggaaacuua agucaacaca acauauacaa aacaaacgaa ucucaagcaa ucaagcauuc       60
uacuucuauu gcagcaauuu aaaucauuuc uuuuaaagca aaagcaauuu ucugaaaauu      120
uucaccauuu acgaacgaua gccaugcagc gcgugaacau gaucauggca gaaagcccag      180 gcccucaucac caucugccug cugggauacc uacucagcgc cgaaugcaca guguuccugg      240
accacgaaaa cgccaacaaa auccugaacc ggccaaagag guacaacagc ggcaaacugg      300
aagaguucgu gcaagggaac cuggagagag aaugcaugga gaaaagugc agcuucgaag      360 aagcacgaga aguguucgaa aacaccgaaa gaacaaccga auucuggaag caguacgugg      420
acggagacca gugcgagagc aacccaugcc ugaacggcgg cagcugcaag gacgacauca      480
acagcuacga augcuggugc cccuucggau ucgaaggaaa gaacugcgaa cuggacguaa      540
caugcaacau caagaacggc agaugcgagc aguucugcaa aaacagcgcc gacaacaagg      600
uggugugcag cugcaccgag ggauaccgac uggcagaaaa ccagaagucc ugcgaaccag      660
```

| | |
|---|---|
| cagugccauu cccaugcgga agagugagcg ugagccaaac cagcaagcuc acccgggccg | 720 |
| agaccguguu ccccgacgug gacuacguaa acagcaccga agccgaaacc auccuggaca | 780 |
| acaucaccca aagcacccaa agcuucaacg acuucacccg gguggugggc ggagaagacg | 840 |
| ccaaaccagg ccaauucccc uggcaggugg ugcugaacgg caaaguggac gcauucugcg | 900 |
| gaggcagcau cgugaacgaa aaauggaucg uaaccgccgc ccacugcgug gaaaccggcg | 960 |
| ugaaaaucac aguggucgca ggcgaacaca caaucgagga gacagaacac acagagcaaa | 1020 |
| agcgaaacgu gauccgaauc aucccccacc acaacuacaa cgcagccauc aacaaguaca | 1080 |
| accacgacau cgcccugcug gaacuggacg aaccccuggu gcuaaacagc uacgugacac | 1140 |
| ccaucugcau cgccgacaag gaauacacga acaucuuccu caaauucgga agcggcuacg | 1200 |
| uaagcggcug gggaagaguc uuccacaaag ggagaagcgc ccuggugcug caguaccuga | 1260 |
| gagugccacu gguggaccga gccacaugcc ugcgaagcac aaaguucacc aucuacaaca | 1320 |
| acauguucug cgccggcuuc cacgaaggag cagagacacu gccaaggga gacagcgggg | 1380 |
| gaccccacgu gaccgaagug gaagggacca gcuuccugac cggaaucauc agcugggggc | 1440 |
| aagagugcgc aaugaaaggc aaauacggaa uauaccaa gguaagccgg uacgucaacu | 1500 |
| ggaucaagga aaaacaaag cucaccuaac ucgagcuagu gacugacuag gaucugguua | 1560 |
| ccacuaaacc agcccaaga acacccgaau ggagucucua agcuacauaa uaccaacuua | 1620 |
| cacuuacaaa auguugucc ccaaaaugua gccauucgua ucugcuccua auaaaagaa | 1680 |
| aguuucuuca cauucuagaa aaaaaaaaa aaaaaaaaa aaaaaaaaa aaaaaaaaa | 1740 |
| aaaaaaaaaa aaaaaaaaa aaaaaaaaa aaaaaaaaa aaaaaaaaa aaaaaaaaa | 1800 |
| aaaaaaaaaa aaaaaaaa | 1818 |

<210> SEQ ID NO 77
<211> LENGTH: 1818
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 77

| | |
|---|---|
| aggaaacuua agucaacaca acauauacaa aacaaacgaa ucucaagcaa ucaagcauuc | 60 |
| uacuucuauu gcagcaauuu aaaucauuuc uuuuaaagca aaagcaauuu ucugaaaauu | 120 |
| uuccaccauuu acgaacgaua gccaugcagc gcgugaacau gaucuggca gaauccaccag | 180 |
| gccucaucac caucugccuu uuaggauauc uacucagugc ugaauguaca guuuccugg | 240 |
| accacgaaaa cgccaacaaa auccugaacc ggccaaagag guacaacagc ggcaaacugg | 300 |
| aagaguucgu gcaagggaac cuggagagag aaugcaugga agaaagugc agcuucgaag | 360 |
| aagcacgaga aguguucgaa acaccgaaa gaacaaccga auucuggaag caguacgugg | 420 |
| acggagacca gugcgagagc aacccaugcc ugaacgcgg cagcugcaag gacgacauca | 480 |
| acagcuacga augcuggugc cccuucggau ucgaggaaa gaacugcgaa cuggacguaa | 540 |
| caugcaacau caagaacggc agaugcgagc aguucugcaa aaacagcgcc gacaacaagg | 600 |
| uggugugcag cugcaccgag ggauaccgac uggcagaaaa ccagaagucc ugcgaaccag | 660 |
| cagugccauu cccaugcgga agagugagcg ugagccaaac cagcaagcuc acccgggccg | 720 |
| agaccguguu ccccgacgug gacuacguaa acagcaccga agccgaaacc auccuggaca | 780 |
| acaucaccca aagcacccaa agcuucaacg acuucacccg gguggugggc ggagaagacg | 840 |

```
ccaaaccagg ccaauucccc uggcaggugg ugcugaacgg caaaguggac gcauucugcg      900
gaggcagcau cgugaacgaa aaauggaucg uaaccgccgc ccacugcgug gaaaccggcg      960
ugaaaaucac aguggucgca ggcgaacaca acaucgagga gacagaacac acagagcaaa     1020
agcgaaacgu gauccgaauc auccccacc acaacuacaa cgcagccauc aacaaguaca      1080
accacgacau cgcccugcug gaacuggacg aaccccuggu gcuaaacagc uacgugacac     1140
ccaucugcau cgccgacaag gaauacacga acaucuuccu caaauucgga agcggcuacg     1200
uaagcggcug gggaagaguc uuccacaaag ggagaagcgc ccuggugcug caguaccuga     1260
gagugccacu ggguggaccga gccacaugcc ugcgaagcac aaaguucacc aucuacaaca     1320
acauguucug cgccggcuuc cacgaaggag gcagagacag cugccaagga gacagcgggg     1380
gaccccacgu gaccgaagug gaagggacca gcuuccugac cggaaucauc agcuggggcg     1440
aagagugcgc aaugaaaggc aaauacggaa uauaccacaa gguaagccgg uacgucaacu     1500
ggaucaagga aaaaacaaag cucaccuaac ucgagcuagu gacugacuag gaucggguua     1560
ccacuaaacc agccucaaga cacccgaauu ggagucucua agcuacauaa uaccaacuua     1620
cacuuacaaa auguugcccc ccaaaaugua gccauucgua ucugcuccua auaaaaagaa     1680
aguuucuuca cauucuagaa aaaaaaaaaa aaaaaaaaaa aaaaaaaaaa aaaaaaaaa     1740 aaaaaaaaaa aaaaaaaaaa aaaaaaaaaa aaaaaaaaaa aaaaaaaaaa aaaaaaaaaa     1800
aaaaaaaaaa aaaaaaaa                                                  1818

<210> SEQ ID NO 78
<211> LENGTH: 1818
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 78
aggaaacuua agucaacaca acauauacaa aacaaacgaa ucucaagcaa ucaagcauuc       60
uacuucuauu gcagcaauuu aaaucauuuc uuuuaaagca aaagcaauuu ucugaaaauu      120
uucaccauuu acgaacgaua gccaugcagc gcgugaacau gaucauggca gaaucaccag      180 gcccucaucac caucugccuu uuaggauauc uacucagugc ugaauguaca guuuuucuug     240
aucaugaaaa cgccaacaaa auucugaauc ggccaaagag guauaauuca gguaaauugg     300
aagaguuugu ucaagggaac cuugagagag aauguaugga agaaaagugu aguuugaag      360 aagcacgaga aguuuugaa aacacugaaa gaacaacuga auuuuggaag caguauguug      420
auggagauca gugcgagagc aacccaugcc ugaacggcgg cagcugcaag gacgacauca     480
acagcuacga augcuggugc cccuucggau ucgaaggaaa gaacugcgaa cuggacguaa     540
caugcaacau caagaacggc agaugcgagc aguucugcaa aaacagcgcc gacaacaagg     600
uggugugcag cugcaccgag ggauaccgac uggcagaaaa ccagaaguc ugcgaaccag       660 cagugccauu cccaugcgga agagugagcg ugagccaaac cagcaagcuc acccgggccg     720
agaccguguu ccccgacgug gacuacguaa acagcaccga agccgaaacc auccuggaca     780 acaucacccca aagcacccaa agcuucaacg acuucacccg gguggugggc ggagaagacg     840
ccaaaccagg ccaauucccc uggcaggugg ugcugaacgg caaaguggac gcauucugcg     900
gaggcagcau cgugaacgaa aaauggaucg uaaccgccgc ccacugcgug gaaaccggcg     960
ugaaaaucac aguggucgca ggcgaacaca acaucgagga gacagaacac acagagcaaa    1020
```

-continued

| | | |
|---|---|---|
| agcgaaacgu gauccgaauc auccccacc acaacuacaa cgcagccauc aacaaguaca | 1080 | |
| accacgacau cgcccugcug gaacuggacg aaccccuggu gcuaaacagc uacgugacac | 1140 | |
| ccaucugcau cgccgacaag gaauacacga acaucuuccu caaauucgga agcggcuacg | 1200 | |
| uaagcggcug gggaagaguc uuccacaaag ggagaagcgc ccggugcug caguaccuga | 1260 | |
| gagugccacu gguggaccga gccacaugcc ugcgaagcac aaaguucacc aucuacaaca | 1320 | |
| acauguucug cgccggcuuc cacgaaggag gcagagacac cugccaagga gacagcgggg | 1380 | |
| gaccccacgu gaccgaagug gaagggacca gcuuccugac cggaaucauc agcuggggcg | 1440 | |
| aagagugcgc aaugaaaggc aaauacgaaa uauaccaccaa gguaagccgg uacgucaacu | 1500 | |
| ggaucaagga aaaaacaaag cucaccuaac ucgagcuagu gacugacuag gaucgguua | 1560 | |
| ccacuaaacc agcccaagaa acacccgaau ggagucucua agcuacauaa uaccaacuua | 1620 | |
| cacuuacaaa auguugucc ccaaaaugua gccauucgua ucugcuccua auaaaaagaa | 1680 | |
| aguuucuuca cauucuagaa aaaaaaaaaa aaaaaaaaaa aaaaaaaaaa aaaaaaaaaa | 1740 | |
| aaaaaaaaaa aaaaaaaaaa aaaaaaaaaa aaaaaaaaaa aaaaaaaaaa aaaaaaaaaa | 1800 | |
| aaaaaaaaaa aaaaaaaa | 1818 | |

<210> SEQ ID NO 79
<211> LENGTH: 1818
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 79

| | | |
|---|---|---|
| aggaaacuua agucaacaca acauauacaa aacaaacgaa ucucaagcaa ucaagcauuc | 60 | |
| uacuucuauu gcagcaauuu aaaucauuuc uuuuaaagca aaagcaauuu ucugaaaauu | 120 | |
| uucaccauuu acgaacgaua gccaugcagc gcgugaacau gaucuggca gaaucaccag | 180 | |
| gccucaucac caucugccuu uuaggauauc uacucagugc ugaauguaca guuuucuug | 240 | |
| aucaugaaaa cgccaacaaa auucugaauc ggccaaagag guauaauuca gguaaauugg | 300 | |
| aagaguuugu ucaagggaac cuugagagag aauguaugga agaaaagugu aguuuugaag | 360 | |
| aagcacgaga aguuuugaa aacacugaaa gaacaacuga auuuggaag caguauguug | 420 | |
| auggagauca gugugagucc aauccauguu uaaauggcgg caguugcaag gaugacauua | 480 | |
| auuccuauga auguuggugu cccuuuggau uugaaggaaa gaacgugaa uuagauguaa | 540 | |
| cauguaacau uaagaauggc agaugcgagc aguuuguaa aaauagugcu gauaacaagg | 600 | |
| uggugugcag cugcaccgag ggauaccgac uggcagaaaa ccagaagucc ugcgaaccag | 660 | |
| cagugccauu cccaugcgga agagugagcg ugagccaaac cagcaagcuc acccgggccg | 720 | |
| agaccguguu cccgacgug gacuacguaa acagcaccga agccgaaacc auccuggaca | 780 | |
| acaucacccca aagcacccaa agcuucaacg acuuacccg ggugguggc ggagaagacg | 840 | |
| ccaaaccagg ccaauucccc uggcaggugg ugcugaacgg caaaguggac gcauucugcg | 900 | |
| gaggcagcau cgugaacgaa aaauggaucg uaaccgccgc ccacugcgug gaaaccggcg | 960 | |
| ugaaaaucac aguggucgca ggcgaacaca acaucgagga gacagaacac acagagcaaa | 1020 | |
| agcgaaacgu gauccgaauc auccccacc acaacuacaa cgcagccauc aacaaguaca | 1080 | |
| accacgacau cgcccugcug gaacuggacg aaccccuggu gcuaaacagc uacgugacac | 1140 | |
| ccaucugcau cgccgacaag gaauacacga acaucuuccu caaauucgga agcggcuacg | 1200 | |

```
uaagcggcug gggaagaguc uuccacaaag ggagaagcgc ccuggugcug caguaccuga    1260
gagugccacu gguggaccga gccacaugcc ugcgaagcac aaaguucacc aucuacaaca    1320
acauguucug cgccggcuuc cacgaaggag gcagagacag cugccaagga gacagcgggg    1380
gaccccacgu gaccgaagug gaagggacca gcuuccugac cggaaucauc agcugggcg     1440 aagagugcgc aaugaaggc aaauacggaa uauacaccaa gguaagccgg uacgucaacu     1500
ggaucaagga aaaaacaaag cucaccuaac ucgagcuagu gacugacuag gaucugguua    1560
ccacuaaacc agccucaaga cacccgaauu ggagucucua agcuacauaa uaccaacuua    1620
cacuuacaaa auguugcccc ccaaaaugua gccauucgua ucugcuccua auaaaaagaa    1680
aguuucuuca cauucuagaa aaaaaaaaa aaaaaaaaaa aaaaaaaaaa aaaaaaaaaa     1740
aaaaaaaaaa aaaaaaaaaa aaaaaaaaaa aaaaaaaaaa aaaaaaaaaa aaaaaaaaaa    1800
aaaaaaaaaa aaaaaaaa                                                  1818

<210> SEQ ID NO 80
<211> LENGTH: 1818
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 80
aggaaacuua agucaacaca acauauacaa aacaaacgaa ucucaagcaa ucaagcauuc      60
uacuucuauu gcagcaauuu aaaucauuuc uuuuaaagca aaagcaauuu ucugaaaauu     120
uucaccauuu acgaacgaua gccaugcagc gcgugaacau gaucauggca gaaucaccag     180
gccucaucac caucugccuu uuaggauauc uacucagugc ugaauguaca guuuuucuug     240
aucaugaaaa cgccaacaaa auucugaauc ggccaaagag guauaauuca gguaaauugg     300
aagaguuugu ucaagggaac cuugagagag aauguaugga agaaaagugu aguuugaag      360 aagcacgaga aguuuugaa aacacugaaa gaacaacuga auuuggaag caguauguug       420 auggagauca gugugagucc aauccauguu uaaauggcgg caguugcaag gaugacauua     480
auuccuauga auguuggugu cccuuuggau uugaaggaaa gaacugugaa uuagauguaa     540
cauguaacau uaagaauggc agaugcgagc aguuuuguaa aaauagugcu gauaacaagg     600
ugguuugcuc cuguacugag ggauaucgac uugcagaaaa ccagaagucc ugugaaccag     660
cagugccauu uccauguggp agaguuucug uuucacaaac uucuaagcuc acccgugcug     720
agacuguuuu uccugaugug gacuauguaa auagcaccga agccgaaacc auccuggaca     780
acaucaccca aagcacccaa agcuucaacg acuucacccg ggugguggge ggagaagacg     840 ccaaaccagg ccaauucccc uggcagguge ugcugaacgg caaaguggac gcauucugcg     900
gaggcagcau cgugaacgaa aaauggaucg uaaccgccgc ccacugcgug gaaaccggcg     960
ugaaaaucac aguggucgca ggcgaacaca acaucgagga gacagaacac acagagcaaa    1020
agcgaaacgu gauccgaauc auccccccacc acaacuacaa cgcagccauc aacaaguaca    1080
accacgacau cgcccugcug gaacuggacg aaccccuggu gcuaaacagc uacgugacac    1140
ccaucugcau cgccgacaag gaauacacga acaucuuccu caaauucgga agcggcuacg    1200
uaagcggcug gggaagaguc uuccacaaag ggagaagcgc ccuggugcug caguaccuga    1260
gagugccacu gguggaccga gccacaugcc ugcgaagcac aaaguucacc aucuacaaca    1320
acauguucug cgccggcuuc cacgaaggag gcagagacag cugccaagga gacagcgggg    1380
```

```
gaccccacgu gaccgaagug gaagggacca gcuuccugac cggaaucauc agcuggggcg    1440
aagagugcgc aaugaaaggc aaauacggaa uauacaccaa gguaagccgg uacgucaacu    1500
ggaucaagga aaaaacaaag cucaccuaac ucgagcuagu gacugacuag gaucugguua    1560
ccacuaaacc agcccuaaga acacccgaau ggagucucua agcuacauaa uaccaacuua    1620
cacuuacaaa auguugcccc ccaaaaugua gccauucgua ucugcuccua auaaaaagaa    1680
aguuucuuca cauucuagaa aaaaaaaaaa aaaaaaaaaa aaaaaaaaaa aaaaaaaaaa    1740
aaaaaaaaaa aaaaaaaaaa aaaaaaaaaa aaaaaaaaaa aaaaaaaaaa aaaaaaaaaa    1800
aaaaaaaaaa aaaaaaaa                                                  1818

<210> SEQ ID NO 81
<211> LENGTH: 1818
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 81
aggaaacuua agucaacaca acauauacaa aacaaacgaa ucucaagcaa ucaagcauuc      60
uacuucuauu gcagcaauuu aaaucauuuc uuuuaaagca aaagcaauuu ucugaaaauu     120
uucaccauuu acgaacgaua gccaugcagc gcgugaacau gaucuggca gaaagcccag      180 gccucaucac caucugccug cugggauacc uacucagcgc cgaaugcaca guguuccugg     240
accacgaaaa cgccaacaaa uccugaacc ggccaaagag guacaacagc ggcaaacugg      300
aagaguucgu gcaagggaac cuggagagag aaugcaugga agaaaagugc agcuucgaag     360
aagcacgaga aguguucgaa aacaccgaaa gaacaaccga auucuggaag caguacgugg     420
acggagacca gugcgagagc aacccaugcc ugaacggcgg cagcugcaag gacgacauca     480 acaqcuacga augcugguqc cccuucggau ucgaaggaaa gaacugcgaa cuggacguaa     540
caugcaacau caagaacggc agaugcgagc aguucugcaa aaacagcgcc gacaacaagg     600
uggugugcag cugcaccgag ggauaccgac uggcagaaaa ccagaaguc cugcgaaccag     660 cagugccauu cccaugcgga agagugagcg ugagccaaac cagcaagcuc acccgggccg     720 agaccgguguu cccccgacgug gacuacguaa acagcaccga agccgaaacc auccuggaca    780 acaucacccca aagcacccaa agcuucaacg acuucacccg ggugguqggc ggagaagacg     840 ccaaaccagg ccaauucccc uggcaggugg ugcugaacgg caaaguggac gcauucugcg     900
gaggcagcau cgugaacgaa aaauggaucg uaaccgccgc ccacugcgug gaaaccggcg     960
ugaaaaucac aguggucgca ggcgaacaca caucgagga dacagaacac acagagcaaa     1020
agcgaaacgu gaucgaauc auccccacc acaacuacaa cgcagccauc aacaaguaca     1080
accacgacau cgcccugcug gaacuggacg aaccccuggu gcuaaacagc uacgugacac     1140
ccaucugcau cgccgacaag gaauacacga acaucuuccu caaauucgga agcggcuacg     1200
uaagcggcug gggaagaguc uuccacaaag ggagaagcgc ccuggugcug caguaccuga     1260
gagugccacu gguggaccga gccacaugcc ugcgaagcac aaaguucacc aucuacaaca     1320 acaugucug cgccggcuuc cacgaaggag gcagagacag cugccaagga gacagcgggg    1380
gaccccacgu gaccgaagug gaagggacca gcuuccugac cggaaucauc agcuggggug    1440
aagagugugc aaugaaaggc aaauauggaa uauauaccaa gguauccgg uaugucaacu     1500 ggauuaagga aaaaacaaag cucacuuaac ucgagcuagu gacugacuag gaucugguua    1560
```

```
ccacuaaacc agccucaaga acacccgaau ggagucucua agcuacauaa uaccaacuua    1620
cacuuacaaa auguugucccc ccaaaaugua gccauucgua ucugcuccua auaaaaagaa   1680
aguuucuuca cauucuagaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaa                                                 1818
```

<210> SEQ ID NO 82
<211> LENGTH: 1818
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 82

```
aggaaacuua agucaacaca acauauacaa acaaacgaa ucucaagcaa ucaagcauuc      60
uacuucuauu gcagcaauuu aaaucauuuc uuuuaaagca aaagcaauuu ucugaaaauu    120
uucaccauuu acgaacgaua gccaugcagc gcgugaacau gaucauggca gaaagcccag    180
gccucaucac caucugccug cugggauacc uacucagcgc cgaaugcaca guguuccugg    240
accacgaaaa cgccaacaaa auccugaacc ggccaaagag guacaacagc ggcaaacugg    300
aagaguucgu gcaagggaac cuggagagag aaugcaugga agaaaaguge agcuucgaag    360 aagcacgaga aguuucgaa acaccgaaa gaacaaccga auucuggaag caguacgugg     420
acggagacca gugcgagagc aacccaugcc ugaacggcgg cagcugcaag gacgacauca    480
acagcuacga augcugguge cccuucggau ucgaaggaaa gaacugcgaa cuggacguaa    540
caugcaacau caagaacggc agaugcgagc aguucgcaa aaacagcgcc gacaacaagg    600
uggugugcag cugcaccgag ggauaccgac uggcagaaaa ccagaagucc ugcgaaccag    660
cagugccauu cccaugcgga agagugagcg ugagccaaac cagcaagcuc acccgggccg    720
agaccguguu cccccgacgug gacuacguaa acagcaccga agccgaaacc auccuggaca    780
acaucaccca aagcacccaa agcuucaacg acuucacccg gguggugggc ggagaagacg    840
ccaaaccagg ccaauucccc uggcaggugg ugcugaacgg caaaguggac gcauucugcg    900
gaggcagcau cgugaacgaa aaauggaucu uaaccgccgc ccacugcgug gaaaccggcg    960
ugaaaaucac aguggucgca ggcgaacaca acaucgagga gacagaacac acagagcaaa   1020
agcgaaacgu gauccgaauc auccccccacc acaacuacaa cgcagccauc aacaaguaca   1080
accacgacau cgcccugcug gaacuggacg aaccccuggu gcuaaacagc uacgugacac    1140
ccaucugcau cgccgacaag gaauacacga acaucuuccu caaauucgga agcggcuacg   1200
uaagcggcug gggaagaguc uuccacaaag ggagaagcgc ccuggugcuu caguaccuua    1260 gaguccacu uguugaccga gccacaugu cuucgaucuac aaaguucacc aucuauaaca    1320
acaguuucug ugcuggcuuc caugaaggag guagagauuc augucaagga gauaguggggg    1380 gaccccaugu uacugaagug gaagggacca guucuuaac uggaauuauu agcuggggug    1440
aagagugugc aaugaaaggc aaaaaugaa uauauaccaa gguacccgg uaugucaacu    1500 ggauuaagga aaaacaaag cucacuuaac ucgagcuagu gacugacuag gaucgguua    1560 ccacuaaacc agccucaaga acacccgaau ggagucucua agcuacauaa uaccaacuua    1620
cacuuacaaa auguugucccc ccaaaaugua gccauucgua ucugcuccua auaaaaagaa   1680
aguuucuuca cauucuagaa aaaaaaaaaa aaaaaaaaaa aaaaaaaaaa aaaaaaaaaa   1740
```
aaaaaaaaaa aaaaaaaaaa aaaaaaaaaa aaaaaaaaaa aaaaaaaaaa aaaaaaaaaa    1800
aaaaaaaaaa aaaaaaaa                                                   1818

<210> SEQ ID NO 83
<211> LENGTH: 1818
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 83
aggaaacuua agucaacaca acauauacaa aacaaacgaa ucucaagcaa ucaagcauuc       60
uacuucuauu gcagcaauuu aaaucauuuc uuuuaaagca aaagcaauuu ucugaaaauu      120
uucaccauuu acgaacgaua gccaugcagc gcgugaacau gaucauggca gaaagcccag      180
gccucaucac caucugccug cugggauacc uacucagcgc cgaaugcaca guguuccugg      240
accacgaaaa cgccaacaaa auccugaacc ggccaaagag guacaacagc ggcaaacugg      300
aagaguucgu gcaagggaac cuggagagag aaugcaugga agaaaagugc agcuucgaag      360
aagcacgaga auguucgaa acaccgaaa gaacaaccga auucuggaag caguacgugg       420
acggagacca gugcgagagc aacccaugcc ugaacggcgg cagcugcaag gacgacauca      480
acagcuacga augcugguge cccuucggau ucgaaggaaa gaacugcgaa cuggacguaa      540
caugcaacau caagaacggc agaugcgagc aguucugcaa aaacagcgcc gacaacaagg      600
uggugugcag cugcaccgag ggauaccgac uggcagaaaa ccagaaguce ugcgaaccag      660 cagugccauu cccaugcgga agagugagcg ugagccaaac cagcaagcuc acccgggccg      720
agaccguguu ccccgacgug gacuacguaa acagcaccga agccgaaacc auccuggaca      780
acaucaccca aagcacccaa agcuucaacg acuucacccg ggugguggge ggagaagacg      840 ccaaaccagg ccaauucccc uggcaggugg ugcugaacgg caaaguggac gcauucugcg      900
gaggcagcau cgugaacgaa aaauggaucg uaaccgccgc ccacugcgug gaaaccggcg      960
ugaaaaucac agugguegca ggcgaacaca caucgagga gacagaacau acagagcaaa     1020
agcgaaaugu gauucgaauu auuccucacc acaacuacaa ugcagcuauu aauaaguaca     1080
accaugacau ugcccuucug gaacuggacg aacccuuagu gcuaaacagc uacguuacac     1140
cuauuugcau ugcugacaag gaauacacga acaucuuccu caaauuugga ucuggcuaug     1200
uaaguggcug gggaagaguc uuccacaaag ggagaucagc uuuaguucuu caguaccuua     1260
gaguuccacu uguugaccga gccacaugue uucgaucuac aaaguucacc aucuauaaca     1320 acaguucug ugcuggcuuc caugaaggag guagagauuc augucaagga gaugugggg       1380 gaccccaugu uacugaagug gaagggacca guuucuuaac uggaauuauu agcuggggug     1440
aagagugugc aaugaaaggc aaauauggaa uauauaccaa gguaucccgg uaugucaacu     1500
ggauuaagga aaaacaaag cucacuuaac ucgagcuagu gacugacuag gaucgguua      1560 ccacuaaacc agccucaaga cacccgaau ggagucucua agcuacauaa uaccaacuua      1620
cacuuacaaa auguugucc ccaaaaugua gccauucgua ucugcuccua auaaaagaa       1680 aguuucuuca cauucuagaa aaaaaaaaa aaaaaaaaaa aaaaaaaaaa aaaaaaaaaa      1740
aaaaaaaaaa aaaaaaaaaa aaaaaaaaaa aaaaaaaaaa aaaaaaaaaa aaaaaaaaaa     1800
aaaaaaaaaa aaaaaaaa                                                  1818

<210> SEQ ID NO 84
<211> LENGTH: 1818
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 84

| | |
|---|---|
| aggaaacuua agucaacaca acauauacaa aacaaacgaa ucucaagcaa ucaagcauuc | 60 |
| uacuucuauu gcagcaauuu aaaucauuuc uuuuaaagca aaagcaauuu ucugaaaauu | 120 |
| uuccaccauuu acgaacgaua gccaugcagc gcgugaacau gaucauggca gaaagcccag | 180 |
| gccucaucac caucugccug cugggauacc uacucagcgc cgaaugcaca guguuccugg | 240 |
| accacgaaaa cgccaacaaa uccugaaccc ggccaaagag guacaacagc ggcaaacugg | 300 |
| aagaguucgu gcaagggaac cuggagagag aaugcaugga agaaaagugc agcuucgaag | 360 |
| aagcacgaga aguguucgaa aacaccgaaa gaacaaccga auucuggaag caguacgugg | 420 |
| acggagacca gugcgagagc aacccaugcc ugaacggcgg cagcugcaag gacgacauca | 480 |
| acagcuacga augcugguge cccuucggau ucgaaggaaa gaacugcgaa cuggacguaa | 540 |
| caugcaacau caagaacggc agaugcgagc aguucgcaa aacagcgcc gacaacaagg | 600 |
| uggugugcag cugcaccgag ggauaccgac uggcagaaaa ccagaaguce ugcgaaccag | 660 |
| cagugccauu cccaugcgga agagugagcg ugagccaaac cagcaagcuc acccgggccg | 720 |
| agaccguguu ccccgacgug gacuacguaa acagcaccga agccgaaacc auccuggaca | 780 |
| acaucaccca aagcacccaa agcuucaacg acuucacccg ggugguggc ggagaagacg | 840 |
| ccaaaccagg ucaauucccu uggcagguug uuugaaugg uaaaguugau gcauucugug | 900 |
| gaggcucuau cguuaaugaa aaauggauug uaacugcugc ccacugugu gaaacuggug | 960 |
| uuaaaauuac aguugucgca ggugaacaua auauugagga gacagaacau acagagcaaa | 1020 |
| agcgaaaugu gauucgaauu auccucacc acaacuacaa ugcagcuauu aauaaguaca | 1080 |
| accaugacau ugcccuucug gaacuggacg aacccuuagu gcuaaacagc uacguuacac | 1140 |
| cuauuugcau ugcugacaag gaauacacga acaucuuccu caaauuugga ucuggcuaug | 1200 |
| uaaguggcug gggaagaguc uuccacaaag ggagaucagc uuuaguucuu caguaccuua | 1260 |
| gaguccacu uguugaccga gccacauguc uucgaucuac aaaguucacc aucuauaaca | 1320 |
| acauguucug ugcuggcuuc caugaaggag guagagauuc augucaagga gauagugggg | 1380 |
| gaccccaugu uacugaagug gaagggacca guucuuaac uggaauuauu agcuggggug | 1440 |
| aagaguguge aaugaaaggc aaauauggaa uauauaccaa gguauccegg uaugucaacu | 1500 |
| ggauuaagga aaaacaaag cucacuuaac ucgagcuagu gacugacuag gaucugguua | 1560 |
| ccacuaaacc agccucaaga cacccgaauu ggagucucua agcuacauaa uaccaacuua | 1620 |
| cacuuacaaa auguugucc ccaaaaugua gccaucgua ucugcuccua auaaaaagaa | 1680 |
| aguuucuuca cauucuagaa aaaaaaaaa aaaaaaaaa aaaaaaaaa aaaaaaaaa | 1740 |
| aaaaaaaaaa aaaaaaaaa aaaaaaaaa aaaaaaaaa aaaaaaaaa aaaaaaaaa | 1800 |
| aaaaaaaaaa aaaaaaaa | 1818 |

<210> SEQ ID NO 85
<211> LENGTH: 1818
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 85

| | | | | | |
|---|---|---|---|---|---|
| aggaaacuua | agucaacaca | acauauacaa | aacaaacgaa | ucucaagcaa | ucaagcauuc | 60 |
| uacuucuauu | gcagcaauuu | aaaucauuuc | uuuuaaagca | aaagcaauuu | ucugaaaauu | 120 |
| uucaccauuu | acgaacgaua | gccaugcagc | gcgugaacau | gaucauggca | gaaagcccag | 180 |
| gccucaucac | caucugccug | cugggauauc | uacucagcgc | cgaaugcaca | guguccugg | 240 |
| accacgaaaa | cgccaacaaa | auccugaacc | ggccaaagag | guacaacagc | gguaaacugg | 300 |
| aagaguucgu | gcaagggaac | cuggagagag | aaugcaugga | agaaaagugc | agcuucgaag | 360 |
| aagcacgaga | aguguucgaa | acaccgaaaa | gaacaaccga | auucuggaag | caguacgugg | 420 |
| acggagacca | gugcgagagc | aacccaugcc | ugaacggcgg | cagcugcaag | gacgacauca | 480 |
| acagcuacga | augcugguge | cccuucggau | ucgaaggaaa | gaacugcgaa | cuggacguaa | 540 |
| caugcaacau | caagaacggc | agaugcgagc | aguucugcaa | aaacagcgcc | gacaacaagg | 600 |
| uggugugecag | cugcaccgag | ggauaccgac | uucagaaaaa | ccagaagucc | ugcgaaccag | 660 |
| cagugccauu | cccaugcgga | agagugagcg | uuagccaaac | cagcaagcuc | acccgggccg | 720 |
| agaccguguu | ccccgacgug | gacuacguaa | acagcaccga | agccgaaacc | auccuggaca | 780 |
| acaucaccca | aagcacccaa | agcuucaacg | acuucacccg | gguggugggc | ggagaagacg | 840 |
| ccaaaccagg | ccaauucccc | uggcaggugg | ugcugaacgg | caaaguggac | gcauucugcg | 900 |
| gaggcagcau | cguuaacgaa | aaauggaucg | uaaccgccgc | ccacugcgug | gaaaccggcg | 960 |
| ugaaaaucac | aguggucgca | ggcgaacaca | acaucgagga | gacagaacac | acagagcaaa | 1020 |
| agcgaaacgu | gauccgaauc | aucccucacc | acaacuacaa | cgcagccauc | aacaaguaca | 1080 |
| accacgacau | cgcccugcug | gaacuggacg | aacccuuagu | gcuaaacagc | uacgugacac | 1140 |
| ccaucugcau | cgccgacaag | gaauacacga | acaucuuccu | caaauucgga | agcggcuacg | 1200 |
| uaagcggcug | gggaagaguc | uuccacaaag | ggagaagcgc | ccuggugcug | caguaccuga | 1260 |
| gagugccacu | gguggaccga | gccacaugcc | ugcgaagcac | aaaguucacc | aucuacaaca | 1320 |
| acauguucug | cgccggcuuc | cacgaaggag | gcagagacag | cugccaagga | gacagcgggg | 1380 |
| gaccccacgu | gaccgaagug | gaagggacca | gcuuccugac | cggaaucauc | agcuggggcg | 1440 |
| aagagugugc | aaugaaaggc | aaauacggaa | uauacaccaa | gguaagccgg | uacgucaacu | 1500 |
| ggaucaagga | aaaaacaaag | cucaccuaac | ucgagcuagu | gacugacuag | gaucugguua | 1560 |
| ccacuaaacc | agcccaagac | acaccgaauu | ggagucucua | agcuacauaa | uaccaacuua | 1620 |
| cacuuacaaa | auguugugccc | ccaaaaugua | gccauucgua | ucugcuccua | auaaaaagaa | 1680 |
| aguuucuuca | cauucuagaa | aaaaaaaaaa | aaaaaaaaaa | aaaaaaaaaa | aaaaaaaaaa | 1740 |
| aaaaaaaaaa | aaaaaaaaaa | aaaaaaaaaa | aaaaaaaaaa | aaaaaaaaaa | aaaaaaaaaa | 1800 |
| aaaaaaaaaa | aaaaaaaa | | | | | 1818 |

<210> SEQ ID NO 86
<211> LENGTH: 1818
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 86

| | | | | | |
|---|---|---|---|---|---|
| aggaaacuua | agucaacaca | acauauacaa | aacaaacgaa | ucucaagcaa | ucaagcauuc | 60 |

| | |
|---|---|
| uacuucuauu gcagcaauuu aaaucauuuc uuuuaaagca aaagcaauuu ucugaaaauu | 120 |
| uucaccauuu acgaacgaua gccaugcagc gcgugaacau gaucauggca gaaagcccag | 180 |
| gccucaucac caucugccug cugggauacc uacucagugc cgaauguaca guguuccugg | 240 |
| accacgaaaa cgccaacaaa auccugaacc ggccaaagag guacaacuca ggcaaacugg | 300 |
| aagaguucgu gcaagggaac cuggagagag aaugcaugga agaaaagugc agcuucgaag | 360 |
| aagcacgaga aguguuugaa aacacugaaa gaacaaccga auuuuggaag caguacgugg | 420 |
| auggagauca gugcgagagc aacccaugcc ugaauggcgg cagcugcaag gacgacauca | 480 |
| acagcuacga augcuggugc cccuucggau ucgaaggaaa gaacugcgaa cuggacguaa | 540 |
| caugcaacau caagaacggc agaugcgagc aguuuguaa aaacagcgcc gacaacaagg | 600 |
| ugguguugcag cugcaccgag ggauaccgac uggcagaaaa ccagaagucc ugcgaaccag | 660 |
| cagugccauu cccaugcgga agagugucug ugucacaaac cagcaagcuc acccgggccg | 720 |
| agaccguguu ccccgacgug gacuacguaa acagcaccga agccgaaacc auccuggaua | 780 |
| acaucacccca aagcacccaa agcuucaaug acuucacccg gguggugggc ggagaagacg | 840 |
| ccaaaccagg ccaauucccc uggcagguug ugcugaacgg caaaguugac gcauucugcg | 900 |
| gaggcagcau cgugaacgaa aaauggaucg uaaccgcugc ccacugcguu gaaaccggcg | 960 |
| ugaaaaucac aguggucgca ggcgaacaca acauugagga gacagaacac acagagcaaa | 1020 |
| agcgaaacgu gauccgaauu auccccccacc acaacuacaa cgcagccauu aauaaguaca | 1080 |
| accaugacau cgcccugcug gaacuggacg aacccuuagu gcuaaacagc uacgugacac | 1140 |
| ccaucugcau cgccgacaag gaauacacga acaucuccu caaauucgga agcggcuacg | 1200 |
| uaagcggcug gggaagaguc uuccacaaag ggagaagcgc ccugguucug caguaccuga | 1260 |
| gagugccacu gguugaccga gccacaugcc ugcgaagcac aaaguucacc aucuacaaca | 1320 |
| acauguucug cgccggcuuc cauggaggag guagagacag cugucaagga gacagcgggg | 1380 |
| gaccccacgu uacugaagug gaagggacca gcuuccugac cggaaucauc agcuggggcg | 1440 |
| aagagugcgc aaugaaaggc aaauacggaa uauauaccaa gguaagccgg uacgucaacu | 1500 |
| ggaucaagga aaaaacaaag cucacuuaac ucgagcuagu gacugacuag gaucugguua | 1560 |
| ccacuaaacc agccucaaga cacccgaauu ggagucucua agcuacauaa uaccaacuua | 1620 |
| cacuuacaaa auguugucc ccaaaaugua gccauucgua ucugcuccua auaaaagaa | 1680 |
| aguuucuuca cauucuagaa aaaaaaaaa aaaaaaaaa aaaaaaaaa aaaaaaaaa | 1740 |
| aaaaaaaaa aaaaaaaaa aaaaaaaaa aaaaaaaaa aaaaaaaaa aaaaaaaaa | 1800 |
| aaaaaaaaa aaaaaaaa | 1818 |

<210> SEQ ID NO 87
<211> LENGTH: 1818
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 87

| | |
|---|---|
| aggaaacuua agucaacaca acauauacaa aacaaacgaa ucucaagcaa ucaagcauuc | 60 |
| uacuucuauu gcagcaauuu aaaucauuuc uuuuaaagca aaagcaauuu ucugaaaauu | 120 |
| uucaccauuu acgaacgaua gccaugcagc gcgugaacau gaucauggca gaaucaccag | 180 |
| gccucaucac caucugccug uuaggauacc uacucagcgc cgaauguaca guguucuug | 240 |

| | |
|---|---|
| accacgaaaa cgccaacaaa auccugaauc ggccaaagag guauaacuca gguaaacugg | 300 |
| aagaguuugu gcaagggaac cuggagagag aaugcaugga agaaaagugc agcuucgaag | 360 |
| aagcacgaga aguguucgaa aacacugaaa gaacaaccga auuuuggaag caguaugugg | 420 |
| auggagacca gugcgagucc aacccaugcu uaaacggcgg caguugcaag gacgacauca | 480 |
| acagcuauga augcuggugc cccuucggau uugaaggaaa gaacugcgaa cuggacguaa | 540 |
| cauguaacau caagaauggc agaugcgagc aguucguaa aaauagcgcc gacaacaagg | 600 |
| uggugugcag cuguaccgag ggauaccgac uggcagaaaa ccagaaguc ugcgaaccag | 660 |
| cagugccauu cccaugcgga agaguuagcg ugagccaaac cagcaagcuc acccgggccg | 720 |
| agaccuguu cccugacgug gacuacguaa acucuaccga agcugaaacc auccuggaca | 780 |
| acaucacuca aagcacccaa ucauucaacg acuucacccg gguggugggc ggagaagaug | 840 |
| ccaaaccagg ucaauucccu uggcaggugg uguugaacgg caaagugac gcauucugug | 900 |
| gaggcagcau cgugaacgaa aaauggaucg uaacugccgc ccacgcgug gaaaccggcg | 960 |
| ugaaaaucac aguggucgca ggcgaacaca auauugagga gacagaacac acagagcaaa | 1020 |
| agcgaaaugu gauccgaauu aucccucacc acaacuacaa cgcagcuauu aacaaguaca | 1080 |
| accacgacau ugcccugcug gaacuggacg aaccccuggu gcuaaacagc uacguuacac | 1140 |
| cuaucugcau cgccgacaag gaauacgaca acaucuuccu caaauucgga ucggcuacg | 1200 |
| uaagcggcug gggaagaguc uuccacaaag ggagaucagc ccuggugcuu caguaccuua | 1260 |
| gagugccacu uguggaccga gccacaugcc ugcgaagcac aaaguucacc aucuacaaca | 1320 |
| acauguucug ugcuggcuuc cacgaaggag guagagacag cugucaagga gauagcgggg | 1380 |
| gaccccacgu uaccgaagug gaagggacca gcuucuuaac uggaaucauc agcuggggcg | 1440 |
| aagagugcgc aaugaaggc aaauacgaa uauacaccaa gguaucccgg uaugucaacu | 1500 |
| ggaucaagga aaaacaaag cucaccuaac ucgagcuagu gacugacuag gaucgguua | 1560 |
| ccacuaaacc agcccuaaga acacccgaau ggagucucua agcuacauaa uaccaacuua | 1620 |
| cacuuacaaa auguugucc ccaaaaugua gccauucgua ucugcuccua auaaaagaa | 1680 |
| aguuucuuca cauucuagaa aaaaaaaaa aaaaaaaaaa aaaaaaaaa aaaaaaaaa | 1740 |
| aaaaaaaaaa aaaaaaaaaa aaaaaaaaaa aaaaaaaaaa aaaaaaaaaa aaaaaaaaaa | 1800 |
| aaaaaaaaaa aaaaaaaa | 1818 |

<210> SEQ ID NO 88
<211> LENGTH: 1818
<212> TYPE: RNA
<213> ORGANISM: Artificial Sequence
<220> FEATURE:
<223> OTHER INFORMATION: Description of Artificial Sequence: Synthetic
    polynucleotide

<400> SEQUENCE: 88

| | |
|---|---|
| aggaaacuua agucaacaca acauauacaa aacaaacgaa ucucaagcaa ucaagcauuc | 60 |
| uacuucuauu gcagcaauuu aaaucauuuc uuuuaaagca aaagcaauuu ucugaaaauu | 120 |
| uucaccauuu acgaacgaua gccaugcagc gcgugaacau gaucauggca gaaagcccag | 180 |
| gccucaucac caucugccuu cugggauauc uacucagcgc gaaugcaca guuuccuug | 240 |
| accacgaaaa cgccaacaaa auccugaauc ggccaaagag guauaauuca gguaaacugg | 300 |
| aagaguuugu ucaagggaac cuugagagag aaugcaugga agaaaagugu aguuuugaag | 360 |
| aagcacgaga aguguucgaa aacaccgaaa gaacaaccga auuuuggaag caguaugugg | 420 |

| auggagacca gugcgagagc aauccaugcu uaaauggcgg cagcugcaag gacgacauua | 480 |
| auuccuauga augcuggugc cccuuuggau ucgaaggaaa gaacugcgaa uuagacguaa | 540 |
| caugcaacau caagaacggc agaugcgagc aguuuuguaa aaauagugcu gacaacaagg | 600 |
| ugguuugcag cugcaccgag ggauaccgac uggcagaaaa ccagaagucc ugcgaaccag | 660 |
| cagugccauu cccaugugga agaguuucug ugagccaaac uucuaagcuc acccgugccg | 720 |
| agaccguuuu cccugacgug gacuauguaa auucuaccga agccaaaccc auuuuggaua | 780 |
| acaucaccca aagcacccaa agcuuuaacg acuucacucg ggugguuggc ggagaagacg | 840 |
| ccaaaccagg ccaauucccu uggcaggugg uucugaaugg caagugggau gcauucugug | 900 |
| gaggcucuau cgugaacgaa aaauggaucg uaacugccgc ccacugcguu gaaaccggcg | 960 |
| uuaaaauuac agguggucgc aggcgaacaca uauugagga gacagaacac acagagcaaa | 1020 |
| agcgaaacgu gauucgaauu aucccucacc acaacuacaa ugcagccauu aacaaguaca | 1080 |
| accaugacau cgcccugcug gaacuggacg aacccuggu gcuaaacagc uacguuacac | 1140 |
| cuauuugcau cgccgacaag gaauacacga acaucuuccu caaauuugga ucuggcuaug | 1200 |
| uaagcggcug gggaagaguc uuccacaaag ggagaagcgc ccuggugcuu caguaccuga | 1260 |
| gagugccacu ugguggaccga gccacaugu cugcgaagcac aaaguucacc aucuacaaca | 1320 |
| acauguucug cgccggcuuc cacgaaggag guagagacuc augccaagga gauagcgggg | 1380 |
| gaccccacgu gaccgaagug gaagggacca gcuuccugac uggaauuauu agcugggcg | 1440 |
| aagagugcgc aaugaaggc aaauauggaa uauacaccaa gguaagccgg uaugucaacu | 1500 |
| ggaucaagga aaaaacaaag cucaccuaac ucgagcuagu gacugacuag gaucugguua | 1560 |
| ccacuaaacc agccucaaga cacccgaau ggagucucua agcuacauaa uaccaacuua | 1620 |
| cacuuacaaa auguugucc ccaaaaugua gccauucgua ucugcuccua auaaaaagaa | 1680 |
| aguuucuuca cauucuagaa aaaaaaaaa aaaaaaaaa aaaaaaaaaa aaaaaaaaaa | 1740 |
| aaaaaaaaaa aaaaaaaaa aaaaaaaaa aaaaaaaaa aaaaaaaaaa aaaaaaaaaa | 1800 |
| aaaaaaaaaa aaaaaaaa | 1818 |

```
<210> SEQ ID NO 89
<211> LENGTH: 1257
<212> TYPE: DNA
<213> ORGANISM: Homo sapiens

<400> SEQUENCE: 89
```

| atgccgtctt ctgtctcgtg gggcatcctc ctgctggcag gcctgtgctg cctggtccct | 60 |
| gtctccctgg ctgaggatcc ccaggagat gctgcccaga agacagatac atcccaccat | 120 |
| gatcaggatc acccaacctt caacaagatc accccaaccc tggctgagtt cgccttcagc | 180 |
| ctataccgcc agctggcaca ccagtccaac agcaccaata tcttcttctc cccagtgagc | 240 |
| atcgctacag ccttttgcaat gctctccctg gggaccaagg ctgacactca cgatgaaatc | 300 |
| ctggagggcc tgaatttcaa cctcacggag attccggagg ctcagatcca tgaaggcttc | 360 |
| caggaactcc tccgtaccct caaccagcca gacagccagc tccagctgac caccggcaat | 420 |
| ggcctgttcc tcagcgaggg cctgaagcta gtggataagt ttttggagga tgttaaaaag | 480 |
| ttgtaccact cagaagcctt cactgtcaac ttcggggaca ccgaagaggc caagaaacag | 540 |
| atcaacgatt acgtggagaa gggtactcaa gggaaaattg tggatttggt caaggagctt | 600 |
| gacagagaca cagttttttgc tctggtgaat tacatcttct ttaaaggcaa atggagagag | 660 |
| cccctttgaag tcaaggacac cgaggaagag gacttccacg tggaccaggt gaccaccgtg | 720 |

```
aaggtgccta tgatgaagcg tttaggcatg tttaacatcc agcactgtaa gaagctgtcc    780
agctgggtgc tgctgatgaa atacctgggc aatgccaccg ccatcttctt cctgcctgat    840
gaggggaaac tacagcacct ggaaaatgaa ctcacccacg atatcatcac caagttcctg    900
gaaaatgaag acagaaggtc tgccagctta catttaccca actgtccat  tactggaacc    960 tatgatctga gagcgtcct  gggtcaactg gcatcacta  aggtcttcag caatggggct   1020
gacctctccg gggtcacaga ggaggcaccc ctgaagctct ccaaggccgt gcataaggct   1080
gtgctgacca tcgacgagaa agggactgaa gctgctgggg ccatgttttt agaggccata   1140
cccatgtcta tccccccga  ggtcaagttc aacaaaccct ttgtcttctt aatgattgaa   1200
caaaatacca agtctcccct cttcatggga aaagtggtga atcccaccca aaaataa     1257

<210> SEQ ID NO 90
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
atgccgagca gcgtcagctg gggcatcctc ctgctggcag gcctgtgctg cctggtcccc     60
gtcagcctgg ccgaggaccc ccagggagac gccgcccaga agacagacac aagccaccac    120
gaccaggacc acccaacctt caacaagatc accccccaacc tggccgagtt cgccttcagc    180
ctataccgcc agctggcaca ccagagcaac agcaccaaca tcttcttcag cccagtgagc    240
atcgccacag ccttcgcaat gctcagcctg gggaccaagg ccgacaccca cgacgaaatc    300
ctggagggcc tgaacttcaa cctcacggag atcccggagg cccagatcca cgaaggcttc    360
caggaactcc tccggaccct caaccagcca gacagccagc tccagctgac caccggcaac    420
ggcctgttcc tcagcgaggg cctgaagcta gtggacaagt tcctggagga cgtgaaaaag    480
ctgtaccaca gcgaagcctt caccgtcaac ttcggggaca ccgaagaggc caagaaacag    540
atcaacgact acgtggagaa gggcacccaa gggaaaatcg tggacctggt caaggagctg    600
gacagagaca cagtgttcgc cctggtgaac tacatcttct tcaaaggcaa atgggagaga    660
cccttcgaag tcaaggacac cgaggaagag gacttccacg tggaccaggt gaccaccgtg    720
aaggtgccca tgatgaagcg gctgggcatg ttcaacatcc agcactgcaa gaagctgagc    780
agctgggtgc tgctgatgaa atacctgggc aacgccaccg ccatcttctt cctgcccgac    840 gagggggaaac tacagcacct ggaaaacgaa ctcacccacg acatcatcac caagttcctg    900
gaaaacgaag acagaaggag cgccagcctg cacctgccca actgagcat  caccggaacc    960 tacgacctga gtccgtgct  gggccaactg gcatcacca  aggtcttcag caacggggcc   1020
gacctcagcg gggtcacaga ggaggcaccc ctgaagctca gcaaggccgt gcacaaggcc   1080
gtgctgacca tcgacgagaa agggaccgaa gccgccgggg ccatgttcct ggaggccata   1140
cccatgagca tccccccga  ggtcaagttc aacaaaccct tcgtcttcct gatgatcgaa   1200
caaaacacca agagccccct cttcatggga aaagtggtga accccaccca aaaataa     1257

<210> SEQ ID NO 91
<211> LENGTH: 1257
<212> TYPE: DNA
<213> ORGANISM: Artificial Sequence
<220> FEATURE:
<223> OTHER INFORMATION: Description of Artificial Sequence: Synthetic
```

-continued polynucleotide

<400> SEQUENCE: 91

| | |
|---|---|
| atgccgtctt ctgtctcgtg gggcatcctc ctgctggcag gcctgtgctg cctggtccct | 60 |
| gtctccctgg ctgaggatcc cagggagat gctgcccaga agacagatac atcccaccat | 120 |
| gatcaggatc acccaacctt caacaagatc accccccaacc tggctgagtt cgccttcagc | 180 |
| ctataccgcc agctggcaca ccagtccaac agcaccaata tcttcttctc cccagtgagc | 240 |
| atcgctacag cctttgcaat gctctccctg gggaccaagg ctgacactca cgatgaaatc | 300 |
| ctggagggcc tgaacttcaa cctcacggag atcccggagg cccagatcca cgaaggcttc | 360 |
| caggaactcc tccggaccct caaccagcca gacagccagc tccagctgac caccggcaac | 420 |
| ggcctgttcc tcagcgaggg cctgaagcta gtggacaagt tcctggagga cgtgaaaaag | 480 |
| ctgtaccaca gcgaagcctt caccgtcaac ttcggggaca ccgaagaggc caagaaacag | 540 |
| atcaacgact acgtggagaa gggcacccaa gggaaaatcg tggacctggt caaggagctg | 600 |
| gacagagaca cagtgttcgc cctggtgaac tacatcttct tcaaaggcaa atgggagaga | 660 |
| cccttcgaag tcaaggacac cgaggaagag gacttccacg tggaccaggt gaccaccgtg | 720 |
| aaggtgccca tgatgaagcg gctgggcatg ttcaacatcc agcactgcaa gaagctgagc | 780 |
| agctgggtgc tgctgatgaa atacctgggc aacgccaccg ccatcttctt cctgcccgac | 840 |
| gaggggaaac tacagcacct ggaaaacgaa ctcacccacg acatcatcac caagttcctg | 900 |
| gaaaacgaag acagaaggag cgccagcctg cacctgccca aactgagcat caccggaacc | 960 |
| tacgacctga gtccgtgct gggccaactg gcatcacca aggtcttcag caacggggc | 1020 |
| gacctcagcg gggtcacaga ggaggcaccc ctgaagctca gcaaggccgt gcacaaggcc | 1080 |
| gtgctgacca tcgacgagaa agggaccgaa gccgccgggg ccatgttcct ggaggccata | 1140 |
| cccatgagca tccccccga ggtcaagttc aacaaaccct tcgtcttcct gatgatcgaa | 1200 |
| caaaacacca agagccccct cttcatggga aagtggtga accccaccca aaaataa | 1257 |

<210> SEQ ID NO 92
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

| | |
|---|---|
| atgccgtctt ctgtctcgtg gggcatcctc ctgctggcag gcctgtgctg cctggtccct | 60 |
| gtctccctgg ctgaggatcc cagggagat gctgcccaga agacagatac atcccaccat | 120 |
| gatcaggatc acccaacctt caacaagatc accccccaacc tggctgagtt cgccttcagc | 180 |
| ctataccgcc agctggcaca ccagtccaac agcaccaata tcttcttctc cccagtgagc | 240 |
| atcgctacag cctttgcaat gctctccctg gggaccaagg ctgacactca cgatgaaatc | 300 |
| ctggagggcc tgaatttcaa cctcacggag attccggagg ctcagatcca tgaaggcttc | 360 |
| caggaactcc tccgtaccct caaccagcca gacagccagc tccagctgac caccggcaat | 420 |
| ggcctgttcc tcagcgaggg cctgaagcta gtggataagt ttttggagga tgttaaaaag | 480 |
| ttgtaccact cagaagcctt cactgtcaac ttcggggaca ccgaagaggc caagaaacag | 540 |
| atcaacgatt acgtggagaa gggtactcaa gggaaaattg tggatttggt caaggagctt | 600 |
| gacagagaca cagtttttgc tctggtgaat tacatcttct tcaaaggcaa atgggagaga | 660 |

```
cccttcgaag tcaaggacac cgaggaagag gacttccacg tggaccaggt gaccaccgtg    720
aaggtgccca tgatgaagcg gctgggcatg ttcaacatcc agcactgcaa gaagctgagc    780
agctgggtgc tgctgatgaa atacctgggc aacgccaccg ccatcttctt cctgcccgac    840 gagggggaaac tacagcacct ggaaaacgaa ctcacccacg acatcatcac caagttcctg    900
gaaaacgaag acagaaggag cgccagcctg cacctgccca aactgagcat caccggaacc    960
tacgacctga gtccgtgctg ggccaactg gcatcacca aggtcttcag caacggggcc    1020
gacctcagcg gggtcacaga ggaggcaccc ctgaagctca gcaaggccgt gcacaaggcc    1080
gtgctgacca tcgacgagaa agggaccgaa gccgccgggg ccatgttcct ggaggccata    1140
cccatgagca tccccccccga ggtcaagttc aacaaaccct tcgtcttcct gatgatcgaa    1200
caaaacacca agagccccct cttcatggga aaagtggtga accccaccca aaaataa      1257
```

<210> SEQ ID NO 93
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

```
atgccgtctt ctgtctcgtg gggcatcctc ctgctggcag gcctgtgctg cctggtccct     60
gtctccctgg ctgaggatcc ccaggagat gctgcccaga agacagatac atcccaccat    120
gatcaggatc acccaacctt caacaagatc accccccaacc tggctgagtt cgccttcagc    180
ctataccgcc agctggcaca ccagtccaac agcaccaata tcttcttctc cccagtgagc    240
atcgctacag cctttgcaat gctctccctg gggaccaagg ctgacactca cgatgaaatc    300
ctggagggcc tgaattttcaa cctcacgag attccggagg ctcagatcca tgaaggcttc    360
caggaactcc tccgtacccct caaccagcca gacagccagc tccagctgac caccggcaat    420
ggcctgttcc tcagcgaggg cctgaagcta gtggataagt ttttggagga tgttaaaaag    480
ttgtaccact cagaagcctt cactgtcaac ttcggggaca ccgaagaggc caagaaacag    540
atcaacgatt acgtggagaa gggtactcaa gggaaaattg tggatttggt caaggagctt    600
gacagagaca cagttttgc tctggtgaat tacatcttct ttaaaggcaa atgggagaga    660
ccctttgaag tcaaggacac cgaggaagag gacttccacg tggaccaggt gaccaccgtg    720
aaggtgccta tgatgaagcg tttaggcatg tttaacatcc agcactgtaa gaagctgtcc    780
agctgggtgc tgctgatgaa atacctgggc aatgccaccg ccatcttctt cctgcctgat    840 gagggggaaac tacagcacct ggaaaatgaa ctcacccacg atatcatcac caagttcctg    900
gaaaatgaag acagaaggtc tgccagctta catttaccca aactgtccat tactggaacc    960
tatgatctga gtccgtgctg gggtcaactg gcatcacca aggtcttcag caacggggcc    1020
gacctcagcg gggtcacaga ggaggcaccc ctgaagctca gcaaggccgt gcacaaggcc    1080
gtgctgacca tcgacgagaa agggaccgaa gccgccgggg ccatgttcct ggaggccata    1140
cccatgagca tccccccccga ggtcaagttc aacaaaccct tcgtcttcct gatgatcgaa    1200
caaaacacca agagccccct cttcatggga aaagtggtga accccaccca aaaataa      1257
```

<210> SEQ ID NO 94
<211> LENGTH: 1257
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 94

```
atgccgagca gcgtcagctg gggcatcctc ctgctggcag gcctgtgctg cctggtcccc      60
gtcagcctgg ccgaggaccc ccagggagac gccgcccaga agacagacac aagccaccac     120
gaccaggacc acccaacctt caacaagatc accccccaacc tggccgagtt cgccttcagc    180
ctataccgcc agctggcaca ccagagcaac agcaccaaca tcttcttcag cccagtgagc    240
atcgccacag ccttcgcaat gctcagcctg gggaccaagg ccgacaccca cgacgaaatc    300
ctggagggcc tgaacttcaa cctcacggag atcccggagg cccagatcca cgaaggcttc    360
caggaactcc tccggaccct caaccagcca gacagccagc tccagctgac caccggcaac    420
ggcctgttcc tcagcgaggg cctgaagcta gtggacaagt tcctggagga cgtgaaaaag    480
ctgtaccaca gcgaagcctt caccgtcaac ttcggggaca ccgaagaggc caagaaacag    540
atcaacgact acgtggagaa gggcacccaa gggaaaatcg tggacctggt caaggagctg    600
gacagagaca cagtgttcgc cctggtgaac tacatcttct tcaaaggcaa atgggagaga    660
cccttcgaag tcaaggacac cgaggaagag gacttccacg tggaccaggt gaccaccgtg    720
aaggtgccca tgatgaagcg gctgggcatg ttcaacatcc agcactgcaa gaagctgagc    780
agctgggtgc tgctgatgaa atacctgggc aacgccaccg ccatcttctt cctgccgac    840
gaggggaaac tacagcacct ggaaaacgaa ctcacccacg acatcatcac caagttcctg    900
gaaaacgaag acagaaggag cgccagcctg cacctgccca aactgagcat tactggaacc    960
tatgatctga gtccgtgct gggtcaactg ggcatcacta aggtcttcag caatggggct   1020
gacctctccg gggtcacaga ggaggcaccc ctgaagctct ccaaggccgt gcataaggct   1080
gtgctgacca tcgacgagaa agggactgaa gctgctgggg ccatgttttt agaggccata   1140
cccatgtcta tccccccga ggtcaagttc aacaaaccct tgtcttctt aatgattgaa    1200
caaaatacca agtctcccct cttcatggga aaagtggtga atccccaccca aaaataa    1257
```

<210> SEQ ID NO 95
<211> LENGTH: 1257
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 95

```
atgccgagca gcgtcagctg gggcatcctc ctgctggcag gcctgtgctg cctggtcccc      60
gtcagcctgg ccgaggaccc ccagggagac gccgcccaga agacagacac aagccaccac     120
gaccaggacc acccaacctt caacaagatc accccccaacc tggccgagtt cgccttcagc    180
ctataccgcc agctggcaca ccagagcaac agcaccaaca tcttcttcag cccagtgagc    240
atcgccacag ccttcgcaat gctcagcctg gggaccaagg ccgacaccca cgacgaaatc    300
ctggagggcc tgaacttcaa cctcacggag atcccggagg cccagatcca cgaaggcttc    360
caggaactcc tccggaccct caaccagcca gacagccagc tccagctgac caccggcaac    420
ggcctgttcc tcagcgaggg cctgaagcta gtggacaagt tcctggagga cgtgaaaaag    480
ctgtaccaca gcgaagcctt caccgtcaac ttcggggaca ccgaagaggc caagaaacag    540
atcaacgact acgtggagaa gggcacccaa gggaaaatcg tggacctggt caaggagctt    600
gacagagaca cagttttgc tctggtgaat tacatcttct ttaaaggcaa atgggagaga    660
```

```
ccctttgaag tcaaggacac cgaggaagag gacttccacg tggaccaggt gaccaccgtg    720
aaggtgccta tgatgaagcg tttaggcatg tttaacatcc agcactgtaa gaagctgtcc    780
agctgggtgc tgctgatgaa atacctgggc aatgccaccg ccatcttctt cctgcctgat    840
gaggggaaac tacagcacct ggaaaatgaa ctcacccacg atatcatcac caagttcctg    900
gaaaatgaag acagaaggtc tgccagctta catttaccca aactgtccat tactggaacc    960
tatgatctga gtccgtgct gggtcaactg gcatcacta aggtcttcag caatgggct     1020 gacctctccg gggtcacaga ggaggcaccc ctgaagctct ccaaggccgt gcataaggct    1080
gtgctgacca tcgacgagaa agggactgaa gctgctgggg ccatgttttt agaggccata    1140
cccatgtcta tccccccga ggtcaagttc aacaaaccct tgtcttctt aatgattgaa    1200 caaaatacca agtctcccct cttcatggga aaagtggtga atcccaccca aaataa     1257
```

<210> SEQ ID NO 96
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96

```
atgccgagca gcgtcagctg gggcatcctc ctgctggcag gcctgtgctg cctggtcccc     60
gtcagcctgg ccgaggaccc ccagggagac gccgcccaga agacagacac aagccaccac    120
gaccaggacc acccaaacctt caacaagatc acccccaacc tggccgagtt cgccttcagc    180
ctataccgcc agctggcaca ccagagcaac agcaccaaca tcttcttcag cccagtgagc    240
atcgccacag cctttgcaat gctctccctg gggaccaagg ctgacactca cgatgaaatc    300
ctggagggcc tgaatttcaa cctcacggag attccggagg ctcagatcca tgaaggcttc    360
caggaactcc tccgtaccct caaccagcca gacagccagc tccagctgac caccggcaat    420
ggcctgttcc tcagcgaggg cctgaagcta gtggataagt ttttggagga tgttaaaaag    480
ttgtaccact cagaagcctt cactgtcaac ttcggggaca ccgaagaggc caagaaacag    540
atcaacgatt acgtggagaa gggtactcaa gggaaaattg tggatttggt caaggagctt    600
gacagagaca cagttttgc tctggtgaat tacatcttct taaaggcaa atgggagaga    660 ccctttgaag tcaaggacac cgaggaagag gacttccacg tggaccaggt gaccaccgtg    720
aaggtgccta tgatgaagcg tttaggcatg tttaacatcc agcactgtaa gaagctgtcc    780
agctgggtgc tgctgatgaa atacctgggc aatgccaccg ccatcttctt cctgcctgat    840
gaggggaaac tacagcacct ggaaaatgaa ctcacccacg atatcatcac caagttcctg    900
gaaaatgaag acagaaggtc tgccagctta catttaccca aactgtccat tactggaacc    960
tatgatctga gtccgtgct gggtcaactg gcatcacta aggtcttcag caatgggct     1020 gacctctccg gggtcacaga ggaggcaccc ctgaagctct ccaaggccgt gcataaggct    1080
gtgctgacca tcgacgagaa agggactgaa gctgctgggg ccatgttttt agaggccata    1140
cccatgtcta tccccccga ggtcaagttc aacaaaccct tgtcttctt aatgattgaa    1200 caaaatacca agtctcccct cttcatggga aaagtggtga atcccaccca aaataa     1257
```

<210> SEQ ID NO 97
<211> LENGTH: 1257
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 97
atgccgagca gcgtctcgtg gggcatcctc ctgctggcag gcctgtgctg cctggtcccc      60
gtcagcctgg ccgaggaccc ccagggagat gctgcccaga agacagacac atcccaccac     120
gaccaggacc acccaacctt caacaagatc accccaacc tggctgagtt cgccttcagc      180
ctataccgcc agctggcaca ccagagcaac agcaccaata tcttcttcag cccagtgagc     240
atcgctacag ccttcgcaat gctcagcctg gggaccaagg ccgacaccca cgatgaaatc     300
ctggagggcc tgaatttcaa cctcacggag atcccggagg ctcagatcca cgaaggcttc     360
caggaactcc tccggaccct caaccagcca gacagccagc tccagctgac caccggcaac     420
ggcctgttcc tcagcgaggg cctgaagcta gtggacaagt tcctggagga cgttaaaaag     480
ctgtaccaca gcgaagcctt caccgtcaac ttcggggaca ccgaagaggc caagaaacag     540
atcaacgatt acgtggagaa gggcacccaa gggaaaatcg tggacctggt caaggagctt     600
gacagagaca cagtgtttgc cctggtgaac tacatcttct tcaaaggcaa atgggagaga     660
cccttcgaag tcaaggacac cgaggaagag gacttccacg tggaccaggt gaccaccgtg     720
aaggtgccca tgatgaagcg gttaggcatg ttcaacatcc agcactgcaa gaagctgagc     780
agctgggtgc tgctgatgaa atacctgggc aacgccaccg ccatcttctt cctgcccgac     840 gagggaaac tacagcacct ggaaaacgaa ctcacccacg acatcatcac caagttcctg     900
gaaaacgaag acagaaggag cgccagcctg catctgccca aactgagcat tactggaacc     960
tacgatctga agtccgtgct gggtcaactg gcatcacca aggtcttcag caatggggcc     1020
gacctcagcg gggtcacaga ggaggcaccc ctgaagctca gcaaggccgt gcacaaggct     1080
gtgctgacca tcgacgagaa agggaccgaa gccgctgggg ccatgttcct ggaggccata     1140
cccatgagca tcccccccga ggtcaagttc aacaaaccct tgtcttcct gatgatcgaa      1200 caaaacacca gtctcccct cttcatggga aagtggtga acccacccca aaaataa         1257

<210> SEQ ID NO 98
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
atgccgtctt ctgtctcgtg gggcatcctc ctgctggcag gcctgtgctg cctggtcccc      60
gtctccctgg ctgaggaccc ccagggagat gccgcccaga agacagacac atcccaccat     120
gaccaggacc acccaacctt caacaagatc accccaacc tggccgagtt cgccttcagc      180
ctataccgcc agctggcaca ccagagcaac agcaccaaca tcttcttctc cccagtgagc     240
atcgccacag cctttgcaat gctctccctg gggaccaagg ccgacaccca cgacgaaatc     300
ctggagggcc tgaatttcaa cctcacggag atcccggagg ctcagatcca tgaaggcttc     360
caggaactcc tccggaccct caaccagcca gacagccagc tccagctgac caccggcaat     420
ggcctgttcc tcagcgaggg cctgaagcta gtggataagt tcctggagga tgttaaaaag     480
ctgtaccaca gcgaagcctt caccgtcaac ttcggggaca ccgaagaggc caagaaacag     540
atcaacgatt acgtggagaa gggcacccaa gggaaaatcg tggacctggt caaggagctt     600
```

| | |
|---|---|
| gacagagaca cagtgtttgc tctggtgaat tacatcttct ttaaaggcaa atgggagaga | 660 |
| cccttttgaag tcaaggacac cgaggaagag gacttccacg tggaccaggt gaccaccgtg | 720 |
| aaggtgccta tgatgaagcg gttaggcatg tttaacatcc agcactgcaa gaagctgagc | 780 |
| agctgggtgc tgctgatgaa atacctgggc aatgccaccg ccatcttctt cctgcctgat | 840 |
| gaggggaaac tacagcacct ggaaaacgaa ctcacccacg acatcatcac caagttcctg | 900 |
| gaaaatgaag acagaaggtc tgccagctta cacttaccca aactgagcat tactggaacc | 960 |
| tacgatctga agtccgtgct gggccaactg ggcatcacta aggtcttcag caacggggct | 1020 |
| gacctctccg gggtcacaga ggaggcaccc ctgaagctca gcaaggccgt gcacaaggct | 1080 |
| gtgctgacca tcgacgagaa agggaccgaa gctgccgggg ccatgttttct ggaggccata | 1140 |
| cccatgtcta tcccccccga ggtcaagttc aacaaaccct ttgtcttcct gatgatcgaa | 1200 |
| caaaatacca agagcccccct cttcatggga aaagtggtga accccaccca aaaataa | 1257 |

<210> SEQ ID NO 99
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

| | |
|---|---|
| atgccgagca gcgtcagctg gggcatcctc ctgctggcag gcctgtgctg cctggtccct | 60 |
| gtctccctgg ctgaggatcc ccagggagat gctgcccaga agacagatac atcccaccat | 120 |
| gatcaggatc acccaacctt caacaagatc accccccaacc tggctgagtt cgccttcagc | 180 |
| ctataccgcc agctggcaca ccagtccaac agcaccaata tcttcttctc cccagtgagc | 240 |
| atcgctacag ccttcgcaat gctctccctg gggaccaagg ctgacactca cgatgaaatc | 300 |
| ctggagggcc tgaatttcaa cctcacggag attccgagg cccagatcca tgaaggcttc | 360 |
| caggaactcc tccgtaccct caaccagcca gacagccagc tccagctgac caccggcaat | 420 |
| ggcctgttcc tcagcgaggg cctgaagcta gtggataagt ttttggagga tgttaaaaag | 480 |
| ctgtaccaca gcgaagcctt cactgtcaac ttcggggaca ccgaagaggc caagaaacag | 540 |
| atcaacgatt acgtggagaa gggtactcaa gggaaaattg tggatttggt caaggagctt | 600 |
| gacagagaca cagtttttgc tctggtgaat tacatcttct tcaaaggcaa atgggagaga | 660 |
| cccttttgaag tcaaggacac cgaggaagag gacttccacg tggaccaggt gaccaccgtg | 720 |
| aaggtgccta tgatgaagcg gttaggcatg ttcaacatcc agcactgtaa gaagctgtcc | 780 |
| agctgggtgc tgctgatgaa atacctgggc aatgccaccg ccatcttctt cctgcctgat | 840 |
| gaggggaaac tacagcacct ggaaaatgaa ctcacccacg atatcatcac caagttcctg | 900 |
| gaaaatgaag acagaaggag cgccagctta catttaccca aactgagcat tactggaacc | 960 |
| tacgatctga agtccgtgct gggtcaactg ggcatcacta aggtcttcag caacggggct | 1020 |
| gacctctccg gggtcacaga ggaggcaccc ctgaagctct ccaaggccgt gcataaggct | 1080 |
| gtgctgacca tcgacgagaa agggactgaa gctgctgggg ccatgttttt agaggccata | 1140 |
| cccatgtcta tcccccccga ggtcaagttc aacaaaccct ttgtcttcct gatgatcgaa | 1200 |
| caaaatacca agagcccccct cttcatggga aaagtggtga atcccaccca aaaataa | 1257 |

<210> SEQ ID NO 100
<211> LENGTH: 1689
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 100

```
aggaaactta agtcaacaca acatatacaa aacaaacgaa tctcaagcaa tcaagcattc    60
tacttctatt gcagcaattt aaatcatttc ttttaaagca aaagcaattt tctgaaaatt   120
ttcaccattt acgaacgata gccatgccga gcagcgtcag ctggggcatc ctcctgctgg   180
caggcctgtg ctgcctggtc cccgtcagcc tggccgagga cccccaggga gacgccgccc   240
agaagacaga cacaagccac cacgaccagg accaccaaac cttcaacaag atcaccccca   300
acctggccga gttcgccttc agcctatacc gccagctggc acaccagagc aacagcacca   360
acatcttctt cagcccagtg agcatcgcca gccttcgc aatgctcagc ctggggacca   420
aggccgacac ccacgacgaa atcctggagg gcctgaactt caacctcacg gagatcccgg   480
aggcccagat ccacgaaggc ttccaggaac tcctccggac cctcaaccag ccagacagcc   540
agctccagct gaccaccggc aacggcctgt tcctcagcga gggcctgaag ctagtggaca   600
agttcctgga ggacgtgaaa aagctgtacc acagcgaagc cttcaccgtc aacttcgggg   660
acaccgaaga ggccaagaaa cagatcaacg actacgtgga aagggcacc caagggaaaa   720
tcgtggacct ggtcaaggag ctggacagag acacagtgtt cgccctggtg aactacatct   780
tcttcaaagg caaatgggag agacccttcg aagtcaagga caccgaggaa gaggacttcc   840
acgtggacca ggtgaccacc gtgaaggtgc ccatgatgaa gcggctgggc atgttcaaca   900
tccagcactg caagaagctg agcagctggg tgctgctgat gaaatacctg ggcaacgcca   960
ccgccatctt cttcctgccc gacgagggga actacagca cctggaaaac gaactcaccc  1020
acgacatcat caccaagttc ctggaaaacg aagacagaag gagcgccagc ctgcacctgc  1080
ccaaactgag catcaccgga acctacgacc tgaagtccgt gctgggccaa ctgggcatca  1140
ccaaggtctt cagcaacggg gccgacctca gcggggtcac agaggaggca cccctgaagc  1200
tcagcaaggc cgtgcacaag gccgtgctga ccatcgacga aaagggacc gaagccgccg  1260
gggccatgtt cctggaggcc atacccatga gcatccccc cgaggtcaag ttcaacaaac  1320
ccttcgtctt cctgatgatc gaacaaaaca ccaagagccc cctcttcatg ggaaagtgg  1380
tgaaccccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga agtttcttc  1560
acattctaga aaaaaaaaa aaaaaaaaaa aaaaaaaaa aaaaaaaaaa aaaaaaaaa    1620
aaaaaaaaa aaaaaaaaa aaaaaaaaa aaaaaaaaa aaaaaaaaa aaaaaaaaa    1680
aaaaaaaaa                                                        1689
```

<210> SEQ ID NO 101
<211> LENGTH: 1689
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 101

```
aggaaactta agtcaacaca acatatacaa aacaaacgaa tctcaagcaa tcaagcattc    60
tacttctatt gcagcaattt aaatcatttc ttttaaagca aaagcaattt tctgaaaatt   120
```

```
ttcaccattt acgaacgata gccatgccgt cttctgtctc gtggggcatc ctcctgctgg    180
caggcctgtg ctgcctggtc cctgtctccc tggctgagga tccccaggga gatgctgccc    240
agaagacaga tacatcccac catgatcagg atcacccaac cttcaacaag atcacccca    300 acctggctga gttcgccttc agcctatacc gccagctggc acaccagtcc aacagcacca    360
atatcttctt ctccccagtg agcatcgcta cagcctttgc aatgctctcc ctggggacca    420
aggctgacac tcacgatgaa atcctggagg gcctgaactt caacctcacg agatcccgg    480 aggcccagat ccacgaaggc ttccaggaac tcctccggac cctcaaccag ccagacagcc    540
agctccagct gaccaccggc aacggcctgt tcctcagcga gggcctgaag ctagtggaca    600
agttcctgga ggacgtgaaa aagctgtacc acagcgaagc cttcaccgtc aacttcgggg    660
acaccgaaga ggccaagaaa cagatcaacg actacgtgga aagggcacc caagggaaaa    720 tcgtggacct ggtcaaggag ctggacagag acacagtgtt cgccctggtg aactacatct    780
tcttcaaagg caaatgggag agaccccttcg aagtcaagga caccgaggaa gaggacttcc    840
acgtggacca ggtgaccacc gtgaaggtgc ccatgatgaa gcggctgggc atgttcaaca    900
tccagcactg caagaagctg agcagctggg tgctgctgat gaaatacctg ggcaacgcca    960
ccgccatctt cttcctgccc gacgagggga aactacagca cctggaaaac gaactcaccc    1020
acgacatcat caccagttc ctggaaaacg aagacagaag gagcgccagc ctgcacctgc    1080
ccaaactgag catcaccgga acctacgacc tgaagtccgt gctgggccaa ctgggcatca    1140
ccaaggtctt cagcaacggg gccgacctca gcggggtcac agaggaggca cccctgaagc    1200
tcagcaaggc cgtgcacaag gccgtgctga ccatcgacga aaagggacc gaagccgccg    1260 gggccatgtt cctggaggcc atacccatga gcatccccc cgaggtcaag ttcaacaaac    1320
ccttcgtctt cctgatgatc gaacaaaaca ccaagagccc cctcttcatg ggaaaagtgg    1380
tgaaccccac ccaaaaataa ctcgagctag tgactgacta ggatctggtt accactaaac    1440
cagcctcaag aacacccgaa tggagtctct aagctacata ataccaactt acacttacaa    1500
aatgttgtcc cccaaaatgt agccattcgt atctgctcct aataaaaaga agtttcttc    1560 acattctaga aaaaaaaaa aaaaaaaaaa aaaaaaaaaa aaaaaaaaaa aaaaaaaaaa    1620
aaaaaaaaaa aaaaaaaaaa aaaaaaaaaa aaaaaaaaaa aaaaaaaaaa aaaaaaaaaa    1680
aaaaaaaaa                                                           1689

<210> SEQ ID NO 102
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
aggaaactta agtcaacaca acatatacaa aacaaacgaa tctcaagcaa tcaagcattc     60
tacttctatt gcagcaattt aaatcatttc ttttaaagca aaagcaattt tctgaaaatt    120
ttcaccattt acgaacgata gccatgccgt cttctgtctc gtggggcatc ctcctgctgg    180
caggcctgtg ctgcctggtc cctgtctccc tggctgagga tccccaggga gatgctgccc    240
agaagacaga tacatcccac catgatcagg atcacccaac cttcaacaag atcacccca    300 acctggctga gttcgccttc agcctatacc gccagctggc acaccagtcc aacagcacca    360
atatcttctt ctccccagtg agcatcgcta cagcctttgc aatgctctcc ctggggacca    420
```

```
aggctgacac tcacgatgaa atcctggagg gcctgaattt caacctcacg gagattccgg    480
aggctcagat ccatgaaggc ttccaggaac tcctccgtac cctcaaccag ccagacagcc    540
agctccagct gaccaccggc aatggcctgt tcctcagcga gggcctgaag ctagtggata    600 agttttttgga ggatgttaaa aagttgtacc actcagaagc cttcactgtc aacttcgggg   660
acaccgaaga ggccaagaaa cagatcaacg attacgtgga aagggtact caagggaaaa    720 ttgtggattt ggtcaaggag cttgacagag acacagtttt tgctctggtg aattacatct    780
tcttcaaagg caaatgggag agacccttcg aagtcaagga caccgaggaa gaggacttcc    840
acgtggacca ggtgaccacc gtgaaggtgc ccatgatgaa cggctgggc atgttcaaca    900 tccagcactg caagaagctg agcagctggg tgctgctgat gaaatacctg gcaacgcca    960 ccgccatctt cttcctgccc gacgagggga actacagca cctggaaaac gaactcaccc    1020
acgacatcat caccaagttc ctggaaacg aagacagaag gagcgccagc ctgcacctgc     1080
ccaaactgag catcaccgga acctacgacc tgaagtccgt gctgggccaa ctgggcatca   1140
ccaaggtctt cagcaacggg gccgacctca gcggggtcac agaggaggca cccctgaagc   1200
tcagcaaggc cgtgcacaag gccgtgctga ccatcgacga aaagggacc gaagccgccg    1260 gggccatgtt cctggaggcc atacccatga gcatccccc cgaggtcaag ttcaacaaac    1320
ccttcgtctt cctgatgatc gaacaaaaca ccaagagccc cctcttcatg ggaaaagtgg   1380
tgaaccccac ccaaaaataa ctcgagctag tgactgacta ggatctggtt accactaaac   1440
cagcctcaag aacacccgaa tggagtctct aagctacata ataccaactt acacttacaa    1500
aatgttgtcc cccaaaatgt agccattcgt atctgctcct aataaaaaga agtttcttc    1560 acattctaga aaaaaaaaa aaaaaaaaaa aaaaaaaaaa aaaaaaaaaa aaaaaaaaaa    1620 aaaaaaaaa aaaaaaaaa aaaaaaaaaa aaaaaaaaa aaaaaaaaaa aaaaaaaaaa      1680
aaaaaaaaa                                                            1689
```

<210> SEQ ID NO 103
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
aggaaactta agtcaacaca acatatacaa aacaaacgaa tctcaagcaa tcaagcattc     60
tacttctatt gcagcaattt aaatcatttc ttttaaagca aaagcaattt tctgaaaatt    120
ttcaccattt acgaacgata gccatgccgt cttctgtctc gtggggcatc ctcctgctgg    180
caggcctgtg ctgcctggtc cctgtctccc tggctgagga tccccaggga gatgctgccc   240
agaagacaga tacatcccac catgatcagg atcacccaac cttcaacaag atcacccccca   300 acctggctga gttcgccttc agcctatacc gccagctggc acaccagtcc aacagcacca   360
atatcttctt ctccccagtg agcatcgcta cagcctttgc aatgctctcc ctggggacca   420
aggctgacac tcacgatgaa atcctggagg gcctgaattt caacctcacg gagattccgg    480
aggctcagat ccatgaaggc ttccaggaac tcctccgtac cctcaaccag ccagacagcc    540
agctccagct gaccaccggc aatggcctgt tcctcagcga gggcctgaag ctagtggata    600 agttttttgga ggatgttaaa aagttgtacc actcagaagc cttcactgtc aacttcgggg   660
acaccgaaga ggccaagaaa cagatcaacg attacgtgga aagggtact caagggaaaa    720
```

```
ttgtggattt ggtcaaggag cttgacagag acacagtttt tgctctggtg aattacatct    780
tctttaaagg caaatgggag agacccttttg aagtcaagga caccgaggaa gaggacttcc    840
acgtggacca ggtgaccacc gtgaaggtgc ctatgatgaa gcgtttaggc atgtttaaca    900
tccagcactg taagaagctg tccagctggg tgctgctgat gaaatacctg ggcaatgcca    960
ccgccatctt cttcctgcct gatgagggga aactacagca cctggaaaat gaactcaccc   1020
acgatatcat caccagttc ctggaaaatg aagacagaag gtctgccagc ttacatttac    1080
ccaaactgtc cattactgga acctatgatc tgaagtccgt gctgggtcaa ctgggcatca    1140
ccaaggtctt cagcaacggg gccgacctca gcggggtcac agaggaggca cccctgaagc    1200
tcagcaaggc cgtgcacaag gccgtgctga ccatcgacga gaagggacc gaagccgccg    1260 gggccatgtt cctggaggcc atacccatga gcatccccccc cgaggtcaag ttcaacaaac    1320
ccttcgtctt cctgatgatc gaacaaaaca ccaagagccc cctcttcatg ggaaaagtgg    1380
tgaaccccac ccaaaaataa ctcgagctag tgactgacta ggatctggtt accactaaac    1440
cagcctcaag aacacccgaa tggagtctct aagctacata taccaactt acacttacaa    1500 aatgttgtcc cccaaaatgt agccattcgt atctgctcct aataaaaga agtttcttc    1560 acattctaga aaaaaaaaaa aaaaaaaaaa aaaaaaaaaa aaaaaaaaaa aaaaaaaaaa    1620
aaaaaaaaaa aaaaaaaaaa aaaaaaaaaa aaaaaaaaaa aaaaaaaaaa aaaaaaaaaa    1680
aaaaaaaaa                                                          1689

<210> SEQ ID NO 104
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
aggaaactta agtcaacaca acatatacaa aacaaacgaa tctcaagcaa tcaagcattc     60
tacttctatt gcagcaattt aaatcatttc ttttaaagca aaagcaattt tctgaaaatt    120
ttcaccattt acgaacgata gccatgccga gcagcgtcag ctggggcatc ctcctgctgg    180
caggcctgtg ctgcctggtc cccgtcagcc tggccgagga cccccaggga gacgccgccc    240
agaagacaga cacaagccac cacgaccagg accacccaac cttcaacaag atcaccccca    300
acctggccga gttcgccttc agcctatacc gccagctggc acaccagagc aacagcacca    360
acatcttctt cagcccagtg agcatcgcca cagccttcgc aatgctcagc ctggggacca    420
aggccgacac ccacgacgaa atcctggagg gcctgaactt caacctcacg agatcccgg    480 aggcccagat ccacgaaggc ttccaggaac tcctccggac cctcaaccag ccagacagcc    540
agctccagct gaccaccggc aacggcctgt tcctcagcga gggcctgaag ctagtggaca    600
agttcctgga ggacgtgaaa aagctgtacc acagcgaagc cttcaccgtc aacttcgggg    660
acaccgaaga ggccaagaaa cagatcaacg actacgtgga aagggcacc caagggaaaa    720 tcgtggacct ggtcaaggag ctggacagag acacagtgtt cgccctggtg aactacatct    780
tcttcaaagg caaatgggag agacccttcg aagtcaagga caccgaggaa gaggacttcc    840
acgtggacca ggtgaccacc gtgaaggtgc ccatgatgaa gcggctgggc atgttcaaca    900
tccagcactg caagaagctg agcagctggg tgctgctgat gaaatacctg ggcaacgcca    960
ccgccatctt cttcctgccc gacgagggga aactacagca cctggaaaac gaactcaccc   1020
```

```
acgacatcat caccaagttc ctggaaaacg aagacagaag gagcgccagc ctgcacctgc    1080
ccaaactgag cattactgga acctatgatc tgaagtccgt gctgggtcaa ctgggcatca    1140
ctaaggtctt cagcaatggg gctgacctct ccggggtcac agaggaggca cccctgaagc    1200
tctccaaggc cgtgcataag gctgtgctga ccatcgacga gaaagggact gaagctgctg    1260
gggccatgtt tttagaggcc atacccatgt ctatcccccc cgaggtcaag ttcaacaaac    1320
cctttgtctt cttaatgatt gaacaaaata ccaagtctcc cctcttcatg ggaaaagtgg    1380
tgaatcccac ccaaaaataa ctcgagctag tgactgacta ggatctggtt accactaaac    1440
cagcctcaag aacacccgaa tggagtctct aagctacata ataccaactt acacttacaa    1500
aatgttgtcc cccaaaatgt agccattcgt atctgctcct aataaaaaga agtttcttc    1560 acattctaga aaaaaaaaaa aaaaaaaaaa aaaaaaaaaa aaaaaaaaaa aaaaaaaaaa    1620
aaaaaaaaaa aaaaaaaaaa aaaaaaaaaa aaaaaaaaaa aaaaaaaaaa aaaaaaaaaa    1680
aaaaaaaaa                                                           1689
```

<210> SEQ ID NO 105
<211> LENGTH: 1689
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105

```
aggaaactta agtcaacaca acatatacaa aacaaacgaa tctcaagcaa tcaagcattc      60
tacttctatt gcagcaattt aaatcatttc ttttaaagca aaagcaattt tctgaaaatt     120
ttcaccattt acgaacgata gccatgccga gcagcgtcag ctggggcatc ctcctgctgg     180
caggcctgtg ctgcctggtc cccgtcagcc tggccgagga ccccagggga gacgccgccc     240
agaagacaga cacaagccac cacgaccagg accaccaaac cttcaacaag atcaccccca     300
acctggccga gttcgccttc agcctatacc gccagctggc acaccagagc aacagcacca     360
acatcttctt cagcccagtg agcatcgcca cagccttcgc aatgctcagc ctggggacca     420
aggccgacac ccacgacgaa atcctggagg gcctgaactt caacctcacg gagatcccgg     480
aggcccagat ccacgaaggc ttccaggaac tcctccggac cctcaaccag ccagacagcc     540
agctccagct gaccaccggc aacggcctgt tcctcagcga gggcctgaag ctagtggaca     600
agttcctgga ggacgtgaaa aagctgtacc acagcgaagc cttcaccgtc aacttcgggg     660
acaccgaaga ggccaagaaa cagatcaacg actacgtgga aagggcacc caagggaaaa     720 tcgtggacct ggtcaaggag cttgacagag acacagtttt tgctctggtg aattacatct     780
tctttaaagg caaatgggag agaccctttg aagtcaagga caccgaggaa gaggacttcc     840
acgtggacca ggtgaccacc gtgaaggtgc ctatgatgaa gcgtttaggc atgtttaaca     900
tccagcactg taagaagctg tccagctggg tgctgctgat gaaatacctg ggcaatgcca     960
ccgccatctt cttcctgcct gatgagggga aactacagca cctggaaaat gaactcaccc    1020
acgatatcat caccaagttc ctggaaaatg aagacagaag gtctgccagc ttacatttac    1080
ccaaactgtc cattactgga acctatgatc tgaagtccgt gctgggtcaa ctgggcatca    1140
ctaaggtctt cagcaatggg gctgacctct ccggggtcac agaggaggca cccctgaagc    1200
tctccaaggc cgtgcataag gctgtgctga ccatcgacga gaaagggact gaagctgctg    1260
gggccatgtt tttagaggcc atacccatgt ctatcccccc cgaggtcaag ttcaacaaac    1320
```

```
cctttgtctt cttaatgatt gaacaaaata ccaagtctcc cctcttcatg ggaaaagtgg    1380
tgaatcccac ccaaaaataa ctcgagctag tgactgacta ggatctggtt accactaaac    1440
cagcctcaag aacacccgaa tggagtctct aagctacata ataccaactt acacttacaa    1500
aatgttgtcc cccaaaatgt agccattcgt atctgctcct aataaaaaga aagtttcttc    1560
acattctaga aaaaaaaaa aaaaaaaaaa aaaaaaaaaa aaaaaaaaaa aaaaaaaaaa    1620 aaaaaaaaa aaaaaaaaaa aaaaaaaaaa aaaaaaaaaa aaaaaaaaaa aaaaaaaaaa    1680
aaaaaaaaa                                                            1689
```

<210> SEQ ID NO 106
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

```
aggaaactta agtcaacaca acatatacaa acaaacgaa tctcaagcaa tcaagcattc      60
tacttctatt gcagcaattt aaatcatttc ttttaaagca aaagcaattt tctgaaaatt    120
ttcaccattt acgaacgata gccatgccga gcagcgtcag ctggggcatc ctcctgctgg    180
caggcctgtg ctgcctggtc cccgtcagcc tggccgagga ccccaggga gacgccgccc     240 agaagacaga cacaagccac cacgaccagg accacccaac cttcaacaag atcaccccca    300
acctggccga gttcgccttc agcctatacc gccagctggc acaccagagc aacagcacca    360
acatcttctt cagcccagtg agcatcgcca cagcctttgc aatgctctcc ctggggacca    420
aggctgacac tcacgatgaa atcctggagg gcctgaattt caacctcacg gagattccgg    480
aggctcagat ccatgaaggc ttccaggaac tcctccgtac cctcaaccag ccagacagcc    540
agctccagct gaccaccggc aatggcctgt tcctcagcga gggcctgaag ctagtggata    600 agttttttgga ggatgttaaa aagttgtacc actcagaagc cttcactgtc aacttcgggg    660
acaccgaaga ggccaagaaa cagatcaacg attacgtgga aagggtact caagggaaaa    720 ttgtggattt ggtcaaggag cttgacagag acacagtttt tgctctggtg aattacatct    780
tctttaaagg caaatgggag agacccttg aagtcaagga caccgaggaa gaggacttcc    840
acgtggacca ggtgaccacc gtgaaggtgc ctatgatgaa gcgtttaggc atgtttaaca    900
tccagcactg taagaagctg tccagctggg tgctgctgat gaaatacctg ggcaatgcca    960
ccgccatctt cttcctgcct gatgagggga aactacagca cctggaaaat gaactcaccc    1020
acgatatcat caccagttc ctggaaaatg aagacagaag gtctgccagc ttacatttac    1080
ccaaactgtc cattactgga acctatgatc tgaagtccgt gctgggtcaa ctgggcatca    1140
ctaaggtctt cagcaatggg gctgacctct ccggggtcac agaggaggca ccctgaagc    1200 tctccaaggc cgtgcataag gctgtgctga ccatcgacga aaagggact gaagctgctg    1260 gggccatgtt tttagaggcc atacccatgt ctatccccc cgaggtcaag ttcaacaaac    1320
cctttgtctt cttaatgatt gaacaaaata ccaagtctcc cctcttcatg ggaaaagtgg    1380
tgaatcccac ccaaaaataa ctcgagctag tgactgacta ggatctggtt accactaaac    1440
cagcctcaag aacacccgaa tggagtctct aagctacata ataccaactt acacttacaa    1500
aatgttgtcc cccaaaatgt agccattcgt atctgctcct aataaaaaga aagtttcttc    1560
acattctaga aaaaaaaaa aaaaaaaaaa aaaaaaaaaa aaaaaaaaaa aaaaaaaaaa    1620
```

| aaaaaaaaaa aaaaaaaaaa aaaaaaaaaa aaaaaaaaaa aaaaaaaaaa aaaaaaaaaa | 1680 |
| aaaaaaaaa | 1689 |

<210> SEQ ID NO 107
<211> LENGTH: 1689
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 107

| aggaaactta agtcaacaca acatatacaa acaaacgaa tctcaagcaa tcaagcattc | 60 |
| tacttctatt gcagcaattt aaatcatttc ttttaaagca aaagcaattt tctgaaaatt | 120 |
| ttcaccattt acgaacgata gccatgccga gcagcgtctc gtggggcatc ctcctgctgg | 180 |
| caggcctgtg ctgcctggtc cccgtcagcc tggccgagga cccccaggga gatgctgccc | 240 |
| agaagacaga cacatcccac cacgaccagg accacccaac cttcaacaag atcaccccca | 300 |
| acctggctga gttcgccttc agcctatacc gccagctggc acaccagagc aacagcacca | 360 |
| atatcttctt cagcccagtg agcatcgcta cagccttcgc aatgctcagc ctggggacca | 420 |
| aggccgacac ccacgatgaa atcctggagg gcctgaattt caacctcacg gagatcccgg | 480 |
| aggctcagat ccacgaaggc ttccaggaac tcctccggac cctcaaccag ccagacagcc | 540 |
| agctccagct gaccaccggc aacggcctgt tcctcagcga gggcctgaag ctagtggaca | 600 |
| agttcctgga ggacgttaaa agctgtacc acagcgaagc cttcaccgtc aacttcgggg | 660 |
| acaccgaaga ggccaagaaa cagatcaacg attacgtgga agggcacc caagggaaaa | 720 |
| tcgtggacct ggtcaaggag cttgacagag acacagtgtt tgccctggtg aactacatct | 780 |
| tcttcaaagg caaatgggag agacccttcg aagtcaagga caccgaggaa gaggacttcc | 840 |
| acgtggacca ggtgaccacc gtgaaggtgc ccatgatgaa gcggttaggc atgttcaaca | 900 |
| tccagcactg caagaagctg agcagctggg tgctgctgat gaaatacctg gcaacgcca | 960 |
| ccgccatctt cttcctgccc gacgagggga aactacagca cctggaaaac gaactcaccc | 1020 |
| acgacatcat caccaagttc ctggaaaacg aagacagaag gagcgccagc ctgcatctgc | 1080 |
| ccaaactgag cattactgga acctacgatc tgaagtccgt gctgggtcaa ctgggcatca | 1140 |
| ccaaggtctt cagcaatggg gccgacctca gcggggtcac agaggaggca cccctgaagc | 1200 |
| tcagcaaggc cgtgcacaag gctgtgctga ccatcgacga gaagggacc gaagccgctg | 1260 |
| gggccatgtt cctggaggcc atacccatga gcatcccccc cgaggtcaag ttcaacaaac | 1320 |
| cctttgtctt cctgatgatc gaacaaaaca ccaagtctcc cctcttcatg ggaaaagtgg | 1380 |
| tgaaccccac ccaaaaataa ctcgagctag tgactgacta ggatctggtt accactaaac | 1440 |
| cagcctcaag aacacccgaa tggagtctct aagctacata ataccaactt acacttacaa | 1500 |
| aatgttgtcc cccaaaatgt agccattcgt atctgctcct aataaaaaga agtttcttc | 1560 |
| acattctaga aaaaaaaaaa aaaaaaaaaa aaaaaaaaaa aaaaaaaaaa aaaaaaaaaa | 1620 |
| aaaaaaaaaa aaaaaaaaaa aaaaaaaaaa aaaaaaaaaa aaaaaaaaaa aaaaaaaaaa | 1680 |
| aaaaaaaaa | 1689 |

<210> SEQ ID NO 108
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108

| | | | | | |
|---|---|---|---|---|---|
| aggaaactta | agtcaacaca | acatatacaa | acaaacgaa | tctcaagcaa | tcaagcattc | 60 |
| tacttctatt | gcagcaattt | aaatcatttc | ttttaaagca | aaagcaattt | tctgaaaatt | 120 |
| ttcaccattt | acgaacgata | gccatgccgt | cttctgtctc | gtggggcatc | ctcctgctgg | 180 |
| caggcctgtg | ctgcctggtc | cccgtctccc | tggctgagga | ccccaggga | gatgccgccc | 240 |
| agaagacaga | cacatcccac | catgaccagg | accacccaac | cttcaacaag | atcacccca | 300 |
| acctggccga | gttcgccttc | agcctatacc | gccagctggc | acaccagagc | aacagcacca | 360 |
| acatcttctt | ctccccagtg | agcatcgcca | cagcctttgc | aatgctctcc | ctggggacca | 420 |
| aggccgacac | ccacgacgaa | atcctggagg | gcctgaattt | caacctcacg | gagatcccgg | 480 |
| aggctcagat | ccatgaaggc | ttccaggaac | tcctccggac | cctcaaccag | ccagacagcc | 540 |
| agctccagct | gaccaccggc | aatggcctgt | tcctcagcga | gggcctgaag | ctagtggata | 600 |
| agttcctgga | ggatgttaaa | aagctgtacc | acagcgaagc | cttcaccgtc | aacttcgggg | 660 |
| acaccgaaga | ggccaagaaa | cagatcaacg | attacgtgga | aagggcacc | caagggaaaa | 720 |
| tcgtggacct | ggtcaaggag | cttgacagag | acacagtgtt | tgctctggtg | aattacatct | 780 |
| tctttaaagg | caaatgggag | agacccttg | aagtcaagga | caccgaggaa | gaggacttcc | 840 |
| acgtggacca | ggtgaccacc | gtgaaggtgc | ctatgatgaa | gcggttaggc | atgtttaaca | 900 |
| tccagcactg | caagaagctg | agcagctggg | tgctgctgat | gaaatacctg | ggcaatgcca | 960 |
| ccgccatctt | cttcctgcct | gatgagggga | aactacagca | cctggaaaac | gaactcaccc | 1020 |
| acgacatcat | caccaagttc | ctggaaaatg | aagacagaag | gtctgccagc | ttacacttac | 1080 |
| ccaaactgag | cattactgga | acctacgatc | tgaagtccgt | gctgggccaa | ctgggcatca | 1140 |
| ctaaggtctt | cagcaacggg | gctgacctct | ccggggtcac | agaggaggca | ccctgaagc | 1200 |
| tcagcaaggc | cgtgcacaag | gctgtgctga | ccatcgacga | gaaagggacc | gaagctgccg | 1260 |
| gggccatgtt | tctggaggcc | atacccatgt | ctatccccc | cgaggtcaag | ttcaacaaac | 1320 |
| cctttgtctt | cctgatgatc | gaacaaaata | ccaagagccc | cctcttcatg | ggaaaagtgg | 1380 |
| tgaaccccac | ccaaaaataa | ctcgagctag | tgactgacta | ggatctggtt | accactaaac | 1440 |
| cagcctcaag | aacacccgaa | tggagtctct | aagctacata | ataccaactt | acacttacaa | 1500 |
| aatgttgtcc | cccaaaatgt | agccattcgt | atctgctcct | aataaaaaga | agtttcttc | 1560 |
| acattctaga | aaaaaaaaaa | aaaaaaaaa | aaaaaaaaa | aaaaaaaaa | aaaaaaaaa | 1620 |
| aaaaaaaaa | aaaaaaaaa | aaaaaaaaa | aaaaaaaaa | aaaaaaaaa | aaaaaaaaa | 1680 |
| aaaaaaaaa | | | | | | 1689 |

<210> SEQ ID NO 109
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

| | | | | | |
|---|---|---|---|---|---|
| aggaaactta | agtcaacaca | acatatacaa | acaaacgaa | tctcaagcaa | tcaagcattc | 60 |
| tacttctatt | gcagcaattt | aaatcatttc | ttttaaagca | aaagcaattt | tctgaaaatt | 120 |

| | |
|---|---|
| ttcaccattt acgaacgata gccatgccga gcagcgtcag ctggggcatc ctcctgctgg | 180 |
| caggcctgtg ctgcctggtc cctgtctccc tggctgagga tccccaggga gatgctgccc | 240 |
| agaagacaga tacatcccac catgatcagg atcacccaac cttcaacaag atcaccccca | 300 |
| acctggctga gttcgccttc agcctatacc gccagctggc acaccagtcc aacagcacca | 360 |
| atatcttctt ctccccagtg agcatcgcta cagccttcgc aatgctctcc ctggggacca | 420 |
| aggctgacac tcacgatgaa atcctggagg gcctgaattt caacctcacg agattccgg | 480 |
| aggcccagat ccatgaaggc ttccaggaac tcctccgtac cctcaaccag ccagacagcc | 540 |
| agctccagct gaccaccggc aatggcctgt tcctcagcga gggcctgaag ctagtggata | 600 |
| agttttgga ggatgttaaa aagctgtacc acagcgaagc cttcactgtc aacttcgggg | 660 |
| acaccgaaga ggccaagaaa cagatcaacg attacgtgga aagggtact caagggaaaa | 720 |
| ttgtggattt ggtcaaggag cttgacagag acacagtttt tgctctggtg aattacatct | 780 |
| tcttcaaagg caaatgggag agaccctttg aagtcaagga caccgaggaa gaggacttcc | 840 |
| acgtggacca ggtgaccacc gtgaaggtgc ctatgatgaa gcggttaggc atgttcaaca | 900 |
| tccagcactg taagaagctg tccagctggg tgctgctgat gaaatacctg ggcaatgcca | 960 |
| ccgccatctt cttcctgcct gatgagggga aactacagca cctggaaaat gaactcaccc | 1020 |
| acgatatcat caccaagttc ctggaaaatg aagacagaag gagcgccagc ttacatttac | 1080 |
| ccaaactgag cattactgga acctacgatc tgaagtccgt gctgggtcaa ctgggcatca | 1140 |
| ctaaggtctt cagcaacggg gctgacctct ccggggtcac agaggaggca cccctgaagc | 1200 |
| tctccaaggc cgtgcataag gctgtgctga ccatcgacga aaagggact gaagctgctg | 1260 |
| gggccatgtt tttagaggcc atacccatgt ctatccccc cgaggtcaag ttcaacaaac | 1320 |
| cctttgtctt cctgatgatc gaacaaaata ccaagagccc cctcttcatg ggaaaagtgg | 1380 |
| tgaatcccac ccaaaaataa ctcgagctag tgactgacta ggatctggtt accactaaac | 1440 |
| cagcctcaag aacacccgaa tggagtctct aagctacata ataccaactt acacttacaa | 1500 |
| aatgttgtcc cccaaaatgt agccattcgt atctgctcct aataaaaaga agtttcttc | 1560 |
| acattctaga aaaaaaaaa aaaaaaaaa aaaaaaaaa aaaaaaaaa aaaaaaaaa | 1620 |
| aaaaaaaaa aaaaaaaaa aaaaaaaaa aaaaaaaaa aaaaaaaaa aaaaaaaaa | 1680 |
| aaaaaaaaa | 1689 |

```
<210> SEQ ID NO 110
<211> LENGTH: 1689
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 110
```

| | |
|---|---|
| aggaaacuua agucaacaca acauauacaa aacaaacgaa ucucaagcaa ucaagcauuc | 60 |
| uacuucuauu gcagcaauuu aaaucauuuc uuuuaaagca aaagcaauuu ucugaaaauu | 120 |
| uucaccauuu acgaacgaua gccaugccga gcagcgucag cuggggcauc cuccugcugg | 180 |
| caggccugug cugccugguc cccgucagcc uggccgagga ccccaggga gacgccgccc | 240 |
| agaagacaga cacaagccac cacgaccagg accacccaac cuucaacaag aucaccccca | 300 |
| accuggccga guucgccuuc agccuauacc gccagcuggc accagagc aacagcacca | 360 |
| acaucuucuu cagcccagug agcaucgcca cagccuucgc aaugcucagc cuggggacca | 420 |

| | |
|---|---|
| aggccgacac ccacgacgaa auccuggagg gccugaacuu caaccucacg gagaucccgg | 480 |
| aggcccagau ccacgaaggc uuccaggaac uccuccggac ccucaaccag ccagacagcc | 540 |
| agcuccagcu gaccaccggc aacggccugu uccucagcga gggccugaag cuaguggaca | 600 |
| aguuccugga ggacgugaaa aagcuguacc acagcgaagc cuucaccguc aacuucgggg | 660 |
| acaccgaaga ggccaagaaa cagaucaacg acuacgugga aagggcacc caagggaaaa | 720 |
| ucguggaccu ggucaaggag cuggacagag acacagguu cgcccuggug aacuacaucu | 780 |
| ucuucaaagg caaaugggag agacccuucg aagucaagga caccgaggaa gaggacuucc | 840 |
| acguggacca ggugaccacc gugaaggugc ccaugaugaa gcggcuggc auguucaaca | 900 |
| uccagcacug caagaagcug agcagcuggg ugcugcugau gaaauaccug ggcaacgcca | 960 |
| ccgccaucuu cuuccugccc gacgagggga acuacagca ccuggaaaac gaacucaccc | 1020 |
| acgacaucau caccaaguuc cuggaaaacg aagacagaag gagcgccagc cugcaccugc | 1080 |
| ccaaacugag caucaccgga accuacgacc ugaaguccgu gcugggccaa cugggcauca | 1140 |
| ccaaggucuu cagcaacggg gccgaccuca gcggggucac agaggaggca ccccugaagc | 1200 |
| ucagcaaggc cgugcacaag gccgugcuga ccaucgacga gaaagggacc gaagccgccg | 1260 |
| gggccauguu ccuggaggcc auccccauga gcaucccccc cgaggucaag uucaacaaac | 1320 |
| ccuucgucuu ccugaugauc gaacaaaaca ccaagagccc ccucuucaug ggaaaagugg | 1380 |
| ugaaccccac ccaaaaauaa cucgagcuag ugacugacua ggaucgguu accacuaaac | 1440 |
| cagccucaag aacacccgaa uggagucucu aagcuacaua auaccaacuu acacuuacaa | 1500 |
| aauguuguc cccaaaaugu agccauucgu aucugcuccu aauaaaaga aaguucuuc | 1560 |
| acauucuaga aaaaaaaaa aaaaaaaaaa aaaaaaaaaa aaaaaaaaaa aaaaaaaaaa | 1620 |
| aaaaaaaaaa aaaaaaaaa aaaaaaaaaa aaaaaaaaaa aaaaaaaaaa aaaaaaaaaa | 1680 |
| aaaaaaaaa | 1689 |

<210> SEQ ID NO 111
<211> LENGTH: 1689
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 111

| | |
|---|---|
| aggaaacuua agucaacaca acauauacaa aacaaacgaa ucucaagcaa ucaagcauuc | 60 |
| uacuucuauu gcagcaauuu aaaucauuuc uuuuaaagca aaagcaauuu ucugaaaauu | 120 |
| uucaccauuu acgaacgaua gccaugccgu cuucugucuc gugggcauc ucccugcugg | 180 |
| caggccugug cugccugguc ccugucuccc uggcugagga uccccaggga gaugcugccc | 240 |
| agaagacaga uacaucccac caugaucagg aucacccaac cuucaacaag aucacccca | 300 |
| accuggcuga guucgccuuc agccauauacc gccagcuggc acaccaguc aacagccacca | 360 |
| auaucuucuu cuccccagug agcaucgcua cagccuuugc aaugcucucc cugggaccaa | 420 |
| aggcugacac ucacgaugaa auccuggagg ccugaacuu caaccucacg gagaucccgg | 480 |
| aggcccagau ccacgaaggc uuccaggaac uccuccggac ccucaaccag ccagacagcc | 540 |
| agcuccagcu gaccaccggc aacggccugu uccucagcga gggccugaag cuaguggaca | 600 |
| aguuccugga ggacgugaaa aagcuguacc acagcgaagc cuucaccguc aacuucgggg | 660 |
| acaccgaaga ggccaagaaa cagaucaacg acuacgugga aagggcacc caagggaaaa | 720 |

-continued

| | |
|---|---|
| ucguggaccu ggucaaggag cuggacagag acacaguguu cgcccuggug aacuacaucu | 780 |
| ucuucaaagg caaaugggag agacccuucg aagucaagga caccgaggaa gaggacuucc | 840 |
| acguggacca ggugaccacc gugaaggugc ccaugaugaa gcggcugggc auguucaaca | 900 |
| uccagcacug caagaagcug agcagcuggg ugcugcugau gaaauaccug gcaacgcca | 960 |
| ccgccaucuu cuuccugccc gacgagggga aacuacagca ccuggaaaac gaacucaccc | 1020 |
| acgacaucau caccaaguuc cuggaaaacg aagacagaag gagcgccagc cugcaccugc | 1080 |
| ccaaacugag caucaccgga accuacgacc ugaaguccgu gcugggccaa cugggcauca | 1140 |
| ccaaggucuu cagcaacggg gccgaccuca gcggggucac agaggaggca ccccugaagc | 1200 |
| ucagcaaggc cgugcacaag gccgugcuga ccaucgacga gaaagggacc gaagccgccg | 1260 |
| ggccauguu ccuggaggcc auacccauga gcaucccccc cgaggucaag uucaacaaac | 1320 |
| ccuucgucuu ccugaugauc gaacaaaaca ccaagagccc ccucuucaug ggaaaagugg | 1380 |
| ugaaccccac ccaaaaauaa cucgagcuag ugacugacua ggaucugguu accacuaaac | 1440 |
| cagccucaag aacacccgaa uggagucucu aagcuacaua uaccaacuu acacuuacaa | 1500 |
| aauguugucc cccaaaaugu agccauucgu aucugcuccu aauaaaaaga aaguuucuuc | 1560 |
| acauucuaga aaaaaaaaa aaaaaaaaaa aaaaaaaaaa aaaaaaaaaa aaaaaaaaaa | 1620 |
| aaaaaaaaaa aaaaaaaaaa aaaaaaaaaa aaaaaaaaaa aaaaaaaaaa aaaaaaaaaa | 1680 |
| aaaaaaaaa | 1689 |

<210> SEQ ID NO 112
<211> LENGTH: 1689
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 112

| | |
|---|---|
| aggaaacuua agucaacaca acauauacaa aacaaacgaa ucucaagcaa ucaagcauuc | 60 |
| uacuucuauu gcagcaauuu aaaucauuuc uuuuaaagca aaagcaauuu ucugaaaauu | 120 |
| uucaccauuu acgaacgaua gccaugccgu cuucugucuc guggggcauc ucccugcugg | 180 |
| caggccugug cugccugguc ccugucuccc uggcugagga uccccaggga gaugcugccc | 240 |
| agaagacaga uacaucccac caugaucagg ucacccaac cuucaacaag aucacccca | 300 |
| accuggcuga guucgccuuc agccuauacc gccagcuggc acaccagucc aacagcacca | 360 |
| auaucuucuc cuccccagug agcaucgcua cagcccuugc aaugcucucc cugggacca | 420 |
| aggcugacac ucacgaugaa auccuggagg gccugaauuu caaccucacg gagauuccgg | 480 |
| aggcucagau ccaugaaggc uuccaggaac uccccguac ccucaaccag ccagacagcc | 540 |
| agcuccagcu gaccaccggc aauggccugu uccagcga gggccugaag cuaguggaua | 600 |
| aguuuuugga ggauguuaaa aaguugacc acucagaagc cuucacuguc aacuucgggg | 660 |
| acaccgaaga ggcaagaaa cagaucaacg auuacgugga aaggguacu caagggaaaa | 720 |
| uuguggauuu ggucaaggag cuugacagag acacaguuuu ugcucuggug aauuacaucu | 780 |
| ucuucaaagg caaaugggag agacccuucg aagucaagga caccgaggaa gaggacuucc | 840 |
| acguggacca ggugaccacc gugaaggugc ccaugaugaa gcggcugggc auguucaaca | 900 |
| uccagcacug caagaagcug agcagcuggg ugcugcugau gaaauaccug gcaacgcca | 960 |
| ccgccaucuu cuuccugccc gacgagggga aacuacagca ccuggaaaac gaacucaccc | 1020 |

| acgacaucau caccaaguuc cuggaaaacg aagacagaag gagcgccagc cugcaccugc | 1080 |
| ccaaacugag caucaccgga accuacgacc ugaagucccgu gcugggccaa cugggcauca | 1140 |
| ccaaggucuu cagcaacggg gccgaccuca gcggggucac agaggaggca ccccugaagc | 1200 |
| ucagcaaggc cgugcacaag gccgugcuga ccaucgacga gaaagggacc gaagccgccg | 1260 |
| gggccauguu ccuggaggcc auccccauga gcaucccccc cgaggucaag uucaacaaac | 1320 |
| ccuucgucuu ccugaugauc gaacaaaaca ccaagagccc ccucuucaug ggaaaagugg | 1380 |
| ugaaccccac ccaaaaauaa cucgagcuag ugacugacua ggaucugguu accacuaaac | 1440 |
| cagccucaag aacacccgaa uggagucucu aagcuacaua auaccaacuu acacuuacaa | 1500 |
| aauguugucc cccaaaaugu agccauucgu aucugcuccu aauaaaaaga aaguuucuuc | 1560 |
| acauucuaga aaaaaaaaaa aaaaaaaaaa aaaaaaaaaa aaaaaaaaaa aaaaaaaaaa | 1620 |
| aaaaaaaaaa aaaaaaaaaa aaaaaaaaaa aaaaaaaaaa aaaaaaaaaa aaaaaaaaaa | 1680 |
| aaaaaaaaa | 1689 |

<210> SEQ ID NO 113
<211> LENGTH: 1689
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 113

| aggaaacuua agucaacaca acauauacaa aacaaacgaa ucucaagcaa ucaagcauuc | 60 |
| uacuucuauu gcagcaauuu aaaucauuuc uuuuaaagca aaagcaauuu ucugaaaauu | 120 |
| uucaccauuu acgaacgaua gccaugccgu cuucugucuc gugggcauc uccugcugg | 180 |
| caggccugug cugccugguc ccugucuccc uggcugagga uccccaggga gaugcugccc | 240 |
| agaagacaga uacaucccac caugaucagg aucacccaac cuucaacaag aucacccccca | 300 |
| accuggcuga guucgccuuc agccauacc gccagcuggc acaccagucc aacagcacca | 360 |
| auaucuucuu cuccccagug agcaucgcua cagcccuugc aaugcucucc cuggggacca | 420 |
| aggcugacac ucacgaugaa auccuggagg gccugaauuu caaccucacg agauuccgg | 480 |
| aggcucagau ccaugaaggc uuccaggaac uccuccguac ccucaaccag ccagacagcc | 540 |
| agcuccagcu gaccaccggc aauggccugu ccucagcga gggccugaag cuaguggaua | 600 |
| aguuuuugga ggauguuaaa aaguuguacc acucagaagc cuucacuguc aacuucgggg | 660 |
| acaccgaaga ggccaagaaa cagaucaacg auuacgugga aagggacu caagggaaaa | 720 |
| uuguggauuu ggucaaggag cuugacagag acacaguuuu ugcucuggug aauuacaucu | 780 |
| ucuuuaaagg caaaugggag agacccuuug aagucaagga caccgaggaa gaggacuucc | 840 |
| acguggacca ggugaccacc gugaaggugc cuaugaugaa gcguuaggc auguuuaaca | 900 |
| uccagcacug uaagaagcug uccagcuggg ugcugcugau gaaauaccug ggcaaugcca | 960 |
| ccgccaucuu cuuccugccu gaugaggga aacuacagca ccuggaaaau gaacucaccc | 1020 |
| acgauaucau caccaaguuc cuggaaaaug aagacagaag gucugccagc uuacauuuac | 1080 |
| ccaaacuguc cauuacugga accaugauc ugaagucccgu gcuggucaa cugggcauca | 1140 |
| ccaaggucuu cagcaacggg gccgaccuca gcggggucac agaggaggca ccccugaagc | 1200 |
| ucagcaaggc cgugcacaag gccgugcuga ccaucgacga gaaagggacc gaagccgccg | 1260 |
| gggccauguu ccuggaggcc auccccauga gcaucccccc cgaggucaag uucaacaaac | 1320 |

```
ccuucgucuu ccugaugauc gaacaaaaca ccaagagccc ccucuucaug ggaaaagugg   1380
ugaaccccac ccaaaaauaa cucgagcuag ugacugacua ggaucgdsinvalid... 
```

<br>

```
ccuucgucuu ccugaugauc gaacaaaaca ccaagagccc ccucuucaug ggaaaagugg   1380
ugaaccccac ccaaaaauaa cucgagcuag ugacugacua ggaucgguu accacuaaac    1440 cagccucaag aacacccgaa uggagucucu aagcuacaua auaccaacuu acacuuacaa   1500
aauguugucc cccaaaaugu agccauucgu aucugcuccu aauaaaaaga aaguuucuuc   1560
acauucuaga aaaaaaaaa aaaaaaaaaa aaaaaaaaaa aaaaaaaaaa aaaaaaaaaa    1620
aaaaaaaaaa aaaaaaaaaa aaaaaaaaaa aaaaaaaaaa aaaaaaaaaa aaaaaaaaaa   1680
aaaaaaaaa                                                           1689

<210> SEQ ID NO 114
<211> LENGTH: 1689
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 114
aggaaacuua agucaacaca acauauacaa aacaaacgaa ucucaagcaa ucaagcauuc     60
uacuucuauu gcagcaauuu aaaucauuuc uuuuaaagca aaagcaauuu ucugaaaauu    120
uucaccauuu acgaacgaua gccaugccga gcagcgucag cuggggcauc ucccugcugg    180
caggccugug cugccuqquc cccqucaqcc uggccgagga cccccaggga gacgccgccc    240
agaagacaga cacaagccac cacgaccagg accacccaac cuucaacaag aucaccccca    300
accuggccga guucgccuuc agccauaucc gccagcuggc acaccagagc aacagcacca    360
acaucuucuu cagcccagug agcaucgcca cagccuucgc aaugcucagc cuggggacca    420
aggccgacac ccacgacgaa auccggagg ggccugaacuu caaccucacg agauccccgg    480
aggcccagau ccacgaaggc uuccaggaac uccuccggac ccucaaccag ccagacagcc    540
agcuccagcu gaccaccggc aacggccugu uccucagcga gggccugaag cuaguggaca    600
aguuccugga ggacgugaaa aagcuguacc acagcgaagc cuucaccguc aacuucgggg    660
acaccgaaga ggccaagaaa cagaucaacg acuacguqqa aagggcacc caagggaaaa    720 ucguggaccu ggucaaggag cuggacagag acacagugug cgcccuggug aacuacaucu    780
ucuucaaagg caaaugggag agacccuucg aagucaagga caccgaggaa gaggacuucc    840
acguggacca ggugaccacc gugaagguqc ccaugauga gcggcuggqc auguucaaca    900 uccagcacug caagaagcug agcagcuggg ugcugcugau gaaauaccug gcaacgcca    960 ccgccaucuu cuuccugccc gacgaqggga acuacagca ccuggaaaac gaacucaccc   1020
acgacaucau caccaaguuc cuggaaaacg aagacagaag gagcgccagc cugcaccugc   1080
ccaaacugag cauuacugga accaugauc ugaagucccgu gcuggucaa cugggcauca   1140 cuaaggucuu cagcaaauggg gcugaccucu ccgggguacc agaqgaggca ccccugaagc   1200 ucuccaaggc cgugcauaag gcuqugcuga ccaucgacga gaaagggacu gaagcugcug   1260 ggccauguu uuaqgaggcc auaccccaugu cuaucccccc cgaqgucaaq uucaacaaac   1320 ccuuuqucuu cuuaaugauu gaacaaaaua ccaaqucucc ccucuucauq ggaaaaquqq   1380 ugaaccccac ccaaaaauaa cucgagcuag ugacugacua ggaucgqguu accacuaaac   1440 cagccucaag aacacccgaa uggagucucu aagcuacaua auaccaacuu acacuuacaa   1500 aauguuqucc cccaaaauqu agccauucgu aucuqcuccu aauaaaaaqa aaquuucuuc   1560 acauucuaga aaaaaaaaa aaaaaaaaaa aaaaaaaaaa aaaaaaaaaa aaaaaaaaaa    1620
```
aaaaaaaaaa aaaaaaaaa aaaaaaaaaa aaaaaaaaaa aaaaaaaaaa aaaaaaaaaa    1680
aaaaaaaaa                                                              1689

<210> SEQ ID NO 115
<211> LENGTH: 1689
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 115
aggaaacuua agucaacaca acauauacaa aacaaacgaa ucucaagcaa ucaagcauuc     60
uacuucuauu gcagcaauuu aaaucauuuc uuuuaaagca aaagcaauuu ucugaaaauu    120
uucaccauuu acgaacgaua gccaugccga gcagcgucag cuggggcauc uccugcugg     180 caggccugug cugccugguc cccgucagcc uggccgagga cccccaggga gacgccgccc    240
agaagacaga cacaagccac cacgaccagg accacccaac cuucaacaag aucacccca    300 accuggccga guucgccuuc agccuauacc gccagcuggc acaccagagc aacagcacca    360
acaucuucuu cagcccagug agcaucgcca cagccuucgc aaugcucagc cuggggacca    420
aggccgacac ccacgacgaa auccuggagg gccugaacuu caaccucacg gagaucccgg    480
aggcccagau ccacgaaggc uuccaggaac uccuccggac ccucaaccag ccagacagcc    540
agcuccagcu gaccaccggc aacggccugu ccucagcga gggccugaag cuaguggaca    600
aguuccugga ggacgugaaa aagcuguacc acagcgaagc cuucaccguc aacuucgggg    660
acaccgaaga ggccaagaaa cagaucaacg acuacgugga aagggcacc caagggaaaa    720 ucguggaccu ggucaaggag cuugacagag acacaguuuu ugcucuggug aauuacaucu    780
ucuuuaaagg caaauggggag agacccuuug aagucaagga caccgaggaa gaggacuucc    840
acguggacca ggugaccacc gugaaggugc cuaugaugaa gcguuuaggc auguuuaaca    900
uccagcacug uaagaagcug uccagcuggg ugcugcugau gaaauaccug ggcaaugcca    960
ccgccaucuu cuuccugccu gaugagggga acuacagca ccuggaaaau gaacucaccc    1020
acgauaucau caccaaguuc cuggaaaaug aagacagaag gucugccagc uuacauuuac    1080
ccaaacuguc cauuacugga accuaugauc ugaaguccgu gcuggucaa cugggcauca    1140 cuaaggucuu cagcaauggg gcugaccucu ccggggucac agaggaggca ccccugaagc    1200
ucuccaaggc cgugcauaag gcugugcuga ccaucgacga gaaagggacu gaagcugcug    1260
gggccauguu uuuagaggcc auacccaugu cuauccccc cgaggucaag uucaacaaac    1320
ccuuugucuu cuuaaugauu gaacaaaaua ccaagcuccc ccucuucaug ggaaagugg    1380 ugaaucccac ccaaaaauaa cucgagcuag ugacugacua ggaucugguu accacuaaac    1440
cagccucaag aacacccgaa uggagucucu aagcuacaua uaccaacuu acacuuacaa    1500 aauguugucc cccaaaaugu agccauucgu aucugcuccu aauaaaaaga aguuucuuc    1560 acauucuaga aaaaaaaaaa aaaaaaaaa aaaaaaaaa aaaaaaaaaa aaaaaaaaaa    1620
aaaaaaaaaa aaaaaaaaaa aaaaaaaaaa aaaaaaaaaa aaaaaaaaaa aaaaaaaaaa    1680
aaaaaaaaa                                                              1689

<210> SEQ ID NO 116
<211> LENGTH: 1689
<212> TYPE: RNA
<213> ORGANISM: Artificial Sequence
<220> FEATURE:

<223> OTHER INFORMATION: Description of Artificial Sequence: Synthetic
      polynucleotide

<400> SEQUENCE: 116

```
aggaaacuua agucaacaca acauauacaa acaaacgaa ucucaagcaa ucaagcauuc      60
uacuucuauu gcagcaauuu aaaucauuuc uuuuaaagca aaagcaauuu ucugaaaauu    120
uucaccauuu acgaacgaua gccaugccga gcagcgucag cuggggcauc cuccugcugg    180
caggccugug cugccugguc cccgucagcc uggccgagga cccccaggga gacgccgccc    240
agaagacaga cacaagccac cacgaccagg accacccaac cuucaacaag aucaccccca    300
accuggccga guucgccuuc agccuauacc gccagcuggc acaccagagc aacagcacca    360
acaucuucuu cagcccagug agcaucgcca cagccuuugc aaugcucucc cuggggacca    420
aggcugacac ucacgaugaa auccuggagg gccugaauuu caaccucacg gagauuccgg    480
aggcucagau ccaugaaggc uuccaggaac uccuccguac ccucaaccag ccagacagcc    540
agcuccagcu gaccaccggc aauggccugu uccuagcga gggccugaag cuagguggaua    600
aguuuuugga ggauguuaaa aaguuguacc acucagaagc cuucacuguc aacuucgggg    660
acaccgaaga ggccaagaaa cagaucaacg auuacgugga aagggguacu caagggaaaa    720
uuguggauuu ggucaaggag cuugacagag acacaguuuu ugcucuggug aauuacaucu    780
ucuuuaaagg caaaugggag agacccuuug aagucaagga caccgaggaa gaggacuucc    840
acguggacca ggugaccacc gugaaggugc uaugaugaa gcguuaggc auguuuaaca    900
uccagcacug uaagaagcug uccagcuggg ugcugcugau gaaauaccug ggcaaugcca    960
ccgccaucuu cuuccugccu gaugagggga acuacagca ccuggaaaau gaacucaccc   1020
acgauaucau caccaaguuc cuggaaaaug aagacagaag gucugccagc uuacauuuac   1080
ccaaacuguc cauuacugga accaugauc ugaaguccgu gcggucaa cugggcauca   1140
cuaaggucuu cagcaauggg gcugaccucu ccggggucac agaggaggca ccccugaagc   1200
ucuccaaggc cgugcauaag gcugugcuga ccaucgacga gaaagggacu gaagcugcug   1260
gggccauguu uuuagaggcc auacccaugu cuauccccc cgaggucaag uucaacaaac   1320
ccuuugucuu cuuaaugauu gaacaaaaua ccaagucucc ccucuucaug ggaaaagugg   1380
ugaaucccac ccaaaaauaa cucgagcuag ugacugacua ggaucugguu accacuaaac   1440
cagccucaag aacacccgaa uggagucucu aagcuacaua auaccaacuu acacuuacaa   1500
aauguugucc cccaaaaugu agccauucgu aucugcuccu aauaaaaaga aaguuucuuc   1560
acauucuaga aaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaa                                                          1689
```

<210> SEQ ID NO 117
<211> LENGTH: 1689
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 117

```
aggaaacuua agucaacaca acauauacaa acaaacgaa ucucaagcaa ucaagcauuc      60
uacuucuauu gcagcaauuu aaaucauuuc uuuuaaagca aaagcaauuu ucugaaaauu    120
uucaccauuu acgaacgaua gccaugccga gcagcgucuc guggggcauc cuccugcugg    180
```

-continued

```
caggccugug cugccugguc ccgucagcc uggccgagga cccccaggga gaugcugccc      240
agaagacaga cacaucccac cacgaccagg accacccaac cuucaacaag aucaccccca      300
accuggcuga guucgccuuc agccauacc gccagcuggc acaccagagc aacagcacca      360
auaucuucuu cagcccagug agcaucgcua cagccuucgc aaugcucagc cuggggacca      420
aggccgacac ccacgaugaa auccuggagg gccugaauuu caaccucacg gagaucccgg      480
aggcucagau ccacgaaggc uuccaggaac uccuccggac ccucaaccag ccagacagcc      540
agcuccagcu gaccaccggc aacggccugu uccucagcga gggccugaag cuaguggaca      600
aguuccugga ggacguuaaa aagcuguacc acagcgaagc cuucaccguc aacuucgggg      660
acaccgaaga ggccaagaaa cagaucaacg auuacgugga aagggcacc caagggaaaa      720 ucguggaccu ggucaaggag cuugacagag acacaguguu ugcccggug aacuacaucu      780 ucuucaaagg caaaugggag agacccuucg aagucaagga caccgaggaa gaggacuucc      840
acguggacca ggugaccacc gugaaggugc ccaugaugaa gcgguuaggc auguucaaca      900
uccagcacug caagaagcug agcagcuggg ugcugcugau gaaauaccug ggcaacgcca      960
ccgccaucuu cuuccugccc gacgagggga acuacagca ccuggaaaac gaacucaccc     1020
acgacaucau caccaaguuc cuggaaaacg aagacagaag gagcgccagc cugcaucugc     1080
ccaaacugag cauuacugga accuacgauc ugaaguccgu gcuggucaa cuggcauca      1140 ccaaggucuu cagcaauggg gccgaccuca gcggggucac agaggaggca cccugaagc      1200 ucagcaaggc cgugcacaag gcugugcuga ccaucgacga gaaagggacc gaagccgcug     1260
gggccauguu ccuggaggcc auacccauga gcauccccc cgaggucaag uucaacaaac     1320
ccuuugucuu ccugaugauc gaacaaaaca ccaagcuccc ccucuucaug ggaaaagugg     1380
ugaaccccac ccaaaaauaa cucgagcuag ugacugacua ggaucgguu accacuaaac     1440 cagccucaag aacacccgaa uggagucucu aagcuacaua auccaacuu acacuuacaa     1500 aauguugucc cccaaaaugu agccauucgu aucugcuccu aauaaaaga aguuucuuc      1560 acauucuaga aaaaaaaaaa aaaaaaaaaa aaaaaaaaaa aaaaaaaaaa aaaaaaaaaa     1620
aaaaaaaaaa aaaaaaaaaa aaaaaaaaaa aaaaaaaaaa aaaaaaaaaa aaaaaaaaaa     1680
aaaaaaaaa                                                            1689
```

<210> SEQ ID NO 118
<211> LENGTH: 1689
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 118

```
aggaaacuua agucaacaca acauauacaa aacaaacgaa ucucaagcaa ucaagcauuc       60
uacuucuauu gcagcaauuu aaaucauuuc uuuuaaagca aaagcaauuu ucugaaaauu      120
uucaccauuu acgaacgaua gccaugccgu cuucugucuc guggggcauc cuccugcugg      180
caggccugug cugccugguc ccgucagcc uggcugagga cccccaggga gaugccgccc      240
agaagacaga cauccccac caugaccagg accacccaac cuucaacaag aucaccccca      300
accuggccga guucgccuuc agccauacc gccagcuggc acaccagagc aacagcacca      360
acaucucucu cuccccagug agcaucgcca cagccuuugc aaugcucucc cuggggacca      420
aggccgacac ccacgacgaa auccuggagg gccugaauuu caaccucacg gagaucccgg      480
```

```
aggcucagau ccaugaaggc uuccaggaac uccuccggac ccucaaccag ccagacagcc      540
agcuccagcu gaccaccggc aauggccugu uccucagcga gggccugaag cuaguggaua      600
aguuccugga ggauguuaaa aagcuguacc acagcgaagc cuucaccguc aacuucgggg      660
acaccgaaga ggccaagaaa cagaucaacg auuacgugga aagggcacc caagggaaaa       720 ucguggaccu ggucaaggag cuugacagag acacagugu ugcucuggug aauuacaucu       780
ucuuuaaagg caaugggag agacccuuug aagucaagga caccgaggaa gaggacuucc       840
acguggacca ggugaccacc gugaaggugc cuaugaugaa gcgguuaggc auguuuaaca     900
uccagcacug caagaagcug agcagcggg ugcugcugau gaaauaccug gcaaugcca       960 ccgccaucuu cuuccugccu gaugagggga acuacagca ccuggaaaac gaacucaccc      1020
acgacaucau caccaaguuc cuggaaaaug aagacagaag gucugccagc uuacacuuac     1080
ccaaacugag cauuacugga accuacgauc ugaagccgu gcugggccaa cugggcauca     1140
cuaaggucuu cagcaacggg gcugaccucu ccggggucac agaggaggca ccccugaagc    1200
ucagcaaggc cgugcacaag gcugugcuga ccaucgacga gaaagggacc gaagcugccg    1260
gggccauguu ucuggaggcc auacccaugu cuauccccccc cgaggucaag uucaacaaac    1320
ccuuugucuu ccugaugauc gaacaaaaua ccaagagccc ccucuucaug ggaaaagugg    1380
ugaaccccac ccaaaaauaa cucgagcuag ugacugacua ggaucugguu accacuaaac     1440
cagccucaag aacacccgaa uggagucucu aagcuacaua auaccaacuu acacuuacaa     1500
aauguugucc cccaaaaugu agccauucgu aucugcuccu aauaaaaaga aguuucuuc     1560 acauucuaga aaaaaaaaa aaaaaaaaa aaaaaaaaaa aaaaaaaaa aaaaaaaaa        1620 aaaaaaaaa aaaaaaaaa aaaaaaaaa aaaaaaaaa aaaaaaaaa aaaaaaaaa          1680 aaaaaaaaa                                                                1689

<210> SEQ ID NO 119
<211> LENGTH: 1689
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 119
aggaaacuua agucaacaca acauauacaa aacaaacgaa ucucaagcaa ucaagcauuc       60
uacuucuauu gcagcaauuu aaaucauuuc uuuuaaagca aaagcaauuu ucugaaaauu      120
uucaccauuu acgaacgaua gccaugccga gcagcgucag cuggggcauc ucccugcugg      180
caggccugug cugccugguc ccugucuccc uggcugagga uccccaggga gaugcugccc      240
agaagacaga uacaucccac caugaucagg aucacccaac cuucaacaag aucaccccca      300
accuggcuga guucgccuuc agccuauacc gccagcuggc acaccagucc aacagcacca     360
auaucuucuu cucccccaguc agcaucgcua cagccuucgc aaugcucucc cuggggacca    420
aggcugacac ucacgaugaa auccuggagg ccugaauuu caaccucacg gagauuccgg     480
aggcccagau ccaugaaggc uuccaggaac uccuccguac ccucaaccag ccagacagcc     540
agcuccagcu gaccaccggc aauggccugu uccucagcga gggccugaag cuaguggaua      600
aguuuuugga ggauguuaaa aagcuguacc acagcgaagc cuucaccguc aacuucgggg     660
acaccgaaga ggccaagaaa cagaucaacg auuacgugga aaggguacu caagggaaaa       720 uuguggauuu ggucaaggag cuugacagag acacaguuuu ugcucuggug aauuacaucu     780
```

| | |
|---|---|
| ucuucaaagg caaaugggag agacccuuug aagucaagga caccgaggaa gaggacuucc | 840 |
| acguggacca ggugaccacc gugaaggugc cuaugaugaa gcgguuaggc auguucaaca | 900 |
| uccagcacug uaagaagcug uccagcuggg ugcugcugau gaaauaccug ggcaaugcca | 960 |
| ccgccaucuu cuuccugccu gaugagggga aacuacagca ccuggaaaau gaacucaccc | 1020 |
| acgauaucau caccaaguuc cuggaaaaug aagacagaag gagcgccagc uuacauuuac | 1080 |
| ccaaacugag cauuacugga accuacgauc ugaagucccu gcugggucaa cugggcauca | 1140 |
| cuaaggucuu cagcaacggg gcugaccucu ccggggucac agaggaggca ccccugaagc | 1200 |
| ucuccaaggc cgugcauaag gcugugcuga ccaucgacga gaaagggacu gaagcugcug | 1260 |
| gggccauguu uuuagaggcc auacccaugu cuauccccc cgaggucaag uucaacaaac | 1320 |
| ccuuugucuu ccugaugauc gaacaaaaua ccaagagccc ccucuucaug ggaaaagugg | 1380 |
| ugaaucccac ccaaaaauaa cucgagcuag ugacugacua ggaucugguu accacuaaac | 1440 |
| cagccucaag aacacccgaa uggagucucu aagcuacaua auaccaacuu acacuuacaa | 1500 |
| aauguugucc cccaaaaugu agccauucgu aucugcuccu aauaaaaaga aaguuucuuc | 1560 |
| acauucuaga aaaaaaaaaa aaaaaaaaaa aaaaaaaaaa aaaaaaaaaa aaaaaaaaaa | 1620 |
| aaaaaaaaaa aaaaaaaaaa aaaaaaaaaa aaaaaaaaaa aaaaaaaaaa aaaaaaaaaa | 1680 |
| aaaaaaaaa | 1689 |

<210> SEQ ID NO 120
<211> LENGTH: 735
<212> TYPE: DNA
<213> ORGANISM: Homo sapiens

<400> SEQUENCE: 120

| | |
|---|---|
| atgctgttgc tgggagctgt tctactgcta ttagctctgc ccggtcatga ccaggaaacc | 60 |
| acgactcaag ggcccggagt cctgcttccc ctgcccaagg gggcctgcac aggttggatg | 120 |
| gcgggcatcc cagggcatcc gggccataat ggggccccag gccgtgatgg cagagatggc | 180 |
| acccctggtg agaagggtga gaaggagatc caggtctta ttggtcctaa gggagacatc | 240 |
| ggtgaaaccg gagtacccgg ggctgaaggt ccccgaggct ttccgggaat ccaaggcagg | 300 |
| aaaggagaac ctggagaagg tgcctatgta taccgctcag cattcagtgt gggattggag | 360 |
| acttacgtta ctatcccaa catgcccatt cgctttacca agatcttcta caatcagcaa | 420 |
| aaccactatg atggctccac tggtaaattc cactgcaaca ttcctgggct gtactacttt | 480 |
| gcctaccaca tcacagtcta tatgaaggat gtgaaggtca gcctcttcaa gaaggacaag | 540 |
| gctatgctct tcacctatga tcagtaccag gaaaataatg tggaccaggc ctccggctct | 600 |
| gtgctcctgc atctggaggt gggcgaccaa gtctggctcc aggtgtatgg ggaaggagag | 660 |
| cgtaatggac tctatgctga taatgacaat gactccacct tcacaggctt tcttctctac | 720 |
| catgacacca actga | 735 |

<210> SEQ ID NO 121
<211> LENGTH: 735
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 121

| | |
|---|---|
| atgctgctgc tgggagccgt gctactgcta ctggccctgc ccggccacga ccaggaaacc | 60 |

```
acgacccaag ggcccggagt cctgctgccc ctgcccaagg gggcctgcac aggctggatg      120
gcgggcatcc cagggcaccc gggccacaac ggggccccag gccgggacgg cagagacggc      180 accccccggcg agaagggcga gaaaggagac ccaggcctga tcggcccaa gggagacatc      240 ggcgaaaccg gagtacccgg ggccgaaggc ccccgaggct tcccgggaat ccaaggcagg      300
aaaggagaac ccggagaagg cgcctacgta taccgcagcg cattcagcgt gggactggag      360
acctacgtga ccatccccaa catgcccatc cgcttcacca agatcttcta caaccagcaa      420
aaccactacg acggcagcac cggcaaattc cactgcaaca tccccgggct gtactacttc      480
gcctaccaca tcacagtcta catgaaggac gtgaaggtca gcctcttcaa gaaggacaag      540
gccatgctgt tcacctacga ccagtaccag gaaaacaacg tggaccaggc cagcggcagc      600
gtgctcctgc acctggaggt gggcgaccaa gtctggctcc agtgtacgg ggaaggagag      660 cggaacggac tctacgccga caacgacaac gacagcacct tcacaggctt cctgctctac      720
cacgacacca actga                                                      735
```

<210> SEQ ID NO 122
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

```
atgctgttgc tgggagctgt tctactgcta ttagctctgc ccggtcatga ccaggaaacc       60
acgactcaag ggcccggagt cctgcttccc ctgcccaagg gggcctgcac aggttggatg      120
gcgggcatcc cagggcatcc gggccataac ggggccccag gccgggacgg cagagacggc      180 accccccggcg agaagggcga gaaaggagac ccaggcctga tcggcccaa gggagacatc      240 ggcgaaaccg gagtacccgg ggccgaaggc ccccgaggct tcccgggaat ccaaggcagg      300
aaaggagaac ccggagaagg cgcctacgta taccgcagcg cattcagcgt gggactggag      360
acctacgtga ccatccccaa catgcccatc cgcttcacca agatcttcta caaccagcaa      420
aaccactacg acggcagcac cggcaaattc cactgcaaca tccccgggct gtactacttc      480
gcctaccaca tcacagtcta catgaaggac gtgaaggtca gcctcttcaa gaaggacaag      540
gccatgctgt tcacctacga ccagtaccag gaaaacaacg tggaccaggc cagcggcagc      600
gtgctcctgc acctggaggt gggcgaccaa gtctggctcc agtgtacgg ggaaggagag      660 cggaacggac tctacgccga caacgacaac gacagcacct tcacaggctt cctgctctac      720
cacgacacca actga                                                      735
```

<210> SEQ ID NO 123
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123

```
atgctgttgc tgggagctgt tctactgcta ttagctctgc ccggtcatga ccaggaaacc       60
acgactcaag ggcccggagt cctgcttccc ctgcccaagg gggcctgcac aggttggatg      120
gcgggcatcc cagggcatcc gggccataat ggggccccag gccgtgatgg cagagatggc      180
```

| | |
|---|---|
| acccctggtg agaagggtga aaaggagat ccaggtctta ttggtcctaa gggagacatc | 240 |
| ggtgaaaccg gagtacccgg ggctgaaggc ccccgaggct tcccgggaat ccaaggcagg | 300 |
| aaaggagaac ccggagaagg cgcctacgta taccgcagcg cattcagcgt gggactggag | 360 |
| acctacgtga ccatcccaa catgcccatc cgcttcacca agatcttcta caaccagcaa | 420 |
| aaccactacg acggcagcac cggcaaattc cactgcaaca tccccgggct gtactacttc | 480 |
| gcctaccaca tcacagtcta catgaaggac gtgaaggtca gcctcttcaa gaaggacaag | 540 |
| gccatgctgt tcacctacga ccagtaccag gaaaacaacg tggaccaggc cagcggcagc | 600 |
| gtgctcctgc acctggaggt gggcgaccaa gtctggctcc aggtgtacgg ggaaggagag | 660 |
| cggaacggac tctacgccga caacgacaac gacagcacct tcacaggctt cctgctctac | 720 |
| cacgacacca actga | 735 |

<210> SEQ ID NO 124
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 124

| | |
|---|---|
| atgctgttgc tgggagctgt tctactgcta ttagctctgc ccggtcatga ccaggaaacc | 60 |
| acgactcaag ggcccggagt cctgcttccc ctgcccaagg gggcctgcac aggttggatg | 120 |
| gcgggcatcc cagggcatcc gggccataat ggggccccag gccgtgatgg cagagatggc | 180 |
| acccctggtg agaagggtga aaaggagat ccaggtctta ttggtcctaa gggagacatc | 240 |
| ggtgaaaccg gagtacccgg ggctgaaggt ccccgaggct ttccgggaat ccaaggcagg | 300 |
| aaaggagaac ctggagaagg tgcctatgta taccgctcag cattcagtgt gggattggag | 360 |
| acttacgtta ctatcccaa catgcccatt cgctttacca agatcttcta caatcagcaa | 420 |
| aaccactatg acggcagcac cggcaaattc cactgcaaca tccccgggct gtactacttc | 480 |
| gcctaccaca tcacagtcta catgaaggac gtgaaggtca gcctcttcaa gaaggacaag | 540 |
| gccatgctgt tcacctacga ccagtaccag gaaaacaacg tggaccaggc cagcggcagc | 600 |
| gtgctcctgc acctggaggt gggcgaccaa gtctggctcc aggtgtacgg ggaaggagag | 660 |
| cggaacggac tctacgccga caacgacaac gacagcacct tcacaggctt cctgctctac | 720 |
| cacgacacca actga | 735 |

<210> SEQ ID NO 125
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 125

| | |
|---|---|
| atgctgttgc tgggagctgt tctactgcta ttagctctgc ccggtcatga ccaggaaacc | 60 |
| acgactcaag ggcccggagt cctgcttccc ctgcccaagg gggcctgcac aggttggatg | 120 |
| gcgggcatcc cagggcatcc gggccataat ggggccccag gccgtgatgg cagagatggc | 180 |
| acccctggtg agaagggtga aaaggagat ccaggtctta ttggtcctaa gggagacatc | 240 |
| ggtgaaaccg gagtacccgg ggctgaaggt ccccgaggct ttccgggaat ccaaggcagg | 300 |
| aaaggagaac ctggagaagg tgcctatgta taccgctcag cattcagtgt gggattggag | 360 |

```
acttacgtta ctatccccaa catgcccatt cgctttacca agatcttcta caatcagcaa    420
aaccactatg atggctccac tggtaaattc cactgcaaca ttcctgggct gtactacttt    480
gcctaccaca tcacagtcta tatgaaggat gtgaaggtca gcctcttcaa gaaggacaag    540
gctatgctgt tcacctatga tcagtaccag gaaaataatg tggaccaggc ctccggcagc    600
gtgctcctgc acctggaggt gggcgaccaa gtctggctcc aggtgtacgg ggaaggagag    660
cggaacggac tctacgccga caacgacaac gacagcacct tcacaggctt cctgctctac    720
cacgacacca actga                                                    735
```

<210> SEQ ID NO 126
<211> LENGTH: 735
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 126

```
atgctgctgc tgggagccgt gctactgcta ctggccctgc ccggccacga ccaggaaacc    60
acgacccaag ggcccggagt cctgctgccc ctgcccaagg gggcctgcac aggctggatg    120
gcgggcatcc cagggcaccc gggccacaac ggggccccag gccgggacgg cagagacggc    180 accccccggcg agaagggcga gaaggagacc ccaggcctga tcggcccaa gggagacatc    240 ggcgaaaccg gagtacccgg ggccgaaggc ccccgaggct tcccgggaat ccaaggcagg    300
aaaggagaac ccgagaagg cgcctacgta taccgcagcg cattcagcgt gggactggag    360
acctacgtga ccatccccaa catgcccatc cgcttcacca agatcttcta caaccagcaa    420
aaccactacg acggcagcac cggcaaattc cactgcaaca tccccgggct gtactacttc    480
gcctaccaca tcacagtcta catgaaggac gtgaaggtca gcctcttcaa gaaggacaag    540
gccatgctgt tcacctacga ccagtaccag gaaaacaacg tggaccaggc cagcggcagc    600
gtgctcctgc acctggaggt gggcgaccaa gtctggctcc aggtgtatgg ggaaggagag    660
cgtaatggac tctatgctga taatgacaat gactccacct tcacaggctt tcttctctac    720
catgacacca actga                                                    735
```

<210> SEQ ID NO 127
<211> LENGTH: 735
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 127

```
atgctgctgc tgggagccgt gctactgcta ctggccctgc ccggccacga ccaggaaacc    60
acgacccaag ggcccggagt cctgctgccc ctgcccaagg gggcctgcac aggctggatg    120
gcgggcatcc cagggcaccc gggccacaac ggggccccag gccgggacgg cagagacggc    180 accccccggcg agaagggcga gaaggagacc ccaggcctga tcggcccaa gggagacatc    240 ggcgaaaccg gagtacccgg ggccgaaggc ccccgaggct tcccgggaat ccaaggcagg    300
aaaggagaac ccgagaagg cgcctacgta taccgcagcg cattcagcgt gggactggag    360
acctacgtga ccatccccaa catgcccatc cgcttcacca agatcttcta caaccagcaa    420
aaccactacg acggcagcac cggtaaattc cactgcaaca ttcctgggct gtactacttt    480
```

```
gcctaccaca tcacagtcta tatgaaggat gtgaaggtca gcctcttcaa gaaggacaag    540
gctatgctgt tcacctatga tcagtaccag gaaaataatg tggaccaggc ctccggctct    600
gtgctcctgc atctggaggt gggcgaccaa gtctggctcc aggtgtatgg ggaaggagag    660
cgtaatggac tctatgctga taatgacaat gactccacct tcacaggctt tcttctctac    720
catgacacca actga                                                    735
```

<210> SEQ ID NO 128  
<211> LENGTH: 735  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 128

```
atgctgctgc tgggagccgt gctactgcta ctggccctgc ccggccacga ccaggaaacc    60
acgacccaag ggcccggagt cctgctgccc ctgcccaagg gggcctgcac aggctggatg    120
gcgggcatcc cagggcaccc gggccacaac ggggcccag gccgggacgg cagagacggc    180 accccggcg agaagggcga gaaggagac ccaggcctga tcggcccaa gggagacatc    240 ggcgaaaccg gagtacccgg ggccgaaggc ccccgaggct tcccgggaat ccaaggcagg    300
aaaggagaac ccgagaagg tgcctatgta taccgctcag cattcagtgt gggattggag    360
acttacgtta ctatccccaa catgcccatt cgctttacca agatcttcta caatcagcaa    420
aaccactatg atggctccac tggtaaattc cactgcaaca ttcctgggct gtactacttt    480
gcctaccaca tcacagtcta tatgaaggat gtgaaggtca gcctcttcaa gaaggacaag    540
gctatgctgt tcacctatga tcagtaccag gaaaataatg tggaccaggc ctccggctct    600
gtgctcctgc atctggaggt gggcgaccaa gtctggctcc aggtgtatgg ggaaggagag    660
cgtaatggac tctatgctga taatgacaat gactccacct tcacaggctt tcttctctac    720
catgacacca actga                                                    735
```

<210> SEQ ID NO 129  
<211> LENGTH: 735  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 129

```
atgctgctgc tgggagccgt gctactgcta ctggccctgc ccggccacga ccaggaaacc    60
acgacccaag ggcccggagt cctgctgccc ctgcccaagg gggcctgcac aggctggatg    120
gcgggcatcc cagggcaccc gggccacaac ggggcccag gccgggacgg cagagatggc    180 accccctggtg agaagggtga aaaggagat ccaggtctta ttggtcctaa gggagacatc    240
ggtgaaaccg gagtacccgg ggctgaaggt ccccgaggct ttccgggaat ccaaggcagg    300
aaaggagaac ctggagaagg tgcctatgta taccgctcag cattcagtgt gggattggag    360
acttacgtta ctatccccaa catgcccatt cgctttacca agatcttcta caatcagcaa    420
aaccactatg atggctccac tggtaaattc cactgcaaca ttcctgggct gtactacttt    480
gcctaccaca tcacagtcta tatgaaggat gtgaaggtca gcctcttcaa gaaggacaag    540
gctatgctgt tcacctatga tcagtaccag gaaaataatg tggaccaggc ctccggctct    600
gtgctcctgc atctggaggt gggcgaccaa gtctggctcc aggtgtatgg ggaaggagag    660
```

```
cgtaatggac tctatgctga taatgacaat gactccacct tcacaggctt tcttctctac    720
catgacacca actga                                                     735

<210> SEQ ID NO 130
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
atgctgttgc tgggagccgt gctactgcta ctggccctgc ccggccacga ccaggaaacc     60
acgactcaag ggcccggagt cctgctgccc ctgcccaagg gggcctgcac aggttggatg    120
gcgggcatcc cagggcaccc gggccacaat ggggccccag gccgggatgg cagagacggc    180 accccggcg agaagggcga gaaggagat ccaggcctga tcggtcccaa gggagacatc    240
ggcgaaaccg gagtacccgg ggccgaaggc ccccgaggct tcccgggaat ccaaggcagg    300
aaaggagaac ccggagaagg cgcctatgta taccgcagcg cattcagtgt gggattggag    360
acctacgtga ccatccccaa catgcccatc cgcttcacca agatcttcta caaccagcaa    420
aaccactacg acgcagcac cggcaaattc cactgcaaca tccccgggct gtactacttt    480
gcctaccaca tcagtgtcta catgaaggac gtgaaggtca gcctcttcaa gaaggacaag    540
gccatgctgt tcacctacga ccagtaccag gaaaacaacg tggaccaggc cagcggcagc    600
gtgctcctgc acctggaggt gggcgaccaa gtctggctcc aggtgtacgg ggaaggagag    660
cgtaacggac tctacgccga caacgacaac gacagcacct tcacaggctt cctgctctac    720
cacgacacca actga                                                    735

<210> SEQ ID NO 131
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
atgctgctgc tgggagccgt gctactgcta ctggctctgc ccggtcacga ccaggaaacc     60
acgactcaag ggcccggagt cctgctgccc ctgcccaagg gggcctgcac aggttggatg    120
gcgggcatcc cagggcatcc gggccataac ggggccccag gccgggatgg cagagacggc    180
acccctggcg agaagggtga gaaggagac ccaggcctga tcggccctaa gggagacatc    240
ggcgaaaccg gagtacccgg ggccgaaggc ccccgaggct tcccgggaat ccaaggcagg    300
aaaggagaac ccggagaagg cgcctatgta taccgcagcg cattcagtgt gggattggag    360
acttacgtta ccatccccaa catgcccatt cgcttcacca agatcttcta caaccagcaa    420
aaccactacg acgcagcac cggtaaattc cactgcaaca tccctgggct gtactacttt    480
gcctaccaca tcagtgtcta tatgaaggat gtgaaggtca gcctcttcaa gaaggacaag    540
gctatgctgt tcacctacga tcagtaccag gaaaataatg tggaccaggc cagcggcagc    600
gtgctcctgc acctggaggt gggcgaccaa gtctggctcc aggtgtacgg ggaaggagag    660
cggaacggac tctacgccga caacgacaat gacagcacct tcacaggctt cctgctctac    720
catgacacca actga                                                    735
```

<210> SEQ ID NO 132
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 132

```
atgctgttgc tgggagccgt tctactgcta ctggctctgc ccggccatga ccaggaaacc      60
acgacccaag ggcccggagt cctgcttccc ctgcccaagg gggcctgcac aggttggatg     120
gcgggcatcc cagggcaccc gggccatatt ggggccccag gccgtgatgg cagagacggc     180
acccccggcg agaagggtga aaaggagatc caggtctga tcggtcctaa gggagacatc      240
ggcgaaaccg gagtacccgg ggctgaaggt ccccgaggct ttccgggaat ccaaggcagg     300
aaaggagaac ctggagaagg cgcctacgta taccgcagcg cattcagcgt gggactggag     360
acctacgtga ccatcccaa catgcccatc cgctttacca agatcttcta caatcagcaa      420
aaccactatg acggctccac tggcaaattc cactgcaaca ttcccgggct gtactacttt     480
gcctaccaca tcacagtcta tatgaaggat gtgaaggtca gcctcttcaa gaaggacaag     540
gccatgctgt tcacctacga tcagtaccag gaaaacaatg tggaccaggc cagcggctct     600
gtgctcctgc atctggaggt gggcgaccaa gtctggctcc aggtgtacgg ggaaggagag     660
cgtaacggac tctatgccga taatgacaat gactccacct tcacaggctt tcttctctac     720
catgacacca actga                                                      735
```

<210> SEQ ID NO 133
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133

```
atgctgttgc tgggagccgt tctactgcta ttagctctgc ccggtcatga ccaggaaacc      60
acgactcaag ggcccggagt cctgctgccc ctgcccaagg gggcctgcac aggttggatg     120
gcgggcatcc cagggcatcc gggccatatt ggggccccag gccgtgacgg cagagatggc     180
acccccggtg agaagggtga aaaggagac ccaggtctta ttggccctaa gggagacatc       240
ggtgaaaccg gagtacccgg ggctgaaggc ccccgaggct ttccgggaat ccaaggcagg     300
aaaggagaac ctggagaagg cgcctatgta taccgcagcg cattcagtgt gggattggag     360
acttacgtta ctatcccaa catgcccatt cgctttacca agatcttcta caatcagcaa       420
aaccactatg atggcagcac cggtaaattc cactgcaaca tccctgggct gtactacttt     480
gcctaccaca tcacagtcta tatgaaggat gtgaaggtca gcctcttcaa gaaggacaag     540
gctatgctgt tcacctatga ccagtaccag gaaaataatg tggaccaggc ctccggctct     600
gtgctcctgc atctggaggt gggcgaccaa gtctggctcc aggtgtatgg ggaaggagag     660
cgtaatggac tctacgctga taatgacaat gactccacct tcacaggctt tctgctctac     720
catgacacca actga                                                      735
```

<210> SEQ ID NO 134
<211> LENGTH: 1167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134

```
aggaaactta agtcaacaca acatatacaa aacaaacgaa tctcaagcaa tcaagcattc    60
tacttctatt gcagcaattt aaatcatttc ttttaaagca aaagcaattt tctgaaaatt   120
ttcaccattt acgaacgata gccatgctgc tgctgggagc cgtgctactg ctactggccc   180
tgcccggcca cgaccaggaa accacgaccc aagggcccgg agtcctgctg cccctgccca   240
aggggggcctg cacaggctgg atggcgggca tcccagggca cccggggccac aacggggccc   300
caggccggga cggcagagac ggcacccccg gcgagaaggg cgagaaagga gacccaggcc   360
tgatcggccc caagggagac atcggcgaaa ccggagtacc cggggccgaa ggccccgag   420
gcttcccggg aatccaaggc aggaaaggag aacccggaga aggcgcctac gtataccgca   480
gcgcattcag cgtgggactg gagacctacg tgaccatccc caacatgccc atccgcttca   540
ccaagatctt ctacaaccag caaaaccact acgacggcag caccggcaaa ttccactgca   600
acatccccgg gctgtactac ttcgcctacc acatcacagt ctacatgaag gacgtgaagg   660
tcagcctctt caagaaggac aaggccatgc tgttcaccta cgaccagtac caggaaaaca   720
acgtggacca ggccagcggc agcgtgctcc tgcacctgga ggtgggcgac caagtctggc   780
tccaggtgta cggggaagga gagcggaacg gactctacgc cgacaacgac aacgacagca   840
ccttcacagg cttcctgctc taccacgaca ccaactgact cgagctagtg actgactagg   900
atctggttac cactaaacca gcctcaagaa cacccgaatg gagtctctaa gctacataat   960
accaacttac acttacaaaa tgttgtcccc caaaatgtag ccattcgtat ctgctcctaa  1020
taaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167
```

<210> SEQ ID NO 135
<211> LENGTH: 1167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135

```
aggaaactta agtcaacaca acatatacaa aacaaacgaa tctcaagcaa tcaagcattc    60
tacttctatt gcagcaattt aaatcatttc ttttaaagca aaagcaattt tctgaaaatt   120
ttcaccattt acgaacgata gccatgctgt tgctgggagc tgttctactg ctattagctc   180
tgcccggtca tgaccaggaa accacgactc aagggcccgg agtcctgctt cccctgccca   240
aggggggcctg cacaggttgg atggcgggca tcccagggca tccggggccat aacggggccc   300
caggccggga cggcagagac ggcacccccg gcgagaaggg cgagaaagga gacccaggcc   360
tgatcggccc caagggagac atcggcgaaa ccggagtacc cggggccgaa ggccccgag   420
gcttcccggg aatccaaggc aggaaaggag aacccggaga aggcgcctac gtataccgca   480
gcgcattcag cgtgggactg gagacctacg tgaccatccc caacatgccc atccgcttca   540
ccaagatctt ctacaaccag caaaaccact acgacggcag caccggcaaa ttccactgca   600
acatccccgg gctgtactac ttcgcctacc acatcacagt ctacatgaag gacgtgaagg   660
```

```
tcagcctctt caagaaggac aaggccatgc tgttcaccta cgaccagtac caggaaaaca    720
acgtggacca ggccagcggc agcgtgctcc tgcacctgga ggtgggcgac caagtctggc    780
tccaggtgta cggggaagga gagcggaacg gactctacgc cgacaacgac aacgacagca    840
ccttcacagg cttcctgctc taccacgaca ccaactgact cgagctagtg actgactagg    900
atctggttac cactaaacca gcctcaagaa cacccgaatg gagtctctaa gctacataat    960
accaacttac acttacaaaa tgttgtcccc caaaatgtag ccattcgtat ctgctcctaa   1020 taaaagaaa gtttcttcac attctagaaa aaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaa                                       1167
```

<210> SEQ ID NO 136
<211> LENGTH: 1167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136

```
aggaaactta agtcaacaca acatatacaa aacaaacgaa tctcaagcaa tcaagcattc     60
tacttctatt gcagcaattt aaatcatttc ttttaaagca aaagcaattt tctgaaaatt    120
ttcaccattt acgaacgata gccatgctgt tgctgggagc tgttctactg ctattagctc    180
tgcccggtca tgaccaggaa accacgactc aagggcccgg agtcctgctt cccctgccca    240 aggggggcctg cacaggttgg atggcgggca tcccaggggca tccgggccat aatggggccc    300
caggccgtga tggcagagat ggcaccccctg gtgagaaggg tgagaaagga gatccaggtc    360
ttattggtcc taagggagac atcggtgaaa ccggagtacc cggggctgaa ggcccccgag    420
gcttcccggg aatccaaggc aggaaaggag aacccggaga aggcgcctac gtataccgca    480
gcgcattcag cgtgggactg gagacctacg tgaccatccc caacatgccc atccgcttca    540
ccaagatctt ctacaaccag caaaaccact acgacggcag caccggcaaa ttccactgca    600
acatccccgg gctgtactac ttcgcctacc acatcacagt ctacatgaag gacgtgaagg    660
tcagcctctt caagaaggac aaggccatgc tgttcaccta cgaccagtac caggaaaaca    720
acgtggacca ggccagcggc agcgtgctcc tgcacctgga ggtgggcgac caagtctggc    780
tccaggtgta cggggaagga gagcggaacg gactctacgc cgacaacgac aacgacagca    840
ccttcacagg cttcctgctc taccacgaca ccaactgact cgagctagtg actgactagg    900
atctggttac cactaaacca gcctcaagaa cacccgaatg gagtctctaa gctacataat    960
accaacttac acttacaaaa tgttgtcccc caaaatgtag ccattcgtat ctgctcctaa   1020 taaaagaaa gtttcttcac attctagaaa aaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaa                                       1167
```

<210> SEQ ID NO 137
<211> LENGTH: 1167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137

```
aggaaactta agtcaacaca acatatacaa aacaaacgaa tctcaagcaa tcaagcattc      60
tacttctatt gcagcaattt aaatcatttc ttttaaagca aaagcaattt tctgaaaatt     120
ttcaccattt acgaacgata gccatgctgt tgctgggagc tgttctactg ctattagctc     180
tgcccggtca tgaccaggaa accacgactc aagggcccgg agtcctgctt ccctgccca      240 aggggcctg cacaggttgg atggcgggca tcccagggca tccgggccat aatgggccc       300 caggccgtga tggcagagat ggcacccctg gtgagaaggg tgagaaagga gatccaggtc     360
ttattggtcc taagggagac atcggtgaaa ccggagtacc cggggctgaa ggtccccgag     420
gctttccggg aatccaaggc aggaaaggag aacctggaga aggtgcctat gtataccgct     480
cagcattcag tgtgggattg gagacttacg ttactatccc caacatgccc attcgcttta     540
ccaagatctt ctacaatcag caaaaccact atgacggcag caccggcaaa ttccactgca     600
acatccccgg gctgtactac ttcgcctacc acatcacagt ctacatgaag gacgtgaagg     660
tcagcctctt caagaaggac aaggccatgc tgttcaccta cgaccagtac caggaaaaca     720
acgtggacca ggccagcggc agcgtgctcc tgcacctgga ggtgggcgac caagtctggc     780
tccaggtgta cggggaagga gagcggaacg gactctacgc cgacaacgac aacgacagca     840
ccttcacagg cttcctgctc taccacgaca ccaactgact cgagctagtg actgactagg     900
atctggttac cactaaacca gcctcaagaa caccgaatg gagtctctaa gctacataat      960
accaacttac acttacaaaa tgttgtcccc caaaatgtag ccattcgtat ctgctcctaa    1020 taaaagaaa gtttcttcac attctagaaa aaaaaaaaa aaaaaaaaaa aaaaaaaaaa      1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaa                                        1167
```

<210> SEQ ID NO 138
<211> LENGTH: 1167
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 138

```
aggaaactta agtcaacaca acatatacaa aacaaacgaa tctcaagcaa tcaagcattc      60
tacttctatt gcagcaattt aaatcatttc ttttaaagca aaagcaattt tctgaaaatt     120
ttcaccattt acgaacgata gccatgctgt tgctgggagc tgttctactg ctattagctc     180
tgcccggtca tgaccaggaa accacgactc aagggcccgg agtcctgctt ccctgccca      240 aggggcctg cacaggttgg atggcgggca tcccagggca tccgggccat aatgggccc       300 caggccgtga tggcagagat ggcacccctg gtgagaaggg tgagaaagga gatccaggtc     360
ttattggtcc taagggagac atcggtgaaa ccggagtacc cggggctgaa ggtccccgag     420
gctttccggg aatccaaggc aggaaaggag aacctggaga aggtgcctat gtataccgct     480
cagcattcag tgtgggattg gagacttacg ttactatccc caacatgccc attcgcttta     540
ccaagatctt ctacaatcag caaaaccact atgatggctc cactggtaaa ttccactgca     600
acattcctgg gctgtactac tttgcctacc acatcacagt ctatatgaag gatgtgaagg     660
tcagcctctt caagaaggac aaggctatgc tgttcaccta tgatcagtac caggaaaata     720
atgtggacca ggcctccggc agcgtgctcc tgcacctgga ggtgggcgac caagtctggc     780
tccaggtgta cggggaagga gagcggaacg gactctacgc cgacaacgac aacgacagca     840
```

```
ccttcacagg cttcctgctc taccacgaca ccaactgact cgagctagtg actgactagg      900
atctggttac cactaaacca gcctcaagaa cacccgaatg gagtctctaa gctacataat      960
accaacttac acttacaaaa tgttgtcccc caaaatgtag ccattcgtat ctgctcctaa     1020
taaaaagaaa gtttcttcac attctagaaa aaaaaaaaa aaaaaaaaaa aaaaaaaaaa      1080
aaaaaaaaaa aaaaaaaaaa aaaaaaaaaa aaaaaaaaaa aaaaaaaaaa aaaaaaaaaa     1140
aaaaaaaaaa aaaaaaaaaa aaaaaaa                                        1167
```

<210> SEQ ID NO 139
<211> LENGTH: 1167
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 139

```
aggaaactta agtcaacaca acatatacaa aacaaacgaa tctcaagcaa tcaagcattc       60
tacttctatt gcagcaattt aaatcatttc ttttaaagca aaagcaattt tctgaaaatt      120
ttcaccattt acgaacgata gccatgctgc tgctgggagc cgtgctactg ctactggccc      180
tgcccggcca cgaccaggaa accacgaccc aagggcccgg agtcctgctg cccctgccca      240 aggggggcctg cacaggctgg atggcgggca tcccagggca cccggccac aacggggccc      300 caggccggga cggcagagac ggcaccccg gcgagaaggg cgagaaggga gacccaggcc      360
tgatcggccc caagggagac atcggcgaaa ccggagtacc cggggccgaa ggccccccgag     420 gcttcccggg aatccaaggc aggaaaggag aacccggaga aggcgcctac gtataccgca      480
gcgcattcag cgtgggactg gagacctacg tgaccatccc caacatgccc atccgcttca      540
ccaagatctt ctacaaccag caaaaccact acgacggcag caccggcaaa ttccactgca      600
acatccccgg gctgtactac ttcgcctacc acatcacagt ctacatgaag gacgtgaagg      660
tcagcctctt caagaaggac aaggccatgc tgttcaccta cgaccagtac caggaaaaca      720
acgtggacca ggccagcggc agcgtgctcc tgcacctgga ggtgggcgac caagtctggc      780
tccaggtgta tggggaagga gagcgtaatg gactctatgc tgataatgac aatgactcca      840
ccttcacagg cttctcttctc taccatgaca ccaactgact cgagctagtg actgactagg      900
atctggttac cactaaacca gcctcaagaa cacccgaatg gagtctctaa gctacataat      960
accaacttac acttacaaaa tgttgtcccc caaaatgtag ccattcgtat ctgctcctaa     1020
taaaaagaaa gtttcttcac attctagaaa aaaaaaaaa aaaaaaaaaa aaaaaaaaaa      1080
aaaaaaaaaa aaaaaaaaaa aaaaaaaaaa aaaaaaaaaa aaaaaaaaaa aaaaaaaaaa     1140
aaaaaaaaaa aaaaaaaaaa aaaaaaa                                        1167
```

<210> SEQ ID NO 140
<211> LENGTH: 1167
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 140

```
aggaaactta agtcaacaca acatatacaa aacaaacgaa tctcaagcaa tcaagcattc       60
tacttctatt gcagcaattt aaatcatttc ttttaaagca aaagcaattt tctgaaaatt      120
```

```
ttcaccattt acgaacgata gccatgctgc tgctgggagc cgtgctactg ctactggccc      180
tgcccggcca cgaccaggaa accacgaccc aagggcccgg agtcctgctg cccctgccca      240 aggggggcctg cacaggctgg atggcgggca tcccagggca cccggccac aacggggccc      300 caggccggga cggcagagac ggcacccccg gcgagaaggg cgagaaagga gacccaggcc      360
tgatcggccc caagggagac atcggcgaaa ccggagtacc cggggccgaa ggcccccgag      420
gcttcccggg aatccaaggc aggaaaggag aacccggaga aggcgcctac gtataccgca      480
gcgcattcag cgtgggactg gagacctacg tgaccatccc caacatgccc atccgcttca      540
ccaagatctt ctacaaccag caaaaccact acgacggcag caccggtaaa ttccactgca      600
acattcctgg gctgtactac tttgcctacc acatcacagt ctatatgaag gatgtgaagg      660
tcagcctctt caagaaggac aaggctatgc tgttcaccta tgatcagtac caggaaaata      720
atgtggacca ggcctccggc tctgtgctcc tgcatctgga ggtgggcgac caagtctggc      780
tccaggtgta tggggaagga gagcgtaatg gactctatgc tgataatgac aatgactcca      840
ccttcacagg ctttcttctc taccatgaca ccaactgact cgagctagtg actgactagg      900
atctggttac cactaaacca gcctcaagaa cacccgaatg gagtctctaa gctacataat      960
accaacttac acttacaaaa tgttgtcccc caaaatgtag ccattcgtat ctgctcctaa     1020 taaaagaaa gtttcttcac attctagaaa aaaaaaaaa aaaaaaaaaa aaaaaaaaa       1080 aaaaaaaaaa aaaaaaaaaa aaaaaaaaaa aaaaaaaaaa aaaaaaaaaa aaaaaaaaaa     1140
aaaaaaaaaa aaaaaaaaaa aaaaaaa                                        1167
```

<210> SEQ ID NO 141
<211> LENGTH: 1167
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 141

```
aggaaactta agtcaacaca acatatacaa aacaaacgaa tctcaagcaa tcaagcattc       60
tacttctatt gcagcaattt aaatcatttc ttttaaagca aaagcaattt tctgaaaatt      120
ttcaccattt acgaacgata gccatgctgc tgctgggagc cgtgctactg ctactggccc      180
tgcccggcca cgaccaggaa accacgaccc aagggcccgg agtcctgctg cccctgccca      240 aggggggcctg cacaggctgg atggcgggca tcccagggca cccggccac aacggggccc      300 caggccggga cggcagagac ggcacccccg gcgagaaggg cgagaaagga gacccaggcc      360
tgatcggccc caagggagac atcggcgaaa ccggagtacc cggggccgaa ggcccccgag      420
gcttcccggg aatccaaggc aggaaaggag aacccggaga aggtgcctat gtataccgct      480
cagcattcag tgtgggattg gagacttacg ttactatccc caacatgccc attcgcttta      540
ccaagatctt ctacaatcag caaaaccact atgatggctc cactggtaaa ttccactgca      600
acattcctgg gctgtactac tttgcctacc acatcacagt ctatatgaag gatgtgaagg      660
tcagcctctt caagaaggac aaggctatgc tgttcaccta tgatcagtac caggaaaata      720
atgtggacca ggcctccggc tctgtgctcc tgcatctgga ggtgggcgac caagtctggc      780
tccaggtgta tggggaagga gagcgtaatg gactctatgc tgataatgac aatgactcca      840
ccttcacagg ctttcttctc taccatgaca ccaactgact cgagctagtg actgactagg      900
atctggttac cactaaacca gcctcaagaa cacccgaatg gagtctctaa gctacataat      960
```

```
accaacttac acttacaaaa tgttgtcccc caaaatgtag ccattcgtat ctgctcctaa    1020
taaaaagaaa gtttcttcac attctagaaa aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaa                                       1167
```

<210> SEQ ID NO 142
<211> LENGTH: 1167
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 142

```
aggaaactta agtcaacaca acatatacaa aacaaacgaa tctcaagcaa tcaagcattc      60
tacttctatt gcagcaattt aaatcatttc ttttaaagca aaagcaattt tctgaaaatt     120
ttcaccattt acgaacgata gccatgctgc tgctgggagc cgtgctactg ctactggccc     180
tgcccggcca cgaccaggaa accacgaccc aagggcccgg agtcctgctg cccctgccca     240
agggggcctg cacaggctgg atggcgggca tcccagggca cccggccac aacgggccc      300 caggccggga cggcagagat ggcacccctg gtgagaaggg tgagaaagga gatccaggtc     360
ttattggtcc taagggagac atcggtgaaa ccggagtacc cggggctgaa ggtccccgag     420
gctttccggg aatccaaggc aggaaaggag aacctggaga aggtgcctat gtataccgct     480
cagcattcag tgtgggattg gagacttacg ttactatccc caacatgccc attcgcttta     540
ccaagatctt ctacaatcag caaaaccact atgatggctc cactggtaaa ttccactgca     600
acattcctgg gctgtactac tttgcctacc acatcacagt ctatatgaag gatgtgaagg     660
tcagcctctt caagaaggac aaggctatgc tgttcaccta tgatcagtac caggaaaata     720
atgtggacca ggcctccggc tctgtgctcc tgcatctgga ggtgggcgac caagtctggc     780
tccaggtgta tggggaagga gagcgtaatg gactctatgc tgataatgac aatgactcca     840
ccttcacagg ctttcttctc taccatgaca ccaactgact cgagctagtg actgactagg     900
atctggttac cactaaacca gcctcaagaa cacccgaatg gagtctctaa gctacataat     960
accaacttac acttacaaaa tgttgtcccc caaaatgtag ccattcgtat ctgctcctaa    1020
taaaaagaaa gtttcttcac attctagaaa aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaa                                       1167
```

<210> SEQ ID NO 143
<211> LENGTH: 1167
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 143

```
aggaaactta agtcaacaca acatatacaa aacaaacgaa tctcaagcaa tcaagcattc      60
tacttctatt gcagcaattt aaatcatttc ttttaaagca aaagcaattt tctgaaaatt     120
ttcaccattt acgaacgata gccatgctgt tgctgggagc cgtgctactg ctactggccc     180
tgcccggcca cgaccaggaa accacgactc aagggcccgg agtcctgctg cccctgccca     240
agggggcctg cacaggttgg atggcgggca tcccagggca cccggccac aatgggccc      300
```

```
caggccggga tggcagagac ggcaccccg gcgagaaggg cgagaaagga gatccaggcc    360
tgatcggtcc caagggagac atcggcgaaa ccggagtacc cggggccgaa ggcccccgag    420
gcttcccggg aatccaaggc aggaaaggag aacccggaga aggcgcctat gtataccgca    480
gcgcattcag tgtgggattg gagacctacg tgaccatccc caacatgccc atccgcttca    540
ccaagatctt ctacaaccag caaaaccact acgacggcag caccggcaaa ttccactgca    600
acatccccgg gctgtactac tttgcctacc acatcacagt ctacatgaag gacgtgaagg    660
tcagcctctt caagaaggac aaggccatgc tgttcaccta cgaccagtac caggaaaaca    720
acgtggacca ggccagcggc agcgtgctcc tgcacctgga ggtgggcgac caagtctggc    780
tccaggtgta cggggaagga gagcgtaacg gactctacgc cgacaacgac aacgacagca    840
ccttcacagg cttcctgctc taccacgaca ccaactgact cgagctagtg actgactagg    900
atctggttac cactaaacca gcctcaagaa cacccgaatg gagtctctaa gctacataat    960
accaacttac acttacaaaa tgttgtcccc caaaatgtag ccattcgtat ctgctcctaa    1020
taaaaagaaa gtttcttcac attctagaaa aaaaaaaaaa aaaaaaaaaa aaaaaaaaa     1080 aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaa                                        1167
```

<210> SEQ ID NO 144
<211> LENGTH: 1167
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 144

```
aggaaactta agtcaacaca acatatacaa aacaaacgaa tctcaagcaa tcaagcattc     60
tacttctatt gcagcaattt aaatcatttc ttttaaagca aaagcaattt tctgaaaatt    120
ttcaccattt acgaacgata gccatgctgc tgctgggagc cgtgctactg ctactggctc    180
tgcccggtca cgaccaggaa accacgactc aagggcccgg agtcctgctg cccctgccca    240 aggggggcctg cacaggttgg atggcgggca tcccagggca tccgggccat aacggggccc    300
caggccggga tggcagagac ggcacccctg gcgagaaggg tgagaaagga gacccaggcc    360
tgatcggccc taagggagac atcggcgaaa ccggagtacc cggggccgaa ggcccccgag    420
gcttcccggg aatccaaggc aggaaaggag aacccggaga aggcgcctat gtataccgca    480
gcgcattcag tgtgggattg gagacttacg ttaccatccc caacatgccc attcgcttca    540
ccaagatctt ctacaaccag caaaaccact acgacggcag caccggtaaa ttccactgca    600
acatccctgg gctgtactac tttgcctacc acatcacagt ctatatgaag gatgtgaagg    660
tcagcctctt caagaaggac aaggctatgc tgttcaccta cgatcagtac caggaaaata    720
atgtggacca ggccagcggc agcgtgctcc tgcacctgga ggtgggcgac caagtctggc    780
tccaggtgta cggggaagga gagcggaacg gactctacgc cgacaacgac aatgacagca    840
ccttcacagg cttcctgctc taccatgaca ccaactgact cgagctagtg actgactagg    900
atctggttac cactaaacca gcctcaagaa cacccgaatg gagtctctaa gctacataat    960
accaacttac acttacaaaa tgttgtcccc caaaatgtag ccattcgtat ctgctcctaa    1020
taaaaagaaa gtttcttcac attctagaaa aaaaaaaaaa aaaaaaaaaa aaaaaaaaa     1080 aaaaaaaaaa aaaaaaaaaa aaaaaaaaaa aaaaaaaaaa aaaaaaaaaa aaaaaaaaaa    1140
```

```
aaaaaaaaaa aaaaaaaaaa aaaaaaa                                       1167

<210> SEQ ID NO 145
<211> LENGTH: 1167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
aggaaactta agtcaacaca acatatacaa aacaaacgaa tctcaagcaa tcaagcattc         60
tacttctatt gcagcaattt aaatcatttc ttttaaagca aaagcaattt tctgaaaatt        120
ttcaccattt acgaacgata gccatgctgt tgctgggagc cgttctactg ctactggctc        180
tgcccggcca tgaccaggaa accacgaccc aagggcccgg agtcctgctt ccctgccca         240 aggggggcctg cacaggttgg atggcgggca tcccagggca cccgggccat aatgggccc       300 caggccgtga tggcagagac ggcaccccg gcgagaaggt tgagaaagga gatccaggtc        360
tgatcggtcc taaggagac atcggcgaaa ccggagtacc cggggctgaa ggtccccgag        420
gctttccggg aatccaaggc aggaaaggag aacctggaga aggcgcctac gtataccgca        480
gcgcattcag cgtgggactg gagacctacg tgaccatccc caacatgccc atccgcttta       540
ccaagatctt ctacaatcag caaaaccact atgacggctc cactggcaaa ttccactgca       600
acattcccgg gctgtactac tttgcctacc acatcacagt ctatatgaag gatgtgaagg       660
tcagcctctt caagaaggac aaggccatgc tgttcaccta cgatcagtac caggaaaaca       720
atgtggacca ggccagcggc tctgtgctcc tgcatctgga ggtgggcgac caagtctggc       780
tccaggtgta cggggaagga gagcgtaacg gactctatgc cgataatgac aatgactcca       840
ccttcacagg ctttcttctc taccatgaca ccaactgact cgagctagtg actgactagg       900
atctggttac cactaaacca gcctcaagaa cacccgaatg gagtctctaa gctacataat       960
accaacttac acttacaaaa tgttgtcccc caaaatgtag ccattcgtat ctgctcctaa      1020
taaaaagaaa gtttcttcac attctagaaa aaaaaaaaa aaaaaaaaaa aaaaaaaaaa       1080
aaaaaaaaaa aaaaaaaaaa aaaaaaaaaa aaaaaaaaaa aaaaaaaaaa aaaaaaaaaa      1140
aaaaaaaaaa aaaaaaaaaa aaaaaaa                                          1167

<210> SEQ ID NO 146
<211> LENGTH: 1167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
aggaaactta agtcaacaca acatatacaa aacaaacgaa tctcaagcaa tcaagcattc         60
tacttctatt gcagcaattt aaatcatttc ttttaaagca aaagcaattt tctgaaaatt        120
ttcaccattt acgaacgata gccatgctgt tgctgggagc cgttctactg ctattagctc        180
tgcccggtca tgaccaggaa accacgactc aagggcccgg agtcctgctg ccctgccca         240 aggggggcctg cacaggttgg atggcgggca tcccagggca tccgggccat aatgggccc       300 caggccgtga cggcagagat ggcaccccg gtgagaaggg tgagaaagga gacccaggtc        360
ttattggccc taagggagac atcggtgaaa ccggagtacc cggggctgaa ggcccccgag        420
```

| | |
|---|---|
| gctttccggg aatccaaggc aggaaaggag aacctggaga aggcgcctat gtataccgca | 480 |
| gcgcattcag tgtgggattg gagacttacg ttactatccc caacatgccc attcgcttta | 540 |
| ccaagatctt ctacaatcag caaaaccact atgatggcag caccggtaaa ttccactgca | 600 |
| acatccctgg gctgtactac tttgcctacc acatcacagt ctatatgaag gatgtgaagg | 660 |
| tcagcctctt caagaaggac aaggctatgc tgttcaccta tgaccagtac caggaaaata | 720 |
| atgtggacca ggcctccggc tctgtgctcc tgcatctgga ggtgggcgac caagtctggc | 780 |
| tccaggtgta tggggaagga gagcgtaatg gactctacgc tgataatgac aatgactcca | 840 |
| ccttcacagg ctttctgctc taccatgaca ccaactgact cgagctagtg actgactagg | 900 |
| atctggttac cactaaacca gcctcaagaa cacccgaatg gagtctctaa gctacataat | 960 |
| accaacttac acttacaaaa tgttgtcccc caaaatgtag ccattcgtat ctgctcctaa | 1020 |
| taaaagaaa gtttcttcac attctagaaa aaaaaaaaa aaaaaaaaaa aaaaaaaaaa | 1080 |
| aaaaaaaaaa aaaaaaaaaa aaaaaaaaaa aaaaaaaaaa aaaaaaaaaa aaaaaaaaaa | 1140 |
| aaaaaaaaaa aaaaaaaaaa aaaaaaa | 1167 |

<210> SEQ ID NO 147
<211> LENGTH: 1167
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 147

| | |
|---|---|
| aggaaacuua agucaacaca acauauacaa acaaacgaa ucucaagcaa ucaagcauuc | 60 |
| uacuucuauu gcagcaauuu aaaucauuuc uuuuaaagca aaagcaauuu ucugaaaauu | 120 |
| uucaccauuu acgaacgaua gccaugcugc ugcugggagc cgugcuacug cuacuggccc | 180 |
| ugcccggcca cgaccaggaa accacgaccc aagggcccgg aguccugcug ccccugccca | 240 |
| aggggggccug cacaggcugg auggcgggca ucccagggca cccgggccac aacggggccc | 300 |
| caggccggga cggcagagac ggcacccccg gcgagaaggg cgagaaagga gacccaggcc | 360 |
| ugaucggccc caagggagac aucggcgaaa ccggaguacc cggggccgaa ggcccccgag | 420 |
| gcuucccggg aauccaaggc aggaaaggag aacccggaga aggcgccuac guauaccgca | 480 |
| gcgcauucag cgugggacug gagaccuacg ugaccauccc caacaugccc aucgccuuca | 540 |
| ccaagaucuu cuacaaccag caaaaccacu acgacggcag caccggcaaa uuccacugca | 600 |
| acaucccgg gcuguacuac uucgccuacc acaucacagu cuacaugaag gacgugaagg | 660 |
| ucagccucuu caagaaggac aaggccaugc uguuccaccua cgaccaguac caggaaaaca | 720 |
| acguggacca ggccagcggc agcgugcucc ugcaccugga ggugggcgac caagucuggc | 780 |
| uccaggugua cggggaagga gagcggaacg gacucuacgc cgacaacgac aacgacagca | 840 |
| ccuucacagg cuuccugcuc uaccacgaca ccaacgacu cgagcuagug acugacuagg | 900 |
| aucugguuac cacuaaacca gccucaagaa cacccgaaug gagucucuaa gcuacauaau | 960 |
| accaacuuac acuuacaaaa uguugucccc caaaauguag ccauucguau cugcuccuaa | 1020 |
| uaaaagaaa guucuucac auucuagaaa aaaaaaaaa aaaaaaaaaa aaaaaaaaaa | 1080 |
| aaaaaaaaaa aaaaaaaaaa aaaaaaaaaa aaaaaaaaaa aaaaaaaaaa aaaaaaaaaa | 1140 |
| aaaaaaaaaa aaaaaaaaaa aaaaaaa | 1167 |

<210> SEQ ID NO 148

<211> LENGTH: 1167
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 148

| | | | | | |
|---|---|---|---|---|---|
| aggaaacuua | agucaacaca | acauauacaa | aacaaacgaa | ucucaagcaa | ucaagcauuc | 60 |
| uacuucuauu | gcagcaauuu | aaaucauuuc | uuuuaaagca | aaagcaauuu | ucugaaaauu | 120 |
| uucaccauuu | acgaacgaua | gccaugcugu | ugcugggagc | uguucuacug | cuauuagcuc | 180 |
| ugcccgguca | ugaccaggaa | accacgacuc | aagggcccgg | aguccugcuu | ccccugccca | 240 |
| aggggggccug | cacagguugg | auggcgggca | ucccagggca | uccgggccau | aacggggccc | 300 |
| caggccggga | cggcagagac | ggcaccccg | gcgagaaggg | cgagaaagga | gacccaggcc | 360 |
| ugaucggccc | caagggagac | aucggcgaaa | ccggaguacc | cggggccgaa | ggccccgag | 420 |
| gcuucccggg | aauccaaggc | aggaaaggag | aacccggaga | aggcgccuac | guauaccgca | 480 |
| gcgcauucag | cgugggacug | gagaccuacg | ugaccauccc | caacaugccc | auccgcuuca | 540 |
| ccaagaucuu | cuacaaccag | caaaaccacu | acgacggcag | caccggcaaa | uuccacugca | 600 |
| acaucccccgg | gcuguacuac | uucgccuacc | acaucacagu | cuacaugaag | gacgugaagg | 660 |
| ucagccucuu | caagaaggac | aaggccaugc | uguucaccua | cgaccaguac | caggaaaaca | 720 |
| acguggacca | ggccagcggc | agcgugcucc | ugcaccugga | ggugggcgac | caagucuggc | 780 |
| uccaggugua | cggggaagga | gagcggaacg | gacucuacgc | cgacaacgac | aacgacagca | 840 |
| ccuucacagg | cuuccugcuc | uaccacgaca | ccaacugacu | cgagcuagug | acugacuagg | 900 |
| aucugguuac | cacuaaacca | gccucaagaa | cacccgaaug | gagucucuaa | gcuacauaau | 960 |
| accaacuuac | acuuacaaaa | uguugucccc | caaaauguag | ccauucguau | cugcuccuaa | 1020 |
| uaaaagaaa | guuucuucac | auucuagaaa | aaaaaaaaa | aaaaaaaaaa | aaaaaaaaaa | 1080 |
| aaaaaaaaaa | aaaaaaaaaa | aaaaaaaaaa | aaaaaaaaaa | aaaaaaaaaa | aaaaaaaaaa | 1140 |
| aaaaaaaaaa | aaaaaaaaaa | aaaaaaa | | | | 1167 |

<210> SEQ ID NO 149
<211> LENGTH: 1167
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 149

| | | | | | |
|---|---|---|---|---|---|
| aggaaacuua | agucaacaca | acauauacaa | aacaaacgaa | ucucaagcaa | ucaagcauuc | 60 |
| uacuucuauu | gcagcaauuu | aaaucauuuc | uuuuaaagca | aaagcaauuu | ucugaaaauu | 120 |
| uucaccauuu | acgaacgaua | gccaugcugu | ugcugggagc | uguucuacug | cuauuagcuc | 180 |
| ugcccgguca | ugaccaggaa | accacgacuc | aagggcccgg | aguccugcuu | ccccugccca | 240 |
| aggggggccug | cacagguugg | auggcgggca | ucccagggca | uccgggccau | aaugggggccc | 300 |
| caggccguga | uggcagagau | ggcacccccug | gugagaaggg | ugagaaagga | gauccagguc | 360 |
| uuauuggucc | uaagggagac | aucggugaaa | ccggaguacc | cggggcugaa | ggccccgag | 420 |
| gcuucccggg | aauccaaggc | aggaaaggag | aacccggaga | aggcgccuac | guauaccgca | 480 |
| gcgcauucag | cgugggacug | gagaccuacg | ugaccauccc | caacaugccc | auccgcuuca | 540 |
| ccaagaucuu | cuacaaccag | caaaaccacu | acgacggcag | caccggcaaa | uuccacugca | 600 |

```
acaucccegg gcuguacuac uucgccuacc acaucacagu cuacaugaag gacgugaagg    660
ucagccucuu caagaaggac aaggccaugc uguuccacuua cgaccaguac caggaaaaca   720
acguggacca ggccagcggc agcgugcucc ugcaccugga gguggcgac caagucuggc     780 uccaggugua cggggaagga gagcggaacg gacucuacgc cgacaacgac aacgacagca    840
ccuucacagg cuuccugcuc uaccacgaca ccaacugacu cgagcuagug acugacuagg    900
aucugguuac cacuaaacca gccucaagaa cacccgaaug gagucucuaa gcuacauaau    960
accaacuuac acuuacaaaa uguugucccc caaaauguag ccauucguau cugcuccuaa   1020
uaaaaagaaa guuucuucac auucuagaaa aaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaa                                       1167

<210> SEQ ID NO 150
<211> LENGTH: 1167
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 150
aggaaacuua agucaacaca acauauacaa aacaaacgaa ucucaagcaa ucaagcauuc     60
uacuucuauu gcagcaauuu aaaucauuuc uuuuaaagca aaagcaauuu ucugaaaauu    120 uuccauuu acgaacgaua gccaugcugu ugcugggagc uguucuacug cuauuagcuc     180
ugcccgguca ugaccaggaa accacgacuc aagggcccgg aguccugcuu ccccugccca    240 aggggggccug cacagguugg auggcgggca ucccaggca uccgggccau aauggggccc    300
caggccguga uggcagagau ggcaccccug gugagaaggg ugagaaagga gauccagguc    360
uuauuggucc uaagggagac aucgugaaa ccggaguacc cggggcugaa ggucccgag     420 gcuuccgggg aauccaaggc aggaaaggag aaccuggaga aggugccuau guauaccgcu    480
cagcauucag ugugggauug gagacuuacg uuacuauccc caacaugccc auucgcuuua    540
ccaagaucuu cuacaaucag caaaaccacu augacggcag caccggcaaa uuccacugca    600 acaucccegg gcuguacuac uucgccuacc acaucacagu cuacaugaag gacgugaagg    660
ucagccucuu caagaaggac aaggccaugc uguuccacuua cgaccaguac caggaaaaca   720
acguggacca ggccagcggc agcgugcucc ugcaccugga gguggcgac caagucuggc     780 uccaggugua cggggaagga gagcggaacg gacucuacgc cgacaacgac aacgacagca    840
ccuucacagg cuuccugcuc uaccacgaca ccaacugacu cgagcuagug acugacuagg    900
aucugguuac cacuaaacca gccucaagaa cacccgaaug gagucucuaa gcuacauaau    960
accaacuuac acuuacaaaa uguugucccc caaaauguag ccauucguau cugcuccuaa   1020
uaaaaagaaa guuucuucac auucuagaaa aaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaa                                       1167

<210> SEQ ID NO 151
<211> LENGTH: 1167
<212> TYPE: RNA
<213> ORGANISM: Artificial Sequence
<220> FEATURE:
<223> OTHER INFORMATION: Description of Artificial Sequence: Synthetic
```

-continued polynucleotide

<400> SEQUENCE: 151
aggaaacuua agucaacaca acauauacaa aacaaacgaa ucucaagcaa ucaagcauuc      60
uacuucuauu gcagcaauuu aaaucauuuc uuuuaaagca aaagcaauuu ucugaaaauu     120
uucaccauuu acgaacgaua gccaugcugu ugcugggagc uguucuacug cuauuagcuc     180
ugcccgguca ugaccaggaa accacgacuc aagggcccgg agccugcuu ccccugccca      240 aggggggccug cacagguugg auggcgggca ucccagggca uccgggccau aaugggggccc   300 caggccguga uggcagagau ggcaccccug gugagaaggg ugagaaagga gauccagguc    360
uuauuggucc uaagggagac aucggugaaa ccggaguacc cggggcugaa gguccccgag    420
gcuuuccggg aauccaaggc aggaaaggag aaccuggaga aggugccuau guauaccgcu    480
cagcauucag gugggauug gagacuuacg uuacuauccc caacaugccc auucgcuuua    540
ccaagaucuu cuacaaucag caaaaccacu augauggcuc cacugguaaa uccacugca    600 acauuccugg gcuguacuac uuugccuacc acaucacagu cuauaugaag gaugugaagg    660
ucagccucuu caagaaggac aaggcuaugc uguucaccua ugaucaguac caggaaaaua    720
auguggacca ggccuccggc agcgugcucc ugcaccugga ggugggcgac caagucuggc    780
uccaggugua cggggaagga gagcggaacg gacucuacgc cgacaacgac aacgacagca    840
ccuucacagg cuuccugcuc uaccacgaca ccaacgacu cgagcuagug acugacuagg    900
aucugguuac cacuaaaacca gccucaagaa cacccgaaug gagucucuaa gcuacauaau    960
accaacuuac acuuacaaaa uguugucccc caaaauguag ccauucguau cugcuccuaa   1020 uaaaagaaa guuucuucac auucuagaaa aaaaaaaaa aaaaaaaaaa aaaaaaaaaa     1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaa                                       1167

<210> SEQ ID NO 152
<211> LENGTH: 1167
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 152
aggaaacuua agucaacaca acauauacaa aacaaacgaa ucucaagcaa ucaagcauuc     60
uacuucuauu gcagcaauuu aaaucauuuc uuuuaaagca aaagcaauuu ucugaaaauu    120
uucaccauuu acgaacgaua gccaugcugc ugcugggagc cgugcuacug cuacuggccc    180
ugcccggcca cgaccaggaa accacgaccc aagggcccgg agccugcug ccccugccca     240 aggggggccug cacaggcugg auggcgggca ucccagggca cccgggccac aacgggccc     300 caggccggga cggcagagac ggcaccccg gcgagaaggg cgagaaagga gacccaggcc    360
ugaucggccc caagggagac aucggcgaaa ccggaguacc cggggccgaa ggccccgag    420 gcuuuccggg aauccaaggc aggaaaggag aacccggaga aggcgccuac guauaccgca    480
gcgcauucag cgugggacug gagacuuacg ugaccauccc caacaugccc auccgcuuca    540
ccaagaucuu cuacaaccag caaaaccacu acgacggcag caccggcaaa uccacugca    600 acauccccgg gcuguacuac uucgccuacc acaucacagu cuacaugaag gacgugaagg    660
ucagccucuu caagaaggac aaggccaugc uguucaccua cgaccaguac caggaaaaca    720

| | |
|---|---|
| acguggacca ggccagcggc agcgugcucc ugcaccugga gguggcgac caagucuggc | 780 |
| uccaggugua uggggaagga gagcguaaug gacucuaugc ugauaaugac aaugacucca | 840 |
| ccuucacagg cuuucuucuc uaccaugaca ccaacugacu cgagcuagug acugacuagg | 900 |
| aucugguuac cacuaaacca gccucaagaa cacccgaaug gagucucuaa gcuacauaau | 960 |
| accaacuuac acuuacaaaa uguugucccc caaaauguag ccauucguau cugcuccuaa | 1020 |
| uaaaaagaaa guuucuucac auucagaaa aaaaaaaaa aaaaaaaaaa aaaaaaaaaa | 1080 |
| aaaaaaaaaa aaaaaaaaaa aaaaaaaaaa aaaaaaaaaa aaaaaaaaaa aaaaaaaaaa | 1140 |
| aaaaaaaaaa aaaaaaaaaa aaaaaaa | 1167 |

<210> SEQ ID NO 153
<211> LENGTH: 1167
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 153

| | |
|---|---|
| aggaaacuua agucaacaca acauauacaa aacaaacgaa ucucaagcaa ucaagcauuc | 60 |
| uacuucuauu gcagcaauuu aaaucauuuc uuuuaaagca aaagcaauuu ucugaaaauu | 120 |
| uucaccauuu acgaacgaua gccaugcugc ugcgggagc cgugcuacug cuacuggccc | 180 |
| ugcccggcca cgaccaggaa accacgaccc aagggcccgg aguccugcug ccccugccca | 240 |
| aggggcccug cacaggcugg auggcgggca ucccagggca cccggccac aacggggccc | 300 |
| caggccggga cggcagagac ggcacccccg gcgagaaggg cgagaaagga gacccaggcc | 360 |
| ugaucggccc caagggagac aucggcgaaa ccggaguacc cggggccgaa ggcccccgag | 420 |
| gcuucccggg aauccaaggc aggaaaggag aacccggaga aggcgccuac guauaccgca | 480 |
| gcgcauucag cgugggacug gagaccuacg ugaccauccc caacaugccc auccgcuuca | 540 |
| ccaagaucuu cuacaaccag caaaaccacu acgacggcag caccgguaaa uuccacugca | 600 |
| acauuccugg gcuguacuac uuugccuacc acaucacagu cuauaugaag gaugugaagg | 660 |
| ucagccucuu caagaaggac aaggcuaugc uguuaccua ugaucaguac caggaaaaua | 720 |
| augguggacca ggccuccggc ucugugcucc ugcaucugga gguggcgac caagucuggc | 780 |
| uccaggugua uggggaagga gagcguaaug gacucuaugc ugauaaugac aaugacucca | 840 |
| ccuucacagg cuuucuucuc uaccaugaca ccaacugacu cgagcuagug acugacuagg | 900 |
| aucugguuac cacuaaacca gccucaagaa cacccgaaug gagucucuaa gcuacauaau | 960 |
| accaacuuac acuuacaaaa uguugucccc caaaauguag ccauucguau cugcuccuaa | 1020 |
| uaaaaagaaa guuucuucac auucagaaaa aaaaaaaaa aaaaaaaaaa aaaaaaaaaa | 1080 |
| aaaaaaaaaa aaaaaaaaaa aaaaaaaaaa aaaaaaaaaa aaaaaaaaaa aaaaaaaaaa | 1140 |
| aaaaaaaaaa aaaaaaaaaa aaaaaaa | 1167 |

<210> SEQ ID NO 154
<211> LENGTH: 1167
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 154

| | |
|---|---|
| aggaaacuua agucaacaca acauauacaa aacaaacgaa ucucaagcaa ucaagcauuc | 60 |

```
uacuucuauu gcagcaauuu aaaucauuuc uuuuaaagca aaagcaauuu ucugaaaauu      120
uucaccauuu acgaacgaua gccaugcugc ugcugggagc cgugcuacug cuacuggccc      180
ugcccggcca cgaccaggaa accacgaccc aagggcccgg aguccugcug ccccugccca      240
agggggccug cacaggcugg auggcgggca ucccagggca cccgggccac aacgggcccc      300
caggccggga cggcagagac ggcaccccccg gcgagaaggg cgagaaagga gacccaggcc     360
ugaucggccc caaggagac aucggcgaaa ccggaguacc cggggccgaa ggcccccgag       420
gcuucccggg aauccaaggc aggaaaggag aacccggaga aggugccuau guauaccgcu      480
cagcauucag gugggauug gagacuuacg uuacuauccc caacaugccc auucgcuuua      540
ccaagaucuu cuacaaucag caaaaccacu augauggcuc cacugguaaa uuccacugca     600
acauuccugg gcuguacuac uuugccuacc acaucacagu cuauaugaag gaugugaagg     660
ucagccucuu caagaaggac aaggcuaugc uguuaccua ugaucaguac caggaaaaua     720
auguggacca ggccuccggc ucugugcucc ugcaucugga ggugggcgac caagucuggc     780
uccaggugua uggggaagga gagcguaaug gacucuaugc ugauaaugac aaugacucca     840
ccuucacagg cuuucuucuc uaccaugaca ccaacugacu cgagcuagug acugacuagg     900
aucugguuac cacuaaacca gccucaagaa caccccgaaug gagucucuaa gcuacauaau    960
accaacuuac acuuacaaaa uguugucccc caaauguag ccauucguau cugcuccuaa     1020 uaaaagaaa guuucuucac auucuagaaa aaaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaa                                        1167

<210> SEQ ID NO 155
<211> LENGTH: 1167
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 155
aggaaacuua agucaacaca acauauacaa aacaaacgaa ucucaagcaa ucaagcauuc      60
uacuucuauu gcagcaauuu aaaucauuuc uuuuaaagca aaagcaauuu ucugaaaauu    120
uucaccauuu acgaacgaua gccaugcugc ugcugggagc cgugcuacug cuacuggccc    180
ugcccggcca cgaccaggaa accacgaccc aagggcccgg aguccugcug ccccugccca    240
agggggccug cacaggcugg auggcgggca ucccagggca cccgggccac aacgggcccc    300
caggccggga cggcagagau ggcaccccug gugagaaggg ugagaaagga gauccagguc    360
uuauuggucc uaagggagac aucggugaaa ccggaguacc cggggcugaa ggucccccgag  420 gcuucccggg aauccaaggc aggaaaggag aaccuggaga aggugccuau guauaccgcu    480
cagcauucag gugggauug gagacuuacg uuacuauccc caacaugccc auucgcuuua    540
ccaagaucuu cuacaaucag caaaaccacu augauggcuc cacugguaaa uuccacugca    600
acauuccugg gcuguacuac uuugccuacc acaucacagu cuauaugaag gaugugaagg    660
ucagccucuu caagaaggac aaggcuaugc uguucaccua ugaucaguac caggaaaaua    720
auguggacca ggccuccggc ucugugcucc ugcaucugga ggugggcgac caagucuggc    780
uccaggugua uggggaagga gagcguaaug gacucuaugc ugauaaugac aaugacucca    840
ccuucacagg cuuucuucuc uaccaugaca ccaacugacu cgagcuagug acugacuagg    900
```

```
aucugguuac cacuaaacca gccucaagaa cacccgaaug gagucucuaa gcuacauaau    960
accaacuuac acuuacaaaa uguuguccc caaaauguag ccauucguau cugcuccuaa    1020
uaaaaagaaa guuucuucac auucagaaa aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaa                                         1167
```

<210> SEQ ID NO 156
<211> LENGTH: 1167
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 156

```
aggaaacuua agucaacaca acauauacaa acaaacgaa ucucaagcaa ucaagcauuc      60
uacuucuauu gcagcaauuu aaaucauuuc uuuuaaagca aaagcaauuu ucugaaaauu    120
uucaccauuu acgaacgaua gccaugcugu ugcugggagc cgugcuacug cuacuggccc    180
ugcccggcca cgaccaggaa accacgcacu aagggcccgg aguccugcug ccccugccca    240
agggggccug cacagguugg auggcgggca ucccagggca ccgggccac aaugggggccc    300 caggccggga uggcagagac ggcaccccg gcgagaaggg cgagaaagga gauccaggcc    360
ugaucggucc caagggagac aucggcgaaa ccggaguacc cggggccgaa ggccccgag     420 gcuucccggg aauccaaggc aggaaaggag acccggaga aggcgccuau guauaccgca    480
gcgcauucag ugugggauug gagaccuacg ugaccauccc caacaugccc auccgcuuca    540
ccaagaucuu cuacaaccag caaaaccacu acgacggcag caccggcaaa uuccacugca    600
acauccccgg gcuguacuac uuugccuacc acaucacagu cuacaugaag gacgugaagg    660
ucagccucuu caagaaggac aaggccaugc uguucaccua cgaccaguac caggaaaaca    720 acgugggacca ggccagcggc agcgugcucc ugcaccugga gguggcgac caagucuggc    780 uccaggugua cggggaagga gagcguaacg gacgcuacgc cgacaacgac aacgacagca    840
ccuucacagg cuuccugcuc uaccacgaca ccaacugacu cgagcuagug acugacuagg    900
aucugguuac cacuaaacca gccucaagaa cacccgaaug gagucucuaa gcuacauaau    960
accaacuuac acuuacaaaa uguugucccc caaaauguag ccauucguau cugcuccuaa    1020
uaaaaagaaa guuucuucac auucagaaaa aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaa                                         1167
```

<210> SEQ ID NO 157
<211> LENGTH: 1167
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 157

```
aggaaacuua agucaacaca acauauacaa acaaacgaa ucucaagcaa ucaagcauuc      60
uacuucuauu gcagcaauuu aaaucauuuc uuuuaaagca aaagcaauuu ucugaaaauu    120
uucaccauuu acgaacgaua gccaugcugc ugcugggagc cgugcuacug cuacuggcuc    180
```

```
ugcccgguca cgaccaggaa accacgacuc aagggcccgg aguccugcug ccccugccca      240
agggggccug cacagguugg auggcgggca ucccagggca uccgggccau aacgggcccc      300
caggccggga uggcagagac ggcaccccug gcgagaaggg ugagaaagga gacccaggcc      360
ugaucggccc uaaggagac aucggcgaaa ccggaguacc cggggccgaa ggcccccgag      420
gcuucccggg aauccaaggc aggaaaggag aacccggaga aggcgccuau guauaccgca      480
gcgcauucag gugggauug gagacuuacg uuaccaucc caacaugccc auucgcuuca        540
ccaagaucuu cuacaaccag caaaaccacu acgacggcag caccgguaaa uccacugca       600 acaucccugg gcuguacuac uuugccuacc acaucacagu cuauaugaag gaugugaagg      660
ucagccucuu caagaaggac aaggcuaugc uguucaccua cgaucaguac caggaaaaua     720 augguggacca ggccagcggc agcgugcucc ugcaccugga ggugggcgac caagucuggc    780
uccaggugua cggggaagga gagcggaacg gacucuacgc cgacaacgac aaugacagca    840
ccuucacagg cuuccugcuc uaccaugaca ccaacugacu cgagcuagug acugacuagg    900
aucugguuac cacuaaaacca gccucaagaa cacccgaaug gagucucuaa gcuacauaau    960
accaacuuac acuuacaaaa uguugucccc caaaauguag ccaucgauau cugcuccuaa    1020
uaaaagaaaa guuucuucac auucuagaaaa aaaaaaaaaa aaaaaaaaaa aaaaaaaaaa   1080 aaaaaaaaaaaa aaaaaaaaaaa aaaaaaaaaaa aaaaaaaaaa aaaaaaaaaa aaaaaaaaaaa 1140 aaaaaaaaaaa aaaaaaaaaa aaaaaaa                                       1167

<210> SEQ ID NO 158
<211> LENGTH: 1167
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 158
aggaaacuua agucaacaca acauauacaa aacaaacgaa ucucaagcaa ucaagcauuc      60
uacuucuauu gcagcaauuu aaaucauuuc uuuuaaagca aaagcaauuu ucugaaaauu     120
uucaccauuu acgaacgaua gccaugcugu ugcugggagc cguucuacug cuacuggcuc    180
ugcccggcca ugaccaggaa accacgaccc aagggcccgg aguccugcuu ccccugccca     240
agggggccug cacagguugg auggcgggca ucccagggca cccggggccau aauggggccc   300 caggccguga uggcagagac ggcacccccg gcgagaaggg ugagaaagga gauccagguc     360
ugaucggucc uaaggagac aucggcgaaa ccggaguacc cggggcugaa ggucccgag      420 gcuuuccggg aauccaaggc aggaaaggag aaccggaga aggcgccuac guauaccgca      480
gcgcauucag cguggacug gagaccuacu gaccauccc caacaugccc auccgcuuua      540
ccaagaucuu cuacaaucag caaaaccacu augacggcuc cacuggcaaa uccacugca     600 acauccccgg gcuguacuac uuugccuacc acaucacagu cuauaugaag gaugugaagg    660
ucagccucuu caagaaggac aaggccaugc uguucaccua cgaucaguac caggaaaaca   720 augguggacca ggccagcggc ucugugcucc ugcaucugga ggugggcgac caagucuggc   780
uccaggugua cggggaagga gagcguaacg gacucuaugc cgauaaugac aaugaccca    840 ccuucacagg cuuucuucuc uaccaugaca ccaacugacu cgagcuagug acugacuagg    900
aucugguuac cacuaaaacca gccucaagaa cacccgaaug gagucucuaa gcuacauaau    960
accaacuuac acuuacaaaa uguugucccc caaaauguag ccaucgauau cugcuccuaa   1020
```

| | |
|---|---|
| uaaaaagaaa guuucuucac auucuagaaa aaaaaaaaaa aaaaaaaaaa aaaaaaaaaa | 1080 |
| aaaaaaaaaa aaaaaaaaaa aaaaaaaaaa aaaaaaaaaa aaaaaaaaaa aaaaaaaaaa | 1140 |
| aaaaaaaaaa aaaaaaaaaa aaaaaaa | 1167 |

<210> SEQ ID NO 159
<211> LENGTH: 1167
<212> TYPE: RNA
<213> ORGANISM: Artificial Sequence
<220> FEATURE:
<223> OTHER INFORMATION: Description of Artificial Sequence: Synthetic
    polynucleotide

<400> SEQUENCE: 159

| | |
|---|---|
| aggaaacuua agucaacaca acauauacaa aacaaacgaa ucucaagcaa ucaagcauuc | 60 |
| uacuucuauu gcagcaauuu aaaucauuuc uuuuaaagca aaagcaauuu ucugaaaauu | 120 |
| uucaccauuu acgaacgaua gccaugcugu ugcugggagc cguucuacug cuauuagcuc | 180 |
| ugcccgguca ugaccaggaa accacgacuc aagggcccgg aguccugcug ccccugccca | 240 |
| aggggggccug cacagguugg auggcgggca ucccagggca uccgggccau aauggggccc | 300 |
| caggccguga cggcagagau ggcaccccg gugagaaggg ugagaaagga gacccaagguc | 360 |
| uuauuggccc uaagggagac aucggugaaa ccggaguacc cggggcugaa ggccccgag | 420 |
| gcuuuccggg aauccaaggc aggaaaggag aaccuggaga aggcgccuau guauaccgca | 480 |
| gcgcauucag uguggauug gagacuuacg uuacuauccc caacaugccc auucgcuuua | 540 |
| ccaagaucuu cuacaaucag caaaaccacu augauggcag caccgguaaa uuccacugca | 600 |
| acaucccugg gcuguacuac uuugccuacc acaucacagu cuauaugaag gaugugaagg | 660 |
| ucagccucuu caagaaggac aaggcuaugc uguucaccua ugaccaguac caggaaaaua | 720 |
| auguggacca ggccuccggc ucugugcucc ugcaucugga gguggcgac caagucuggc | 780 |
| uccaggugua uggggaagga gagcguaaug gacucuacgc ugauaaugac aaugacucca | 840 |
| ccuucacagg cuuucugcuc uaccaugaca ccaacugacu cgagcuagug acugacuagg | 900 |
| aucugguuac cacuaaacca gccucaagaa cacccgaaug gagucucuaa gcuacauaau | 960 |
| accaacuuac acuacaaaa uguugucccc caaaauguag ccauucguau cugcuccuaa | 1020 |
| uaaaaagaaa guuucuucac auucuagaaa aaaaaaaaa aaaaaaaaaa aaaaaaaaaa | 1080 |
| aaaaaaaaaa aaaaaaaaaa aaaaaaaaaa aaaaaaaaaa aaaaaaaaaa aaaaaaaaaa | 1140 |
| aaaaaaaaaa aaaaaaaaaa aaaaaaa | 1167 |

<210> SEQ ID NO 160
<211> LENGTH: 579
<212> TYPE: DNA
<213> ORGANISM: Macaca fascicularis

<400> SEQUENCE: 160

| | |
|---|---|
| atgggggtgc acgaatgtcc tgcctggctg tggcttctcc tgtctctgct gtcgctccct | 60 |
| ctgggcctcc cagtcccggg cgccccacca cgcctcatct gtgacagccg agtcctggag | 120 |
| aggtacctct tggaggccaa ggaggccgag aatgtcacga tggctgtttc cgaaagctgc | 180 |
| agcttgaatg agaatatcac cgtcccagac accaaagtta acttctatgc ctggaagagg | 240 |
| atggaggtcg gcagcaggc tgtagaagtc tggcagggcc tggccctgct ctcagaagct | 300 |
| gtcctgcggg gccaggccgt gttggccaac tcttcccagc ctttcgagcc cctgcagctg | 360 |
| cacatggata agccatcag tggccttcgc agcatcacca ctctgcttcg ggcgctggga | 420 |

| | |
|---|---|
| gcccaggaag ccatctccct cccagatgcg gcctcggctg ctccactccg aaccatcact | 480 |
| gctgacactt tctgcaaact cttccgagtc tactccaatt tcctccgggg aaagctgaag | 540 |
| ctgtacacgg gggaggcctg caggagaggg gacagatga | 579 |

```
<210> SEQ ID NO 161
<211> LENGTH: 579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161
```

| | |
|---|---|
| atgggggtgc acgaatgccc cgcctggctg tggctgctcc tgagcctgct gagcctcccc | 60 |
| ctgggcctcc cagtcccggg cgccccacca cgcctcatct gcgacagccg agtcctggag | 120 |
| aggtacctcc tggaggccaa ggaggccgag aacgtcacga tgggctgcag cgaaagctgc | 180 |
| agcctgaacg agaacatcac cgtcccagac accaaagtga acttctacgc ctggaagagg | 240 |
| atggaggtcg ggcagcaggc cgtagaagtc tggcagggcc tggccctgct cagcgaagcc | 300 |
| gtcctgcggg gccaggccgt gctggccaac agcagccagc cttcgagcc cctgcagctg | 360 |
| cacatggaca aagccatcag cggcctgcgc agcatcacca ccctgctgcg ggcgctggga | 420 |
| gcccaggaag ccatcagcct cccagacgcg gccagcgccg ccccactccg aaccatcacc | 480 |
| gccgacacct tctgcaaact cttccgagtc tacagcaact tcctccgggg aaagctgaag | 540 |
| ctgtacacgg gggaggcctg caggagaggg gacagatga | 579 |

```
<210> SEQ ID NO 162
<211> LENGTH: 579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162
```

| | |
|---|---|
| atgggggtgc acgaatgtcc tgcctggctg tggcttctcc tgagcctgct gagcctcccc | 60 |
| ctgggcctcc cagtcccggg cgccccacca cgcctcatct gcgacagccg agtcctggag | 120 |
| aggtacctcc tggaggccaa ggaggccgag aacgtcacga tgggctgcag cgaaagctgc | 180 |
| agcctgaacg agaacatcac cgtcccagac accaaagtga acttctacgc ctggaagagg | 240 |
| atggaggtcg ggcagcaggc cgtagaagtc tggcagggcc tggccctgct cagcgaagcc | 300 |
| gtcctgcggg gccaggccgt gctggccaac agcagccagc cttcgagcc cctgcagctg | 360 |
| cacatggaca aagccatcag cggcctgcgc agcatcacca ccctgctgcg ggcgctggga | 420 |
| gcccaggaag ccatcagcct cccagacgcg gccagcgccg ccccactccg aaccatcacc | 480 |
| gccgacacct tctgcaaact cttccgagtc tacagcaact tcctccgggg aaagctgaag | 540 |
| ctgtacacgg gggaggcctg caggagaggg gacagatga | 579 |

```
<210> SEQ ID NO 163
<211> LENGTH: 579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 163
```

| | |
|---|---|
| atggggtgc acgaatgtcc tgcctggctg tggcttctcc tgtctctgct gtcgctccct | 60 |
| ctgggcctcc cagtcccggg cgccccacca cgcctcatct gtgacagccg agtcctggag | 120 |
| aggtacctct tggaggccaa ggaggccgag aatgtcacga tgggctgttc cgaaagctgc | 180 |
| agcttgaatg agaacatcac cgtcccagac accaaagtga acttctacgc ctggaagagg | 240 |
| atggaggtcg ggcagcaggc cgtagaagtc tggcagggcc tggccctgct cagcgaagcc | 300 |
| gtcctgcggg gccaggccgt gctggccaac agcagccagc ccttcgagcc cctgcagctg | 360 |
| cacatggaca aagccatcag cggcctgcgc agcatcacca ccctgctgcg ggcgctggga | 420 |
| gcccaggaag ccatcagcct cccagacgcg ccagcgccg ccccactccg aaccatcacc | 480 |
| gccgacacct tctgcaaact cttccgagtc tacagcaact tcctccgggg aaagctgaag | 540 |
| ctgtacacgg gggaggcctg caggagaggg gacagatga | 579 |

<210> SEQ ID NO 164
<211> LENGTH: 579
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 164

| | |
|---|---|
| atggggtgc acgaatgtcc tgcctggctg tggcttctcc tgtctctgct gtcgctccct | 60 |
| ctgggcctcc cagtcccggg cgccccacca cgcctcatct gtgacagccg agtcctggag | 120 |
| aggtacctct tggaggccaa ggaggccgag aatgtcacga tgggctgttc cgaaagctgc | 180 |
| agcttgaatg agaatatcac cgtcccagac accaaagtta acttctatgc ctggaagagg | 240 |
| atggaggtcg ggcagcaggc tgtagaagtc tggcagggcc tggccctgct ctcagaagct | 300 |
| gtcctgcggg gccaggccgt gttggccaac tcttcccagc ctttcgagcc cctgcagctg | 360 |
| cacatggata aagccatcag cggcctgcgc agcatcacca ccctgctgcg ggcgctggga | 420 |
| gcccaggaag ccatcagcct cccagacgcg ccagcgccg ccccactccg aaccatcacc | 480 |
| gccgacacct tctgcaaact cttccgagtc tacagcaact tcctccgggg aaagctgaag | 540 |
| ctgtacacgg gggaggcctg caggagaggg gacagatga | 579 |

<210> SEQ ID NO 165
<211> LENGTH: 579
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 165

| | |
|---|---|
| atggggtgc acgaatgtcc tgcctggctg tggcttctcc tgtctctgct gtcgctccct | 60 |
| ctgggcctcc cagtcccggg cgccccacca cgcctcatct gtgacagccg agtcctggag | 120 |
| aggtacctct tggaggccaa ggaggccgag aatgtcacga tgggctgttc cgaaagctgc | 180 |
| agcttgaatg agaatatcac cgtcccagac accaaagtta acttctatgc ctggaagagg | 240 |
| atggaggtcg ggcagcaggc tgtagaagtc tggcagggcc tggccctgct ctcagaagct | 300 |
| gtcctgcggg gccaggccgt gttggccaac tcttcccagc ctttcgagcc cctgcagctg | 360 |
| cacatggata aagccatcag tggccttcgc agcatcacca ctctgcttcg ggcgctggga | 420 |
| gcccaggaag ccatctccct cccagatgcg gcctcggctg ctccactccg aaccatcact | 480 |
| gctgacacct tctgcaaact cttccgagtc tacagcaact tcctccgggg aaagctgaag | 540 |

```
ctgtacacgg gggaggcctg caggagaggg gacagatga                               579
```

<210> SEQ ID NO 166
<211> LENGTH: 579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166

```
atgggggtgc acgaatgccc cgcctggctg tggctgctcc tgagcctgct gagcctcccc        60
ctgggcctcc cagtcccggg cgccccacca cgcctcatct gcgacagccg agtcctggag       120
aggtacctcc tggaggccaa ggaggccgag aacgtcacga tgggctgcag cgaaagctgc       180
agcctgaacg agaacatcac cgtcccagac accaaagtga acttctacgc ctggaagagg       240
atggaggtcg ggcagcaggc cgtagaagtc tggcagggcc tggccctgct cagcgaagcc       300
gtcctgcggg gccaggccgt gctggccaac agcagccagc cttcgagcc cctgcagctg       360
cacatggaca aagccatcag cggcctgcgc agcatcacca ccctgctgcg ggcgctggga       420
gcccaggaag ccatcagcct cccagacgcg gccagcgccg ccccactccg aaccatcacc       480
gccgacactt tctgcaaact cttccgagtc tactccaatt tcctccgggg aaagctgaag       540
ctgtacacgg gggaggcctg caggagaggg gacagatga                               579
```

<210> SEQ ID NO 167
<211> LENGTH: 579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167

```
atgggggtgc acgaatgccc cgcctggctg tggctgctcc tgagcctgct gagcctcccc        60
ctgggcctcc cagtcccggg cgccccacca cgcctcatct gcgacagccg agtcctggag       120
aggtacctcc tggaggccaa ggaggccgag aacgtcacga tgggctgcag cgaaagctgc       180
agcctgaacg agaacatcac cgtcccagac accaaagtga acttctacgc ctggaagagg       240
atggaggtcg ggcagcaggc cgtagaagtc tggcagggcc tggccctgct cagcgaagcc       300
gtcctgcggg gccaggccgt gctggccaac agcagccagc cttcgagcc cctgcagctg       360
cacatggaca aagccatcag tggccttcgc agcatcacca ctctgcttcg ggcgctggga       420
gcccaggaag ccatctccct cccagatgcg gcctcggctg ctccactccg aaccatcact       480
gctgacactt tctgcaaact cttccgagtc tactccaatt tcctccgggg aaagctgaag       540
ctgtacacgg gggaggcctg caggagaggg gacagatga                               579
```

<210> SEQ ID NO 168
<211> LENGTH: 579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 168

```
atgggggtgc acgaatgccc cgcctggctg tggctgctcc tgagcctgct gagcctcccc        60
ctgggcctcc cagtcccggg cgccccacca cgcctcatct gcgacagccg agtcctggag       120
```

```
aggtacctcc tggaggccaa ggaggccgag aacgtcacga tgggctgcag cgaaagctgc    180
agcctgaacg agaatatcac cgtcccagac accaaagtta acttctatgc ctggaagagg    240
atggaggtcg ggcagcaggc tgtagaagtc tggcagggcc tggccctgct ctcagaagct    300
gtcctgcggg gccaggccgt gttggccaac tcttcccagc ctttcgagcc cctgcagctg    360
cacatggata aagccatcag tggccttcgc agcatcacca ctctgcttcg ggcgctggga    420
gcccaggaag ccatctccct cccagatgcg gcctcggctg ctccactccg aaccatcact    480
gctgacactt tctgcaaact cttccgagtc tactccaatt cctccgggg aaagctgaag    540 ctgtacacgg gggaggcctg caggagaggg gacagatga                          579
```

<210> SEQ ID NO 169
<211> LENGTH: 579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169

```
atggggtgc acgaatgccc cgcctggctg tggctgctcc tgtctctgct gtcgctccct     60
ctgggcctcc cagtcccggg cgccccacca cgcctcatct gtgacagccg agtcctggag    120
aggtacctct tggaggccaa ggaggccgag aatgtcacga tgggctgttc cgaaagctgc    180
agcttgaatg agaatatcac cgtcccagac accaaagtta acttctatgc ctggaagagg    240
atggaggtcg ggcagcaggc tgtagaagtc tggcagggcc tggccctgct ctcagaagct    300
gtcctgcggg gccaggccgt gttggccaac tcttcccagc ctttcgagcc cctgcagctg    360
cacatggata aagccatcag tggccttcgc agcatcacca ctctgcttcg ggcgctggga    420
gcccaggaag ccatctccct cccagatgcg gcctcggctg ctccactccg aaccatcact    480
gctgacactt tctgcaaact cttccgagtc tactccaatt cctccgggg aaagctgaag    540 ctgtacacgg gggaggcctg caggagaggg gacagatga                          579
```

<210> SEQ ID NO 170
<211> LENGTH: 579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170

```
atggggtgc acgaatgccc cgcctggctg tggctgctcc tgagcctgct gagcctccct     60
ctgggcctcc cagtcccggg cgccccacca cgcctcatct gcgacagccg agtcctggag    120
aggtacctcc tggaggccaa ggaggccgag aacgtcacga tgggctgcag cgaaagctgc    180
agcctgaacg agaatatcac cgtcccagac accaaagtga acttctacgc ctggaagagg    240
atggaggtcg ggcagcaggc cgtagaagtc tggcagggcc tggccctgct cagcgaagcc    300
gtcctgcggg gccaggccgt gctggccaac agcagccagc ctttcgagcc cctgcagctg    360
cacatggaca aagccatcag cggcctgcgc agcatcacca ccctgctgcg ggcgctggga    420
gcccaggaag ccatcagcct cccagacgcg gccagcgccg cccactccg aaccatcacc    480 gccgacacct tctgcaaact cttccgagtc tacagcaact cctccggggg aaagctgaag    540
ctgtacacgg gggaggcctg caggagaggg gacagatga                          579
```

<210> SEQ ID NO 171
<211> LENGTH: 579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 171

```
atggggtgc acgaatgccc cgcctggctg tggcttctcc tgagcctgct gtcgctcccc      60
ctgggcctcc cagtcccggg cgccccacca cgcctcatct gcgacagccg agtcctggag     120
aggtacctcc tggaggccaa ggaggccgag aacgtcacga tgggctgctc cgaaagctgc    180
agcttgaatg agaacatcac cgtcccagac accaaagtga acttctacgc ctggaagagg     240
atggaggtcg ggcagcaggc cgtagaagtc tggcagggcc tggccctgct ctcagaagcc    300
gtcctgcggg gccaggccgt gctggccaac agcagccagc ctttcgagcc cctgcagctg    360
cacatggata aagccatcag cggccttcgc agcatcacca ctctgctgcg ggcgctggga    420
gcccaggaag ccatctccct cccagatgcg gccagcgctg ccccactccg aaccatcact    480
gccgacacct tctgcaaact cttccgagtc tacagcaact tcctccgggg aaagctgaag    540
ctgtacacgg gggaggcctg caggagaggg gacagatga                           579
```

<210> SEQ ID NO 172
<211> LENGTH: 579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172

```
atggggtgc acgaatgccc cgcctggctg tggcttctcc tgtctctgct gagcctccct      60
ctgggcctcc cagtcccggg cgccccacca cgcctcatct gtgacagccg agtcctggag     120
aggtacctct tggaggccaa ggaggccgag aacgtcacga tgggctgttc cgaaagctgc    180
agcttgaacg agaatatcac cgtcccagac accaaagtga acttctatgc ctggaagagg     240
atggaggtcg ggcagcaggc tgtagaagtc tggcagggcc tggccctgct cagcgaagcc    300
gtcctgcggg gccaggccgt gttggccaac agctcccagc ccttcgagcc cctgcagctg    360
cacatggaca aagccatcag tggcctgcgc agcatcacca ctctgcttcg ggcgctggga    420
gcccaggaag ccatctccct cccagatgcg gccagcgctg ctccactccg aaccatcact    480
gctgacactt tctgcaaact cttccgagtc tactccaatt tcctccgggg aaagctgaag    540
ctgtacacgg gggaggcctg caggagaggg gacagatga                           579
```

<210> SEQ ID NO 173
<211> LENGTH: 579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 173

```
atggggtgc acgaatgccc tgcctggctg tggcttctcc tgtctctgct gtcgctccct      60
ctgggcctcc cagtcccggg cgccccacca cgcctcatct gtgacagccg agtcctggag     120
aggtacctct tggaggccaa ggaggccgag aatgtcacga tgggctgttc cgaaagctgc    180
```

```
agcctgaatg agaatatcac cgtcccagac accaaagtta acttctatgc ctggaagagg    240
atggaggtcg ggcagcaggc tgtagaagtc tggcagggcc tggccctgct ctcagaagct    300
gtcctgcggg gccaggccgt gttggccaac tcttcccagc ctttcgagcc cctgcagctg    360
cacatggata aagccatcag tggccttcgc agcatcacca ctctgctgcg ggcgctggga    420
gcccaggaag ccatctccct cccagatgcg gcctcggctg ctccactccg aaccatcact    480
gctgacactt tctgcaaact cttccgagtc tactccaatt cctccgggg aaagctgaag     540 ctgtacacgg gggaggcctg caggagaggg gacagatga                           579
```

<210> SEQ ID NO 174
<211> LENGTH: 913
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 174

```
aggaaactta agaacttaaa aaaaaaaatc aaaatggccg ccaccatggg ggtgcacgaa    60
tgccccgcct ggctgtggct gctcctgagc ctgctgagcc tcccctgggg cctcccagtc   120
ccgggcgccc caccacgcct catctgcgac agccgagtcc tggagaggta cctcctggag   180
gccaaggagg ccgagaacgt cacgatgggc tgcagcgaaa gctgcagcct gaacgagaac   240
atcaccgtcc agacaccaa agtgaacttc tacgcctgga gaggatgga ggtcgggcag    300 caggccgtag aagtctggca gggcctggcc ctgctcagcg aagccgtcct gcggggccag   360
gccgtgctgg ccaacagcag ccagcccttc gagcccctgc agctgcacat ggacaaagcc   420
atcagcggcc tgcgcagcat caccaccctg ctgcgggcgc tgggagccca ggaagccatc   480
agcctcccag acgcggccag cgccgcccca ctccgaacca tcaccgccga caccttctgc   540
aaactcttcc gagtctacag caacttcctc cggggaaagc tgaagctgta cacggggag   600 gcctgcagga gagggacag atgactcgag ctagtgactg actaggatct ggttaccact    660
aaaccagcct caagaacacc cgaatggagt ctctaagcta cataatacca acttacactt    720
acaaaatgtt gtcccccaaa atgtagccat tcgtatctgc tcctaataaa aagaaagttt    780
cttcacattc tagaaaaaaa aaaaaaaaaa aaaaaaaaa aaaaaaaaa aaaaaaaaa    840 aaaaaaaaaa aaaaaaaaaa aaaaaaaaaa aaaaaaaaa aaaaaaaaa aaaaaaaaa    900 aaaaaaaaaa aaa                                                      913
```

<210> SEQ ID NO 175
<211> LENGTH: 913
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175

```
aggaaactta agaacttaaa aaaaaaaatc aaaatggccg ccaccatggg ggtgcacgaa    60
tgtcctgcct ggctgtggct tctcctgagc ctgctgagcc tcccctgggg cctcccagtc   120
ccgggcgccc caccacgcct catctgcgac agccgagtcc tggagaggta cctcctggag   180
gccaaggagg ccgagaacgt cacgatgggc tgcagcgaaa gctgcagcct gaacgagaac   240
atcaccgtcc agacaccaa agtgaacttc tacgcctgga gaggatgga ggtcgggcag    300 caggccgtag aagtctggca gggcctggcc ctgctcagcg aagccgtcct gcggggccag   360
```

```
gccgtgctgg ccaacagcag ccagcccttc gagcccctgc agctgcacat ggacaaagcc      420
atcagcggcc tgcgcagcat caccaccctg ctgcgggcgc tgggagccca ggaagccatc      480
agcctcccag acgcggccag cgccgcccca ctccgaacca tcaccgccga cccttctgc       540 aaactcttcc gagtctacag caacttcctc cggggaaagc tgaagctgta cacggggag       600 gcctgcagga gagggacag atgactcgag ctagtgactg actaggatct ggttaccact        660
aaaccagcct caagaacacc cgaatggagt ctctaagcta cataatacca acttacactt      720
acaaaatgtt gtcccccaaa atgtagccat tcgtatctgc tcctaataaa agaaagttt       780 cttcacattc tagaaaaaaa aaaaaaaaaa aaaaaaaaaa aaaaaaaaaa aaaaaaaaaa      840
aaaaaaaaaa aaaaaaaaaa aaaaaaaaaa aaaaaaaaaa aaaaaaaaaa aaaaaaaaaa      900
aaaaaaaaaa aaa                                                        913

<210> SEQ ID NO 176
<211> LENGTH: 913
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 176
aggaaactta agaacttaaa aaaaaaaatc aaaatggccg ccaccatggg ggtgcacgaa      60
tgccccgcct ggctgtggct gctcctgagc ctgctgagcc tcccctgggg cctcccagtc     120
ccgggcgccc caccacgcct catctgcgac agccgagtcc tggagaggta cctcctggag     180
gccaaggagg ccgagaacgt cacgatgggc tgcagcgaaa gctgcagcct gaacgagaac     240
atcaccgtcc cagacaccaa agtgaacttc tacgcctgga gaggatgga ggtcgggcag     300 caggccgtag aagtctggca gggcctggcc ctgctcagcg aagccgtcct gcggggccag      360
gccgtgctgg ccaacagcag ccagcccttc gagcccctgc agctgcacat ggacaaagcc      420
atcagcggcc tgcgcagcat caccaccctg ctgcgggcgc tgggagccca ggaagccatc      480
agcctcccag acgcggccag cgccgcccca ctccgaacca tcaccgccga cactttctgc     540
aaactcttcc gagtctactc caatttcctc cggggaaagc tgaagctgta cacggggag      600 gcctgcagga gagggacag atgactcgag ctagtgactg actaggatct ggttaccact        660
aaaccagcct caagaacacc cgaatggagt ctctaagcta cataatacca acttacactt      720
acaaaatgtt gtcccccaaa atgtagccat tcgtatctgc tcctaataaa agaaagttt       780 cttcacattc tagaaaaaaa aaaaaaaaaa aaaaaaaaaa aaaaaaaaaa aaaaaaaaaa      840
aaaaaaaaaa aaaaaaaaaa aaaaaaaaaa aaaaaaaaaa aaaaaaaaaa aaaaaaaaaa      900
aaaaaaaaaa aaa                                                        913

<210> SEQ ID NO 177
<211> LENGTH: 913
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177
aggaaactta agaacttaaa aaaaaaaatc aaaatggccg ccaccatggg ggtgcacgaa      60
tgccccgcct ggctgtggct gctcctgagc ctgctgagcc tccctctggg cctcccagtc     120
```

| | |
|---|---|
| ccgggcgccc caccacgcct catctgcgac agccgagtcc tggagaggta cctcctggag | 180 |
| gccaaggagg ccgagaacgt cacgatgggc tgcagcgaaa gctgcagcct gaacgagaat | 240 |
| atcaccgtcc cagacaccaa agtgaacttc tacgcctgga agaggatgga ggtcgggcag | 300 |
| caggccgtag aagtctggca gggcctggcc ctgctcagcg aagccgtcct gcggggccag | 360 |
| gccgtgctgg ccaacagcag ccagcctttc gagcccctgc agctgcacat ggacaaagcc | 420 |
| atcagcggcc tgcgcagcat caccaccctg ctgcgggcgc tgggagccca ggaagccatc | 480 |
| agcctcccag acgcggccag cgccgcccca ctccgaacca tcaccgccga caccttctgc | 540 |
| aaactcttcc gagtctacag caacttcctc cggggaaagc tgaagctgta cacggcggag | 600 |
| gcctgcagga gagggacag atgactcgag ctagtgactg actaggatct ggttaccact | 660 |
| aaaccagcct caagaacacc cgaatggagt ctctaagcta cataatacca acttacactt | 720 |
| acaaaatgtt gtcccccaaa atgtagccat tcgtatctgc tcctaataaa agaaagttt | 780 |
| cttcacattc tagaaaaaaa aaaaaaaaaa aaaaaaaaaa aaaaaaaaaa aaaaaaaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaa | 913 |

<210> SEQ ID NO 178
<211> LENGTH: 913
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 178

| | |
|---|---|
| aggaaacuua agaacuuaaa aaaaaaaauc aaaauggccg ccaccauggg ggugcacgaa | 60 |
| ugccccgccu ggcuguggcu gcuccugagc cugcugagcc uccccuggg ccucccaguc | 120 |
| ccgggcgccc caccacgccu caucugcgac agccgaguc uggagaggua ccuccuggag | 180 |
| gccaaggagg ccgagaacgu cacgaugggc ugcagcgaaa gcugcagccu gaacgagaac | 240 |
| aucaccgucc cagacaccaa agugaacuuc uacgccugga agaggaugga ggucgggcag | 300 |
| caggccguag aagucuggca gggccuggcc cugcucagcg aagccguccu gcggggccag | 360 |
| gccgugcugg ccaacagcag ccagcccuuc gagccccugc agcugcacau ggacaaagcc | 420 |
| aucagcggcc ugcgcagcau caccacccug cugcgggcgc ugggagccca ggaagccauc | 480 |
| agccucccag acgcggccag cgccgcccca cuccgaacca ucaccgccga caccuucugc | 540 |
| aaacucuucc gagucuacag caacuuccuc cggggaaagc ugaagcugua cacggcggag | 600 |
| gccugcagga gagggacag augacucgag cuagugacug acuaggaucu gguuaccacu | 660 |
| aaaccagccu caagaacacc cgaauggagu cucuaagcua cauaauacca acuuacacuu | 720 |
| acaaaauguu gucccccaaa auguagccau ucguaucugc uccuaauaaa agaaaguuu | 780 |
| cuucacauuc uagaaaaaaa aaaaaaaaaa aaaaaaaaaa aaaaaaaaaa aaaaaaaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaa | 913 |

<210> SEQ ID NO 179
<211> LENGTH: 913
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 179

```
aggaaacuua agaacuuaaa aaaaaaaauc aaaauggccg ccaccauggg ggugcacgaa      60
uguccugccu ggcuguggcu ucuccugagc cugcugagcc uccccugggg ccucccaguc     120
ccgggcgccc caccacgccu caucugcgac agccgagucc uggagaggua ccuccuggag     180
gccaaggagg ccgagaacgu cacgaugggc ugcagcgaaa gcugcagccu gaacgagaac     240
aucaccgucc cagacaccaa agugaacuuc uacgccugga agaggaugga ggucgggcag     300
caggccguag aagucuggca gggccuggcc cugcucagcg aagccguccu gcggggccag     360
gccgugcugg ccaacagcag ccagcccuuc gagccccugc agcugcacau ggacaaagcc     420
aucagcggcc ugcgcagcau caccacccug cugcgggcgc ugggagccca ggaagccauc     480
agccucccag acgcggccag cgccgcccca cuccgaacca ucaccgccga caccuucugc     540
aaacucuucc gagucuacag caacuuccuc cggggaaagc ugaagcugua cacggggag      600
gccugcagga gagggacag augacucgag cuagugacug acuaggaucu gguuaccacu      660
aaaccagccu caagaacacc cgaauggagu cucuaagcua cauaauacca acuuacacuu     720
acaaaauguu gucccccaaa auguagccau ucguaucugc uccuaauaaa aagaaaguuu     780
cuucacauuc uagaaaaaaa aaaaaaaaaa aaaaaaaaaa aaaaaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaa                                                        913
```

<210> SEQ ID NO 180
<211> LENGTH: 913
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 180

```
aggaaacuua agaacuuaaa aaaaaaaauc aaaauggccg ccaccauggg ggugcacgaa      60
ugccccgccu ggcuguggcu gcuccugagc cugcugagcc uccccugggg ccucccaguc     120
ccgggcgccc caccacgccu caucugcgac agccgagucc uggagaggua ccuccuggag     180
gccaaggagg ccgagaacgu cacgaugggc ugcagcgaaa gcugcagccu gaacgagaac     240
aucaccgucc cagacaccaa agugaacuuc uacgccugga agaggaugga ggucgggcag     300
caggccguag aagucuggca gggccuggcc cugcucagcg aagccguccu gcggggccag     360
gccgugcugg ccaacagcag ccagcccuuc gagccccugc agcugcacau ggacaaagcc     420
aucagcggcc ugcgcagcau caccacccug cugcgggcgc ugggagccca ggaagccauc     480
agccucccag acgcggccag cgccgcccca cuccgaacca ucaccgccga cacuuucugc     540
aaacucuucc gagucuacuc caauuuccuc cggggaaagc ugaagcugua cacggggag      600
gccugcagga gagggacag augacucgag cuagugacug acuaggaucu gguuaccacu      660
aaaccagccu caagaacacc cgaauggagu cucuaagcua cauaauacca acuuacacuu     720
acaaaauguu gucccccaaa auguagccau ucguaucugc uccuaauaaa aagaaaguuu     780
cuucacauuc uagaaaaaaa aaaaaaaaaa aaaaaaaaaa aaaaaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaa                                                        913
```

```
<210> SEQ ID NO 181
<211> LENGTH: 913
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 181
aggaaacuua agaacuuaaa aaaaaaaauc aaaauggccg ccaccauggg ggugcacgaa      60
ugccccgccu ggcuguggcu gcuccugagc cugcugagcc ucccucuggg ccucccaguc     120
ccgggcgccc caccacgccu caucgcgac agccgaguccu uggagaggua ccuccuggag     180
gccaaggagg ccgagaacgu cacgauggg cugcagcgaaa gcugcagccu gaacgagaau    240
aucaccgucc cagacaccaa agugaacuuc uacgccugga agaggaugga ggucgggcag     300
caggccguag aagucuggca gggccuggcc cugcucagcg aagccguccu gcggggccag     360
gccgugcugg ccaacagcag ccagccuuuc gagccccugc agcugcacau ggacaaagcc     420
aucagcggcc ugcgcagcau caccacccug cugcgggcg ugggagccca ggaagccauc     480
agccucccag acgcggccag cgccgcccca cuccgaacca ucaccgccga caccuucugc    540
aaacucuucc gagucuacag caacuuccuc cggggaaagc ugaagcugua cacggggag     600 gccugcagga gagggacag augacucgag cuagugacug acuaggaucu gguuaccacu     660
aaaccagccu caagaacacc cgaauggagu cucuaagcua cauaauacca acuuacacuu     720
acaaaauguu gucccccaaa auguagccau ucguaucugc uccuaauaaa agaaaguuu     780 cuucacauuc uagaaaaaaa aaaaaaaaaa aaaaaaaaa aaaaaaaaa aaaaaaaaa       840 aaaaaaaaaa aaaaaaaaa aaaaaaaaa aaaaaaaaa aaaaaaaaa aaaaaaaaa          900 aaaaaaaaaa aaa                                                        913

<210> SEQ ID NO 182
<211> LENGTH: 1011
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 182
aggaaactta agtcaacaca acatatacaa aacaaacgaa tctcaagcaa tcaagcattc      60
tacttctatt gcagcaattt aaatcatttc ttttaaagca aaagcaattt tctgaaaatt     120
ttcaccattt acgaacgata gccatggggg tgcacgaatg ccccgcctgg ctgtggctgc     180
tcctgagcct gctgagcctc cccctgggcc tcccagtccc gggcgcccca ccacgcctca     240
tctgcgacag ccgagtcctg gagaggtacc tcctggaggc caaggaggcc gagaacgtca     300
cgatgggctg cagcgaaagc tgcagcctga acgagaacat caccgtccca gacaccaaag     360
tgaacttcta cgcctggaag aggatggagg tcgggcagca ggccgtagaa gtctggcagg     420
gcctggccct gctcagcgaa gccgtcctgc ggggccaggc cgtgctggcc aacagcagcc     480
agcccttcga gcccctgcag ctgcacatgg acaaagccat cagcggcctg cgcagcatca     540
ccaccctgct gcgggcgctg ggagcccagg aagccatcag cctcccagac gcggccagcg     600 ccgcccccact ccgaaccatc accgccgaca ccttctgcaa actcttccga gtctacagca     660
acttcctccg ggaaagctg aagctgtaca cggggggagc ctgcaggaga ggggacagat       720
gactcgagct agtgactgac taggatctgg ttaccactaa accagcctca agaacacccg     780
```

| aatggagtct ctaagctaca taataccaac ttacacttac aaaatgttgt cccccaaaat | 840 |
| gtagccattc gtatctgctc ctaataaaaa gaaagtttct tcacattcta gaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa a | 1011 |

<210> SEQ ID NO 183
<211> LENGTH: 1011
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 183

| aggaaactta agtcaacaca acatatacaa aacaaacgaa tctcaagcaa tcaagcattc | 60 |
| tacttctatt gcagcaattt aaatcatttc ttttaaagca aaagcaattt tctgaaaatt | 120 |
| ttcaccattt acgaacgata gccatggggg tgcacgaatg tcctgcctgg ctgtggcttc | 180 |
| tcctgagcct gctgagcctc cccctgggcc tcccagtccc gggcgcccca ccacgcctca | 240 |
| tctgcgacag ccgagtcctg gagaggtacc tcctggaggc caaggaggcc gagaacgtca | 300 |
| cgatgggctg cagcgaaagc tgcagcctga acgagaacat caccgtccca gacaccaaag | 360 |
| tgaacttcta cgcctggaag aggatggagg tcgggcagca ggccgtagaa gtctggcagg | 420 |
| gcctggccct gctcagcgaa gccgtcctgc ggggccaggc cgtgctggcc aacagcagcc | 480 |
| agcccttcga gccctgcag ctgcacatgg acaaagccat cagcggcctg cgcagcatca | 540 |
| ccaccctgct gcgggcgctg ggagcccagg aagccatcag cctcccagac gcggccagcg | 600 |
| ccgccccact ccgaaccatc accgccgaca ccttctgcaa actcttccga gtctacagca | 660 |
| acttcctccg gggaaagctg aagctgtaca cgggggaggc ctgcaggaga ggggacagat | 720 |
| gactcgagct agtgactgac taggatctgg ttaccactaa accagcctca agaacacccg | 780 |
| aatggagtct ctaagctaca taataccaac ttacacttac aaaatgttgt cccccaaaat | 840 |
| gtagccattc gtatctgctc ctaataaaaa gaaagtttct tcacattcta gaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa a | 1011 |

<210> SEQ ID NO 184
<211> LENGTH: 1011
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 184

| aggaaactta agtcaacaca acatatacaa aacaaacgaa tctcaagcaa tcaagcattc | 60 |
| tacttctatt gcagcaattt aaatcatttc ttttaaagca aaagcaattt tctgaaaatt | 120 |
| ttcaccattt acgaacgata gccatggggg tgcacgaatg ccccgcctgg ctgtggctgc | 180 |
| tcctgagcct gctgagcctc cccctgggcc tcccagtccc gggcgcccca ccacgcctca | 240 |
| tctgcgacag ccgagtcctg gagaggtacc tcctggaggc caaggaggcc gagaacgtca | 300 |
| cgatgggctg cagcgaaagc tgcagcctga acgagaacat caccgtccca gacaccaaag | 360 |
| tgaacttcta cgcctggaag aggatggagg tcgggcagca ggccgtagaa gtctggcagg | 420 |
| gcctggccct gctcagcgaa gccgtcctgc ggggccaggc cgtgctggcc aacagcagcc | 480 |

```
agcccttcga gcccctgcag ctgcacatgg acaaagccat cagcggcctg cgcagcatca        540
ccaccctgct gcgggcgctg ggagcccagg aagccatcag cctcccagac gcggccagcg        600 ccgcccact  ccgaaccatc accgccgaca ctttctgcaa actcttccga gtctactcca        660
atttcctccg gggaaagctg aagctgtaca cgggggaggc ctgcaggaga ggggacagat        720
gactcgagct agtgactgac taggatctgg ttaccactaa accagcctca agaacacccg        780
aatggagtct ctaagctaca taataccaac ttacacttac aaaatgttgt cccccaaaat        840
gtagccattc gtatctgctc ctaataaaaa gaaagtttct tcacattcta gaaaaaaaaa        900
aaaaaaaaaa aaaaaaaaaa aaaaaaaaaa aaaaaaaaaa aaaaaaaaaa aaaaaaaaaa        960
aaaaaaaaaa aaaaaaaaaa aaaaaaaaaa aaaaaaaaaa aaaaaaaaaa a                1011
```

<210> SEQ ID NO 185
<211> LENGTH: 1011
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185

```
aggaaactta agtcaacaca acatatacaa aacaaacgaa tctcaagcaa tcaagcattc         60
tacttctatt gcagcaattt aaatcatttc ttttaaagca aaagcaattt tctgaaaatt        120
ttcaccattt acgaacgata gccatggggg tgcacgaatg ccccgcctgg ctgtggctgc        180
tcctgagcct gctgagcctc cctctgggcc tcccagtccc gggcgcccca ccacgcctca        240
tctgcgacag ccgagtcctg gagaggtacc tcctggaggc caaggaggcc gagaacgtca        300
cgatgggctg cagcgaaagc tgcagcctga acgagaatat caccgtccca gacaccaaag        360
tgaacttcta cgcctggaag aggatggagg tcgggcagca ggccgtagaa gtctggcagg        420
gcctggccct gctcagcgaa gccgtcctgc ggggccaggc cgtgctggcc aacagcagcc        480 agccttcga  gcccctgcag ctgcacatgg acaaagccat cagcggcctg cgcagcatca        540
ccaccctgct gcgggcgctg ggagcccagg aagccatcag cctcccagac gcggccagcg        600 ccgcccact  ccgaaccatc accgccgaca ccttctgcaa actcttccga gtctacagca        660
acttcctccg gggaaagctg aagctgtaca cgggggaggc ctgcaggaga ggggacagat        720
gactcgagct agtgactgac taggatctgg ttaccactaa accagcctca agaacacccg        780
aatggagtct ctaagctaca taataccaac ttacacttac aaaatgttgt cccccaaaat        840
gtagccattc gtatctgctc ctaataaaaa gaaagtttct tcacattcta gaaaaaaaaa        900
aaaaaaaaaa aaaaaaaaaa aaaaaaaaaa aaaaaaaaaa aaaaaaaaaa aaaaaaaaaa        960
aaaaaaaaaa aaaaaaaaaa aaaaaaaaaa aaaaaaaaaa aaaaaaaaaa a                1011
```

<210> SEQ ID NO 186
<211> LENGTH: 1011
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 186

```
aggaaacuua agucaacaca acauauacaa aacaaacgaa ucucaagcaa ucaagcauuc         60
uacuucuauu gcagcaauuu aaaucauuuc uuuuaaagca aaagcaauuu ucugaaaauu        120
```

-continued

| | |
|---|---|
| uucaccauuu acgaacgaua gccauggggg ugcacgaaug ccccgccugg cuguggcugc | 180 |
| uccugagccu gcugagccuc ccccugggcc ucccagcccc gggcgcccca ccacgccuca | 240 |
| ucugcgacag ccgagucccug gagagguacc uccuggaggc caaggaggcc gagaacguca | 300 |
| cgaugggcug cagcgaaagc ugcagccuga acgagaacau caccgucccca gacaccaaag | 360 |
| ugaacuucua cgccuggaag aggauggagg ucgggcagca ggccguagaa gucuggcagg | 420 |
| gccuggcccu gcucagcgaa gccguccugc ggggccaggc cgugcuggcc aacagcagcc | 480 |
| agcccuucga gccccugcag cugcacaugg acaaagccau cagcggccug cgcagcauca | 540 |
| ccacccugcu gcgggcgcug ggagcccagg aagccaucag ccucccagac gcggccagcg | 600 |
| ccgccccacu ccgaaccauc accgccgaca ccuucugcaa acucuuccga gucuacagca | 660 |
| acuuccuccg gggaaagcug aagcuguaca cgggggaggc cugcaggaga ggggacagau | 720 |
| gacucgagcu agugacugac uaggaucugg uuaccacuaa accagccuca agaacacccg | 780 |
| aauggagucu cuaagcuaca uaauaccaac uuacacuuac aaaauguugu ccccaaaaau | 840 |
| guagccauuc guaucugcuc cuauaaaaa gaaaguuucu ucacauucua gaaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa a | 1011 |

<210> SEQ ID NO 187
<211> LENGTH: 1011
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 187

| | |
|---|---|
| aggaaacuua agucaacaca acauauacaa aacaaacgaa ucucaagcaa ucaagcauuc | 60 |
| uacuucuauu gcagcaauuu aaaucauuuc uuuuaaagca aaagcaauuu ucugaaaauu | 120 |
| uucaccauuu acgaacgaua gccauggggg ugcacgaaug uccugccugg cuguggcuuc | 180 |
| uccugagccu gcugagccuc ccccugggcc ucccagcccc gggcgcccca ccacgccuca | 240 |
| ucugcgacag ccgagucccug gagagguacc uccuggaggc caaggaggcc gagaacguca | 300 |
| cgaugggcug cagcgaaagc ugcagccuga acgagaacau caccgucccca gacaccaaag | 360 |
| ugaacuucua cgccuggaag aggauggagg ucgggcagca ggccguagaa gucuggcagg | 420 |
| gccuggcccu gcucagcgaa gccguccugc ggggccaggc cgugcuggcc aacagcagcc | 480 |
| agcccuucga gccccugcag cugcacaugg acaaagccau cagcggccug cgcagcauca | 540 |
| ccacccugcu gcgggcgcug ggagcccagg aagccaucag ccucccagac gcggccagcg | 600 |
| ccgccccacu ccgaaccauc accgccgaca ccuucugcaa acucuuccga gucuacagca | 660 |
| acuuccuccg gggaaagcug aagcuguaca cgggggaggc cugcaggaga ggggacagau | 720 |
| gacucgagcu agugacugac uaggaucugg uuaccacuaa accagccuca agaacacccg | 780 |
| aauggagucu cuaagcuaca uaauaccaac uuacacuuac aaaauguugu ccccaaaaau | 840 |
| guagccauuc guaucugcuc cuauaaaaa gaaaguuucu ucacauucua gaaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa a | 1011 |

<210> SEQ ID NO 188
<211> LENGTH: 1011
<212> TYPE: RNA

<213> ORGANISM: Artificial Sequence
<220> FEATURE:
<223> OTHER INFORMATION: Description of Artificial Sequence: Synthetic polynucleotide

<400> SEQUENCE: 188

```
aggaaacuua agucaacaca acauauacaa aacaaacgaa ucucaagcaa ucaagcauuc      60
uacuucuauu gcagcaauuu aaaucauuuc uuuuaaagca aaagcaauuu ucugaaaauu     120
uucaccauuu acgaacgaua gccauggggg ugcacgaaug ccccgccugg cuguggcugc     180
uccugagccu gcugagccuc cccugggcc ucccaguccc gggcgcccca ccacgccuca      240
ucugcgacag ccgaguccug gagagguacc uccuggaggc caaggaggcc gagaacguca     300
cgaugggcug cagcgaaagc ugcagccuga acgagaacau caccgucccca gacaccaaag    360
ugaacuucua cgccuggaag aggauggagg ucgggcagca ggccguagaa gucuggcagg    420
gccuggcccu gcucagcgaa gccguccugc ggggccaggc cgugcuggcc aacagcagcc    480
agcccuucga gccccugcag cugcacaugg acaaagccau cagcggccug cgcagcauca    540
ccacccugcu gcgggcgcug ggagcccagg aagccaucag ccucccagac gcggccagcg    600
ccgccccacu ccgaaccauc accgccgaca cuuucugcaa acucuuccga gucuacucca    660
auuuccuccg gggaaagcug aagcuguaca cgggggaggc cugcaggaga ggggacagau    720
gacucgagcu agugacugac uaggaucugg uuaccacuaa accagccuca agaacacccg    780
aauggagucu cuaagcuaca uaauaccaac uuacacuuac aaaauguugu cccccaaaau    840
guagccauuc guaucugcuc cuauaaaaa gaaaguuucu ucacauucua gaaaaaaaaa     900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaa a             1011
```

<210> SEQ ID NO 189
<211> LENGTH: 1011
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 189

```
aggaaacuua agucaacaca acauauacaa aacaaacgaa ucucaagcaa ucaagcauuc      60
uacuucuauu gcagcaauuu aaaucauuuc uuuuaaagca aaagcaauuu ucugaaaauu     120
uucaccauuu acgaacgaua gccauggggg ugcacgaaug ccccgccugg cuguggcugc     180
uccugagccu gcugagccuc ccucugggcc ucccaguccc gggcgcccca ccacgccuca     240
ucugcgacag ccgaguccug gagagguacc uccuggaggc caaggaggcc gagaacguca     300
cgaugggcug cagcgaaagc ugcagccuga acgagaauau caccgucccca gacaccaaag    360
ugaacuucua cgccuggaag aggauggagg ucgggcagca ggccguagaa gucuggcagg     420
gccuggcccu gcucagcgaa gccguccugc ggggccaggc cgugcuggcc aacagcagcc     480
agccuuucga gccccugcag cugcacaugg acaaagccau cagcggccug cgcagcauca    540
ccacccugcu gcgggcgcug ggagcccagg aagccaucag ccucccagac gcggccagcg    600
ccgccccacu ccgaaccauc accgccgaca ccuucugcaa acucuuccga gucuacagca    660
acuuccuccg gggaaagcug aagcuguaca cgggggaggc cugcaggaga ggggacagau    720
gacucgagcu agugacugac uaggaucugg uuaccacuaa accagccuca agaacacccg    780
aauggagucu cuaagcuaca uaauaccaac uuacacuuac aaaauguugu cccccaaaau    840
```

| guagccauuc guaucugcuc cuaauaaaaa gaaaguuucu ucacauucua gaaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa a | 1011 |

<210> SEQ ID NO 190
<211> LENGTH: 1653
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 190

| atggaagacg ccaaaaacat aaagaaaggc ccggcgccat tctatccgct ggaagatgga | 60 |
| accgctggag agcaactgca taaggctatg aagagatacg ccctggttcc tggaacaatt | 120 |
| gcttttacag atgcacatat cgaggtggac atcacttacg ctgagtactt cgaaatgtcc | 180 |
| gttcggttgg cagaagctat gaaacgatat gggctgaata caaatcacag aatcgtcgta | 240 |
| tgcagtgaaa actctcttca attctttatg ccggtgttgg gcgcgttatt tatcggagtt | 300 |
| gcagttgcgc ccgcgaacga catttataat gaacgtgaat tgctcaacag tatgggcatt | 360 |
| tcgcagccta ccgtggtgtt cgtttccaaa aaggggttgc aaaaaatttt gaacgtgcaa | 420 |
| aaaaagctcc caatcatcca aaaaattatt atcatggatt ctaaaacgga ttaccaggga | 480 |
| tttcagtcga tgtacacgtt cgtcacatct catctacctc ccggttttaa tgaatacgat | 540 |
| tttgtgccag agtccttcga tagggacaag acaattgcac tgatcatgaa ctcctctgga | 600 |
| tctactggtc tgcctaaagg tgtcgctctg cctcatagaa ctgcctgcgt gagattctcg | 660 |
| catgccagag atcctatttt tggcaatcaa atcattccgg atactgcgat tttaagtgtt | 720 |
| gttccattcc atcacggttt tggaatgttt actacactcg atatttgat atgtggattt | 780 |
| cgagtcgtct taatgtatag atttgaagaa gagctgtttc tgaggagcct tcaggattac | 840 |
| aagattcaaa gtgcgctgct ggtgccaacc ctattctcct tcttcgccaa agcactctg | 900 |
| attgacaaat acgatttatc taatttacac gaaattgctt ctggtggcgc tcccctctct | 960 |
| aaggaagtcg gggaagcggt tgccaagagg ttccatctgc caggtatcag caaggatat | 1020 |
| gggctcactg agactacatc agctattctg attacacccg aggggatga taaaccgggc | 1080 |
| gcggtcggta agttgttcc attttttgaa gcgaaggttg tggatctgga taccgggaaa | 1140 |
| acgctgggcg ttaatcaaag aggcgaactg tgtgtgagag gtcctatgat tatgtccggt | 1200 |
| tatgtaaaca atccggaagc gaccaacgcc ttgattgaca aggatggatg gctacattct | 1260 |
| ggagacatag cttactggga cgaagacgaa cacttcttca tcgttgaccg cctgaagtct | 1320 |
| ctgattaagt acaaaggcta tcaggtggct cccgctgaat ggaatccat cttgctccaa | 1380 |
| caccccaaca tcttcgacgc aggtgtcgca ggtcttcccg acgatgacgc cggtgaactt | 1440 |
| cccgccgccg ttgttgttt ggagcacgga aagacgatga cggaaaaaga gatcgtggat | 1500 |
| tacgtcgcca gtcaagtaac aaccgcgaaa aagttgcgcg gaggagttgt gtttgtggac | 1560 |
| gaagtaccga aaggtcttac cggaaaactc gacgcaagaa aaatcagaga gatcctcata | 1620 |
| aaggccaaga agggcggaaa gatcgccgtg taa | 1653 |

<210> SEQ ID NO 191
<211> LENGTH: 1653
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 191

| | |
|---|---|
| atggaagacg ccaaaaacat aaagaaaggc ccggcgccat tctacccgct ggaagacgga | 60 |
| accgccggag agcaactgca caaggccatg aagagatacg ccctggtgcc cggaacaatc | 120 |
| gccttcacag acgcacacat cgaggtggac atcacctacg ccgagtactt cgaaatgagc | 180 |
| gtgcggctgg cagaagccat gaaacgatac gggctgaaca caaaccacag aatcgtcgta | 240 |
| tgcagcgaaa acagcctgca attcttcatg ccggtgctgg gcgcgctgtt catcggagtg | 300 |
| gcagtggcgc ccgcgaacga catctacaac gaacgggaac tgctcaacag catgggcatc | 360 |
| agccagccca ccgtggtgtt cgtgagcaaa aaggggctgc aaaaaatcct gaacgtgcaa | 420 |
| aaaaagctcc caatcatcca aaaaatcatc atcatggaca gcaaaacgga ctaccaggga | 480 |
| ttccagagca tgtacacgtt cgtcacaagc cacctacccc ccggcttcaa cgaatacgac | 540 |
| ttcgtgccag agagcttcga cagggacaag acaatcgcac tgatcatgaa cagcagcgga | 600 |
| agcaccggcc tgcccaaagg cgtcgccctg ccccacagaa ccgcctgcgt gagattcagc | 660 |
| cacgccagag accccatctt cggcaaccaa atcatcccgg acaccgcgat cctgagcgtg | 720 |
| gtgccattcc accacggctt cggaatgttc accacactcg gatacctgat atgcggattc | 780 |
| cgagtcgtcc tgatgtacag attcgaggag gagctgttcc tgaggagcct gcaggactac | 840 |
| aagatccaaa gcgcgctgct ggtgccaacc ctattcagct tcttcgccaa aagcaccctg | 900 |
| atcgacaaat acgacctgag caacctgcac gaaatcgcca gcggcggcgc cccctcagc | 960 |
| aaggaagtcg gggaagcggt ggccaagagg ttccacctgc aggcatcag gcaaggatac | 1020 |
| gggctcaccg agaccacaag cgccatcctg atcacacccg aggggacga caaaccgggc | 1080 |
| gcggtcggca agtggtgcc attcttcgaa gcgaaggtgg tggacctgga caccgggaaa | 1140 |
| acgctgggcg tgaaccaaag aggcgaactg tgcgtgagag gccccatgat catgagcggc | 1200 |
| tacgtaaaca acccggaagc gaccaacgcc ctgatcgaca aggacggatg gctacacagc | 1260 |
| ggagacatag cctactggga cgaagacgaa cacttcttca tcgtggaccg cctgaagtcc | 1320 |
| ctgatcaagt acaaaggcta ccaggtggcc cccgccgaac tggaaagcat cctgctccaa | 1380 |
| cacccccaaca tcttcgacgc aggcgtcgca ggcctgcccg acgacgacgc cggcgaactg | 1440 |
| cccgccgccg tggtggtgct ggagcacgga aagacgatga cggaaaaaga gatcgtggac | 1500 |
| tacgtcgcca gccaagtaac aaccgcgaaa agctgcgcg gaggagtggt gttcgtggac | 1560 |
| gaagtaccga aaggcctgac cggaaaactc gacgcaagaa aaatcagaga gatcctcata | 1620 |
| aaggccaaga agggcggaaa gatcgccgtg taa | 1653 |

<210> SEQ ID NO 192
<211> LENGTH: 1653
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 192

| | |
|---|---|
| atggaagacg ccaaaaacat aaagaaaggc ccggcgccat tctatccgct ggaagatgga | 60 |
| accgctggag agcaactgca taaggctatg aagagatacg ccctggttcc tggaacaatt | 120 |
| gcttttacag atgcacatat cgaggtggac atcacttacg ctgagtactt cgaaatgtcc | 180 |

-continued

```
gttcggttgg cagaagctat gaaacgatat gggctgaata caaatcacag aatcgtcgta    240
tgcagtgaaa actctcttca attctttatg ccggtgttgg gcgcgttatt tatcggagtg    300
gcagtggcgc ccgcgaacga catctacaac gaacgggaac tgctcaacag catgggcatc    360
agccagccca ccgtggtgtt cgtgagcaaa aaggggctgc aaaaaatcct gaacgtgcaa    420
aaaaagctcc caatcatcca aaaaatcatc atcatggaca gcaaaacgga ctaccaggga    480
ttccagagca tgtacacgtt cgtcacaagc cacctacccc ccggcttcaa cgaatacgac    540
ttcgtgccag agagcttcga cagggacaag acaatcgcac tgatcatgaa cagcagcgga    600
agcaccggcc tgcccaaagg cgtcgccctg ccccacagaa ccgcctgcgt gagattcagc    660
cacgccagag accccatctt cggcaaccaa atcatcccgg acaccgcgat cctgagcgtg    720
gtgccattcc accacggctt cggaatgttc accacactcg gatacctgat atgcggattc    780
cgagtcgtcc tgatgtacag attcgaggag gagctgttcc tgaggagcct gcaggactac    840
aagatccaaa gcgcgctgct ggtgccaacc ctattcagct tcttcgccaa aagcaccctg    900
atcgacaaat acgacctgag caacctgcac gaaatcgcca gcggcggcgc ccccctcagc    960
aaggaagtcg gggaagcggt ggccaagagg ttccacctgc caggcatcag gcaaggatac   1020
gggctcaccg agaccacaag cgccatcctg atcacacccg aggggacga caaaccgggc   1080 gcggtcggca aagtggtgcc attcttcgaa gcgaaggtgg tggacctgga caccgggaaa   1140
acgctgggcg tgaaccaaag aggcgaactg tgcgtgagag gccccatgat catgagcggc   1200
tacgtaaaca acccggaagc gaccaacgcc ctgatcgaca aggacggatg gctacacagc   1260
ggagacatag cctactggga cgaagacgaa cacttcttca tcgtggaccg cctgaagtcc   1320
ctgatcaagt acaaaggcta ccaggtggcc cccgccgaac tggaaagcat cctgctccaa   1380
caccccaaca tcttcgacgc aggcgtcgca ggcctgcccg acgacgacgc cggcgaactg   1440
cccgccgccg tggtggtgct ggagcacgga aagacgatga cggaaaaaga gatcgtggac   1500
tacgtcgcca gccaagtaac aaccgcgaaa aagctgcgcg gaggagtggt gttcgtggac   1560
gaagtaccga aaggcctgac cggaaaactc gacgcaagaa aaatcagaga gatcctcata   1620
aaggccaaga agggcggaaa gatcgccgtg taa                                1653
```